(12) United States Patent
Johns

(10) Patent No.: US 10,064,873 B2
(45) Date of Patent: *Sep. 4, 2018

(54) COMPOUNDS AND COMPOSITIONS FOR TREATING HIV WITH DERIVATIVES OF BETULIN

(71) Applicant: GlaxoSmithKline LLC, Wilmington, DE (US)

(72) Inventor: Brian Alvin Johns, Research Triangle Park, NC (US)

(73) Assignee: GLAXOSMITHKLINE LLC, Wilmington, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/464,553

(22) Filed: Mar. 21, 2017

(65) Prior Publication Data

US 2017/0252356 A1    Sep. 7, 2017

Related U.S. Application Data

(63) Continuation of application No. 14/461,731, filed on Aug. 18, 2014, now abandoned, which is a
(Continued)

(51) Int. Cl.
| | | |
|---|---|---|
| *A61K 31/56* | (2006.01) | |
| *A61K 31/568* | (2006.01) | |
| *C07J 63/00* | (2006.01) | |
| *A61K 31/225* | (2006.01) | |
| *A61K 31/472* | (2006.01) | |

(Continued)

(52) U.S. Cl.
CPC .......... *A61K 31/568* (2013.01); *A61K 31/222* (2013.01); *A61K 31/225* (2013.01); *A61K 31/397* (2013.01); *A61K 31/40* (2013.01); *A61K 31/44* (2013.01); *A61K 31/472* (2013.01); *A61K 31/495* (2013.01); *A61K 31/4985* (2013.01); *A61K 31/505* (2013.01); *A61K 31/506* (2013.01); *A61K 31/5375* (2013.01); *A61K 31/54* (2013.01); *A61K 31/551* (2013.01); *A61K 31/58* (2013.01); *A61K 45/06* (2013.01); *C07C 219/24* (2013.01); *C07C 225/14* (2013.01); *C07D 205/04* (2013.01); *C07D 207/09* (2013.01); *C07D 213/40* (2013.01); *C07D 217/04* (2013.01); *C07D 239/26* (2013.01); *C07D 239/48* (2013.01); *C07D 243/08* (2013.01); *C07D 265/30* (2013.01); *C07D 265/32* (2013.01); *C07D 413/06* (2013.01); *C07D 498/14* (2013.01); *C07J 53/002* (2013.01); *C07J 63/008* (2013.01); *A61K 31/56* (2013.01); *C07C 2601/02* (2017.05); *C07C 2601/14* (2017.05); *C07C 2603/52* (2017.05)

(58) Field of Classification Search
CPC .. A61K 31/568; A61K 31/222; A61K 31/225; A61K 31/397; A61K 31/40; A61K 31/44; A61K 31/472; A61K 31/495; A61K 31/4985; A61K 31/505; A61K 31/506; A61K 31/5375; A61K 31/54; A61K 31/551; A61K 31/58; A61K 31/56; A61K 45/06; C07D 217/04; C07D 239/26; C07D 239/48; C07D 413/06; C07D 243/08; C07D 205/04; C07D 265/30; C07D 265/32; C07D 207/09; C07D 498/14; C07D 213/40; C07J 53/002; C07J 63/008; C07C 219/24; C07C 225/14; C07C 2601/02; C07C 2601/14; C07C 2603/52
USPC .......................................................... 514/177
See application file for complete search history.

(56) References Cited

U.S. PATENT DOCUMENTS

| | | |
|---|---|---|
| 5,034,394 A | 7/1991 | Daluge |
| 5,358,721 A | 10/1994 | Guittard et al. ............... 424/473 |

(Continued)

FOREIGN PATENT DOCUMENTS

| | | |
|---|---|---|
| WO | 200190046 A1 | 11/2001 |
| WO | WO 2005112929 | 12/2005 |

(Continued)

OTHER PUBLICATIONS

U.S. Appl. No. 13/714,627, filed Dec. 14, 2012 Derivatives of Betulin.
(Continued)

*Primary Examiner* — Barbara P Badio
(74) *Attorney, Agent, or Firm* — Robert H. Brink; Edward R. Gimmi; William R. Majarian

(57) ABSTRACT

The present invention relates to compounds characterized by having a structure according to the following Formula I:

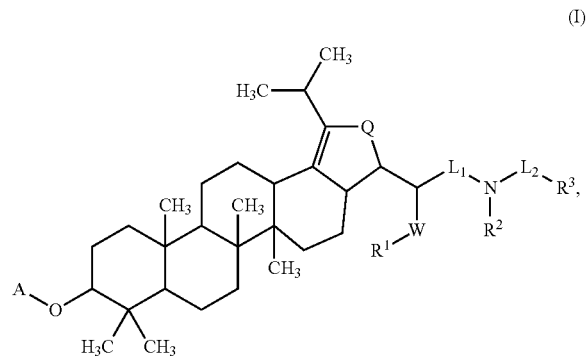

(I)

or a pharmaceutically acceptable salt thereof. Compounds of the present invention are useful for the treatment or prevention of HIV.

8 Claims, 5 Drawing Sheets

Related U.S. Application Data continuation of application No. 13/714,627, filed on Dec. 14, 2012, now Pat. No. 9,102,685.

(60) Provisional application No. 61/576,448, filed on Dec. 16, 2011.

(51) Int. Cl.

| | | |
|---|---|---|
| *A61K 31/495* | (2006.01) | |
| *A61K 31/505* | (2006.01) | |
| *A61K 31/5375* | (2006.01) | |
| *A61K 31/54* | (2006.01) | |
| *A61K 31/551* | (2006.01) | |
| *A61K 45/06* | (2006.01) | |
| *C07D 217/04* | (2006.01) | |
| *C07D 239/26* | (2006.01) | |
| *C07D 243/08* | (2006.01) | |
| *C07D 265/32* | (2006.01) | |
| *C07C 219/24* | (2006.01) | |
| *C07C 225/14* | (2006.01) | |
| *A61K 31/222* | (2006.01) | |
| *A61K 31/4985* | (2006.01) | |
| *C07D 239/48* | (2006.01) | |
| *C07D 498/14* | (2006.01) | |
| *A61K 31/397* | (2006.01) | |
| *A61K 31/40* | (2006.01) | |
| *A61K 31/44* | (2006.01) | |
| *A61K 31/506* | (2006.01) | |
| *C07D 205/04* | (2006.01) | |
| *C07D 207/09* | (2006.01) | |
| *C07D 213/40* | (2006.01) | |
| *C07D 265/30* | (2006.01) | |
| *C07D 413/06* | (2006.01) | |
| *A61K 31/58* | (2006.01) | |
| *C07J 53/00* | (2006.01) | |

(56) References Cited

U.S. PATENT DOCUMENTS

| 9,102,685 B2 | 8/2015 | Johns | |
|---|---|---|---|
| 2003/0026843 A1 | 2/2003 | Bogue | 424/491 |
| 2005/0142205 A1 | 6/2005 | Rashba-Step et al. | 424/490 |
| 2006/0205697 A1 | 9/2006 | Robinson et al. | |
| 2007/0197646 A1 | 8/2007 | Bradbury et al. | |
| 2008/0206161 A1 | 8/2008 | Tamarkin et al. | 424/45 |
| 2009/0023698 A1 | 1/2009 | Krasutsky et al. | |
| 2009/0275583 A1 | 11/2009 | Yager et al. | |
| 2010/0190795 A1 | 7/2010 | Yli-Kauhaluoma et al. | |
| 2011/0144071 A1 | 6/2011 | Grawe et al. | 514/173 |
| 2011/0218204 A1 | 9/2011 | Reddy et al. | |
| 2011/0282055 A1 | 11/2011 | Yoshida et al. | 544/95 |
| 2012/0046291 A1 | 2/2012 | Nitz et al. | 514/169 |
| 2012/0302534 A1 | 11/2012 | Gao et al. | |
| 2015/0313917 A1 | 11/2015 | Cai et al. | 424/497 |

FOREIGN PATENT DOCUMENTS

| WO | 2006106103 A2 | 10/2006 |
|---|---|---|
| WO | WO 2006117666 | 11/2006 |
| WO | 2007141389 A1 | 12/2007 |
| WO | 2007141390 A1 | 12/2007 |
| WO | 2007141391 A1 | 12/2007 |
| WO | 2007141392 A2 | 12/2007 |
| WO | 2007147882 A2 | 12/2007 |
| WO | 2008057420 A2 | 5/2008 |
| WO | 2009082818 A1 | 7/2009 |
| WO | 2009082819 A1 | 7/2009 |
| WO | 2010053817 A1 | 5/2010 |
| WO | 2010054606 A2 | 5/2010 |
| WO | 2011007230 A2 | 1/2011 |
| WO | 2011100308 A1 | 8/2011 |
| WO | WO 2012037320 | 3/2012 |
| WO | 2013020245 A1 | 2/2013 |
| WO | 2013020246 A1 | 2/2013 |
| WO | WO 2013090664 | 6/2013 |
| WO | WO 2013090683 | 6/2013 |
| WO | WO 2014035945 | 3/2014 |
| WO | WO 2014093941 | 6/2014 |
| WO | 2016046786 A1 | 3/2016 |

OTHER PUBLICATIONS

U.S. Appl. No. 14/365,802, filed Jun. 16, 2014 Derivatives of Betulin.
U.S. Appl. No. 14/651,673, filed Jun. 12, 2015 Pharmaceutical Compositions.
U.S. Appl. No. 14/757,754, filed Dec. 23, 2015 Derivatives of Betulin.
Aiken et al. Trends in Molecular Medicine, Jan. 2005, vol. 11, pp. 31-36.
Lan et al Medicinal Chemistry Research, 2011, vol. 20, pp. 1247-1259.
Lansdon et al Medicinal Chemistry Research 2010 vol. 53 pp. 4295-4299.
Andrews et al., Long-acting integrase inhibitor protects macaques from intrarectal simian/human immunodeficiency virus. Science. Mar. 7, 2014;343(6175):1151-4.
Azijn et al., TMC278, a next-generation nonnucleoside reverse transcriptase inhibitor (NNRTI), active against wild-type and NNRTI-resistant HIV-1. Antimicrob Agents Chemother. Feb. 2010;54(2):718-27.
Dolgin, Long-acting HIV drugs advanced to overcome adherence challenge. Nat Med. Apr. 2014;20(4):323-4.
Highleyman, ICAAC 2012: Long-acting Integrase inhibitor S/GSK1265744 Active Against HIV Subtypes. Retrieved online: http://www.hivandhepatitis.com/hiv-aids/hiv-aids-topics/hiv-treatment/3781-icaac-2012-long-acting-integrase-inhibitor-sgsk1265744-active-against-multiple-hiv-subtypes. Sep. 2012.
Knapp et al., In vitro selection of clinically relevant bevirimat resistance mutations revealed by "deep" sequencing of serially passaged, quasispecies-containing recombinant HIV-1. J Clin Microbiol. Jan. 2011;49(1):201-8.
The Merck Index. Abacavir. 14th Edition, p. 9 (2013).
Yoshinaga et al., Antiviral Characteristics of S/GSK1265744, An HIV Integrase Inhibitor (INI) Dosed by Oral or Long-acting Parenteral Injection . . . once monthly or 3 months dosing/PrEP/HAART. 52nd ICAAC Interscience Conference on Antimicrobial Agents and Chemotherapy. Sep. 9-12, 2012.
U.S. Appl. No. 13/714,627 Non Final dated Jul. 1, 2014.
U.S. Appl. No. 13/714,627 Notice of allowance filed Dec. 2, 2014.
U.S. Appl. No. 13/714,627 Notice of allowance dated Mar. 31, 2015.
U.S. Appl. No. 13/714,627 preliminary amendment filed May 27, 2014.
U.S. Appl. No. 13/714,627 RCE amendment filed Mar. 2, 2015.
U.S. Appl. No. 13/714,627 Response filed Sep. 25, 2014.
U.S. Appl. No. 14/365,802 Non Final dated Jun. 26, 2015.
U.S. Appl. No. 14/365,802 preliminary amendment filed Jun. 16, 2014.
U.S. Appl. No. 14/365,802 Response to Office Action dated Dec. 23, 2015.
U.S. Appl. No. 14/461,731, filed Aug. 18, 2014 Derivatives of Betulin.
U.S. Appl. No. 14/461,731 Final dated May 10, 2016.
U.S. Appl. No. 14/461,731 Issue Fee Payment dated Feb. 28, 2017.
U.S. Appl. No. 14/461,731 Non Final dated Nov. 19, 2015.
U.S. Appl. No. 14/461,731 Notice of allowance dated Dec. 9, 2016.
U.S. Appl. No. 14/461,731 Petition to Withdraw dated Mar. 21, 2017.
U.S. Appl. No. 14/461,731 RCE amendment filed Nov. 10, 2016.
U.S. Appl. No. 14/461,731 Response filed Feb. 19, 2016.
U.S. Appl. No. 14/651,673 Non Final dated Mar. 24, 2016.

(56) References Cited

OTHER PUBLICATIONS

U.S. Appl. No. 14/651,673 Notice of Allowance dated Dec. 13, 2016.
U.S. Appl. No. 14/651,673 Notice of Allowance dated Apr. 11, 2017.
U.S. Appl. No. 14/651,673 Preliminary Amendment filed Jun. 12, 2015.
U.S. Appl. No. 14/651,673 Response filed Sep. 26, 2016.
U.S. Appl. No. 14/651,673 Response to Restriction Requirement dated Mar. 7, 2016.
U.S. Appl. No. 14/651,673 Restriction Requirement dated Jan. 6, 2016.
U.S. Appl. No. 14/651,673 Supplemental Response filed Nov. 28, 2016.
U.S. Appl. No. 14/757,754 Non Final Office Action dated Feb. 1, 2017.
U.S. Appl. No. 14/757,754 Preliminary Amendment filed Dec. 23, 2015.
U.S. Appl. No. 14/757,754 Response filed May 1, 2017.
U.S. Appl. No. 15/514,564 filed Mar. 27, 2017 Derivatives of Betulin.
U.S. Appl. No. 15/514,564 Preliminary Amendment filed Mar. 27, 2017.
International Search Report and Written Opinion for Application No. PCT/US2012/069637, dated Feb. 19, 2013.

COMPOUNDS AND COMPOSITIONS FOR TREATING HIV WITH DERIVATIVES OF BETULIN

CROSS REFERENCE TO RELATED PATENTS AND PATENT APPLICATIONS

This is a Continuation application of U.S. application Ser. No. 14/461,731 filed 18 Aug. 2014, now abandoned, which is a Continuation application of U.S. patent application Ser. No. 13/714,627, now granted U.S. Pat. No. 9,102,685, which claims priority to US Provisional Application No. 61/576,448 filed 16 Dec. 2011, which is hereby incorporated by reference in its entirety.

FIELD OF THE INVENTION

The present invention relates to compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Despite the positive impact of HAART on patient survival, drug resistance can still occur.

The HIV Gag polyprotein precursor (Pr55Gag), which is composed of four protein domains—matrix (MA), capsid (CA), nucleocapsid (NC) and p6—and two spacer peptides, SP1 and SP2, represents a new therapeutic target. Although the cleavage of the Gag polyprotein plays a central role in the progression of infectious virus particle production, to date, no antiretroviral drug has been approved for this mechanism.

In most cell types, assembly occurs at the plasma membrane, and the MA domain of Gag mediates membrane binding. Assembly is completed by budding of the immature particle from the cell. Concomitant with particle release, the virally encoded PR cleaves Gag into the four mature protein domains, MA, CA, NC and p6, and the two spacer peptides, SP1 and SP2. Gag-Pol is also cleaved by PR, liberating the viral enzymes PR, RT and IN. Gag proteolytic processing induces a morphological rearrangement within the particle, known as maturation. Maturation converts the immature, donut-shaped particle to the mature virion, which contains a condensed conical core composed of a CA shell surrounding the viral RNA genome in a complex with NC and the viral enzymes RT and IN. Maturation prepares the virus for infection of a new cell and is absolutely essential for particle infectivity.

Bevirimat (PA-457) is a maturation inhibitor that inhibits the final step in the processing of Gag, the conversion of capsid-SP1 (p25) to capsid, which is required for the formation of infectious viral particles. Bevirimat has activity against ART-resistant and wild-type HIV, and has shown synergy with antiretrovirals from all classes. Bevirimat reduced HIV viral load by a mean of 1.3 $\log_{10}$/mL in patients who achieved trough levels of >=20 μg/mL and who did not have any of the key baseline Gag polymorphisms at Q369, V370 or T371. However, Bevirimat users with Gag polymorphisms at Q369, V370 or T371 demonstrated significantly lower load reductions than patients without Gag polymorphisms at these sites.

Other examples of maturation inhibitors can be found in PCT Patent Application No. WO2011/100308, "Derivatives of Betulin"; PCT Patent Application No. PCT/US2012/024288, "Novel Anti-HIV Compounds and Methods of Use Thereof"; Chinese PCT Application No. PCT/CN2011/001302, "Carbonyl Derivatives of Betulin"; Chinese PCT Application No. PCT/CN2011/001303, "Methylene Derivatives of Betulin"; Chinese PCT Application Nos. PCT/CN2011/002105 and PCT/CN2011/002159, "Propenoate Derivatives of Betulin". Maturation inhibitors in the prior art leave open gaps in the areas of polymorphism coverage whereby potency against a broad range of clinically relevant gag sequences is extremely important, along with overall potency including the clinically relevant protein adjusted antiviral activity that will be required for robust efficacy in long term durability trials. To date, no maturation inhibitor has achieved an optimal balance of these properties.

It would therefore be an advance in the art to discover alternative compounds that are an effective balance of the aforementioned properties for the prevention and/or treatment of HIV infections.

SUMMARY OF THE INVENTION

In accordance with one embodiment of the present invention, there is provided a compound of Formula I:

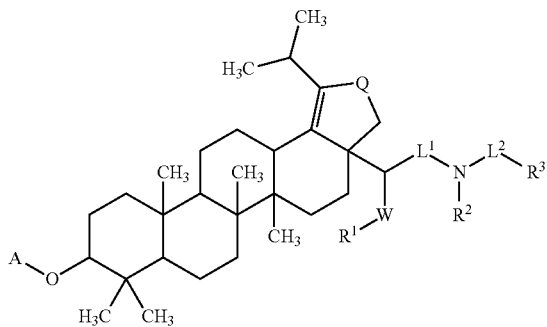

(I)

or a pharmaceutically acceptable salt thereof, wherein:
A is

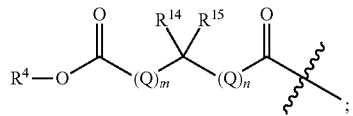

$L_1$ and $L_2$ are independently selected from a bond or $[C(R^6R^{6'})]_q$;

each instance of Q is independently selected from —$CH_2$— or —C(=O)—;

W is selected from a bond or O;

$R^1$ is selected from the group consisting of hydrogen, ($C_1$-$C_{12}$)alkyl, —C(O)$R^5$, —$CH_2$—O—($C_1$-$C_6$)alkyl, 2-tetrahydro-2H-pyran, and

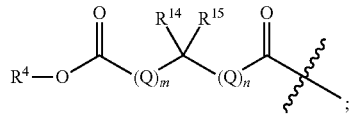

$R^2$ is selected from the group consisting of —H, ($C_1$-$C_{12}$)alkyl, —($C_1$-$C_6$)alkyl-O$R^4$, —($C_1$-$C_6$)alkyl-O—($C_1$-$C_6$)alkyl, —C(O)$R^5$, —($CH_2$)$_r$N$R^7R^8$, and —($CH_2$)$_r$N$^+$($R^4$)$_3$, wherein when W is O, $R^1$ and $R^2$ can optionally be taken together with the O and N to which they are respectively joined to form a 4 to 8 membered heterocyclyl ring, wherein the heterocyclyl ring may be optionally substituted by one to two $R^{11}$ groups;

$R^3$ is selected from the group consisting of hydrogen, ($C_1$-$C_{12}$)alkyl, —N$R^1R^2$, —O$R^5$,

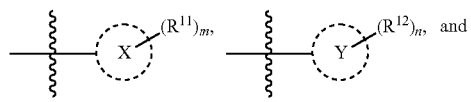

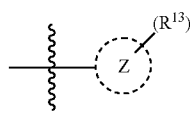

wherein:
X is a monocyclic or bicyclic ($C_5$-$C_{14}$)aryl,
Y is selected from a monocyclic or bicyclic ($C_2$-$C_9$) heterocyclyl or monocyclic or bicyclic ($C_2$-$C_9$)heteroaryl, each having one to three heteroatoms selected from S, N or O, and
Z is a monocyclic or bicyclic ($C_3$-$C_8$)cycloalkyl;

$R^2$ and $R^3$ can optionally be taken together with the nitrogen and $L_2$ to which they are respectively joined to form a 4 to 8 membered heterocyclyl ring, wherein the heterocyclyl ring may be optionally substituted by one to two $R^{11}$ groups;

$R^4$ is selected from the group consisting of —H and ($C_1$-$C_6$)alkyl;

$R^5$ is selected from the group consisting of —H, ($C_1$-$C_6$) alkyl, —$R^3$, —($CH_2$)$_r$N$R^7R^8$, and —($CH_2$)$_r$O$R^7$.

$R^6$ and $R^{6'}$ are independently selected from the group consisting of —H, ($C_1$-$C_6$)alkyl, ($C_3$-$C_8$)cycloalkyl, ($C_1$-$C_6$) alkoxy, haloalkyl, —Y, —($CH_2$)$_r$N$R^7R^8$, —C(O)OH, and —C(O)NH$_2$, wherein the $R^6$ and $R^{6'}$ groups can optionally be taken together with the carbon to which they are joined to form a 3 to 8 membered cycloalkyl ring, and wherein the cycloalkyl ring may be optionally substituted by one to three $R^{11}$ groups;

$R^7$ and $R^8$ are independently selected from the group consisting of —H, ($C_1$-$C_6$)alkyl, ($C_3$-$C_8$)cycloalkyl, -Q-aryl-($R^4$)$_n$, —N$R^{14}R^{15}$, —C(O)$CH_3$, wherein $R^7$ and $R^8$ can optionally be taken together with the nitrogen to which they are joined to form a 4 to 8 membered heterocyclyl or heteroaryl ring containing one to three heteroatoms selected from —N$R^5$—, —O—, —S—, —S(O)—, or —$SO_2$—, wherein the heterocyclyl or heteroaryl ring may be optionally substituted by one to three $R^{11}$ groups;

$R^9$ is halo;

$R^{10}$ is —N($R^{16}$)$_2$;

$R^{11}$, $R^{12}$, and $R^{13}$ are independently selected from the group consisting of oxo, hydroxyl, halo, ($C_1$-$C_6$)alkoxy, —$R^6$($R^9$)$_q$, —O$R^6$($R^9$)$_q$, nitro, —$SO_2R^6$, ($C_1$-$C_6$)alkyl, —C(O)$R^{10}$, —$R^4$Y$R^6$, —CO(O)$R^4$, and —CO(O)$R^5$, wherein any two $R^{11}$, $R^{12}$ or $R^{13}$ groups can optionally join to form a 3 to 8 membered cycloalkyl, aryl, heterocyclyl or heteroaryl ring, wherein the heterocyclyl or heteroaryl ring may contain one to three heteroatoms selected from —N$R^5$—, —O—, —S—, —S(O)—, or —$SO_2$—, and wherein the cycloalkyl, aryl, heterocyclyl or heteroaryl ring may be optionally substituted by one to three $R^{16}$ groups;

$R^{14}$ and $R^{15}$ are independently selected from the group consisting of —H, ($C_1$-$C_6$)alkyl, ($C_3$-$C_8$)cycloalkyl, ($C_1$-$C_6$) alkoxy, —[C($R^6$)$_2$]$_r$—, —O[C($R^6$)$_2$]$_r$—, oxo, hydroxyl, halo, —C(O)$R^7$, —$R^{10}$, and —CO(O)$R^2$, wherein $R^{14}$ and $R^{15}$ can optionally be taken together with the carbon to which they are joined to form a 3 to 8 membered cycloalkyl ring or 4 to 8 membered heterocyclyl ring containing one to three heteroatoms selected from —N$R^5$—, —O—, —S—, —S(O)—, or —$SO_2$—, wherein the cycloalkyl ring or heterocyclyl ring may be optionally substituted by one to three $R^{16}$ groups;

$R^{16}$ is independently selected from the group consisting of —H, halo, oxo, hydroxyl, ($C_1$-$C_6$)alkyl, ($C_1$-$C_6$)alkoxy, ($C_3$-$C_8$)cycloalkyl, —$R^6$($R^9$)$_q$, —O$R^6$($R^9$)$_q$, —N($R^4$)$_2$, —(CH$_2$)$_r$-heterocyclyl, —C(O)OH, —C(O)NH$_2$, —R$^5$(R$^9$)$_q$, —OR$^5$(R$^9$)$_q$, nitro, —SO$_2$R$^6$, —C(O)R$^{10}$, and —CO(O)R$^4$;

m and n in each instance are independently 0, 1, 2, 3, or 4;

p is independently 0, 1, 2, 3, or 4; and r and q in each instance are independently 0, 1, 2, 3, or 4.

In a second aspect, the present invention relates to a pharmaceutical composition comprising a) the compound of Formula I or Formula II or a pharmaceutically acceptable salt the thereof; and b) a pharmaceutically acceptable excipient.

In a third aspect, the present invention is a method of treating an HIV infection comprising administering to a subject suffering therefrom a compound of Formula I or Formula II, or a pharmaceutically acceptable salt thereof.

Compounds of the present invention are useful for the treatment of subjects with an HIV infection or for the treatment of subjects at risk of acquiring an HIV infection.

DETAILED DESCRIPTION OF REPRESENTATIVE EMBODIMENTS

Figure 1:
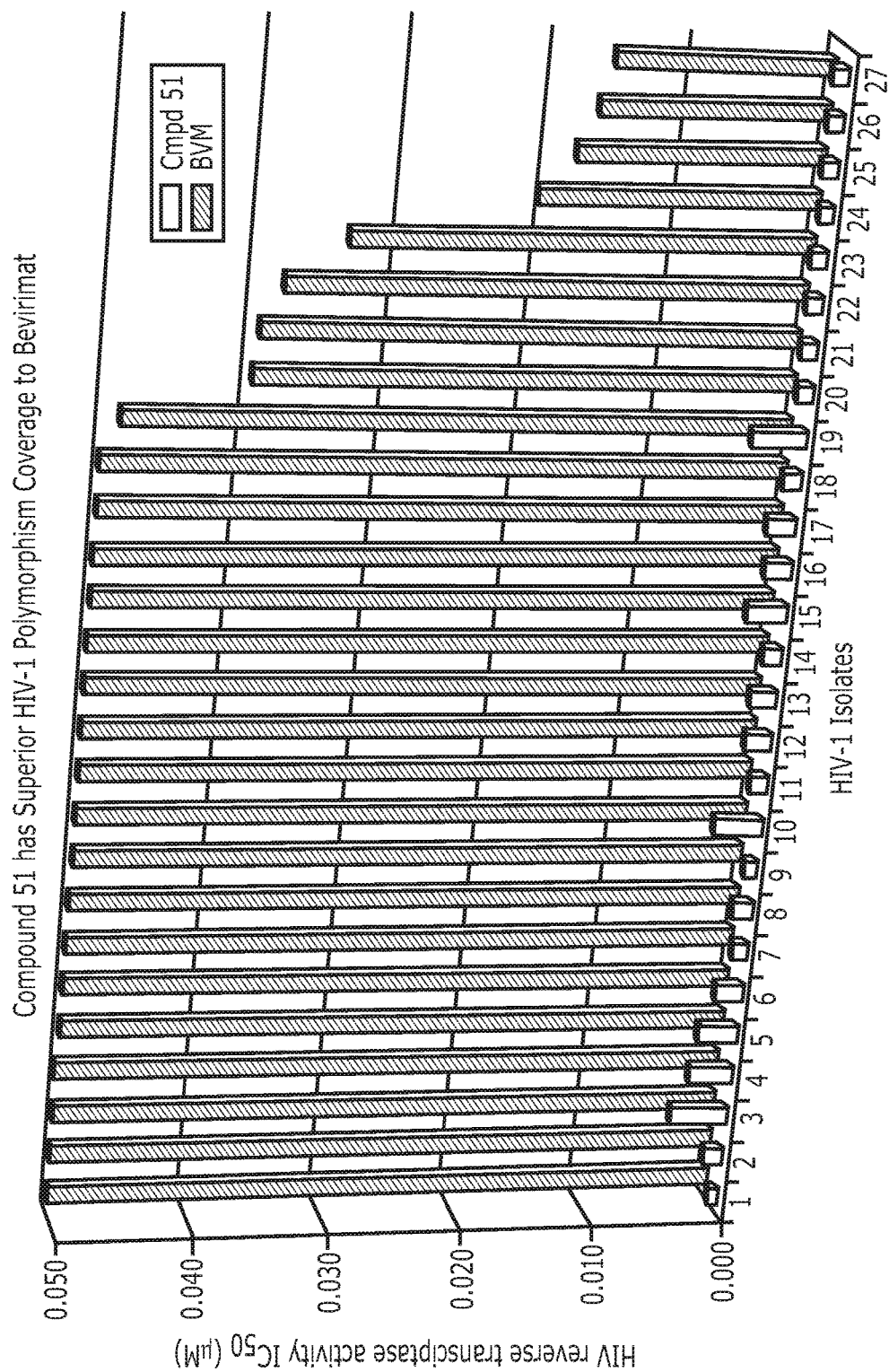
FIG. 1 shows a bar graph representing a comparison between Bevirimat and compound 51 of their relative ability to inhibit HIV reverse transcriptase activity across a broad panel of HIV-1 isolates.

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "(C$_x$-C$_y$)alkyl" refers to alkyl groups having from x to y carbon atoms. The term "alkyl" includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Alkylene" or "alkylene" refers to divalent saturated aliphatic hydrocarbyl groups having from 1 to 10 carbon atoms and, in some embodiments, from 1 to 6 carbon atoms. "(C$_u$-C$_v$)alkylene" refers to alkylene groups having from u to v carbon atoms. The alkylene groups include branched and straight chain hydrocarbyl groups. For example, "(C$_1$-C$_6$)alkylene" is meant to include methylene, ethylene, propylene, 2-methypropylene, dimethylethylene, pentylene, and so forth. As such, the term "propylene" could be exemplified by the following structure:

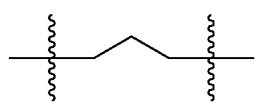

Likewise, the term "dimethylbutylene" could be exemplified by any of the following three structures or more:

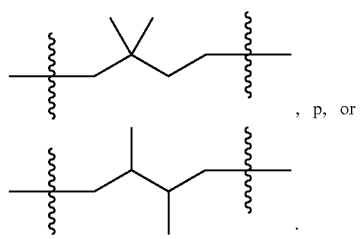

, p, or

Furthermore, the term "(C$_1$-C$_6$)alkylene" is meant to include such branched chain hydrocarbyl groups as cyclopropylmethylene, which could be exemplified by the following structure:

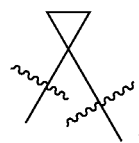

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C═C<). For example, (C$_x$-C$_y$)alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, (C$_2$-C$_6$)alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl- C(O)—, heteroaryl-C(O)—, and heterocyclic-C(O)—. Acyl includes the "acetyl" group CH₃C(O)—.

"Acylamino" refers to the groups —NR²⁰C(O)alkyl, —NR²⁰C(O)cycloalkyl, —NR²⁰C(O)alkenyl, —NR²⁰C(O)alkynyl, —NR²⁰C(O)aryl, —NR²⁰C(O)heteroaryl, and —NR²⁰C(O)heterocyclic, wherein R²⁰ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —NR²¹R²² where R²¹ and R²² are independently selected from hydrogen, alkyl, alkenyl, alkynyl, aryl, cycloalkyl, heteroaryl, heterocyclic, —SO₂-alkyl, —SO₂-alkenyl, —SO₂-cycloalkyl, —SO₂-aryl, —SO₂-heteroaryl, and —SO₂-heterocyclic, and wherein R²¹ and R²² are optionally joined together with the nitrogen bound thereto to form a heterocyclic group. When R²¹ is hydrogen and R²² is alkyl, the amino group is sometimes referred to herein as alkylamino. When R²¹ and R²² are alkyl, the amino group is sometimes referred to herein as dialkylamino. When referring to a monosubstituted amino, it is meant that either R²¹ or R²² is hydrogen but not both. When referring to a disubstituted amino, it is meant that neither R²¹ nor R²² are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR²⁶R²⁷ where R²⁶ and R²⁷ are independently selected from hydrogen, alkyl, alkenyl, alkynyl, aryl, cycloalkyl, heteroaryl, heterocyclic, hydroxy, alkoxy, amino, and acylamino, and where R²⁶ and R²⁷ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"AUC" refers to the area under the plot of plasma concentration of drug (not logarithm of the concentration) against time after drug administration.

"EC₅₀" refers to the concentration of a drug that gives half-maximal response.

"IC₅₀" refers to the half-maximal inhibitory concentration of a drug. Sometimes, it is also converted to the pIC₅₀ scale (-log IC₅₀), in which higher values indicate exponentially greater potency.

"Clade" refers to a hypothetical construct based on experimental data. Clades are found using multiple (sometimes hundreds) of traits from a number of species (or specimens) and analyzing them statistically to find the most likely phylogenetic tree for the group.

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

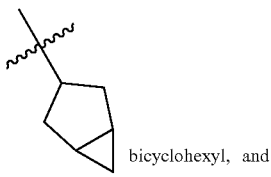 bicyclohexyl, and 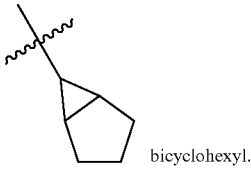 bicyclohexyl.

"(C$_u$-C$_v$)cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

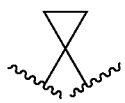

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

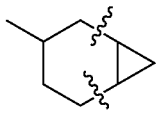

"Carboxy" or "carboxyl" refers interchangeably to the groups

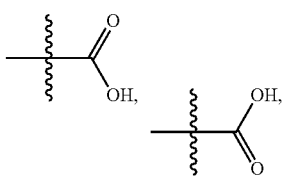

—C(O)O, or —CO₂.

"Halo" or "halogen" refers to fluoro, chloro, bromo, and iodo.

"Haloalkyl" refers to substitution of an alkyl group with 1 to 3 halo groups (e.g., bifluoromethyl or trifluoromethyl).

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Human Serum Protein Shift Assay" refers to an HIV assay using a Luciferase Reporter to determine percent inhibition—pIC$_{50}$. The HIV assay makes use of a two-cell co-culture system. In this assay, an infected cell line J4HxB2 and an indicator cell line HOS (delta LTR+luciferase) are co-cultured in the presence and absence of compound. The assay is designed to find inhibitors that prevent the infection of HOS cells by the J4HxB2 cell line. The assay can detect inhibitors of any stage of the HIV infection cycle.

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., C$_3$-C$_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" or "fused heterocycle" refer to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

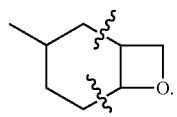

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

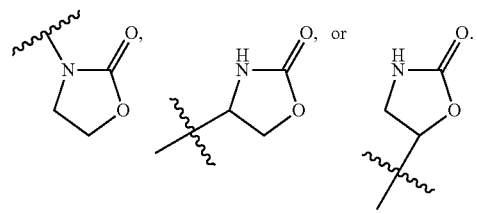 [SMILES: *N1CCOC1=O ; *C1COC(=O)N1 ; "or" ; *C1CNC(=O)O1]

"Oxo" refers to a (=O) group.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the EC$_{50}$ values determined in the absence and presence of human serum.

"QVT" refers to the amino acids at positions 369, 370, and 371, respectively in the Sp1 fragment of HIV-1 Gag.

"Racemates" refers to a mixture of enantiomers. In an embodiment of the invention, the compounds of Formula I, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

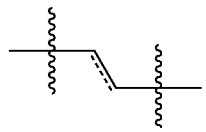

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N-containing heteroaryl ring with one to three double bonds arranged in any position that still depicts the proper valence:

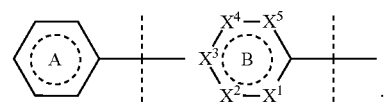

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

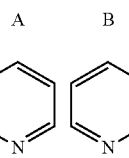

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—$C(R^x)_2$", it should be understood that the two $R^x$ groups can be the same, or they can be different if $R^x$ is defined as having more than one possible identity. In addition, certain substituents are drawn as —$R^xR^y$, where the "—" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

As recited above, Bevirimat is a yet unapproved anti-HIV drug derived from a betulinic acid-like compound, first isolated from *Syzygium claviflorum*, a Chinese herb. It is believed to inhibit HIV by a novel mechanism, so-called maturation inhibition. Like protease inhibitors, Bevirimat and other maturation inhibitors interfere with protease processing of newly translated HIV polyprotein precursor, called gag. Gag is an essential structural protein of the HIV virus. Gag undergoes a chain of interactions both with itself and with other cellular and viral factors to accomplish the assembly of infectious virus particles.

However, naturally occurring polymorphisms in HIV are present in some infected individuals, thus lowering the anti-HIV efficacy of some currently considered therapies. Indeed, studies have shown that presence of a number of single nucleotide polymorphisms in the Capsid/SP1 spacer protein (CA/SP1) cleavage site has resulted in clinical resistance in HIV patients to Bevirimat. Likewise, mutations in the glutamine-valine-threonine (QVT) motif of the SP1 peptide are also known to cause Bevirimat resistance in HIV infected patients. Mutations in the QVT motif of the SP1 peptide are the primary predictors of failure to respond to Bevirimat and the effect of these mutations has been repeatedly demonstrated. These problems eventually led to the cessation of clinical development of Bevirimat. See Knapp, D., et al., *J. Clin. Microbiol.* 49(1): 201-208 (2011).

Bevirimat:

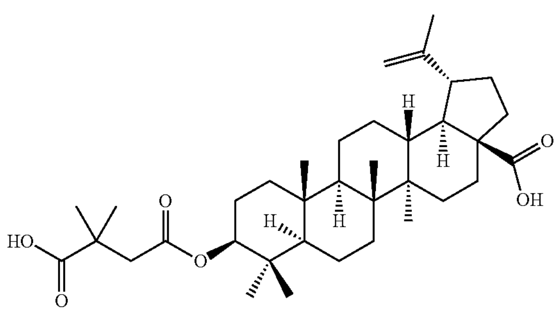

Bevirimat's Clinical Problems:

Polymorphism issues & weak potency.

MT4 antiviral assay NL4-3 strain $EC_{50}$=223 nM.

MT4 antiviral assay NL4-3 strain with V370A site directed mutant polymorphism $EC_{50}$=6062 nM.

In assay fold shift with human serum 157 fold. See Table 6.

$C_{min}$ target >20 μg/mL*.

>40% of clade B patients have QVT polymorphisms*.

*See McCallister, et al., XVII International Drug Resistance Workshop, Jun. 10-14, 2008, Sitges, Spain. Conference poster "*HIV*-1 *Gag Polymorphisms Determine Treatment Response to Bevirimat* (*PA*-457)".

After the above HIV clinical problems with Bevirimat were reported, several new HIV active maturation inhibitor compounds were discovered. For example, certain maturation inhibitor compounds (hereinafter, compounds "A", "B" and "C", as shown below) have been described in PCT Published Application No. WO2011/100308 and PCT Application Serial No. PCT/CN2011/001302. In addition, the present application also describes compounds 51 and 56, among others, as detailed throughout. The present application describes compounds that are novel over the compounds described in PCT Published Application No. WO2011/100308 and PCT Application Serial No. PCT/CN2011/001302. In addition, certain compounds described herein show unexpectedly superior properties over the compounds ("A", "B", and "C") described in PCT Published Application No. WO2011/100308 and PCT Application Serial No. PCT/CN2011/001302.

One difference between the compounds described in those two references and the compounds of the present application is that both of those references have compounds requiring a carbonyl group at a position where, instead, the present application describes compounds that cannot have a carbonyl at the same position. By way of example only, this carbonyl versus non-carbonyl difference is highlighted by the arrows indicated directly below. The generic structures of Formulas (I) and (II) bear this out within the present application because when W is oxygen, there can only be a single bond between the adjacent carbon and the W. In sum, there can be no double bond between W and its adjacent carbon so as to form a carbonyl in the Formulas of the present application.

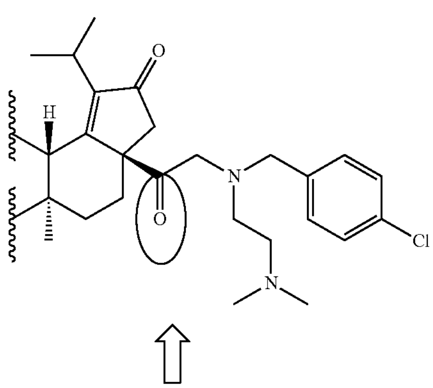

vs.

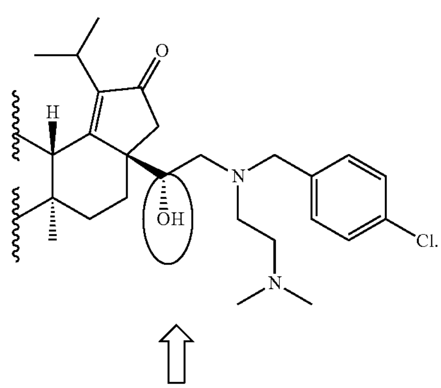

Indeed, this structural difference has now been discovered to unexpectedly improve many of the properties that are involved with creating an efficacious drug for the prevention and/or treatment of viral diseases, such as HIV. One or more of such properties of certain compounds described within the present application, include, but are not limited to, improving the HIV virus polymorphism coverage, improving the in vitro potency ($EC_{50}$), reducing the projected clinical human AUC target, potentially reducing any toxicity window by lowering the required dosage to be efficacious, and reducing the impact of protein binding and/or serum shift upon the projected clinical AUC target.

Such improvements to the pharmacokinetics and projected clinical use of certain compounds described herein are described in more detail within Examples 84-89 below.

Compound A

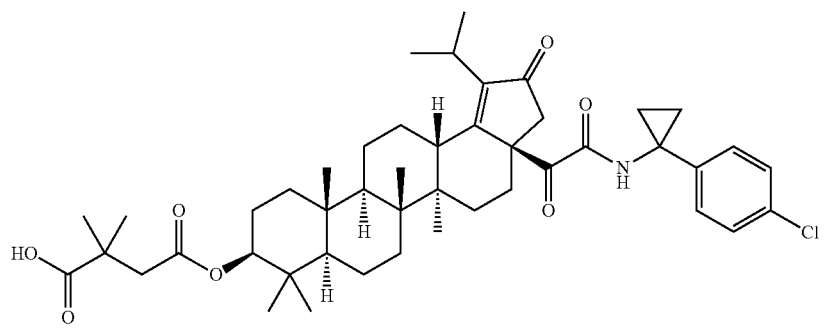

Compound B

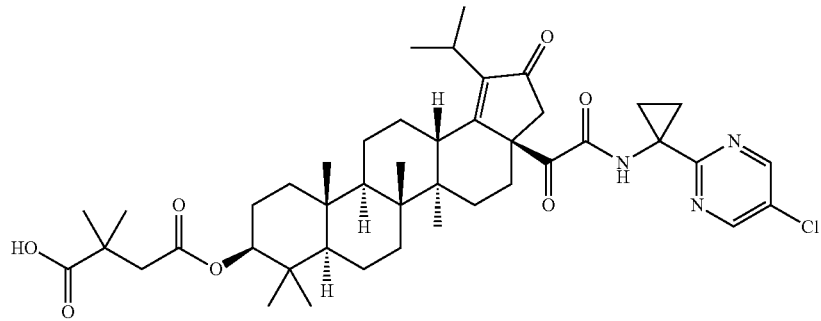

Compound C

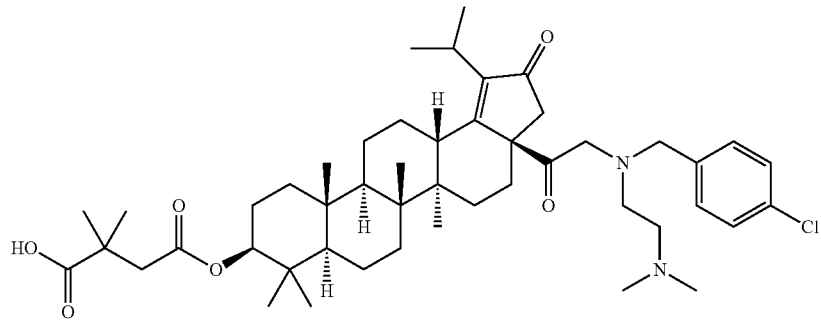

(Example 17-19 from PCT Published Application No. WO/2011/10038)

Compound 51

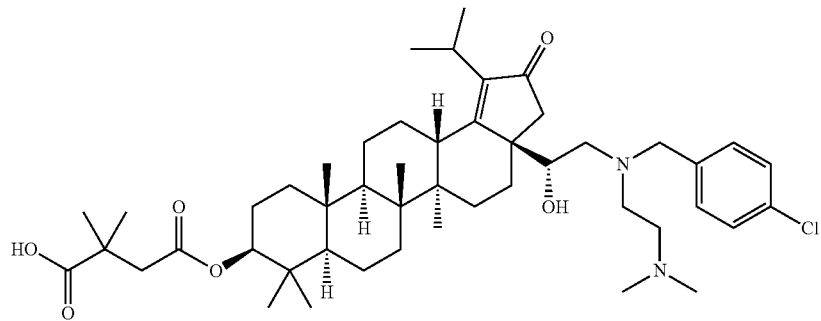

(Example 18 herein)

-continued

Compound 56

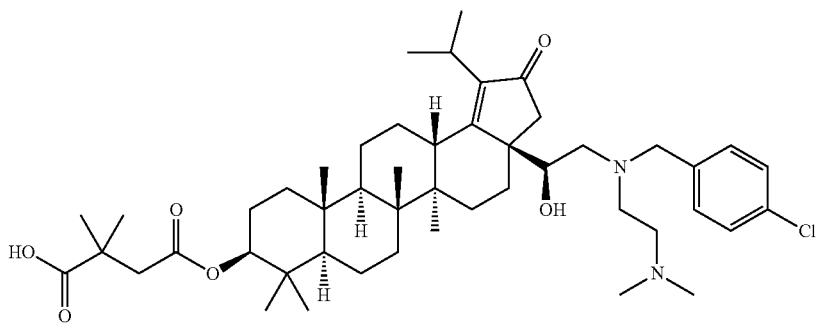

(Example 19 herein)

In accordance with one embodiment of the present invention, there is provided a compound having the structure of Formula I:

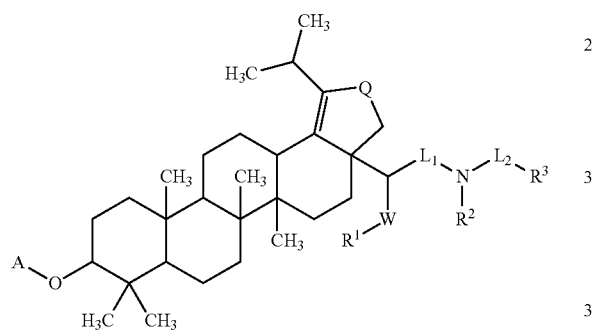

or a pharmaceutically acceptable salt thereof, wherein:

A is

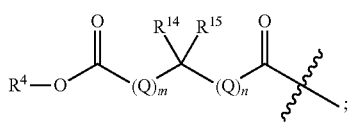

$L_1$ and $L_2$ are independently selected from a bond or $[C(R^6R^{6\prime})]_q$;

each instance of Q is independently selected from —$CH_2$— or —C(=O)—;

W is selected from a bond or O;

$R^1$ is selected from the group consisting of —H, ($C_1$-$C_{12}$) alkyl, —C(O)$R^5$, —$CH_2$—O—($C_1$-$C_6$)alkyl, 2-tetrahydro-2H-pyran, and

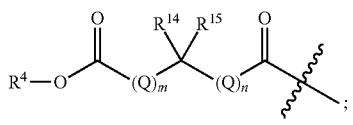

$R^2$ is selected from the group consisting of —H, ($C_1$-$C_{12}$) alkyl, —($C_1$-$C_6$)alkyl-O$R^4$, —($C_1$-$C_6$)alkyl-O—($C_1$-$C_6$) alkyl, —C(O)$R^5$, —$(CH_2)_r$N$R^7R^8$, and —$(CH_2)_r$N$^+$($R^4$)$_3$, wherein when W is O, $R^1$ and $R^2$ can optionally be taken together with the O and N to which they are respectively joined to form a 4 to 8 membered heterocyclyl ring, wherein the heterocyclyl ring may be optionally substituted by one to two $R^{11}$ groups;

$R^3$ is selected from the group consisting of —H, ($C_1$-$C_{12}$) alkyl, —NR$^1$R$^2$, —OR$^5$,

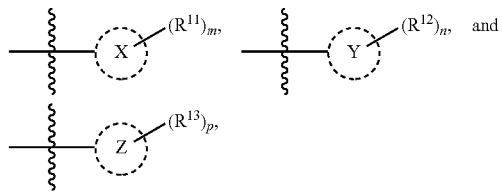

wherein:

X is a monocyclic or bicyclic ($C_5$-$C_{14}$)aryl,

Y is selected from a monocyclic or bicyclic ($C_2$-$C_9$) heterocyclyl or monocylic or bicyclic ($C_2$-$C_9$)heteroaryl, each having one to three heteroatoms selected from S, N or O, and Z is a monocyclic or bicyclic ($C_3$-$C_8$)cycloalkyl;

$R^2$ and $R^3$ can optionally be taken together with the nitrogen and $L_2$ to which they are respectively joined to form a 4 to 8 membered heterocyclyl ring, wherein the heterocyclyl ring may be optionally substituted by one to two $R^{11}$ groups;

$R^4$ is selected from the group consisting of —H and ($C_1$-$C_6$)alkyl;

$R^5$ is selected from the group consisting of —H, ($C_1$-$C_6$) alkyl, —$R^3$, —$(CH_2)_r$N$R^7R^8$, and —$(CH_2)_r$O$R^7$.

$R^6$ and $R^{6\prime}$ are independently selected from the group consisting of —H, ($C_1$-$C_6$)alkyl, ($C_3$-$C_8$)cycloalkyl, ($C_1$-$C_6$) alkoxy, haloalkyl, —Y, —$(CH_2)_r$N$R^7R^8$, —C(O)OH, and —C(O)NH$_2$, wherein the $R^6$ and $R^{6\prime}$ groups can optionally be taken together with the carbon to which they are joined to form a 3 to 8 membered cycloalkyl ring, and wherein the cycloalkyl ring may be optionally substituted by one to three $R^{11}$ groups;

$R^7$ and $R^8$ are independently selected from the group consisting of —H, ($C_1$-$C_6$)alkyl, ($C_3$-$C_8$)cycloalkyl, -Q-aryl-($R^4$)$_n$, —NR$^{14}$R$^{15}$, —C(O)CH$_3$, wherein $R^7$ and $R^8$ can optionally be joined together with the nitrogen to which they are joined to form a 4 to 8 membered heterocyclyl or heteroaryl ring containing one to three heteroatoms selected from —NR$^5$—, —O—, —S—, —S(O)—, or —SO$_2$—, wherein the heterocyclyl or heteroaryl ring may be optionally substituted by one to three $R^{11}$ groups;
$R^9$ is halo;
$R^{10}$ is —N($R^{16}$)$_2$;
$R^{11}$, $R^{12}$, and $R^{13}$ are independently selected from the group consisting of oxo, hydroxyl, halo, ($C_1$-$C_6$)alkoxy, —$R^6(R^9)_q$, —$OR^6(R^9)_q$, nitro, —$SO_2R^6$, ($C_1$-$C_6$)alkyl, —C(O)$R^{10}$, —$R^4YR^6$, —CO(O)$R^4$, and —CO(O)$R^5$, wherein any two $R^{11}$, $R^{12}$ or $R^{13}$ groups can optionally join to form a 3 to 8 membered cycloalkyl, aryl, heterocyclyl or heteroaryl ring, wherein the heterocyclyl or heteroaryl ring may contain one to three heteroatoms selected from —$NR^5$—, —O—, —S—, —S(O)—, or —$SO_2$—, and wherein the cycloalkyl, aryl, heterocyclyl or heteroaryl ring may be optionally substituted by one to three $R^{16}$ groups;
$R^{14}$ and $R^{15}$ are independently selected from the group consisting of —H, ($C_1$-$C_6$)alkyl, ($C_3$-$C_8$)cycloalkyl, ($C_1$-$C_6$)alkoxy, —[C($R^6$)$_2$]$_r$—, —O[C($R^6$)$_2$]$_r$—, oxo, hydroxyl, halo, —C(O)$R^7$, —$R^{10}$, and —CO(O)$R^2$, wherein $R^{14}$ and $R^{15}$ can optionally be taken together with the carbon to which they are joined to form a 3 to 8 membered cycloalkyl ring or 4 to 8 membered heterocyclyl ring containing one to three heteroatoms selected from —$NR^5$—, —O—, —S—, —S(O)—, or —$SO_2$—, wherein the cycloalkyl ring or heterocyclyl ring may be optionally substituted by one to three $R^{16}$ groups;
$R^{16}$ is independently selected from the group consisting of —H, halo, oxo, hydroxyl, ($C_1$-$C_6$)alkyl, ($C_1$-$C_6$)alkoxy, ($C_3$-$C_8$)cycloalkyl, —$R^6(R^9)_q$, —$OR^6(R^9)_q$, —N($R^4$)$_2$, —(CH$_2$)$_r$-heterocycle, —C(O)OH, —C(O)NH$_2$, —$R^5(R^9)_q$, —$OR^5(R^9)_q$, nitro, —$SO_2R^6$, —C(O)$R^{10}$, and —CO(O)$R^4$;
m and n in each instance are independently 0, 1, 2, 3, or 4;
p is independently 0, 1, 2, 3, or 4; and
r and q in each instance are independently 0, 1, 2, 3, or 4.
In accordance with another embodiment of the present invention, there is provided a compound having the structure of Formula I:

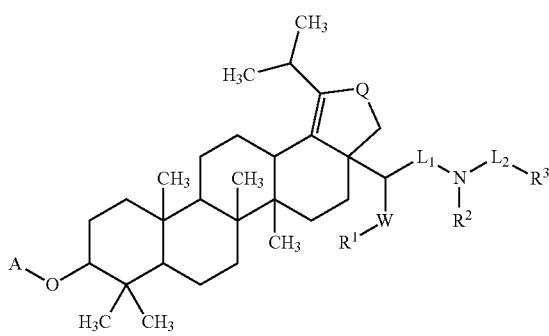
(I)

or a pharmaceutically acceptable salt thereof, wherein:
A is

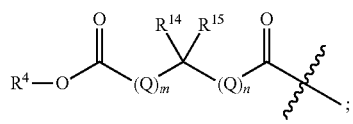

$L_1$ and $L_2$ are [C($R^6R^{6'}$)]$_q$;
each Q is independently selected from —CH$_2$— or —C(=O)—;

W is selected from a bond or O;
$R^1$ is selected from the group consisting of —H, ($C_1$-$C_6$)alkyl, —C(O)$R^4$, and

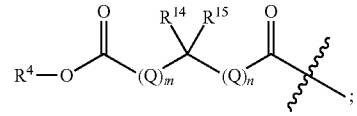

$R^2$ is selected from the group consisting of —H, ($C_1$-$C_6$)alkyl, —($C_1$-$C_6$)alkyl-OR$^4$, —($C_1$-$C_6$)alkyl-O—($C_1$-$C_6$)alkyl, —C(O)$R^5$, —(CH$_2$)$_r$NR$^7R^8$, and —(CH$_2$)$_r$N$^+$($R^4$)$_3$;
$R^3$ is selected from the group consisting of hydrogen, ($C_1$-$C_{12}$)alkyl, —NR$^1R^2$, —OR$^5$,

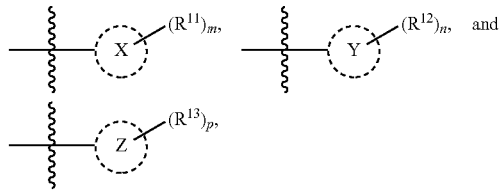
and wherein:
X is a monocyclic or bicyclic ($C_5$-$C_{14}$)aryl,
Y is selected from a monocyclic or bicyclic ($C_2$-$C_9$)heterocyclyl or monocyclic or bicyclic ($C_2$-$C_9$)heteroaryl, each having one to three heteroatoms selected from S, N or O, and
Z is a monocyclic or bicyclic ($C_3$-$C_8$)cycloalkyl;
$R^4$ is selected from the group consisting of —H and ($C_1$-$C_6$)alkyl;
$R^5$ is selected from the group consisting of ($C_1$-$C_6$)alkyl, —(CH$_2$)$_r$NR$^7R^8$, and —(CH$_2$)$_r$OR$^7$;
$R^6$ and $R^{6'}$ are independently selected from the group consisting of —H, ($C_1$-$C_6$)alkyl, ($C_3$-$C_8$)cycloalkyl, ($C_1$-$C_6$)alkoxy, haloalkyl, —(CH$_2$)$_r$NR$^7R^8$, —C(O)OH, and —C(O)NH$_2$, wherein the $R^6$ and $R^{6'}$ groups can optionally be taken together with the carbon to which they are joined to form a 3 to 8 membered cycloalkyl ring, and wherein the cycloalkyl ring may be optionally substituted by one to three $R^{11}$ groups;
$R^7$ and $R^8$ are independently selected from the group consisting of —H, ($C_1$-$C_6$)alkyl, ($C_3$-$C_8$)cycloalkyl, —NR$^{14}R^{15}$, and —C(O)CH$_3$;
$R^9$ is halo;
$R^{10}$ is —N($R^{16}$)$_2$;
$R^{11}$, $R^{12}$, and $R^{13}$ are independently selected from the group consisting of oxo, hydroxyl, halo, ($C_1$-$C_6$)alkoxy, —$R^6(R^9)_q$, —$OR^6(R^9)_q$, nitro, —$SO_2R^6$, ($C_1$-$C_6$)alkyl, —C(O)$R^{10}$, —$R^4YR^6$, —CO(O)$R^4$, and —CO(O)$R^5$;
$R^{14}$ and $R^{15}$ are independently selected from the group consisting of —H, ($C_1$-$C_6$)alkyl, ($C_3$-$C_8$)cycloalkyl, ($C_1$-$C_6$)alkoxy, —[C($R^6$)$_2$]$_r$—, —O[C($R^6$)$_2$]$_r$—, oxo, hydroxyl, halo, —C(O)$R^7$, —$R^{10}$, and —CO(O)$R^2$;
$R^{16}$ is independently selected from the group consisting of —H, oxo, halo, hydroxyl, ($C_1$-$C_6$)alkyl, ($C_1$-$C_6$)alkoxy, ($C_3$-$C_8$)cycloalkyl, —$R^6(R^9)_q$, —$OR^6(R^9)_q$, —N($R^4$)$_2$, —(CH$_2$)$_r$-heterocycle, —C(O)OH, —C(O)NH$_2$, —$R^5(R^9)_q$, —$OR^5(R^9)_q$, nitro, —$SO_2R^6$, —C(O)$R^{10}$, and —CO(O)$R^4$;

m and n in each instance are independently 0, 1, 2, 3, or 4;

p is independently 0, 1, 2, 3, or 4; and r and q in each instance are independently 0, 1, 2, 3, or 4.

In accordance with another embodiment of the present invention, there is provided a compound having the structure of Formula I:

(I)

or a pharmaceutically acceptable salt thereof, wherein:

A is

;

$L_1$ and $L_2$ are both (—$CH_2$—);

Q is —C(=O)—;

W is O;

$R^1$ is —H;

$R^2$ is selected from the group consisting of —H, ($C_1$-$C_6$)alkyl, —($C_1$-$C_6$)alkyl-$OR^4$, —($C_1$-$C_6$)alkyl-O—($C_1$-$C_6$)alkyl, —C(O)$R^5$, and —($CH_2$)$_r$$NR^7R^8$;

$R^3$ is selected from the group consisting of —H, ($C_1$-$C_{12}$)alkyl, —$NR^1R^2$, —$OR^5$, and wherein:

X is a monocyclic or bicyclic ($C_5$-$C_{14}$)aryl,

Y is selected from a monocyclic or bicyclic ($C_2$-$C_9$)heterocyclyl or monocylic or bicyclic ($C_2$-$C_9$)heteroaryl, each having one to three heteroatoms selected from S, N or O, and Z is a monocyclic or bicyclic ($C_3$-$C_8$)cycloalkyl;

$R^4$ is selected from the group consisting of —H and ($C_1$-$C_6$)alkyl;

$R^5$ is selected from the group consisting of ($C_1$-$C_6$)alkyl, —($CH_2$)$_r$$NR^7R^8$, and —($CH_2$)$_r$$OR^7$;

$R^6$ and $R^{6'}$ are independently selected from the group consisting of —H, ($C_1$-$C_6$)alkyl, ($C_3$-$C_8$)cycloalkyl, ($C_1$-$C_6$)alkoxy, haloalkyl, —($CH_2$)$_r$$NR^7R^8$, —C(O)OH, and —C(O)$NH_2$;

$R^7$ and $R^8$ are independently selected from the group consisting of —H, ($C_1$-$C_6$)alkyl, ($C_3$-$C_8$)cycloalkyl, —$NR^{14}R^{15}$, and —C(O)$CH_3$;

$R^9$ is halo;

$R^{10}$ is —N($R^{16}$)$_2$;

$R^{11}$, $R^{12}$, and $R^{13}$ are independently selected from the group consisting of oxo, hydroxyl, halo, ($C_1$-$C_6$)alkoxy, —$R^6(R^9)_q$, —$OR^6(R^9)_q$, nitro, —$SO_2R^6$, ($C_1$-$C_6$)alkyl, —C(O)$R^{10}$, —$R^4YR^6$, —CO(O)$R^4$, and —CO(O)$R^5$;

$R^{14}$ and $R^{15}$ are independently selected from the group consisting of —H, ($C_1$-$C_6$)alkyl, ($C_3$-$C_8$)cycloalkyl, ($C_1$-$C_6$)alkoxy, —[C($R^6$)$_2$]$_r$—, —O[C($R^6$)$_2$]$_r$—, oxo, hydroxyl, halo, —C(O)$R^7$, —$R^{10}$, and —CO(O)$R^2$;

$R^{16}$ is independently selected from the group consisting of —H, oxo, halo, hydroxyl, ($C_1$-$C_6$)alkyl, ($C_1$-$C_6$)alkoxy, ($C_3$-$C_8$)cycloalkyl, —$R^6(R^9)_q$, —$OR^6(R^9)_q$, —N($R^4$)$_2$, —($CH_2$)$_r$-heterocyclyl, —C(O)OH, —C(O)$NH_2$, —$R^5(R^9)_q$, —$OR^5(R^9)_q$, nitro, —$SO_2R^6$, —C(O)$R^{10}$, and —CO(O)$R^4$;

m and n in each instance are independently 0, 1, or 2;

p is independently 0, 1, or 2; and r and q in each instance are independently 0, 1, 2, or 3.

In accordance with another embodiment of the present invention, there is provided a compound having the structure of Formula I:

(I)

or a pharmaceutically acceptable salt thereof, wherein:

A is

;

$L_1$ and $L_2$ are both (—$CH_2$—);

Q is —C(=O)—;

W is O;

$R^1$ is —H;

$R^2$ is selected from the group consisting of —H, ($C_1$-$C_6$)alkyl, —C(O)$R^5$, and —($CH_2$)$_r$$NR^7R^8$;

$R^3$ is

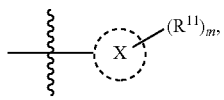

wherein X is a monocyclic or bicyclic $(C_5-C_{14})$aryl;

$R^4$ is selected from the group consisting of —H and $(C_1-C_6)$alkyl;

$R^5$ is selected from the group consisting of $(C_1-C_6)$alkyl, —$(CH_2)_rNR^7R^8$, and —$(CH_2)_rOR^7$;

$R^6$ is selected from the group consisting of —H, $(C_1-C_6)$alkyl, $(C_3-C_8)$cycloalkyl, $(C_1-C_6)$alkoxy, haloalkyl, —$(CH_2)_rNR^7R^8$, —C(O)OH, and —C(O)NH$_2$;

$R^7$ and $R^8$ are independently selected from the group consisting of —H, $(C_1-C_6)$alkyl, $(C_3-C_8)$cycloalkyl, —NR$^{14}$R$^{15}$, and —C(O)CH$_3$;

$R^9$ is halo;

$R^{10}$ is —N(R$^{16}$)$_2$;

$R^{11}$, $R^{12}$, and $R^{13}$ are independently selected from the group consisting of oxo, hydroxyl, halo, $(C_1-C_6)$alkoxy, —R$^6$(R$^9$)$_q$, —OR$^6$(R$^9$)$_q$, nitro, —SO$_2$R$^6$, $(C_1-C_6)$alkyl, —C(O)R$^{10}$, —CO(O)R$^4$, and —CO(O)R$^5$;

$R^{14}$ and $R^{15}$ are independently selected from the group consisting of —H, $(C_1-C_6)$alkyl, $(C_3-C_8)$cycloalkyl, $(C_1-C_6)$alkoxy, —[C(R$^6$)$_2$]$_r$—, —O[C(R$^6$)$_2$]$_r$—, oxo, hydroxyl, halo, —C(O)R$^7$, —R$^{10}$, and —CO(O)R$^2$;

$R^{16}$ is independently selected from the group consisting of —H, oxo, halo, hydroxyl, $(C_1-C_6)$alkyl, $(C_1-C_6)$alkoxy, $(C_3-C_8)$cycloalkyl, —R$^6$(R$^9$)$_q$, —OR$^6$(R$^9$)$_q$, —N(R$^4$)$_2$, —(CH$_2$)$_r$-heterocyclyl, —C(O)OH, —C(O)NH$_2$, —R$^5$(R$^9$)$_q$, —OR(R$^9$)$_q$, nitro, —SO$_2$R$^6$, —C(O)R$^{10}$, and —CO(O)R$^4$;

m and n in each instance are independently 0, 1, or 2;

p is independently 0, 1, or 2; and r and q in each instance are independently 0, 1, 2, or 3.

In accordance with another embodiment of the present invention, there is provided a compound having the structure of Formula I:

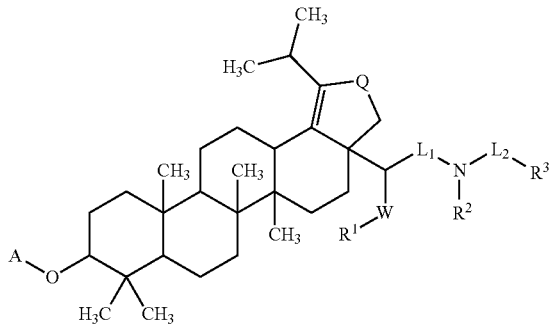

(I)

or a pharmaceutically acceptable salt thereof, wherein:

A is

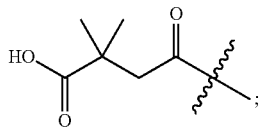

$L_1$ and $L_2$ are both (—CH$_2$—);

Q is —C(=O)—;

W is O;

$R^1$ is —H;

$R^2$ is —(CH$_2$)$_r$NR$^7$R$^8$;

$R^3$ is

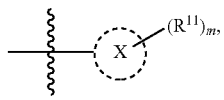

wherein X is phenyl;

$R^7$ and $R^8$ are independently selected from the group consisting of —H and methyl;

$R^9$ is selected from the group consisting of chloro, bromo, and fluoro;

$R^{11}$ is selected from the group consisting of chloro, bromo, and fluoro;

m is 0, 1, or 2; and r is 1, 2, or 3.

In accordance with another embodiment of the present invention, there is provided a compound having the structure of Formula II:

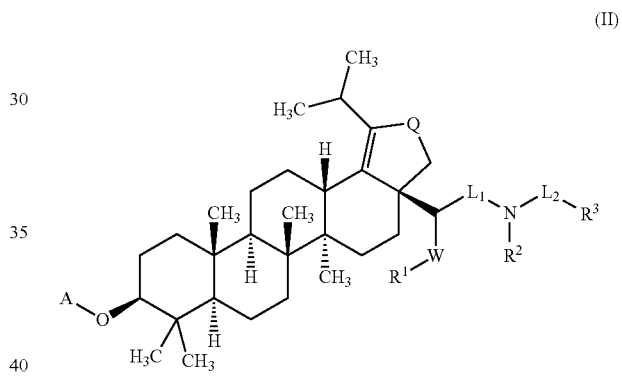

(II)

or a pharmaceutically acceptable salt thereof, wherein:

A is

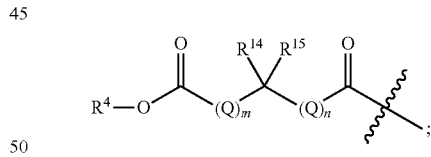

$L_1$ and $L_2$ are independently selected from a bond or [C(R$^6$R$^{6'}$)]$_q$;

each instance of Q is independently selected from —CH$_2$— or —C(=O)—;

W is selected from a bond or O;

$R^1$ is selected from the group consisting of —H, $(C_1-C_{12})$alkyl, —C(O)R$^5$, —CH$_2$—O—$(C_1-C_6)$alkyl, 2-tetrahydro-2H-pyran, and

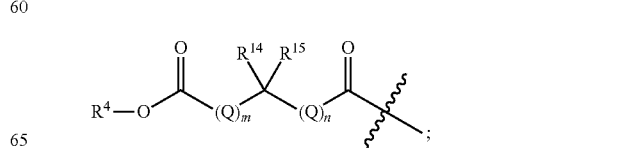

$R^2$ is selected from the group consisting of —H, $(C_1-C_{12})$ alkyl, —$(C_1-C_6)$alkyl-$OR^4$, —$(C_1-C_6)$alkyl-O—$(C_1-C_6)$ alkyl, —$C(O)R^5$, —$(CH_2)_rNR^7R^8$, and —$(CH_2)_rN^+(R^4)_3$, wherein when W is O, $R^1$ and $R^2$ can optionally be taken together with the O and N to which they are respectively joined to form a 4 to 8 membered heterocyclyl ring, wherein the heterocyclyl ring may be optionally substituted by one to two $R^{11}$ groups;

$R^3$ is selected from the group consisting of hydrogen, $(C_1-C_{12})$alkyl, —$NR^1R^2$, —$OR^5$,

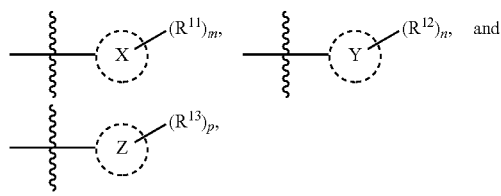

wherein:
X is a monocyclic or bicyclic $(C_5-C_{14})$aryl,
Y is selected from a monocylic or bicyclic $(C_2-C_9)$ heterocyclyl or monocylic or bicyclic $(C_2-C_9)$heteroaryl, each having one to three heteroatoms selected from S, N or O, and
Z is a monocyclic or bicyclic $(C_3-C_8)$cycloalkyl;

$R^2$ and $R^3$ can optionally be taken together with the nitrogen and $L_2$ to which they are respectively joined to form a 4 to 8 membered heterocyclyl ring, wherein the heterocyclyl ring may be optionally substituted by one to two $R^{11}$ groups;

$R^4$ is selected from the group consisting of —H and $(C_1-C_6)$alkyl;

$R^5$ is selected from the group consisting of —H, $(C_1-C_6)$ alkyl, —$R^3$, —$(CH_2)_rNR^7R^8$, and —$(CH_2)_rOR^7$.

$R^6$ and $R^{6'}$ are independently selected from the group consisting of —H, $(C_1-C_6)$alkyl, $(C_3-C_8)$cycloalkyl, $(C_1-C_6)$ alkoxy, haloalkyl, —Y, —$(CH_2)_rNR^7R^8$, —$C(O)OH$, and —$C(O)NH_2$, wherein the $R^6$ and $R^{6'}$ groups can optionally be taken together with the carbon to which they are joined to form a 3 to 8 membered cycloalkyl ring, and wherein the cycloalkyl ring may be optionally substituted by one to three $R^{11}$ groups;

$R^7$ and $R^8$ are independently selected from the group consisting of —H, $(C_1-C_6)$alkyl, $(C_3-C_8)$cycloalkyl, -Q-aryl-$(R^4)_n$, —$NR^{14}R^{15}$, —$C(O)CH_3$, wherein $R^7$ and $R^8$ can optionally be taken together with the nitrogen to which they are joined to form a 4 to 8 membered heterocyclyl or heteroaryl ring containing one to three heteroatoms selected from —$NR^5$—, —O—, —S—, —S(O)—, or —$SO_2$—, wherein the heterocyclyl or heteroaryl ring may be optionally substituted by one to three $R^{11}$ groups;

$R^9$ is halo;
$R^{10}$ is —$N(R^{16})_2$;
$R^{11}$, $R^{12}$, and $R^{13}$ are independently selected from the group consisting of oxo, hydroxyl, halo, $(C_1-C_6)$alkoxy, —$R^6(R^9)_q$, —$OR^6(R^9)_q$, nitro, —$SO_2R^6$, $(C_1-C_6)$alkyl, —$C(O)R^{10}$, —$R^4YR^6$, —$CO(O)R^4$, and —$CO(O)R^5$, wherein any two $R^{11}$, $R^{12}$ or $R^{13}$ groups can optionally join to form a 3 to 8 membered cycloalkyl, aryl, heterocyclyl or heteroaryl ring, wherein the heterocyclyl or heteroaryl ring may contain one to three heteroatoms selected from —$NR^5$—, —O—, —S—, —S(O)—, or —$SO_2$—, and wherein the cycloalkyl, aryl, heterocyclyl or heteroaryl ring may be optionally substituted by one to three $R^{16}$ groups;

$R^{14}$ and $R^{15}$ are independently selected from the group consisting of —H, $(C_1-C_6)$alkyl, $(C_3-C_8)$cycloalkyl, $(C_1-C_6)$ alkoxy, —$[C(R^6)_2]_r$—, —$O[C(R^6)_2]_r$—, oxo, hydroxyl, halo, —$C(O)R^7$, —$R^{10}$, and —$CO(O)R^2$, wherein $R^{14}$ and $R^{15}$ can optionally be taken together with the carbon to which they are joined to form a 3 to 8 membered cycloalkyl ring or 4 to 8 membered heterocyclyl ring containing one to three heteroatoms selected from —$NR^5$—, —O—, —S—, —S(O)—, or —$SO_2$—, wherein the cycloalkyl ring or heterocyclyl ring may be optionally substituted by one to three $R^{16}$ groups;

$R^{16}$ is independently selected from the group consisting of —H, halo, oxo, hydroxyl, $(C_1-C_6)$alkyl, $(C_1-C_6)$alkoxy, $(C_3-C_8)$cycloalkyl, —$R^6(R^9)_q$, —$OR^6(R^9)_q$, —$N(R^4)_2$, —$(CH_2)_r$-heterocycle, —$C(O)OH$, —$C(O)NH_2$, —$R^5(R^9)_q$, —$OR^5(R^9)_q$, nitro, —$SO_2R^6$, —$C(O)R^{10}$, and —$CO(O)R^4$;

m and n in each instance are independently 0, 1, 2, 3, or 4;
p is independently 0, 1, 2, 3, or 4; and
r and q in each instance are independently 0, 1, 2, 3, or 4.

In accordance with another embodiment of the present invention, there is provided a compound having the structure of Formula II:

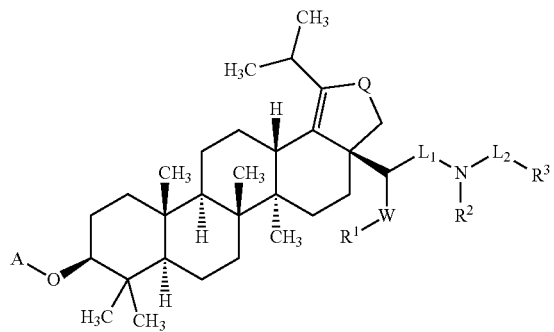

(II)

or a pharmaceutically acceptable salt thereof, wherein:
A is

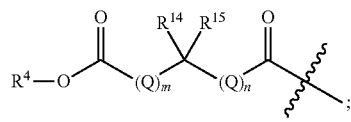

;

$L_1$ and $L_2$ are $[C(R^6R^{6'})]_q$;
each Q is independently selected from —$CH_2$— or —$C(=O)$—;
W is selected from a bond or O;
$R^1$ is selected from the group consisting of —H, $(C_1-C_6)$ alkyl, —$C(O)R^4$, and

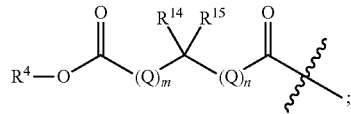

;

$R^2$ is selected from the group consisting of —H, $(C_1-C_6)$ alkyl, —$(C_1-C_6)$alkyl-$OR^4$, —$(C_1-C_6)$alkyl-O—$(C_1-C_6)$ alkyl, —$C(O)R^5$, —$(CH_2)_rNR^7R^8$, and —$(CH_2)_rN^+(R^4)_3$;

$R^3$ is selected from the group consisting of —H, $(C_1-C_{12})$ alkyl, —$NR^1R^2$, —$OR^5$,

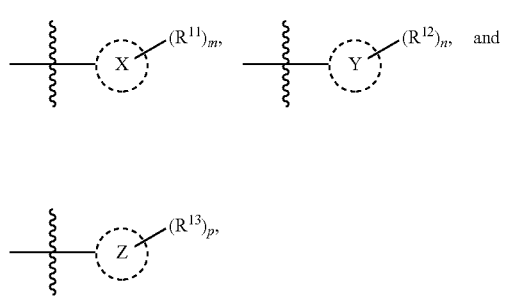

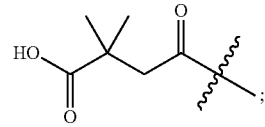

wherein:
X is a monocyclic or bicyclic $(C_5-C_{14})$aryl,
Y is selected from a monocyclic or bicyclic $(C_2-C_9)$ heterocyclyl or monocyclic or bicyclic $(C_2-C_9)$heteroaryl, each having one to three heteroatoms selected from S, N or O, and
Z is a monocyclic or bicyclic $(C_3-C_8)$cycloalkyl;
$R^4$ is selected from the group consisting of —H and $(C_1-C_6)$alkyl;
$R^5$ is selected from the group consisting of $(C_1-C_6)$alkyl, —$(CH_2)_rNR^7R^8$, and —$(CH_2)_rOR^7$;
$R^6$ and $R^{6'}$ are independently selected from the group consisting of —H, $(C_1-C_6)$alkyl, $(C_3-C_8)$cycloalkyl, $(C_1-C_6)$alkoxy, haloalkyl, —$(CH_2)_rNR^7R^8$, —$C(O)OH$, and —$C(O)NH_2$, wherein the $R^6$ and $R^{6'}$ groups can optionally be taken together with the carbon to which they are joined to form a 3 to 8 membered cycloalkyl ring, and wherein the cycloalkyl ring may be optionally substituted by one to three $R^{11}$ groups;
$R^7$ and $R^8$ are independently selected from the group consisting of —H, $(C_1-C_6)$alkyl, $(C_3-C_8)$cycloalkyl, —$NR^{14}R^{15}$, and —$C(O)CH_3$;
$R^9$ is halo;
$R^{10}$ is —$N(R^{16})_2$;
$R^{11}$, $R^{12}$, and $R^{13}$ are independently selected from the group consisting of oxo, hydroxyl, halo, $(C_1-C_6)$alkoxy, —$R^6(R^9)_q$, —$OR^6(R^9)_q$, nitro, —$SO_2R^6$, $(C_1-C_6)$alkyl, —$C(O)R^{10}$, —$R^4YR^6$, —$CO(O)R^4$, and —$CO(O)R^5$;
$R^{14}$ and $R^{15}$ are independently selected from the group consisting of —H, $(C_1-C_6)$alkyl, $(C_3-C_8)$cycloalkyl, $(C_1-C_6)$alkoxy, —$[C(R^6)_2]_r$—, —$O[C(R^6)_2]_r$—, oxo, hydroxyl, halo, —$C(O)R^7$, —$R^{10}$, and —$CO(O)R^2$;
$R^{16}$ is independently selected from the group consisting of —H, oxo, halo, hydroxyl, $(C_1-C_6)$alkyl, $(C_1-C_6)$alkoxy, $(C_3-C_8)$cycloalkyl, —$R^6(R^9)_q$, —$OR^6(R^9)_q$, —$N(R^4)_2$, —$(CH_2)_r$-heterocycle, —$C(O)OH$, —$C(O)NH_2$, —$R^5(R^9)_q$, —$OR^5(R^9)_q$, nitro, —$SO_2R^6$, —$C(O)R^{10}$, and —$CO(O)R^4$;
m and n in each instance are independently 0, 1, 2, 3, or 4;
p is independently 0, 1, 2, 3, or 4; and
r and q in each instance are independently 0, 1, 2, 3, or 4.

In accordance with another embodiment of the present invention, there is provided a compound having the structure of Formula II:

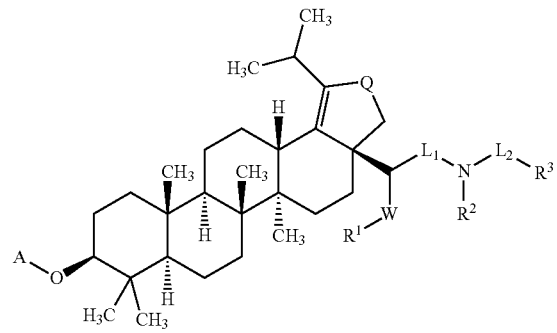

(II)

or a pharmaceutically acceptable salt thereof, wherein:
A is

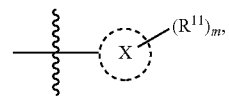

$L_1$ and $L_2$ are both (—$CH_2$—);
Q is —$C(=O)$—;
W is O;
$R^1$ is —H;
$R^2$ is selected from the group consisting of —H, $(C_1-C_6)$ alkyl, —$C(O)R^5$, and —$(CH_2)_rNR^7R^8$;
$R^3$ is

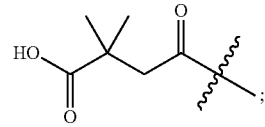

wherein X is a monocyclic or bicyclic $(C_5-C_{14})$aryl;
$R^4$ is selected from the group consisting of —H and $(C_1-C_6)$alkyl;
$R^5$ is selected from the group consisting of $(C_1-C_6)$alkyl, —$(CH_2)_rNR^7R^8$, and —$(CH_2)_rOR^7$;
$R^6$ is selected from the group consisting of —H, $(C_1-C_6)$ alkyl, $(C_3-C_8)$cycloalkyl, $(C_1-C_6)$alkoxy, haloalkyl, —$(CH_2)_rNR^7R^8$, —$C(O)OH$, and —$C(O)NH_2$;
$R^7$ and $R^8$ are independently selected from the group consisting of —H, $(C_1-C_6)$alkyl, $(C_3-C_8)$cycloalkyl, —$NR^{14}R^{15}$, and —$C(O)CH_3$;
$R^9$ is halo;
$R^{10}$ is —$N(R^{16})_2$;
$R^{11}$, $R^{12}$, and $R^{13}$ are independently selected from the group consisting of oxo, hydroxyl, halo, $(C_1-C_6)$alkoxy, —$R^6(R^9)_q$, —$OR^6(R^9)_q$, nitro, —$SO_2R^6$, $(C_1-C_6)$alkyl, —$C(O)R^{10}$, —$CO(O)R^4$, and —$CO(O)R^5$;
$R^{14}$ and $R^{15}$ are independently selected from the group consisting of —H, $(C_1-C_6)$alkyl, $(C_3-C_8)$cycloalkyl, $(C_1-C_6)$alkoxy, —$[C(R^6)_2]_r$—, —$O[C(R^6)_2]_r$—, oxo, hydroxyl, halo, —$C(O)R^7$, —$R^{10}$, and —$CO(O)R^2$;
$R^{16}$ is independently selected from the group consisting of —H, oxo, halo, hydroxyl, $(C_1-C_6)$alkyl, $(C_1-C_6)$alkoxy, $(C_3-C_8)$cycloalkyl, —$R^6(R^9)_q$, —$OR^6(R^9)_q$, —$N(R^4)_2$, —$(CH_2)_r$-heterocycle, —$C(O)OH$, —$C(O)NH_2$, —$R^5(R^9)_q$, —$OR^5(R^9)_q$, nitro, —$SO_2R^6$, —$C(O)R^{10}$, and —$CO(O)R^4$;

m and n in each instance are independently 0, 1, or 2;

p is independently 0, 1, or 2; and r and q in each instance are independently 0, 1, 2, or 3.

In accordance with another embodiment of the present invention, there is provided a compound having the structure of Formula II:

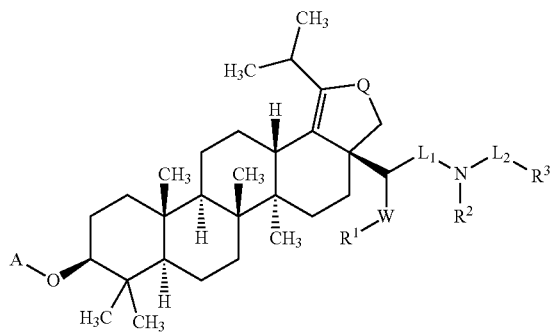
(II)

or a pharmaceutically acceptable salt thereof, wherein:

A is

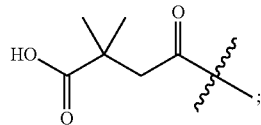 [SMILES: *C(=O)CC(C)(C)C(=O)O]
;

$L_1$ and $L_2$ are both (—$CH_2$—);

Q is —C(=O)—;

W is O;

$R^1$ is —H;

$R^2$ is —($CH_2$)$_r$$NR^7R^8$;

$R^3$ is

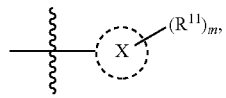

wherein X is phenyl;

$R^7$ and $R^8$ are independently selected from the group consisting of —H and methyl;

$R^9$ is selected from the group consisting of chloro, bromo, and fluoro;

$R^{11}$ is selected from the group consisting of chloro, bromo, and fluoro;

m is 0, 1, or 2; and r is 1, 2, or 3.

In accordance with another embodiment of the present invention, there is provided a compound of Formula II:

Formula II

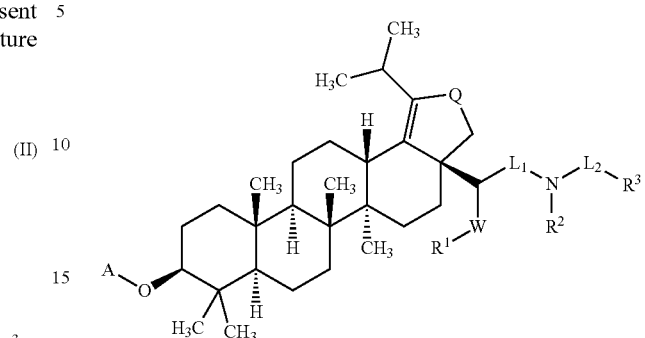
(II)

or a pharmaceutically acceptable salt thereof, wherein:

A is

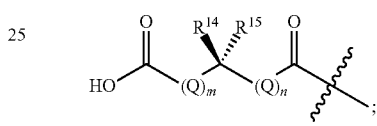
;

$L_1$ and $L_2$ are independently selected from a bond or [C($R^6R^6$)]$_q$;

Q is selected from —$CH_2$— or —C(=O)—;

W is selected from a bond or oxygen;

$R^1$ is selected from the group consisting of —H, ($C_1$-$C_{12}$) alkyl, —C(O)$R^5$, —$CH_2$—O—($C_1$-$C_6$)alkyl, 2-tetrahydro-2H-pyran and

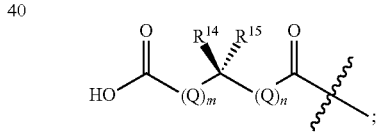
;

$R^2$ is selected from the group consisting of —H, ($C_1$-$C_{12}$) alkyl, —$C_{1-6}$ alkyl-OH, —$C_{1-6}$ alkyl-O—$C_{1-6}$ alkyl, —C(O)$R^5$, and —($CH_2$)$_r$$NR^7R^8$, —C(O)$R^5$, wherein when W is oxygen, $R^1$ and $R^2$ can optionally be taken together with the oxygen and nitrogen to which they are respectively joined to form a 4 to 8 membered heterocyclyl ring. wherein the heterocyclyl ring may be optionally substituted by one to two $R^{11}$ groups;

$R^3$ is selected from the group consisting of hydrogen, ($C_1$-$C_{12}$)alkyl, —$NR^1R^2$, —$OR^5$,

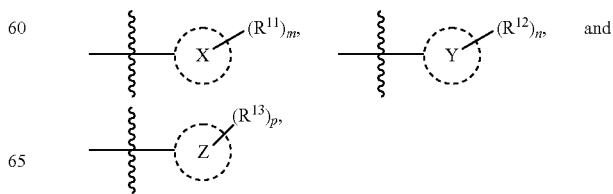

wherein:
X is a monocyclic or bicyclic $(C_5-C_{14})$aryl,
Y is selected from a monocyclic or bicyclic $(C_2-C_9)$ heterocyclyl or monocylic or bicyclic $(C_2-C_9)$heteroaryl, each having one to three heteroatoms selected from S, N or O, and
Z is a monocyclic or bicyclic $(C_3-C_8)$cycloalkyl;
$R^2$ and $R^3$ can optionally be taken together with the nitrogen and $L_2$ to which they are respectively joined to form a 4 to 8 membered heterocyclyl ring, wherein the heterocyclyl ring may be optionally substituted by one to two $R^{11}$ groups;
$R^4$ is selected from —H and $(C_1-C_6)$alkyl;
$R^5$ is selected from $(C_1-C_6)$alkyl, —$R^3$, —$(CH_2)_rNR^7R^8$, or —$(CH_2)_rOR^7$;
$R^6$ and $R^{6'}$ are independently —H, $(C_1-C_6)$alkyl, $(C_3-C_8)$ cycloalkyl, $(C_1-C_6)$alkoxy, haloalkyl, —Y, —$(CH_2)_rNR^7R^8$, —C(O)OH, —C(O)NH$_2$, wherein the $R^6$ and $R^{6'}$ groups can optionally be taken together with the carbon to which they are joined to form a 3 to 8 membered cycloalkyl ring, wherein the cycloalkyl ring may be optionally substituted by one to three $R^{11}$ groups;
$R^7$ and $R^8$ are independently selected from the group consisting of —H, $(C_1-C_6)$alkyl, $(C_3-C_8)$cycloalkyl, -Q-aryl-$(R^4)_n$, —$NR^{14}R^{15}$, —C(O)CH$_3$, wherein $R^7$ and $R^8$ can optionally be taken together with the nitrogen to which they are joined to form a 4 to 8 membered heterocyclyl or heteroaryl ring containing one to three heteroatoms selected from —$NR^5$—, —O—, —S—, —S(O)—, or —SO$_2$—, wherein the heterocyclyl or heteroaryl ring may be optionally substituted by one to three $R^{11}$ groups;
$R^9$ is halo;
$R^{10}$ is —$N(R^{16})_2$;
$R^{11}$, $R^{12}$, and $R^{13}$ are independently selected from the group consisting of oxo, hydroxyl, halo, $(C_1-C_6)$alkoxy, —$R^6(R^9)_q$, —$OR^6(R^9)_q$, nitro, —$SO_2R^6$, $(C_1-C_6)$alkyl, —$C(O)R^{10}$, —$R^4YR^6$, and —$CO(O)R^5$, wherein any two $R^9$, $R^{10}$ or $R^{11}$ groups can optionally join to form a 3 to 8 membered cycloalkyl, aryl, heterocyclyl or heteroaryl ring, wherein the heterocyclyl or heteroaryl ring may contain one to three heteroatoms selected from —$NR^5$—, —O—, —S—, —S(O)—, or —SO$_2$—, and wherein the cycloalkyl, aryl, heterocyclyl or heteroaryl ring may be optionally substituted by one to three $R^{16}$ groups;
$R^{14}$ and $R^{15}$ are independently selected from the group consisting of —H, $(C_1-C_6)$alkyl, $(C_3-C_8)$cycloalkyl, $(C_1-C_6)$ alkoxy, —$[C(R^6)_2]_r$—, —$O[C(R^6)_2]_r$—, oxo, hydroxyl, halo, —C(O)$R^7$, —$R^{10}$, and —CO(O)$R^2$, wherein $R^{14}$ and $R^{15}$ can optionally be taken together with the carbon to which they are joined to form a 3 to 8 membered cycloalkyl ring or 4 to 8 membered heterocyclyl ring containing one to three heteroatoms selected from —$NR^5$—, —O—, —S—, —S(O)—, or —SO$_2$—, wherein the cycloalkyl ring or heterocyclyl ring may be optionally substituted by one to three $R^{16}$ groups;
$R^{16}$ is independently selected from the group consisting of halo, oxo, hydroxyl, $(C_1-C_6)$alkyl, $(C_1-C_6)$alkoxy, $(C_3-C_8)$ cycloalkyl, —$R^6(R^9)_q$, —$OR^6(R^9)_q$, —$N(R^4)_2$, —$(CH_2)_r$-heterocyclyl, —C(O)OH, —C(O)NH$_2$, —$R^5(R^9)_q$, —$OR^5(R^9)_q$, nitro, —$SO_2R^6$, —C(O)$R^{10}$, and —CO(O)$R^4$;
m and n in each instance are independently 0, 1, 2, 3, or 4;
p is independently 0, 1, 2, 3, or 4; and
r and q in each instance are independently 0, 1, 2, 3, or 4.

In accordance with another embodiment of the present invention, there is provided a compound having the structure of Formula I or Formula II above, wherein $L_1$ and $L_2$ are both $[C(R^6R^{6'})]_q$.

In accordance with another embodiment of the present invention, there is provided a compound having the structure of Formula I or Formula II above, wherein $L_1$ and $L_2$ are both —CH$_2$—.

In accordance with another embodiment of the present invention, there is provided a compound having the structure of Formula I or Formula II above, wherein q is independently 1, 2, or 3.

In accordance with another embodiment of the present invention, there is provided a compound having the structure of Formula I or Formula II above, wherein q is 1.

In accordance with another embodiment of the present invention, there is provided a compound having the structure of Formula I or Formula II above, wherein W is O.

In accordance with another embodiment of the present invention, there is provided a compound having the structure of Formula I or Formula II above, wherein W is a bond.

In accordance with another embodiment of the present invention, there is provided a compound having the structure of Formula I or Formula II above, wherein when W is a bond, then $R^1$ is —H.

In accordance with another embodiment of the present invention, there is provided a compound having the structure of Formula I or Formula II above, wherein when W is O, then $R^1$ is —H.

In accordance with another embodiment of the present invention, there is provided a compound having the structure of Formula I or Formula II above, wherein $Q_m$ in the A group is absent and $Q_n$ in the A group is —CH$_2$— and the Q in the Formula I structure is —C(=O)—.

In accordance with another embodiment of the present invention, there is provided a compound having the structure of Formula I or Formula II above, wherein $R^1$ is —H.

In accordance with another embodiment of the present invention, there is provided a compound having the structure of Formula I or Formula II above, wherein $R^2$ is —$(CH_2)_rNR^7R^8$.

In accordance with another embodiment of the present invention, there is provided a compound having the structure of Formula I or Formula II above, wherein $R^2$ is (dimethylamino)ethyl.

In accordance with another embodiment of the present invention, there is provided a compound having the structure of Formula I or Formula II above, wherein r is independently 0, 1, 2, or 3.

In accordance with another embodiment of the present invention, there is provided a compound having the structure of Formula I or Formula II above, wherein r is 2.

In accordance with another embodiment of the present invention, there is provided a compound having the structure of Formula I or Formula II above, wherein $R^3$ is

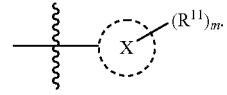

In accordance with another embodiment of the present invention, there is provided a compound having the structure of Formula I or Formula II above, wherein X is a monocyclic $(C_5-C_{14})$aryl.

In accordance with another embodiment of the present invention, there is provided a compound having the structure of Formula I or Formula II above, wherein X is phenyl.

In accordance with another embodiment of the present invention, there is provided a compound having the structure of Formula I or Formula II above, wherein $R^4$ is —H.

In accordance with another embodiment of the present invention, there is provided a compound having the structure of Formula I or Formula II above, wherein m is 0 or 1.

In accordance with another embodiment of the present invention, there is provided a compound having the structure of Formula I or Formula II above, wherein m is 0.

In accordance with another embodiment of the present invention, there is provided a compound having the structure of Formula I or Formula II above, wherein m is 1.

In accordance with another embodiment of the present invention, there is provided a compound having the structure of Formula I or Formula II above, wherein n is 1.

In accordance with another embodiment of the present invention, there is provided a compound having the structure of Formula I or Formula II above, wherein $R^6$ and $R^{6'}$ are both —H.

In accordance with another embodiment of the present invention, there is provided a compound having the structure of Formula I or Formula II above, wherein $R^7$ and $R^8$ are both $(C_1$-$C_6)$alkyl.

In accordance with another embodiment of the present invention, there is provided a compound having the structure of Formula I or Formula II above, wherein $R^7$ is methyl.

In accordance with another embodiment of the present invention, there is provided a compound having the structure of Formula I or Formula II above, wherein $R^8$ is methyl.

In accordance with another embodiment of the present invention, there is provided a compound having the structure of Formula I or Formula II above, wherein $R^7$ and $R^8$ are both methyl.

In accordance with another embodiment of the present invention, there is provided a compound having the structure of Formula I or Formula II above, wherein $R^{11}$ is halo.

In accordance with another embodiment of the present invention, there is provided a compound having the structure of Formula I or Formula II above, wherein $R^{11}$ is selected from chloro, bromo, or fluoro.

In accordance with another embodiment of the present invention, there is provided a compound having the structure of Formula I or Formula II above, wherein $R^{11}$ is chloro.

In accordance with another embodiment of the present invention, there is provided a compound having the structure of Formula I or Formula II above, wherein $R^{11}$ is absent.

In accordance with another embodiment of the present invention, there is provided a compound having the structure of Formula I or Formula II above, wherein $R^{14}$ and $R^{15}$ are both $(C_1$-$C_6)$alkyl.

In accordance with another embodiment of the present invention, there is provided a compound having the structure of Formula I or Formula II above, wherein $R^{14}$ and $R^{15}$ are both methyl.

In accordance with another embodiment of the present invention, there is provided a compound having the structure of Formula I or Formula II above, wherein A is

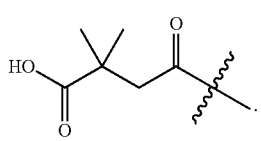 [SMILES: *C(=O)CC(C)(C)C(=O)O]

In accordance with another embodiment of the present invention, there is provided a compound having the structure of Formula I or Formula II above, wherein A is

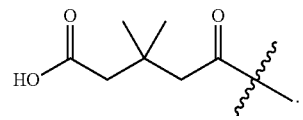 [SMILES: *C(=O)CC(C)(C)CC(=O)O]

In accordance with another embodiment of the present invention, there is provided a compound having the structure of Formula I or Formula II above, wherein A is

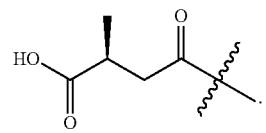

In accordance with another embodiment of the present invention, there is provided a compound having the structure of Formula I or Formula II above, wherein A is

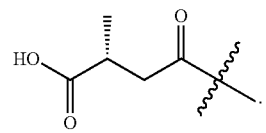

In accordance with another embodiment of the present invention, there is provided a compound having the structure:

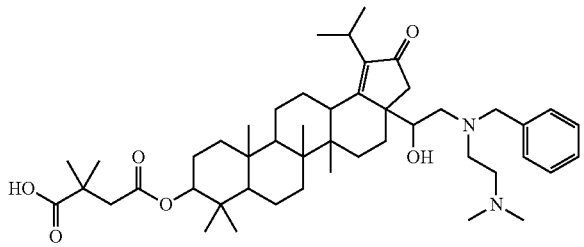

or a pharmaceutically acceptable salt thereof.

In accordance with another embodiment of the present invention, there is provided a compound having the structure:

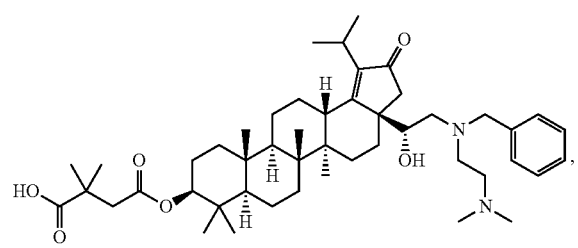

or a pharmaceutically acceptable salt thereof.

In accordance with another embodiment of the present invention, there is provided a compound having the structure:

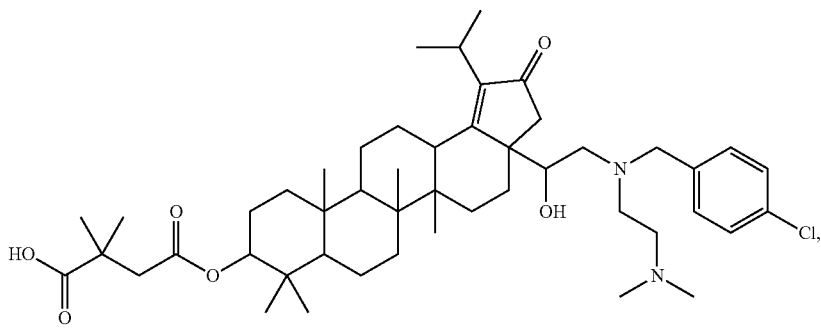

or a pharmaceutically acceptable salt thereof.

In accordance with another embodiment of the present invention, there is provided a compound having the structure:

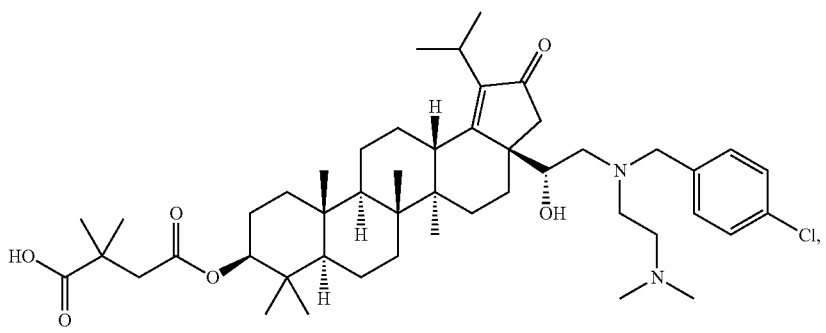

or a pharmaceutically acceptable salt thereof.

In a further embodiment of the present invention, there is provided a pharmaceutical composition comprising a compound of Formula I or Formula II, or a pharmaceutically acceptable salt thereof; and a pharmaceutically acceptable excipient.

In a further embodiment of the present invention, there is provided a method of treating HIV comprising administering to a patient suffering therefrom an effective amount of a compound of Formula I or Formula II, or a pharmaceutically acceptable salt thereof.

In a further embodiment of the present invention, there is provided a pharmaceutical composition comprising a compound of Formula I or Formula II, or a pharmaceutically acceptable salt thereof, and a pharmaceutically acceptable excipient.

In a further embodiment of the present invention, there is provided a pharmaceutical composition comprising a compound of Formula I or Formula II, or a pharmaceutically acceptable salt thereof, and a pharmaceutically acceptable excipient, wherein the compound is present in an amorphous form.

In a further embodiment of the present invention, there is provided a pharmaceutical composition comprising a compound of Formula I or Formula II, or a pharmaceutically acceptable salt thereof, and a pharmaceutically acceptable excipient, wherein the composition is in a tablet form.

In a further embodiment of the present invention, there is provided a pharmaceutical composition comprising a compound of Formula I or Formula II, or a pharmaceutically acceptable salt thereof, and a pharmaceutically acceptable excipient, wherein the compound is present as a spray dried dispersion.

In a further embodiment of the present invention, there is provided a method of treating an HIV infection in a subject comprising administering to the subject a compound of Formula I or Formula II, or a pharmaceutically acceptable salt thereof. In certain embodiments, the subject is a mammal, and in other embodiments, the subject is a human.

In a further embodiment of the present invention, there is provided a method of treating an HIV infection in a subject comprising administering to the subject a pharmaceutical composition comprising a compound of Formula I or Formula II, or a pharmaceutically acceptable salt thereof, and a pharmaceutically acceptable excipient.

In a further embodiment of the present invention, there is provided a method of preventing an HIV infection in a subject at risk for developing an HIV infection, comprising administering to the subject a compound of Formula I or Formula II, or a pharmaceutically acceptable salt thereof.

In a further embodiment of the present invention, there is provided a method of preventing an HIV infection in a subject at risk for developing an HIV infection, comprising administering to the subject a pharmaceutical composition comprising a compound of Formula I or Formula II, or a pharmaceutically acceptable salt thereof, and a pharmaceutically acceptable excipient.

In still other embodiments, the present invention also provides the use of a compound or salt as defined in any of Formula I or Formula II in the manufacture of a medicament for use in the treatment of an HIV infection in a human.

Furthermore, the compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula I or Formula II, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formula I.

In one embodiment, the pharmaceutical formulation containing a compound of Formula I or Formula II or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. Therefore, in other embodiments, the methods of treating and/or preventing an HIV infection in a subject may in addition to administration of a compound of Formula I or Formula II further comprise administration of one or more additional pharmaceutical agents active against HIV.

In such embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

As such, the compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula I or Formula II or salts thereof and the other pharmaceutically active agent(s) and the relative timings of administration will be selected in order to achieve the desired combined therapeutic effect.

In addition, the compounds of the present invention may be used in combination with one or more other agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where the compounds of the present invention may be used in combination with one or more agents useful in the prevention or treatment of HIV are found in Table 1.

TABLE 1

| FDA Approval | Brand Name | Generic Name | Manufacturer |
|---|---|---|---|
| Nucleoside Reverse Transcriptase Inhibitors (NRTIs) | | | |
| 1987 | Retrovir | zidovudine, azidothymidine, AZT, ZDV | GlaxoSmithKline |

TABLE 1-continued

| FDA Approval | Brand Name | Generic Name | Manufacturer |
|---|---|---|---|
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | maraviroc | Pfizer |
| Integrase Inhibitors | | | |
| 2007 | Isentress | raltegravir | Merck |

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formula I or Formula II is used in combination with ritonavir. In one embodiment, the combination is an oral fixed dose combination. In another embodiment, the compound of Formula I or Formula II is formulated as a long acting parenteral injection and ritonavir is formulated as an oral composition. In one embodiment, is a kit containing the compound of Formula I or Formula II formulated as a long acting parenteral injection and ritonavir formulated as an oral composition. In another embodiment, the compound of Formula I or Formula II is formulated as a long acting parenteral injection and ritonavir is formulated as an injectable composition. In one embodiment, is a kit containing the compound of Formula I or Formula II formulated as a long acting parenteral injection and ritonavir formulated as an injectable composition.

In another embodiment of the present invention, a compound of Formula I or Formula II is used in combination with GS-9350. In one embodiment, the combination is an oral fixed dose combination. In another embodiment, the compound of Formula I or Formula II is formulated as a long acting parenteral injection and GS-9350 is formulated as an oral composition. In one embodiment, there is provided a kit containing the compound of Formula I or Formula II formulated as a long acting parenteral injection and GS-9350 formulated as an oral composition. In another embodiment, the compound of Formula I or Formula II is formulated as a long acting parenteral injection and GS-9350 is formulated as an injectable composition. In one embodiment, is a kit containing the compound of Formula I or Formula II is formulated as a long acting parenteral injection and GS-9350 formulated as an injectable composition.

In one embodiment of the present invention, a compound of Formula I or Formula II is used in combination with SPI-452. In one embodiment, the combination is an oral fixed dose combination. In another embodiment, the compound of Formula I or Formula II is formulated as a long acting parenteral injection and SPI-452 is formulated as an oral composition. In one embodiment, there is provided a kit containing the compound of Formula I or Formula II formulated as a long acting parenteral injection and SPI-452 formulated as an oral composition. In another embodiment, the compound of Formula I or Formula II is formulated as a long acting parenteral injection and SPI-452 is formulated as an injectable composition. In one embodiment, there is provided a kit containing the compound of Formula I or Formula II formulated as a long acting parenteral injection and SPI-452 formulated as an injectable composition.

In one embodiment of the present invention, a compound of Formula I or Formula II is used in combination with compounds which are found in previously filed PCT/CN2011/0013021, which is herein incorporated by reference.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I or Formula II.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I or Formula II, wherein said virus is an HIV virus. In some embodiments, the HIV virus is the HIV-1 virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I or Formula II, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I or Formula II, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 2.

TABLE 2

| Example No. | Parent Structure | Chemical Name |
|---|---|---|
| 1 | 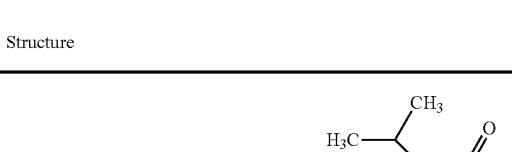 | 4-[(1R)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl]amino}ethoxy]-2,2-dimethyl-4-oxobutanoic acid |

TABLE 2-continued

| Example No. | Parent Structure | Chemical Name |
|---|---|---|
| 2 | | 4-[(1R)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl][2-(dimethylamino)ethyl]amino}ethoxy]-2,2-dimethyl-4-oxobutanoic acid |
| 3 | | 4-[(1S)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl]amino}ethoxy]-2,2-dimethyl-4-oxobutanoic acid |
| 4 | | 4-[(1S)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl][2-(dimethylamino)ethyl]amino}ethoxy]-2,2-dimethyl-4-oxobutanoic acid |
| 5 | | 4-{[(1R,2R,5R,10S,13R,14R,17S,19R)-5-(2-{[(4-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 6 | 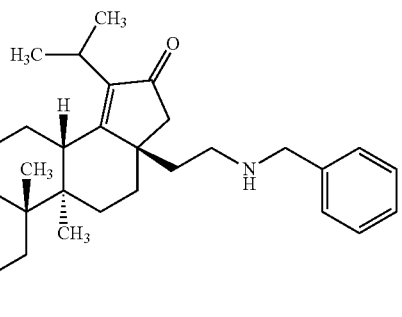 | 4-{[(1R,2R,5R,10S,13R,14R,17S,19R)-5-[2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 7 | 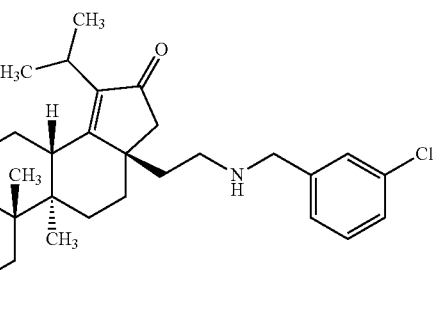 | 4-{[(1R,2R,5R,10S,13R,14R,17S,19R)-5-(2-{[(3-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 8 | 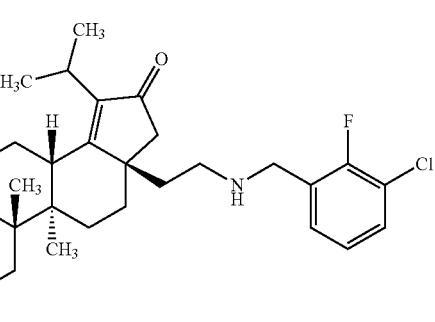 | 4-{[(1R,2R,5R,10S,13R,14R,17S,19R)-5-(2-{[(3-chloro-2-fluorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 9 | 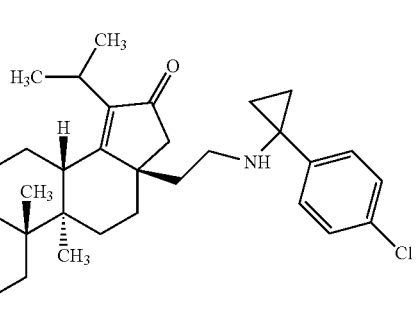 | 4-{[(1R,2R,5R,10S,13R,14R,17S,19R)-5-(2-{[1-(4-chlorophenyl)cyclopropyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 10 | | 4-{[(1R,2R,5R,10S,13R,14R,17S,19R)-5-(2-{[(4-chlorophenyl)methyl][2-(dimethylamino)ethyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 11 | | 4-{[(1R,2R,5R,10S,13R,14R,17S,19R)-5-(2-{[1-(4-chlorophenyl)cyclopropyl][2-(dimethylamino)ethyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 12 | | 4-{[(1R,2R,5R,10S,13R,14R,17S,19R)-5-(2-{[(4-chlorophenyl)methyl](methyl)amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 13 | | 4-{[(1R,2R,5R,10S,13R,14R,17S,19R)-5-(2-{N-[(4-chlorophenyl)methyl]acetamido}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 14 | | 4-{[(1R,2R,5R,10S,13R,14R,17S,19R)-5-[(1R)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 15 | | 4-{[(1R,2R,5R,10S,13R,14R,17S,19R)-5-[(1S)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 16 | | 4-{[(1R,2R,5R,10S,13R,14R,17S,19R)-5-[(1S)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 17 | | 4-{[(1R,2R,5R,10S,13R,14R,17S,19R)-5-[(1R)-1-(acetyloxy)-2-{[(4-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 18 | | 4-{[(1R,2R,5R,10S,13R,14R,17S,19R)-5-[(1R)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 19 | | 4-{[(1R,2R,5R,10S,13R,14R,17S,19R)-5-[(1S)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 20 | | 4-{[(1R,2R,5R,10S,13R,14R,17S,19R)-5-[(1S)-1-(acetyloxy)-2-{[(4-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 21 | | 4-{[(1R,2R,5R,10S,13R,14R,17S,19R)-5-[(1R)-1-(acetyloxy)-2-{[(4-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 22 | | 5-{[(1R,2R,5R,10S,13R,14R,17S,19R)-5-[(1R)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
| 23 | | 5-{[(1R,2R,5R,10S,13R,14R,17S,19R)-5-[(1S)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
| 24 | | 4-{[(1R,2R,5R,10S,13R,14R,17S,19R)-5-[(1S)-2-{[(2-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 25 | | 4-{[(1R,2R,5R,10S,13R,14R,17S,19R)-5-[(1R)-2-{[(2-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 26 | 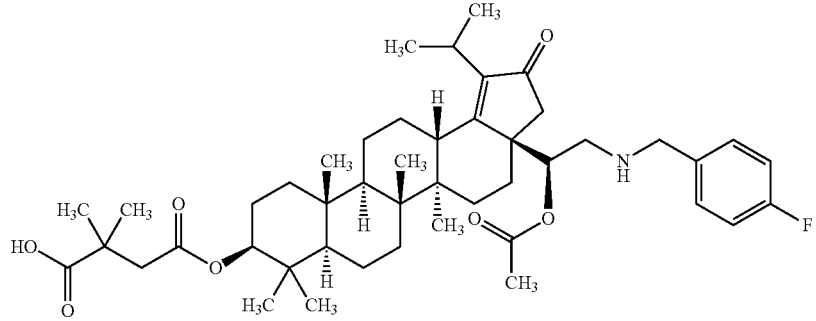 | 4-{[(1R,2R,5R,10S,13R,14R,17S,19R)-5-[(1S)-1-(acetyloxy)-2-{[(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 27 | 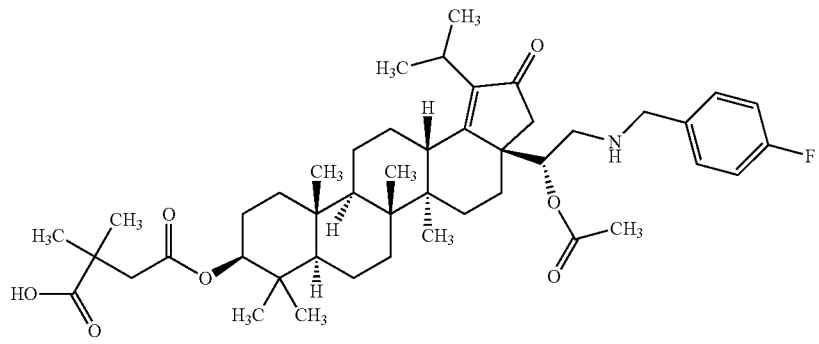 | 4-{[(1R,2R,5R,10S,13R,14R,17S,19R)-5-[(1R)-1-(acetyloxy)-2-{[(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 28 | 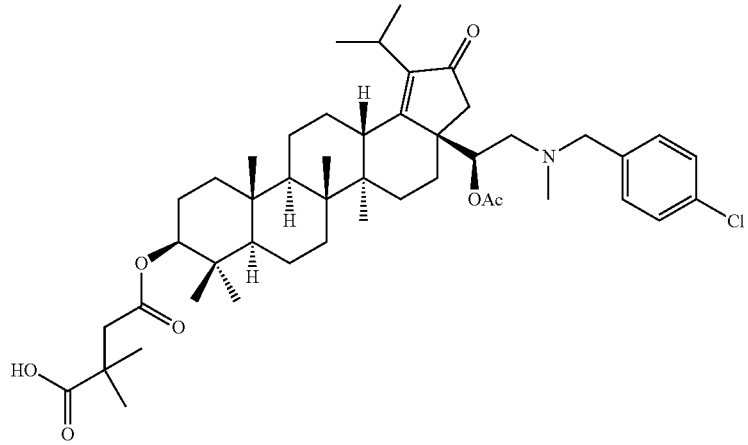 | 4-(((3aR,5aR,5bR,7aR,9S,11aR,11bR,13aS)-3a-((S)-1-acetoxy-2-((4-fluorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 29 | 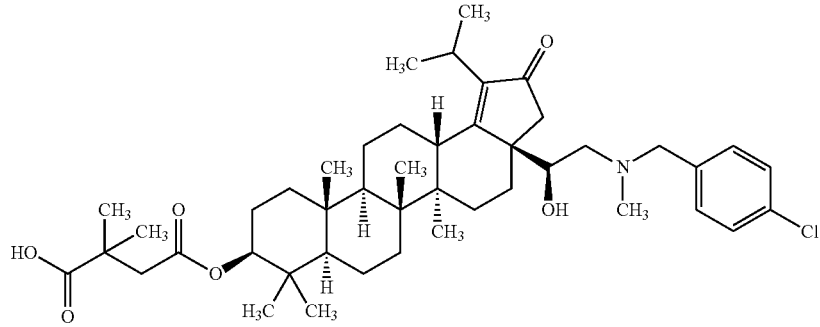 | 4-{[(1R,2R,5R,10S,13R,14R,17S,19R)-5-[(1S)-2-{[(4-chlorophenyl)methyl](methyl)amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 30 | | 4-(((3aR,5aR,5bR,7aR,9S,11aR,11bR,13aS)-3a-((R)-1-Acetoxy-2-((4-chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 31 | | 4-{[(1R,2R,5R,10S,13R,14R,17S,19R)-5-[(1R)-2-{[(4-chlorophenyl)methyl](methyl)amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 32 | | 4-(((3aR,5aR,5bR,7aR,9S,11aR,11bR,13aS)-3a-((S)-1-Acetoxy-2-(N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 32 | | 4-{[(1R,2R,5R,10S,13R,14R,17S,19R)-5-[(1S)-2-{N-[(4-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 33 | | 4-(((3aR,5aR,5bR,7aR,9S,11aR,11bR,13aS)-3a-((S)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 34 | | 4-(((3aR,5aR,5bR,7aR,9S,11aR,11bR,13aS)-3a-((R)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 35 | | 4-(((3aR,5aR,5bR,7aR,9S,11aR,11bR,13aS)-3a-((S)-2-(N-(2-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 36 | | 4-{[(1R,2R,5R,10S,13R,14R,17S,19R)-5-[(1S)-1-(acetyloxy)-2-{[(2-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 37 | | 4-{[(1R,2R,5R,10S,13R,14R,17S,19R)-5-[(1S)-2-{[(3-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 38 | | 4-{[(1R,2R,5R,10S,13R,14R,17S,19R)-5-[(1R)-2-{[(3-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 37 | | 4-{[(1R,2R,5R,10S,13R,14R,17S,19R)-5-[(1S)-2-{[(3-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 38 | | 4-{[(1R,2R,5R,10S,13R,14R,17S,19R)-5-[(1R)-2-{[(3-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 39 | | 4-{[(1R,2R,5R,10S,13R,14R,17S,19R)-5-[(1S)-1-(acetyloxy)-2-{[(3-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 40 | | 4-{[(1R,2R,5R,10S,13R,14R,17S,19R)-5-[(1R)-1-(acetyloxy)-2-{[(3-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 41 | | 4-(((3aR,5aR,5bR,7aR,9S,11aR,11bR,13aS)-3a-((S)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 42 | | 4-(((3aR,5aR,5bR,7aR,9S,11aR,11bR,13aS)-3a-((R)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 43 | | 4-(((3aR,5aR,5bR,7aR,9S,11aR,11bR,13aS)-3a-((R)-2-((3-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 44 | | 4-(((3aR,5aR,5bR,7aR,9S,11aR,11bR,13aS)-3a-((S)-2-((3-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 45 | | 4-(((3aR,5aR,5bR,7aR,9S,11aR,11bR,13aS)-3a-((R)-2-((3-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid. |
| 46 | | 4-{[(1R,2R,5R,10S,13R,14R,17S,19R)-5-[(1R)-2-{N-[(3-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 47 | | 4-{[(1R,2R,5R,10S,13R,14R,17S,19R)-5-[(1S)-2-{N-[(3-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 48 | | 4-(((3aR,5aR,5bR,7aR,9S,11aR,11bR,13aS)-3a-((R)-1-acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 49 | 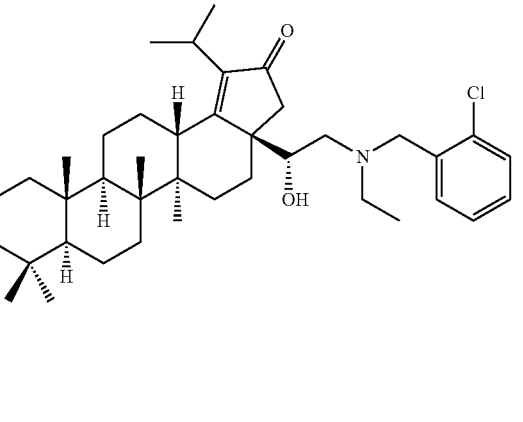 | 4-(((3aR,5aR,5bR,7aR,9S,11aR,11bR,13aS)-3a-((R)-2-((2-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 50 | 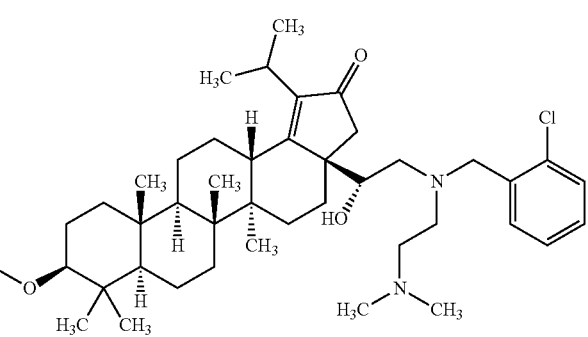 | 4-{[(1R,2R,5R,10S,13R,14R,17S,19R)-5-[(1R)-2-{[(2-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 51 | 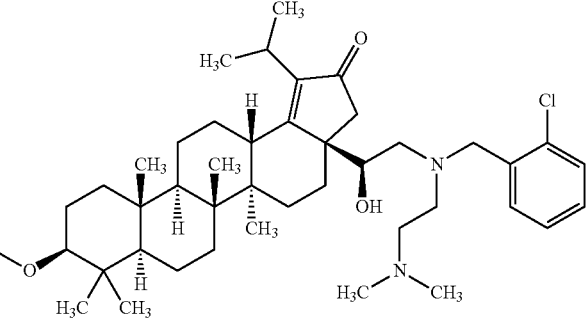 | 4-{[(1R,2R,5R,10S,13R,14R,17S,19R)-5-[(1S)-2-{[(2-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 52 | 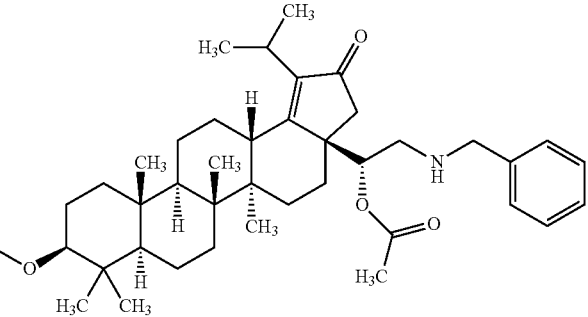 | 4-{[(1R,2R,5R,10S,13R,14R,17S,19R)-5-[(1R)-1-(acetyloxy)-2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 53 | | 4-{[(1R,2R,5R,10S,13R,14R,17S,19R)-5-[(1S)-1-(acetyloxy)-2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 54 | | 4-(((3aR,5aR,5bR,7aR,9S,11aR,11bR,13aS)-3a-((R)-2-((3-Chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 55 | | 4-(((3aR,5aR,5bR,7aR,9S,11aR,11bR,13aS)-3a-((S)-2-((3-chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 56 | | 4-{[(1R,2R,5R,10S,13R,14R,17S,19R)-5-[(1R)-2-{[(3-chloro-2-fluorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 57 | | 4-{[(1R,2R,5R,10S,13R,14R,17S,19R)-5-[(1S)-2-{[(3-chloro-2-fluorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 58 | | 4-{[(1R,2R,5R,10S,13R,14R,17S,19R)-5-[(1R)-1-hydroxy-2-[(propan-2-yl)amino]ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 59 | | 4-{[(1R,2R,5R,10S,13R,14R,17S,19R)-5-[(1R)-2-(cyclohexylamino)-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 53 | | 4-{[(1R,2R,5S,10S,13R,14R,17S,19R)-5-[1-hydroxy-2-(4-methylpiperazin-1-yl)ethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 54 | 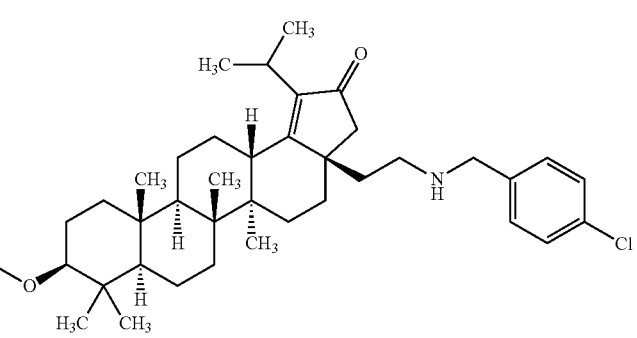 | 4-{[(1R,2R,5R,10S,13R,14R,17S,19R)-5-(2-{[(4-chlorophenyl)methyl]amino}ethyl)-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 55 | 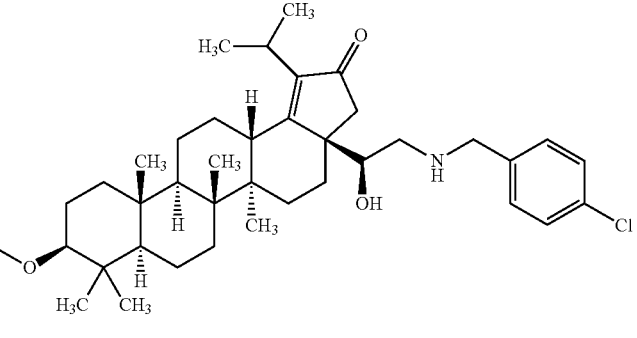 | 4-{[(1R,2R,5S,10S,13R,14R,17S,19R)-5-[(1S)-2-{[(4-chlorophenyl)methyl]amino}-1-hydroxyethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 56 | 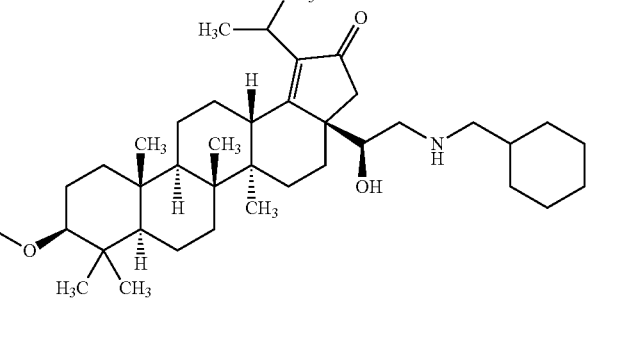 | 4-{[(1R,2R,5S,10S,13R,14R,17S,19R)-5-[(1S)-2-[(cyclohexylmethyl)amino]-1-hydroxyethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 57 | 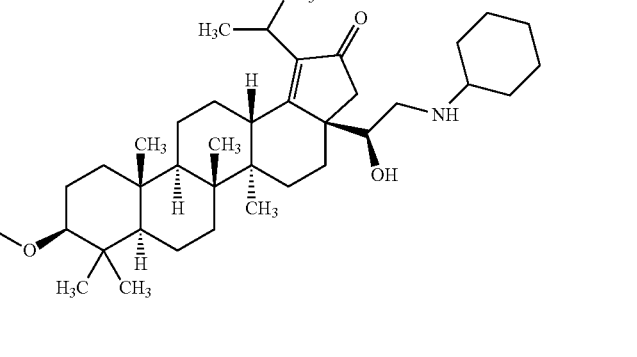 | 4-{[(1R,2R,5R,10S,13R,14R,17S,19R)-5-[(1S)-2-(cyclohexylamino)-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 58 | | 4-{[(1R,2R,5R,10S,13R,14R,17S,19R)-5-[(1R)-1-hydroxy-2-(1,2,3,4-tetrahydroisoquinolin-2-yl)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 59 | | 4-{[(1R,2R,5R,10S,13R,14R,17S,19R)-5-[(1S)-1-hydroxy-2-(1,2,3,4-tetrahydroisoquinolin-2-yl)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 60 | | 4-{[(1R,2R,10S,13R,14R,17S,19R)-5-[(5S)-3-[1-(5-chloropyrimidin-2-yl)cyclopropyl]-2-oxo-1,3-oxazolidin-5-yl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 61 | | 4-{[(1R,2R,10S,13R,14R,17S,19R)-5-[(5R)-3-[1-(5-chloropyrimidin-2-yl)cyclopropyl]-2-oxo-1,3-oxazolidin-5-yl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 62 | | 5-{[(1R,2R,5R,10S,13R,14R,17S,19R)-5-[(1S)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
| 63 | | 4-(((3aR,5aR,5bR,7aR,9S,11aR,11bR,13aS)-3a-((R)-2-(3,4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 64 | | 4-(((3aR,5aR,5bR,7aR,9S,11aR,11bR,13aS)-3a-((S)-2-(3,4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 65 | | 4-(((3aS,5aR,5bR,7aR,9S,11aR,11bR,13aS)-3a-((R)-1-hydroxy-2-(4-methylpiperazin-1-yl)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 66 | 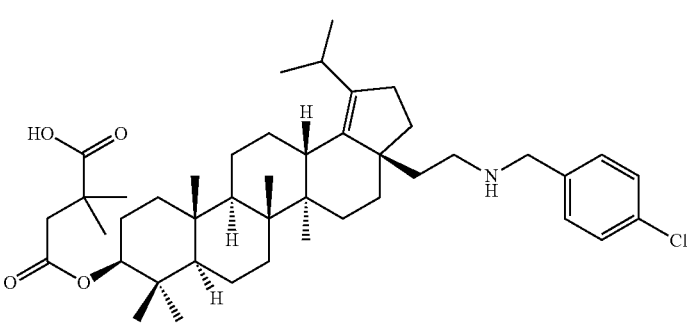 | 4-(((3aR,5aR,5bR,7aR,9S,11aR,11bR,13aS)-3a-(2-((4-chlorobenzyl)amino)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 67 | 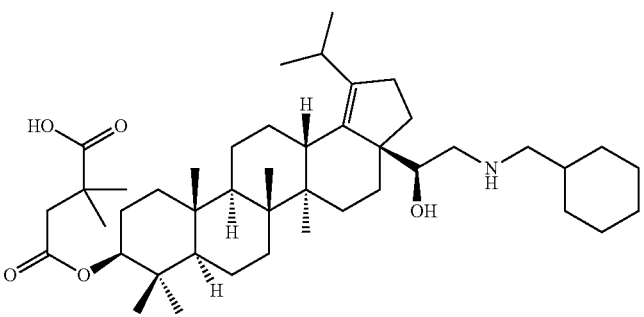 | 4-(((3aS,5aR,5bR,7aR,9S,11aR,11bR,13aS)-3a-((S)-2-((cyclohexylmethyl)amino)-1-hydroxyethyl)-1-isopropyl-5a,5b,8,8,11a-pentamethyl-3,3a,4,5,5a,5b,6,7,7a,8,9,10,11,11a11b,12,13,13a-octadecahydro-2H-cyclopenta[a]chrysen-9-yl)oxy)-2,2-dimethyl-4-oxobutanoic acid |
| 68 | 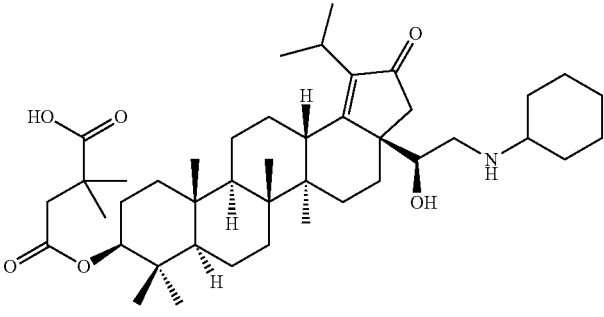 | 4-(((3aR,5aR,5bR,7aR,9S,11aR,11bR,13aS)-3a-((S)-2-(cyclohexylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 69 | 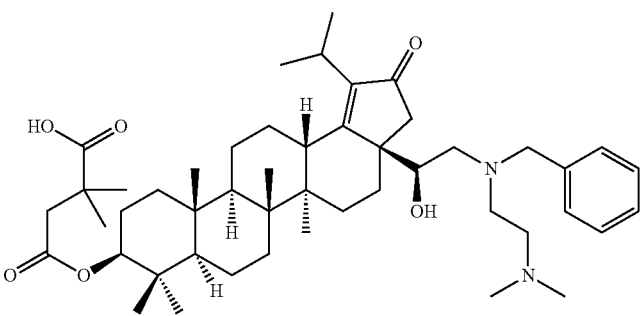 | 4-(((3aR,5aR,5bR,7aR,9S,11aR,11bR,13aS)-3a-((S)-2-(benzyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 2-continued

| Example No. | Parent Structure | Chemical Name |
|---|---|---|
| 70 | | 4-{[(1R,2R,5R,10S,13R,14R,17S,19R)-5-[(1S)-1-(acetyloxy)-2-{[2-(dimethylamino)ethyl][(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 71 | | 4-{[(1R,2R,5R,10S,13R,14R,17S,19R)-5-[(1R)-1-(acetyloxy)-2-{[2-(dimethylamino)ethyl][(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 72 | | 5-{[(1R,2R,5R,10S,13R,14R,17S,19R)-5-[(1R)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
| 73 | | 5-(((3aR,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid |

TABLE 2-continued

| Example No. | Parent Structure | Chemical Name |
|---|---|---|
| 74 | | 4-{[(1R,2R,5R,10S,13R,14R,17S,19R)-5-[(1S)-2-{[(2,4-dichlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 75 | | 4-{[(1R,2R,5R,10S,13R,14R,17S,19R)-5-[(1R)-2-{benzyl[2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 76 | | 4-{[(1R,2R,5R,10S,13R,14R,17S,19R)-5-[(1R)-2-{[2-(dimethylamino)ethyl][(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 77 | | 4-{[(1R,2R,5R,10S,13R,14R,17S,19R)-5-[(1R)-2-{[(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 78 | | 4-{[(1R,2R,5R,10S,13R,14R,17S,19R)-5-[(1S)-2-{[2-(dimethylamino)ethyl][(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 79 | | 4-{[(1R,2R,5R,10S,13R,14R,17S,19R)-5-[(1S)-2-{[(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 80 | | 4-{[(1R,2R,5R,10S,13R,14R,17S,19R)-5-[(1R)-2-{[(2,4-dichlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 81 | | 4-{[(1R,2R,5R,10S,13R,14R,17S,19R)-5-[(1R)-2-[1-(4-chlorophenyl)-N-[2-(dimethylamino)ethyl]formamido]-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 2-continued

| Example No. | Parent Structure | Chemical Name |
|---|---|---|
| 82 | 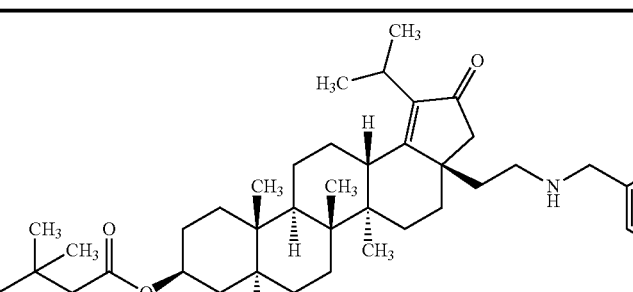 | 4-{[(1R,2R,5R,10S,13R,14R,17S,19R)-5-(2-{[(2-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 83 | 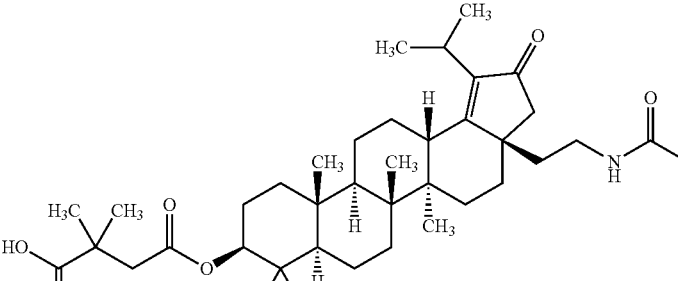 | 2,2-dimethyl-4-oxo-4-{[(1R,2R,5R,10S,13R,14R,17S,19R)-1,2,14,18,18-pentamethyl-7-oxo-5-[2-(phenylformamido)ethyl]-8-(propan-2-yl)pentacyclo[11.8.0.0^{2,10}.0^{5,9}.0^{14,19}]henicos-8-en-17-yl]oxy)butanoic acid |

The compounds of Table 2 were synthesized according to the Synthetic Methods, General Schemes, and the Examples described below.

In certain embodiments, the compound(s) of the present invention, or a pharmaceutically acceptable salt thereof, is chosen from the compounds set forth in Table 2.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million
q.s.=sufficient amount
s=singlet
RT=room temperature
sat.=saturated
t=triplet
TFA=trifluoroacetic acid Equipment Description $^1$H NMR spectra were recorded on a Bruker Avance-III 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Agilent 1200 HPLC/6110 or Agilent 1200 HPLC/6130 using a SunFire C18, 4.6×50 mm, 3.5 μm using a gradient elution method.

Solvent A: 0.01% trifluoroacetic acid (TFA) in water;
Solvent B: 0.01% TFA in acetonitrile;
Constant A for 1.2 min followed by 5%-95% or 20%-95% B over 4 min.

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention. All examples exhibited LHIV $IC_{50}$ values between 1 μM and 1 nM using the assay disclosed herein.

For several of the examples the stereochemistry of the C28 secondary alcohol when present was not definitively confirmed as to its absolute configuration. Unless stated otherwise, the compounds exemplified in the present application were isolated as optically pure stereoisomers and initially assigned to a configuration as drawn. There is the possibility that some of these may be listed as the opposite stereochemistry at that single C28 position as shown. This in no way is meant to limit the scope of the invention or utility of the compounds of Formula I. Additional examples contained within were determined to have the shown configuration by spectroscopic methods well known to those skilled in the art including, but not limited to, 1D and 2D NMR methods, vibrational circular dichroism and X-ray crystallography. These examples and the methods to make both diastereomers should serve to clearly exemplify the pure stereoisomers of both R and S configuration at the C28 position are readily obtained, separated and characterized and any remaining undefined examples could be readily confirmed by similar methods well known to one skilled in the art.

Synthesis of Aldehyde Intermediate 6.

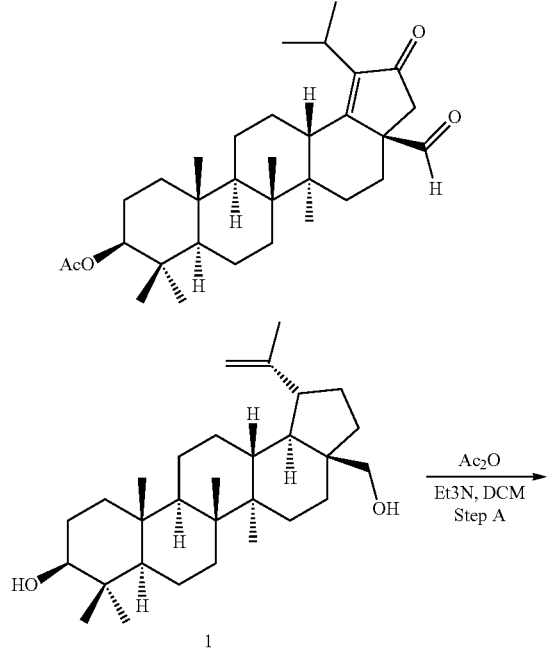

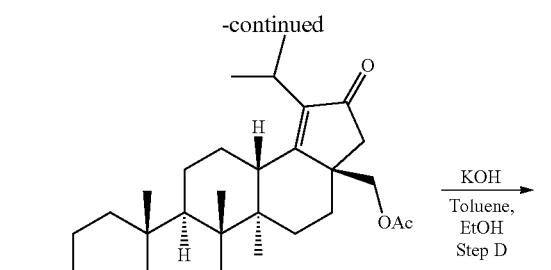

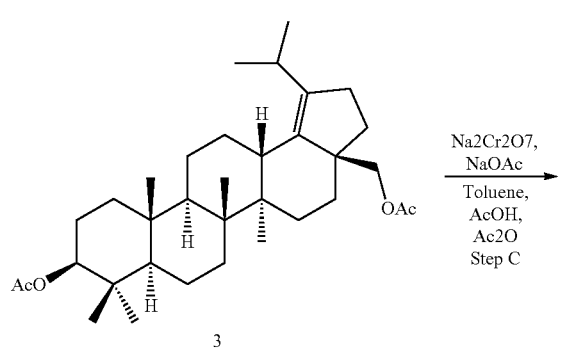

Step A: Intermediate 2

((1R,3aS,5aR,5bR,7aR,9S,11aR,11bR,13aR,13bR)-9-Acetoxy-5a,5b,8,8,11a-pentamethyl-1-(prop-1-en-2-yl)icosahydro-1H-cyclopenta[a]chrysen-3a-yl) methyl acetate To a solution of the intermediate 1 (20 g, 45.2 mmol), 4-dimethylaminopyridine (DMAP, 1.66 g, 13.6 mmol), and Et$_3$N (63 mL, 136 mmol) in CH$_2$Cl$_2$ (DCM, 100 mL) at room temperature was added acetic anhydride (Ac$_2$O, 17.1 mL, 113 mmol). After it was heated at reflux overnight, and cooled down to room temperature, the reaction was quenched with water (50 mL). The organic phase was then washed with water (50 mL×2) and dried over sodium sulfate. After removing most of the organic solvent under reduced pressure, anhydrous ethanol (50 mL) was added and the resulting precipitates were collected by filtration as a white solid (intermediate 2, 20 g, 84%). $^1$H NMR (400 MHz, CDCl$_3$) δ ppm 4.69 (1H, m), 4.59 (1H, m), 4.51-4.43 (1H, m), 4.25 (1H, d, J=11.2 Hz), 3.85 (1H, d, J=10.8 Hz), 2.49-2.40 (1H, m), 2.07 (3H, s), 2.04 (3H, s), 1.98-0.77 (42H, m). LC/MS: m/z calculated 526.4. found 527.7 (M+1)+.

Step B: Intermediate 3

((3aS,5aR,5bR,7aR,9S,11aR,11bR,13aS)-9-acetoxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)methyl acetate HBr in acetic acid (40 mL, 33%) was added to a suspension of the intermediate 2 (20 g, 38 mmol) in toluene (40 mL), Ac$_2$O (40 mL), and acetic acid (AcOH, 40 mL) previously heated at 105° C. The reaction mixture was stirred and heated at this temperature for 1.5 h. After cooling down, sodium acetate (24 g) was added and the resulting reaction mixture was evaporated to dryness. The pale brownish residue was taken up in DCM (200 mL) and the organic phase was washed with water (100 mL×3), dried over sodium sulfate, and evaporated to dryness under reduced pressure to provide a residue, which was then recrystallized from ethanol (EtOH, 95%) and DCM, to afford the intermediate 3 (13.8 g, 69%) as a white solid. $^1$H NMR (400 MHz, CDCl$_3$) δ ppm 4.50-4.46 (1H, m), 4.02 (1H, d, J=10.8 Hz), 3.98 (1H, d, J=10.8 Hz), 3.18-3.10 (1H, m), 2.43-2.40 (1H, m), 2.26-2.22 (2H, m), 2.04 (3H, s), 2.05 (3H, s), 2.00-1.95 (1H, m), 1.90-1.85 (1H, m), 1.77-0.83 (39 H, m). LC/MS: m/z calculated 526.4. found 549.2 (M+Na)+.

Step C: Intermediate 4

((3aR,5aR,5bR,7aR,9S,11aR,11bR,13aS)-9-Acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)methyl acetate A mixture of the intermediate 3 (7 g, 13.29 mmol), sodium acetate (NaOAc, 6.21 g, 76 mmol) and sodium dichromate dihydrate (4.75 g, 15.95 mmol) in anhydrous toluene (90 mL), AcOH (119 mL), and Ac$_2$O (29 mL) was stirred at 60° C. overnight. After cooling down, the reaction mixture was partitioned between water (150 mL) and ethyl acetate (EtOAc, 250 mL). The organic phase was washed successively with: water (100 mL), a saturated solution of sodium carbonate (100 mL×2) and brine (100 mL×2), then dried over sodium sulfate, and concentrated under reduced pressure to afford a sticky oil. The sticky oil was triturated with MeOH (250 mL) and the precipitates were collected to give the intermediate 4 (6 g, 11.1 mmol, 83%) as a white solid. $^1$H NMR (400 MHz, CDCl$_3$) δ ppm 4.52-4.46 (1H, m), 4.33 (1H, d, J=10.8 Hz), 4.06 (1H, d, J=11.2 Hz), 3.21-3.16 (1H, m), 2.86 (1H, dd, J=12.8, 3.2 Hz), 2.42-2.36 (1H, m), 2.05 (3H, s), 2.00 (3H, s), 1.94-0.84 (40H, m). LC/MS: m/z calculated 540.4. found 563.3 (M+Na)+.

Step D: Intermediate 5

(3aR,5aR,5bR,7aR,9S,11aR,11bR,13aS)-3a-(Hydroxymethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate A mixture of the intermediate 4 (7 g, 12.94 mmol) and potassium hydroxide (KOH, 0.872 g, 15.5 mmol) in EtOH (200 mL) and toluene (200 mL) was stirred vigorously at room temperature for 1 h. The reaction mixture was neutralized with aqueous HCl (1N) to pH 7 and evaporated to dryness. The obtained residue was taken up in water and a small amount of acetone. The precipitates were collected and then washed with water and dried in vacuo to obtain the intermediate 5 (6.0 g, 93%) as a white solid. LC/MS: m/z calculated 498.4. found 499.3 (M+1)+.

Step E: Intermediate 6

(3aR,5aR,5bR,7aR,9S,11aR,11bR,13aS)-3a-Formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of the intermediate 5 (5.1 g, 10.23 mmol) in DCM (300 mL) at room temperature were added pyridinium chlorochromate (PCC, 6.61 g, 30.7 mmol), and silica gel (6.6 g). The reaction mixture was stirred at room temperature for 1 h. After the reaction was quenched with water, the organic phase was washed with saturated sodium bicarbonate solution (100 mL), dried over sodium sulfate, and evaporated under reduced pressure to provide a crude product, which was purified by column chromatography on silica gel (EtOAc:PE=1:10 to 1:5) to provide the intermediate 6 (4.2 g, 83%) as a white solid. LC/MS: m/z calculated 496.4. found 497.2 (M+1)+.

Synthesis of the oxo-butanoate intermediate 10 was accomplished according to the following procedures.

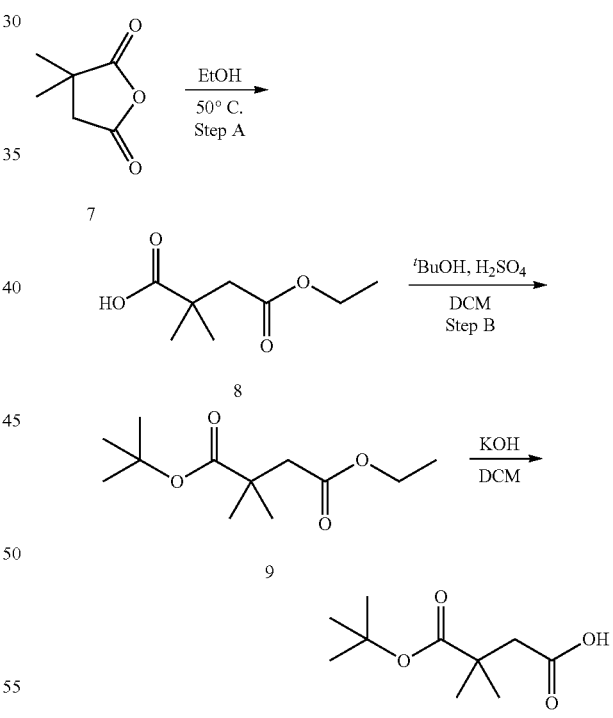

Step A: Intermediate 8

4-Ethoxy-2,2-dimethyl-4-oxobutanoic acid

A solution of 3,3-dimethyl-dihydrofuran-2,5-dione 7 (25 g, 195 mmol) in anhydrous EtOH (150 mL) was stirred at 50° C. overnight. After cooling down to room temperature, the solvent was removed under reduced pressure with a rotary evaporator and the residue was triturated with hexane at −50° C. to afford the intermediate 8 (25 g, 133 mmol, 67.9%) as a white solid. $^1$H NMR (400 MHz, CDCl$_3$) δ ppm 4.13-4.18 (2H, q, J=7.2 Hz), 2.62 (2H, s), 1.28 (6H, s), 1.32-1.25 (3H, t, J=7.6 Hz). LC/MS: m/z calculated 174.1. found 173.1 (M−1)−.

Step B: Intermediate 9

1-Tert-butyl 4-ethyl 2,2-dimethylsuccinate

To a mixture of the intermediate 8 (20 g, 109 mmol), magnesium sulfate (52.5 g, 436 mmol), and tert-butanol (60 mL) in DCM (480 mL) was added to sulfuric acid (8.72 mL, 164 mmol). After stirring at room temperature overnight, the reaction mixture was poured into saturated sodium bicarbonate solution (300 mL) and water (300 mL). DCM was added to extract the desired product, and the organic phase was washed with brine, dried, and concentrated to afford the intermediate 9 (19 g, 83 mmol, 80%) as a colorless oil. $^1$H NMR (400 MHz, CDCl$_3$) δ ppm 4.02-4.08 (2H, q, J=7.2 Hz), 2.46 (2H, s), 1.07 (9H, s), 1.14-1.20 (9H, m). LC/MS: m/z calculated 230.2. found 253.1 (M+Na)+.

Step C: Intermediate 10

4-(Tert-butoxy)-3,3-dimethyl-4-oxobutanoic acid

To a solution of the intermediate 9 (10 g, 41.3 mmol) in EtOH (200 mL) was added to potassium hydroxide (12.86 g, 206 mmol) in water (100 mL) at room temperature. The reaction mixture was stirred at room temperature for 2 h. The pH of the reaction mixture was adjusted to 3-4 by 1N HCl. The resulting solution was extracted with ether (300 mL), and the ether phase was dried and concentrated to afford a crude product, which was re-crystallized from hexane at −10° C. to afford the intermediate 10 (4 g, 19.78 mmol, 47.9%) as a white solid. $^1$H NMR (400 MHz, CDCl$_3$) δ ppm 2.58 (2H, s), 1.43 (9H, s), 1.25 (6H, s). LC/MS: m/z calculated 202.1. found 201.1 (M−1)−.

Synthesis of diastereomeric intermediates 18 and 19.

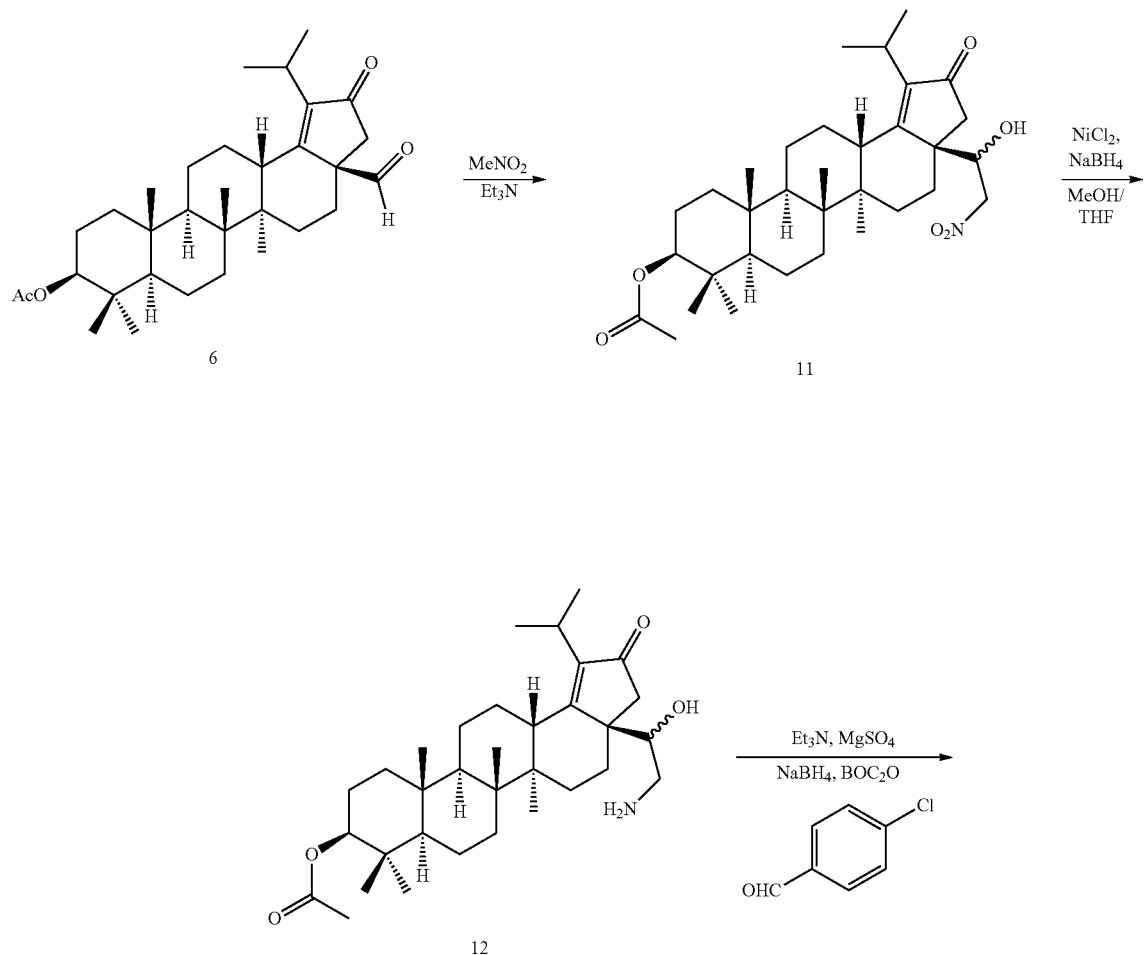

-continued
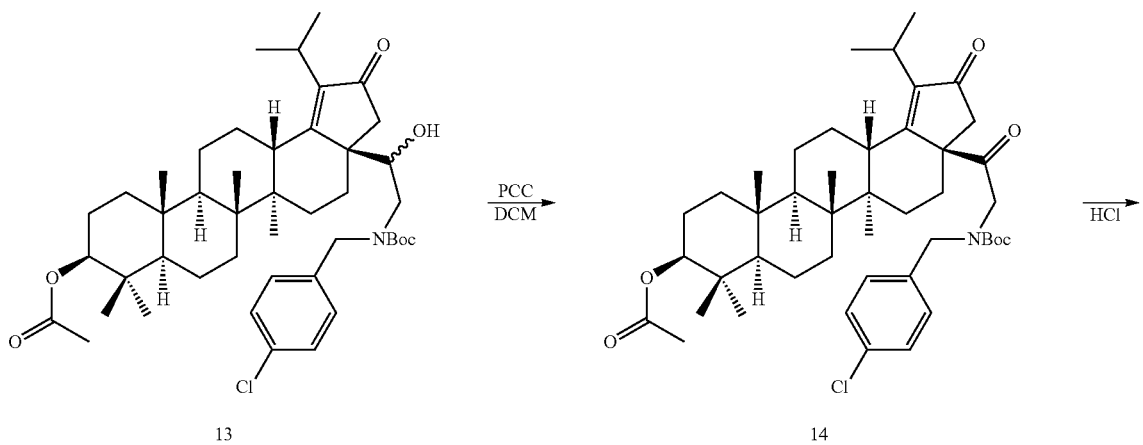
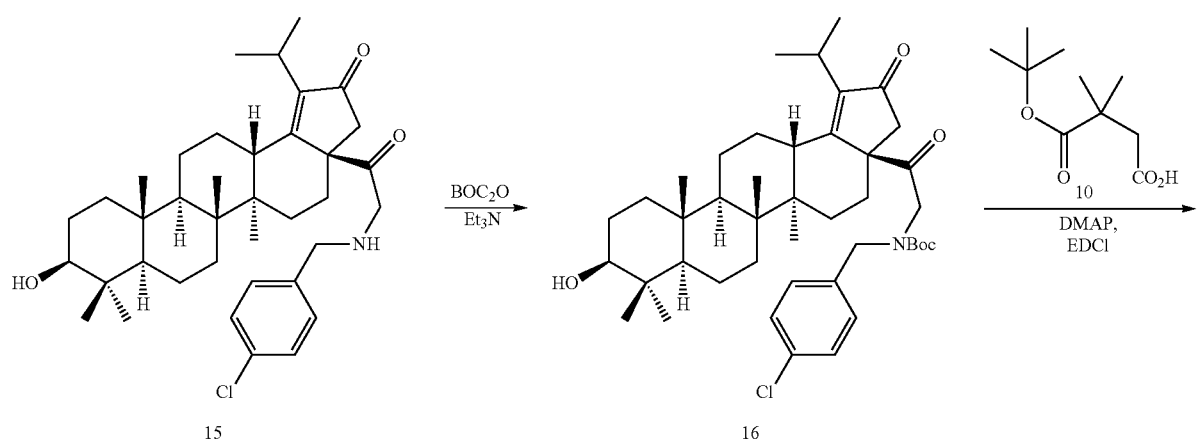
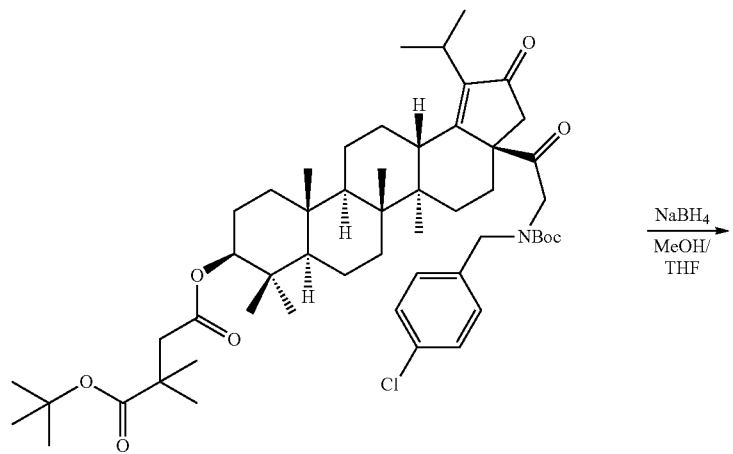

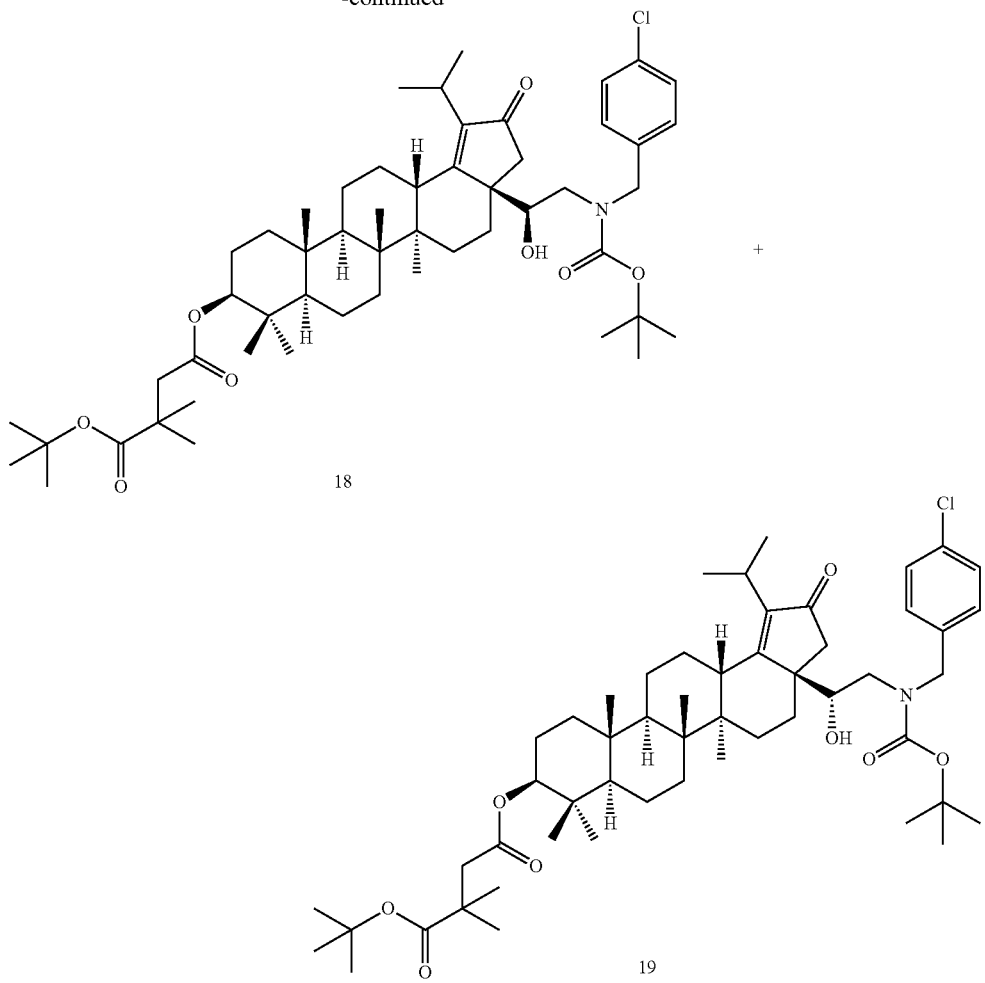

Step A: Intermediate 11

(3aR,5aR,5bR,7aR,9S,11aR,11bR,13aS)-3a-(1-Hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a mixture of (3b)-21,28-dioxolup-18-en-3-yl acetate (6) (25 g, 50.3 mmol) and nitromethane (150 ml, 2782 mmol) stirred at room temp was added to triethylamine (75 ml, 538 mmol) in one charge. The reaction mixture was stirred at rt overnight. The reaction mixture was concentrated and washed with petroleum ether/EtOAc (2:1, 100 mL) to give the product of (24 g, 43.0 mmol, 85% yield) as a white solid. LC/MS: m/z calculated 557.4, found 558.2 (M+1)$^+$.

Step B: Intermediate 12

(3aR,5aR,5bR,7aR,9S,11aR,11bR,13aS)-3a-(2-Amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of 11 (15.0 g, 26.9 mmol) in methanol (300 mL) was added NiCl$_2$.6H$_2$O (9.59 g, 40.3 mmol) at −5° C. and was slowly added sodium borohydride (10.17 g, 269 mmol) at 5~10° C. (internal temp). The reaction mixture was stirred at −5° C. (bath temp) for 30 min. The mixture was then quenched with saturated NH$_4$Cl (200 mL), diluted with EtOAc (1500 mL), then stirred at rt overnight. And the organic layer was washed with saturated NH$_4$Cl (50 mL), water (800 mL), brine (800 mL) and was dried over MgSO$_4$, filtered and concentrated to afford a solid, which was washed with petroleum ether to give the 12 (14 g, 24.40 mmol, 91% yield) as a white solid. LC/MS: m/z calculated 527.4, found 528.3 (M+1)$^+$.

Step C: Intermediate 13

(3aR,5aR,5bR,7aR,9S,11aR,11bR,13aS)-3a-(2-((Tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of 12 (8 g, 14.58 mmol), triethylamine (0.813 ml, 5.83 mmol) and MgSO$_4$ (2.63 g, 21.87 mmol) in methanol (225 ml) stirred at rt was added 4-chlorobenzaldehyde (2.056 ml, 17.50 mmol). The reaction mixture was stirred at rt for 2 h, then cooled to −5° C. and NaBH$_4$ was added in small portions during 10 min and stirred for 30 min.

Following this, Boc₂O (4.06 ml, 17.50 mmol) was added. The reaction was warmed to rt. and stirred for 1 h. The reaction mixture was poured into ice water (300 ml) and the solids were collected and dried to give 13 (7 g, 8.56 mmol, 58.7% yield) as a white foam. LC/MS: m/z calculated 751.5, found 774.3 (M+Na)⁺.

Step D: Intermediate 14

(3aR,5aR,5bR,7aR,9S,11aR,11bR,13aS)-3a-(2-((Tert-butoxycarbonyl)(4-chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a mixture of 13 (25 g, 29.9 mmol) in dichloromethane (200 mL), was added PCC (50 g, 232 mmol) and silica gel 50 g, This mixture was stirred at rt overnight. The solids were removed by fitration to obtain black solution, which was concentrated and purified by silica gel column chromatography eluting with hex/EtOAc (10:1) to afford the 14 (20 g, 23.99 mmol, 80% yield) as a white solid. LC/MS: m/z calculated 749.4, found 772.2 (M+Na)⁺.

Step E: Intermediate 15

(3aR,5aR,5bR,7aR,9S,11aR,11bR,13aS)-3a-(2-((4-Chlorobenzyl)amino)acetyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one To a solution of 14 in 1,4-dioxane (200 mL) and methanol (200 mL) stirred at rt was added con HCl (100 mL) in one charge. The reaction mixture was stirred overnight at 45° C. The reaction mixture was concentrated and washed with acetone to give 15 (12.5 g, 17.45 mmol, 87% yield) as a white foam. LC/MS: m/z calculated 607.38, found 608.0 (M+1)⁺.

Step F: Intermediate 16

Tert-butyl 4-chlorobenzyl(2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-oxoethyl)carbamate To a solution of 15 (6 g, 9.86 mmol) and Et₃N (5.50 mL, 39.5 mmol) in dichloromethane (30 mL) stirred at rt was added Boc₂O (2.290 mL, 9.86 mmol) in one charge. The reaction mixture was stirred at rt for 2 h. From TLC, the reaction was fininshed. The solvent was removed in vacuo. The crude product 16 (6 g, 8.47 mmol, 86% yield) was used without further purification.

Step G: Intermediate 17

4-((3aR,5aR,5bR,7aR,9S,11aR,11bR,13aS)-3a-(2-((Tert-butoxycarbonyl)(4-chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate To a solution of 10 (5.14 g, 25.4 mmol), DMAP (5.17 g, 42.3 mmol) and 16 (6 g, 8.47 mmol) in dichloromethane (50 mL) stirred at rt was added EDC (8.12 g, 42.3 mmol). The reaction mixture was stirred at rt until starting material disappeared as monitored by TLC. After the reaction was finished, the mixture was diluted with CH₂Cl₂, and washed with aq NH₄Cl. The organic layer was dried with Na₂SO₄ and the solvent was removed in vacuo. The material was purified by silica gel chromatography (hex:EtOAc, 12:1 to 5:1) to give 17 (5.4 g, 6.05 mmol, 71.4% yield) as a light white solid. The proton NMR consists of a mixture of rotomers. ¹H NMR (400 MHz, CHLOROFORM-d) δ 7.34-7.24 (m, 2 H), 7.23-7.08 (m, 2 H), 4.63-4.29 (m, 3 H), 4.11-3.39 (m, 2 H), 3.28-3.06 (m, 1 H), 2.69-0.69 (m, 68 H).

Step H: Intermediates 18 and 19

4-((3aR,5aR,5bR,7aR,9S,11aR,11bR,13aS)-3a-((R)-2-(Ttert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (18) & 4-((3aR,5aR,5bR,7aR,9S,11aR,11bR,13aS)-3a-((S)-2-((tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (19)

To a solution of and 17 (1.5 g, 1.680 mmol) in methanol (10 mL) and THF (10.00 mL) stirred at 0° C. was added NaBH₄ (0.127 g, 3.36 mmol). The reaction mixture was stirred at 0° C. until starting material disappeared (about 2 hours) as monitored by TLC. Upon completion the mixture was diluted with water, extracted with EtOAc and the organic layer was dried with Na₂SO₄. The residue was purified by silica gel chromatography (hex:EtOAc, 7:1 to 5:1) to give the diastereomer with the S configuration 4-((3aR,5aR,5bR,7aR,9S,11aR,11bR,13aS)-3a-((S)-2-((tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (18) (700 mg, 0.782 mmol, 46.6% yield) and the diastereomer with the R configuration 4-((3aR,5aR,5bR,7aR,9S,11aR,11bR,13aS)-3a-((R)-2-((tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (19) (500 mg, 0.559 mmol, 33.3% yield) both as a light white solids. For 18 ¹H NMR (400 MHz, CHLOROFORM-d) δ 7.40-7.24 (m, 2 H), 7.18 (d, J=8.3 Hz, 2 H), 4.87-4.57 (m, 1 H), 4.51 (dd, J=5.3, 11.0 Hz, 1 H), 4.42-4.13 (m, 2 H), 3.43-3.05 (m, 3 H), 2.97-2.78 (m, 1 H), 2.62-2.47 (m, 2 H), 2.47-2.29 (m, 1 H), 2.01-0.70 (m, 64 H); LC/MS: m/z calculated 893.6, found 916.5 (M+Na)⁺. For 19 ¹H NMR (400 MHz, CHLOROFORM-d) δ 7.36-7.23 (m, 2 H), 7.12 (d, J=8.3 Hz, 2 H), 4.56-4.14 (m, 4 H), 3.45-3.18 (m, 1 H), 3.15-2.97 (m, 1 H), 2.76-0.71 (m, 69 H); LC/MS: m/z calculated 893.6, found 916.7 (M+Na)⁺.

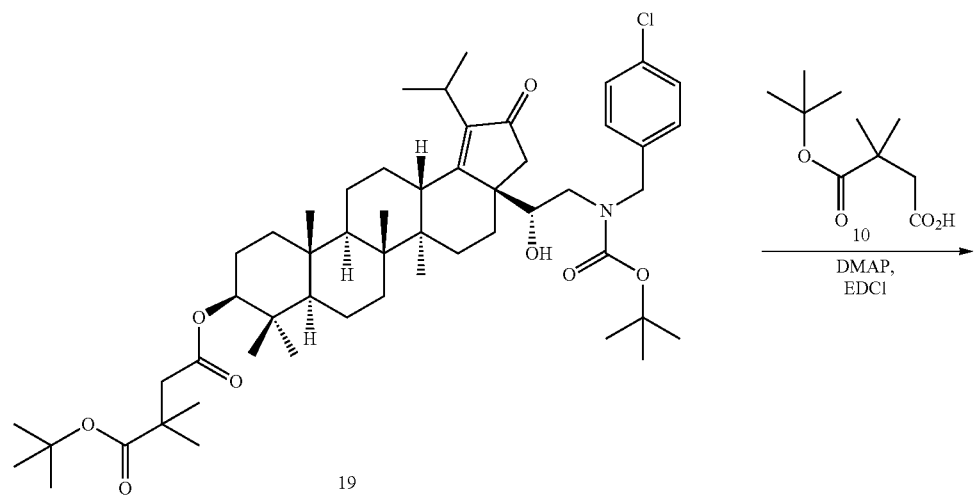
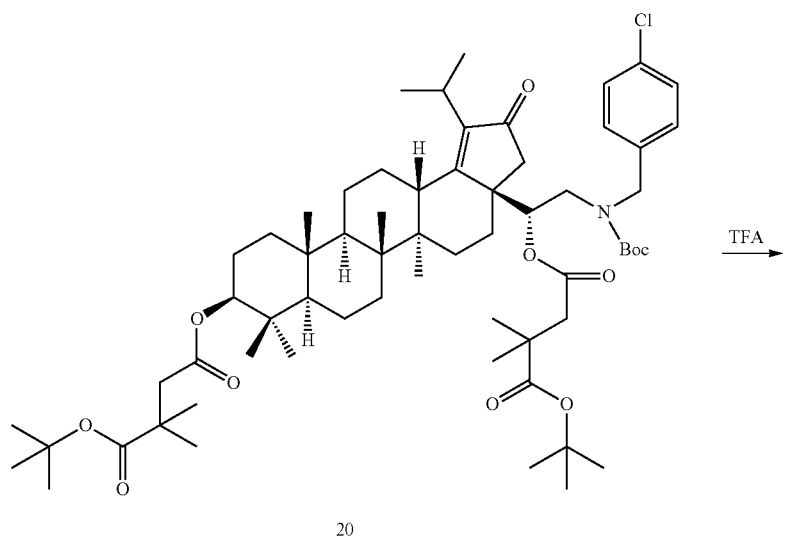
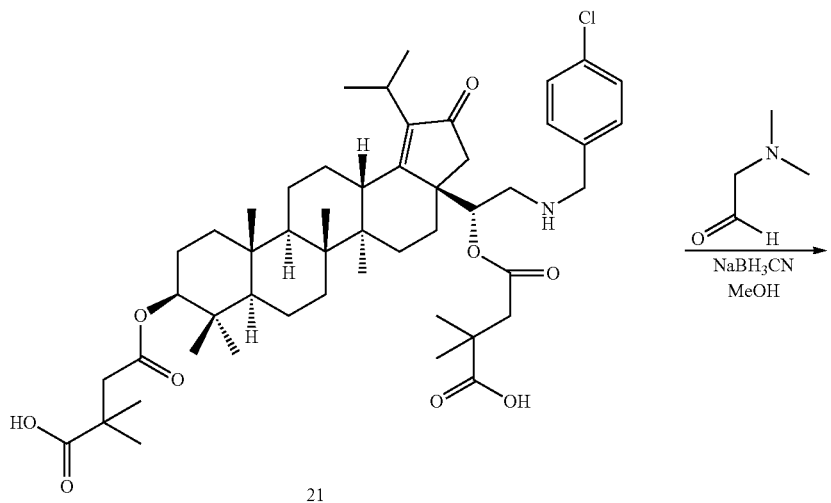

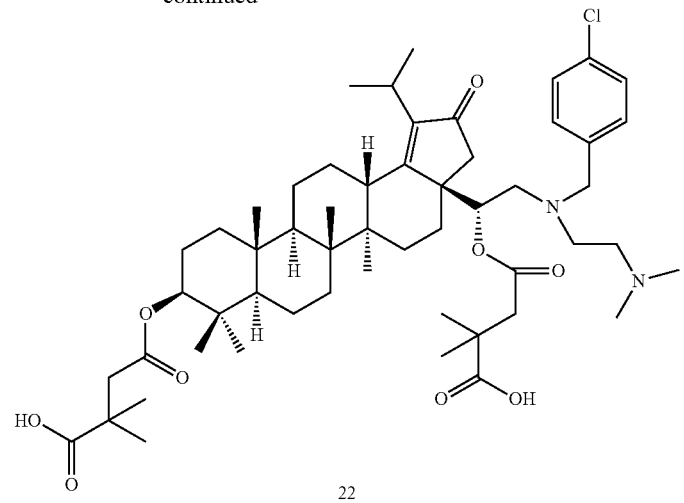

22

Example 1

Compound 21

4-((R)-1-((3aR,5aR,5bR,7aR,9S,11aR,11bR,13aS)-9-((3-carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((4-chlorobenzyl)amino)ethoxy)-2,2-dimethyl-4-oxobutanoic acid

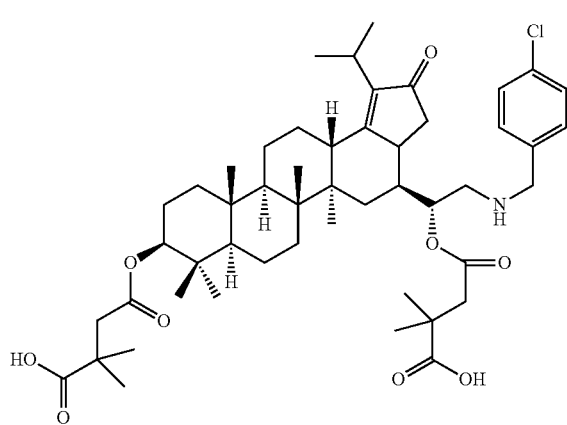

21

Step A: Intermediate 20

4-((R)-1-((3aR,5aR,5bR,7aR,9S,11aR,11bR,13aS)-9-((4-(tert-butoxy)-3,3-dimethyl-4-oxobutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysTn-3a-yl)-2-((tert-butoxycarbonyl)(4-chlorobenzyl)amino)ethyl) 1-tert-butyl 2,2-dimethylsuccinate To a solution of 10 (543 mg, 2.68 mmol), DMAP (205 mg, 1.677 mmol) in dichloromethane (5 mL) stirred at rt was added EDC (514 mg, 2.68 mmol). The reaction mixture was stirred at rt for 1 h. Then 19 (300 mg, 0.335 mmol) was added to the reaction mixture. Upon completion, the mixture was washed with 2 M HCl, water and brine. The organic layer was dried over $Na_2SO_4$ and concentrated to give the crude product 20 (400 mg, 0.278 mmol, 83% yield) as an oil. This material was used in the next step without further purification.

Step B: Compound 21

4-((R)-1-((3aR,5aR,5bR,7aR,9S,11aR,11bR,13aS)-9-((3-Carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((4-chlorobenzyl)amino)ethoxy)-2,2-dimethyl-4-oxobutanoic acid To a solution of 20 (400 mg, 0.371 mmol) in dichloromethane (5 mL) stirred at rt was added TFA (2 mL, 26.0 mmol). The reaction mixture was stirred at rt for 1 h. The mixture was evaporated to afford the TFA salt of intermediate 21 (350 mg, 0.343 mmol, 93% yield) as a light oil. $^1$H NMR (400 MHz, CHLOROFORM-d) δ 7.33-7.12 (m, 4 H), 5.76-5.60 (m, 1 H), 4.48-4.32 (m, 1 H), 4.26-3.98 (m, 2 H), 3.18-2.89 (m, 2 H), 2.89-2.68 (m, 2 H), 2.69-0.60 (m, 58 H); LC/MS: m/z calculated 865.5, found 866.3 (M+1)$^+$.

Example 2

Compound 22

4-((R)-1-((3aR,5aR,5bR,7aR,9S,11aR,11bR,13aS)-9-((3-Carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((4-chlorobenzyl)(2-(dimethylamino)ethyl)amino)ethoxy)-2,2-dimethyl-4-oxobutanoic acid

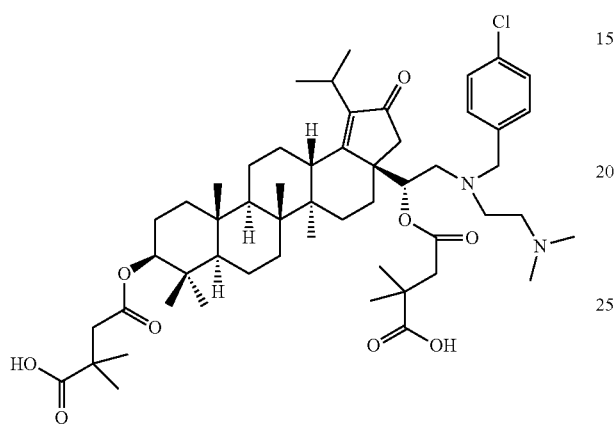

To a solution of 2-(dimethylamino)acetaldehyde, hydrochloride (441 mg, 3.57 mmol) in methanol (12 mL) was added 21, (as it's trifluoroacetic acid salt) (350 mg, 0.357 mmol). The mixture's pH was adjusted to 7-8 with Et$_3$N. The reaction mixture was stirred at rt for 2 h then NaBH$_3$CN (224 mg, 3.57 mmol) was added and mixture was stirred overnight. The reaction was filtered and evaporated to afford a crude product. The residue was purified by preparative-HPLC to obtain compound 22 as a TFA salt (200 mg, 0.168 mmol, 47.2% yield) as a white solid. $^1$H NMR (400 MHz, CHLOROFORM-d) δ 7.33 (d, J=8.3 Hz, 2 H), 7.22 (d, J=8.3 Hz, 2 H), 5.83-5.67 (m, 1 H), 4.54-4.42 (m, 1 H), 3.88-3.75 (m, 1 H), 3.65-3.49 (m, 1 H), 3.04-0.60 (m, 71 H); LC/MS: m/z calculated 936.6, found 937.4 (M+1)$^+$.

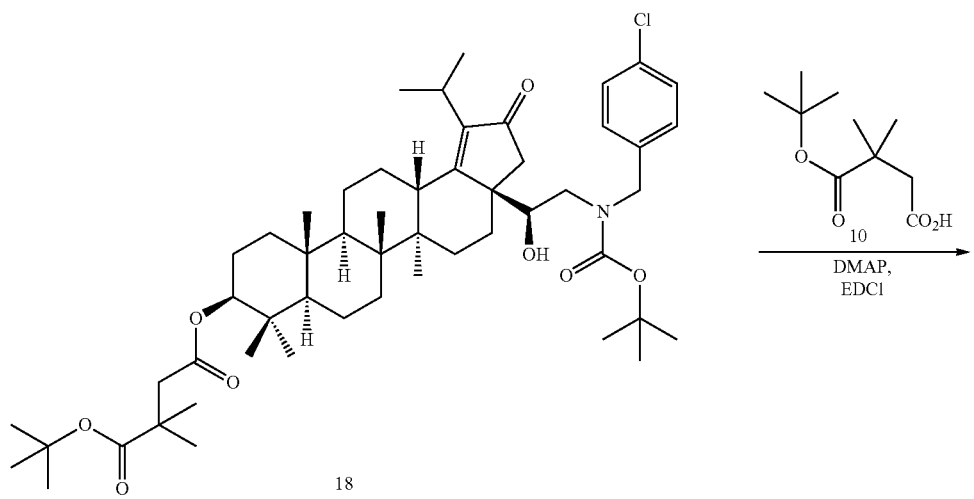

-continued
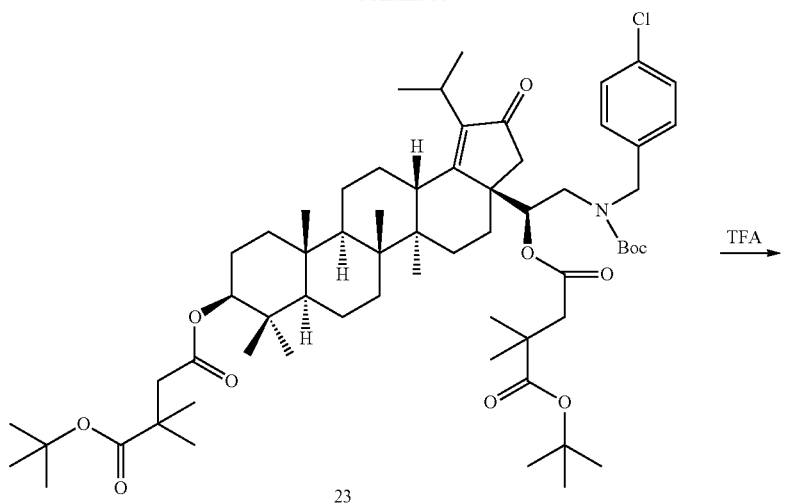
23
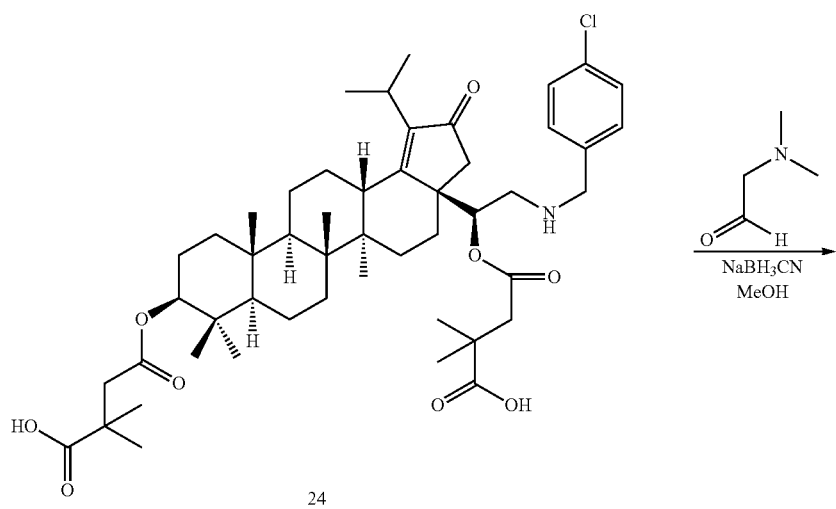
24
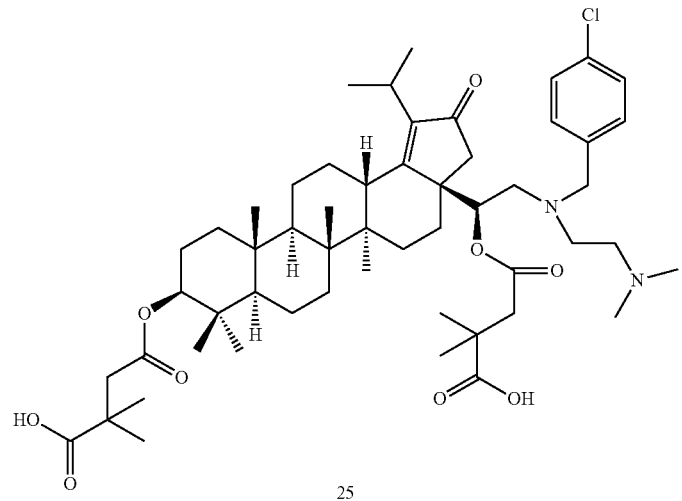
25

Example 3

Compound 25

4-((S)-1-((3aR,5aR,5bR,7aR,9S,11aR,11bR,13aS)-9-((3-Carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((4-chlorobenzyl)(2-(dimethylamino)ethyl)amino)ethoxy)-2,2-dimethyl-4-oxobutanoic acid

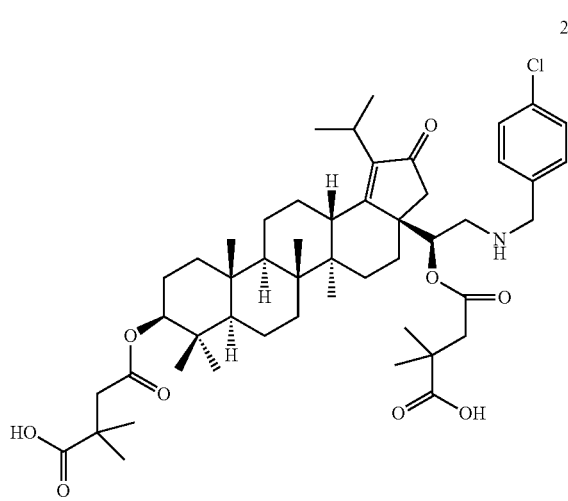

Step A: Intermediate 23

4-((S)-1-((3aR,5aR,5bR,7aR,9S,11aR,11bR,13aS)-9-((4-(Tert-butoxy)-3,3-dimethyl-4-oxobutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((tert-butoxycarbonyl)(4-chlorobenzyl)amino)ethyl) 1-tert-butyl 2,2-dimethylsuccinate To a solution of 10 (203 mg, 1.006 mmol), DMAP (123 mg, 1.006 mmol) in dichloromethane (10 ml) stirred at rt was added EDC (321 mg, 1.677 mmol). The reaction mixture was stirred at rt for 1 h, then 18 (300 mg, 0.335 mmol) was added to the reaction. Upon completion, silica gel was added, the mixture was concentrated and purified by chromatography (petroleum ether:EtOAc 6:1 to 3:1) to give the 23 (344 mg, 0.319 mmol, 95% yield) as a light white solid.

Step B: Compound 24

4-((S)-1-((3aR,5aR,5bR,7aR,9S,11aR,11bR,13aS)-9-((4-(Tert-butoxy)-3,3-dimethyl-4-oxobutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((tert-butoxycarbonyl)(4-chlorobenzyl)amino)ethyl) 1-tert-butyl 2,2-dimethylsuccinate

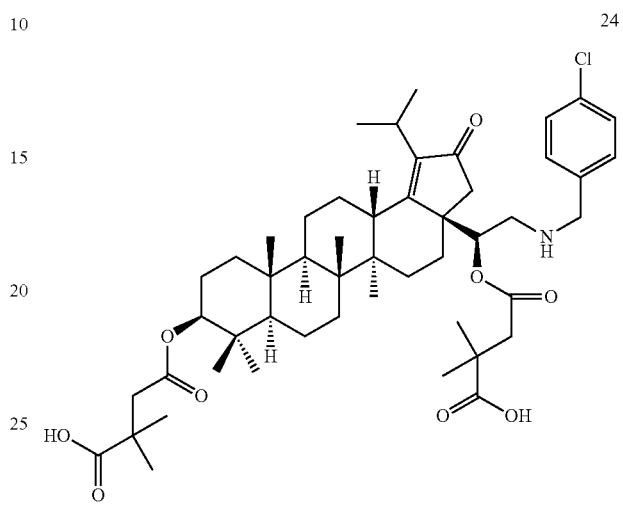

To a solution of 23 (115 mg, 0.107 mmol) in DCM (5 mL) was added TFA (2.5 mL, 0.107 mmol). The reaction mixture was stirred at rt for 2 h and evaporated in vacuo to afford crude product. This material was then washed with satd. sodium bicarbonate solution, water and brine. The organics were filtered and concentrated to give the 24 (89 mg, 0.023 mmol, 21.17% yield) as a white solid. $^1$H NMR (400 MHz, CHLOROFORM-d) δ 7.40 (s, 4 H), 5.97-5.65 (m, 1 H), 4.93-3.75 (m, 3 H), 3.59-3.27 (m, 1 H), 3.27-2.92 (m, 3 H), 2.83-2.11 (m, 5 H), 1.98-0.59 (m, 52 H) LC/MS: m/z calculated 865.5, found 866.4 (M+1)$^+$.

Example 4

Compound 25

4-((S)-1-((3aR,5aR,5bR,7aR,9S,11aR,11bR,13aS)-9-((3-Carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-((4-chlorobenzyl)(2-(dimethylamino)ethyl)amino)ethoxy)-2,2-dimethyl-4-oxobutanoic acid

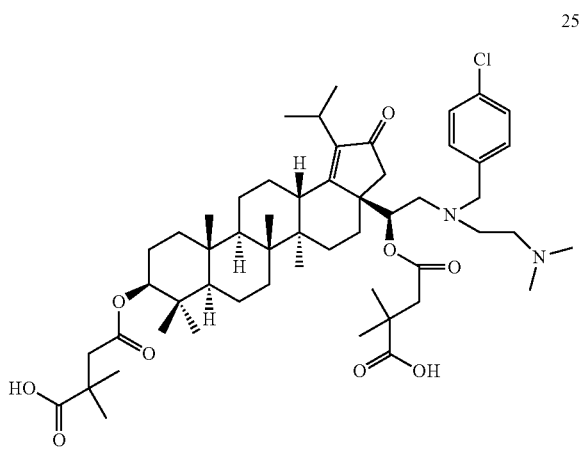

To a solution of 2-(dimethylamino)acetaldehyde (325 mg, 2.63 mmol) in methanol (5 ml) and DCE (50 ml) was added 24 (228 mg, 0.263 mmol) and triethylamine (0.110 ml, 0.789 mmol). The reaction mixture was stirred at rt for 3 h. The reaction was cooled to 0° C., and sodium cyanoborohydride (24.80 mg, 0.395 mmol) was added and resultant mixture was stirred overnight. The reaction was filtered and the filter cake was washed with DCM. The filtrate was concentrated under reduced pressure and the residue was purified by preparative-HPLC to give the title compound 25 as a TFA salt (76 mg, 0.065 mmol, 24.78% yield) as a white solid. $^1$H NMR (400 MHz, CHLOROFORM-d) δ 7.38-7.30 (m, 2 H), 7.30-7.19 (m, 2 H), 5.82-5.69 (m, 1 H), 4.53-4.44 (m, 1 H), 4.05-3.89 (m, 1 H), 3.70-3.54 (m, 1 H), 3.41-2.51 (m, 15 H), 2.45-2.12 (m, 2 H), 1.97-0.65 (m, 54 H); LC/MS: m/z calculated 936.6, found 937.4 (M+1)$^+$.

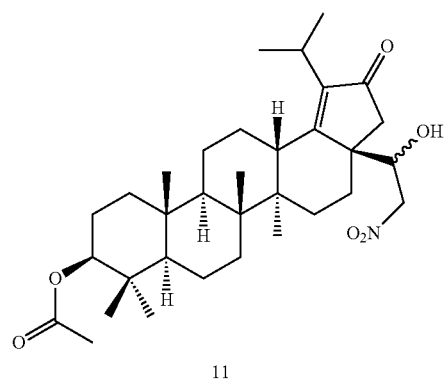

11

Ac$_2$O,
p-TsOH

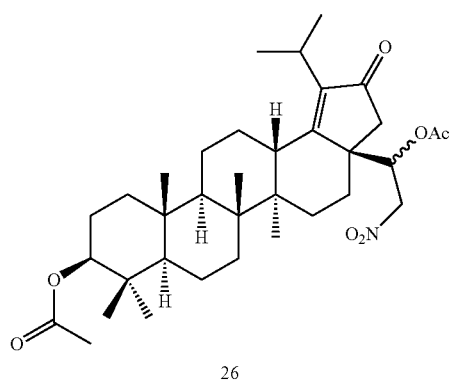

26

NaBH$_4$
EtOH,
THF

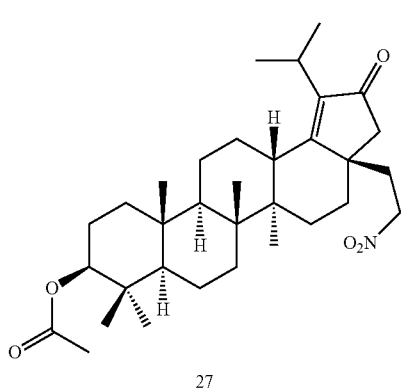

27

KMnO$_4$

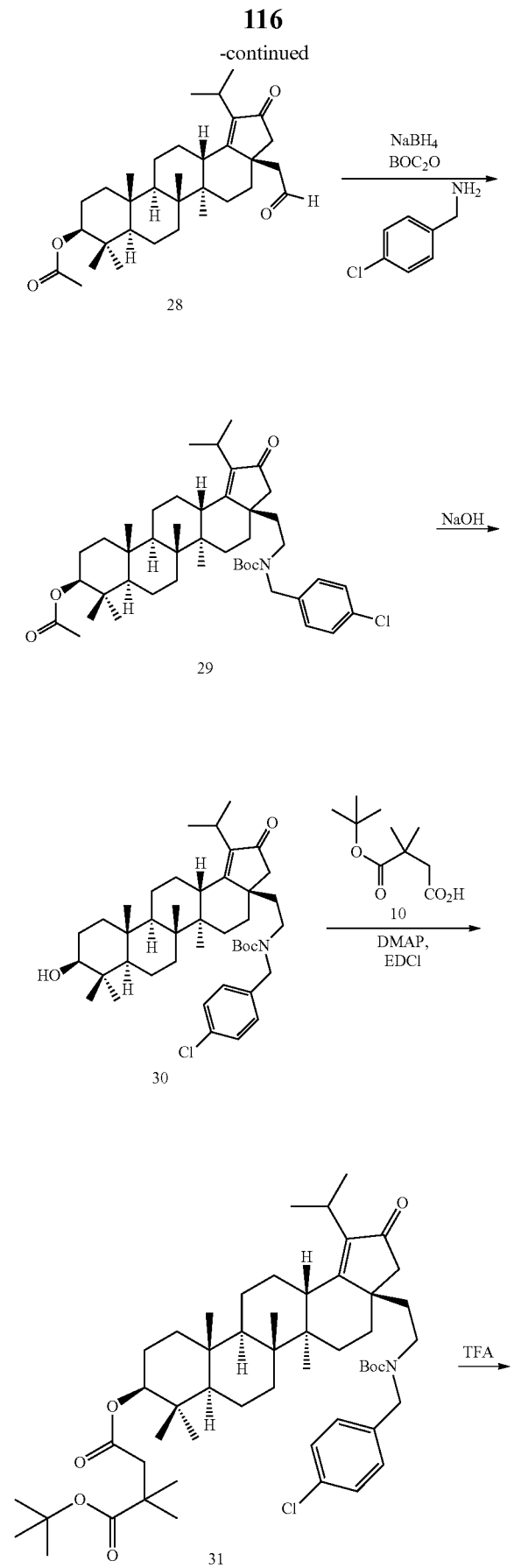

Example 5

Compound 32

4-(((3aR,5aR,5bR,7aR,9S,11aR,11bR,13aS)-3a-(2-((4-Chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

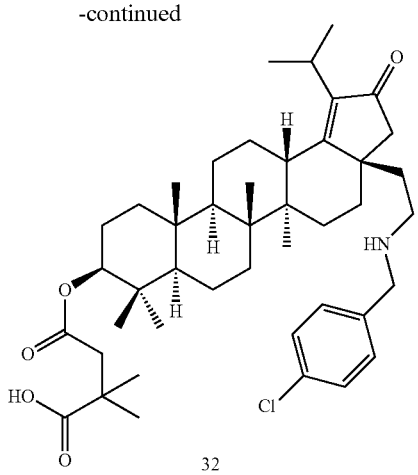

32

Step A: Intermediate 26

1-((3aR,5aR,5bR,7aR,9S,11aR,11bR,13aS)-9-Acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-nitroethyl acetate To a solution of 11 (20 g, 35.9 mmol) in acetic anhydride (100 mL, 1065 mmol) was added 4-methylbenzenesulfonic acid (1.852 g, 10.76 mmol). The reaction mixture was stirred at rt overnight. EtOAc (50 ml) and NaHCO$_3$ aq. (100 ml) were added. The organic layer was separated, washed with water, brine, and dried(Na$_2$SO$_4$). Removal of the solvent resulted in the crude product which was used directly in the next step. LC/MS: m/z calculated 599.4, found 600.3 (M+1)$^+$.

Step B: Intermediate 27

(3aR,5aR,5bR,7aR,9S,11aR,11bR,13aS)-1-Isopropyl-5a,5b,8,8,11a-pentamethyl-3a-(2-nitroethyl)-2-oxo-3,3a,4,5,5a,5b,6,7,7a,8,9,10,11,11a,11b,12,13,13a-octadecahydro-2H-cyclopenta[a]chrysen-9-yl acetate To a solution of 26 (21 g, 35.0 mmol) in THF (30 mL) and EtOH (80 mL) in an ice bath was added NaBH$_4$ (5.30 g, 140 mmol). The mixture was then kept at rt for about 1 h, diluted with ethyl acetate (200 mL) and extracted with aqueous 10% citric acid solution (150 mL), saturated aqueous NaHCO$_3$ (150 mL), and brine (150 mL). The organic layer was dried (Na$_2$SO$_4$) and evaporated to give the crude product 27 (19 g, 27.2 mmol, 78% yield). This was used directly for the next step. LC/MS: m/z calculated 541.4, found 542.3 (M+1)$^+$.

Step C: Intermediate 28

(3aR,5aR,5bR,7aR,9S,11aR,11bR,13aS)-1-Isopropyl-5a,5b,8,8,11a-pentamethyl-2-oxo-3a-(2-oxoethyl)-3,3a,4,5,5a,5b,6,7,7a,8,9,10,11,11a,11b,12,13,13a-octadecahydro-2H-cyclopenta[a]chrysen-9-yl acetate To a stirred solution of 27 (10 g, 18.46 mmol) in acetone (90.00 mL) and methanol (90 mL) at −5° C. was added

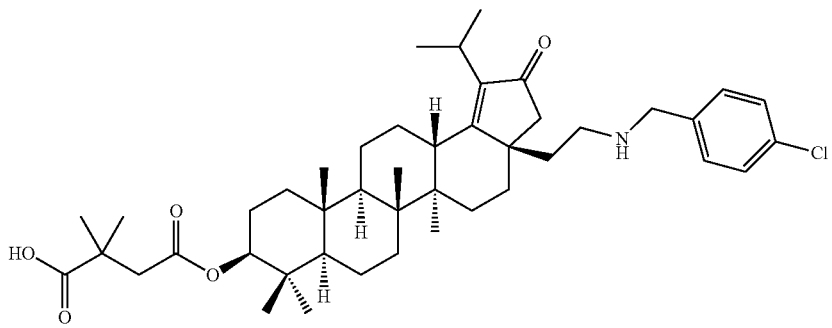

32 dropwise a solution of KOH (1.036 g,18.46 mmol) in 5 mL water, then followed by KMnO4 (1.896 g, 12.00 mmol) and MgSO$_4$ (1.666 g, 13.84 mmol) in 90 mL of water. The temperature was held below 0° C. for 1 h and for another 1 h at room temperature. The reaction mixture was diluted with DCM (100 mL), then filtered on CELITE™ diatomaceous earth and washed with DCM. The organic phase was concentrated, then extracted with DCM, to give the crude product 28 (5 g,8.12 mmol, 44.0% yield) which was used directly for the next step without further purification. $^1$H NMR (400 MHz, CHLOROFORM-d) δ 9.64 (s, 1 H), 4.49 (dd, J=5.5,11.0 Hz, 1 H), 3.27-3.06 (m, 1 H), 2.87-2.76 (m, 1 H), 2.76-2.64 (m, 1 H), 2.64-2.54 (m, 1 H), 2.45 (d, J=18.8 Hz, 1 H), 2.20 (d, J=18.8 Hz, 1 H), 2.05 (s, 3 H), 1.99-0.67 (m, 39 H); LC/MS: m/z calculated 510.4, found 533.3 (M+Na)$^+$.

Step D: Intermediate 29

(3aR,5aR,5bR,7aR,9S,11aR,11bR,13aS)-3a-(2-
((Tert-butoxycarbonyl)(4-chlorobenzyl)amino)
ethyl)-1-isopropyl-5a,5b,8,8,11a-pentamethyl-2-oxo-
3,3a,4,5,5a,5b,6,7,7a,8,9,10,11,11a,11b,12,13,13a-
octadecahydro-2H-cyclopenta[a]chrysen-9-yl acetate To a solution of 28 (1.5 g, 2.94 mmol), TEA (0.164 ml, 1.175 mmol) and MgSO$_4$ (0.530 g, 4.41 mmol) in methanol (15 ml) stirred at rt was added 4-chlorobenzylamine (0.487 ml, 4.11 mmol). The reaction mixture was stirred at 20° C. for 2 h, then cooled to −5° C. and NaBH$_4$ (0.167 g, 4.41 mmol) was added in small portions during 10 min and stirred for 30 min. BOC$_2$O (0.750 ml, 3.23 mmol) was then added. The reaction was warmed to rt and stirred for 1 h. The reaction mixture was poured into ice water (300 ml) and solids were collected and dried to give 29 (1.8 g, 2.106 mmol, 72%) as a white foam. This material was used without further purification. LC/MS: m/z calculated 735.5, found 758.3 (M+Na)$^+$.

Step E: Intermediate 30

Tert-butyl 4-chlorobenzyl(2-((3aR,5aR,5bR,7aR,9S,
11aR,11bR,13aS)-9-hydroxy-1-isopropyl-5a,5b,8,8,
11a-pentamethyl-2-oxo-3,3a,4,5,5a,5b,6,7,7a,8,9,10,
11,11a,11b,12,13,13a-octadecahydro-2H-cyclopenta
[a]chrysen-3a-yl)ethyl)carbamate To a solution of 29 (1.6 g, 2.173 mmol) in methanol (6 mL) and THF (6 mL), and water (6 mL) was added NaOH (5.21 g, 130 mmol). The reaction mixture was stirred at rt for 1 h. Water and EtOAc were added upon completion and the layers separated. The organic layer was washed with water, brine, and dried (Na$_2$SO$_4$). Removal of the solvent gave 30 (1.4 g, 1.590 mmol, 73%) as a white solid. LC/MS: m/z calculated 693.5, found 716.3 (M+Na)$^+$.

Step F: Intermediate 31

4-((3aR,5aR,5bR,7aR,9S,11aR,11bR,13aS)-3a-(2-
((Tert-butoxycarbonyl)(4-chlorobenzyl)amino)
ethyl)-1-isopropyl-5a,5b,8,8,11a-pentamethyl-2-oxo-
3,3a,4,5,5a,5b,6,7,7a,8,9,10,11,11a,11b,12,13,13a-
octadecahydro-2H-cyclopenta[a]chrysen-9-yl)
1-tert-butyl 2,2-dimethylsuccinate To a solution of DMAP (0.862 g, 7.06 mmol), EDC (1.932 g, 10.08 mmol) and 4-tert-butoxy-3,3-dimethyl-4-oxobutanoic acid (10) (1.631 g, 8.06 mmol) in DCM (60 mL) stirred at 20° C. for 30 min was added 30 (1.4 g, 2.016 mmol). The reaction mixture was stirred at 20° C. for 1 h. The mixture was washed with saturated ammonium chloride, water, and saturated NaHCO$_3$, water, and lastly brine. The organic layer was dried over Na$_2$SO$_4$, filtered and concentrated to give the crude product, which was purified by silica gel column eluting with petrol ether/Ethyl acetate (4:1) to afford the product 4-((3aR,5aR,5bR,7aR,9S,11aR, 11bR,13aS)-3a-(2-((tert-butoxycarbonyl)(4-chlorobenzyl) amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (1.4 g, 0.986 mmol, 49%) as a yellow solid.

Step G: Compound 32

4-(((3aR,5aR,5bR,7aR,9S,11aR,11bR,13aS)-3a-(2-
((4-Chlorobenzyl)amino)ethyl)-1-isopropyl-5a,5b,8,
8,11a-pentamethyl-2-oxo-3,3a,4,5,5a,5b,6,7,7a,8,9,
10,11,11a,11b,12,13,13a-octadecahydro-2H-
cyclopenta[a]chrysen-9-yl)oxy)-2,2-dimethyl-4-
oxobutanoic acid To a solution of 31 (1.4 g, 1.593 mmol) in DCM (6 mL) was added TFA (3 mL). The reaction mixture was stirred at 20° C. for 2 h and evaporated in vacuo to afford crude product which was purified by preparative-HPLC to give the title compound trifluoroacetic acid salt (1 g, 73%) as a white solid. $^1$H NMR (400 MHz, METHANOL-d$_4$) δ=7.57-7.42 (m, 4 H), 4.51 (dd, J=5.1, 11.2 Hz, 1 H), 4.29-4.15 (m, 2 H), 3.30-3.18 (m, 1 H), 2.98-2.69 (m, 3 H), 2.62 (q, J=16.0 Hz, 2 H), 2.29 (d, J=19.1 Hz, 1 H), 2.17-0.79 (m, 48 H); LC/MS: m/z calculated 721.5, found 722.3 (M+1)$^+$.

Example 6

Compound 33

4-(((3aR,5aR,5bR,7aR,9S,11aR,11bR,13aS)-3a-(2-
(Benzylamino)ethyl)-1-isopropyl-5a,5b,8,8,11a-pen-
tamethyl-2-oxo-3,3a,4,5,5a,5b,6,7,7a,8,9,10,11,11a,
11b,12,13,13a-octadecahydro-2H-cyclopenta[a]
chrysen-9-yl)oxy)-2,2-dimethyl-4-oxobutanoic acid

33

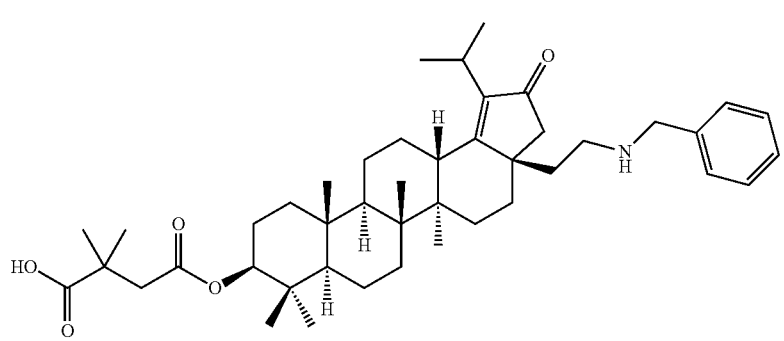

The title compound was made in a similar manner to example 5 as a TFA salt. $^1$H NMR (400 MHz, METHANOL-$d_4$) δ=7.48 (s, 5 H), 4.51 (dd, J=5.1, 11.2 Hz, 1 H), 4.30-4.17 (m, 2 H), 3.31-3.19 (m, 1 H), 2.96-2.71 (m, 3 H), 2.62 (q, J=15.9 Hz, 2 H), 2.29 (d, J=18.8 Hz, 1 H), 2.21-0.78 (m, 48 H); LC/MS: m/z calculated 687.5, found 688.4 (M+1)$^+$.
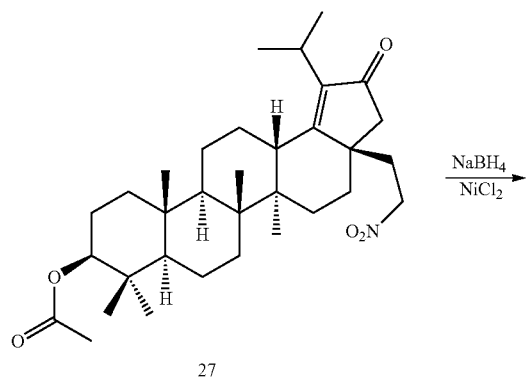
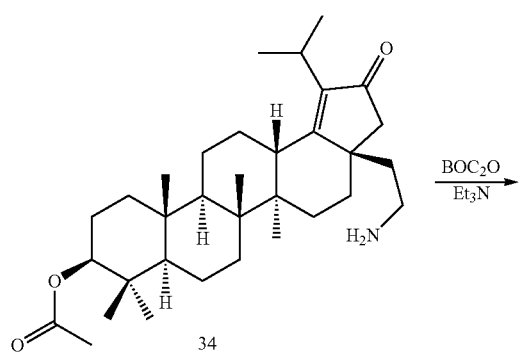
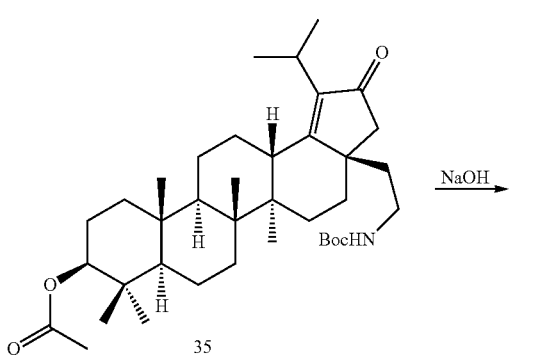
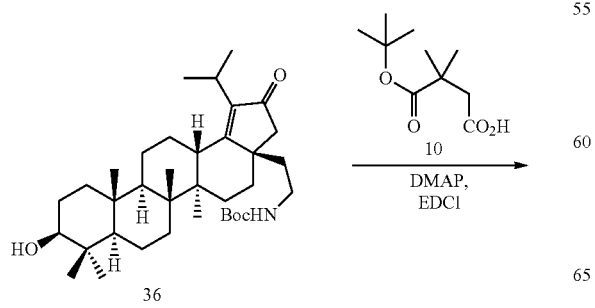
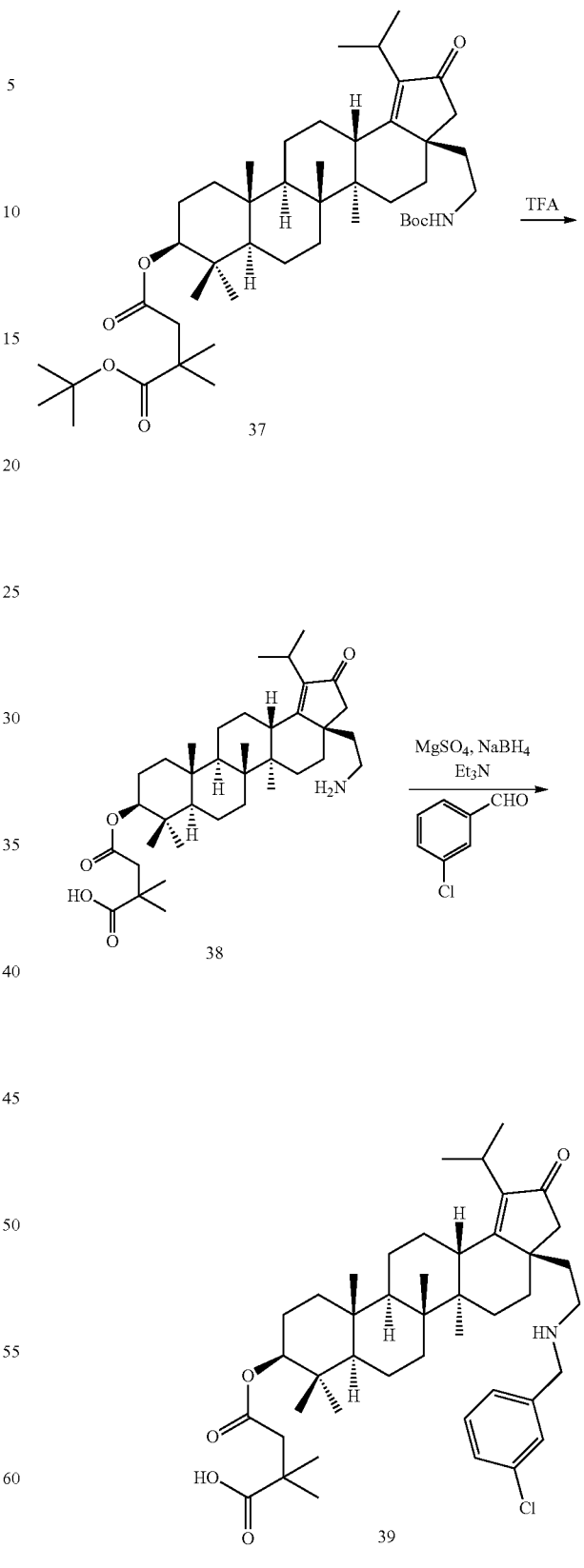

Example 7

Compound 39

4-(((3aR,5aR,5bR,7aR,9S,11aR,11bR,13aS)-3a-(2-((3-Chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

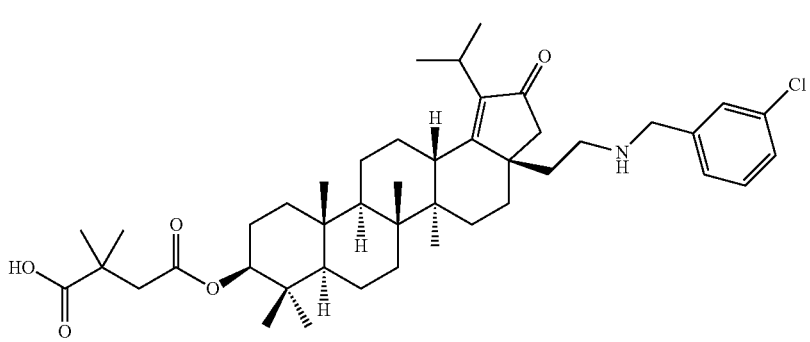

Step A: Compound 34

(3aR,5aR,5bR,7aR,9S,11aR,11bR,13aS)-3a-(2-Aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of (3aR,5aR,5bR,7aR,9S,11aR,11bR,13aS)-1-isopropyl-5a,5b,8,8,11a-pentamethyl-3a-(2-nitroethyl)-2-oxo-3,3a,4,5,5a,5b,6,7,7a,8,9,10,11,11a,11b,12,13,13a-octadecahydro-2H-cyclopenta[a]chrysen-9-yl acetate (27) (10 g, 18.46 mmol) and nickel(II) chloride (7.18 g, 55.4 mmol) in methanol (100 ml) was added sodium borohydride (6.98 g, 185 mmol) portionwise during 1 hour. The reaction mixture was stirred at 0° C. for 1 h. The mixture was diluted with EtOAc (250 mL). The organic phase was washed with sat. NH$_4$Cl (50 mL) until the organic layer change to colorless. The combined organic layers were dried over anhydrous Na$_2$SO$_4$, and concentrated in vacuo to get the crude product (3aR,5aR,5bR,7aR,9S,11aR,11bR,13aS)-3a-(2-aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (34) (7 g, 12.63 mmol, 68.4% yield), which was used without further purification. $^1$H NMR (400 MHz, CHLOROFORM-d) δ=9.15 (dd, J=4.9, 11.4 Hz, 1 H), 8.12 (br. s., 2 H), 7.97-7.81 (m, 1 H), 7.63-7.49 (m, 1 H), 7.26-7.15 (m, 1 H), 7.15-7.04 (m, 1 H), 6.98 (d, J=18.6 Hz, 1 H), 6.81-5.38 (m, 47 H); LC/MS: m/z calculated 511.4, found 512.3 (M+1)$^+$.

Step B: Compound 35

(3aR,5aR,5bR,7aR,9S,11aR,11bR,13aS)-3a-(2-((Tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of (3aR,5aR,5bR,7aR,9S,11aR,11bR,13aS)-3a-(2-aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (34) (5.3 g, 10.36 mmol), TEA (2.165 mL, 15.53 mmol) and TEA (2.165 mL, 15.53 mmol) in dichloromethane (DCM) (100 mL) stirred at room temp was added BOC$_2$O (2.404 mL, 10.36 mmol). The reaction mixture was stirred at 20° C. for 2 h. The reaction mixture was poured into ice water (300 ml) and the solids were collected and dried to give (3aR,5aR,5bR,7aR,9S,11aR,11bR,13aS)-3a-(2-((tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (35) (5.8 g, 8.34 mmol, 81% yield) as a white foam. This was used crude in next reaction without further purification. $^1$H NMR (400 MHz, CHLOROFORM-d) δ=4.58-4.37 (m, 2 H), 3.26-2.96 (m, 4 H), 2.93-2.72 (m, 2 H), 2.28 (d, J=18.8 Hz, 1 H), 2.11-0.71 (m, 53 H); LC/MS: m/z calculated 611.5, found 634.3 (M+Na)$^+$.

Step C: Compound 36

Tert-butyl (2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)ethyl)carbamate A solution of (3aR,5aR,5bR,7aR,9S,11aR,11bR,13aS)-3a-(2-((tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (35) (5.8 g, 9.48 mmol), NaOH (11.37 g, 284 mmol) in methanol (4 mL), THF (6 mL), and Water (2 mL) was stirred at room temperature for 1 h. EtOAc was added and the reaction mixture was washed with water. The organic layer was separated, washed with water and brine, and dried (Na$_2$SO$_4$). Removal of the solvent provide tert-butyl (2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)ethyl)carbamate (36) (5.4 g, 7.87 mmol, 83% yield) as a white solid. $^1$H NMR (400 MHz, CHLOROFORM-d) δ=4.53-4.36 (m, 1 H), 3.30-2.94 (m, 4 H), 2.94-2.67 (m, 2 H), 2.28 (d, J=18.8 Hz, 1 H), 2.11-0.55 (m, 50 H); LC/MS: m/z calculated 569.4, found 592.3 (M+Na)$^+$.

Step D: Compound 37

4-((3aR,5aR,5bR,7aR,9S,11aR,11bR,13aS)-3a-(2-((Tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate A solution of 4-tert-butoxy-3,3-dimethyl-4-oxobutanoic acid (10) (4.79 g, 23.69 mmol), DMAP (3.47 g, 28.4 mmol) and tert-butyl (2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)ethyl)carbamate (36) (5.4 g, 9.48 mmol) EDC (9.08 g, 47.4 mmol) in dichloromethane (DCM) (25 mL) was stirred at rt overnight. NH$_4$Cl was added and the mixture was extracted with DCM, and purified by chromatography with PE:EA (10:1) to give the 4-((3aR,5aR,5bR,7aR,9S,11aR,11bR,13aS)-3a-(2-((tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (37) (6.7 g, 8.75 mmol, 92% yield). $^1$H NMR (400 MHz, CHLOROFORM-d) δ=4.62-4.39 (m, 2 H), 3.24-3.10 (m, 1 H), 3.10-2.93 (m, 1 H), 2.93-2.68 (m, 2 H), 2.62-2.49 (m, 1 H), 2.28 (d, J=18.8 Hz, 1 H), 2.11-0.69 (m, 66 H); LC/MS: m/z calculated 753.6, found 776.5 (M+Na)$^+$.

Step E: Compound 38

4-(((3aR,5aR,5bR,7aR,9S,11aR,11bR,13aS)-3a-(2-Aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 4-(((3aR,5aR,5bR,7aR,9S,11aR,11bR,13aS)-3a-(2-((tert-butoxycarbonyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (37) (6.7 g, 8.88 mmol) in DCM (20 mL) stirred at rt was added TFA (4 ml, 51.9 mmol). The reaction mixture was stirred at rt for 2 h. The reaction mixture was washed with sat. NaHCO$_3$. A solid was formed and collected by filtration to give 4-(((3aR,5aR,5bR,7aR,9S,11aR,11bR,13aS)-3a-(2-aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (38) (4 g, 6.55 mmol, 73.7% yield) as a white solid. $^1$H NMR (400 MHz, DMSO-d$_6$) δ=4.44-4.28 (m, 1 H), 3.20-3.05 (m, 1 H), 2.87-2.75 (m, 1 H), 2.46-2.16 (m, 6 H), 1.97-0.66 (m, 47 H); LC/MS: m/z calculated 597.4, found 598.3 (M+1)$^+$.

Step F: Compound 39

4-(((3aR,5aR,5bR,7aR,9S,11aR,11bR,13aS)-3a-(2-((3-Chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 4-(((3aR,5aR,5bR,7aR,9S,11aR,11bR,13aS)-3a-(2-aminoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (38) (300 mg, 0.502 mmol), TEA (0.028 ml, 0.201 mmol) and MgSO$_4$ (91 mg, 0.753 mmol) in methanol (15 ml) stirred at room temp was added 3-chlorobenzaldehyde (85 mg, 0.602 mmol). The reaction mixture was stirred at 20° C. for 2 h. The reaction mixture was then cooled to 0° C. and NaBH$_4$ (1.541 g, 40.7 mmol) was added in portions within 30 min, after which the solution was allowed to stirred for 1 h. The mixture was purified by preparative-TLC eluting with DCM/MeOH (20:1) to give 39 (108 mg, 0.147 mmol, 29%). $^1$H NMR (500 MHz, METHANOL-d$_4$) δ=7.41 (s, 1 H), 7.38-7.24 (m, 3 H), 4.48 (dd, J=5.7, 10.7 Hz, 1 H), 3.89-3.67 (m, 2 H), 3.26-3.11 (m, 1 H), 2.84-2.73 (m, 1 H), 2.66-2.47 (m, 2 H), 2.46-2.34 (m, 1 H), 2.34-2.21 (m, 2 H), 2.08-0.77 (m, 48 H).

Example 8

Compound 40

4-(((3aR,5aR,5bR,7aR,9S,11aR,11bR,13aS)-3a-(2-((3-Chloro-2-fluorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

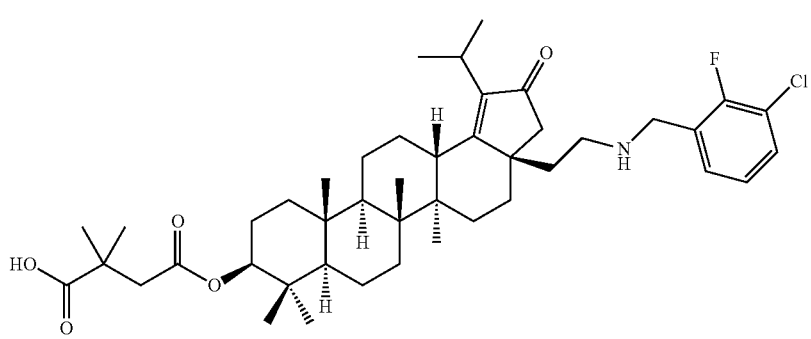

40

The title compound was made in a similar manner to Example 7, but as a TFA salt. $^1$H NMR (500 MHz, METHANOL-d$_4$) δ=7.46-7.38 (m, 1 H), 7.35 (t, J=6.6 Hz, 1 H), 7.17 (t, J=7.7 Hz, 1 H), 4.48 (dd, J=5.5, 10.6 Hz, 1 H), 3.97-3.72 (m, 2 H), 3.27-3.12 (m, 1 H), 2.85-2.73 (m, 1 H), 2.67-2.45 (m, 2 H), 2.44-2.16 (m, 3 H), 2.09-0.73 (m, 48 H).

Example 9

Compound 41

4-(((3aR,5aR,5bR,7aR,9S,11aR,11bR,13aS)-3a-(2-((1-(4-chlorophenyl)cyclopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

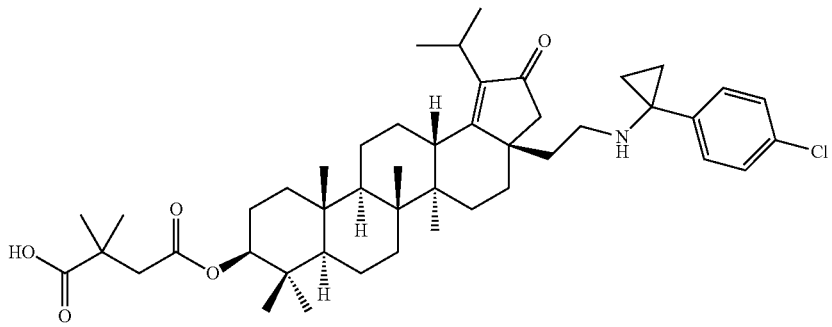

41

The title compound was made in a similar manner to Example 5, but as a TFA salt. The final step was performed according to the following procedure. To a solution of 4-(tert-butoxy)-3,3-dimethyl-4-oxobutanoic acid (10) (0.988 g, 4.89 mmol), EDC (1.171 g, 6.11 mmol) and DMAP (0.522 g, 4.28 mmol) in DCM (12 mL) stirred at room temp was added tert-butyl (1-(4-chlorophenyl)cyclopropyl)(2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)ethyl)carbamate (1.1 g, 1.221 mmol). The reaction mixture was stirred at rt for 2 h. Next, TFA (6 mL) was added to the reaction mixture. Then, the reaction solution was stirred at rt for another 1.5 h, and the product was extracted with DCM (60 mL*3), and the combined organic phase was washed with brine (100 ml), dried over $Na_2SO_4$, concentrated and the residue was purified by recrystallization from DCM and hexane (1:6) resulting in 800 mg of the TFA salt of 41 as white solid. $^1$H NMR (400 MHz, METHANOL-$d_4$) δ=7.64-7.44 (m, 4 H), 4.50 (dd, J=5.1, 11.2 Hz, 1 H), 3.26-3.10 (m, 1 H), 2.84-2.41 (m, 5 H), 2.24-2.12 (m, 1 H), 2.12-0.78 (m, 52 H); LC/MS: m/z calculated 747.5, found 748.3 (M+1)$^+$.

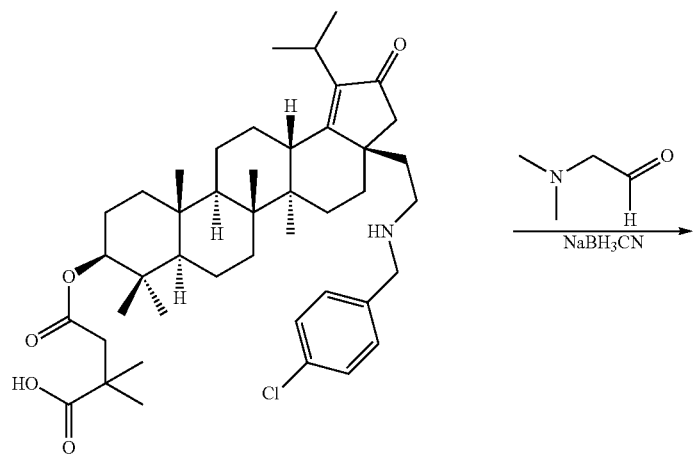

32

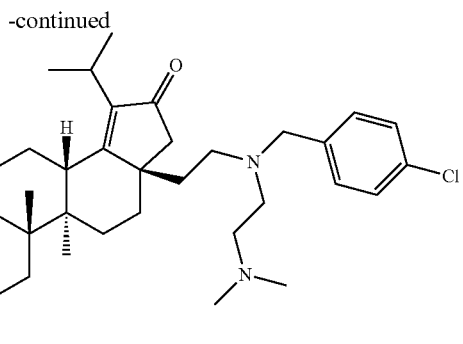

42

Example 10

Compound 42

4-(((3aR,5aR,5bR,7aR,9S,11aR,11bR,13aS)-3a-(2-((4-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

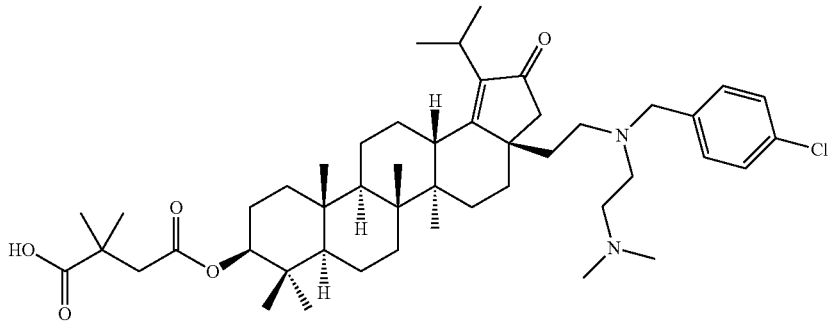

42

To a solution of 2-(dimethylamino)acetaldehyde (244 mg, 1.977 mmol) in methanol (100 ml) was added 4-(((3aR,5aR,5bR,7aR,9S,11aR,11bR,13aS)-3a-(2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, hydrochloride (32) (300 mg, 0.395 mmol). The reaction mixture was stirred at 40° C. for 2 h. The reaction was cooled to rt and sodium cyanoborohydride (24.84 mg, 0.395 mmol) was added and the resultant solution was stirred overnight. The reaction was diluted with ammonium chloride (40 ml), and extracted with DCM (60 ml×3). The combined organic layers were washed with brine (20 ml), dried over sodium sulfate, filtered and concentrated in vacuo. The residue was purified by preparative-HPLC to afford 42 as a trifluoroacetic acid salt (200 mg, 49% yield) as a white solid. $^1$H NMR (400 MHz, METHANOL-$d_4$) δ=7.52-7.34 (m, 4 H), 4.50 (dd, J=5.0, 11.0 Hz, 1 H), 4.07-3.88 (m, 1 H), 3.83-3.62 (m, 1 H), 3.53-3.35 (m, 2 H), 3.22-2.89 (m, 9 H), 2.71-2.54 (m, 2 H), 2.50-2.21 (m, 4 H), 2.06-0.83 (m, 48 H); LC/MS: m/z calculated 792.5, found 793.4 (M+1)$^+$.

Example 11

Compound 43

4-(((3aR,5aR,5bR,7aR,9S,11aR,11bR,13aS)-3a-(2-((1-(4-Chlorophenyl)cyclopropyl)(2-(dimethyl-amino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

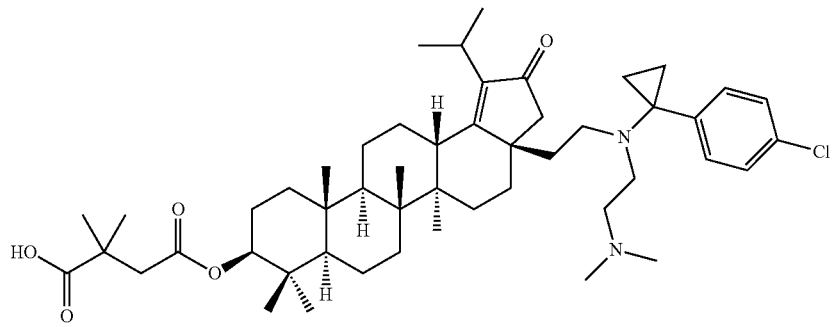

The title compound was made in a similar manner to Example 10, as a TFA salt. $^1$H NMR (400 MHz, METHANOL-$d_4$) δ=7.35 (s, 4 H), 4.51 (dd, J=5.1, 11.2 Hz, 1 H), 3.31-3.17 (m, 2 H), 3.12-2.73 (m, 9 H), 2.73-2.51 (m, 2 H), 2.44-2.17 (m, 3 H), 2.14-0.77 (m, 53 H); LC/MS: m/z calculated 818.4, found 819.4 (M+1)$^+$.

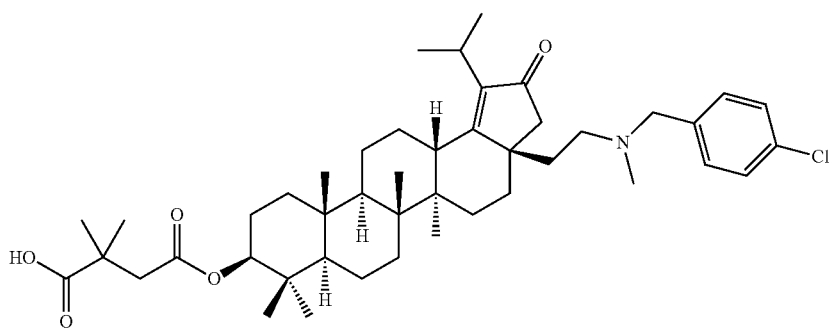

Example 12

Compound 44

4-(((3aR,5aR,5bR,7aR,9S,11aR,11bR,13aS)-3a-(2-((4-Chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

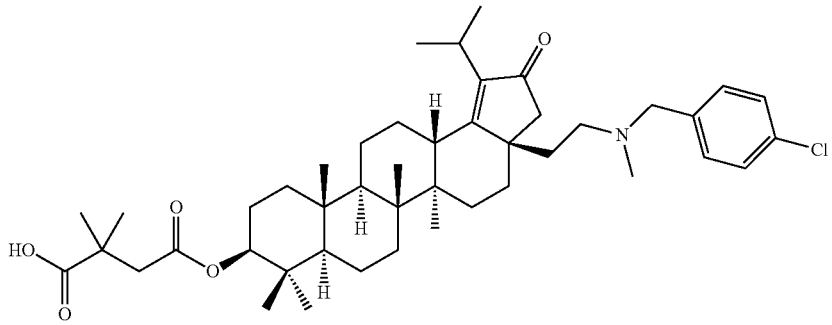

44

To a solution of 32 (150 mg, 0.208 mmol) in MeOH (6 mL) at rt was added formaldehyde (33.7 mg, 0.415 mmol). The reaction mixture was stirred at rt for 2 h. NaCNBH$_4$ (104 mg, 1.661 mmol) was added portionwise and the mixture stirred for overnight. The solvent was evaporated, and the mixture was purified by preparative HPLC to provide the TFA salt of 44 (60 mg, 34%). $^1$H NMR (400 MHz, METHANOL-d$_4$) δ=7.60-7.44 (m, 4 H), 4.56-4.37 (m, 2 H), 4.36-4.24 (m, 1 H), 3.28-3.14 (m, 1 H), 2.89 (m, 5 H), 2.73-2.50 (m, 2 H), 2.28 (d, J=19.1 Hz, 1 H), 2.20-0.83 (m, 49 H); LC/MS: m/z calculated 735.5, found 736.3 (M+1)$^+$.

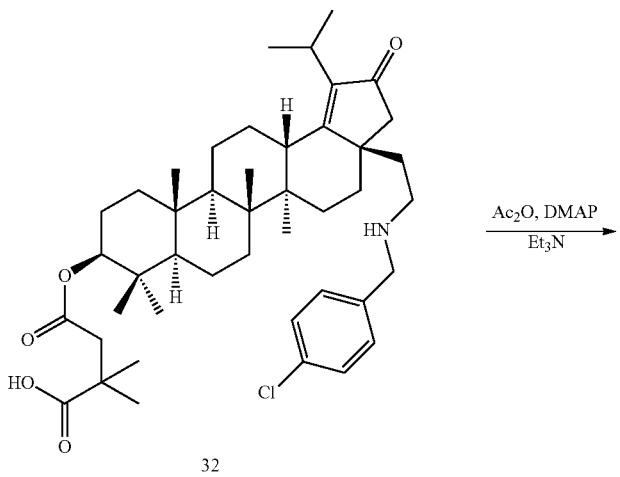

32

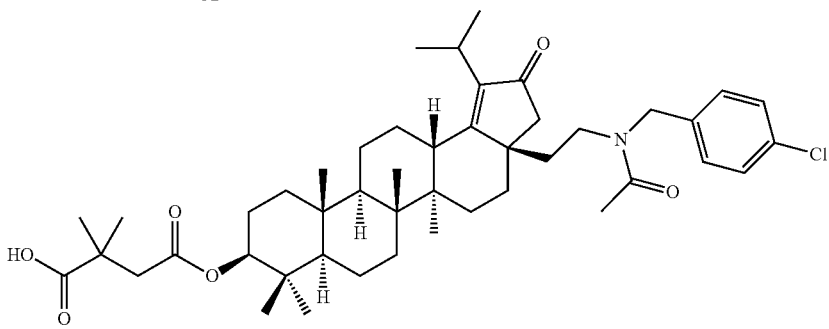

45

Example 13

Compound 45

4-(((3aR,5aR,5bR,7aR,9S,11aR,11bR,13aS)-3a-(2-(N-(4-Chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

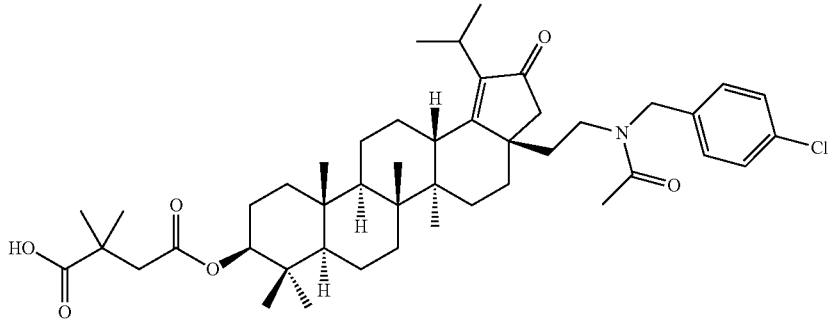

45

A mixture of 32 (150 mg, 0.208 mmol), TEA (210 mg, 2.076 mmol) and DMAP (5 mg, 0.042 mmol) in DCM (5 ml) was stirred for 3 hours. Next, the mixture was quenched with water (50 ml). The organics were then washed with water (2×50 ml), dried over $Na_2SO_4$, and evaporated in vacuo to afford crude product. This was then purified by preparative HPLC to give 45 (65 mg, 0.085 mmol, 41%) as a white solid. Mixture of rotomers. $^1$H NMR (400 MHz, METHANOL-$d_4$) δ=7.49-7.18 (m, 4 H), 4.80-4.42 (m, 3 H), 3.27-2.81 (m, 4 H), 2.76-2.52 (m, 2 H), 2.36-2.10 (m, 4 H), 2.08-0.82 (m, 48 H); LC/MS: m/z calculated 763.5, found 764.3 (M+1)$^+$.

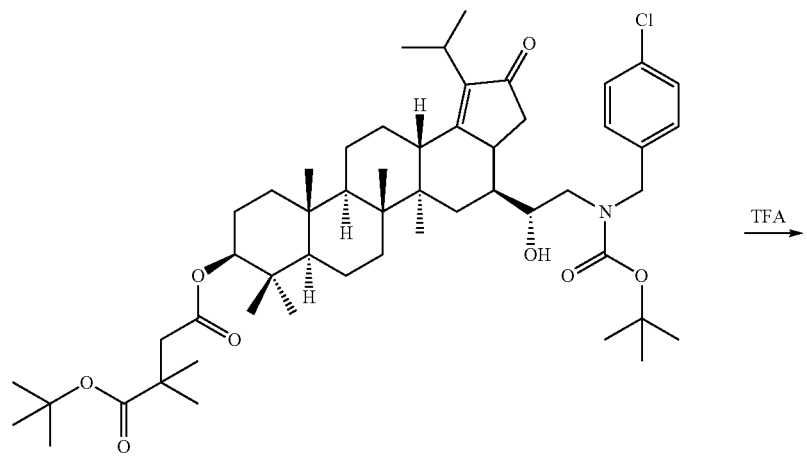

19

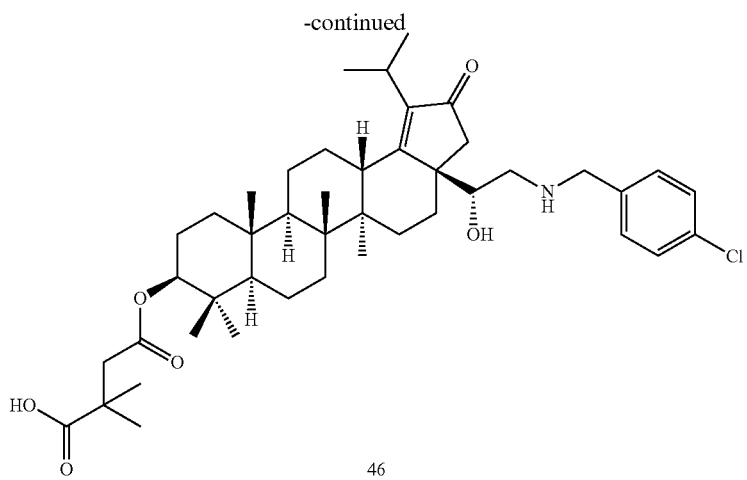

46

Example 14

Compound 46

4-(((3aR,5aR,5bR,7aR,9S,11aR,11bR,13aS)-3a-((R)-2-((4-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

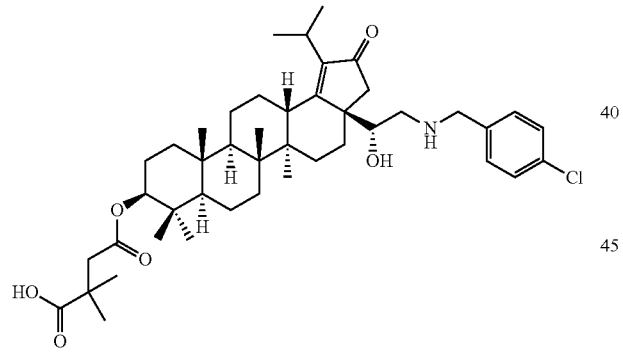

46

To a solution of 4-(((3aR,5aR,5bR,7aR,9S,11aR,11bR,13aS)-3a-((R)-2-((tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (19) (300 mg, 0.335 mmol) in DCM (30 mL) stirred at rt was added TFA (15 mL, 195 mmol). The reaction mixture was stirred at rt until LCMS and TLC indicated SM disappeared. The solvent was removed in vacuo and the residue was purified by preparative HPLC to give 4-(((3aR,5aR,5bR,7aR,9S,11aR,11bR,13aS)-3a-((R)-2-((4-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (46) (100 mg, 0.135 mmol, 40.4% yield) as a TFA salt. $^1$H NMR (400 MHz, CHLOROFORM-d) δ=7.38-7.18 (m, 4 H), 4.54-4.42 (m, 1 H), 4.28-4.14 (m, 1 H), 3.93-3.70 (m, 2 H), 3.19-3.00 (m, 1 H), 2.75-0.69 (m, 52 H); LC/MS: m/z calculated 737.4, found 738.2 (M+1)$^+$.

Example 15

Compound 47

4-(((3aR,5aR,5bR,7aR,9S,11aR,11bR,13aS)-3a-((S)-2-((4-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

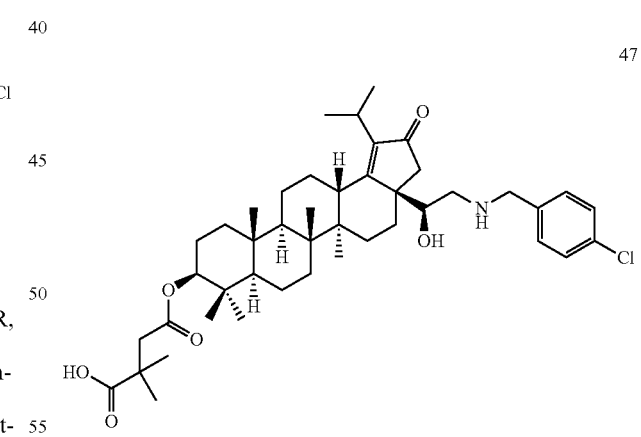

47

To a solution of 4-(((3aR,5aR,5bR,7aR,9S,11aR,11bR,13aS)-3a-((S)-2-((tert-butoxycarbonyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (18) (130 mg, 0.145 mmol) in DCM (30 mL) stirred at rt was added TFA (15 mL, 195 mmol). The reaction mixture was stirred at rt until LCMS and TLC indicated starting material disappeared. The solvent was evaporated and then CH$_3$CN and H$_2$O was added and the material was lyophilized to give 4-(((3aR,5aR,5bR, 7aR,9S,11aR,11bR,13aS)-3a-((S)-2-((4-Chlorobenzyl) amino)-1-hydroxyethyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) oxy)-2,2-dimethyl-4-oxobutanoic acid (47), trifluoroacetic acid salt (120 mg, 0.139 mmol, 96% yield). $^1$H NMR (400 MHz, CHLOROFORM-d) δ=10.30 (br. s., 1 H), 8.08 (br. s., 1 H), 7.38 (s, 4 H), 4.73-4.33 (m, 2 H), 4.28-4.07 (m, 2 H), 3.34-3.06 (m, 2 H), 2.99-2.74 (m, 2 H), 2.73-2.50 (m, 2 H), 2.48-2.29 (m, 1 H), 2.05-0.64 (m, 47 H); LC/MS: m/z calculated 737.4, found 738.3 (M+1)$^+$.
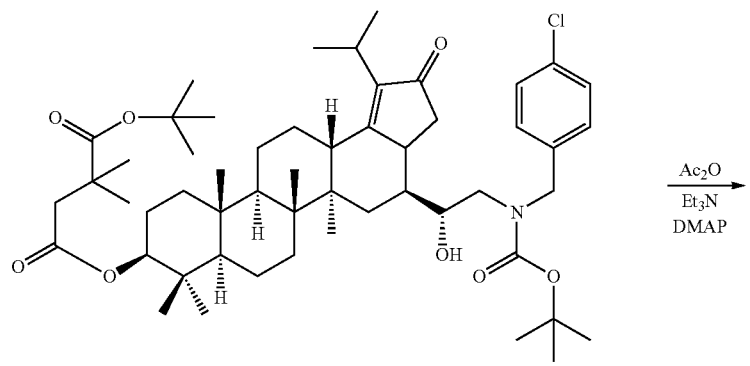
19
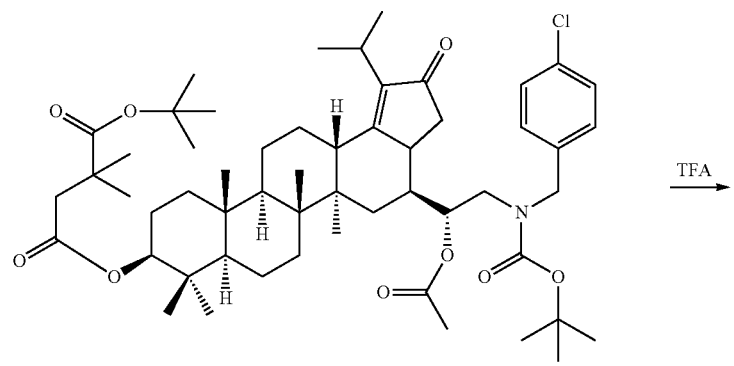
48
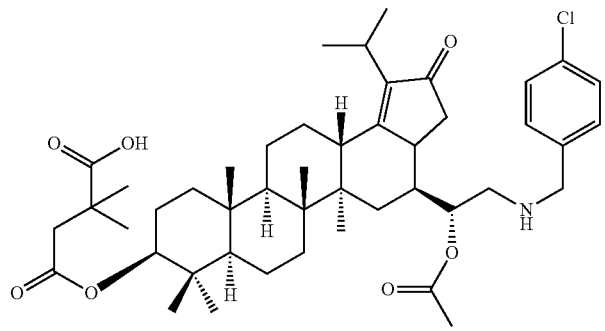
49

Example 16

Compound 49

4-(((3aR,5aR,5bR,7aR,9S,11aR,11bR,13aS)-3a-((R)-1-Acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

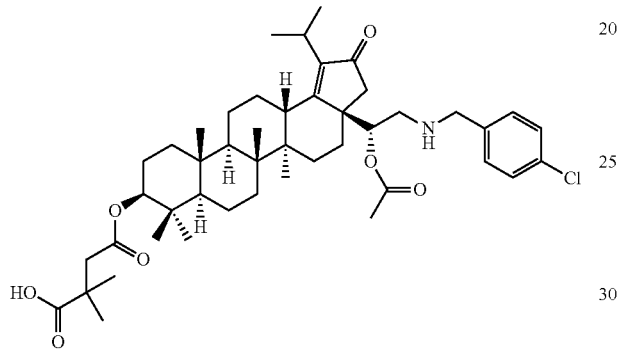

49

Step A: Compound 48

4-((3aR,5aR,5bR,7aR,9S,11aR,11bR,13aS)-3a-((R)-1-acetoxy-2-((tert-butoxycarbonyl)(4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate To a solution of 19 (500 mg, 0.559 mmol) in dichloromethane (30 mL) stirred at rt was added Ac$_2$O (0.158 mL, 1.677 mmol), triethylamine (0.195 mL, 1.397 mmol) and DMAP (6.83 mg, 0.056 mmol). The reaction mixture was stirred at rt until TLC indicated SM disappeared. The mixture was worked up and purified by silica gel chromatography (PE:EA=5:1) to give 48 (510 mg, 0.517 mmol, 93% yield). The product consisted of a mixture of rotomers. $^1$H NMR (400 MHz, CHLOROFORM-d) δ=7.39-7.20 (m, 2 H), 7.21-6.99 (m, 2 H), 5.92-5.56 (m, 1 H), 5.00-3.88 (m, 2 H), 3.40-1.96 (m, 8 H), 1.97-0.58 (m, 67 H).

Step B: Compound 49

4-(((3aR,5aR,5bR,7aR,9S,11aR,11bR,13aS)-3a-((R)-1-Acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 48 (500 mg, 0.534 mmol) in DCM (30 mL) stirred at rt was added TFA (15 mL, 195 mmol). The reaction mixture was stirred at rt until LCMS and TLC indicated SM had disappeared. The solvent was evaporated and CH$_3$CN and H$_2$O were added and mixture was lyophilized to give 49 as a trifluoroacetic acid salt (400 mg, 0.439 mmol, 82% yield). $^1$H NMR (400 MHz, CHLOROFORM-d) δ=7.46-7.19 (m, 4 H), 5.94-5.70 (m, 1 H), 4.58-4.36 (m, 1 H), 4.25-3.88 (m, 2 H), 3.25-3.02 (m, 1 H), 3.01-2.41 (m, 5 H), 2.08 (s, 3 H), 2.00-0.64 (m, 47 H); LC/MS: m/z calculated 779.5, found 780.4 (M+1)$^+$.

Example 17

Compound 50

4-(((3aR,5aR,5bR,7aR,9S,11aR,11bR,13aS)-3a-((S)-1-Acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

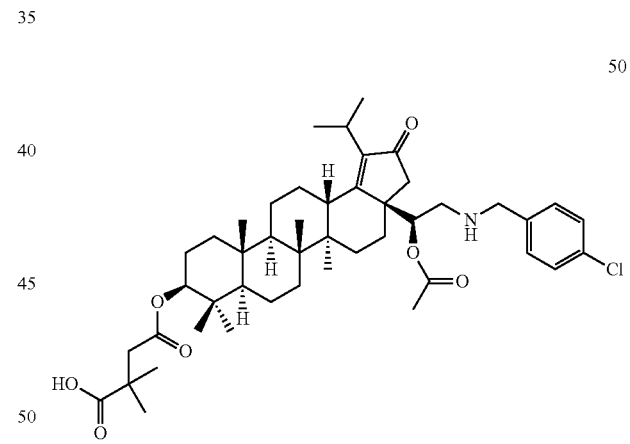

50

The title compound was made in a similar manner to Example 16 and isolated as a TFA salt. $^1$H NMR (400 MHz, CHLOROFORM-d) δ=7.49-7.30 (m, 4 H), 5.85-5.71 (m, 1 H), 4.59-4.40 (m, 1 H), 4.31-4.03 (m, 2 H), 3.41-2.79 (m, 4 H), 2.79-2.50 (m, 2 H), 2.37 (d, J=18.1 Hz, 2 H), 2.02-0.63 (m, 49H); LC/MS: m/z calculated 779.5, found 780.3 (M+1)$^+$.

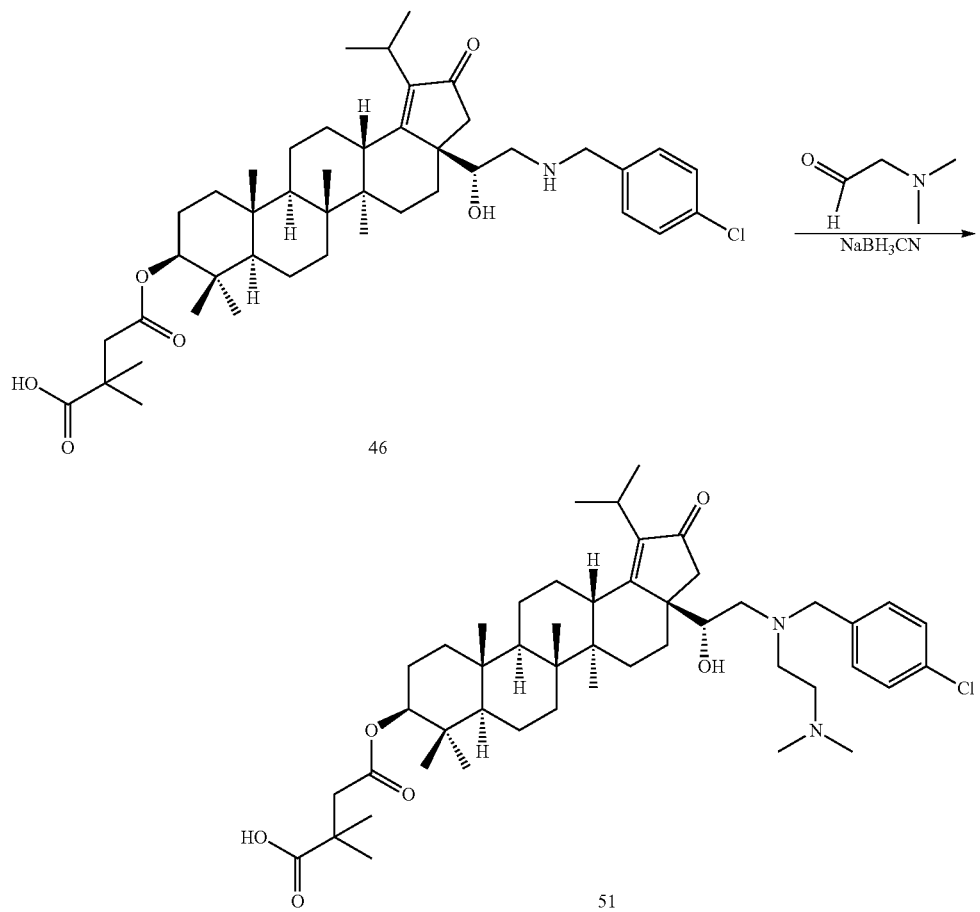

Example 18

Compound 51

4-(((3aR,5aR,5bR,7aR,9S,11aR,11bR,13aS)-3a-((R)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

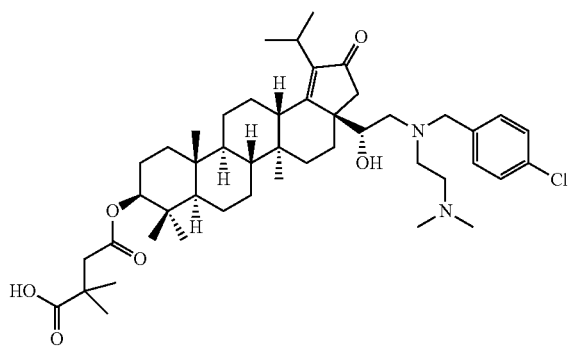

To a solution of 2-(dimethylamino)acetaldehyde, hydrochloride (6.75 g, 54.6 mmol) in methanol (20 mL) was added 4-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, Trifluoroacetic acid salt (46) (9.5 g, 10.92 mmol). The pH was adjusted to 7-8 with $Et_3N$. The reaction mixture was stirred at rt for 2 h. Sodium cyanoborohydride (0.686 g, 10.92 mmol) was then added and the mixture was stirred at rt overnight. After the reaction was complete, water (15 mL) and EtOAc (15 mL) were added, and then the organic phase was removed and concentrated under reduced pressure. The product was extracted with EtOAc (80 mL×3), the combined organic phase was washed with brine, dried, and concentrated. The product was purified by flash chromatography (DCM:EtOAc=2:1 to 1:1, then DCM:MeOH=100:1 to 20:1) to give 4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (51) (6 g, 7.41 mmol, 67.9% yield) as white solid. Multiple batches of this material (were combined 95 g), dissolved in 600 mL of dichloromethane and washed with $NaHCO_3$ (400 mL*3) and the organic phase was dried over $Na_2SO_4$, filtered and concentrated. The solids were washed with a mixture of EtOAc:petroleum ether (600 mL), and filtered followed by lyophilization to provide the final title compound 62 g as a white solid. $^1$H NMR (400 MHz, METHANOL-d$_4$) δ=7.47-7.29 (m, 4 H), 4.48 (dd, J=5.8, 10.3 Hz, 1 H), 4.15-4.04 (m, 1 H), 3.80 (d, J=13.8 Hz, 1 H), 3.57 (d, J=14.1 Hz, 1 H), 3.21-2.82 (m, 5 H), 2.72-2.41 (m, 9 H), 2.37-2.05 (m, 4 H), 2.05-0.74 (m, 45 H); LC/MS: m/z calculated 808.5, found 809.5 (M+1)$^+$.
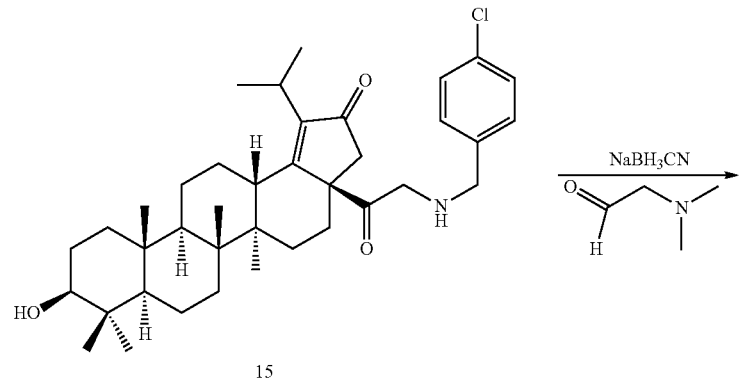
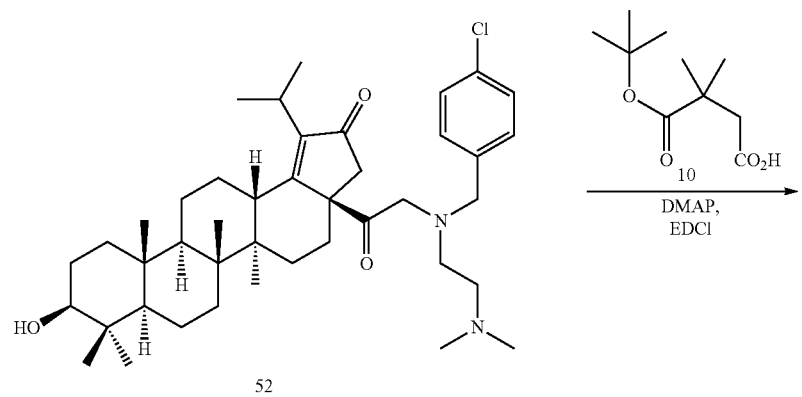
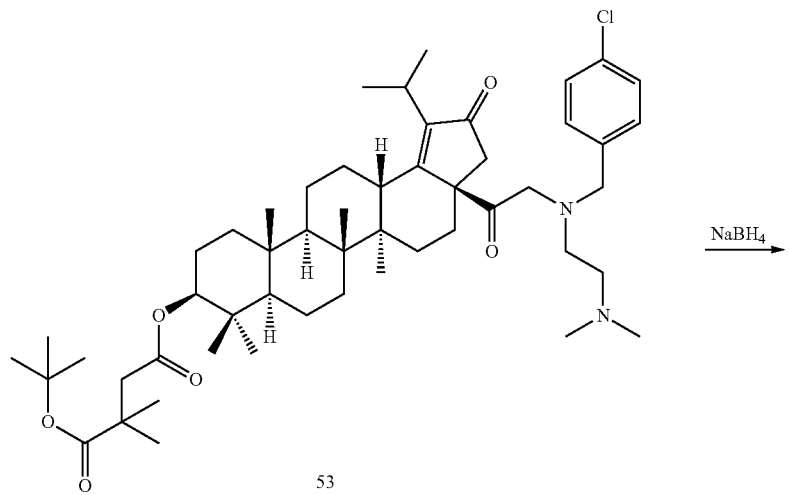

-continued
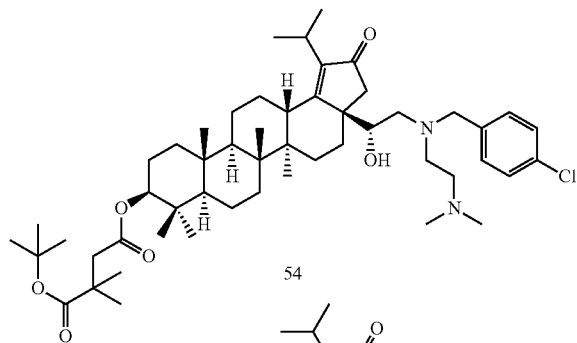
54
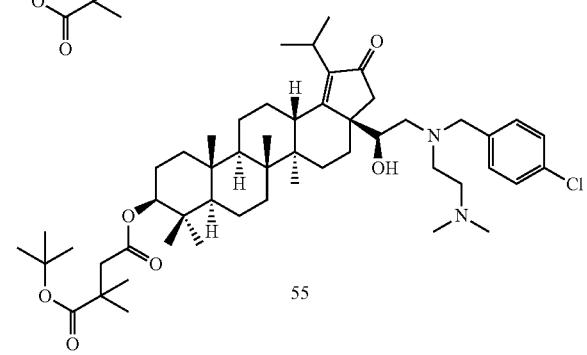
55
54 —TFA→
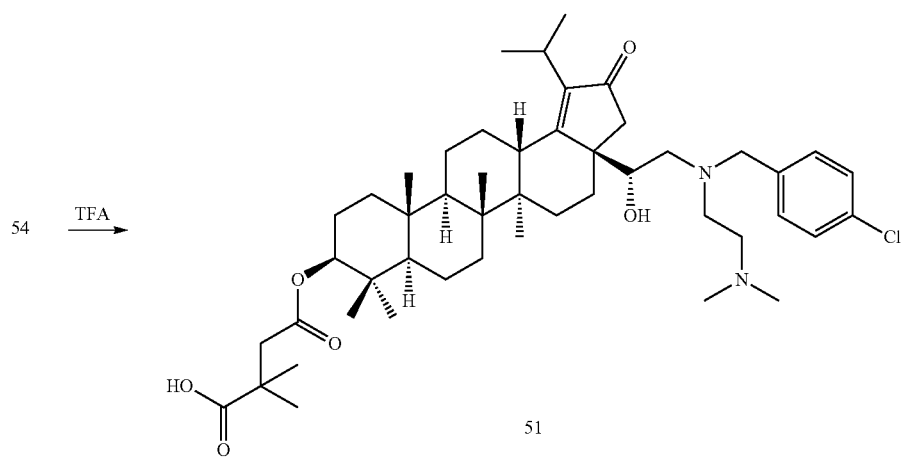
51
55 —TFA→
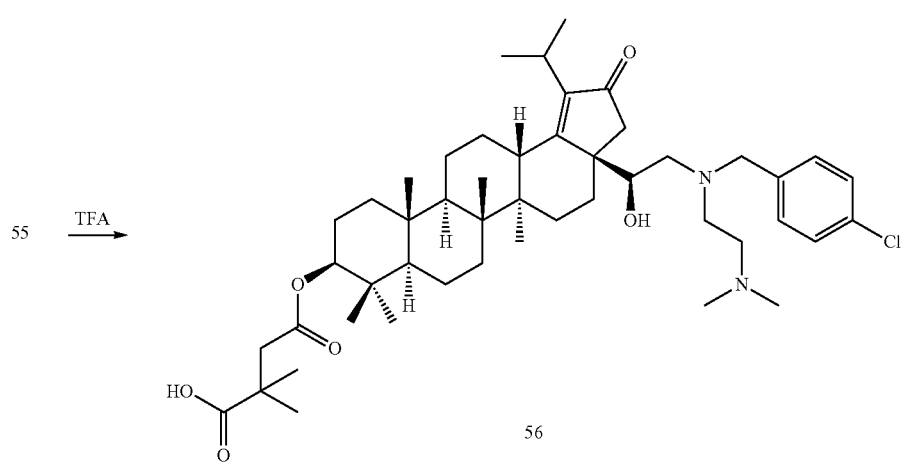
56

Example 19

Compound 56

4-(((3aR,5aR,5bR,7aR,9S,11aR,11bR,13aS)-3a-((S)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

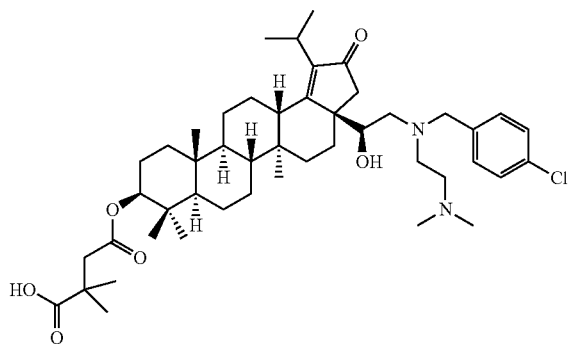

Step A: Compound 52

(3aR,5aR,5bR,7aR,9S,11aR,11bR,13aS)-3a-(2-((4-Chlorobenzyl)(2-(dimethylamino)ethyl)amino)acetyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one To a solution of 2-(dimethylamino)acetaldehyde (4.79 g, 38.8 mmol) in methanol (50 ml) and 1,2-dichloroethane (DCE) (25 ml) was added (3aR,5aR,5bR,7aR,9S,11aR,11bR,13aS)-3a-(2-(4-chlorobenzylamino)acetyl)-9-hydroxy-1-isopropyl-5a,5b,8,8,11a-pentamethyl-3a,4,5,5a,6,7,7a,8,9,10,11,11a,11b,12,13,13a-hexadecahydro-3H-cyclopenta[a]chrysen-2(5bH)-one (15) (5 g, 7.75 mmol) at 0° C. The pH was adjusted to 7 with Et₃N. The reaction mixture was stirred at rt for 1 h. Sodium cyanoborohydride (0.487 g, 7.75 mmol) was added and the mixture was stirred overnight. The reaction was diluted with water (40 ml), and extracted with DCM (60 ml×3). The combined organic layer was washed with brine (20 ml), dried over sodium sulfate and filtered to afford crude product (3aR,5aR,5bR,7aR,9S,11aR,11bR,13aS)-3a-(2-((4-chlorobenzyl)(2-(dimethylamino)ethyl)amino)acetyl)-9-hydroxy-1-isopropyl-5a,5b,8,8,11a-pentamethyl-3a,4,5,5a,6,7,7a,8,9,10,11,11a,11b,12,13,13a-hexadecahydro-3H-cyclopenta[a]chrysen-2(5bH)-one (52) (5 g, 5.89 mmol, 76% yield) as a light yellow solid, which was used in the next step. LC/MS: m/z calculated 678.5, found 679.3 (M+1)⁺.

Step B: Compound 53

1-Tert-butyl 4-((3aR,5aR,5bR,7aR,9S,11aR,11bR,13aS)-3a-(2-((4-chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of 4-(tert-butoxy)-3,3-dimethyl-4-oxobutanoic acid (11.91 g, 58.9 mmol), N,N-dimethylpyridin-4-amine (4.50 g, 36.8 mmol) in DCM (20 mL) was added EDC (11.29 g, 58.9 mmol). The reaction mixture was stirred at rt for 1 h. Then, (3aR,5aR,5bR,7aR,9S,11aR,11bR,13aS)-3a-(2-((4-chlorobenzyl)(2-(dimethylamino)ethyl)amino)acetyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one (52) (5 g, 7.36 mmol) was add. Upon completion, the mixture was washed with 2 M HCl, water and brine. The organic layer was dried over Na₂SO₄, filtered and concentrated to give the crude product. The product was purified by a silica gel column using dichloromethane/methanol (20:1) to afford 1-tert-butyl 4-((3aR,5aR,5bR,7aR,9S,11aR,11bR,13aS)-3a-(2-((4-chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (53) (1.8 g, 1.917 mmol, 26.1% yield) as an oil. ¹H NMR (400 MHz, CHLOROFORM-d) δ=7.27 (s, 4 H), 4.60-4.39 (m, 1 H), 3.82 (d, J=13.8 Hz, 1 H), 3.59 (d, J=13.8 Hz, 1 H), 3.50-3.05 (m, 3 H), 2.82-2.63 (m, 2 H), 2.63-0.53 (m, 67 H).

Step C: Compounds 54 and 55

1-tert-butyl 4-((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (54) and 1-tert-butyl 4-((3aR,5aR,5bR,7aR,9S,11aR,11bR,13aS)-3a-((S)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (55)

To a solution of 1-tert-butyl 4-((3aR,5aR,5bR,7aR,9S,11aR,11bR,13aS)-3a-(2-((4-chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (53) (1.5 g, 1.737 mmol) in methanol (10 mL) was added NaBH₄ (0.131 g, 3.47 mmol). The reaction mixture was stirred at rt for 1 h. The mixture then was extracted with DCM, washed with water and brine. The organic layer was dried over Na₂SO₄, and concentrated to give the crude product. This was purified by preparative-HPLC then purified by SFC to get 54 (230 mg, 15%) and 55 (360 mg 23%). For 54: ¹H NMR (400 MHz, CHLOROFORM-d) δ=7.45-7.18 (m, 4 H), 4.49 (dd, J=5.6, 10.7 Hz, 1 H), 4.04 (d, J=9.8 Hz, 1 H), 3.92-3.47 (m, 3 H), 3.46-0.45 (m, 72 H); LC/MS: m/z calculated 864.6, found 865.4 (M+1)⁺. For 55: ¹H NMR (400 MHz, CHLOROFORM-d)

δ=7.37-7.19 (m, 4 H), 4.50 (dd, J=5.5, 10.5 Hz, 1 H), 4.18-3.98 (m, 1 H), 3.75 (d, J=13.3 Hz, 1 H), 3.55 (d, J=13.3 Hz, 1 H), 3.29-3.10 (m, 1 H), 3.10-2.97 (m, 1 H), 2.81-0.63 (m, 70 H); LC/MS: m/z calculated 864.6, found 865.9 $(M+1)^+$.

Step D: Compound 56

4-(((3aR,5aR,5bR,7aR,9S,11aR,11bR,13aS)-3a-((S)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 55 (360 mg, 0.416 mmol) in DCM (5 mL) stirred at rt was added TFA (2 mL, 26.0 mmol). The reaction mixture was stirred at rt for 1 h. The mixture was evaporated to afford the crude product. This material was purified by preparative-HPLC to provide the title compound 56 as a TFA salt (300 mg, 0.285 mmol, 68.6% yield) as a white solid. $^1$H NMR (400 MHz, METHANOL-$d_4$) δ=7.58-7.34 (m, 4 H), 4.50 (dd, J=5.0, 11.0 Hz, 1 H), 4.23-4.10 (m, 1 H), 4.09-3.74 (m, 2 H), 3.58-3.12 (m, 3 H), 3.12-2.37 (m, 10 H), 2.12-0.67 (m, 50 H); LC/MS: m/z calculated 808.5, found 809.3 $(M+1)^+$.

Example 20

Compound 57

4-(((3aR,5aR,5bR,7aR,9S,11aR,11bR,13aS)-3a-((S)-1-Acetoxy-2-((4-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

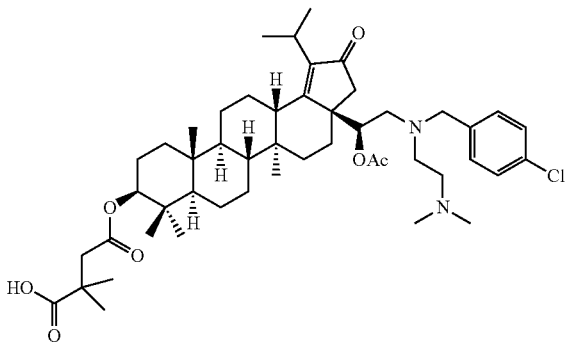

57

To a solution of 2-(dimethylamino)acetaldehyde, hydrochloride (238 mg, 1.922 mmol) in methanol (12 mL) was added 4-(((3aR,5aR,5bR,7aR,9S,11aR,11bR,13aS)-3a-((S)-

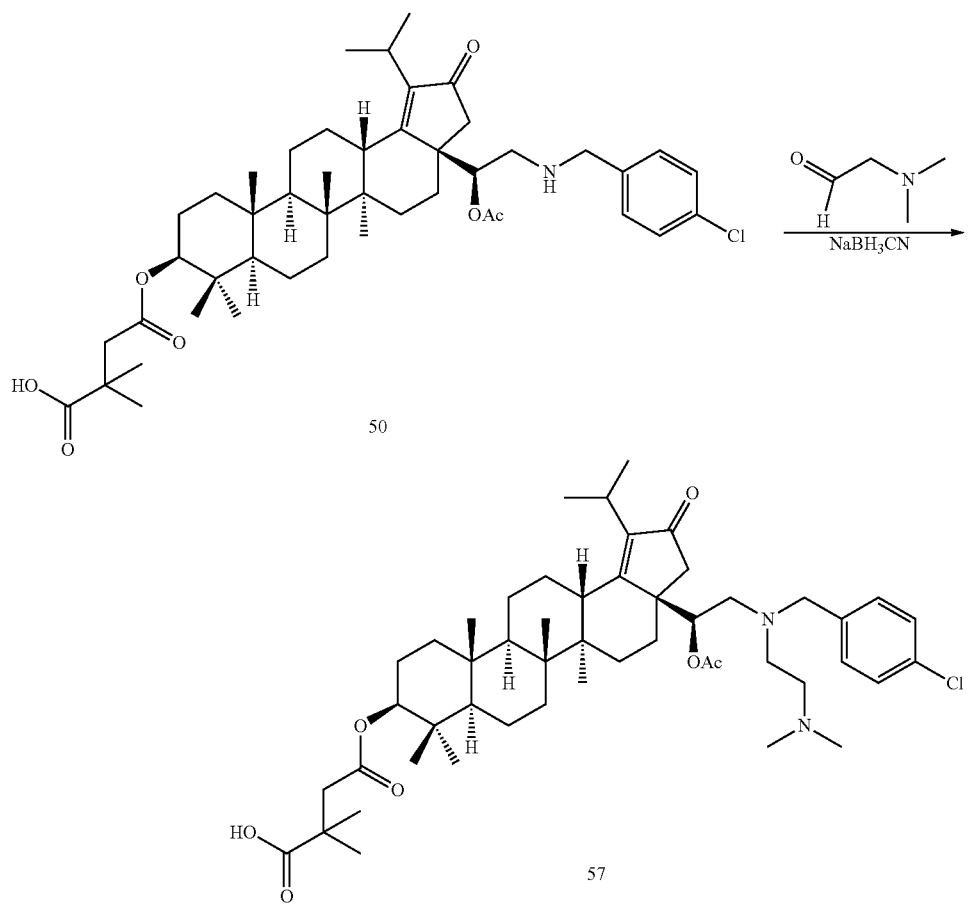

50

57

1-acetoxy-2-((4-chlorobenzyl)amino)ethyl)-1-isopropyl-5a, 5b,8,8,11a-pentamethyl-2-oxo-3,3a,4,5,5a,5b,6,7,7a,8,9,10, 11,11a,11b,12,13,13a-octadecahydro-2H-cyclopenta[a] chrysen-9-yl)oxy)-2,2-dimethyl-4-oxobutanoic acid (50) (150 mg, 0.192 mmol). The reaction mixture was stirred at rt for 2 h then sodium cyanoborohydride (121 mg, 1.922 mmol) was added and the mixture was stirred overnight. Upon completion, the mixture was purified preparative-HPLC to provide the title compound (50 mg, 24%). $^1$H NMR (400 MHz, CHLOROFORM-d) δ=7.35-7.12 (m, 4 H), 5.65 (d, J=9.3 Hz, 1 H), 4.49 (dd, J=5.8, 10.0 Hz, 1 H), 3.83 (d, J=13.6 Hz, 1 H), 3.55 (d, J=13.6 Hz, 1 H), 3.25-2.91 (m, 7 H), 2.91-2.73 (m, 7 H), 2.73-2.52 (m, 3 H), 2.33 (d, J=18.1 Hz, 1 H), 1.99-0.72 (m, 48 H); LC/MS: m/z calculated 850.5, found 851.4 (M+1)$^+$.

Example 21

Compound 58

4-(((3aR,5aR,5bR,7aR,9S,11aR,11bR,13aS)-3a-((R)-1-Acetoxy-2-((4-chlorobenzyl)(2-(dimethylamino) ethyl)amino)ethyl)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a] chrysen-9-yl)oxy)-2,2-dimethyl-4-oxobutanoic acid

58

The title compound was made in a similar manner to example 20. $^1$H NMR (400 MHz, CHLOROFORM-d) δ=7.40-7.10 (m, 4 H), 5.68 (d, J=9.8 Hz, 1 H), 4.55-4.39 (m, 1 H), 3.81 (d, J=13.8 Hz, 1 H), 3.57 (d, J=13.8 Hz, 1 H), 3.29-2.74 (m, 11 H), 2.74-2.27 (m, 6 H), 2.14 (s, 3 H), 2.09-0.68 (m, 46 H); LC/MS: m/z calculated 850.5, found 851.4 (M+1)$^+$.

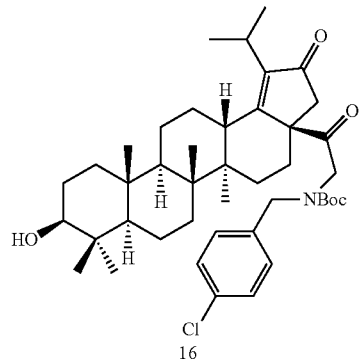

16

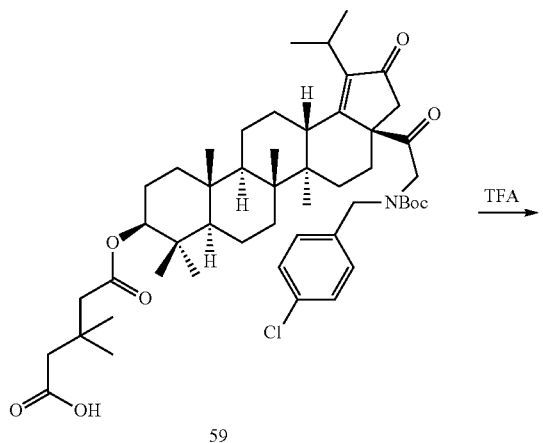

59

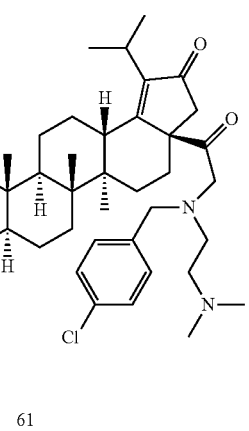

60

61

Example 22 and 23

Compound 62 and 63

5-(((3aR,5aR,5bR,7aR,9S,11aR,11bR,13aS)-3a-((R)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid (62) and 5-(((3aR,5aR,5bR,7aR,9S,11aR,11bR,13aS)-3a-((S)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid (63)

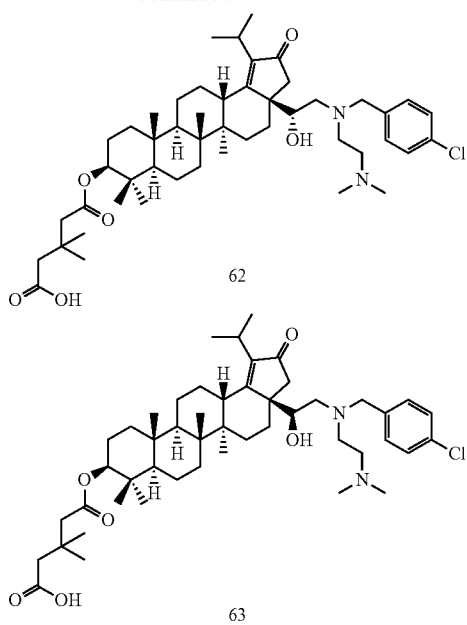

62

63

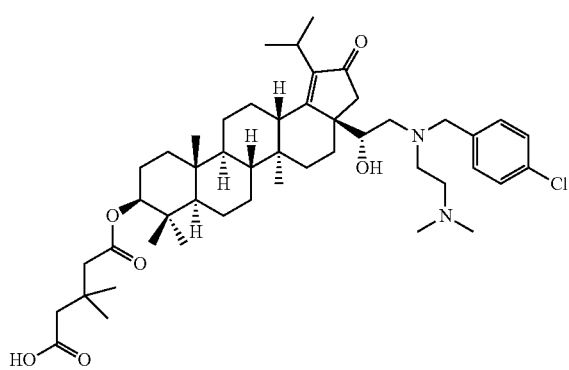

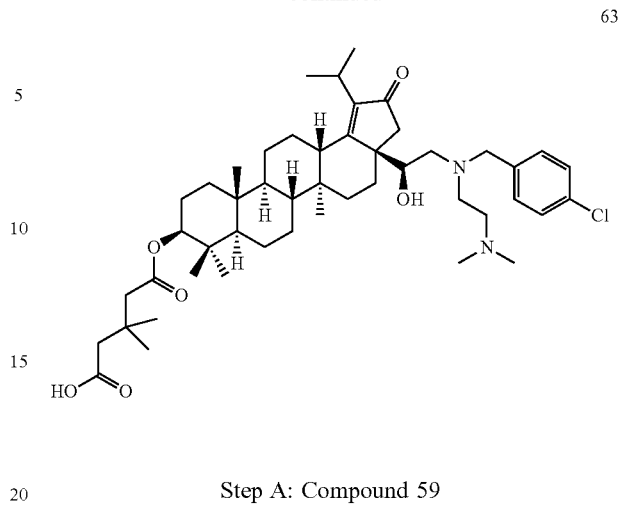

Step A: Compound 59

5-(((3aR,5aR,5bR,7aR,9S,11aR,11bR,13aS)-3a-(2-((Tert-butoxycarbonyl)(4-chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid To a solution of tert-butyl 4-chlorobenzyl(2-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-oxoethyl)carbamate (15) (1 g, 1.412 mmol), DMAP (0.517 g, 4.23 mmol) in pyridine (2 ml) stirred at rt was added 4,4-dimethyl-dihydro-3H-pyran-2,6-dione (1.003 g, 7.06 mmol). The reaction mixture was stirred at 50° C. for 5 h. The mixture was diluted with EtOAc and washed with water. The resultant extract was purified by silica gel column to provide 59 (800 mg, 60%). $^{1}$H NMR (500 MHz, CHLOROFORM-d) δ=8.67 (br. s., 1 H), 7.98-7.36 (m, 1 H), 7.33-7.27 (m, 2 H), 7.21-7.09 (m, 2 H), 4.62-4.26 (m, 3 H), 4.07-3.42 (m, 2 H), 3.30-3.05 (m, 1 H), 2.66-0.66 (m, 61 H).

Step B: Compound 60

5-(((3aR,5aR,5bR,7aR,9S,11aR,11bR,13aS)-3a-(2-((4-Chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid To a solution of 5-(((3aR,5aR,5bR,7aR,9S,11aR,11bR,13aS)-3a-(2-((tert-butoxycarbonyl)(4-chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid (59) (800 mg, 0.941 mmol) in dichloromethane (6 mL) stirred at rt was added trifluoroacetic acid (2 mL, 0.941 mmol). The reaction mixture was stirred at rt for 1 h. The mixture was evaporated to provide the target compound (600 mg, 81%) which was used without further purification. LC/MS: m/z calculated 749.4, found 750.1 (M+1)$^{+}$.

Step C: Compound 61

5-(((3aR,5aR,5bR,7aR,9S,11aR,11bR,13aS)-3a-(2-((4-Chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid To a solution of 5-(((3aR,5aR,5bR,7aR,9S,11aR,11bR,13aS)-3a-(2-((4-chlorobenzyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid, trifluoroacetic acid salt (60) (700 mg, 0.810 mmol) in methanol (30 ml) was added 2-(dimethylamino)acetaldehyde (353 mg, 4.05 mmol) at 00° C. The pH was adjusted to 7 with Et$_3$N. The reaction mixture was stirred at rt for 1 h and sodium cyanoborohydride (50.9 mg, 0.810 mmol) was added and the resultant mixture was stirred overnight. The reaction was diluted with water (40 ml) and extracted with DCM (60 ml×3). The combined organic layer was washed with brine (20 ml), dried over sodium sulfate and filtered to afford crude product 5-(((3aR,5aR,5bR,7aR,9S,11aR,11bR,13aS)-3a-(2-((4-chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid, trifluoroacetic acid salt (61) (200 mg, 23% yield) as a light yellow solid. $^1$H NMR (500 MHz, METHANOL-d$_4$) δ=7.39 (s, 4 H), 4.49 (dd, J=5.7, 10.7 Hz, 1 H), 3.95 (d, J=13.6 Hz, 1 H), 3.57 (d, J=13.2 Hz, 1 H), 3.40-3.29 (m, 1 H), 3.27-3.16 (m, 2 H), 3.05 (s, 6 H), 3.00-2.88 (m, 2 H), 2.57-2.26 (m, 6 H), 2.09 (d, J=19.5 Hz, 1 H), 2.04-0.75 (m, 47 H); LC/MS: m/z calculated 820.5, found 821.3 (M+1)$^+$.

Step D: Compounds 62 and 63

5-(((3aR,5aR,5bR,7aR,9S,11aR,11bR,13aS)-3a-((R)-2-((4-Chlorobenzyl)(isopentyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid (62) and 5-(((3aR,5aR,5bR,7aR,9S,11aR,11bR,13aS)-3a-((S)-2-((4-chlorobenzyl)(isopentyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid (63)

To a solution of 5-(((3aR,5aR,5bR,7aR,9S,11aR,11bR,13aS)-3a-(2-((4-chlorobenzyl)(2-(dimethylamino)ethyl)amino)acetyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid, trifluoroacetic acid salt (61) (140 mg, 0.133 mmol) in methanol (10 mL) stirred at 0° C. was added NaBH$_4$ (10.09 mg, 0.267 mmol). The reaction mixture was stirred at 0° C. for 1 h, then more NaBH$_4$ (10.09 mg, 0.267 mmol) was added. After an additional 1 h at 00° C., the mixture was warmed to rt stirred for another 1 h. LCMS indicated the reaction was complete. EtOAc was added and the mixture was washed with water. The organic phase was evaporated to give the crude which was purified by preparative-HPL to give two diastereomers. 5 mg of isomer A (62) was isolated (3.5% yield) and 10 mg of isomer B (63) was isolated (7%). The stereochemistry of the newly formed stereocenter in each isomer was assigned by spectral similarity to compounds 51 (analogous to 62) and 56 (analogous to 63). For isomer A (62); $^1$H NMR (500 MHz, METHANOL-d$_4$) δ=7.48-7.30 (m, 4 H), 4.57-4.43 (m, 1 H), 4.14 (d, J=10.1 Hz, 1 H), 3.91-3.74 (m, 1 H), 3.67 (d, J=13.9 Hz, 1 H), 3.26-3.10 (m, 2 H), 3.10-2.93 (m, 2 H), 2.93-2.81 (m, 6 H), 2.68-2.10 (m, 9 H), 2.06-0.65 (m, 46 H); LC/MS: m/z calculated 822.5, found 823.5 (M+1)$^+$. For isomer B (63); $^1$H NMR (500 MHz, METHANOL-d$_4$) δ=7.43 (br. s., 4 H), 4.51 (dd, J=5.8, 9.9 Hz, 1 H), 4.16 (d, J=10.1 Hz, 1 H), 3.98-3.75 (m, 2 H), 3.52-3.37 (m, 1 H), 3.31-3.02 (m, 3 H), 3.02-2.71 (m, 9 H), 2.64-2.34 (m, 6 H), 2.19-0.69 (m, 46 H); LC/MS: m/z calculated 822.5, found 823.4 (M+1)$^+$.

Example 24

Compound 64

4-(((3aR,5aR,5bR,7aR,9S,11aR,11bR,13aS)-3a-((S)-2-((2-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

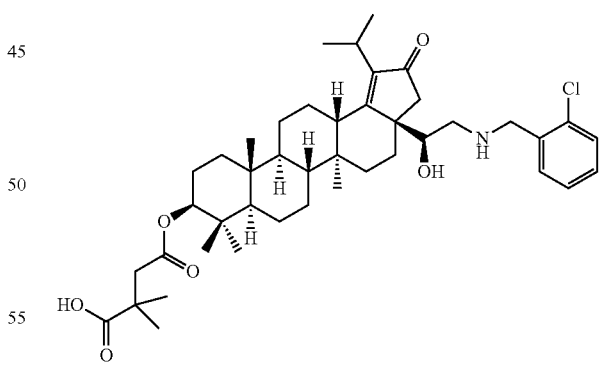

64

The title compound was made in a similar manner to example 14. Stereochemistry was tentatively assigned as drawn but not fully confirmed spectroscopically. $^1$H NMR (400 MHz, METHANOL-d$_4$) δ=7.73-7.38 (m, 4 H), 4.65-4.37 (m, 4 H), 3.44 (d, J=12.3 Hz, 1 H), 3.39-3.22 (m, 1 H), 3.11-2.96 (m, 2 H), 2.62 (q, J=16.0 Hz, 2 H), 2.48 (d, J=18.3 Hz, 1 H), 2.21-0.77 (m, 46 H); LC/MS: m/z calculated 737.4, found 738.3 (M+1)$^+$.

Example 25

Compound 65

4-(((3aR,5aR,5bR,7aR,9S,11aR,11bR,13aS)-3a-((R)-2-((2-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

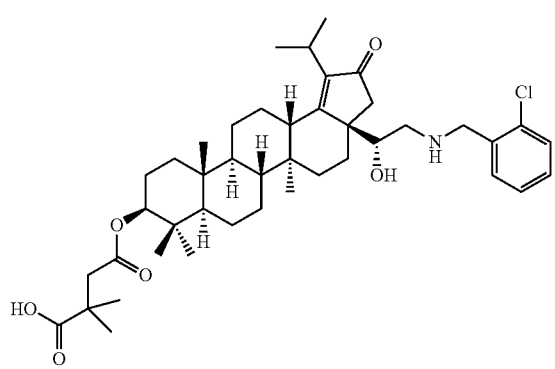

65

The title compound was made in a similar manner to example 14. Stereochemistry was tentatively assigned as drawn but not fully confirmed spectroscopically. $^1$H NMR (400 MHz, METHANOL-$d_4$) δ=7.63-7.37 (m, 4 H), 4.55-4.31 (m, 4 H), 3.26-3.11 (m, 1 H), 3.01-2.46 (m, 6 H), 2.36-2.16 (m, 1 H), 2.15-0.79 (m, 45 H); LC/MS: m/z calculated 737.4, found 738.0 (M+1)$^+$.

Example 26

Compound 66

4-(((3aR,5aR,5bR,7aR,9S,11aR,11bR,13aS)-3a-((S)-1-Acetoxy-2-((4-fluorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

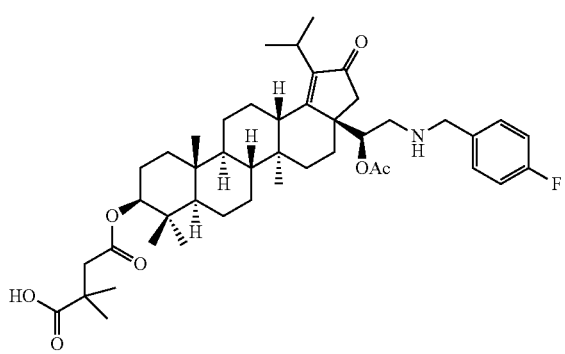

66

The title compound was made as a TFA salt in a similar manner to example 16. Stereochemistry was tentatively assigned as drawn but not fully confirmed spectroscopically. $^1$H NMR (400 MHz, CHLOROFORM-d) δ=10.54-8.79 (m, 1 H), 7.50-7.34 (m, 2 H), 7.19-6.99 (m, 2 H), 5.81 (d, J=9.8 Hz, 1 H), 4.49 (dd, J=5.8, 10.3 Hz, 1 H), 4.31-3.93 (m, 2 H), 3.26 (d, J=12.5 Hz, 1 H), 3.20-3.05 (m, 1 H), 3.05-2.82 (m, 2 H), 2.80-2.47 (m, 2 H), 2.36 (d, J=18.1 Hz, 1 H), 2.05-0.57 (m, 49 H); LC/MS: m/z calculated 763.5, found 764.3 (M+1)$^+$.

Example 27

Compound 67

4-(((3aR,5aR,5bR,7aR,9S,11aR,11bR,13aS)-3a-((R)-1-acetoxy-2-((4-fluorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

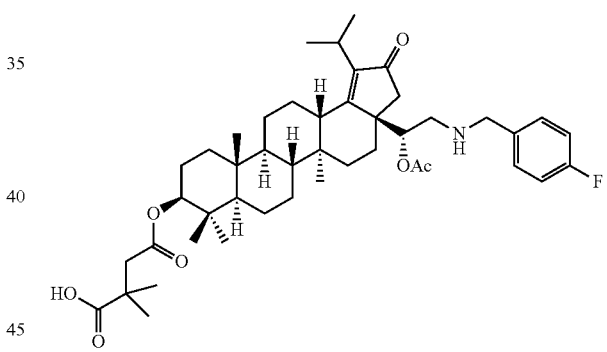

67

The title compound was made as a TFA salt in a similar manner to example 16. Stereochemistry was tentatively assigned as drawn but not fully confirmed spectroscopically. $^1$H NMR (400 MHz, CHLOROFORM-d) δ=9.65 (br. s., 1 H), 7.46-7.28 (m, 2 H), 7.03 (t, J=8.2 Hz, 2 H), 5.86 (br. s., 1 H), 4.50 (dd, J=5.5, 10.3 Hz, 1 H), 4.29-4.06 (m, 1 H), 4.06-3.85 (m, 1 H), 3.19-2.99 (m, 1 H), 2.81-2.39 (m, 6 H), 2.21-0.62 (m, 49 H); LC/MS: m/z calculated 763.5, found 764.3 (M+1)$^+$.

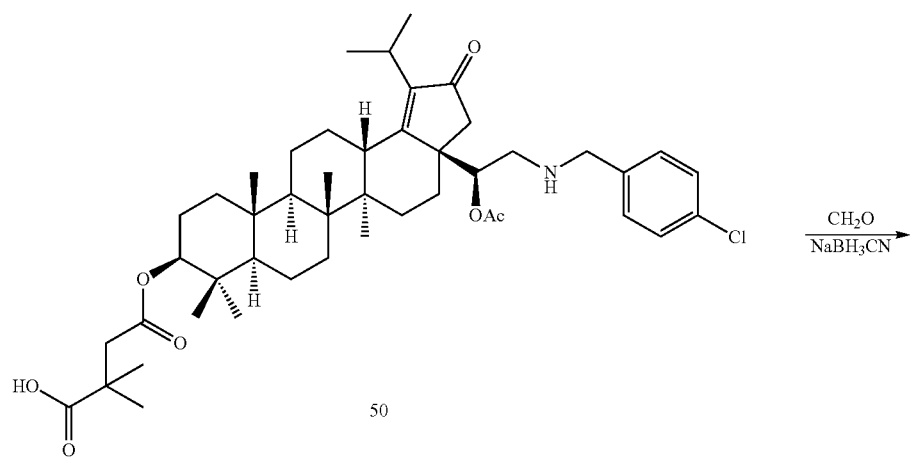
50
$\xrightarrow{\text{CH}_2\text{O}}{\text{NaBH}_3\text{CN}}$
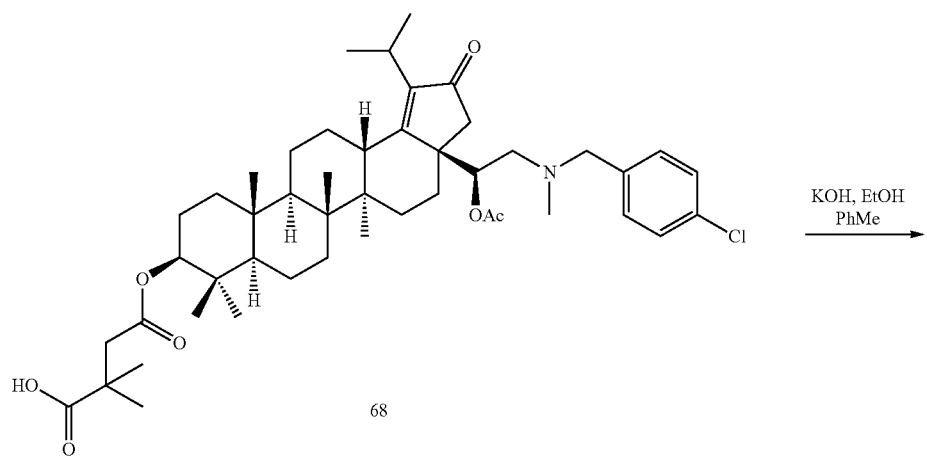
68
$\xrightarrow[\text{PhMe}]{\text{KOH, EtOH}}$
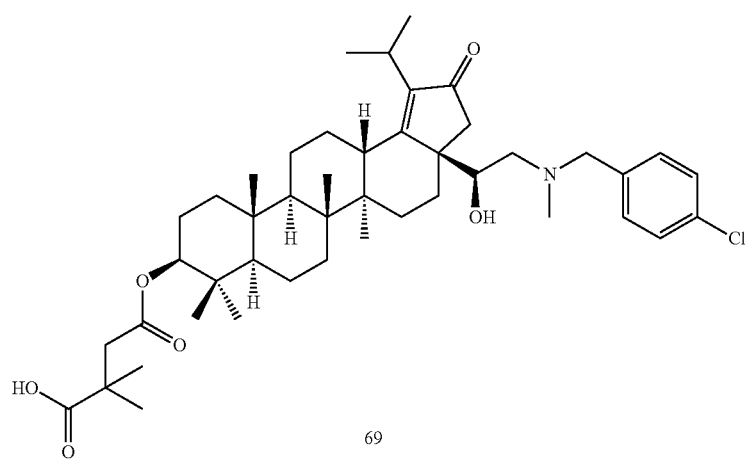
69

Example

Compound 68

4-(((3aR,5aR,5bR,7aR,9S,11aR,11bR,13aS)-3a-((S)-1-acetoxy-2-((4-fluorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

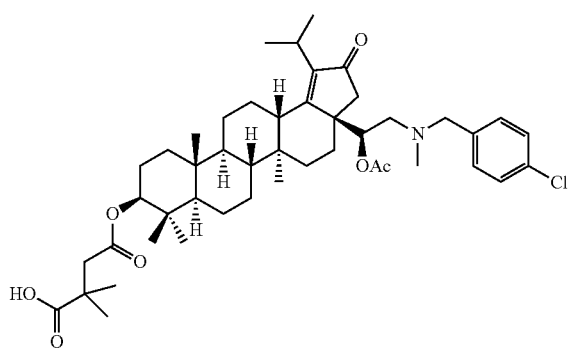

68

Example 29

Compound 69

4-(((3aR,5aR,5bR,7aR,9S,11aR,11bR,13aS)-3a-((S)-2-((4-Chlorobenzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

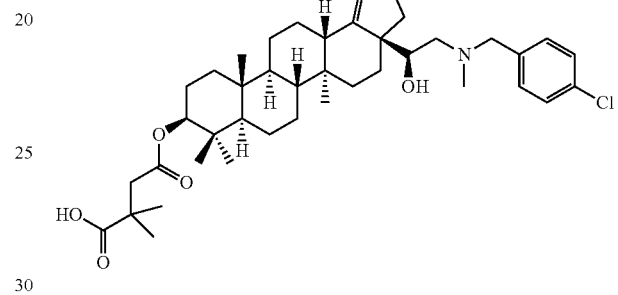

69

To a solution of 4-(((3aR,5aR,5bR,7aR,9S,11aR,11bR,13aS)-3a-((S)-1-acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (50) (150 mg, 0.192 mmol) in MeOH (6 mL) stirred in air at rt was added formaldehyde (31.2 mg, 0.384 mmol). The reaction mixture was stirred at rt for 2 h. Then it was added NaCNBH$_3$ (85 mg, 1.345 mmol) portionwise and stirred for overnight. The solvent was evaporated and the residue diluted with DCM and washed with water and brine. The dried organics were filtered and concentrated to give 4-(((3aR,5aR,5bR,7aR,9S,11aR,11bR,13aS)-3a-((S)-1-acetoxy-2-((4-chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (68) (120 mg, 65% yield) as a white solid. This material was used without further purification. $^1$H NMR (400 MHz, CHLOROFORM-d) δ=7.31-7.26 (m, 2 H), 7.24-7.16 (m, 2 H), 5.65 (d, J=8.5 Hz, 1 H), 4.50 (br. s., 1 H), 3.66-3.51 (m, 1 H), 3.49-3.36 (m, 1 H), 3.27-3.06 (m, 2 H), 2.73-2.32 (m, 5 H), 2.26 (s, 3 H), 2.08-0.73 (m, 49 H); LC/MS: m/z calculated 793.5, found 794.3 (M+1)$^+$.

To a solution of 4-(((3aR,5aR,5bR,7aR,9S,11aR,11bR,13aS)-3a-((S)-1-acetoxy-2-((4-chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (68) (120 mg, 0.151 mmol) in ethanol (2 mL) and toluene (2 mL) was added potassium hydroxide (15.25 mg, 0.272 mmol). The reaction mixture was stirred at rt for 30 min. The reaction mixture was neutralized with aqueous 1N HCl to pH=7 and evaporated to obtain the residue. This was extracted with DCM, washed with water and dried to yield the crude product which was purified by preparative-HPLC to afford 4-(((3aR,5aR,5bR,7aR,9S,11aR,11bR,13aS)-3a-((S)-2-((4-chlorobenzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid as a trifluoroacetate salt (95 mg, 72% yield) as a white solid. $^1$H NMR (400 MHz, METHANOL-d$_4$) δ=7.55 (s, 4 H), 4.60-4.12 (m, 3 H), 3.32-3.19 (m, 1 H), 3.18-2.84 (m, 5 H), 2.71-2.52 (m, 2 H), 2.11-0.78 (m, 49 H); LC/MS: m/z calculated 751.5, found 752.4 (M+1)$^+$.

Example 30

Compound 70

4-(((3aR,5aR,5bR,7aR,9S,11aR,11bR,13aS)-3a-((R)-1-Acetoxy-2-((4-chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 31

Compound 71

4-(((3aR,5aR,5bR,7aR,9S,11aR,11bR,13aS)-3a-((R)-2-((4-Chlorobenzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

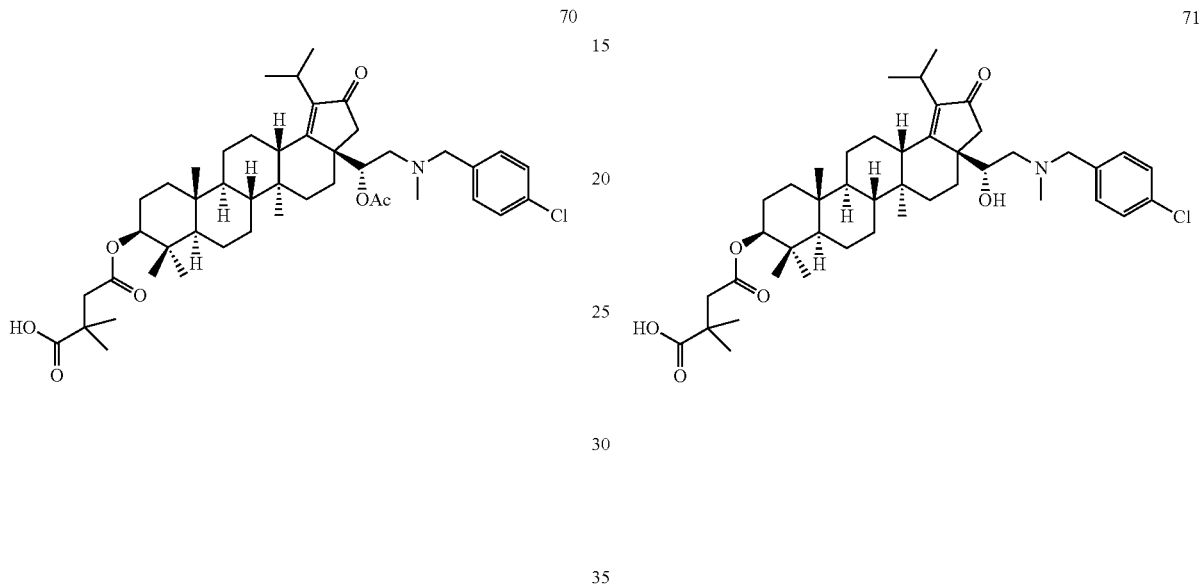

The title compound was made in similar manner to example 28. $^1$H NMR (400 MHz, CHLOROFORM-d) δ=7.31-7.23 (m, 2 H), 7.22-7.13 (m, 2 H), 5.66 (dd, J=2.4, 8.7 Hz, 1 H), 4.55-4.43 (m, 1 H), 3.51-3.35 (m, 2 H), 3.19-3.05 (m, 1 H), 2.74-2.42 (m, 5 H), 2.42-0.66 (m, 53 H); LC/MS: m/z calculated 793.5, found 794.5 (M+1)$^+$.

The title compound was made in similar manner to example 29. $^1$H NMR (500 MHz, METHANOL-d$_4$) δ=7.63-7.38 (m, 4 H), 4.56-4.25 (m, 4 H), 3.25-3.14 (m, 1 H), 2.99 (s, 3 H), 2.82-2.52 (m, 4 H), 2.52-2.32 (m, 2 H), 2.24 (d, J=12.9 Hz, 1 H), 2.09-0.77 (m, 45 H); LC/MS: m/z calculated 751.5, found 752.3 (M+1)$^+$.

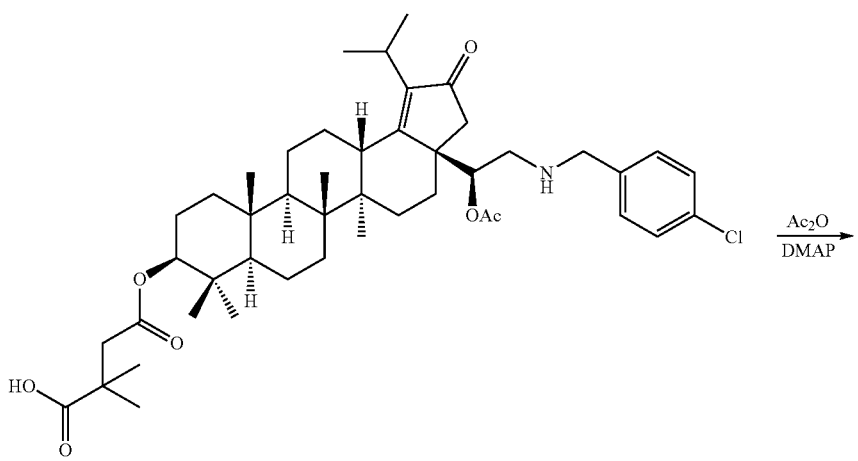

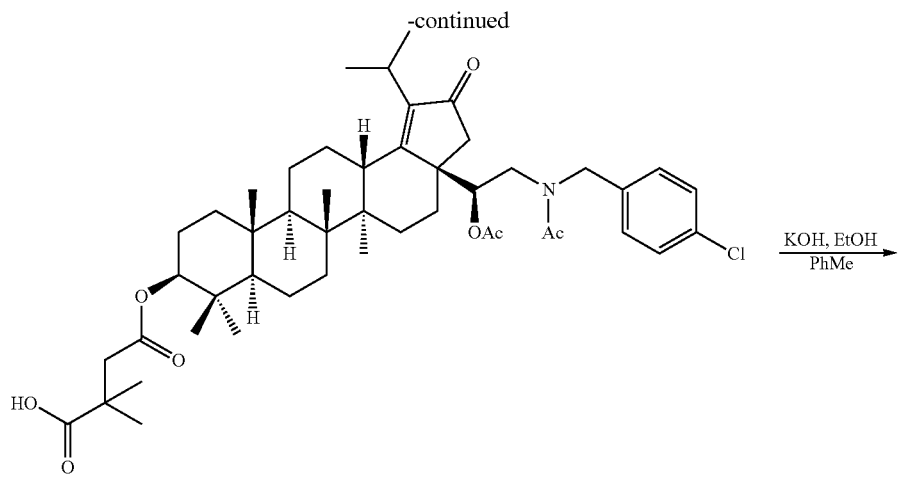

72

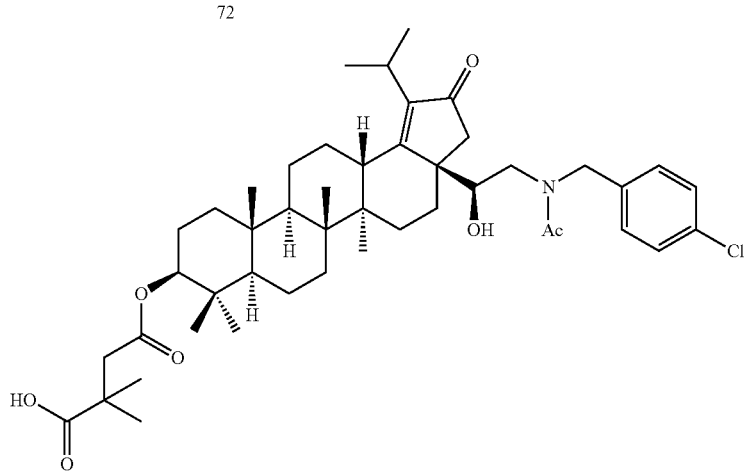

73

Example 32

Compound 72

4-(((3aR,5aR,5bR,7aR,9S,11aR,11bR,13aS)-3a-((S)-1-Acetoxy-2-(N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

72

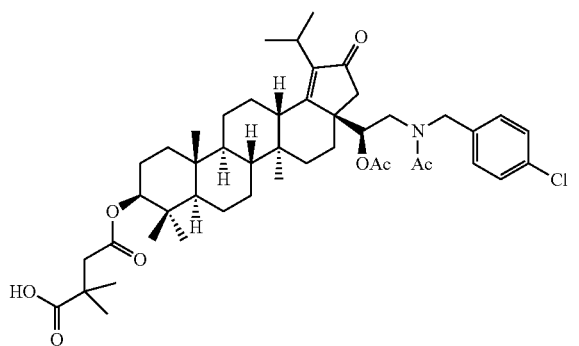

A mixture of 4-(((3aR,5aR,5bR,7aR,9S,11aR,11bR,13aS)-3a-((S)-1-acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (50) (200 mg, 0.256 mmol), TEA (0.332 mL, 2.56 mmol), DMAP (6.3 mg, 0.05 mmol) and in DCM (5 ml) was stirred for 3 h. The mixture was quenched with water (50 ml), washed with water (2×50 ml), dried over Na$_2$SO$_4$, filtered and concentrated in vacuo to afford 4-(((3aR,5aR,5bR,7aR,9S,11aR,11bR,13aS)-3a-((S)-1-acetoxy-2-(N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (72) (160 mg, 0.182 mmol, 71.0% yield) as a white solid. $^1$H NMR (400 MHz, CHLOROFORM-d) δ=7.42-7.24 (m, 2 H), 7.24-6.90 (m, 2 H), 5.98-5.68 (m, 1 H), 5.15-4.56 (m, 1 H), 4.56-4.45 (m, 1 H), 4.40-3.98 (m, 2 H), 2.29-0.68 (m, 66 H), 3.48-0.58 (m, 58 H); LC/MS: m/z calculated 821.5, found 822.3 (M+1)$^+$.

Example 33

Compound 73

4-(((3aR,5aR,5bR,7aR,9S,11aR,11bR,13aS)-3a-((S)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

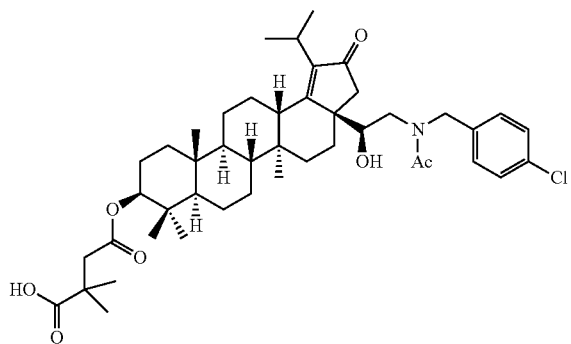

To a solution of 4-(((3aR,5aR,5bR,7aR,9S,11aR,11bR,13aS)-3a-((S)-1-acetoxy-2-(N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (72) (150 mg, 0.182 mmol) in ethanol (2 mL) and toluene (2 mL) was added potassium hydroxide (40.9 mg, 0.729 mmol). The reaction mixture was stirred at rt for 30 min. The reaction mixture was neutralized with aqueous 1N HCl to pH=7 and concentrated to obtain a residue. The residue was extracted with DCM, washed with water and dried to yield the crude product which was purified by preparative-HPLC to afford 4-(((3aR,5aR,5bR,7aR,9S,11aR,11bR,13aS)-3a-((S)-2-(N-(4-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (73) (40 mg, 28%) as a white solid. Compound exists as a mixture of rotomers; $^1$H NMR (400 MHz, DMSO-$d_6$) δ=12.18 (br. s., 1 H), 7.52-7.14 (m, 4 H), 5.03-3.77 (m, 5 H), 3.39-2.80 (m, 3 H), 2.62-2.54 (m, 1 H), 2.27 (t, J=17.2 Hz, 1 H), 2.20-0.58 (m, 51 H); LC/MS: m/z calculated 779.5, found 802.3 (M+Na)$^+$.

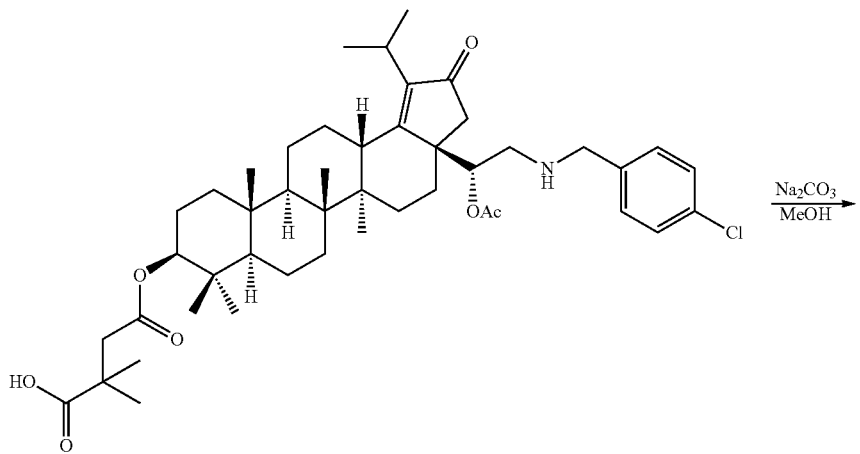

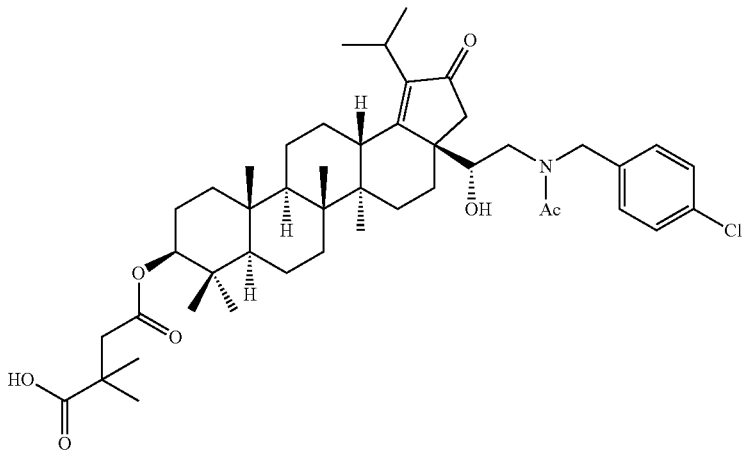

Example 34

Compound 74

4-(((3aR,5aR,5bR,7aR,9S,11aR,11bR,13aS)-3a-((R)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

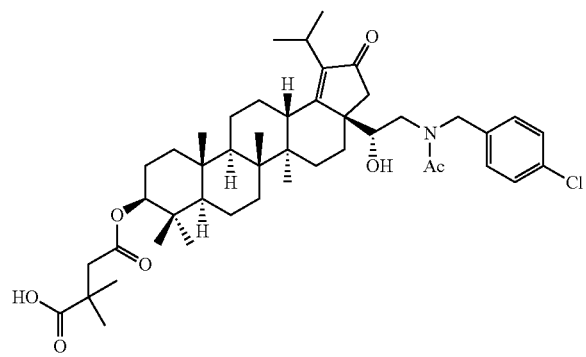

74

A mixture of 4-(((3aR,5aR,5bR,7aR,9S,11aR,11bR,13aS)-3a-((R)-1-acetoxy-2-((4-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (49) (150 mg, 0.192 mmol), Na$_2$CO$_3$ (20.37 mg, 0.192 mmol), in methanol (3 mL) was stirred for 3 h, then purified by preparative-HPLC to afford 4-(((3aR,5aR,5bR,7aR,9S,11aR,11bR,13aS)-3a-((R)-2-(N-(4-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (74) (45 mg, 30%) as a white solid. Compound exists as a mixture of rotamers; $^1$H NMR (500 MHz, METHANOL-d$_4$) δ=7.43-7.27 (m, 2 H), 7.28-7.11 (m, 2 H), 5.30-4.09 (m, 6 H), 3.55-2.09 (m, 11 H), 2.09-0.78 (m, 44 H); LC/MS: m/z calculated 779.5, found 780.4 (M+1)$^+$.

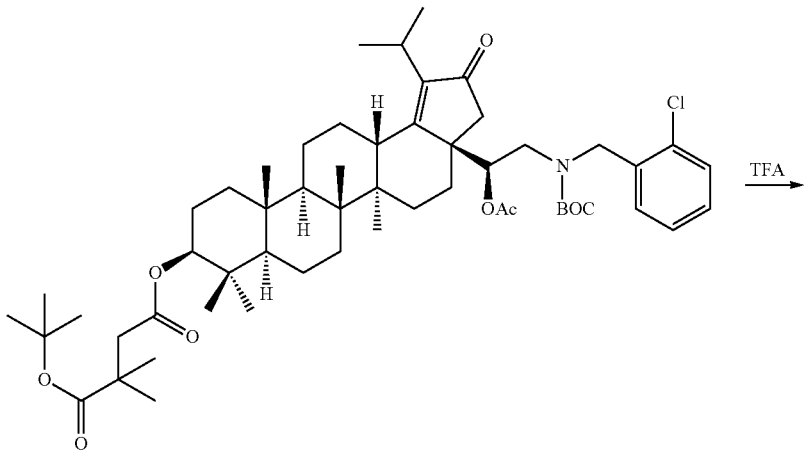

75

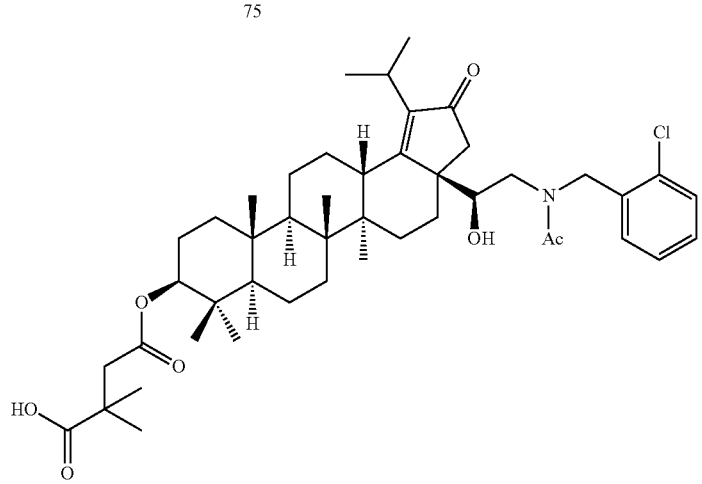

76

Example 35

Compound 76

4-(((3aR,5aR,5bR,7aR,9S,11aR,11bR,13aS)-3a-((S)-2-(N-(2-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

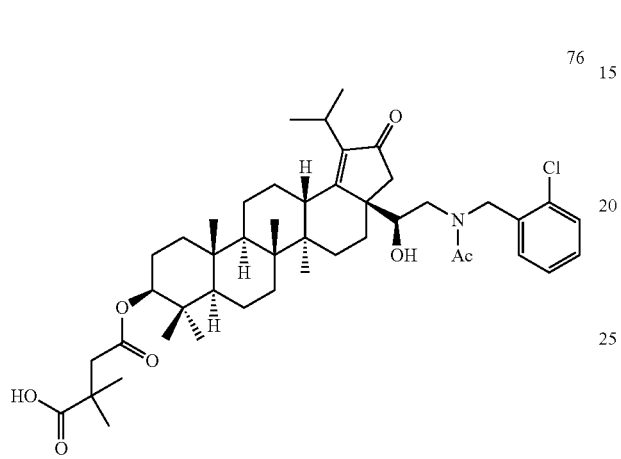

To a solution of 4-(((3aR,5aR,5bR,7aR,9S,11aR,11bR,13aS)-3a-((S)-1-acetoxy-2-((tert-butoxycarbonyl)(2-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (75, made in a similar manner to compound 48) (100 mg, 0.107 mmol) in DCM (30 mL) stirred at rt was added TFA (15 mL, 195 mmol). The reaction mixture was stirred at rt until LCMS and TLC indicated SM disappeared. The solvent was removed to give the crude product purified by preparative HPLC to give 4-(((3aR,5aR,5bR,7aR,9S,11aR,11bR,13aS)-3a-((S)-2-(N-(2-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (40 mg, 48%). Stereochemistry was tentatively assigned as drawn, but not fully confirmed spectroscopically. The compound exists as a mixture of rotomers. $^1$H NMR (400 MHz, METHANOL-$d_4$) δ=7.55-7.14 (m, 4 H), 5.10-4.72 (m, 2 H), 4.72-3.97 (m, 3 H), 3.54-3.39 (m, 1 H), 3.30-3.21 (m, 1 H), 3.13-2.97 (m, 1 H), 2.84-0.69 (m, 53 H); LC/MS: m/z calculated 779.5, found 780.3 (M+1)$^+$.

Example 36

Compound 77

4-(((3aR,5aR,5bR,7aR,9S,11aR,11bR,13aS)-3a-((S)-1-Acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

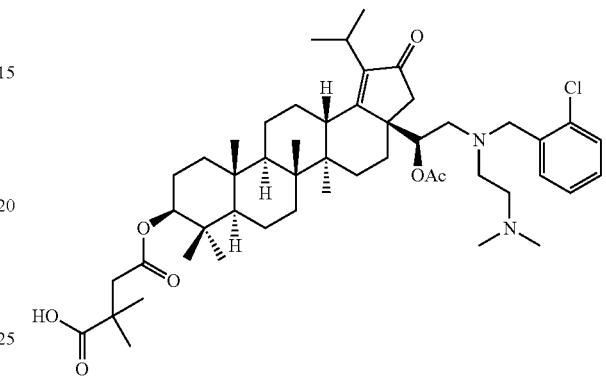

The title compound was made in a similar manner to Example 20. Stereochemistry was tentatively assigned as drawn but not fully confirmed spectroscopically. $^1$H NMR (400 MHz, CHLOROFORM-d) δ=7.64-7.06 (m, 4 H), 5.61 (d, J=8.8 Hz, 1 H), 4.50 (dd, J=5.4, 10.7 Hz, 1 H), 3.82 (d, J=13.8 Hz, 1 H), 3.65 (d, J=13.6 Hz, 1 H), 3.26-2.92 (m, 7 H), 2.89-2.74 (m, 7 H), 2.74-2.53 (m, 3 H), 2.26 (d, J=18.3 Hz, 1 H), 1.93-0.67 (m, 48 H); LC/MS: m/z calculated 850.5, found 851.4 (M+1)$^+$.

Example 37

Compound 78

4-(((3aR,5aR,5bR,7aR,9S,11aR,11bR,13aS)-3a-((S)-2-((3-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

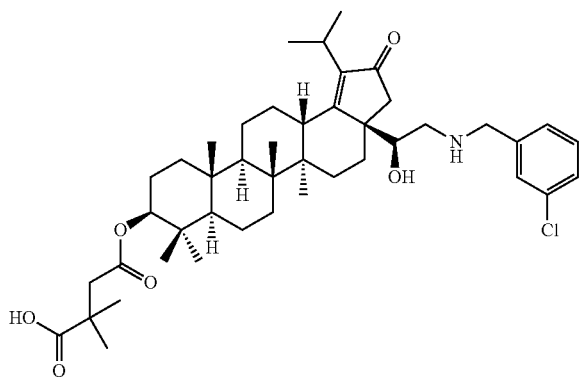

The title compound was made in a similar manner to example 20 as a TFA salt. Stereochemistry was tentatively assigned as drawn but not fully confirmed spectroscopically. $^1$H NMR (400 MHz, METHANOL-d$_4$) δ=7.61 (s, 1 H), 7.56-7.43 (m, 3 H), 4.57-4.44 (m, 2 H), 4.35-4.21 (m, 2 H), 3.38 (dd, J=2.5, 12.5 Hz, 1 H), 3.31-3.23 (m, 1 H), 3.09-3.01 (m, 1 H), 2.96 (t, J=11.8 Hz, 1 H), 2.71-2.51 (m, 1 H), 2.46 (d, J=18.3 Hz, 1 H), 2.15-0.79 (m, 48 H); LC/MS: m/z calculated 737.4, found 738.3 (M+1)$^+$.

Example 38

Compound 79

4-(((3aR,5aR,5bR,7aR,9S,11aR,11bR,13aS)-3a-((R)-2-((3-Chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

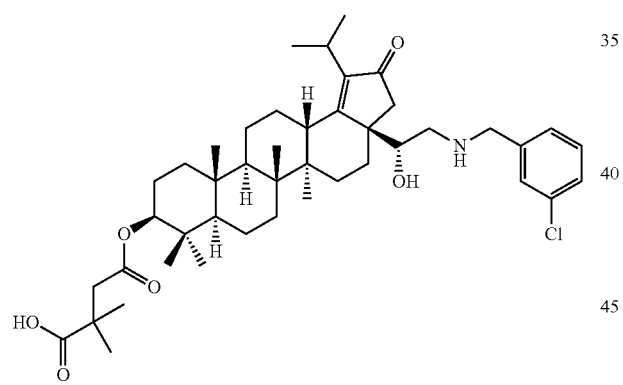

79

The title compound was made in a similar manner to example 20 as a TFA salt. Stereochemistry was tentatively assigned as drawn but not fully confirmed spectroscopically. $^1$H NMR (400 MHz, METHANOL-d$_4$) δ=7.77-7.28 (m, 4 H), 4.68-4.15 (m, 4 H), 3.27-3.11 (m, 1 H), 2.73-2.48 (m, 5 H), 2.38-2.17 (m, 1 H), 2.16-0.71 (m, 4 H); LC/MS: m/z calculated 737.4, found 738.4 (M+1)$^+$.

Example 39

Compound 80

4-(((3aR,5aR,5bR,7aR,9S,11aR,11bR,13aS)-3a-((S)-1-Acetoxy-2-((3-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

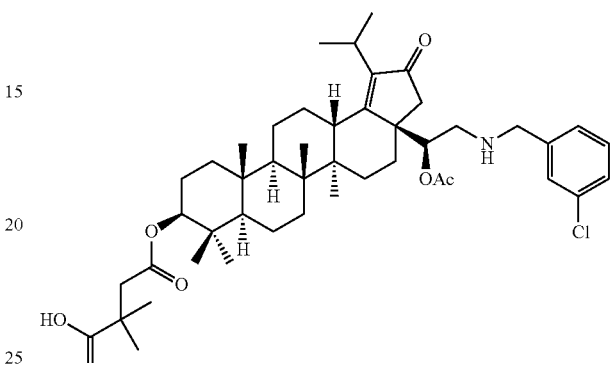

80

The title compound was made in a similar manner to example 16 as a TFA salt. Stereochemistry was tentatively assigned as drawn, but not fully confirmed spectroscopically. $^1$H NMR (500 MHz, CHLOROFORM-d) δ=7.43 (s, 1 H), 7.42-7.32 (m, 3 H), 5.81 (d, J=10.1 Hz, 1 H), 4.49 (dd, J=5.5, 10.2 Hz, 1 H), 4.24 (d, J=13.2 Hz, 1 H), 4.13-3.96 (m, 1 H), 3.34-3.04 (m, 2 H), 3.05-2.82 (m, 2 H), 2.75-2.62 (m, 1 H), 2.62-2.52 (m, 1 H), 2.37 (d, J=18.0 Hz, 1 H), 1.93 (s, 3 H), 1.90-0.65 (m, 47 H); LC/MS: m/z calculated 779.5, found 780.3 (M+1)$^+$.

Example 40

Compound 81

4-(((3aR,5aR,5bR,7aR,9S,11aR,11bR,13aS)-3a-((R)-1-Acetoxy-2-((3-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

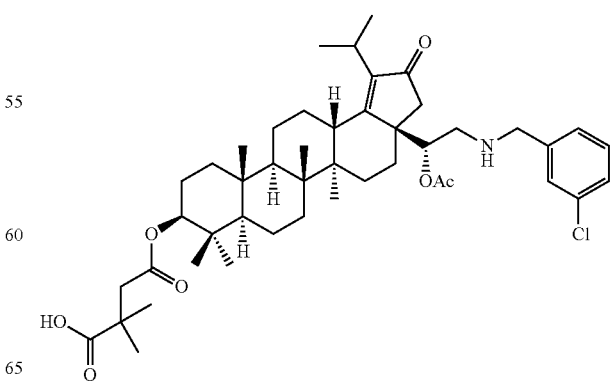

81

The title compound was made in a similar manner to Example 16 as a TFA salt. Stereochemistry was tentatively assigned as drawn but not fully confirmed spectroscopically. $^1$H NMR (500 MHz, CHLOROFORM-d) δ=9.77 (br. s., 1 H), 7.50-7.09 (m, 4 H), 5.87 (br. s., 1 H), 4.57-4.44 (m, 1 H), 4.12 (d, J=1.6 Hz, 1 H), 3.96 (d, J=13.2 Hz, 1 H), 3.23-3.00 (m, 1 H), 2.86-2.37 (m, 5 H), 2.20-0.66 (m, 50 H); LC/MS: m/z calculated 779.5, found 780.2 (M+1)$^+$.

Example 41

Compound 82

4-(((3aR,5aR,5bR,7aR,9S,11aR,11bR,13aS)-3a-((S)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

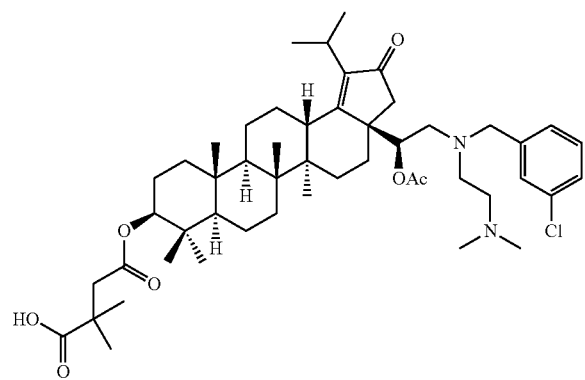

82

The title compound was made in a similar manner to Example 18 as a TFA salt. To a solution of 2-(dimethylamino)acetaldehyde (553 mg, 4.47 mmol) in methanol (10 ml), was added 4-(((3aR,5aR,5bR,7aR,9S,11aR,11bR,13aS)-3a-((S)-1-acetoxy-2-((3-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, trifluoroacetic acid salt (80) (400 mg, 0.447 mmol). The reaction mixture was stirred at 40° C. for 2 h. The reaction was cooled to rt and NaBH$_3$CN (281 mg, 4.47 mmol) was added. The mixture and stirred overnight. Then concentrated in vacuo and purified by preparative-HPLC to afford 4-(((3aR,5aR,5bR,7aR,9S,11aR,11bR,13aS)-3a-((S)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (82) (80 mg, 20%) as a light yellow solid. Stereochemistry was tentatively assigned as drawn but not fully confirmed spectroscopically. LC/MS: m/z calculated 850.5, found 851.5 (M+1)$^+$.

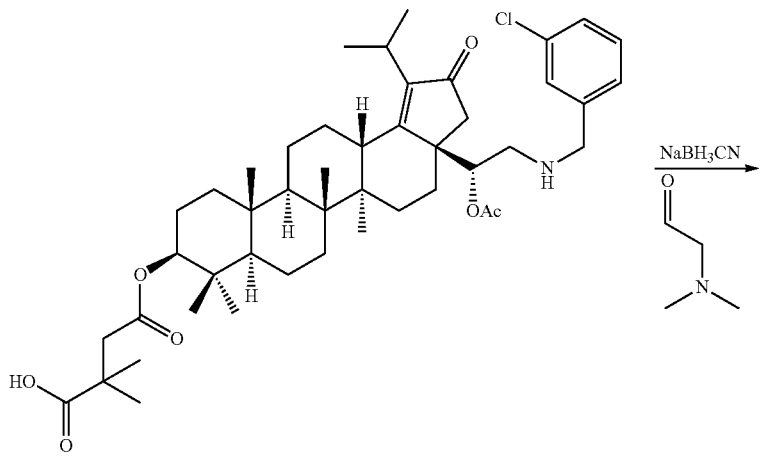

81

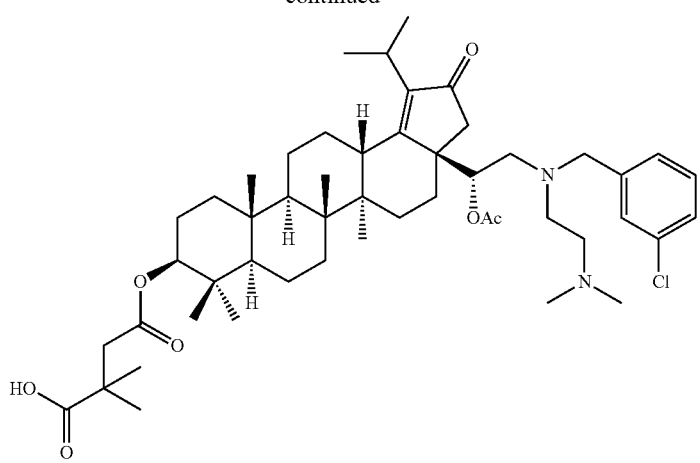
83
+
84

Example 42 and 43

Compound 83 and 84

4-(((3aR,5aR,5bR,7aR,9S,11aR,11bR,13aS)-3a-((R)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (83) and 4-(((3aR,5aR,5bR,7aR,9S,11aR,11bR,13aS)-3a-((R)-2-((3-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (84)

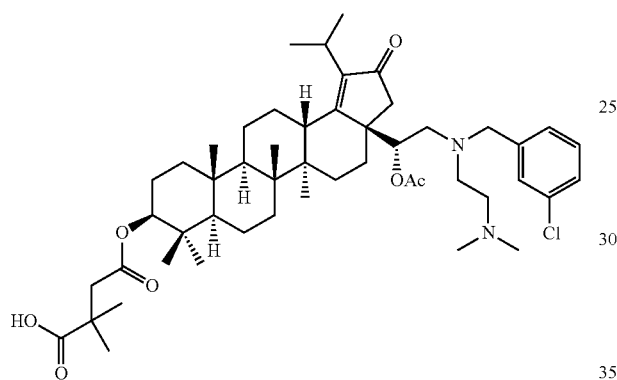

83

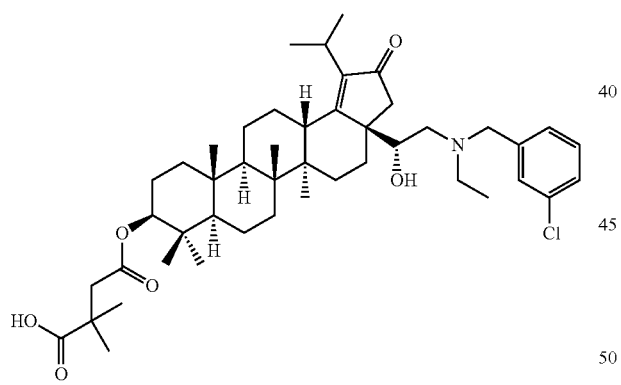

84

To a solution of 2-(dimethylamino)acetaldehyde, hydrochloride (553 mg, 4.47 mmol) in methanol (10 ml) was added (3aR,5aR,5bR,7aR,9S,11aR,11bR,13aS)-3a-(2-(4-chlorobenzylamino)acetyl)-9-hydroxy-1-isopropyl-5a,5b,8,8,11a-pentamethyl-3a,4,5,5a,6,7,7a,8,9,10,11,11a,11b,12,13,13a-hexadecahydro-3H-cyclopenta[a]chrysen-2(5bH)-one (81) (15 g, 24.66 mmol). The reaction mixture was stirred at 40° C. for 2 h. The reaction was cooled to rt and sodium cyanoborohydride (7.75 g, 123 mmol) was added and the resultant mixture was stirred overnight. The reaction was diluted with ammonium chloride solution (40 ml), and extracted with DCM (60 ml×3). The combined organic layer was washed with brine (20 ml), dried over sodium sulfate, filtered and concentrated in vacuo to afford crude product which was purified by preparative-HPLC to give 4-(((3aR,5aR,5bR,7aR,9S,11aR,11bR,13aS)-3a-((R)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (83) (80 mg, 20%) and 4-(((3aR,5aR,5bR,7aR,9S,11aR,11bR,13aS)-3a-((R)-2-((3-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (84) (14 mg, 3%) as their respective TFA salts. Stereochemistry was tentatively assigned as drawn but not fully confirmed spectroscopically. For 83; $^1$H NMR (500 MHz, CHLOROFORM-d) δ=7.25-7.10 (m, 3 H), 7.04 (d, J=3.8 Hz, 1 H), 5.57 (d, J=9.1 Hz, 1 H), 4.42 (dd, J=5.0, 10.7 Hz, 1 H), 3.72 (d, J=13.9 Hz, 1 H), 3.42 (d, J=14.2 Hz, 1 H), 3.16-2.90 (m, 6 H), 2.90-2.79 (m, 1 H), 2.79-2.65 (m, 7 H), 2.65-2.41 (m, 3 H), 2.22 (d, J=18.3 Hz, 1 H), 1.89 (s, 3 H), 1.84-0.62 (m, 45 H); LC/MS: m/z calculated 850.5, found 851.4 (M+1)$^+$. For 84; $^1$H NMR (400 MHz, METHANOL-d$_4$) □=7.65 (s, 1 H), 7.62-7.46 (m, 3 H), 4.58-4.28 (m, 4 H), 3.49-3.38 (m, 1 H), 3.31-3.23 (m, 2 H), 3.13-2.91 (m, 2 H), 2.62 (q, J=15.9 Hz, 2 H), 2.10-0.76 (m, 51 H); LC/MS: m/z calculated 765.5, found 766.5 (M+1)$^+$.

Example 44

Compound 85

4-(((3aR,5aR,5bR,7aR,9S,11aR,11bR,13aS)-3a-((S)-2-((3-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

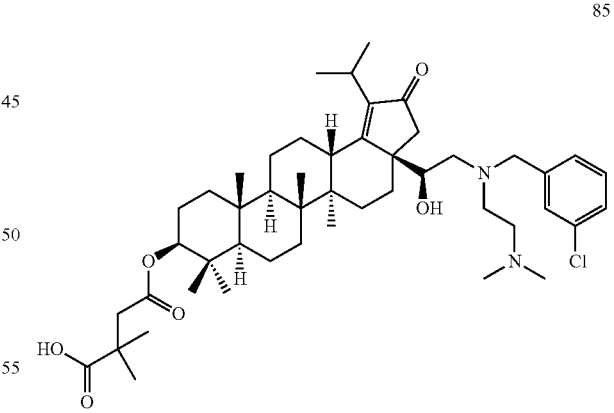

85

The title compound was made in a similar manner to Example 33. Stereochemistry was tentatively assigned as drawn but not fully confirmed spectroscopically. $^1$H NMR (400 MHz, METHANOL-d$_4$) δ=7.57-7.31 (m, 4 H), 4.50 (dd, J=5.0, 11.0 Hz, 1 H), 4.28 (br. s., 1 H), 4.02-3.69 (m, 2 H), 3.53-3.36 (m, 1 H), 3.32-3.07 (m, 4 H), 3.08-2.85 (m, 2 H), 2.78 (s, 6 H), 2.73-2.51 (m, 3 H), 2.45 (d, J=18.3 Hz, 1 H), 2.13-0.75 (m, 46 H); LC/MS: m/z calculated 808.5, found 809.5 (M+1)$^+$.

Example 45

Compound 86

4-(((3aR,5aR,5bR,7aR,9S,11aR,11bR,13aS)-3a-((R)-2-((3-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

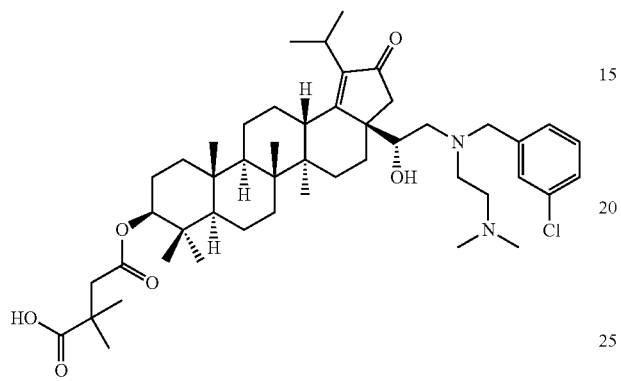

86

The title compound was made in a similar manner to example 33. Stereochemistry was tentatively assigned as drawn but not fully confirmed spectroscopically. $^1$H NMR (400 MHz, METHANOL-d$_4$) δ=7.46-7.23 (m, 4 H), 4.49 (dd, J=5.1, 10.9 Hz, 1 H), 4.19 (d, J=10.0 Hz, 1 H), 3.95-3.78 (m, 1 H), 3.78-3.66 (m, 1 H), 3.41-3.33 (m, 1 H), 3.27-3.00 (m, 3 H), 2.87 (s, 6 H), 2.70-2.50 (m, 3 H), 2.37 (br. s., 1 H), 2.34-2.16 (m, 3 H), 2.08-0.82 (m, 46 H); LC/MS: m/z calculated 808.5, found 809.5 (M+1)$^+$.

Example 46

Compound 87

4-(((3aR,5aR,5bR,7aR,9S,11aR,11bR,13aS)-3a-((R)-2-(N-(3-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

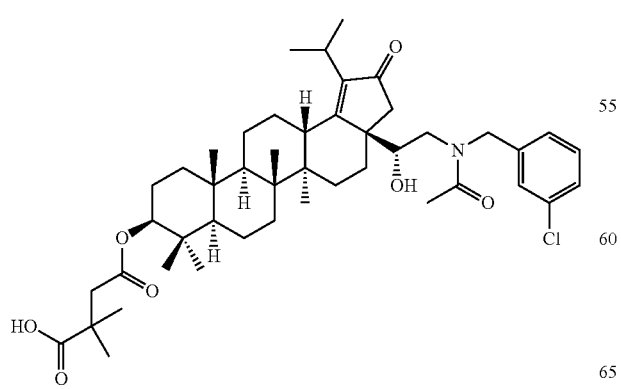

87

The title compound was made in a similar manner to example 33 from compound 81. Stereochemistry was tentatively assigned as drawn but not fully confirmed spectroscopically. The compound exists as a mixture of rotomers. $^1$H NMR (400 MHz, METHANOL-d$_4$) δ=7.42-7.04 (m, 4 H), 5.42-3.97 (m, 3 H), 3.55-3.00 (m, 3 H), 2.82-0.79 (m, 53 H); LC/MS: m/z calculated 779.5, found 780.3 (M+1)$^+$.

Example 47

Compound 88

4-(((3aR,5aR,5bR,7aR,9S,11aR,11bR,13aS)-3a-((S)-2-(N-(3-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

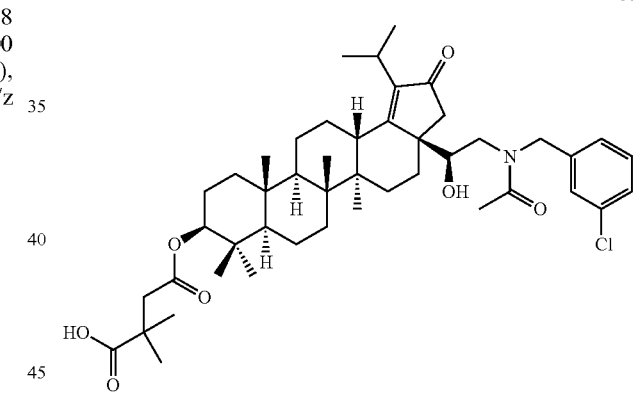

88

The title compound was made in a similar manner to example 33 from compound 80. Stereochemistry was tentatively assigned as drawn but not fully confirmed spectroscopically. $^1$H NMR (400 MHz, METHANOL-d$_4$) δ=7.36-6.99 (m, 4 H), 4.89-3.88 (m, 4 H), 3.39-2.83 (m, 3 H), 2.73-0.66 (m, 53H); LC/MS: m/z calculated 779.5, found 780.3 (M+1)$^+$.

Example 48 and 49

Compounds 89 and 90

4-(((3aR,5aR,5bR,7aR,9S,11aR,11bR,13aS)-3a-((R)-1-acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (89) and 4-(((3aR,5aR,5bR,7aR,9S,11aR,11bR,13aS)-3a-((R)-2-((2-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (90)

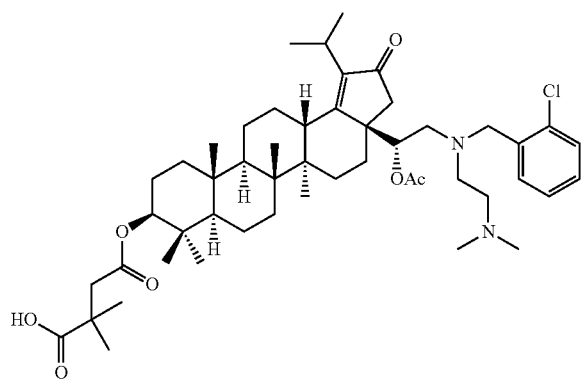

89

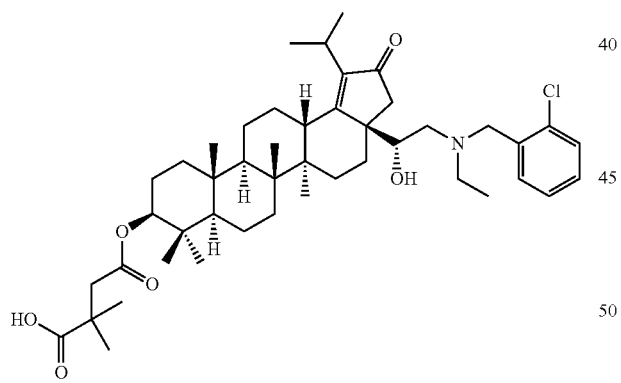

90

The title compounds were made in a similar manner to examples 42 and 43. Stereochemistry was tentatively assigned as drawn but not fully confirmed spectroscopically. For 89; $^1$H NMR (400 MHz, CHLOROFORM-d) δ=7.42-7.18 (m, 4 H), 5.70-5.56 (m, 1 H), 4.57-4.42 (m, 1 H), 3.83-3.51 (m, 2 H), 3.21-2.85 (m, 3 H), 2.79 (s, 6 H), 2.74-2.54 (m, 3 H), 2.54-2.23 (m, 4 H), 2.15-0.65 (m, 50 H); LC/MS: m/z calculated 850.5, found 851.4 (M+1)$^+$. For 90; $^1$H NMR (400 MHz, METHANOL-d$_4$) δ=7.77-7.43 (m, 4 H), 4.69-4.27 (m, 4 H), 3.62-3.37 (m, 2 H), 3.26-3.10 (m, 1 H), 2.97-2.82 (m, 1 H), 2.61 (q, J=16.0 Hz, 2 H), 2.27-2.10 (m, 1 H), 2.10-0.77 (m, 51 H); LC/MS: m/z calculated 765.5, found 766.3 (M+1)$^+$.

Example 50

Compound 91

4-(((3aR,5aR,5bR,7aR,9S,11aR,11bR,13aS)-3a-((R)-2-((2-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

91

The title compound was made in a similar manner to Example 33. Stereochemistry was tentatively assigned as drawn but not fully confirmed spectroscopically. $^1$H NMR (400 MHz, METHANOL-d$_4$) δ=7.55-7.42 (m, 2 H), 7.42-7.32 (m, 2 H), 4.49 (dd, J=5.5, 11.0 Hz, 1 H), 4.43-4.30 (m, 1 H), 4.00-3.89 (m, 1 H), 3.87-3.76 (m, 1 H), 3.42-3.34 (m, 1 H), 3.24-2.91 (m, 3 H), 2.91-2.51 (m, 10 H), 2.52-2.17 (m, 4 H), 2.11-1.84 (m, 2 H), 1.84-0.78 (m, 44 H); LC/MS: m/z calculated 808.5, found 809.4 (M+1)$^+$.

Example 51

Compound 92

4-(((3aR,5aR,5bR,7aR,9S,11aR,11bR,13aS)-3a-((S)-2-((2-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

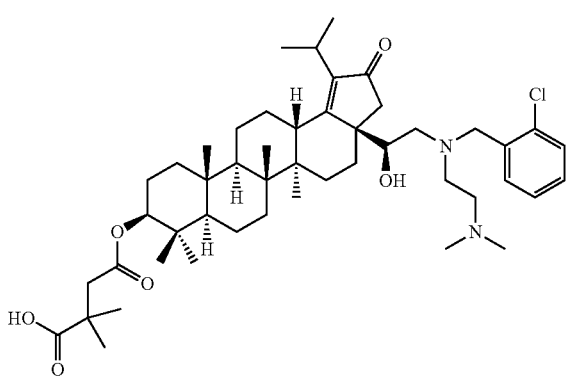

92

The title compound was made in a similar manner to Example 33. Stereochemistry was tentatively assigned as drawn but not fully confirmed spectroscopically. $^1$H NMR (400 MHz, METHANOL-$d_4$) δ=7.57-7.45 (m, 2 H), 7.39 (dd, J=3.6, 5.6 Hz, 2 H), 4.56-4.40 (m, 2 H), 4.02 (d, J=12.8 Hz, 1 H), 3.81 (d, J=12.8 Hz, 1 H), 3.46-3.23 (m, 2 H), 3.13-2.89 (m, 4 H), 2.81-2.41 (m, 10 H), 2.15-1.91 (m, 3 H), 1.89-0.82 (m, 44 H); LC/MS: m/z calculated 808.5, found 809.5 (M+1)$^+$.

Example 52

Compound 93

4-(((3aR,5aR,5bR,7aR,9S,11aR,11bR,13aS)-3a-((R)-1-Acetoxy-2-(benzylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

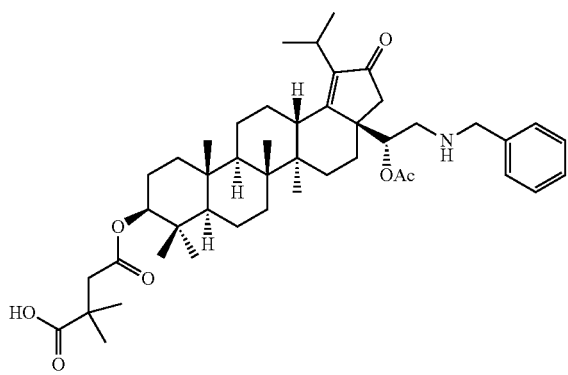

93

The title compound was made as a TFA salt in a similar manner to Example 16. Stereochemistry was tentatively assigned as drawn but not fully confirmed spectroscopically. $^1$H NMR (500 MHz, DMSO-$d_6$) δ=12.17 (br. s., 1 H), 9.49 (br. s., 1 H), 9.19 (br. s., 1 H), 7.66-7.28 (m, 5 H), 5.86-5.53 (m, 1 H), 4.49-3.97 (m, 3 H), 3.16-2.84 (m, 2 H), 2.68-2.55 (m, 1 H), 2.55-2.47 (m, 2 H), 2.41 (d, J=19.5 Hz, 1 H), 2.11 (s, 3 H), 2.04-0.67 (m, 47 H); LC/MS: m/z calculated 745.5, found 746.5 (M+1)$^+$.

Example 53

Compound 94

4-(((3aR,5aR,5bR,7aR,9S,11aR,11bR,13aS)-3a-((S)-1-Acetoxy-2-(benzylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

94

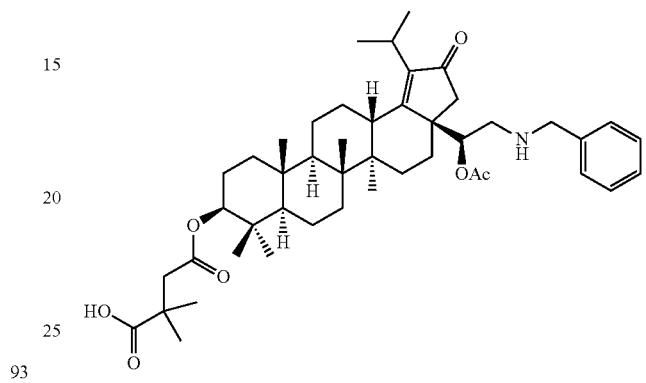

The title compound was made as a TFA salt in a similar manner to Example 16. Stereochemistry was tentatively assigned as drawn but not fully confirmed spectroscopically. $^1$H NMR (500 MHz, CHLOROFORM-d) δ=7.41 (br. s., 5 H), 5.81 (d, J=10.1 Hz, 1 H), 4.48 (dd, J=5.5, 10.2 Hz, 1 H), 4.25 (d, J=13.2 Hz, 1 H), 4.06 (d, J=13.2 Hz, 1 H), 3.27 (d, J=12.3 Hz, 1 H), 3.14 (dt, J=6.8, 13.6 Hz, 1 H), 3.08-2.85 (m, 2 H), 2.74-2.62 (m, 1 H), 2.62-2.54 (m, 1 H), 2.36 (d, J=18.0 Hz, 1H), 1.99-0.63 (m, 49 H); LC/MS: m/z calculated 745.5, found 746.5 (M+1)$^+$.

Example 54

Compound 95

4-(((3aR,5aR,5bR,7aR,9S,11aR,11bR,13aS)-3a-((R)-2-((3-Chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

95

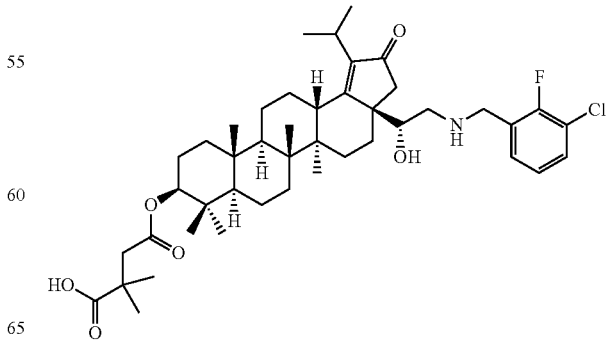

The title compound was made as a TFA salt in a similar manner to Example 14. Stereochemistry was tentatively assigned as drawn but not fully confirmed spectroscopically. LC/MS: m/z calculated 755.4, found 756.3 (M+1)+.

Example 55

Compound 96

4-(((3aR,5aR,5bR,7aR,9S,11aR,11bR,13aS)-3a-((S)-2-((3-chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

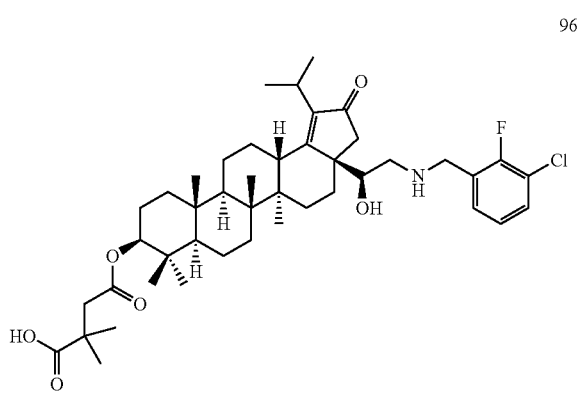

96

The title compound was made as a TFA salt in a similar manner to Example 14. Stereochemistry was tentatively assigned as drawn but not fully confirmed spectroscopically. LC/MS: m/z calculated 755.4, found 756.2 (M+1)+.

Example 56

Compound 97

4-(((3aR,5aR,5bR,7aR,9S,11aR,11bR,13aS)-3a-((R)-2-((3-Chloro-2-fluorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

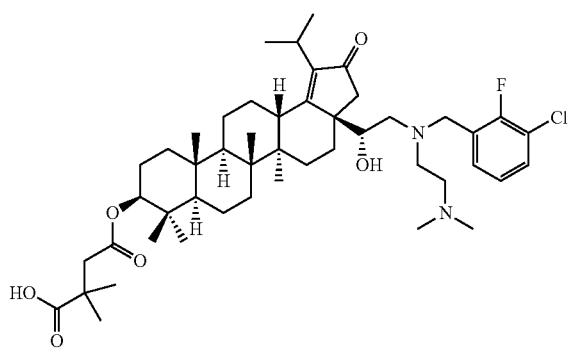

97

The title compound was made as a TFA salt in a similar manner to Example 18. Stereochemistry was tentatively assigned as drawn but not fully confirmed spectroscopically. ¹H NMR (500 MHz, CHLOROFORM-d) δ=7.49-7.35 (m, 2 H), 7.15 (t, J=7.7 Hz, 1 H), 4.46 (dd, J=6.1, 9.9 Hz, 1 H), 4.22 (d, J=10.4 Hz, 1 H), 4.05 (d, J=13.9 Hz, 1 H), 3.90 (d, J=13.6 Hz, 1 H), 3.48 (br. s., 1 H), 3.32-3.02 (m, 4 H), 2.85 (br. s., 6 H), 2.74-2.40 (m, 4 H), 2.40-2.15 (m, 3 H), 1.99-0.58 (m, 43 H); LC/MS: m/z calculated 826.5, found 827.3 (M+1)+.

Example 57

Compound 98

4-(((3aR,5aR,5bR,7aR,9S,11aR,11bR,13aS)-3a-((S)-2-((3-Chloro-2-fluorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

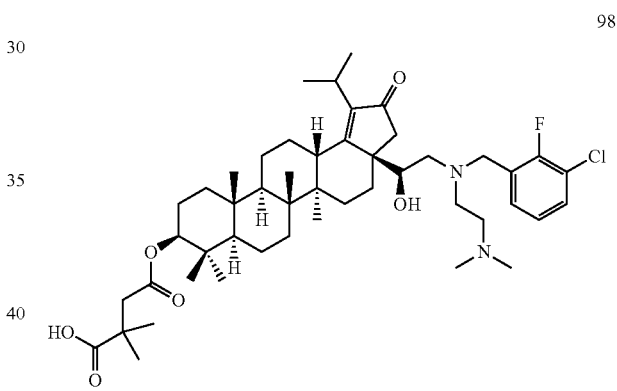

98

The title compound was made as a TFA salt in a similar manner to Example 18. Stereochemistry was tentatively assigned as drawn but not fully confirmed spectroscopically. ¹H NMR (500 MHz, CHLOROFORM-d) δ=7.56-7.32 (m, 2 H), 7.16 (t, J=7.7 Hz, 1 H), 4.53-4.38 (m, 1 H), 4.28 (d, J=9.1 Hz, 1 H), 4.13-3.87 (m, 2 H), 3.44 (br. s., 1 H), 3.33-2.91 (m, 5 H), 2.93-2.21 (m, 11 H), 2.09-1.95 (m, 1 H), 1.95-0.65 (m, 45 H); LC/MS: m/z calculated 826.5, found 827.3 (M+1)+.

Example 58

Compound 99

4-(((3aR,5aR,5bR,7aR,9S,11aR,11bR,13aS)-3a-((R)-1-Hydroxy-2-(isopropylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

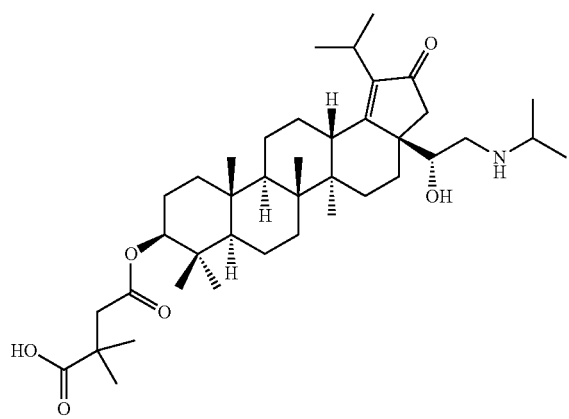

99

The title compound was made as a TFA salt in a similar manner to Example 18. Stereochemistry was tentatively assigned as drawn but not fully confirmed spectroscopically. ¹H NMR (400 MHz, CHLOROFORM-d) δ=10.30 (br. s., 1 H), 4.71-4.26 (m, 2 H), 3.49-2.98 (m, 2 H), 2.87-2.42 (m, 6 H), 2.42-2.21 (m, 1 H), 2.07-0.68 (m, 53 H); LC/MS: m/z calculated 655.5, found 656.5 (M+1)⁺.

Example 59

Compound 100

4-(((3aR,5aR,5bR,7aR,9S,11aR,11bR,13aS)-3a-((R)-2-(cyclohexylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

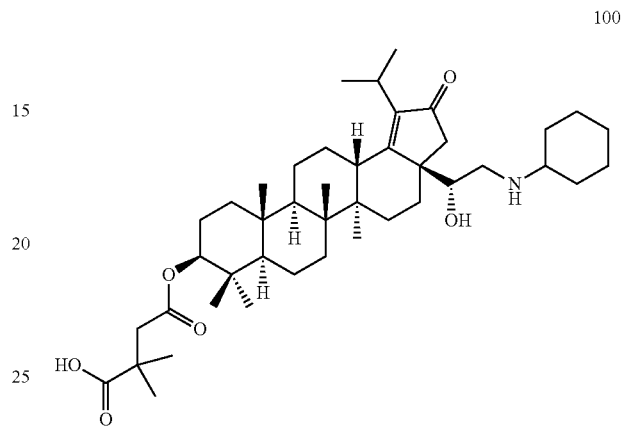

100

The title compound was made as a TFA salt in a similar manner to Example 18. Stereochemistry was tentatively assigned as drawn but not fully confirmed spectroscopically. ¹H NMR (400 MHz, CHLOROFORM-d) δ=10.25 (br. s., 1 H), 7.12 (br. s., 1 H), 4.67-4.34 (m, 2 H), 3.29-3.03 (m, 1 H), 2.92 (br. s., 1 H), 2.83-2.42 (m, 6 H), 2.42-2.26 (m, 1 H), 2.11-0.72 (m, 55 H); LC/MS: m/z calculated 695.5, found 696.4 (M+1)⁺.

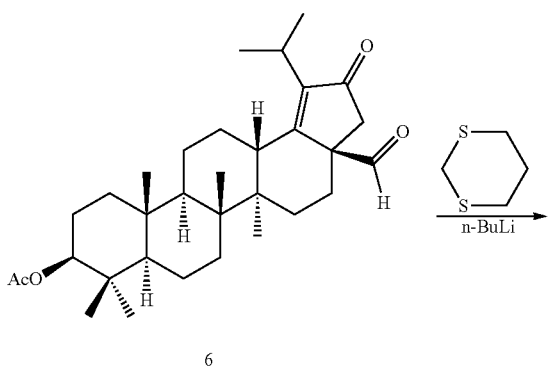

6

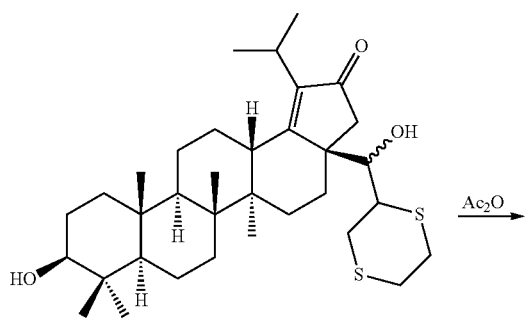

101

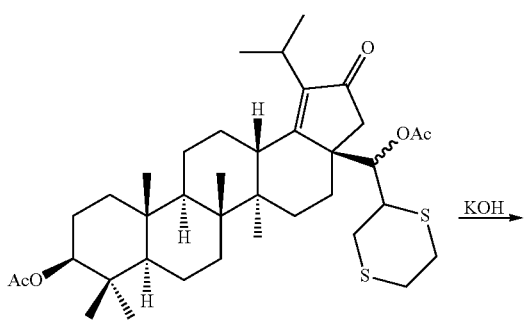

102

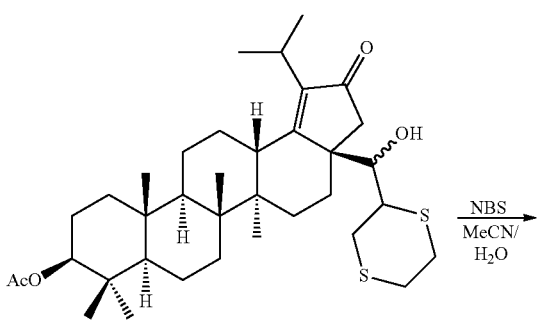

103

-continued
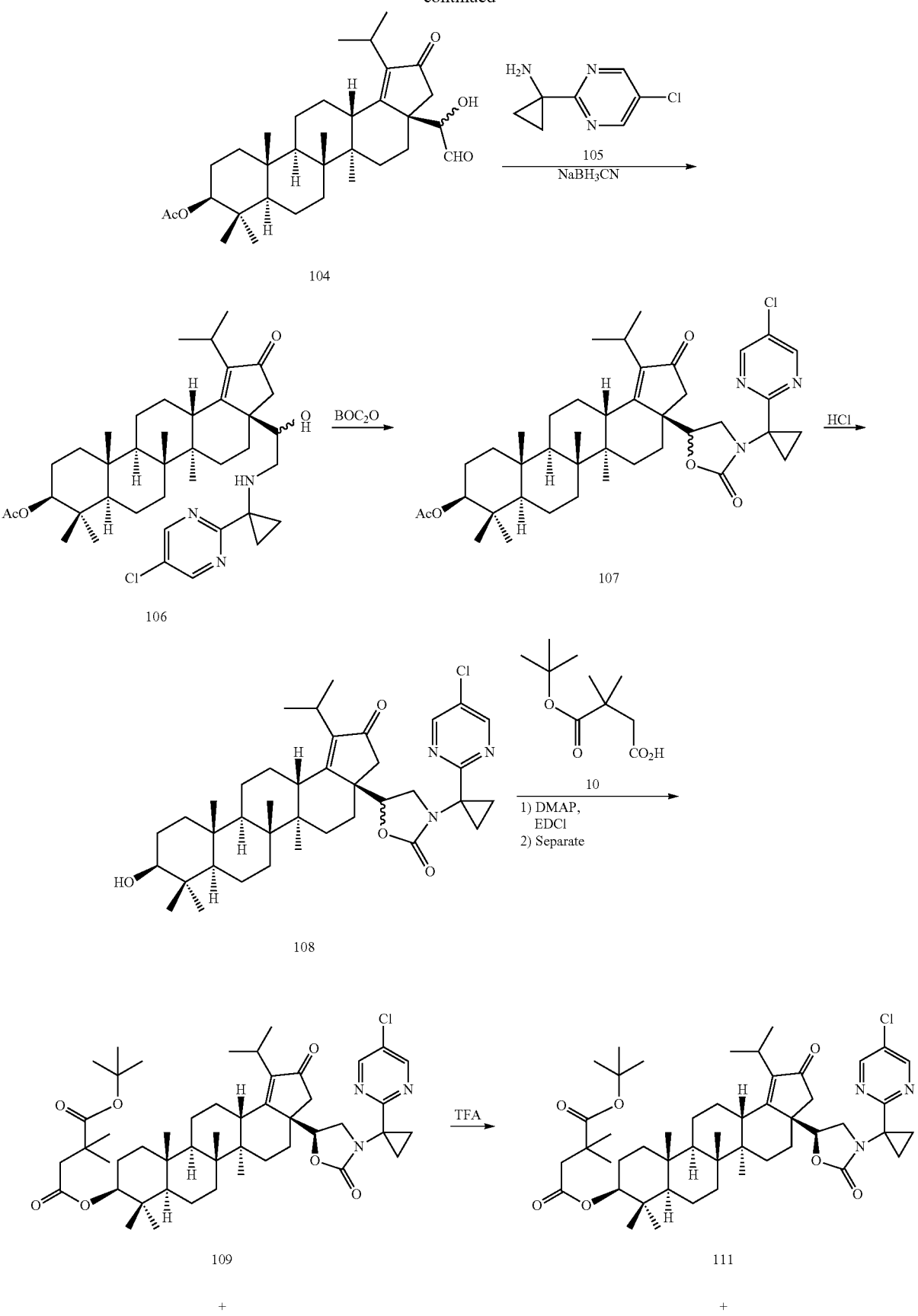

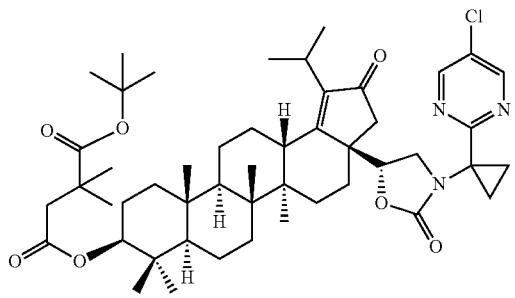

110

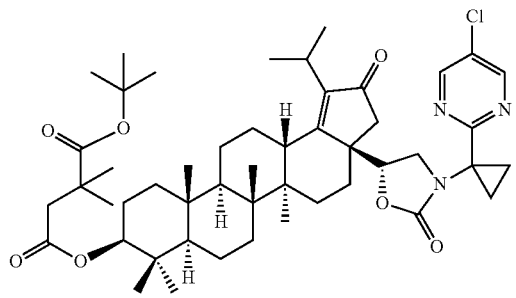

112

TFA

Example 60 and 61

Compound 111 and 112

4-(((3aR,5aR,5bR,7aR,9S,11aR,11bR,13aS)-3a-((S)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (111) and 4-(((3aR,5aR,5bR,7aR,9S,11aR,11bR,13aS)-3a-((R)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (112)

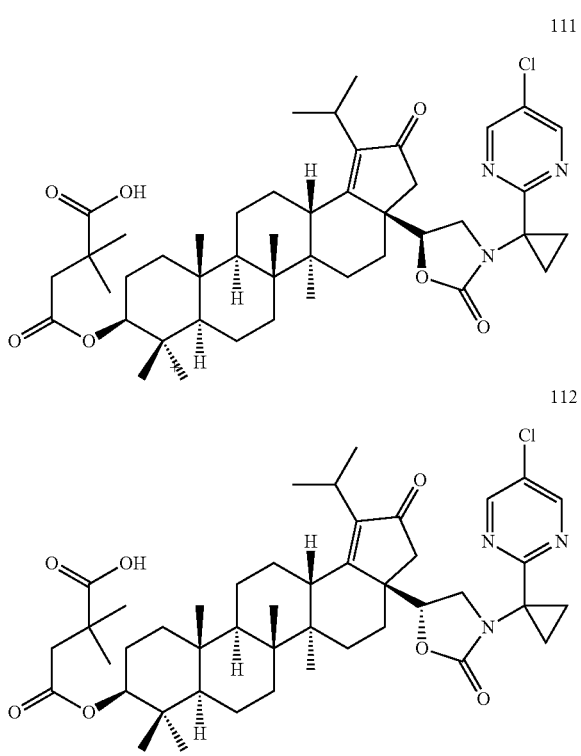

111

112

Step A: Intermediate 101

(3aR,5aR,5bR,7aR,9S,11aR,11bR,13aS)-3a-((1,3-Dithian-2-yl)(hydroxy)methyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one To a solution of 1,3-dithiane (5.7 g, 47.4 mmol) in anhydrous tetrahydrofuran (THF, 60 mL) under an atmosphere of nitrogen at −40° C. was slowly added a solution of n-BuLi (27 mL, 67.5 mmol). After the reaction mixture was stirred at −20° C. for another 2 h, a solution of the intermediate 6 (4.2 g, 8.46 mmol) in anhydrous THF (40 mL) was slowly added under an atmosphere of nitrogen at −70° C. The reaction was then stirred at −78° C. for 1 h before it was quenched with a saturated solution of NaHCO$_3$. Extraction was conducted with EtOAc and the organic phase was washed with water (50 mL), saturated brine (50 mL), dried over sodium sulfate, and evaporated under reduced pressure to provide a crude product, which was purified by column chromatography on silica gel (PE:EtOAc=8:1 to 4:1) to afford the intermediate 101 (3.0 g, 5.22 mmol, 61.7%). LC/MS: m/z calculated 574.4, found 575.0 (M+1)$^+$.

Step B: Intermediate 102

(3aR,5aR,5bR,7aR,9S,11aR,11bR,13aS)-3a-(Acetoxy(1,3-dithian-2-yl)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of the intermediate 101 (3.5 g, 6.09 mmol), Et$_3$N (2.55 mL, 18.26 mmol), and DMAP (0.149 g, 1.218 mmol) in DCM (40 mL) was added Ac$_2$O (3.45 mL, 36.5 mmol) at room temperature. After stirring at 50° C. for 2 h, the reaction mixture was quenched with water. The organic phase was washed with water (100 mL), dried over sodium sulfate, and evaporated under reduced pressure to provide the intermediate 102 (3.41 g, 85%). LC/MS: m/z calculated 658.4, found 659.1 (M+1)$^+$.

Step C: Intermediate 103

(3aR,5aR,5bR,7aR,9S,11aR,11bR,13aS)-3a-((1,3-Dithian-2-yl)(hydroxy)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate A solution of 102 (6.7 g, 10.17 mmol) and potassium hydroxide (1.141 g, 20.33 mmol) in a mixture 1:1 of toluene and ethanol (100 ml) was stirred vigorously at rt for 1 hr. The reaction mixture was neutralized with aqueous 1N HCl to pH 7 and reduced to dryness. The residue was purified on a silica gel using Petroleum ether/EtOAc (5:1) to yield (3aR, 5aR,5bR,7aR,9S,11aR,11bR,13aS)-3a-((1,3-dithian-2-yl) (hydroxy)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (103) (3.4 g, 5.01 mmol, 49%) as a light yellow compound. LC/MS: m/z calculated 616.4, found 617.3 (M+1)+.

Step D: Intermediate 104

(3aR,5aR,5bR,7aR,9S,11aR,11bR,13aS)-3a-(1-hydroxy-2-oxoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of 103 (1.2 g, 1.945 mmol) in acetonitrile (20 ml) and water (5.00 ml) stirred in air at rt was added NBS (1.385 g, 7.78 mmol) in one charge. The reaction mixture was stirred at rt for 0.5 h, then quenched with Na$_2$SO$_3$ (solid), concentrated and the residue was extracted with EtOAc. The organic phase was washed with water and saturated brine, dried over sodium sulphate and concentrated in vacuo to give (3aR,5aR,5bR,7aR,9S,11aR,11bR,13aS)-3a-(1-hydroxy-2-oxoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (104) (1.09 g, 1.083 mmol, 55.7% yield) as a light yellow solid which was used without further purification.

Step E: Intermediate 106

(3aR,5aR,5bR,7aR,9S,11aR,11bR,13aS)-3a-(2-((1-(5-Chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of (3aR,5aR,5bR,7aR,9S,11aR,11bR,13aS)-3a-(1-hydroxy-2-oxoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (104) (545 mg, 1.035 mmol) and 1-(5-chloropyrimidin-2-yl)cyclopropanamine, hydrochloride (105) (213 mg, 1.035 mmol) in methanol (5 ml) and 1,2-dichloroethane (5 ml) was added zinc chloride (141 mg, 1.035 mmol). The reaction mixture was stirred at room temperature overnight. and then sodium cyanoborohydride (65.0 mg, 1.035 mmol) was added. The reaction mixture was allowed to stir for 1 h, then silica gel was added to the mixture and the solvents removed in vacuo to give the residue-silica gel powder which was purified on a silica gel column using petroleum ether/EtOAc (5:1 to 3:1) to afford (3aR,5aR,5bR,7aR,9S, 11aR,11bR,13aS)-3a-(2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (105) as a mixture of diastereomers (200 mg, 0.166 mmol, 16.04% yield) as a yellow foam. LC/MS: m/z calculated 679.4, found 680.3 (M+1)+.

Step F: Intermediate 107

(3aR,5aR,5bR,7aR,9S,11aR,11bR,13aS)-3a-(3-(1-(5-Chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of (3aR,5aR,5bR,7aR,9S,11aR,11bR,13aS)-3a-(2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (106) (400 mg, 0.588 mmol) in dichloromethane (15 ml) stirred at rt was added BOC$_2$O (1.365 ml, 5.88 mmol). The reaction mixture was stirred at rt overnight then evaporated under reduced pressure and the residue was subjected to a silica gel chromatography with petroleum ether/EtOAc (6:1 to 3:1) to give (3aR,5aR,5bR,7aR,9S,11aR,11bR,13aS)-3a-(3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (107) (350 mg, 0.496 mmol, 84% yield) as a white solid.

Step G: Intermediate 108

3-(1-(5-Chloropyrimidin-2-yl)cyclopropyl)-5-((3aR, 5aR,5bR,7aR,9S,11aR,11bR,13aS)-9-hydroxy-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-3a-yl) oxazolidin-2-one To a solution of (3aR,5aR,5bR,7aR,9S,11aR,11bR,13aS)-3a-(3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (107) (350 mg, 0.496 mmol) in 1,4-dioxane (10 mL) and methanol (5 mL) was added hydrochloric acid (5 mL, 165 mmol). The reaction mixture was stirred at 40° C. overnight. The solvents were removed under reduced pressure and taken up in DCM (100 ml), washed with sat. NaHCO$_3$ (20 ml), water (20 ml) and brine (20 ml), dried over sodium sulfate, filtered and concentrated to give residue, which was subjected to a silica gel column eluting with petroleum ether/EtOAc (6:1 to 3:1) to give 3-(1-(5-chloropyrimidin-2-yl)cyclopropyl)-5-((3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)oxazolidin-2-one (130 mg, 0.087 mmol, 17%) as a white solid. LC/MS: m/z calculated 663.4, found 664.3 (M+1)+.

Step H: Intermediates 109 and 110

1-tert-butyl 4-((3aR,5aR,5bR,7aR,9S,11aR,11bR, 13aS)-3a-((S)-3-(1-(5-chloropyrimidin-2-yl)cyclopropyl)-2-oxooxazolidin-5-yl)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl) 2,2-dimethylsuccinate (109) and 1-tert-butyl 4-((3aR,5aR,5bR,7aR,9S,11aR,11bR, 13aS)-3a-((R)-3-(1-(5-chloropyrimidin-2-yl)cyclopropyl)-2-oxooxazolidin-5-yl)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl) 2,2-dimethylsuccinate (110)

A mixture of 4-tert-butoxy-3,3-dimethyl-4-oxobutanoic acid 10 (119 mg, 0.587 mmol), 3-(1-(5-chloropyrimidin-2-yl)cyclopropyl)-5-((3aR,5aR,5bR,7aR,9S,11aR,11bR, 13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)oxazolidin-2-one (108) (130 mg, 0.196 mmol), EDC (188 mg, 0.978 mmol) and DMAP (71.7 mg, 0.587 mmol) in DCM (5 mL) was stirred at rt overnight. After the reaction finished, the mixture was diluted with DCM (25 ml), washed with water (2×15 ml) and brine (20 ml), dried over sodium sulfate, filtered and concentrated under reduced pressure. The residue was purified by silica gel chromatography using petroleum ether/EtOAc (6:1 to 3:1) as eluent to give the two diastereomeric products 1-tert-butyl 4-((3aR,5aR,5bR,7aR, 9S,11aR,11bR,13aS)-3a-((S)-3-(1-(5-chloropyrimidin-2-yl) cyclopropyl)-2-oxooxazolidin-5-yl)-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) 2,2-dimethylsuccinate (109) and 1-tert-butyl 4-((3aR, 5aR,5bR,7aR,9S,11aR,11bR,13aS)-3a-((R)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl) 2,2-dimethylsuccinate (110) in the amounts of (80 mg, 45%) and (50 mg, 22%) as white solids. The stereochemical assignments for each diastereomer were not made. Compound A (tentatively designated as 109): LC/MS: m/z calculated 847.5, found 848.3 (M+1)$^+$. Compound B (tentatively designated as 110): LC/MS: m/z calculated 847.5, found 848 (M+1)$^+$.

Step I: Compound 111

4-(((3aR,5aR,5bR,7aR,9S,11aR,11bR,13aS)-3a-((S)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl)oxy)-2,2-dimethyl-4-oxobutanoic acid To a solution of 1-tert-butyl 4-((3aR,5aR,5bR,7aR,9S, 11aR,11bR,13aS)-3a-((S)-3-(1-(5-chloropyrimidin-2-yl)cyclopropyl)-2-oxooxazolidin-5-yl)-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) 2,2-dimethylsuccinate (109) (80 mg, 0.094 mmol) in DCM (10 mL) was added TFA (1 mL, 0.094 mmol). The reaction mixture was stirred at rt overnight, then diluted with DCM (20 ml) and washed with water (2×15 ml), saturated sodium bicarbonate solution (20 ml) and brine (20 ml), dried over sodium sulfate, filtered and concentrated to get a residue. The residue was purified on silica gel using petroleum ether/EtOAc (4:1 to 1:1) as eluent to give the product 4-(((3aR,5aR,5bR,7aR,9S,11aR,11bR,13aS)-3a-((S)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (111) (50 mg, 67%) as a white solid. This material was lyophilized to give a white powder. Stereochemistry was tentatively assigned as drawn but not fully confirmed spectroscopically. $^1$H NMR (400 MHz, CHLOROFORM-d) δ=8.58 (s, 2 H), 5.04 (t, J=8.5 Hz, 1 H), 4.51 (dd, J=4.6, 10.9 Hz, 1 H), 3.41-3.04 (m, 4 H), 2.75-2.44 (m, 3 H), 2.36 (d, J=13.3 Hz, 1 H), 2.12-0.72 (m, 49 H); LC/MS: m/z calculated 791.4, found 792.3 (M+1)$^+$.

Step J: Compound 112

4-(((3aR,5aR,5bR,7aR,9S,11aR,11bR,13aS)-3a-((R)-3-(1-(5-chloropyrimidin-2-yl)cyclopropyl)-2-oxooxazolidin-5-yl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl)oxy)-2,2-dimethyl-4-oxobutanoic acid The title compound was made in a similar manner to that described for compound 111. Stereochemistry was tentatively assigned as drawn but not fully confirmed spectroscopically. $^1$H NMR (400 MHz, CHLOROFORM-d) δ=8.59 (s, 2 H), 5.10 (t, J=8.8 Hz, 1 H), 4.52 (dd, J=5.3, 10.8 Hz, 1 H), 3.70-3.54 (m, 2 H), 3.28-3.10 (m, 2 H), 3.08-2.92 (m, 2 H), 2.77-2.53 (m, 2 H), 2.14-0.58 (m, 49 H); LC/MS: m/z calculated 791.4, found 792.3 (M+1)$^+$.

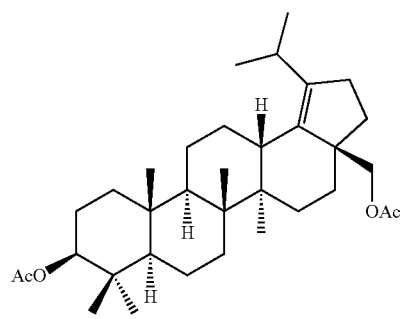
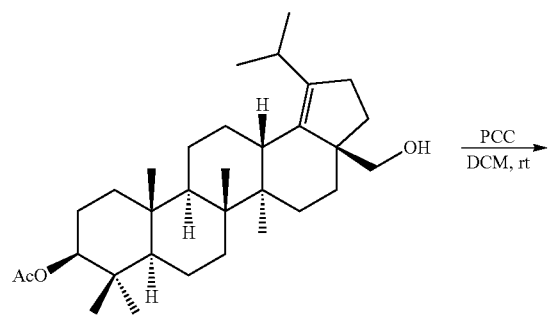

201
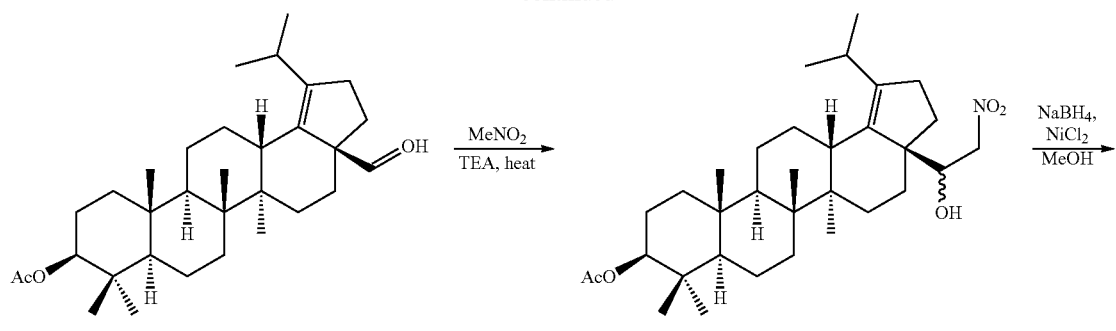
202
-continued
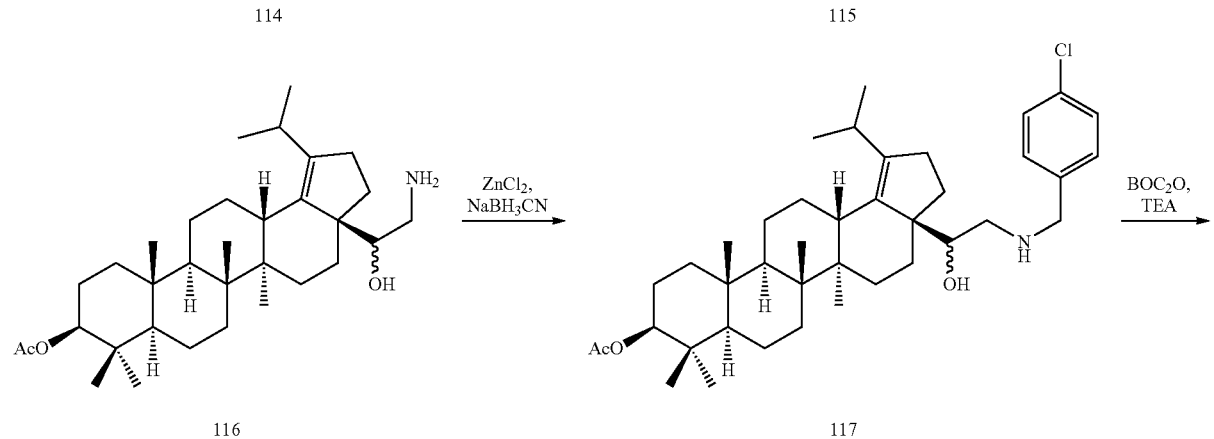
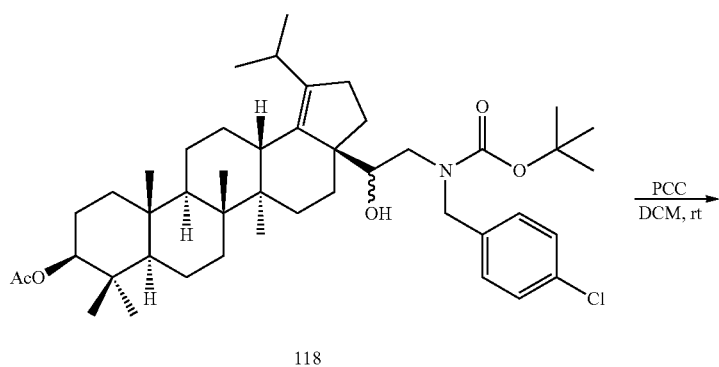
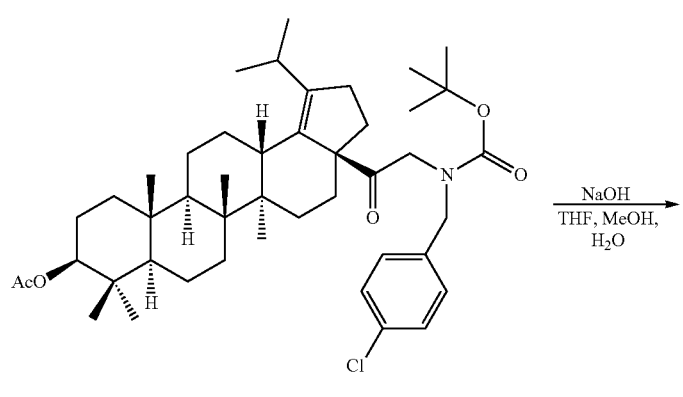

-continued
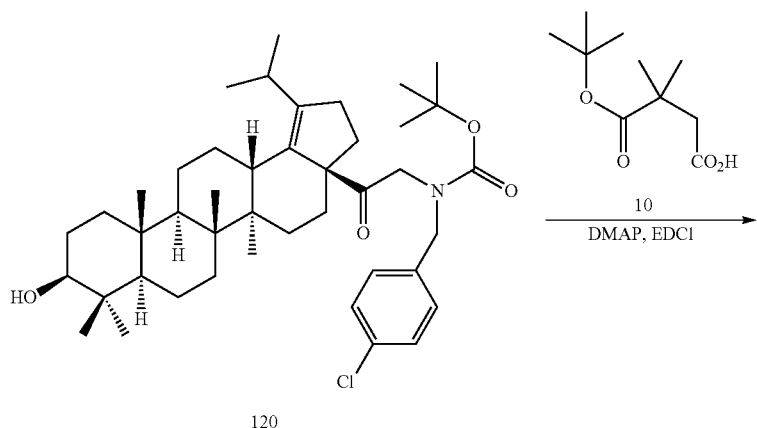
120
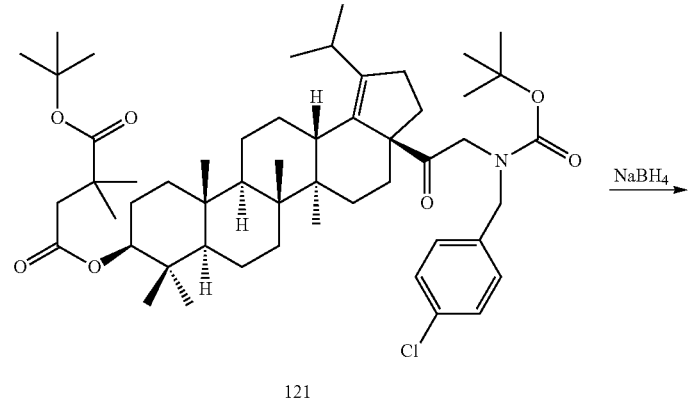
121
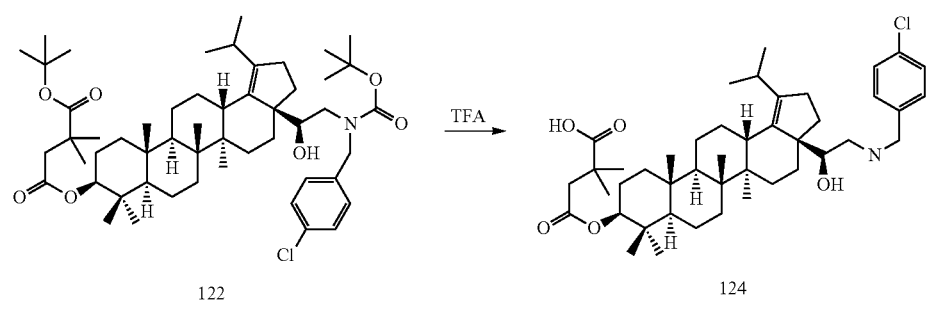
122 124
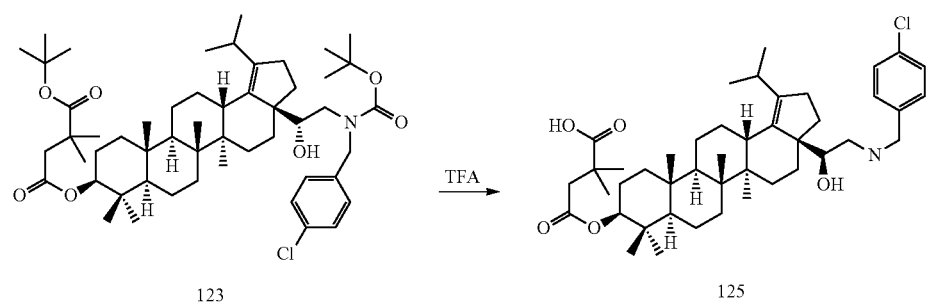
123 125

Example 62

Compound 124

4-(((3aS,5aR,5bR,7aR,9S,11aR,11bR,13aS)-3a-((S)-2-((4-Chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

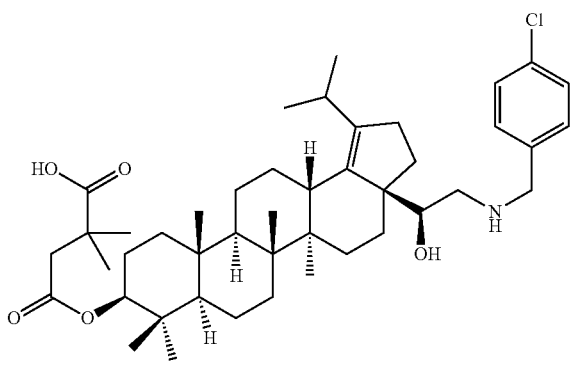

Step A: Intermediate 113

(3aS,5aR,5bR,7aR,9S,11aR,11bR,13aS)-3a-(Hydroxymethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 3 (5 g, 7.59 mmol) in EtOH (100 mL) and toluene (100 mL) was added KOH (0.51 g, 9.11 mmol). After stirring at room temperature for 4 h, the reaction mixture was then partitioned between water (500 mL) and EtOAc (500 mL). The organic phase was washed with water (200 mL×3), brine (100 mL), and dried over sodium sulfate. Removal of the solvent provided a residue, which was purified by column chromatography on silica gel (Hex:EtOAc=6:1 to 4:1) to afford the intermediate 113 (2.5 g, 67.9%) as a white solid. $^1$H NMR (400 Hz, CDCl$_3$) δ ppm 4.50-4.67 (1H, m), 3.68 (1H, d, J=10.4 Hz), 3.32 (1H, d, J=10.4 Hz), 3.23-3.15 (1H, m), 2.42-2.28 (3H, m), 2.05 (3H, s), 2.02-1.89 (2H, m), 1.77-0.83 (40H, m).

Step B: Intermediate 114

(3aS,5aR,5bR,7aR,9S,11aR,11bR,13aS)-3a-Formyl-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 113 (3 g, 6.19 mmol) in DCM (75 mL) at room temperature were added PCC (4 g, 18.57 mmol) and silica gel (3.0 g). After stirring at room temperature for 2 h, the reaction was quenched with water (100 mL). The organic phase was separated, washed with saturated sodium bicarbonate (50 mL), dried over sodium sulfate and concentrated in vacuo to provide a residue, which was purified by column chromatography on silica gel (Hex:EtOAc=10:1) to afford the intermediate 114 (3 g, 100%) as a white solid. $^1$H NMR (400 Hz, CDCl$_3$) δ ppm 9.43 (1H, s), 4.50-4.46 (1H, m), 3.25-3.21 (1H, m), 2.43-2.02 (5H, m), 2.04 (3H, m), 2.00-1.93 (1H, m), 1.75-0.81 (38H, m).

Step C: Intermediate 115

(3aS,5aR,5bR,7aR,9S,11aR,11bR,13aS)-3a-(1-Hydroxy-2-nitroethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 114 (5 g, 10.36 mmol) in MeNO$_2$ (128 mL, 2382 mmol) was added Et$_3$N (10.11 mL, 72.5 mmol). After it was stirred at 60° C. overnight, the reaction mixture was partitioned between water and EtOAc (100 mL each). The organic phase was washed with water (20 mL×3), brine (20 mL), and dried over sodium sulfate. Removal of the solvent provided a residue, which was purified by column chromatography on silica gel (Hex:EtOAc=10:1 to 6:1) to afford the intermediate 115 (2.8 g, 49.7%) as a white powder. LC/MS: m/z calculated 543.4, found 566.3 (M+Na$^+$)+.

Step D: Intermediate 116

(3aS,5aR,5bR,7aR,9S,11aR,11bR,13aS)-3a-(2-Amino-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 115 (2.8 g, 5.15 mmol) in MeOH (166 mL) were added nickel(II) chloride (1.67 g, 12.87 mmol) and sodium borohydride (4.87 g, 129 mmol) at 0° C. After stirring at 0° C. for 10 min, the reaction mixture was partitioned between water and EtOAc (200 mL each), and the organic phase was washed with water (100 mL×3), brine (50 mL), and dried over sodium sulfate. Removal of the solvent provided the intermediate 116 (2.65 g, 100%) as a solid. LC/MS: m/z calculated 513.4, found 514.3 (M+1)+.

Step E: Intermediate 118

(3aS,5aR,5bR,7aR,9S,11aR,11bR,13aS)-3a-(2-((tert-Butoxycarbonyl)(4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 116 (350 mg, 0.613 mmol) and 4-chlorobenzaldehyde (86 mg, 0.613 mmol) in MeOH (15 mL) and dichloroethane (DCE, 15 mL) was added zinc chloride (50.1 mg, 0.368 mmol). After the reaction mixture was stirred at 80° C. for 1 h and cooled down to room temperature, sodium cyanoborohydride (57.8 mg, 0.92 mmol) was added. The resulting mixture was stirred at room temperature for another 1 h to provide the intermediate 117.

To the reaction mixture obtained above were added Et$_3$N (0.18 mL, 1.38 mmol) and di-tert-butyl dicarbonate (0.157 mL, 0.674 mmol). After stirring at room temperature for 30 min, the reaction mixture was partitioned between water (20 mL) and EtOAc (100 mL). The organic phase was washed with water (30 mL×3), brine (20 mL), and dried over sodium sulfate. Removal of the solvent provided a residue, which was purified by column chromatography on silica gel (Hex: EtOAc=15:1) to afford the intermediate 118 (125 mg, 27.6%) as a white solid.

Step F: Intermediate 119

(3aS,5aR,5bR,7aR,9S,11aR,11bR,13aS)-3a-(2-((tert-Butoxycarbonyl)(4-chlorobenzyl)amino)acetyl)-1-isopropyl-5a,5b,8,8,11a-pentamethyl-3,3a,4,5,5a,5b, 6,7,7a,8,9,10,11,11a,11b,12,13,13a-octadecahydro-2H-cyclopenta[a]chrysen-9-yl acetate To a solution of the intermediate 118 (120 mg, 0.162 mmol) in DCM (10 mL) were added PCC (35 mg, 0.162 mmol) and silica gel (100 mg). After stirring at room temperature for 2 h, the insoluble material was removed by filtration and the filtrate was concentrated to afford the intermediate 119 (110 mg, 92%) as a white solid.

Step G: Intermediate 120 tert-butyl 4-Chlorobenzyl(2-((3aS,5aR,5bR,7aR,9S, 11aR,11bR,13aS)-9-hydroxy-1-isopropyl-5a,5b,8,8, 11a-pentamethyl-3,3a,4,5,5a,5b,6,7,7a,8,9,10,11,11a, 11b,12,13,13a-octadecahydro-2H-cyclopenta[a] chrysen-3a-yl)-2-oxoethyl)carbamate To a solution of NaOH (597 mg, 14.94 mmol) in MeOH (1 mL), THF (1 mL), and water (0.5 mL) was added the intermediate 119 (110 mg, 0.149 mmol). After stirring at room temperature for 1 h, the reaction was diluted with water (20 mL), and extracted with EtOAc (50 mL). The organic phase was washed with brine (20 mL), dried over sodium sulfate, and evaporated in vacuo to afford the intermediate 120 (100 mg, 96%) as a white solid.

Step H: Intermediate 121

4-((3aS,5aR,5bR,7aR,9S,11aR,11bR,13aS)-3a-(2-((tert-butoxycarbonyl)(4-chlorobenzyl)amino) acetyl)-1-isopropyl-5a,5b,8,8,11a-pentamethyl-3,3a, 4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate To a solution of 4-tert-butoxy-3,3-dimethyl-4-oxobutanoic acid 10 (1.648 g, 8.15 mmol), DMAP (0.995 g, 8.15 mmol) in DCM (15 ml) stirred at rt was added EDCI (2.60 g, 13.58 mmol). The reaction mixture was stirred at rt. for 2 h. Then tert-butyl 4-chlorobenzyl(2-((3aS,5aR,5bR,7aR,9S, 11aR,11bR,13aS)-9-hydroxy-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-3a-yl)-2-oxoethyl)carbamate 120 (1.886 g, 2.72 mmol) was added to the reaction. The reaction mixture was stirred at rt overnight. Upon completion, the mixture was washed with water (25 mL×2) and brine, dried over sodium sulfate filtered through a short silica gel column and evaporated in vacuo to give the crude product which was further purified on a silica gel column using petroleum ether/EtOAc (50:1 to 10:1) to give intermediate 121 (2.37 g, 99%) as white foam.

Step I: Intermediates 122 and 123

4-((3aS,5aR,5bR,7aR,9S,11aR,11bR,13aS)-3a-((S)-2-((tert-Butoxycarbonyl)(4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-9-yl) 1-tert-butyl 2,2-dimethylsuccinate (122) and 4-((3aS,5aR,5bR,7aR,9S,11aR,11bR,13aS)-3a-((R)-2-((tert-butoxycarbonyl)(4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-9-yl) 1-tert-butyl 2,2-dimethylsuccinate (123)

To a solution of and 4-((3aS,5aR,5bR,7aR,9S,11aR,11bR, 13aS)-3a-(2-((tert-butoxycarbonyl)(4-chlorobenzyl)amino) acetyl)-1-isopropyl-5a,5b,8,8,11a-pentamethyl-3,3a,4,5,5a, 5b,6,7,7a,8,9,10,11,11a,11b,12,13,13a-octadecahydro-2H-cyclopenta[a]chrysen-9-yl) 1-tert-butyl 2,2-dimethylsuccinate (121) (791 mg, 0.90 mmol) in MeOH (10 mL) and THF (10.00 mL) stirred at 0° C. was added NaBH$_4$ (170 mg, 4.50 mmol). The reaction mixture was stirred at rt for 2 h until starting material had disappeared. Upon completion, silica gel was added and the mixture evaporated to dryness and purified by silica gel chromatography (petroleum ether/EtOAc, 40:1 to 10:1) to give the two diastereomeric products: 4-((3aS,5aR,5bR,7aR,9S,11aR,11bR,13aS)-3a-((S)-2-((tert-butoxycarbonyl)(4-chlorobenzyl)amino)-1-hydroxyethyl)-1-isopropyl-5a,5b,8,8,11a-pentamethyl-3,3a, 4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate and 4-((3aS,5aR,5bR,7aR,9S,11aR, 11bR,13aS)-3a-((R)-2-((tert-butoxycarbonyl)(4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-9-yl) 1-tert-butyl 2,2-dimethylsuccinate. Stereochemistry was not confirmed but the diastereomers were produced in the amount of (410 mg, 52%, tentatively assigned as compound 122) and (77 mg, 10%, tentatively assigned as compound 123) as white foams.

Step J: Compound 124

4-(((3aS,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-3,3a,4,5,5a,5b,6,7, 7a,8,9,10,11,11a,11b,12,13,13a-octadecahydro-2H-cyclopenta[a]chrysen-9-yl)oxy)-2,2-dimethyl-4-oxobutanoic acid To a solution of 122 (410 mg, 0.466 mmol) in DCM (10 mL) was added TFA (2 mL, 26.0 mmol). The reaction mixture was stirred at rt for 2 h. The reaction mixture was concentrated to dryness and purified by preparative-HPLC to afford 4-(((3aS,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-3,3a,4,5,5a,5b,6,7,7a,8,9,10, 11,11a,11b,12,13,13a-octadecahydro-2H-cyclopenta[a] chrysen-9-yl)oxy)-2,2-dimethyl-4-oxobutanoic acid, trifluoroacetic acid salt (124) (185 mg, 0.221 mmol, 47.4% yield) as white solid. $^1$H NMR (500 MHz, CHLOROFORM-d) δ=7.36 (q, J=8.5 Hz, 4 H), 4.58-4.41 (m, 1 H), 4.41-4.31 (m, 1 H), 4.20-3.97 (m, 2 H), 3.23-3.05 (m, 2 H), 2.85-2.66 (m, 2 H), 2.56 (d, J=16.1 Hz, 1 H), 2.51-2.38 (m, 1 H), 2.34-2.19 (m, 2 H), 1.93-1.82 (m, 1 H), 1.83-0.67 (m, 46 H); LC/MS: m/z calculated 723.5, found 724.3 (M+1)$^+$.

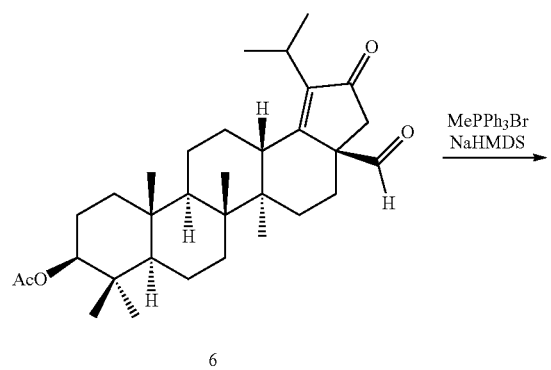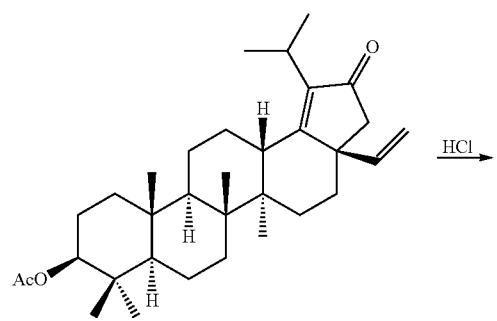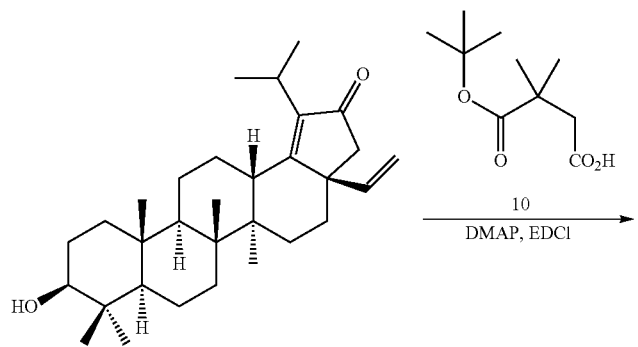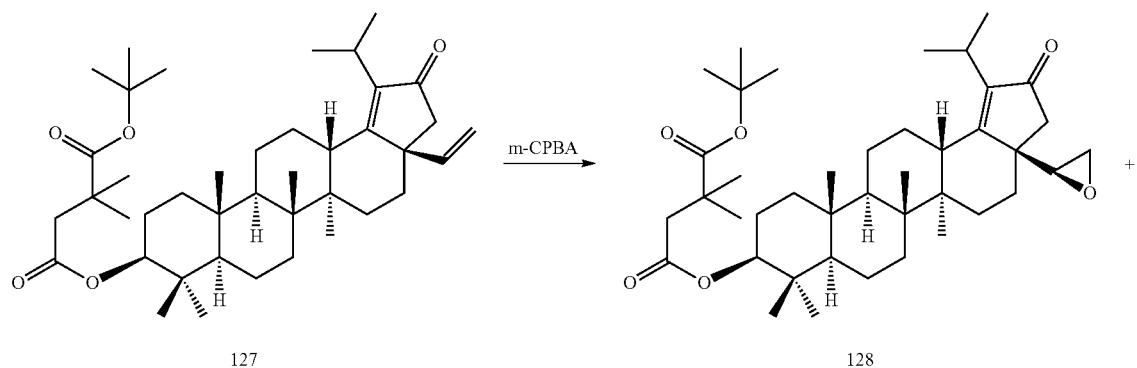

-continued

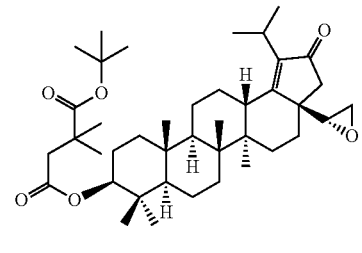
129

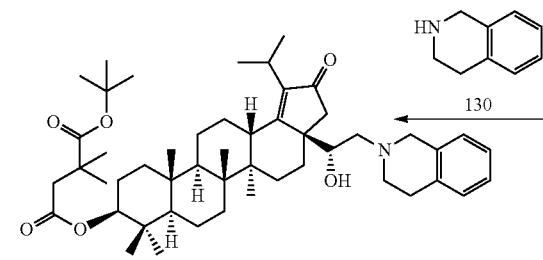
131

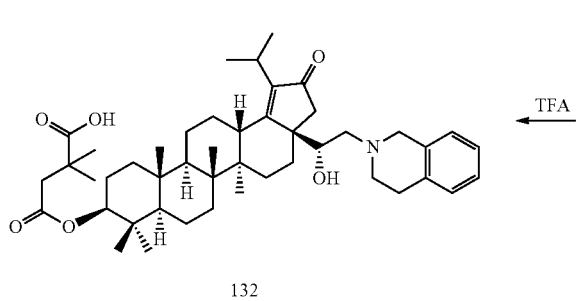
132

Example 63

Compound 132

4-(((3aR,5aR,5bR,7aR,9S,11aR,11bR,13aS)-3a-((R)-2-(3, 4-dihydroisoquinolin-2(1H)-yl)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

132

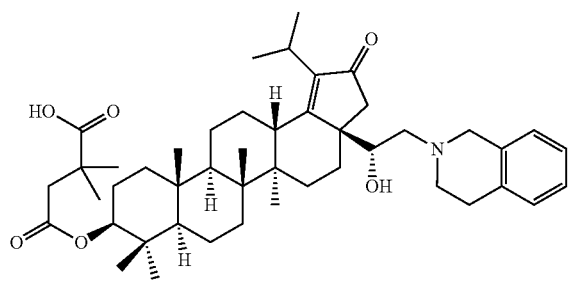

Step A: Intermediate 125

(3aS,5aR,5bR,7aR,9S,11aR,11bR,13aS)-1-isopropyl-5a,5b,8,8,11a-pentamethyl-2-oxo-3a-vinyl-3,3a,4,5,5a,5b,6,7,7a,8,9,10,11,11a,11b,12,13,13a-octadecahydro-2H-cyclopenta[a]chrysen-9-yl acetate To a cold (−78° C.) solution of methyltriphenylphosphonium bromide (8.63 g, 24.16 mmol) in THF (30 mL) was added lithium bis(trimethylsilyl)amide (4.4 g, 24.1 mmol) in THF dropwise. The reaction was stirred at −78° C. for 1 h, then 6 (10.0 g, 20.1 mmol) in THF (60 ml) was added. The mixture was allowed to warm to rt and stirred for 1 h. TLC indicated the reaction was complete. 2N HCl was added to the mixture and it was extracted with ethyl acete and washed with water and brine. The organic phase was dried with Na$_2$SO$_4$ followed by filtration and concentration followed by precipitation of the desired product (10 g of 85% purity, 85% chemical yield) with 5% EtOAc/petroleum ether.

Step B: Intermediate 126

(3aS,5aR,5bR,7aR,9S,11aR,11bR,13aS)-9-hydroxy-1-isopropyl-5a,5b,8,8,11a-pentamethyl-3a-vinyl-3, 3a,4,5,5a,5b,6,7,7a,8,9,10,11,11a,11b,12,13,13a-octadecahydro-2H-cyclopenta[a]chrysen-2-one To a solution of 125 (16 g, 32.3 mmol) in 1,4-dioxane (300 mL) and MeOH (30 ml) stirred at rt was added HCl (37%) (150 mL, 32.3 mmol). The reaction mixture was stirred at 60° C. for 3 h. TLC and LCMS indicated the starting material was consumed completely. Water was added and the volatiles were concentrated, a resultant precipitate was filtered and washed with water. The cake was dried to give 126 (14 g, 81%).

Step C: Intermediate 127

1-tert-butyl 4-((3aS,5aR,5bR,7aR,9S,11aR,11bR, 13aS)-1-isopropyl-5a,5b,8,8,11a-pentamethyl-2-oxo-3a-vinyl-3,3a,4,5,5a,5b,6,7,7a,8,9,10,11,11a,11b,12, 13,13a-octadecahydro-2H-cyclopenta[a]chrysen-9-yl) 2,2-dimethylsuccinate To a solution of 10 (14.52 g, 71.8 mmol), DMAP (10.52 g, 86 mmol) and 126 (13 g, 28.7 mmol) in dichloromethane (150 mL) was added EDC (27.5 g, 144 mmol). The mixture was stirred at rt for 2 h, at which time TLC indicated the reaction was complete. The reaction was washed with 2N HCl, and brine. The organics were dried with Na$_2$SO$_4$, filtered and concentrated. The residue was purified by silica gel chromatography to give 127 (9.5 g, 49%) along with an additional 4 g impure product requiring repurification prior to further use.

Step D: Intermediates 128 and 129

1-tert-butyl 4-((3aR,5aR,5bR,7aR,9S,11aR,11bR,13aS)-1-isopropyl-5a,5b,8,8,11a-pentamethyl-3a-((S)-oxiran-2-yl)-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (128) and 1-tert-butyl 4-((3aR,5aR,5bR,7aR,9S,11aR,11bR,13aS)-1-isopropyl-5a,5b,8,8,11a-pentamethyl-3a-((R)-oxiran-2-yl)-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (129)

To a solution of 127 (8.5 g, 13.34 mmol) in DCM (90 mL) at rt was added m-CPBA (5.42 g, 26.7 mmol). The reaction mixture was stirred at rt overnight. The mixture was further diluted with DCM 150 ml then washed with saturated NaHCO$_3$, water and brine (note for safety reasons this the excess peroxide should be neutralized but was not in this specific procedure). The organic phase was concentrated and purified by silica gel chromatography (EtOAc/PE 5% to 15%) to give 128 (2.0 g, 21%) and 129 (800 mg, 8%) along with 2.4 g of recovered starting material. For 128: $^1$H NMR (500 MHz, CHLOROFORM-d) □=4.51 (dd, J=5.4, 11.3 Hz, 1 H), 3.26-3.12 (m, 3 H), 2.66 (t, J=4.4 Hz, 1 H), 2.54 (s, 2 H), 2.35 (dd, J=2.7, 4.6 Hz, 1 H), 2.18 (d, J=18.3 Hz, 1 H), 2.12-1.93 (m, 3 H), 1.91-0.74 (m, 52 H); LC/MS: m/z calculated 652.5, found 653.3 (M+1)$^+$. For 129: $^1$H NMR (500 MHz, CHLOROFORM-d) δ=4.51 (dd, J=5.0, 11.3 Hz, 1 H), 3.26-3.07 (m, 2 H), 3.00 (dd, J=3.2, 12.6 Hz, 1 H), 2.69 (t, J=4.3 Hz, 1 H), 2.59-2.41 (m, 3 H), 2.21-0.76 (m, 56 H); LC/MS: m/z calculated 652.5, found 653.3 (M+1)$^+$.

Step E: Intermediate 131

1-tert-butyl 4-((3aR,5aR,5bR,7aR,9S,11aR,11bR,13aS)-3a-((R)-2-(3, 4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of 1-tert-butyl 4-((3aR,5aR,5bR,7aR,9S,11aR,11bR,13aS)-1-isopropyl-5a,5b,8,8,11a-pentamethyl-3a-((R)-oxiran-2-yl)-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (0.2 g, 0.306 mmol) in tert-butanol (3 mL) was added 1,2,3,4-tetrahydroisoquinoline (0.408 g, 3.06 mmol). The reaction mixture was stirred at 100° C. for 5 h. Upon completion and cooling, EtOAc was added and the mixture was washed with 4N HCl, and brine, then dried with Na$_2$SO$_4$, filtered and concentrated to give 132 (200 mg, 66%) which was used without further purification. LC/MS: m/z calculated 785.6, found 786.5 (M+1)$^+$.

Step F: Compound 132

4-(((3aR,5aR,5bR,7aR,9S,11aR,11bR,13aS)-3a-((R)-2-(3, 4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 131 (0.2 g, 0.254 mmol) in DCM (2 mL) was added TFA (1 mL, 12.98 mmol). The reaction mixture was stirred at rt for 1 h then concentrated. The residue was purified by preparative-HPLC to give the title compound (106 mg, 48%) as a TFA salt as white solid. $^1$H NMR (500 MHz, METHANOL-d$_4$) δ=7.43-7.15 (m, 4 H), 4.66-4.41 (m, 4 H), 3.28-3.05 (m, 3 H), 3.05-2.83 (m, 2 H), 2.73-2.52 (m, 3 H), 2.30 (d, J=13.9 Hz, 1 H), 2.16-2.03 (m, 1 H), 2.00-0.72 (m, 48 H); LC/MS: m/z calculated 729.5, found 730.5 (M+1)$^+$.

The Examples below were made in a similar manner to the above examples or via combinations or re-ordering of the methods described and/or usage of other methods well known to those skilled in the art.

Example 64

Compound 133

4-(((3aR,5aR,5bR,7aR,9S,11aR,11bR,13aS)-3a-((S)-2-(3, 4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

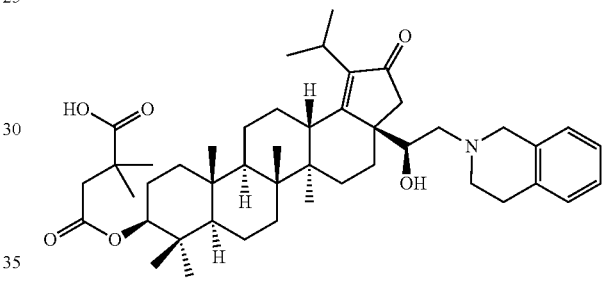

133

Stereochemistry was tentatively assigned as drawn but not fully confirmed spectroscopically. LC/MS: m/z calculated 729.5, found 730.5 (M+1)$^+$.

Example 65

Compound 134

4-(((3aS,5aR,5bR,7aR,9S,11aR,11bR,13aS)-3a-((R)-1-hydroxy-2-(4-methylpiperazin-1-yl)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

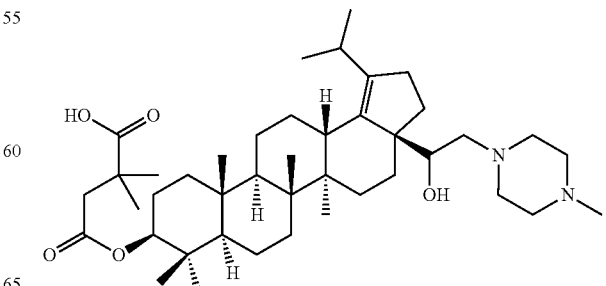

134

Isolated as a mixture of diastereomers. LC/MS: m/z calculated 682.53, found 683.5 (M+1)⁺.

Example 66

Compound 135

4-(((3aR,5aR,5bR,7aR,9S,11aR,11bR,13aS)-3a-(2-((4-chlorobenzyl)amino)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

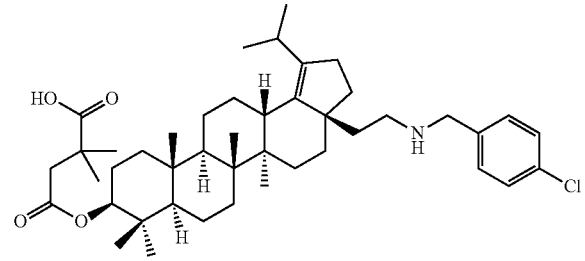

135

LC/MS: m/z calculated 707.5, found 708.3 (M+1)⁺.

Example 67

Compound 136

4-(((3aS,5aR,5bR,7aR,9S,11aR,11bR,13aS)-3a-((S)-2-((cyclohexylmethyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

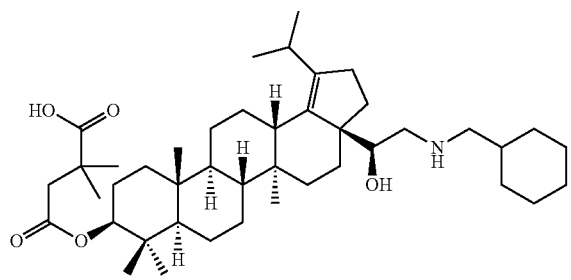

136

Stereochemistry was tentatively assigned as drawn but not fully confirmed spectroscopically. LC/MS: m/z calculated 695.6, found 696.5 (M+1)⁺.

Example 68

Compound 137

4-(((3aR,5aR,5bR,7aR,9S,11aR,11bR,13aS)-3a-((S)-2-(cyclohexylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

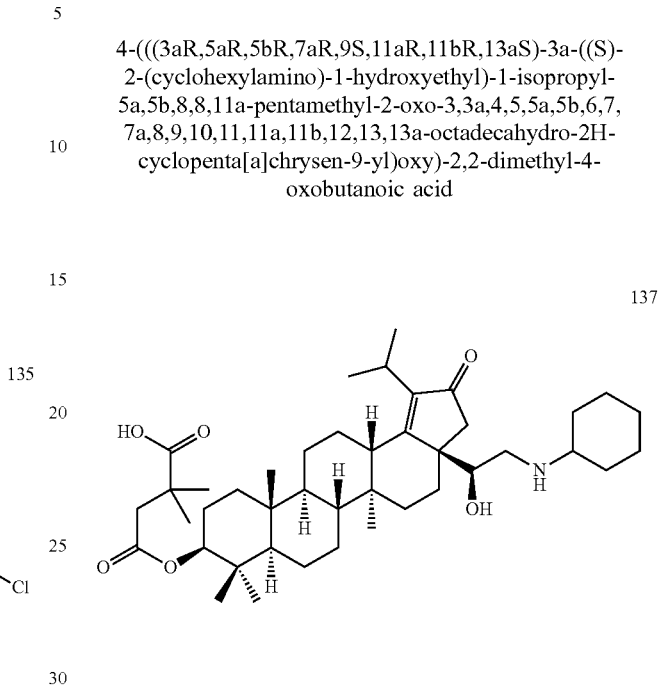

137

Stereochemistry was tentatively assigned as drawn but not fully confirmed spectroscopically. LC/MS: m/z calculated 695.5, found 696.5 (M+1)⁺.

Example 69

Compound 138

4-(((3aR,5aR,5bR,7aR,9S,11aR,11bR,13aS)-3a-((S)-2-(benzyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

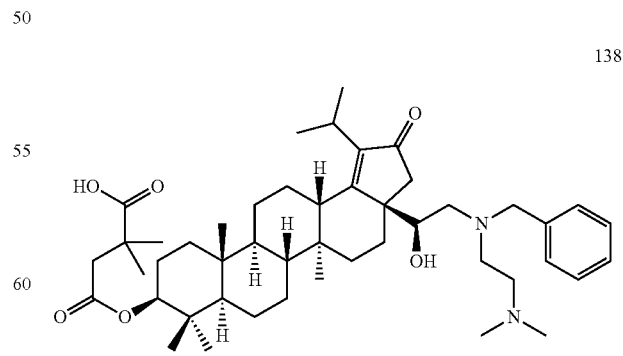

138

Stereochemistry was tentatively assigned as drawn but not fully confirmed spectroscopically. LC/MS: m/z calculated 774.6, found 775.5 (M+1)⁺.

Example 70

Compound 139

4-(((3aR,5aR,5bR,7aR,9S,11aR,11bR,13aS)-3a-((S)-1-acetoxy-2-((2-(dimethylamino)ethyl)(4-fluorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

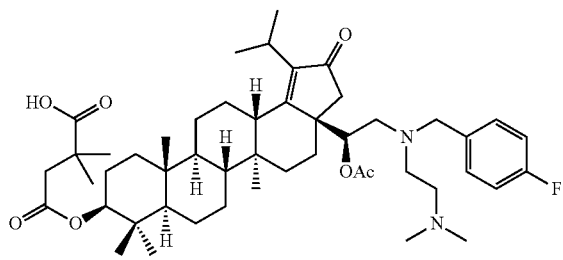

139

Stereochemistry was tentatively assigned as drawn but not fully confirmed spectroscopically. LC/MS: m/z calculated 834.6, found 835 (M+1)+.

Example 71

Compound 140

4-(((3aR,5aR,5bR,7aR,9S,11aR,11bR,13aS)-3a-((R)-1-acetoxy-2-((2-(dimethylamino)ethyl)(4-fluorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

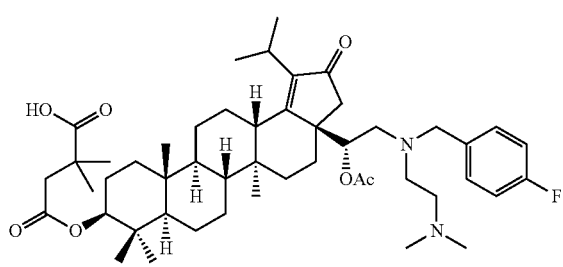

140

Stereochemistry was tentatively assigned as drawn but not fully confirmed spectroscopically. LC/MS: m/z calculated 834.6, found 835 (M+1)+.

Example 72

Compound 141

5-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid

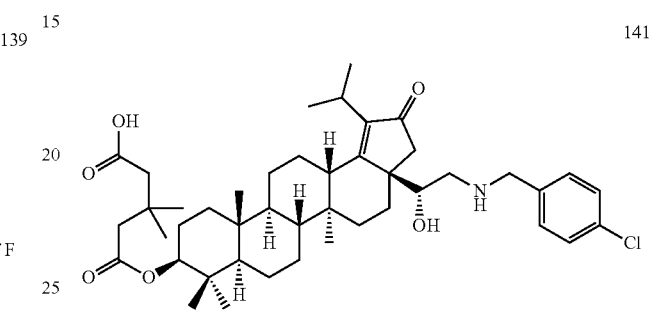

141

Stereochemistry was tentatively assigned as drawn but not fully confirmed spectroscopically. LC/MS: m/z calculated 751.5, found 752.3 (M+1)+.

Example 73

Compound 142

5-(((3aR,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid

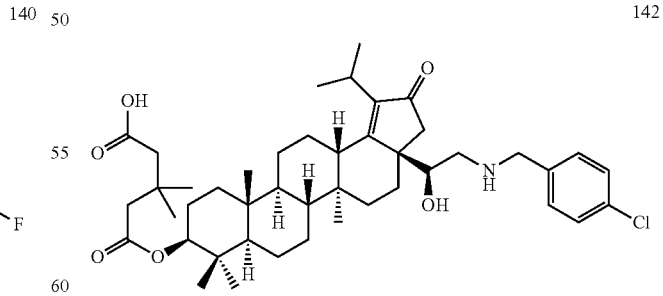

142

Stereochemistry was tentatively assigned as drawn but not fully confirmed spectroscopically. LC/MS: m/z calculated 751.5, found 752.3 (M+1)+.

Example 74

Compound 143

4-(((3aR,5aR,5bR,7aR,9S,11aR,11bR,13aS)-3a-((S)-2-((2,4-dichlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

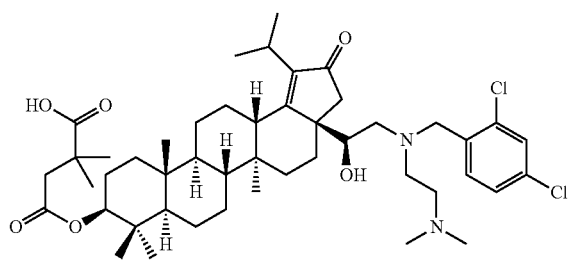

143

Stereochemistry was tentatively assigned as drawn but not fully confirmed spectroscopically. LC/MS: m/z calculated 842.5, found 843.3 (M+1)$^+$.

Example 75

Compound 144

4-(((3aR,5aR,5bR,7aR,9S,11aR,11bR,13aS)-3a-((R)-2-(benzyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

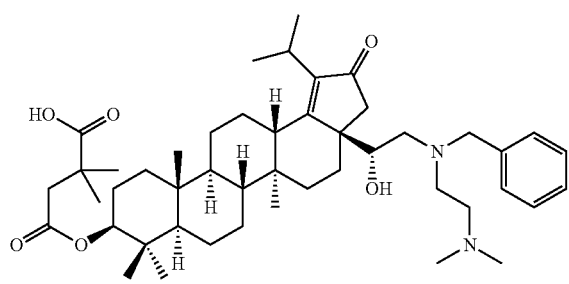

144

Stereochemistry was tentatively assigned as drawn but not fully confirmed spectroscopically. LC/MS: m/z calculated 774.6, found 775.4 (M+1)$^+$.

Example 76

Compound 145

4-(((3aR,5aR,5bR,7aR,9S,11aR,11bR,13aS)-3a-((R)-2-((2-(dimethylamino)ethyl)(4-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

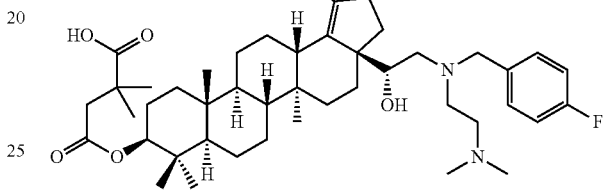

145

Stereochemistry was tentatively assigned as drawn but not fully confirmed spectroscopically. LC/MS: m/z calculated 792.5, found 793.5 (M+1)$^+$.

Example 77

Compound 146

4-(((3aR,5aR,5bR,7aR,9S,11aR,11bR,13aS)-3a-((R)-2-((4-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

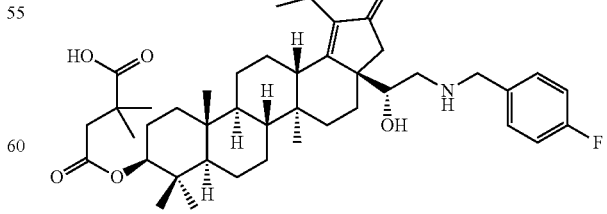

146

Stereochemistry was tentatively assigned as drawn but not fully confirmed spectroscopically. LC/MS: m/z calculated 721.5, found 722.3 (M+1)$^+$.

Example 78

Compound 147

4-(((3aR,5aR,5bR,7aR,9S,11aR,11bR,13aS)-3a-((S)-2-((2-(dimethylamino)ethyl)(4-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

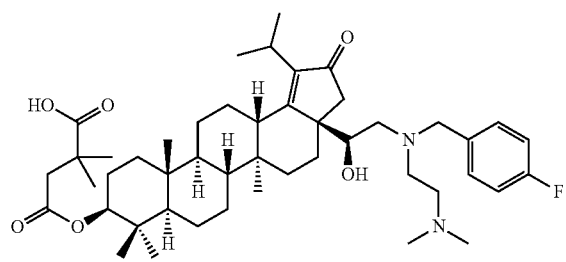

147

Stereochemistry was tentatively assigned as drawn but not fully confirmed spectroscopically. LC/MS: m/z calculated 792.5, found 793.5 (M+1)$^+$.

Example 79

Compound 148

4-(((3aR,5aR,5bR,7aR,9S,11aR,11bR,13aS)-3a-((S)-2-((4-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

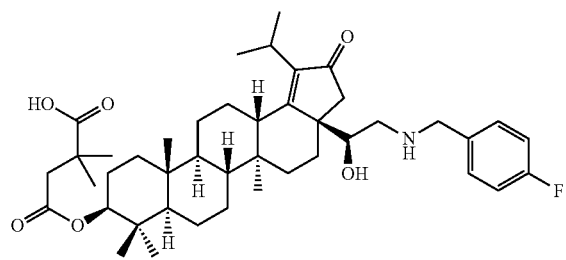

148

Stereochemistry was tentatively assigned as drawn but not fully confirmed spectroscopically. LC/MS: m/z calculated 721.5, found 722.3 (M+1)$^+$.

Example 80

Compound 149

4-(((3aR,5aR,5bR,7aR,9S,11aR,11bR,13aS)-3a-((R)-2-((2,4-dichlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

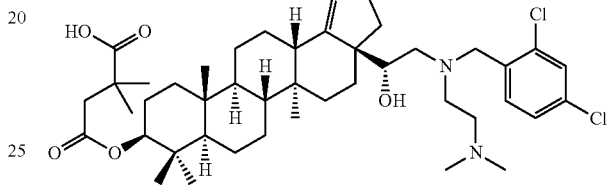

149

Stereochemistry was tentatively assigned as drawn but not fully confirmed spectroscopically. LC/MS: m/z calculated 842.5, found 843.5 (M+1)$^+$.

Example 81

Compound 150

4-(((3aR,5aR,5bR,7aR,9S,11aR,11bR,13aS)-3a-((R)-2-(4-chloro-N-(2-(dimethylamino)ethyl)benzamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

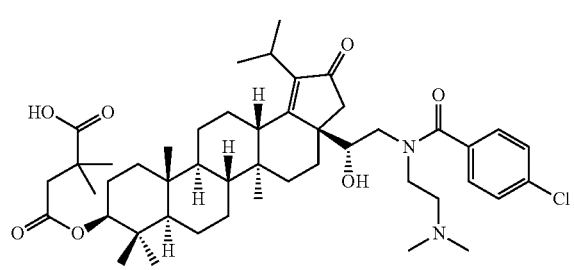

150

Stereochemistry was tentatively assigned as drawn but not fully confirmed spectroscopically. LC/MS: m/z calculated 822.5, found 823.4 (M+1)$^+$.

Example 82

Compound 151

4-(((3aR,5aR,5bR,7aR,9S,11aR,11bR,13aS)-3a-(2-((2-chlorobenzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

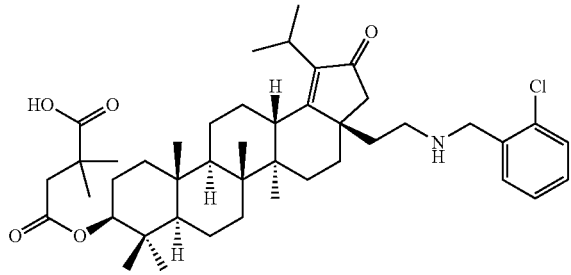

151

LC/MS: m/z calculated 721.5, found 722.3 (M+1)$^+$.

Example 83

Compound 152

4-(((3aR,5aR,5bR,7aR,9S,11aR,11bR,13aS)-3a-(2-benzamidoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

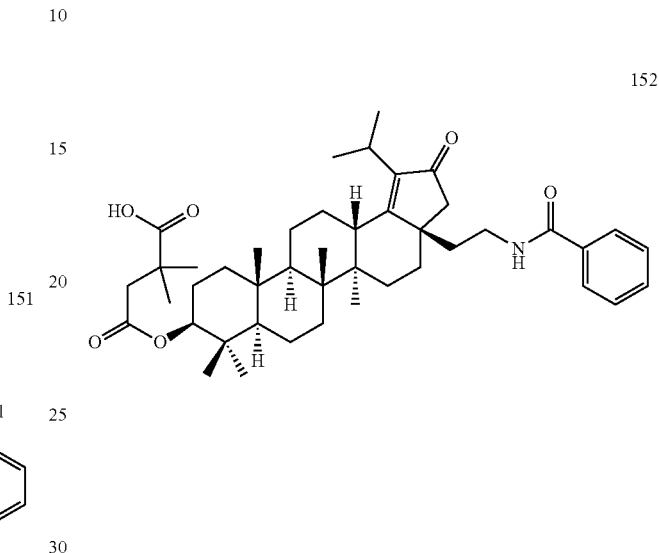

152

LC/MS: m/z calculated 701.5, found 702.5 (M+1)$^+$.

Example 84

Compound 153

4-(((3aR,5aR,5bR,7aR,9S,11aR,11bR,13aS)-3a-(((((R)-1-(4-Chlorophenyl)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

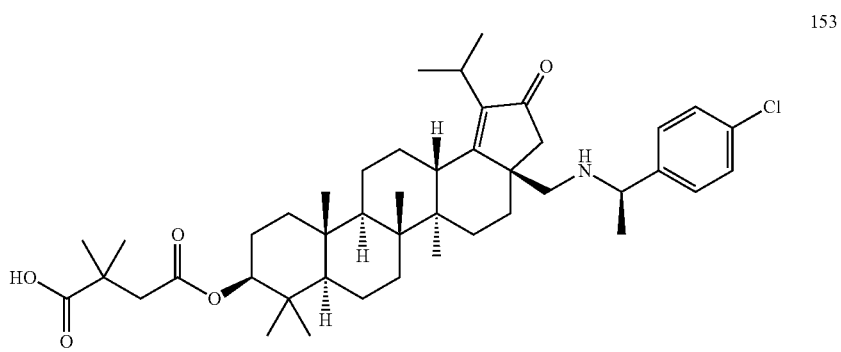

153

LC/MS: m/z calculated 721.5, found 722.3 (M+1)$^+$.

Example 85

Compound 154

4-(((3aR,5aR,5bR,7aR,9S,11aR,11bR,13aS)-3a-((N-(4-chlorobenzyl)acetamido)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

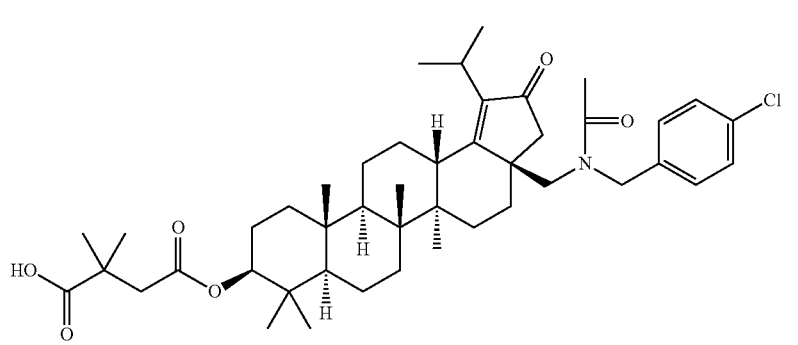

154

LC/MS: m/z calculated 749.4, found 750.3 (M+1)$^+$.

Example 86

Compound 155

4-(((3aR,5aR,5bR,7aR,9S,11aR,11bR,13aS)-3a-(((4-chlorobenzyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

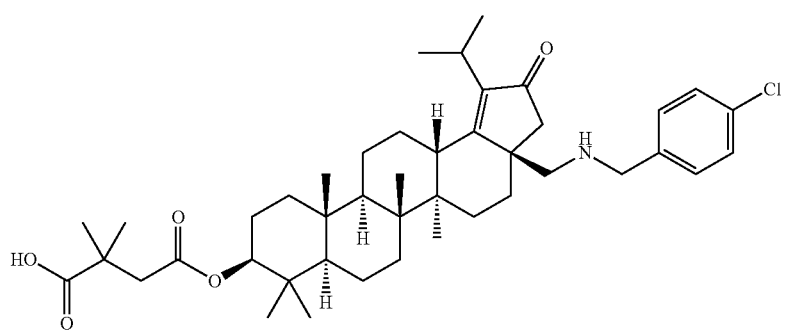

155

LC/MS: m/z calculated 707.4, found 708.3 (M+1)$^+$.

Example 87

Compound 156

4-(((3aR,5aR,5bR,7aR,9S,11aR,11bR,13aS)-3a-((N-(4-chlorophenethyl)acetamido)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

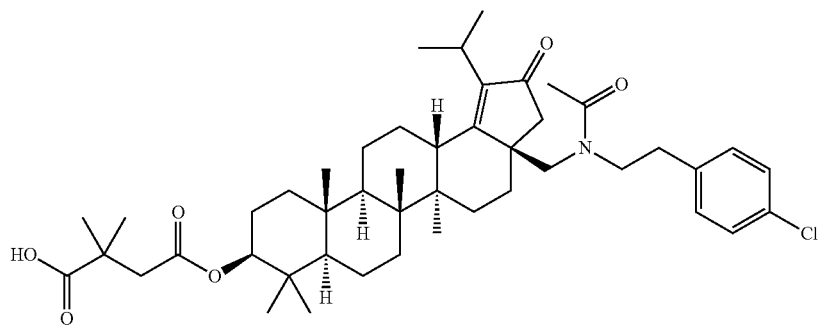

156

LC/MS: m/z calculated 763.5, found 764.3 $(M+1)^+$.

Example 88

Compound 157

4-(((3aR,5aR,5bR,7aR,9S,11aR,11bR,13aS)-3a-(((4-chlorophenethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

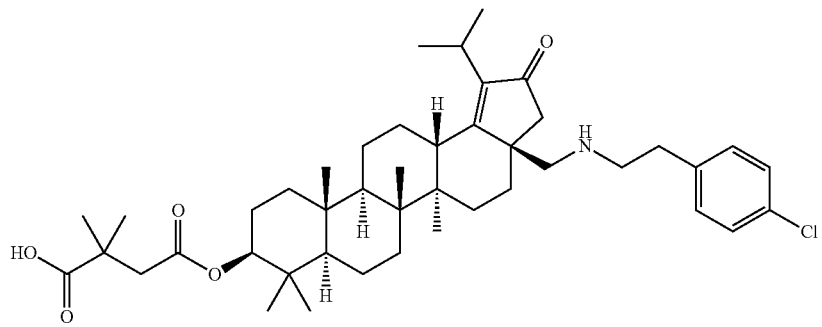

157

LC/MS: m/z calculated 721.5, found 722.3 $(M+1)^+$

Example 89

Compound 158

4-(((3aR,5aR,5bR,7aR,9S,11aR,11bR,13aS)-3a-((R)-2-((4-chlorobenzyl)(3-methoxypropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

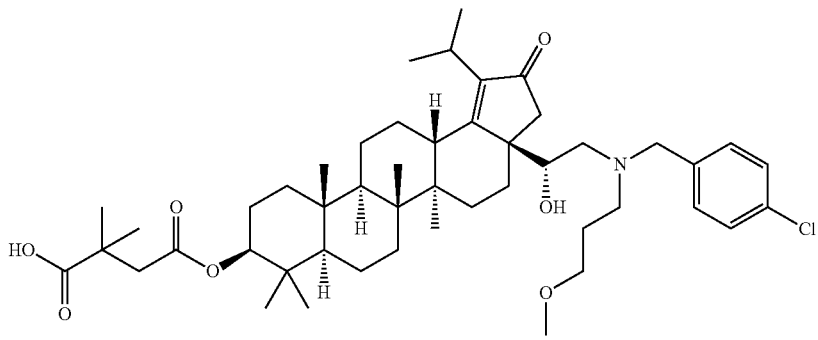

158

LC/MS: m/z calculated 809.50, found 810.7 (M+1)$^+$

Example 90

Compound 159

4-(((3aR,5aR,5bR,7aR,9S,11aR,11bR,13aS)-3a-((S)-2-((4-chlorobenzyl)(3-methoxypropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

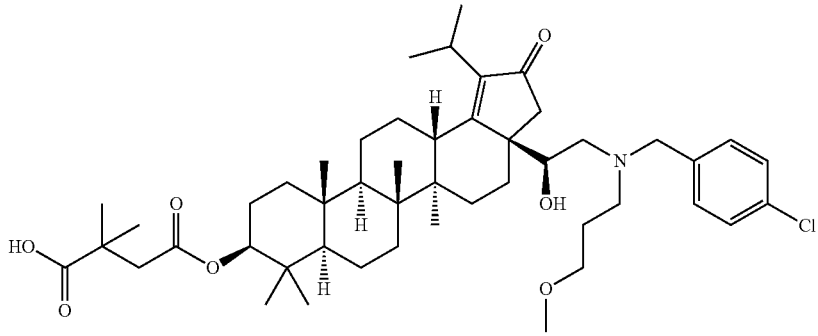

159

LC/MS: m/z calculated 809.5, found 810.4 (M+1)$^+$

Example 91

Compound 160

4-(((3aR,5aR,5bR,7aR,9S,11aR,11bR,13aS)-3a-((R)-2-((4-chlorobenzyl)(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

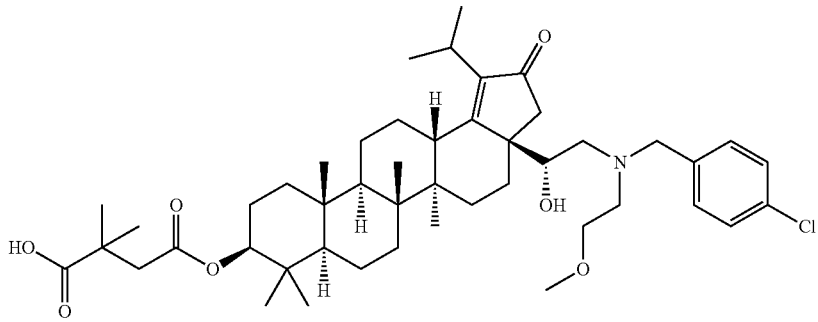

160

LC/MS: m/z calculated 795.5, found 796.3 (M+1)$^+$

Example 92

Compound 161

4-(((3aR,5aR,5bR,7aR,9S,11aR,11bR,13aS)-3a-((S)-2-((4-chlorobenzyl)(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

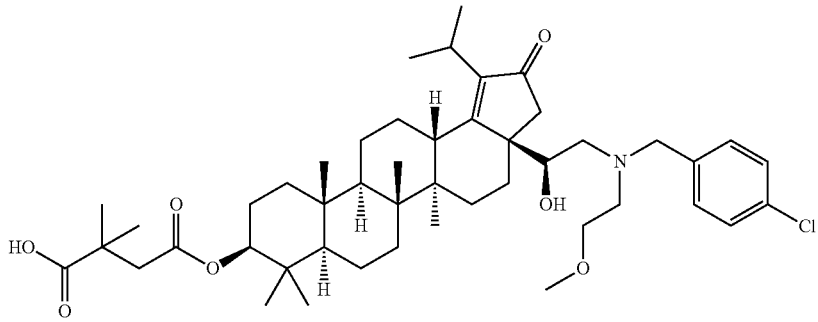

161

LC/MS: m/z calculated 795.5, found 796.3 (M+1)$^+$

Example 93

Compound 162

4-(((3aR,5aR,5bR,7aR,9S,11aR,11bR,13aS)-3a-((S)-2-(4-chloro-N-(2-(dimethylamino)ethyl)benzamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

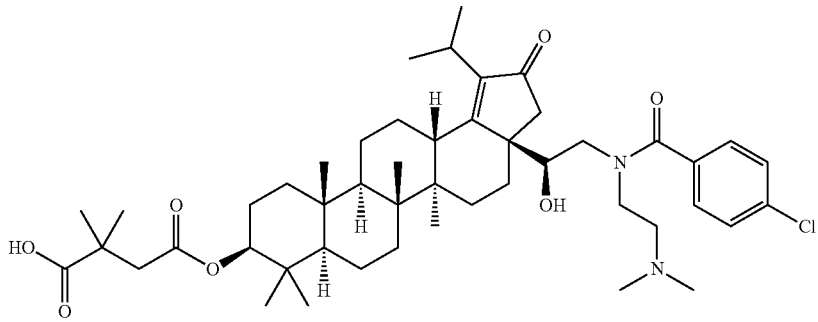

162

LC/MS: m/z calculated 822.5, found 823.5 (M+1)$^+$

Example 94

Compound 163

4-(((3aS,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

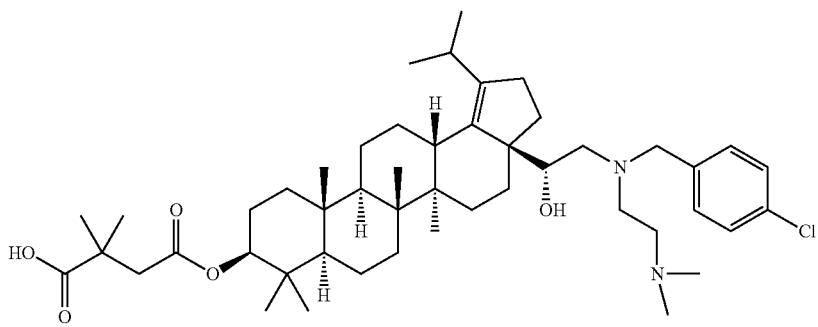

163

LC/MS: m/z calculated 794.5, found 795.5 (M+1)$^+$

Example 95

Compound 164

4-(((3aR,5aR,5bR,7aR,9S,11aR,11bR,13aS)-3a-((R)-2-((4-chlorobenzyl)((R)-pyrrolidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

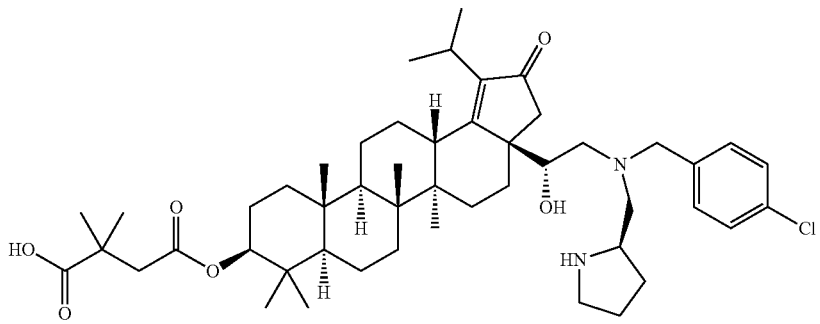

164

LC/MS: m/z calculated 820.5, found 821.5 (M+1)$^+$

Example 96

Compound 165

4-(((3aR,5aR,5bR,7aR,9S,11aR,11bR,13aS)-3a-((S)-2-((4-chlorobenzyl)((R)-pyrrolidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

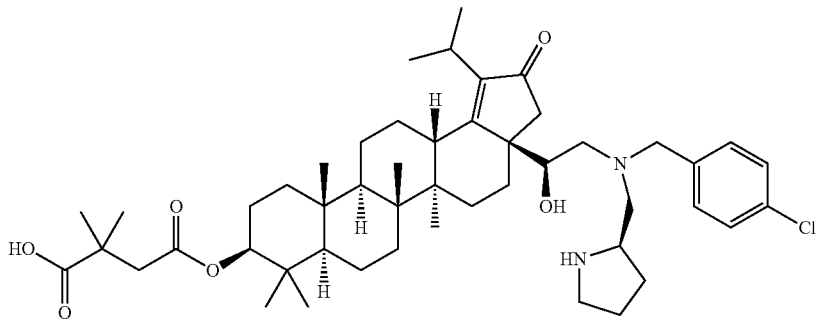

165

LC/MS: m/z calculated 820.5, found 821.5 (M+1)$^+$

Example 97

Compound 166

4-(((3aR,5aR,5bR,7aR,9S,11aR,11bR,13aS)-3a-((R)-2-((4-chlorobenzyl)(2-hydroxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

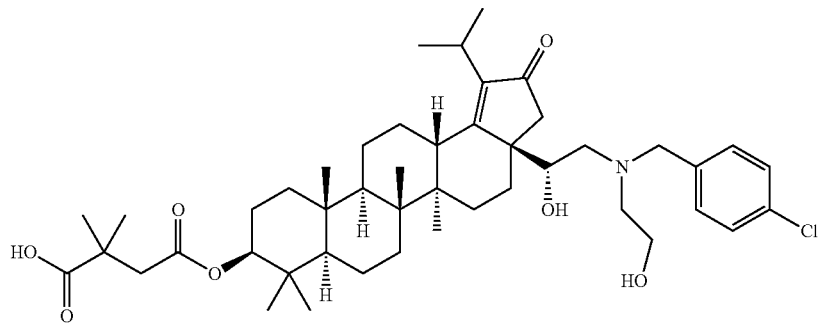

166

LC/MS: m/z calculated 781.5, found 782.5 (M+1)$^+$

Example 98

Compound 167

4-(((3aR,5aR,5bR,7aR,9S,11aR,11bR,13aS)-3a-((R)-4-(4-chlorobenzyl)-5,6-dioxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

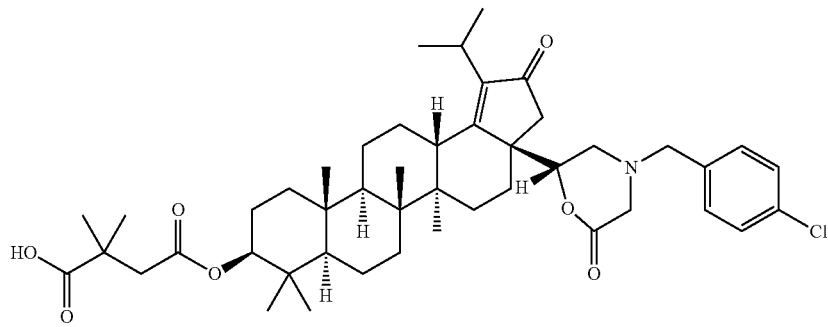

167

LC/MS: m/z calculated 791.4, found 792.5 (M+1)$^+$

Example 99

Compound 168

4-(((3aR,5aR,5bR,7aR,9S,11aR,11bR,13aS)-3a-((S)-2-(((5-chloropyridin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

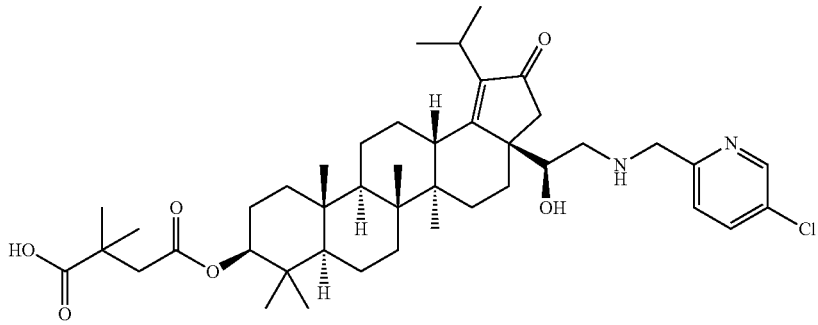

168

LC/MS: m/z calculated 738.4, found 739.5 (M+1)$^+$

Example 100

Compound 169

4-(((3aR,5aR,5bR,7aR,9S,11aR,11bR,13aS)-3a-((R)-4-(4-chlorobenzyl)-5-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

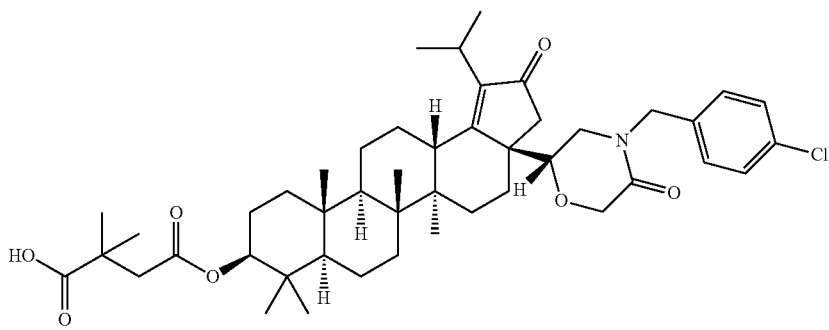

169

LC/MS: m/z calculated 777.4, found 778.6 (M+1)$^+$

Example 101

Compound 170

4-(((3aR,5aR,5bR,7aR,9S,11aR,11bR,13aS)-3a-((R)-4-(4-chlorobenzyl)-6-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

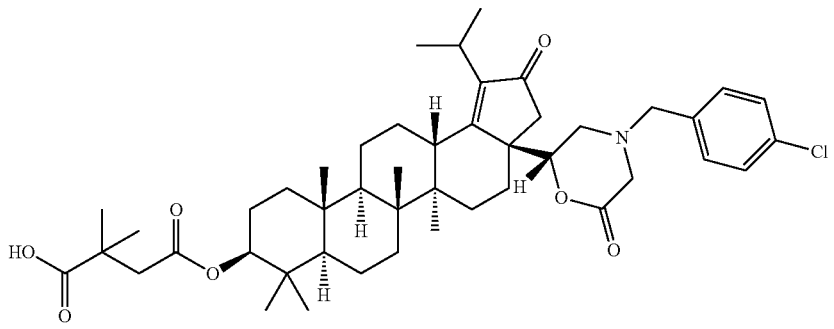

170

LC/MS: m/z calculated 777.4, found 777.9 (M+1)$^+$

Example 102

Compound 171

4-(((3aR,5aR,5bR,7aR,9S,11aR,11bR,13aS)-3a-((S)-4-(4-chlorobenzyl)-5-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

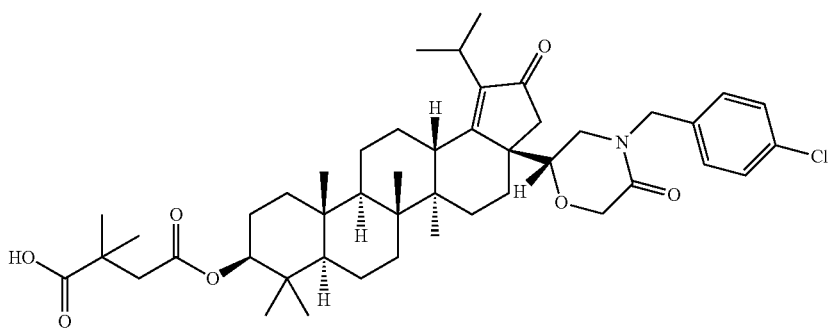

171

LC/MS: m/z calculated 777.4, found 777.9 (M+1)$^+$

Example 103

Compound 172

4-(((3aR,5aR,5bR,7aR,9S,11aR,11bR,13aS)-3a-((R)-2-(((5-chloropyridin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

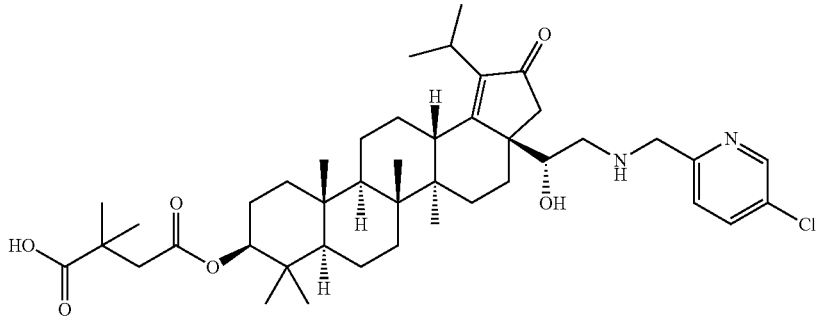

172

LC/MS: m/z calculated 737.4, found 739.4 (M+1)$^+$

Example 104

Compound 173

4-(((3aR,5aR,5bR,7aR,9S,11aR,11bR,13aS)-3a-((S)-2-((4-chlorobenzyl)(2-hydroxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

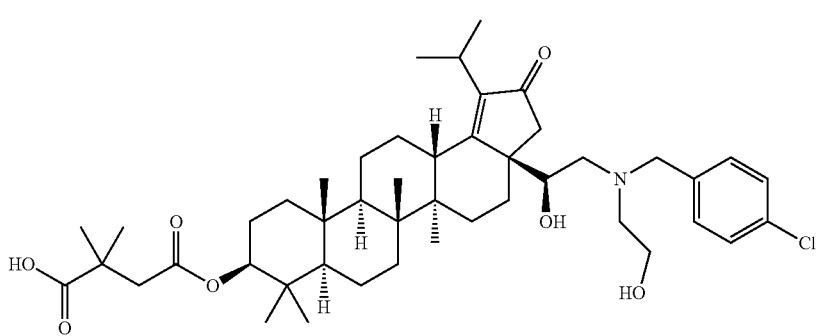

173

LC/MS: m/z calculated 781.5, found 782.3 (M+1)$^+$

Example 105

Compound 174

4-(((3aR,5aR,5bR,7aR,9S,11aR,11bR,13aS)-3a-(((4-chlorobenzyl)(2-(dimethylamino)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

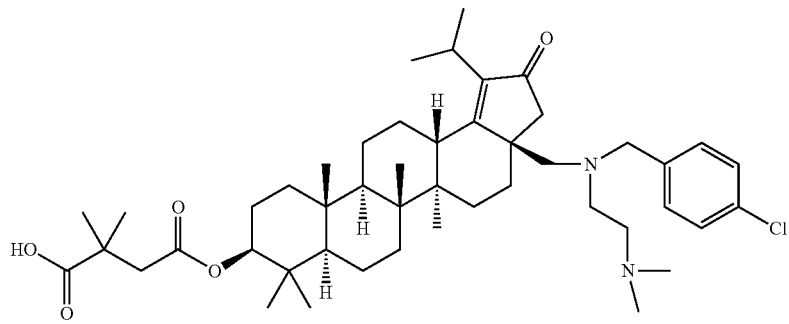

174

LC/MS: m/z calculated 778.5, found 779.5 (M+1)$^+$

Example 106

Compound 175

4-(((3aR,5aR,5bR,7aR,9S,11aR,11bR,13aS)-3a-(((4-chlorophenethyl)(2-(dimethylamino)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

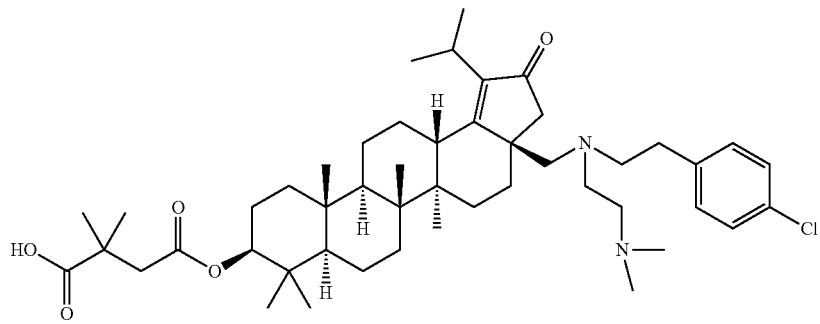

175

LC/MS: m/z calculated 792.5, found 793.5 (M+1)$^+$

Example 107

Compound 176

4-(((3aR,5aR,5bR,7aR,9S,11aR,11bR,13aS)-3a-((S)-2-(N-(4-chlorobenzyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

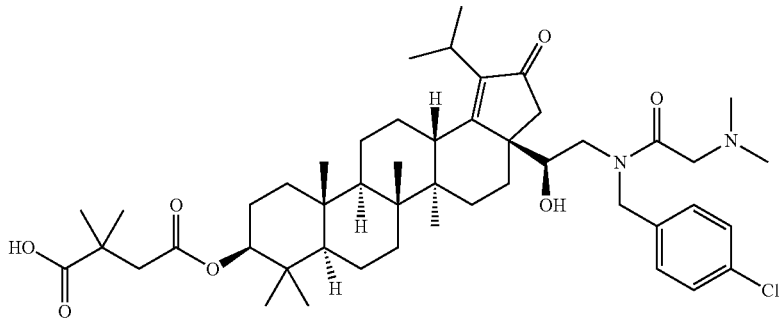

176

LC/MS: m/z calculated 822.5, found 823.5 (M+1)$^+$

Example 108

Compound 177

4-(((3aR,5aR,5bR,7aR,9S,11aR,11bR,13aS)-3a-((R)-2-(N-(4-chlorobenzyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

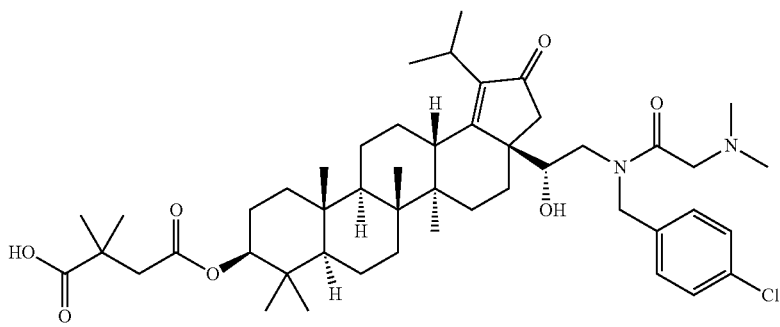

177

LC/MS: m/z calculated 822.5, found 823.5 (M+1)$^+$

Example 109

Compound 178

4-(((3aR,5aR,5bR,7aR,9S,11aR,11bR,13aS)-3a-((R)-2-((4-chlorobenzyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

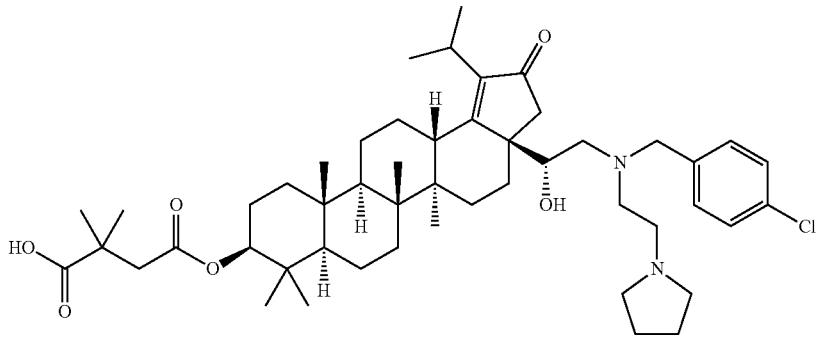

178

LC/MS: m/z calculated 834.5, found 835.5 (M+1)$^+$

Example 110

Compound 179

4-(((3aR,5aR,5bR,7aR,9S,11aR,11bR,13aS)-3a-((S)-2-((4-chlorobenzyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

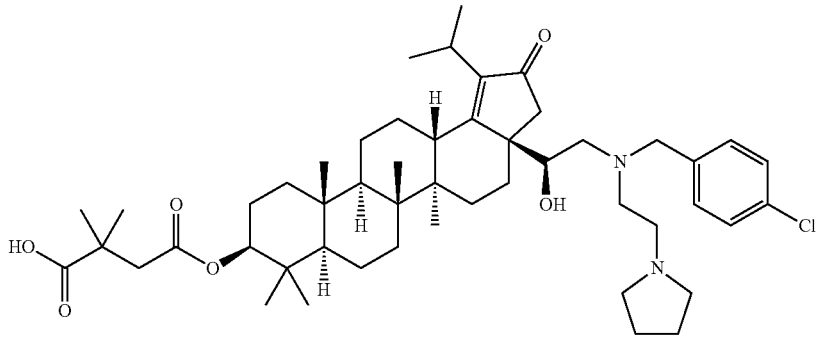

179

LC/MS: m/z calculated 834.5, found 835.5 (M+1)$^+$

Example 111

Compound 180

4-(((3aR,5aR,5bR,7aR,9S,11aR,11bR,13aS)-3a-((R)-2-((4-chlorobenzyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

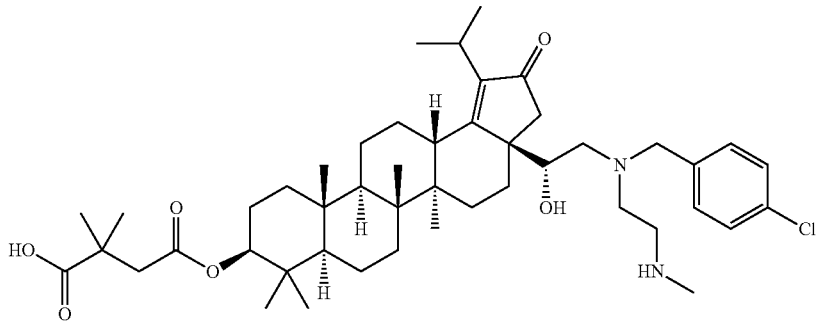

180

LC/MS: m/z calculated 794.5, found 795.4 (M+1)$^+$

Example 112

Compound 181

4-(((3aR,5aR,5bR,7aR,9S,11aR,11bR,13aS)-3a-((S)-2-((2-aminoethyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

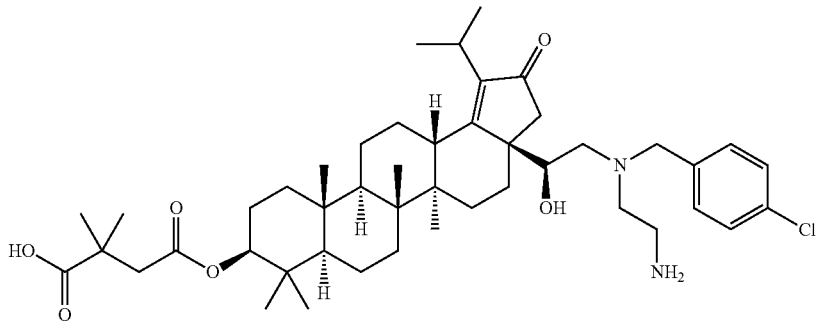

181

LC/MS: m/z calculated 780.5, found 781.4 (M+1)$^+$

Example 113

Compound 182

4-(((3aR,5aR,5bR,7aR,9S,11aR,11bR,13aS)-3a-((R)-2-((2-aminoethyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

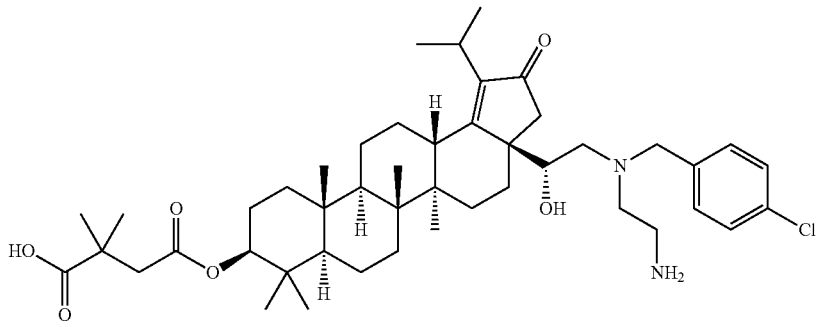

182

LC/MS: m/z calculated 780.5, found 781.4 $(M+1)^+$

Example 114

Compound 183

4-(((3aR,5aR,5bR,7aR,9S,11aR,11bR,13aS)-3a-((S)-2-((4-chlorobenzyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

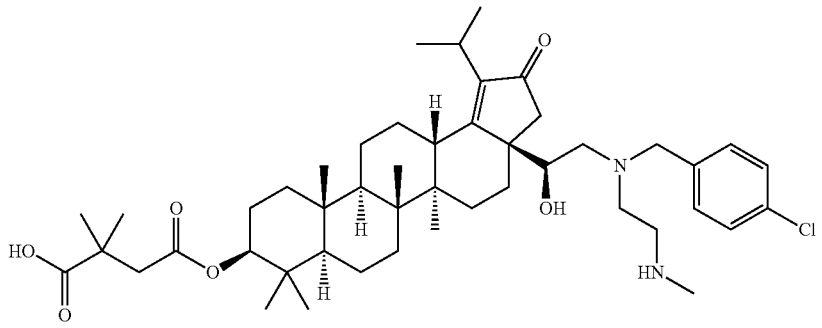

183

LC/MS: m/z calculated 794.5, found 795.5 $(M+1)^+$

Example 115

Compound 184

4-(((3aR,5aR,5bR,7aR,9S,11aR,11bR,13aS)-3a-((R)-2-((4-chlorobenzyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

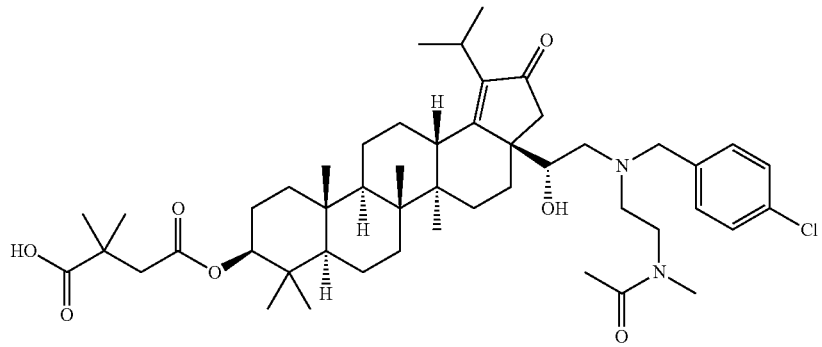

184

LC/MS: m/z calculated 836.5, found 837.5 $(M+1)^+$

Example 116

Compound 185

4-(((3aR,5aR,5bR,7aR,9S,11aR,11bR,13aS)-3a-((S)-2-((4-chlorobenzyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

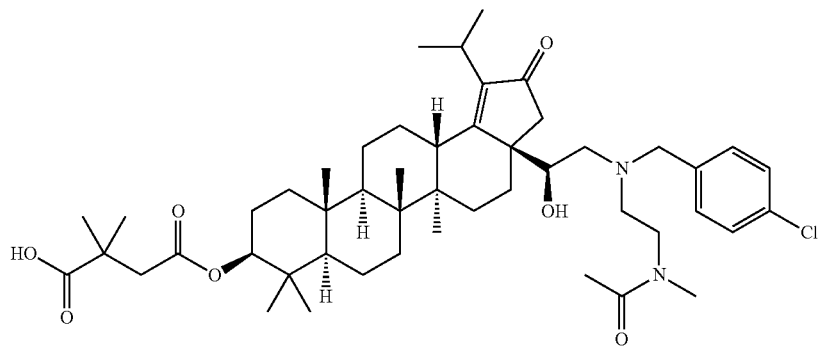

185

LC/MS: m/z calculated 836.5, found 837.5 $(M+1)^+$

Example 117

Compound 186

4-(((3aR,5aR,5bR,7aR,9S,11aR,11bR,13aS)-3a-((S)-2-(((S)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

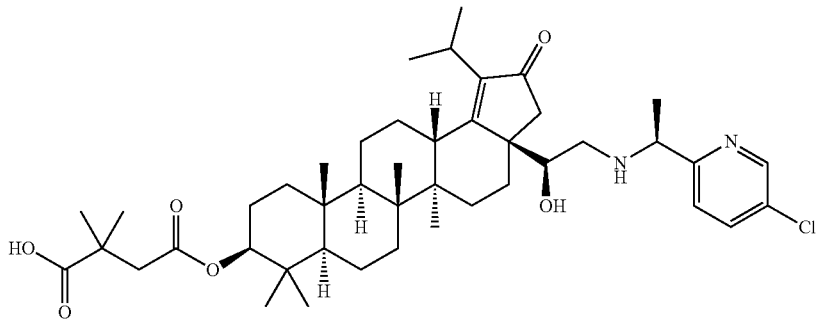

186

LC/MS: m/z calculated 752.5, found 753.4 (M+1)⁺

Example 118

Compound 187

4-(((3aR,5aR,5bR,7aR,9S,11aR,11bR,13aS)-3a-((R)-2-(((S)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

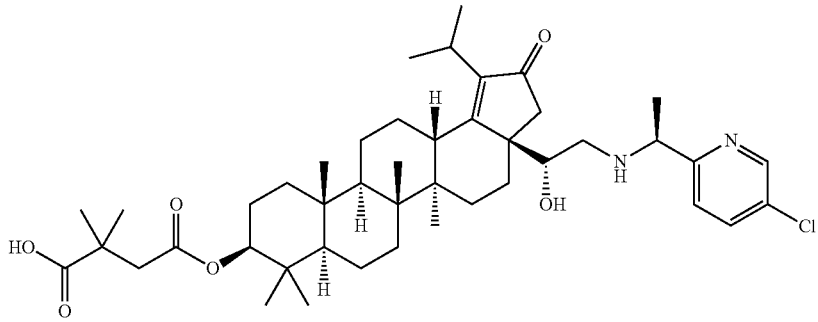

187

LC/MS: m/z calculated 752.5, found 753.4 (M+1)⁺

Example 119

Compound 188

4-(((3aR,5aR,5bR,7aR,9S,11aR,11bR,13aS)-3a-((R)-2-((2-(dimethylamino)ethyl)(phenethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

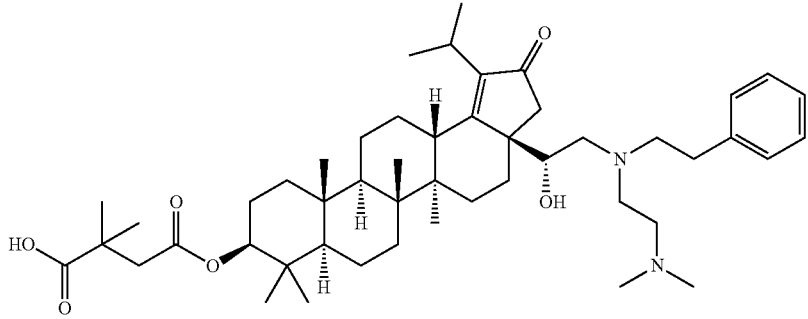

188

LC/MS: m/z calculated 788.6, found 789.5 (M+1)$^+$

Example 120

Compound 189

4-(((3aR,5aR,5bR,7aR,9S,11aR,11bR,13aS)-3a-((S)-2-(cyclohexyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

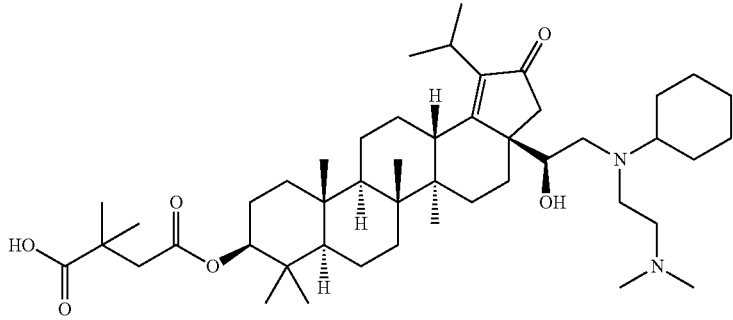

189

LC/MS: m/z calculated 766.6, found 767.6 (M+1)$^+$

Example 121

Compound 190

4-(((3aR,5aR,5bR,7aR,9S,11aR,11bR,13aS)-3a-((R)-2-(cyclohexyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

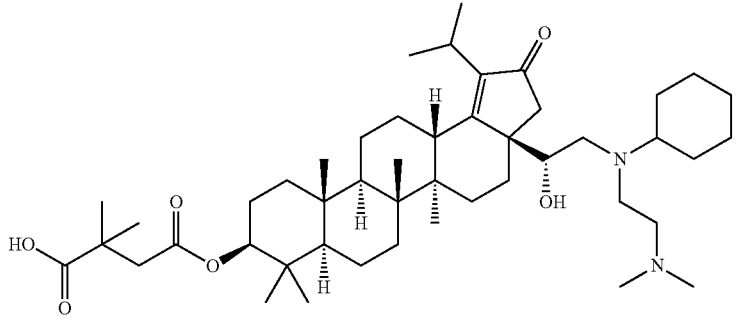

LC/MS: m/z calculated 766.6, found 767.6 (M+1)+

Example 122

Compound 191

4-(((3aR,5aR,5bR,7aR,9S,11aR,11bR,13aS)-3a-((S)-2-(((5-chloropyridin-2-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

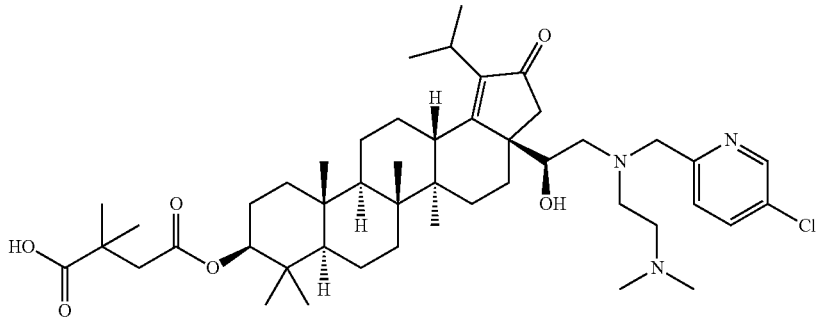

LC/MS: m/z calculated 809.5, found 810.5 (M+1)+

Example 123

Compound 192

4-(((3aR,5aR,5bR,7aR,9S,11aR,11bR,13aS)-3a-(2-(N-(4-chlorobenzyl)-2-(dimethylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

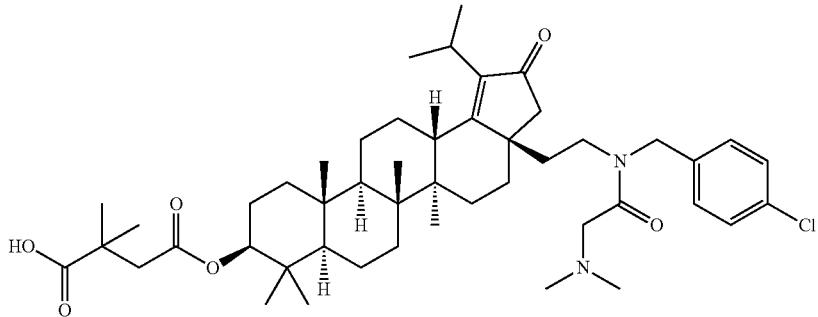

192

LC/MS: m/z calculated 806.5, found 807.4 (M+1)$^+$

Example 124

Compound 193

4-(((3aR,5aR,5bR,7aR,9S,11aR,11bR,13aS)-3a-(2-(2-amino-N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

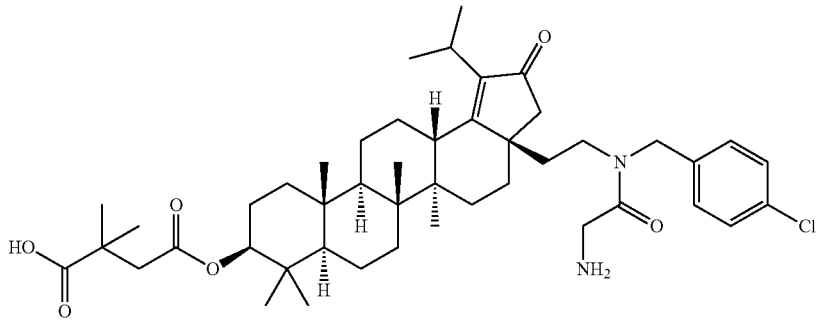

193

LC/MS: m/z calculated 778.5, found 779.4 (M+1)$^+$

Example 125

Compound 194

4-(((3aR,5aR,5bR,7aR,9S,11aR,11bR,13aS)-3a-(2-(N-(4-chlorobenzyl)-2-(methylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

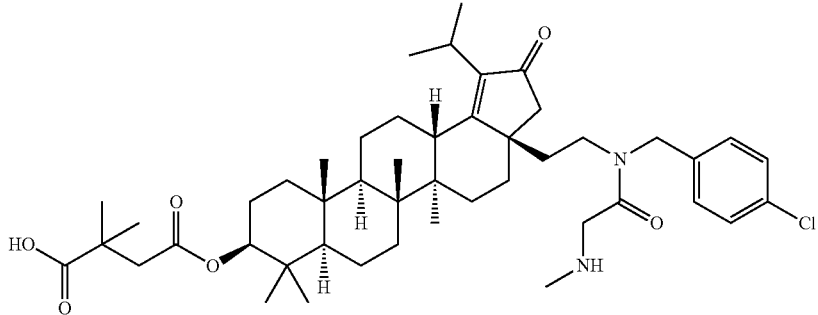

194

LC/MS: m/z calculated 792.5, found 793.4 (M+1)$^+$

Example 126

Compound 195

4-(((3aR,5aR,5bR,7aR,9S,11aR,11bR,13aS)-3a-((S)-2-(((S)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

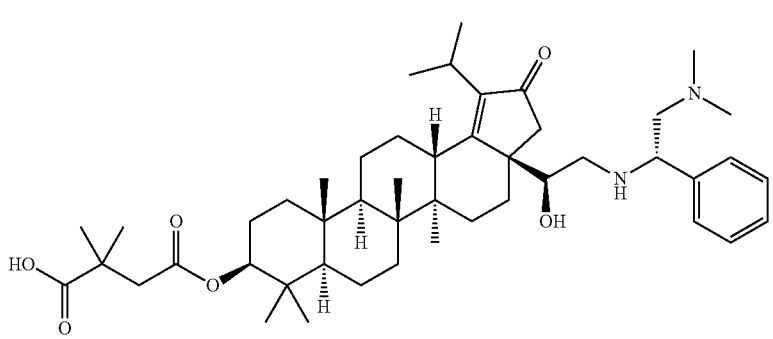

195

LC/MS: m/z calculated 760.5, found 761.5 (M+1)$^+$

Example 127

Compound 196

4-(((3aR,5aR,5bR,7aR,9S,11aR,11bR,13aS)-3a-((R)-2-(((R)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

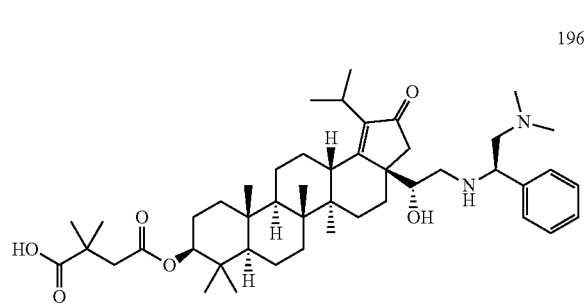

196

LC/MS: m/z calculated 760.5, found 761.5 (M+1)$^+$

Example 128

Compound 197

4-(((3aR,5aR,5bR,7aR,9S,11aR,11bR,13aS)-3a-((R)-2-(((R)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

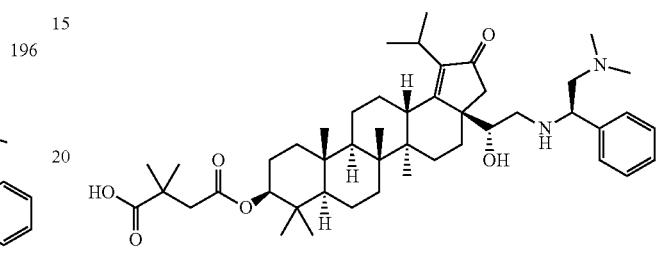

197

LC/MS: m/z calculated 760.5, found 761.5 (M+1)$^+$

Example 129

Compound 198

4-(((3aR,5aR,5bR,7aR,9S,11aR,11bR,13aS)-3a-((R)-2-((4-chlorobenzyl)(3-(dimethylamino)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

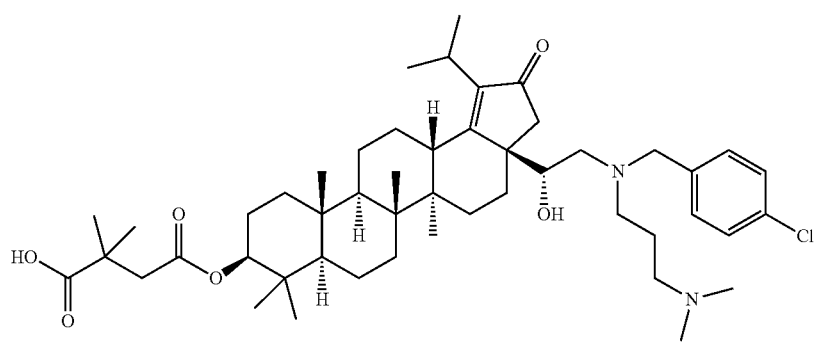

198

LC/MS: m/z calculated 822.5, found 823.5 (M+1)$^+$

Example 130

Compound 199

4-(((3aR,5aR,5bR,7aR,9S,11aR,11bR,13aS)-3a-((S)-2-((4-chlorobenzyl)(3-(dimethylamino)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

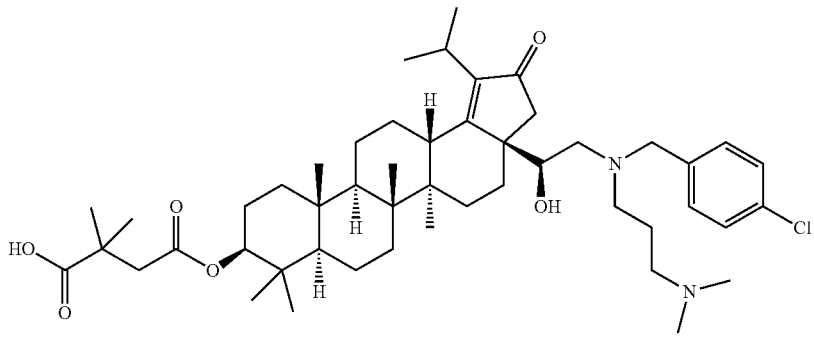

199

LC/MS: m/z calculated 822.5, found 823.5 (M+1)$^+$

Example 131

Compound 200

4-(((3aR,5aR,5bR,7aR,9S,11aR,11bR,13aS)-1-isopropyl-5a,5b,8,8,11a-pentamethyl-2-oxo-3a-(2-(phenethylamino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 132

Compound 201

4-(((3aR,5aR,5bR,7aR,9S,11aR,11bR,13aS)-3a-((R)-2-((2-(dimethylamino)ethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

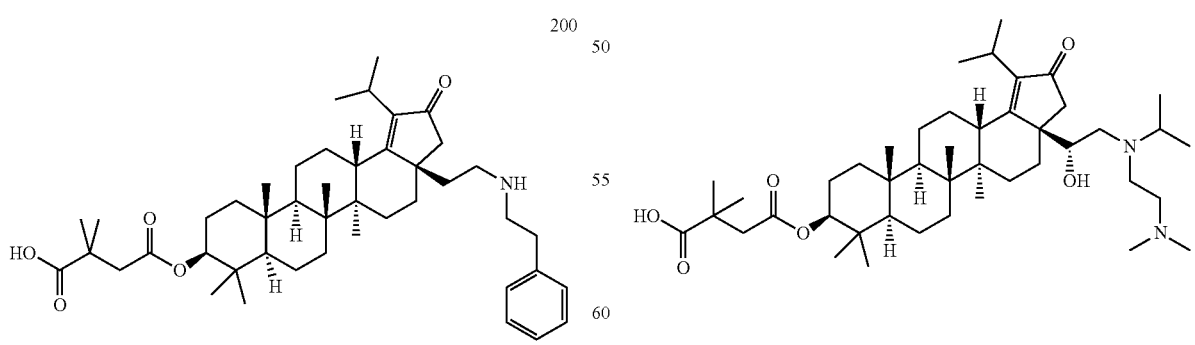

LC/MS: m/z calculated 701.5, found 702.5 (M+1)$^+$

LC/MS: m/z calculated 726.5, found 727.5 (M+1)$^+$

Example 133

Compound 202

2-(((R)-2-((3aR,5aR,5bR,7aR,9S,11aR,11bR,13aS)-9-((3-carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-hydroxyethyl)(4-chlorobenzyl)amino)-N,N,N-trimethylethanaminium trifluoroacetate.

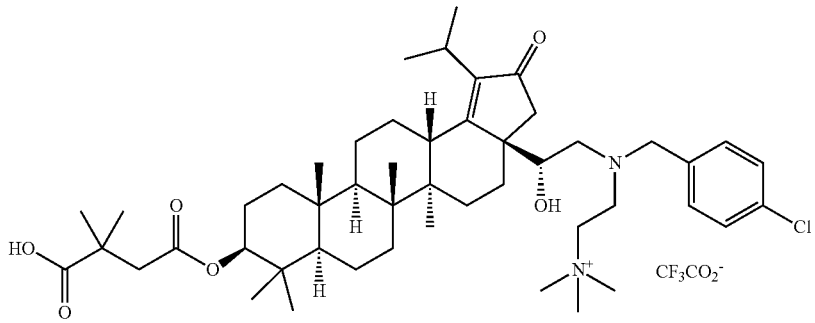

202

LC/MS: m/z calculated 823.5, found 823.5 $(M)^+$

Example 134

Compound 203

4-(((3aR,5aR,5bR,7aR,9S,11aR,11bR,13aS)-3a-((S)-4-(4-chlorobenzyl)-6-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

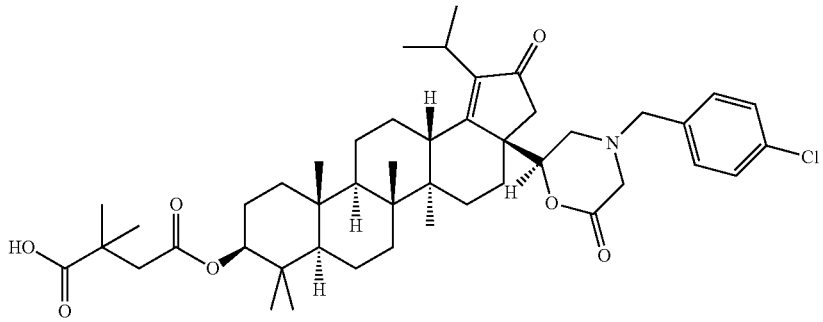

203

LC/MS: m/z calculated 777.4, found 778.4 $(M+1)^+$

Example 135

Compound 204

4-(((3aR,5aR,5bR,7aR,9S,11aR,11bR,13aS)-3a-((R)-2-(((S)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

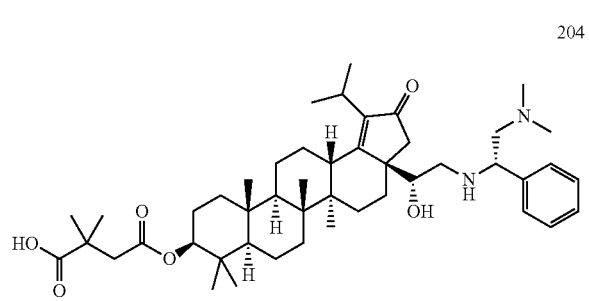

LC/MS: m/z calculated 760.5, found 761.4 (M+1)+

Example 136

Compound 205

4-(((3aR,5aR,5bR,7aR,9S,11aR,11bR,13aS)-3a-((S)-2-((2-(dimethylamino)ethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

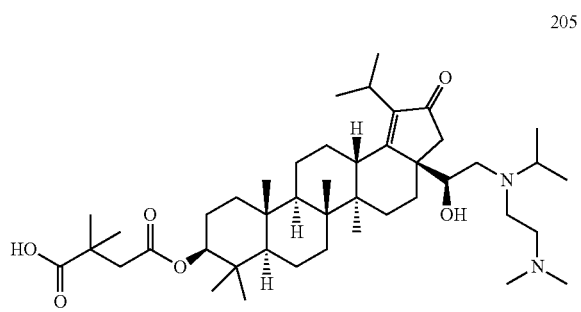

LC/MS: m/z calculated 726.6, found 727.5 (M+1)+

Example 137

Compound 206

4-(((3aR,5aR,5bR,7aR,9S,11aR,11bR,13aS)-3a-((R)-2-(((5-chloropyridin-2-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

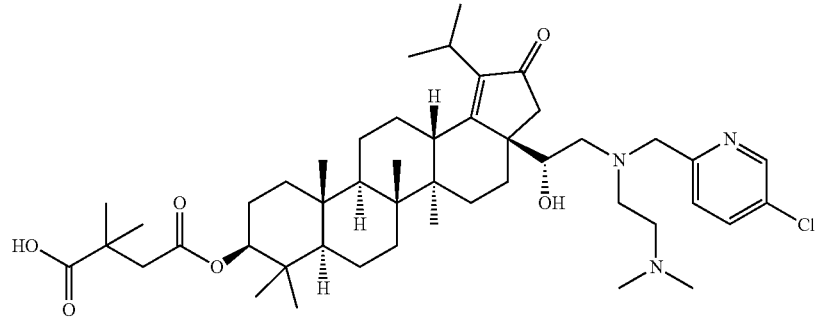

LC/MS: m/z calculated 809.5, found 810.5 (M+1)+

275

Example 138

Compound 207

4-(((3aR,5aR,5bR,7aR,9S,11aR,11bR,13aS)-3a-((S)-1-hydroxy-2-(isopropylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

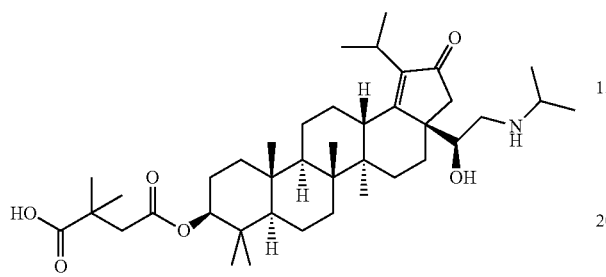

LC/MS: m/z calculated 655.5, found 656.4 (M+1)$^+$

Example 139

Compound 208

4-(((3aR,5aR,5bR,7aR,9S,11aR,11bR,13aS)-3a-(2-(((R)-2-(dimethylamino)-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

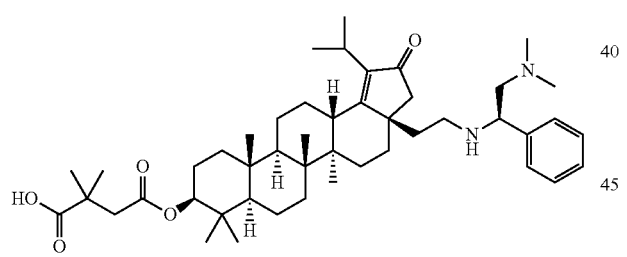

LC/MS: m/z calculated 744.5, found 745.5 (M+1)$^+$

276

Example 140

Compound 209

4-(((3aR,5aR,5bR,7aR,9S,11aR,11bR,13aS)-3a-(2-(((S)-2-(dimethylamino)-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

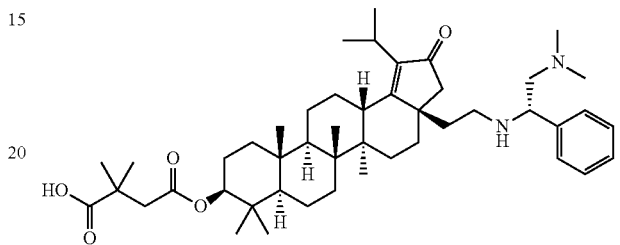

LC/MS: m/z calculated 744.5, found 745.5 (M+1)$^+$

Example 141

Compound 210

2-(((S)-2-((3aR,5aR,5bR,7aR,9S,11aR,11bR,13aS)-9-((3-carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-hydroxyethyl)(4-chlorobenzyl)amino)-N,N,N-trimethylethanaminium trifluoroacetate.

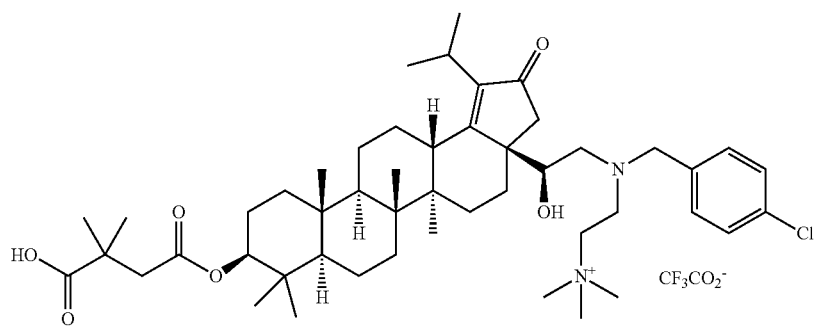

LC/MS: m/z calculated 823.5, found 823.5 (M)$^+$

Example 142

Compound 211

4-(((3aR,5aR,5bR,7aR,9S,11aR,11bR,13aS)-3a-((R)-4-(4-chlorobenzyl)-6-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

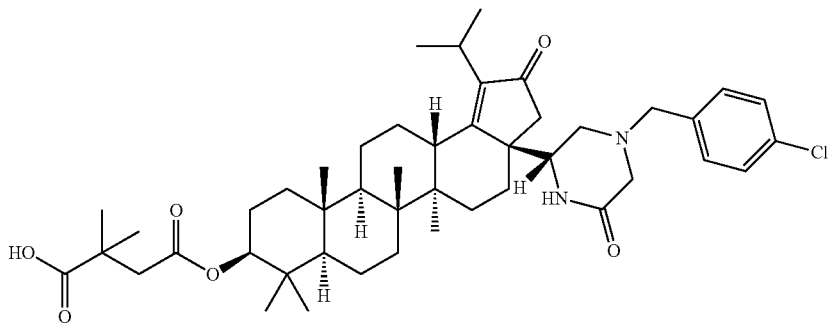

211

LC/MS: m/z calculated 776.5, found 777.4 (M+1)$^+$

Example 143

Compound 212

4-(((3aR,5aR,5bR,7aR,9S,11aR,11bR,13aS)-3a-((S)-4-(4-chlorobenzyl)-1-methyl-6-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

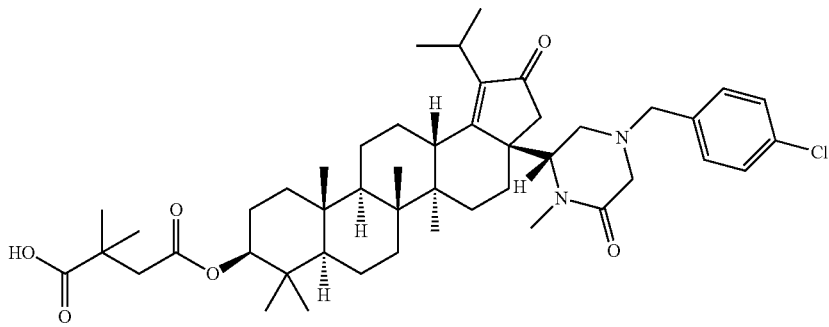

212

LC/MS: m/z calculated 790.5, found 791.4 (M+1)$^+$

Example 144

Compound 213

4-(((3aR,5aR,5bR,7aR,9S,11aR,11bR,13aS)-3a-((R)-2-((4-chlorobenzyl)(2-(dimethylamino)ethyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

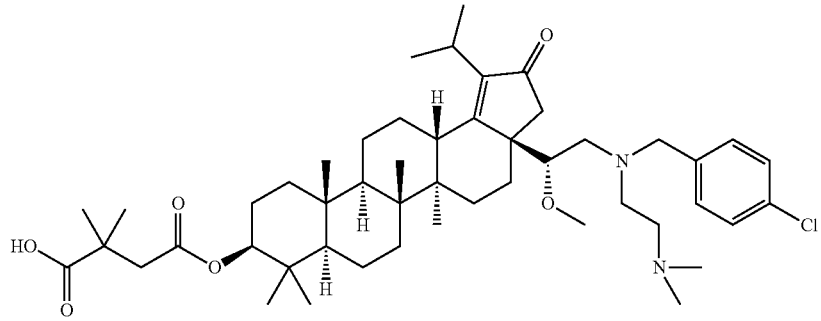

213

LC/MS: m/z calculated 822.5, found 823.5 (M+1)+

Example 145

Compound 214

4-(((3aR,5aR,5bR,7aR,9S,11aR,11bR,13aS)-3a-((S)-1-hydroxy-2-(piperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 146

Compound 215

4-(((3aR,5aR,5bR,7aR,9S,11aR,11bR,13aS)-3a-((R)-1-hydroxy-2-(piperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

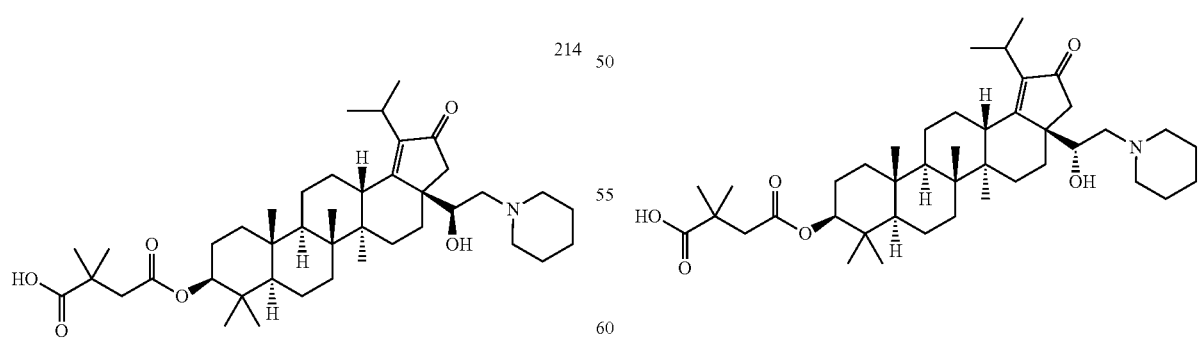

214

215

LC/MS: m/z calculated 681.5, found 682.5 (M+1)+

LC/MS: m/z calculated 681.5, found 682.5 (M+1)+

Example 147

Compound 216

4-(((3aS,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

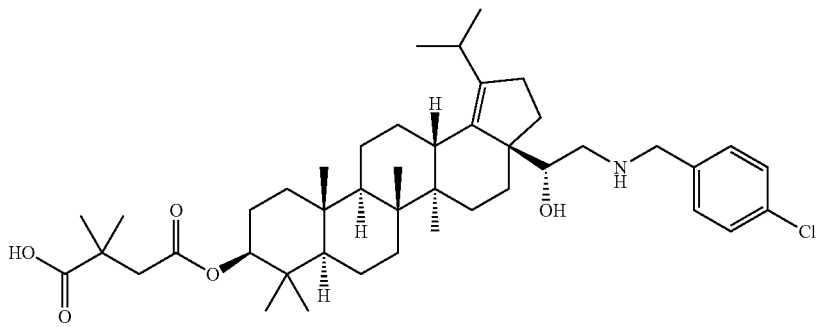

216

LC/MS: m/z calculated 723.5, found 724.4 (M+1)$^+$

Example 148

Compound 217

4-(((3aS,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

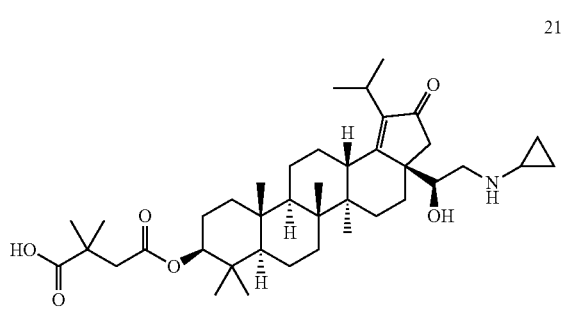

217

LC/MS: m/z calculated 653.5, found 654.4 (M+1)$^+$

Example 149

Compound 218

4-(((3aS,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

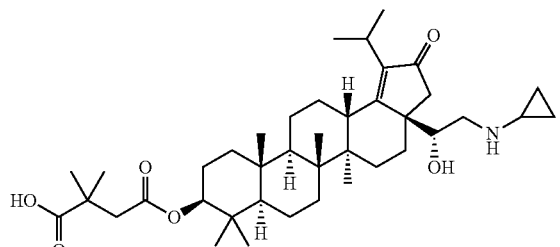

218

LC/MS: m/z calculated 653.5, found 654.4 (M+1)$^+$

Example 150

Compound 219

4-(((3aR,5aR,5bR,7aR,9S,11aR,11bR,13aS)-3a-((S)-2-((4-chlorobenzyl)(2-(dimethylamino)ethyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

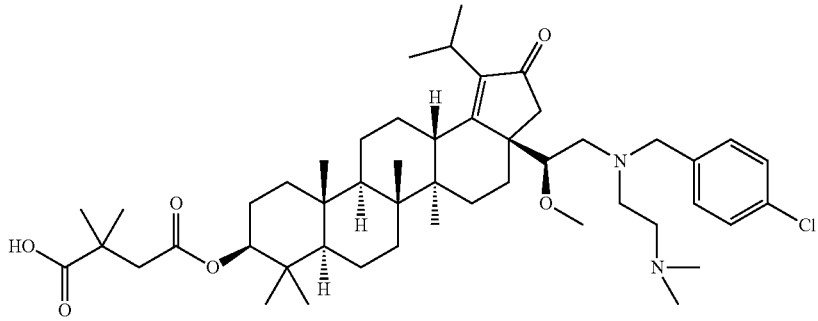

219

LC/MS: m/z calculated 822.5, found 823.5 (M+1)$^+$

Example 151

Compound 220

5-(((3aR,5aR,5bR,7aR,9S,11aR,11bR,13aS)-3a-((R)-2-(benzylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid.

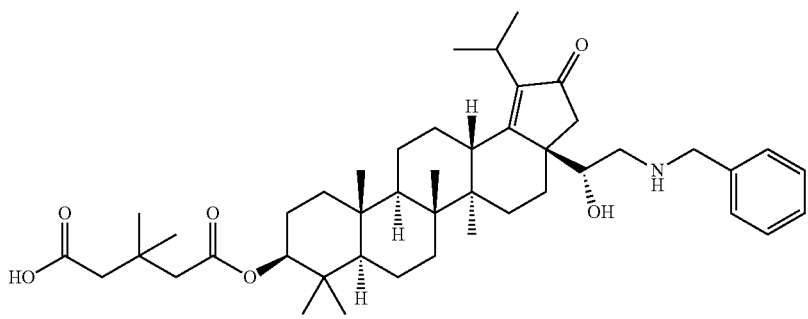

220

LC/MS: m/z calculated 717.5, found 718.5 (M+1)$^+$

Example 152

Compound 221

4-(((3aR,5aR,5bR,7aR,9S,11aR,11bR,13aS)-3a-((R)-2-((4-chlorobenzyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

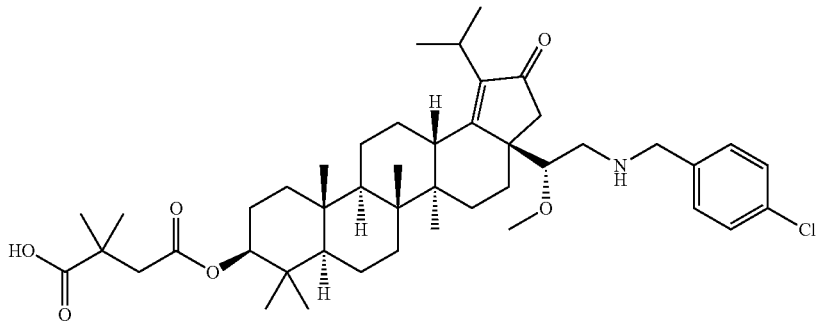

221

LC/MS: m/z calculated 751.5, found 752.5 (M+1)$^+$

Example 153

Compound 222

4-(((3aR,5aR,5bR,7aR,9S,11aR,11bR,13aS)-3a-((S)-2-((4-chlorobenzyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

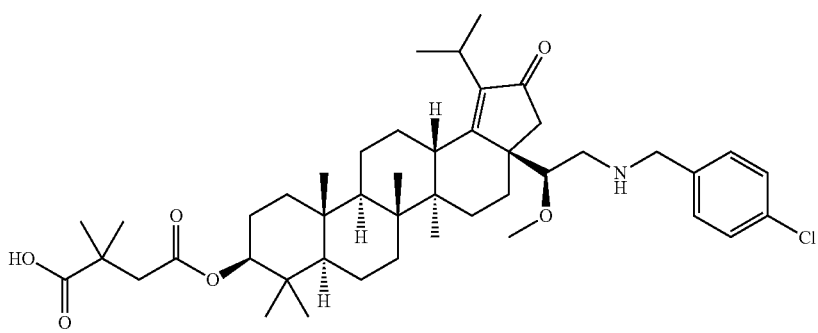

222

LC/MS: m/z calculated 751.5, found 752.5 (M+1)$^+$

Example 154

Compound 223

5-(((3aR,5aR,5bR,7aR,9S,11aR,11bR,13aS)-3a-((R)-2-(2-(dimethylamino)-N-(4-fluorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid.

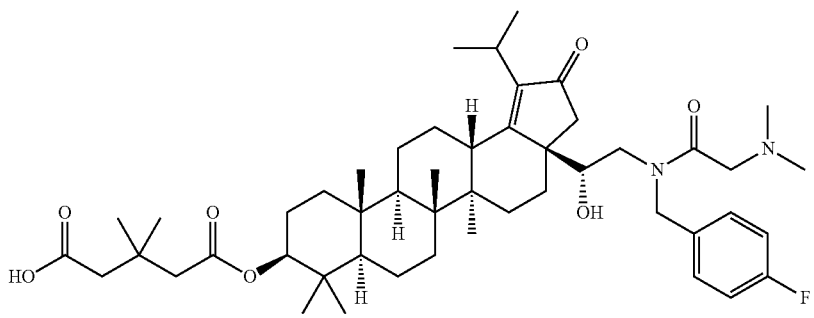

LC/MS: m/z calculated 820.5, found 821.5 (M+1)$^+$

Example 155

Compound 224

4-(((3aR,5aR,5bR,7aR,9S,11aR,11bR,13aS)-3a-((R)-2-((cyclohexylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

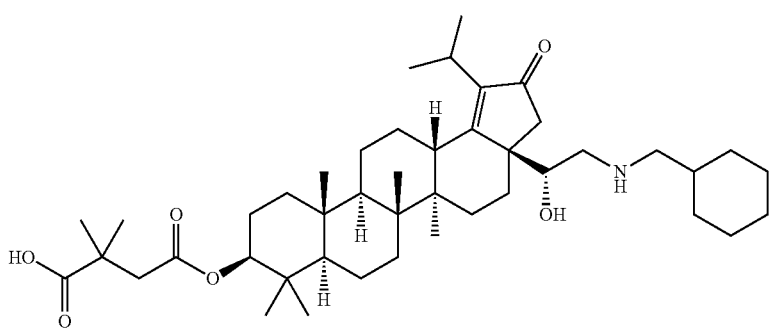

LC/MS: m/z calculated 709.5, found 710.6 (M+1)$^+$

Example 156

Compound 225

4-(((3aR,5aR,5bR,7aR,9S,11aR,11bR,13aS)-3a-((S)-4-(4-chlorobenzyl)-1-methyl-5-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

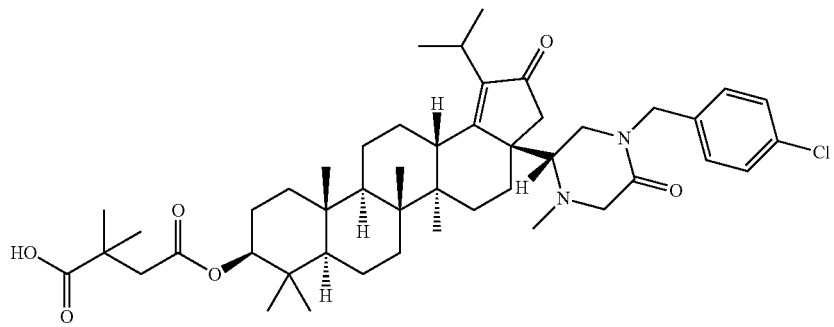

225

LC/MS: m/z calculated 790.5, found 791.5 (M+1)+

Example 157

Compound 226

4-(((3aR,5aR,5bR,7aR,9S,11aR,11bR,13aS)-3a-((R)-2-((cyclohexylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

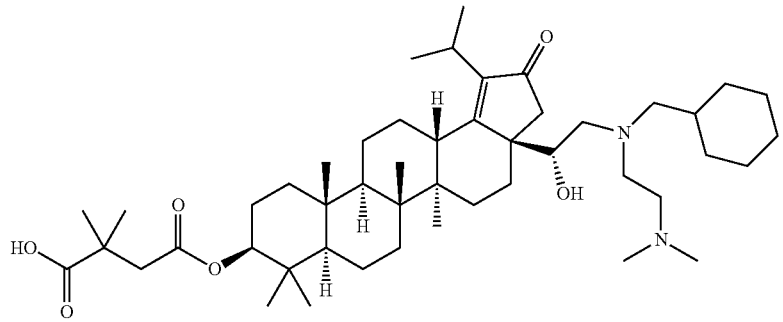

226

LC/MS: m/z calculated 780.6, found 781.5 (M+1)+

Example 158

Compound 227

4-(((3aR,5aR,5bR,7aR,9S,11aR,11bR,13aS)-3a-((R)-2-((cyclopropylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

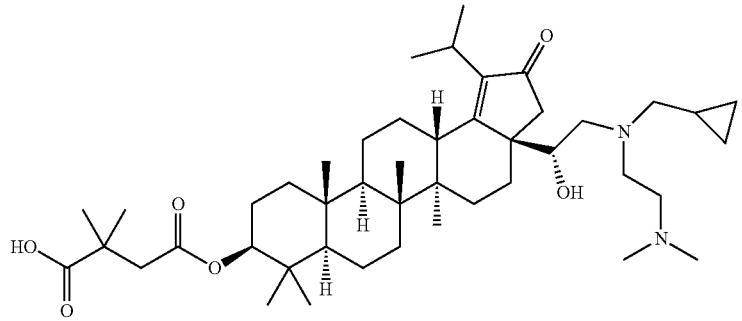

LC/MS: m/z calculated 738.6, found 739.8 (M+1)$^+$

Example 159

Compound 228

2-(2-(((3aR,5aR,5bR,7aR,9S,11aR,11bR,13aS)-3a-((R)-2-(benzylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-oxoethoxy)acetic acid.

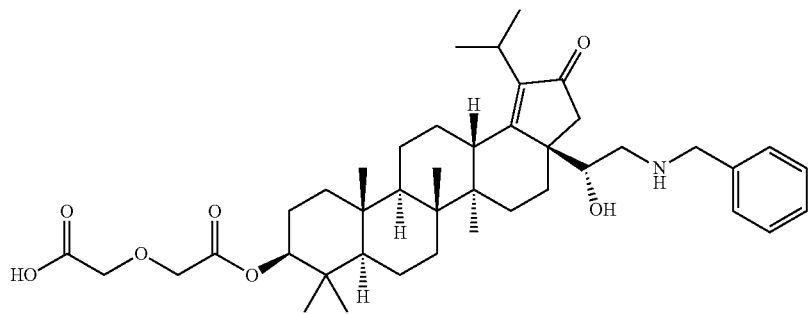

LC/MS: m/z calculated 691.4, found 692.5 (M+1)$^+$

Example 160

Compound 229

4-(((3aR,5aR,5bR,7aR,9S,11aR,11bR,13aS)-3a-(2-((4-chloro-2-((dimethylamino)methyl)benzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

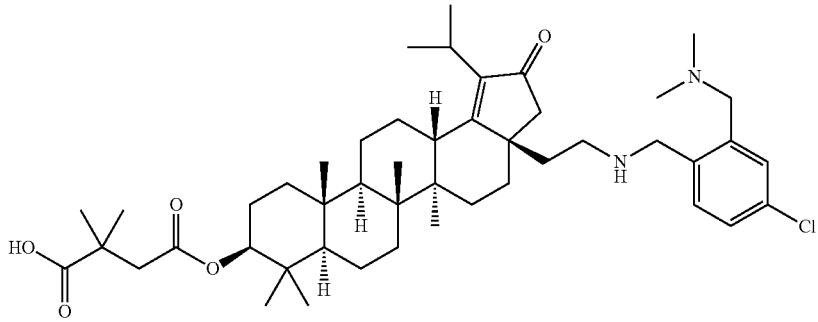

229

LC/MS: m/z calculated 778.5, found 779.5 (M+1)$^+$

Example 161

Compound 230

4-(((3aR,5aR,5bR,7aR,9S,11aR,11bR,13aS)-3a-(2-(N-(4-chloro-2-((dimethylamino)methyl)benzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

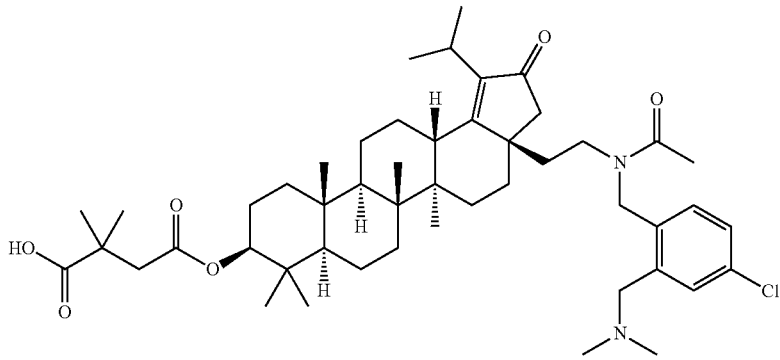

230

LC/MS: m/z calculated 820.5, found 821.7 (M+1)$^+$

Example 162

Compound 231

4-(((3aR,5aR,5bR,7aR,9S,11aR,11bR,13aS)-3a-(2-(N-(4-chloro-2-((dimethylamino)methyl)benzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

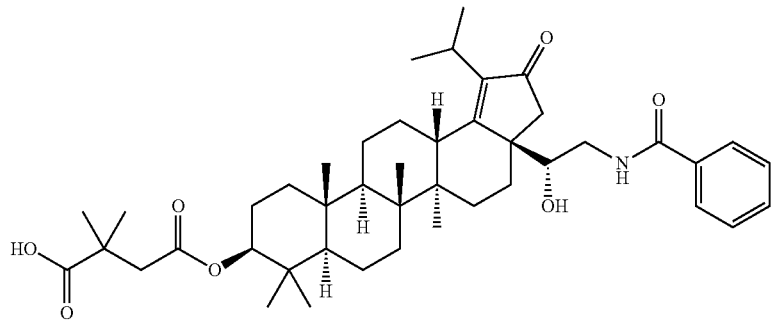

231

LC/MS: m/z calculated 717.5, found 718.5 (M+1)$^+$

Example 163

Compound 232

4-(((3aR,5aR,5bR,7aR,9S,11aR,11bR,13aS)-3a-((S)-2-benzamido-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

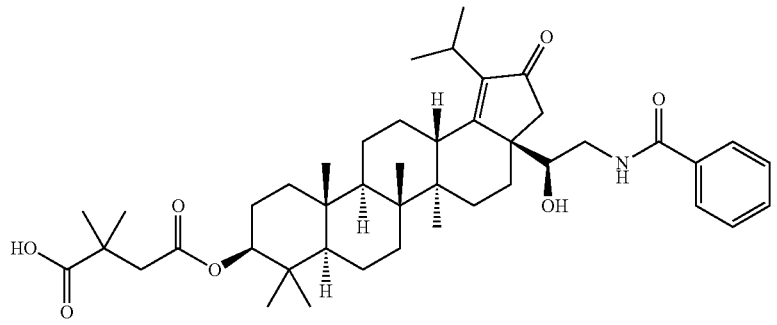

232

LC/MS: m/z calculated 717.5, found 718.5 (M+1)$^+$

Example 164

Compound 233

4-(((3aR,5aR,5bR,7aR,9S,11aR,11bR,13aS)-3a-((R)-1-hydroxy-2-(N-methylbenzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

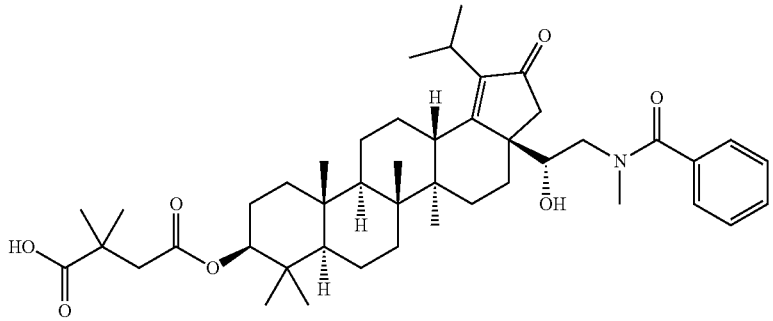

233

LC/MS: m/z calculated 731.5, found 732.3 (M+1)$^+$

Example 165

Compound 234

4-(((3aR,5aR,5bR,7aR,9S,11aR,11bR,13aS)-3a-((S)-1-hydroxy-2-(N-methylbenzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

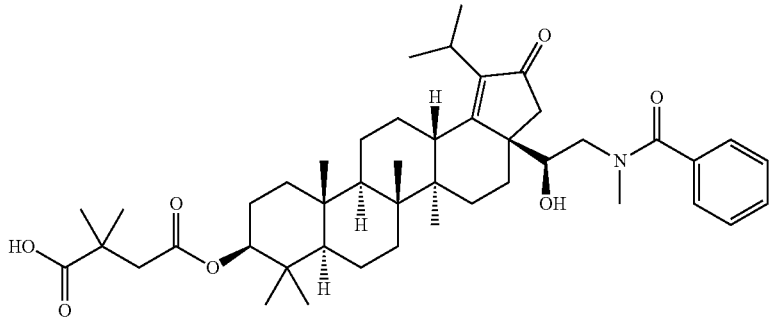

234

LC/MS: m/z calculated 731.5, found 732.5 (M+1)$^+$

Example 166

Compound 235

4-(((3aS,5aR,5bR,7aR,9S,11aR,11bR,13aS)-3a-((S)-2-((4-chlorobenzyl)(2-(dimethylamino)ethyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

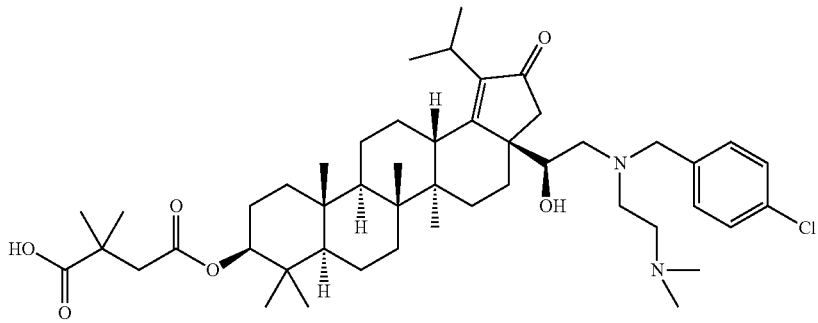

235

LC/MS: m/z calculated 794.5, found 795.7 (M+1)$^+$

Example 167

Compound 236

4-(((3aR,5aR,5bR,7aR,9S,11aR,11bR,13aS)-3a-((R)-2-(2-(dimethylamino)-N-(pyridin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

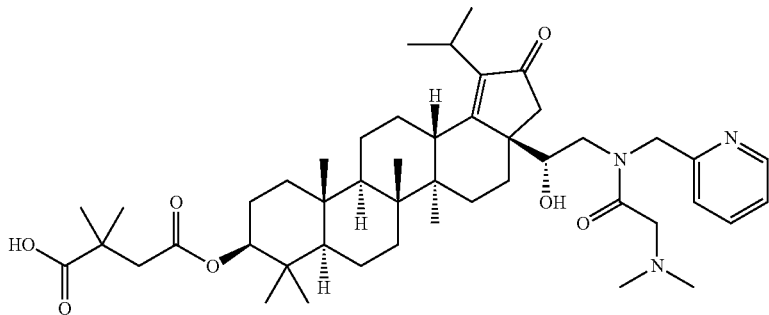

236

LC/MS: m/z calculated 789.5, found 790.5 (M+1)$^+$

Example 168

Compound 237

4-(((3aR,5aR,5bR,7aR,9S,11aR,11bR,13aS)-3a-((R)-1-hydroxy-2-(2-(methylamino)-N-(pyridin-2-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

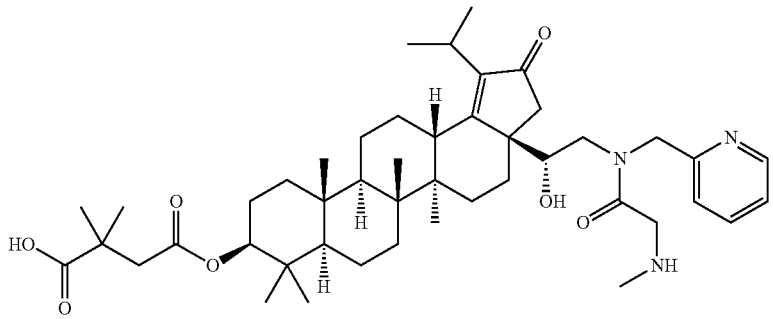

237

LC/MS: m/z calculated 775.5, found 776.5 (M+1)$^+$

Example 169

Compound 238

4-(((3aR,5aR,5bR,7aR,9S,11aR,11bR,13aS)-3a-(2-((4-chloro-2-((dimethylamino)methyl)benzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

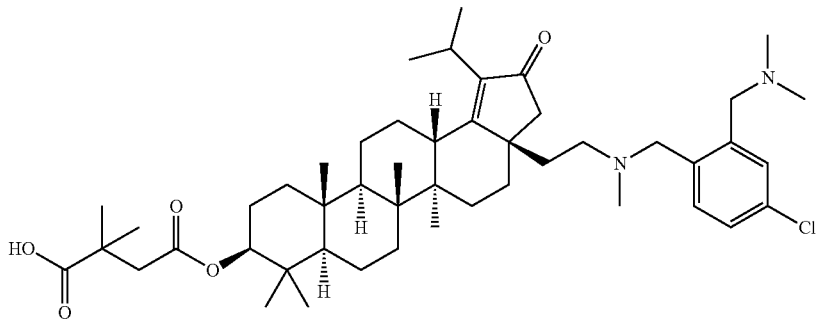

238

LC/MS: m/z calculated 792.5, found 793.5 (M+1)$^+$

Example 170

Compound 239

4-(((3aR,5aR,5bR,7aR,9S,11aR,11bR,13aS)-3a-((R)-1-acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

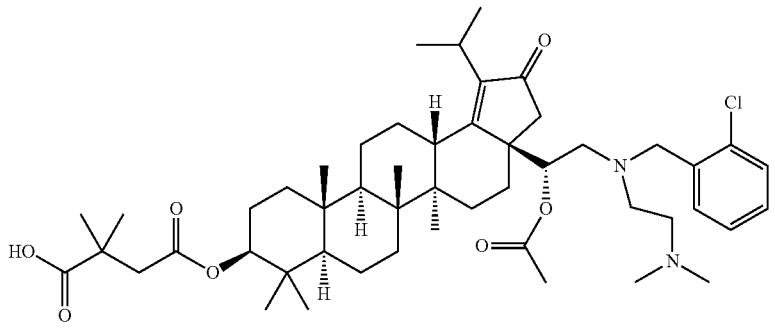

239

LC/MS: m/z calculated 850.5, found 851.5 (M+1)$^+$

Example 171

Compound 240

4-(((3aR,5aR,5bR,7aR,9S,11aR,11bR,13aS)-3a-((R)-2-(2-amino-N-benzylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

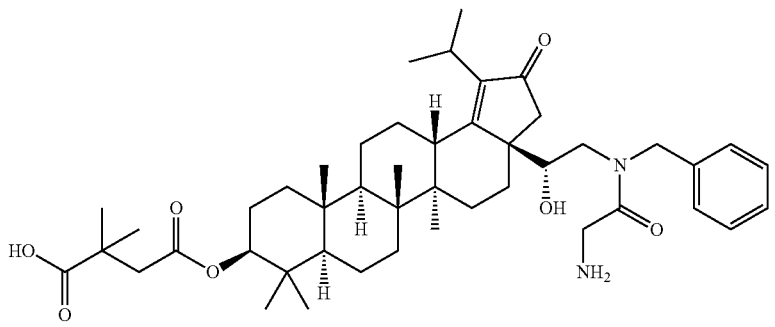

240

LC/MS: m/z calculated 760.5, found 761.5 (M+1)$^+$

Example 172

Compound 241

4-(((3aR,5aR,5bR,7aR,9S,11aR,11bR,13aS)-3a-((R)-2-(N-benzyl-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

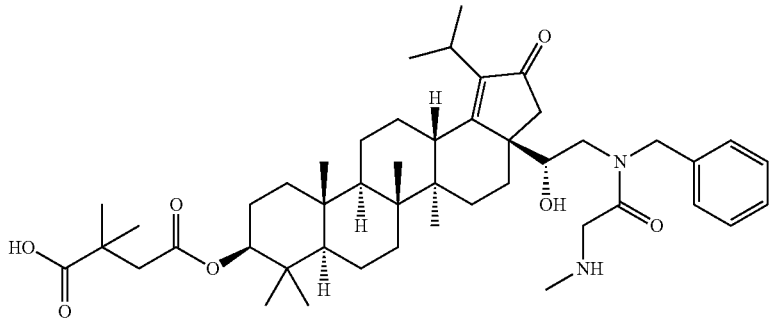

241

LC/MS: m/z calculated 774.5, found 775.5 (M+1)$^+$

Example 173

Compound 242

4-(((3aR,5aR,5bR,7aR,9S,11aR,11bR,13aS)-3a-((R)-2-(N-benzyl-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

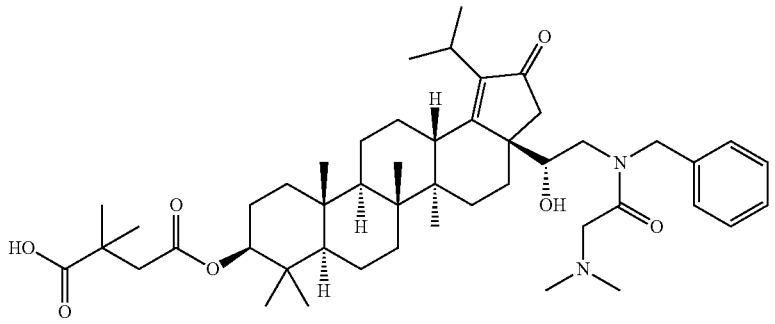

242

LC/MS: m/z calculated 788.5, found 789.5 (M+1)$^+$

Example 174

Compound 243

4-(((3aR,5aR,5bR,7aR,9S,11aR,11bR,13aS)-3a-((R)-2-(2-amino-N-(pyridin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

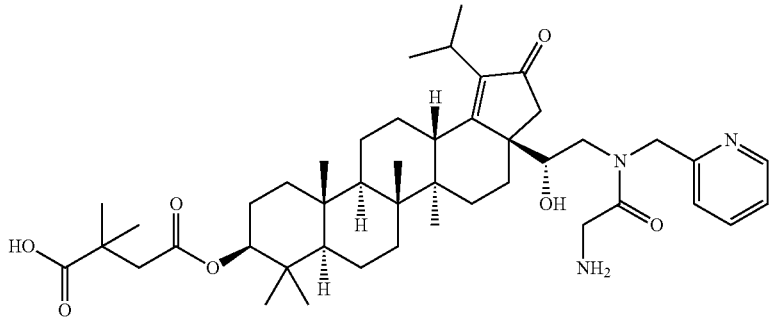

243

LC/MS: m/z calculated 761.5, found 762.5 (M+1)$^+$

Example 175

Compound 244

4-(((3aR,5aR,5bR,7aR,9S,11aR,11bR,13aS)-3a-((S)-2-(((R)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

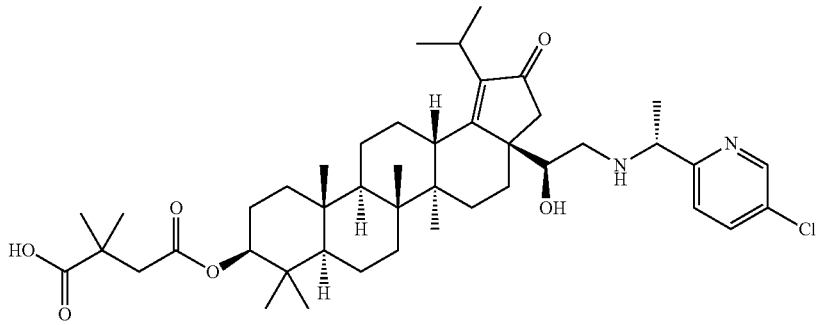

244

LC/MS: m/z calculated 752.5, found 753.5 (M+1)$^+$

Example 176

Compound 245

4-(((3aR,5aR,5bR,7aR,9S,11aR,11bR,13aS)-3a-((R)-2-(((R)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

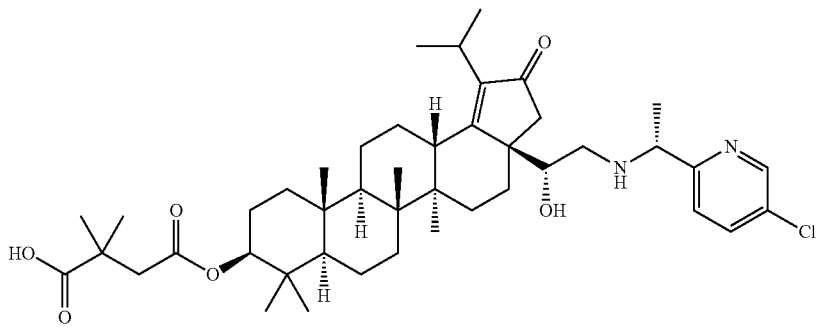

245

LC/MS: m/z calculated 752.5, found 753.4 (M+1)$^+$

Example 177

Compound 246

4-(((3aR,5aR,5bR,7aR,9S,11aR,11bR,13aS)-3a-((R)-2-(N—((R)-1-(5-chloropyridin-2-yl)ethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

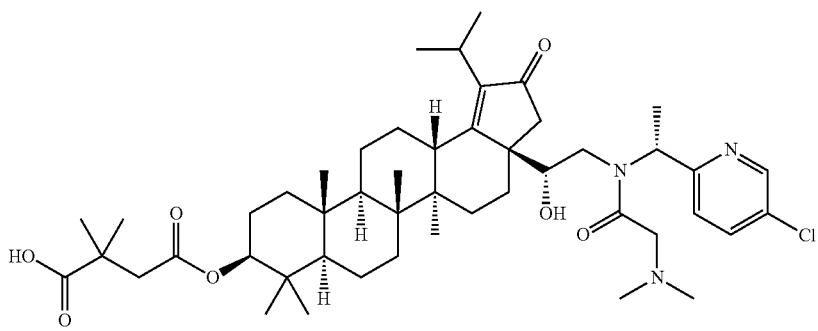

246

LC/MS: m/z calculated 837.5, found 838.5 (M+1)$^+$

Example 178

Compound 247

4-(((3aR,5aR,5bR,7aR,9S,11aR,11bR,13aS)-3a-((S)-2-((2-(dimethylamino)ethyl)(phenethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

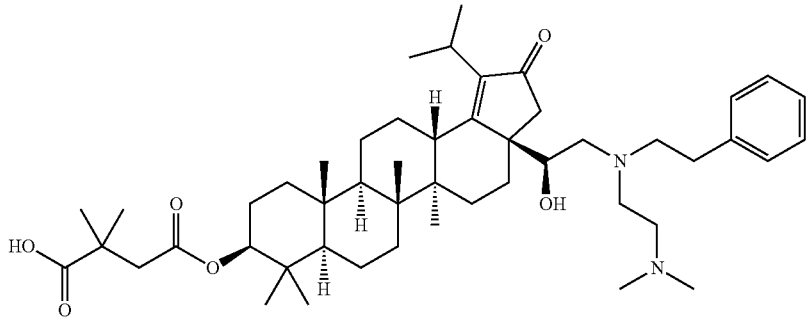

247

LC/MS: m/z calculated 788.6, found 789.5 (M+1)+

Example 179

Compound 248

5-(((3aR,5aR,5bR,7aR,9S,11aR,11bR,13aS)-3a-((R)-2-(N-benzyl-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid.

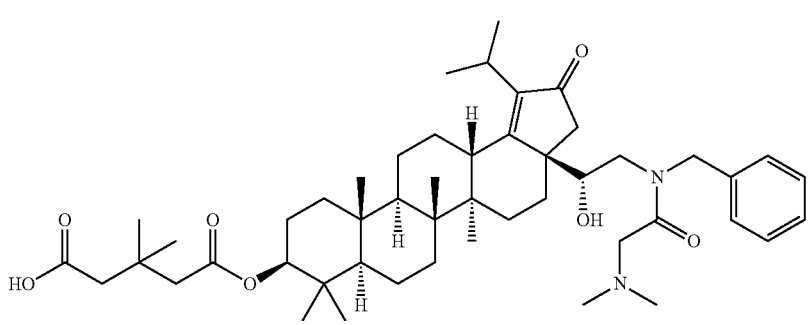

248

LC/MS: m/z calculated 802.6, found 803.5 (M+1)+

Example 180

Compound 249

4-(((3aR,5aR,5bR,7aR,9S,11aR,11bR,13aS)-3a-((R)-2-(N-(2-(dimethylamino)ethyl)cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

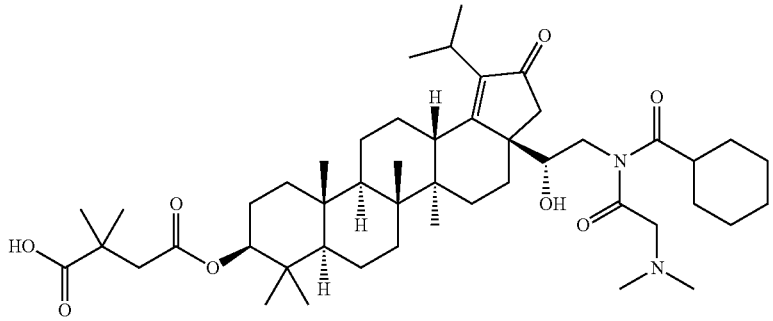

LC/MS: m/z calculated 794.6, found 795.5 (M+1)$^+$

Example 181

Compound 250

4-(((3aR,5aR,5bR,7aR,9S,11aR,11bR,13aS)-3a-((R)-2-(cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

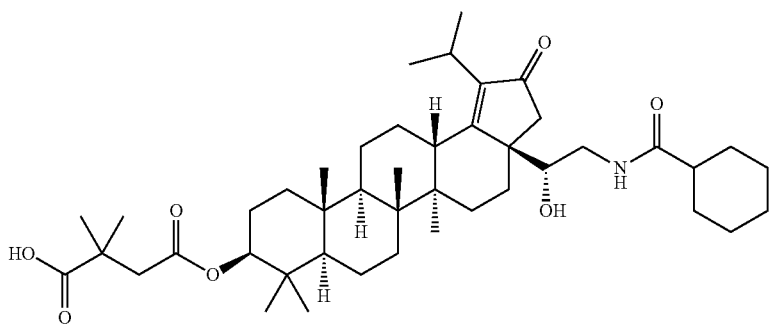

LC/MS: m/z calculated 723.5, found 724.5 (M+1)$^+$

Example 182

Compound 251

4-(((3aR,5aR,5bR,7aR,9S,11aR,11bR,13aS)-3a-((R)-2-(2-amino-N—((S)-1-(5-chloropyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

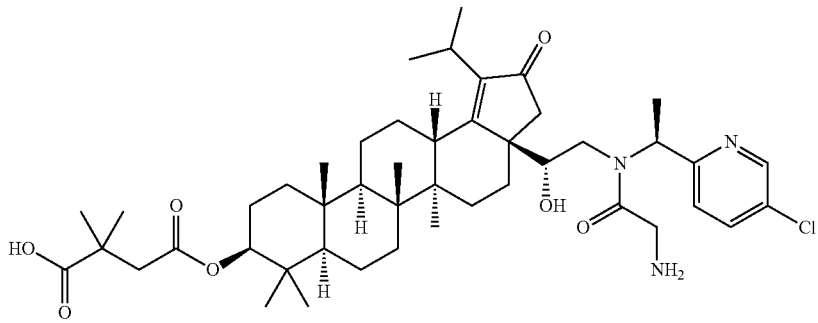

251

LC/MS: m/z calculated 809.5, found 810.4 $(M+1)^+$

Example 183

Compound 252

4-(((3aR,5aR,5bR,7aR,9S,11aR,11bR,13aS)-3a-((R)-2-(N—((S)-1-(5-chloropyridin-2-yl)ethyl)-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

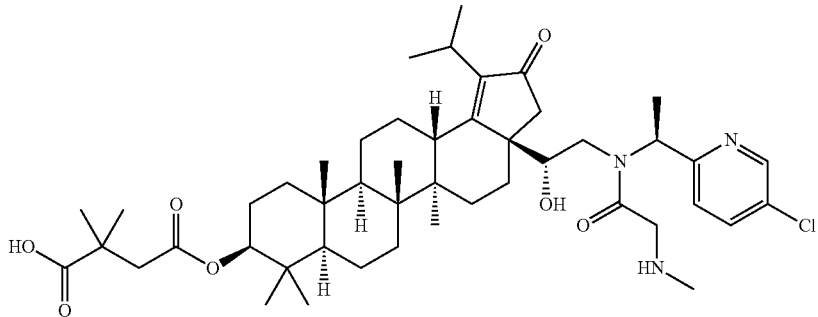

252

LC/MS: m/z calculated 823.5, found 824.5 $(M+1)^+$

Example 184

Compound 253

4-(((3aR,5aR,5bR,7aR,9S,11aR,11bR,13aS)-3a-((R)-2-(N—((S)-1-(5-chloropyridin-2-yl)ethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

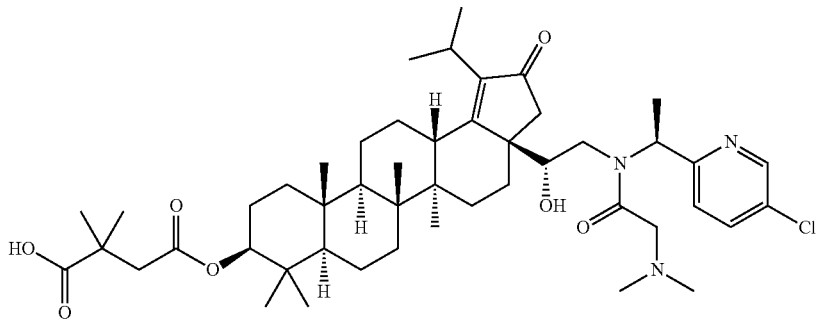

253

LC/MS: m/z calculated 837.5, found 838.5 (M+1)$^+$

Example 185

Compound 254

4-(((3aR,5aR,5bR,7aR,9S,11aR,11bR,13aS)-3a-((R)-2-((2-aminoethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

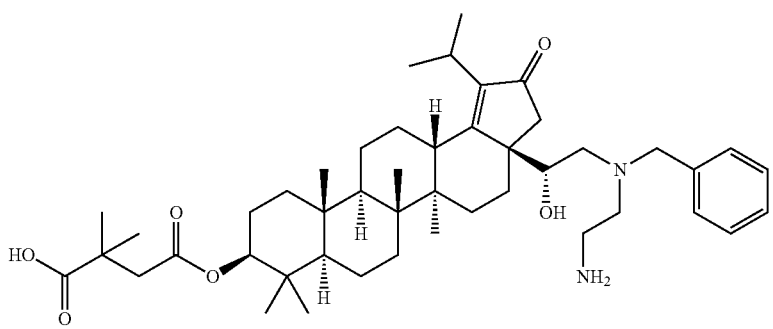

254

LC/MS: m/z calculated 746.5, found 747.5 (M+1)$^+$

Example 186

Compound 255

4-(((3aR,5aR,5bR,7aR,9S,11aR,11bR,13aS)-3a-((R)-2-((cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

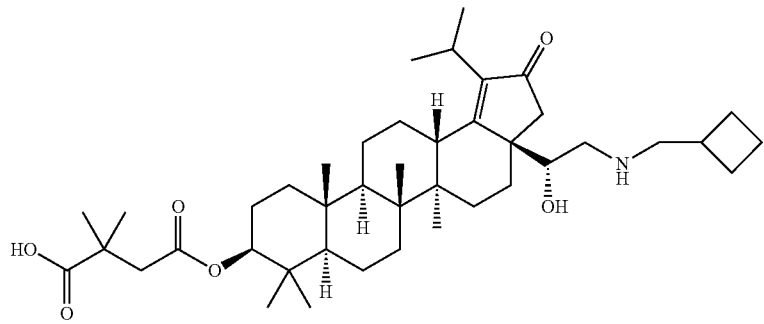

255

LC/MS: m/z calculated 681.5, found 682.5 (M+1)$^+$

Example 187

Compound 256

4-(((3aR,5aR,5bR,7aR,9S,11aR,11bR,13aS)-3a-((R)-1-acetoxy-2-(benzyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 188

Compound 257

4-(((3aR,5aR,5bR,7aR,9S,11aR,11bR,13aS)-3a-((S)-1-acetoxy-2-(benzyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

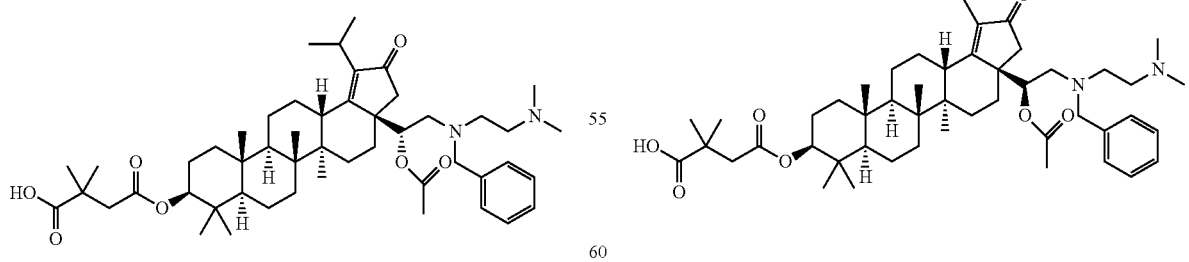

256

257

LC/MS: m/z calculated 816.6, found 817.5 (M+1)$^+$

LC/MS: m/z calculated 816.6, found 817.5 (M+1)$^+$

321

Example 189

Compound 258

4-(((3aR,5aR,5bR,7aR,9S,11aR,11bR,13aS)-3a-((S)-2-(cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

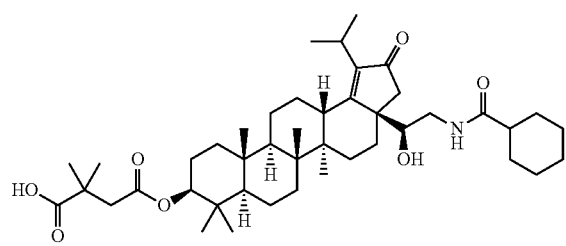

258

LC/MS: m/z calculated 723.5, found 724.5 (M+1)$^+$

Example 190

Compound 259

4-(((3aR,5aR,5bR,7aR,9S,11aR,11bR,13aS)-3a-((S)-2-((cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

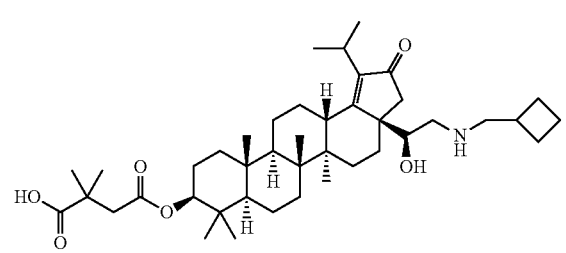

259

LC/MS: m/z calculated 681.5, found 682.5 (M+1)$^+$

322

Example 191

Compound 260

4-(((3aR,5aR,5bR,7aR,9S,11aR,11bR,13aS)-3a-((S)-2-(N-(2-(dimethylamino)ethyl)cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

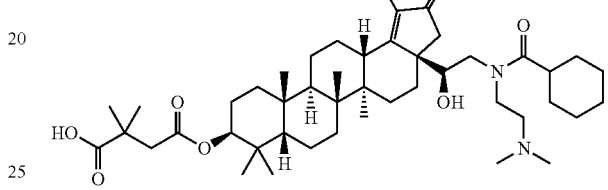

260

LC/MS: m/z calculated 794.6, found 795.6 (M+1)$^+$

Example 192

Compound 261

4-(((3aR,5aR,5bR,7aR,9S,11aR,11bR,13aS)-3a-((S)-2-((cyclobutylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

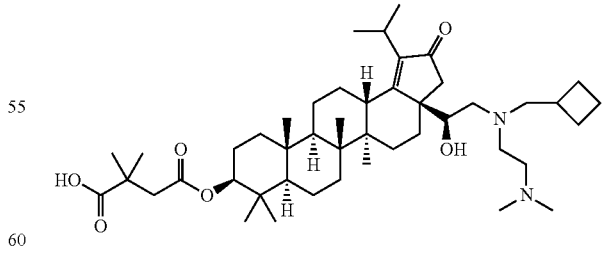

261

LC/MS: m/z calculated 752.6, found 753.6 (M+1)$^+$

Example 193

Compound 262

4-(((3aR,5aR,5bR,7aR,9S,11aR,11bR,13aS)-3a-((R)-2-(((1H-pyrazol-3-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

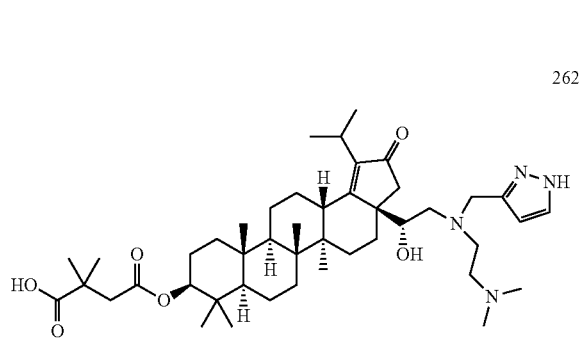

262

LC/MS: m/z calculated 764.6, found 765.5 (M+1)⁺

Example 194

Compound 263

4-(((3aR,5aR,5bR,7aR,9S,11aR,11bR,13aS)-3a-((R)-2-((cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

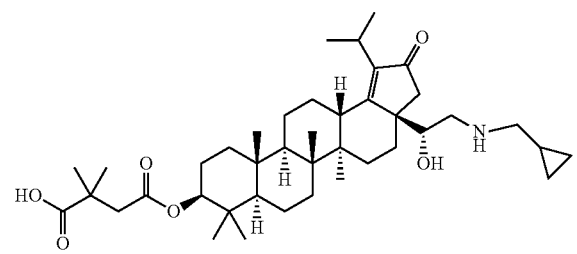

263

LC/MS: m/z calculated 667.5, found 668.5 (M+1)⁺

Example 195

Compound 264

4-(((3aR,5aR,5bR,7aR,9S,11aR,11bR,13aS)-3a-((1S)-1-hydroxy-2-((2-hydroxy-2-phenylethyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

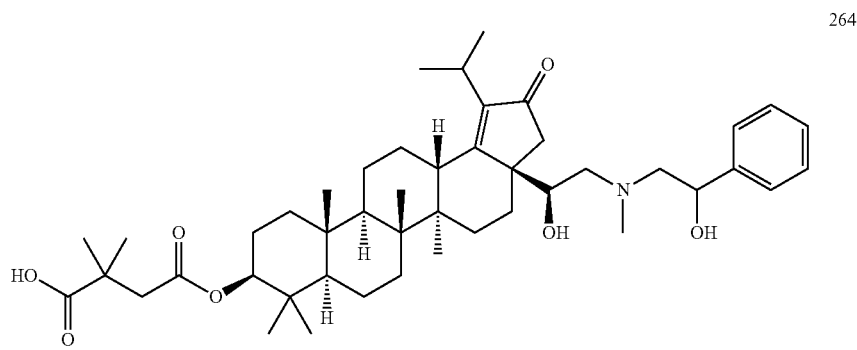

264

LC/MS: m/z calculated 747.5, found 748.5 (M+1)⁺

Example 196

Compound 265

4-(((3aR,5aR,5bR,7aR,9S,11aR,11bR,13aS)-3a-((S)-1-hydroxy-2-((2-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

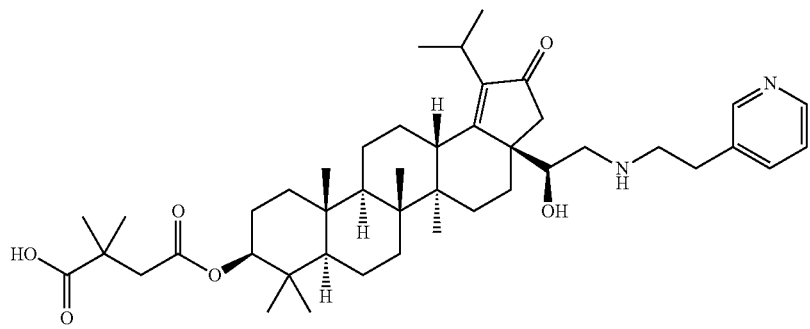

LC/MS: m/z calculated 718.5, found 719.5 $(M+1)^+$

Example 197

Compound 266

4-(((3aR,5aR,5bR,7aR,9S,11aR,11bR,13aS)-3a-((S)-1-hydroxy-2-((R)-3-hydroxypiperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

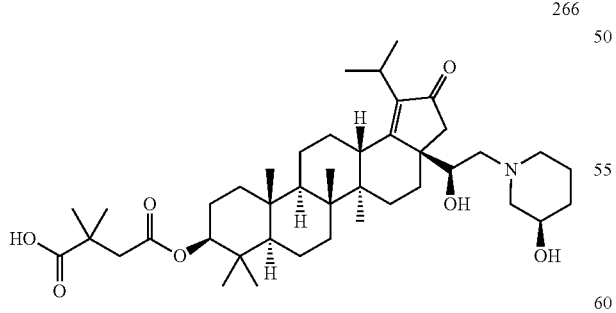

LC/MS: m/z calculated 697.5, found 698.5 $(M+1)^+$

Example 198

Compound 267

4-(((3aR,5aR,5bR,7aR,9S,11aR,11bR,13aS)-3a-((S)-1-hydroxy-2-((3-(2-oxopyrrolidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

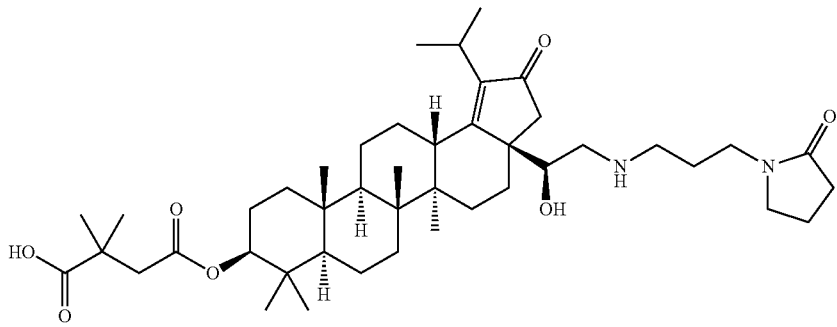

267

LC/MS: m/z calculated 738.5, found 739.5 (M+1)$^+$

Example 199

Compound 268

4-(((3aR,5aR,5bR,7aR,9S,11aR,11bR,13aS)-3a-((S)-1-hydroxy-2-((2-phenoxyethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

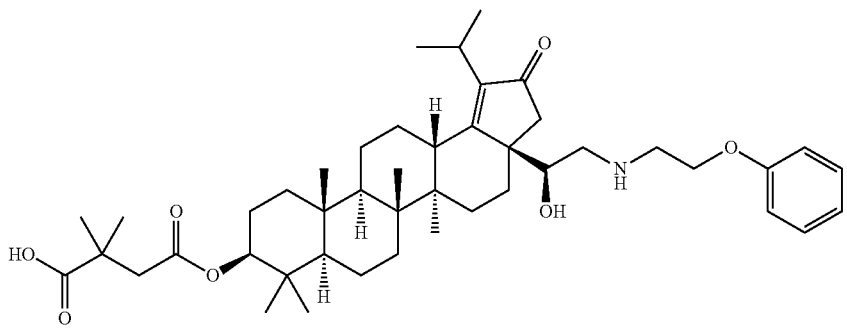

268

LC/MS: m/z calculated 733.5, found 734.5 (M+1)$^+$

Example 200

Compound 269

4-(((3aR,5aR,5bR,7aR,9S,11aR,11bR,13aS)-3a-((S)-1-hydroxy-2-(4-(2-hydroxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

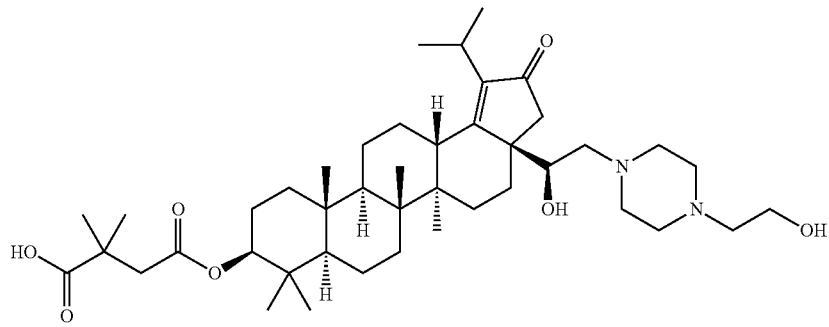

269

LC/MS: m/z calculated 726.5, found 727.5 (M+1)$^+$

Example 201

Compound 270

4-(((3aR,5aR,5bR,7aR,9S,11aR,11bR,13aS)-3a-((1S)-2-(2,6-dimethylmorpholino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 202

Compound 271

4-(((3aR,5aR,5bR,7aR,9S,11aR,11bR,13aS)-3a-((S)-1-hydroxy-2-thiomorpholinoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

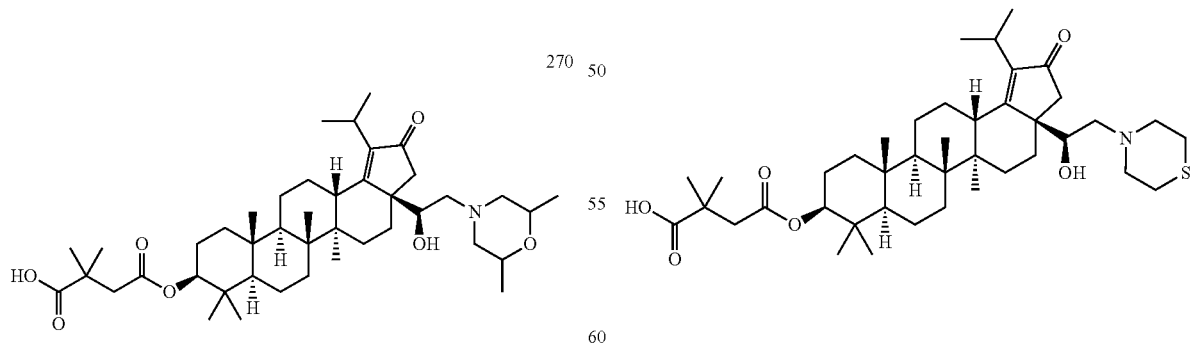

270

271

LC/MS: m/z calculated 711.5, found 712.5 (M+1)$^+$

LC/MS: m/z calculated 699.5, found 700.4 (M+1)$^+$

Example 203

Compound 272

4-(((3aR,5aR,5bR,7aR,9S,11aR,11bR,13aS)-3a-((S)-1-hydroxy-2-((3-morpholinopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

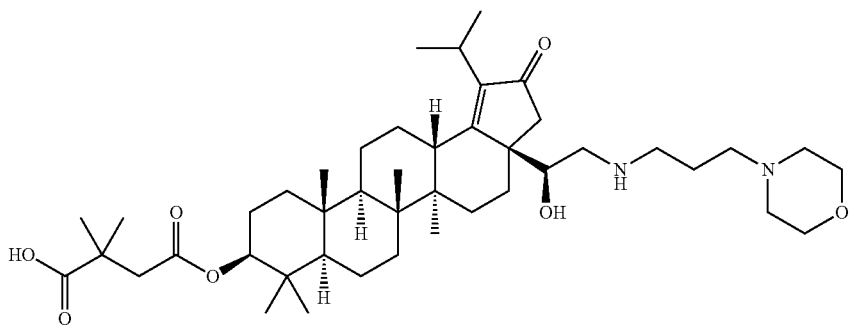

272

LC/MS: m/z calculated 740.5, found 741.5 (M+1)$^+$

Example 204

Compound 273

4-(((3aR,5aR,5bR,7aR,9S,11aR,11bR,13aS)-3a-((S)-2-((3-(1H-imidazol-1-yl)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

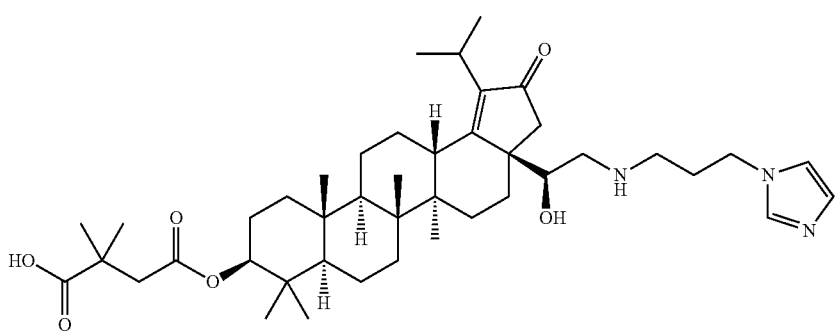

273

LC/MS: m/z calculated 721.5, found 722.5 (M+1)$^+$

Example 205

Compound 274

4-(((3aR,5aR,5bR,7aR,9S,11aR,11bR,13aS)-3a-((S)-1-hydroxy-2-((4-hydroxyphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

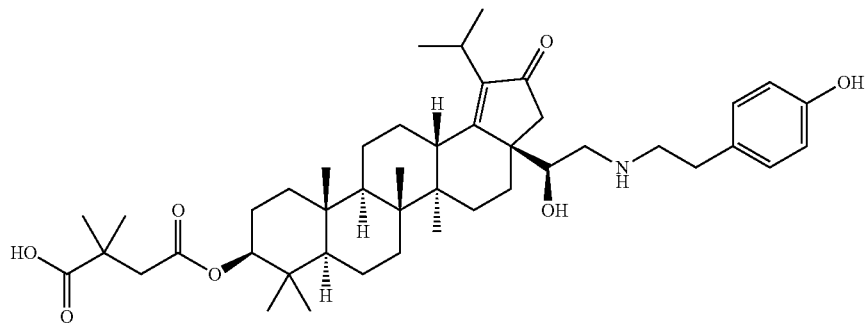

274

LC/MS: m/z calculated 733.5, found 734.5 (M+1)$^+$

Example 206

Compound 275

4-(((3aR,5aR,5bR,7aR,9S,11aR,11bR,13aS)-3a-((R)-2-(cyclopentylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

275

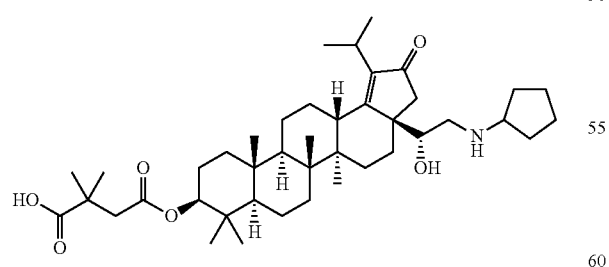

LC/MS: m/z calculated 681.5, found 682.5 (M+1)$^+$

Example 207

Compound 276

4-(((3aR,5aR,5bR,7aR,9S,11aR,11bR,13aS)-3a-((S)-2-((cyclohexylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

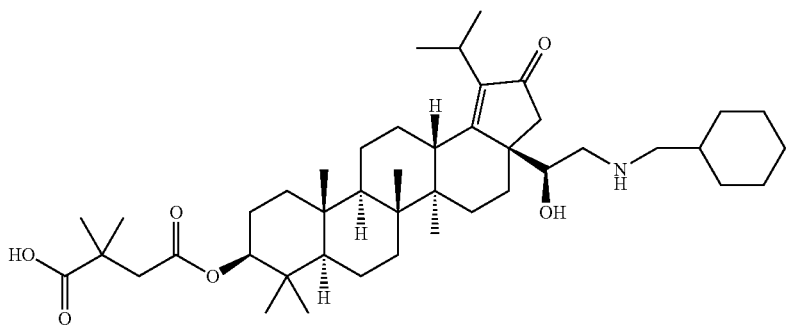

276

LC/MS: m/z calculated 709.5, found 710.5 (M+1)$^+$

Example 208

Compound 277

4-(((3aR,5aR,5bR,7aR,9S,11aR,11bR,13aS)-3a-((R)-2-((cyclobutylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

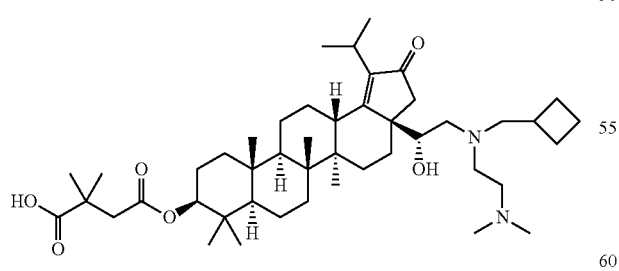

277

LC/MS: m/z calculated 752.6, found 753.6 (M+1)$^+$

Example 209

Compound 278

4-(((3aR,5aR,5bR,7aR,9S,11aR,11bR,13aS)-3a-((R)-2-(((1H-pyrazol-4-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

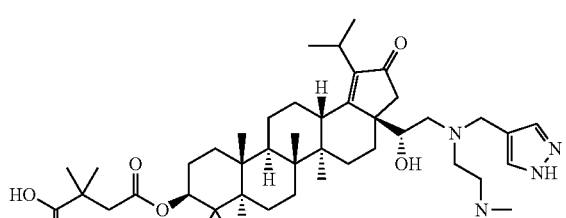

278

LC/MS: m/z calculated 764.6, found 765.5 (M+1)$^+$

337

Example 210

Compound 279

4-(((3aR,5aR,5bR,7aR,9S,11aR,11bR,13aS)-3a-((S)-2-((cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

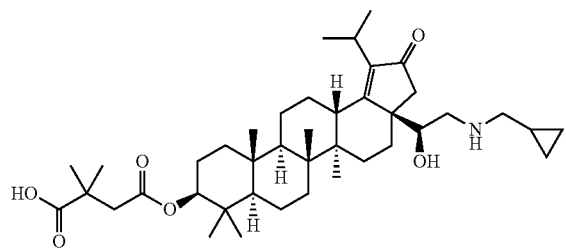

279

LC/MS: m/z calculated 667.5, found 668.5 (M+1)⁺

Example 211

Compound 280

4-(((3aR,5aR,5bR,7aR,9S,11aR,11bR,13aS)-3a-((S)-2-(cyclobutylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

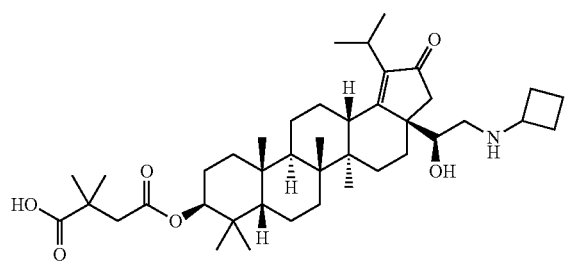

280

LC/MS: m/z calculated 667.5, found 668.5 (M+1)⁺

338

Example 212

Compound 281

4-(((3aR,5aR,5bR,7aR,9S,11aR,11bR,13aS)-3a-((R)-2-(cyclobutylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

281

LC/MS: m/z calculated 667.5, found 668.5 (M+1)⁺

Example 213

Compound 282

4-(((3aR,5aR,5bR,7aR,9S,11aR,11bR,13aS)-3a-((S)-1-hydroxy-2-((3-(pyrrolidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

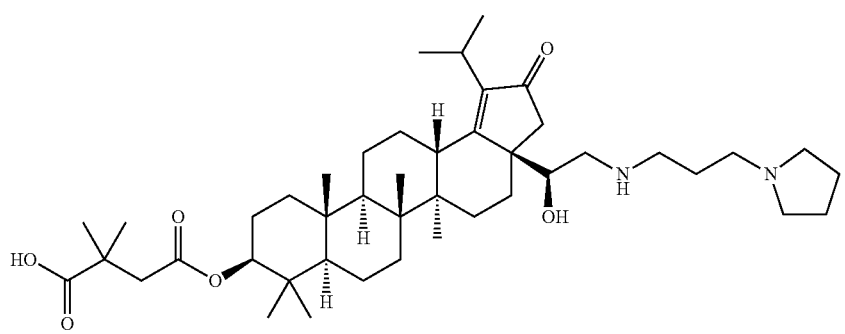

282

LC/MS: m/z calculated 724.5, found 725.5 (M+1)⁺

Example 214

Compound 283

4-(((3aR,5aR,5bR,7aR,9S,11aR,11bR,13aS)-3a-((S)-1-hydroxy-2-(4-(pyridin-2-yl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

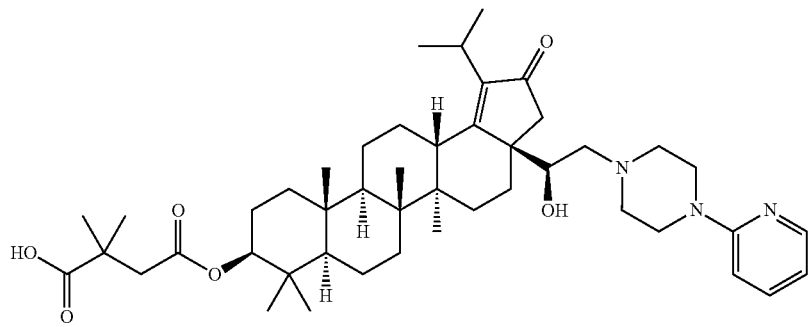

283

LC/MS: m/z calculated 759.5, found 760.5 (M+1)$^+$

Example 215

Compound 284

4-(((3aR,5aR,5bR,7aR,9S,11aR,11bR,13aS)-3a-((S)-1-hydroxy-2-(4-methyl-1,4-diazepan-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

284

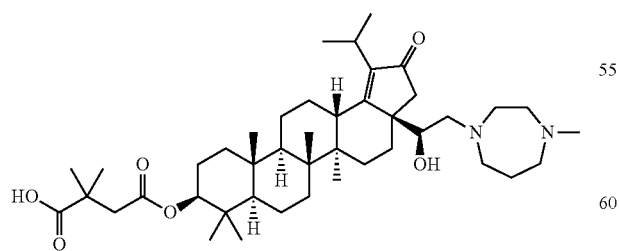

LC/MS: m/z calculated 710.5, found 711.5 (M+1)$^+$

Example 216

Compound 285

4-(((3aR,5aR,5bR,7aR,9S,11aR,11bR,13aS)-3a-((S)-1-hydroxy-2-((4-sulfamoylphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

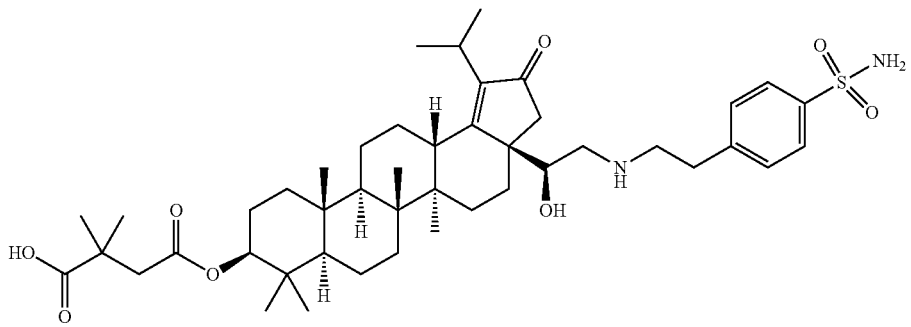

285

LC/MS: m/z calculated 796.5, found 797.5 (M+1)$^+$

Example 217

Compound 286

4-(((3aR,5aR,5bR,7aR,9S,11aR,11bR,13aS)-3a-((S)-2-(4-carbamoylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

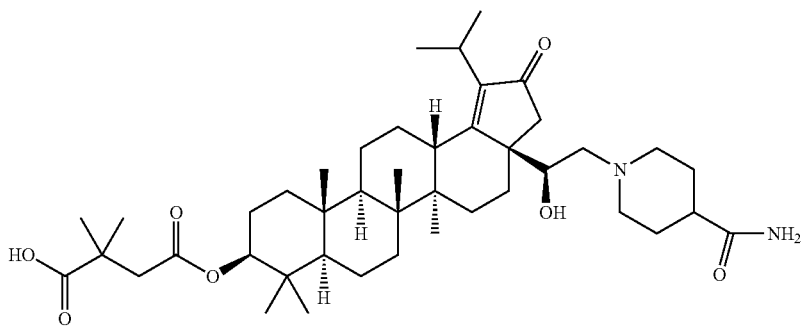

286

LC/MS: m/z calculated 724.5, found 725.5 (M+1)$^+$

Example 218

Compound 287

4-(((3aR,5aR,5bR,7aR,9S,11aR,11bR,13aS)-3a-((S)-1-hydroxy-2-(4-(2-methoxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

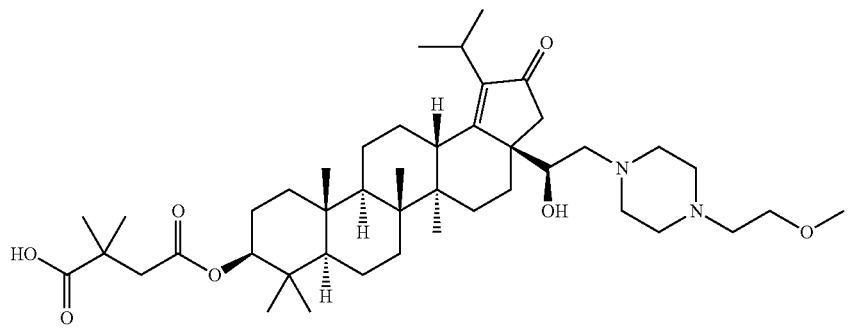

287

LC/MS: m/z calculated 740.5, found 741.5 (M+1)$^+$

Example 219

Compound 288

4-(((3aR,5aR,5bR,7aR,9S,11aR,11bR,13aS)-3a-((S)-1-hydroxy-2-(((R)-2-hydroxy-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

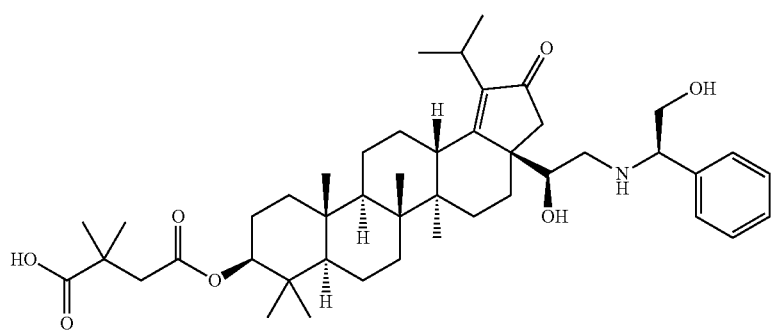

288

LC/MS: m/z calculated 733.5, found 734.5 (M+1)$^+$

Example 220

Compound 289

4-(((3aR,5aR,5bR,7aR,9S,11aR,11bR,13aS)-3a-((1S)-1-hydroxy-2-(octahydroisoquinolin-2(1H)-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

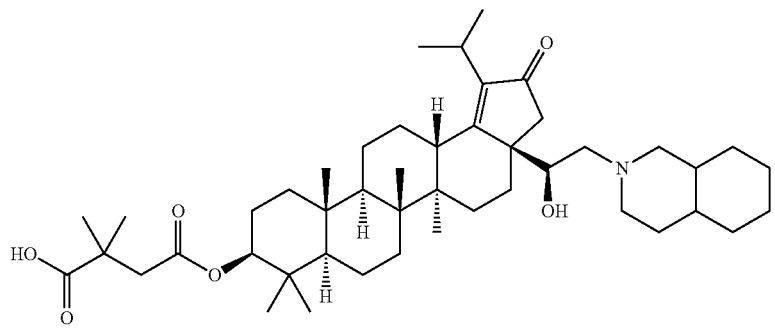

289

LC/MS: m/z calculated 735.5, found 736.5 (M+1)$^+$

Example 221

Compound 290

4-(((3aR,5aR,5bR,7aR,9S,11aR,11bR,13aS)-3a-((S)-1-hydroxy-2-((3-(piperidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

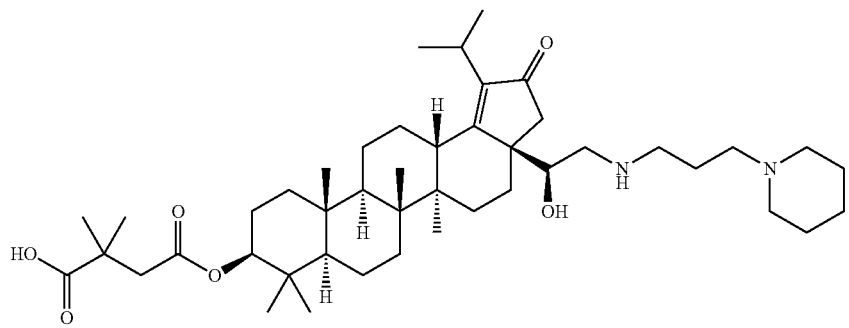

290

LC/MS: m/z calculated 738.5, found 739.5 (M+1)$^+$

Example 222

Compound 291

4-(((3aR,5aR,5bR,7aR,9S,11aR,11bR,13aS)-3a-((R)-2-(2-(dimethylamino)-N—((S)-1-(pyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

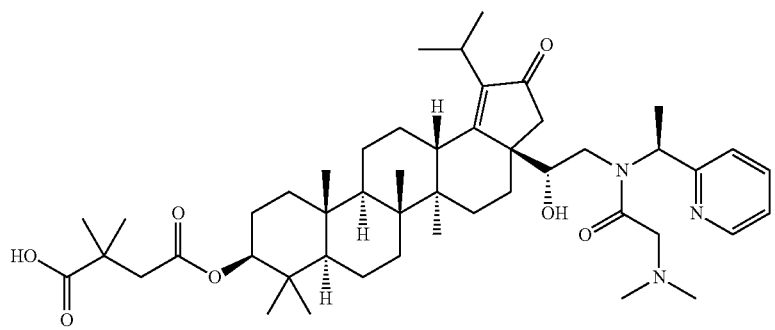

291

LC/MS: m/z calculated 803.5, found 804.5 (M+1)$^+$

Example 223

Compound 292

4-(((3aR,5aR,5bR,7aR,9S,11aR,11bR,13aS)-3a-((S)-2-(cyclopentylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

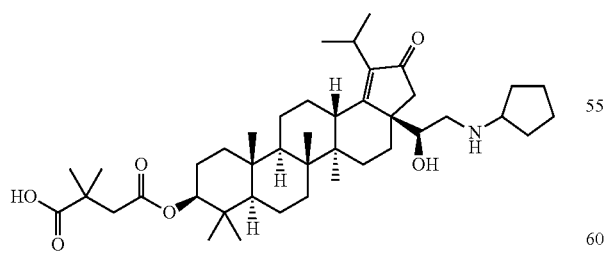

292

LC/MS: m/z calculated 681.5, found 682.5 (M+1)$^+$

Example 224

Compound 293

4-(((3aR,5aR,5bR,7aR,9S,11aR,11bR,13aS)-3a-((S)-2-(benzo[d][1,3]dioxol-5-ylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

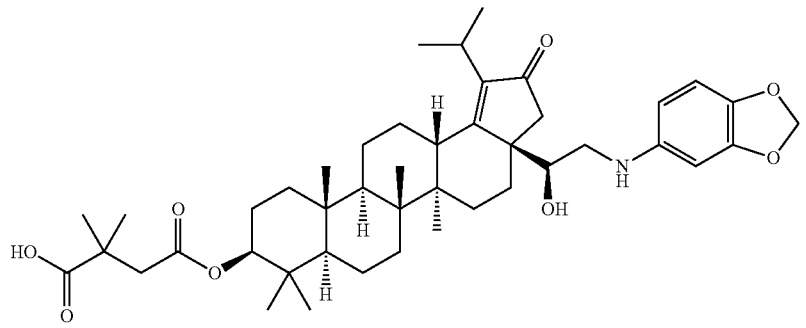

293

LC/MS: m/z calculated 733.5, found 734.5 (M+1)$^+$

Example 225

Compound 294

4-(((3aR,5aR,5bR,7aR,9S,11aR,11bR,13aS)-3a-((S)-1-hydroxy-2-((2-(thiophen-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

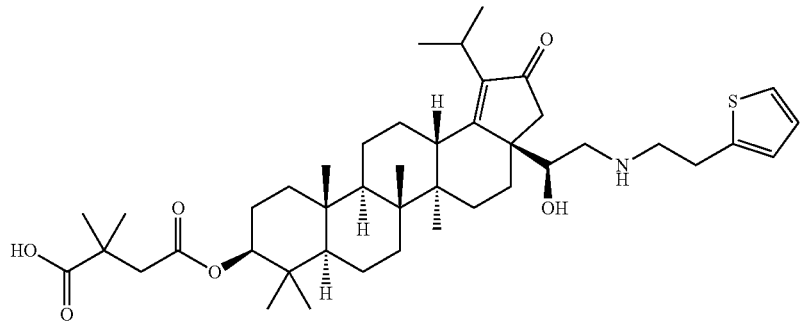

294

LC/MS: m/z calculated 723.5, found 724.4 (M+1)$^+$

Example 226

Compound 295

4-(((3aR,5aR,5bR,7aR,9S,11aR,11bR,13aS)-3a-((S)-1-hydroxy-2-(4-(4-methylbenzyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

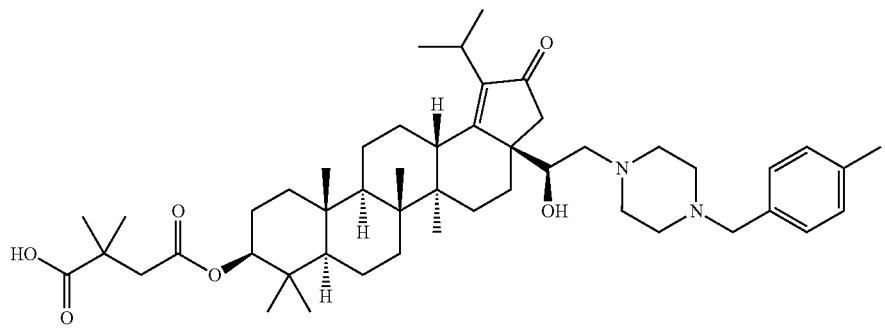

295

LC/MS: m/z calculated 786.5, found 787.5 (M+1)$^+$

Example 227

Compound 296

4-(((3aR,5aR,5bR,7aR,9S,11aR,11bR,13aS)-3a-((S)-2-(bis(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 228

Compound 297

4-(((3aR,5aR,5bR,7aR,9S,11aR,11bR,13aS)-3a-((1S)-1-hydroxy-2-((2-methylcyclohexyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

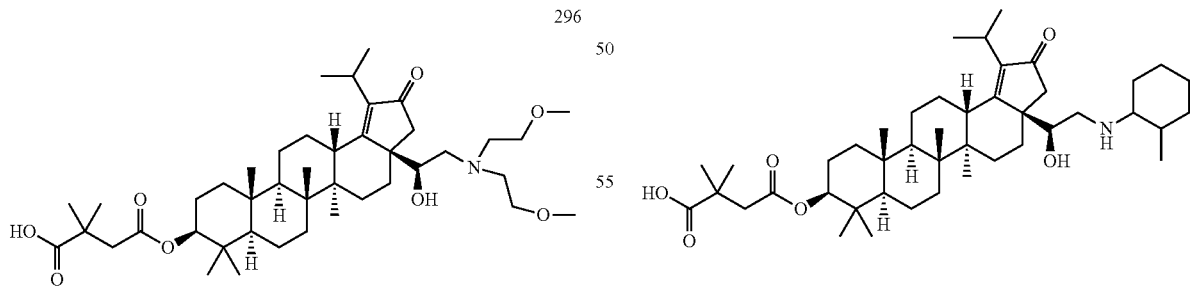

296

297

LC/MS: m/z calculated 729.5, found 730.5 (M+1)$^+$

LC/MS: m/z calculated 709.5, found 710.5 (M+1)$^+$

Example 229

Compound 298

4-(((3aR,5aR,5bR,7aR,9S,11aR,11bR,13aS)-3a-((1S)-1-hydroxy-2-((2-(1-methylpyrrolidin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

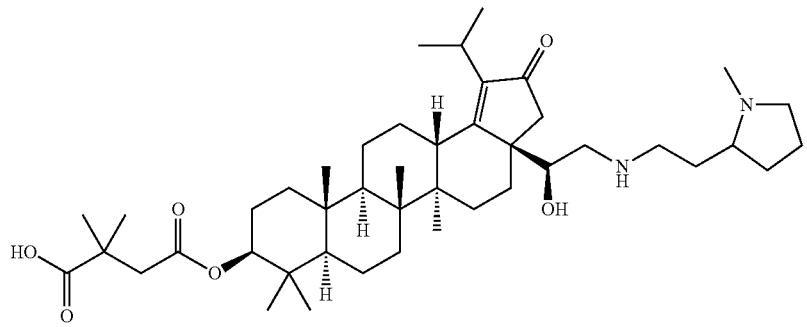

298

LC/MS: m/z calculated 724.5, found 725.5 (M+1)$^+$

Example 230

Compound 299

4-(((3aR,5aR,5bR,7aR,9S,11aR,11bR,13aS)-3a-((S)-1-hydroxy-2-((((1r,4S)-4-hydroxycyclohexyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

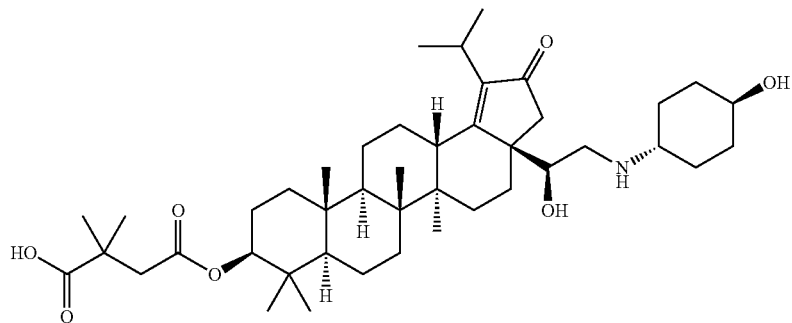

299

LC/MS: m/z calculated 711.5, found 712.4 (M+1)$^+$

Example 231

Compound 300

4-(((3aR,5aR,5bR,7aR,9S,11aR,11bR,13aS)-3a-((S)-2-(4-ethylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

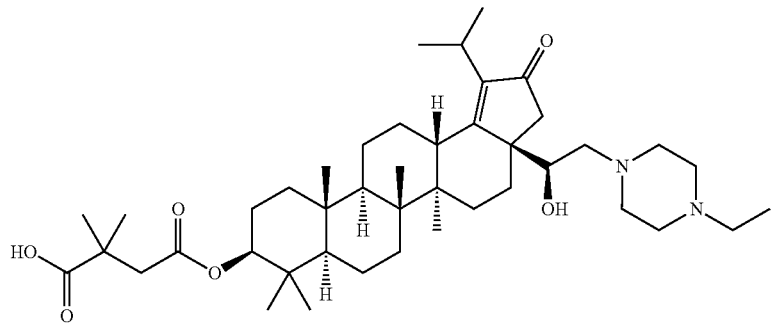

300

LC/MS: m/z calculated 710.5, found 711.5 (M+1)$^+$

Example 232

Compound 301

4-(((3aR,5aR,5bR,7aR,9S,11aR,11bR,13aS)-3a-((S)-1-hydroxy-2-(((S)-2-hydroxypropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

301

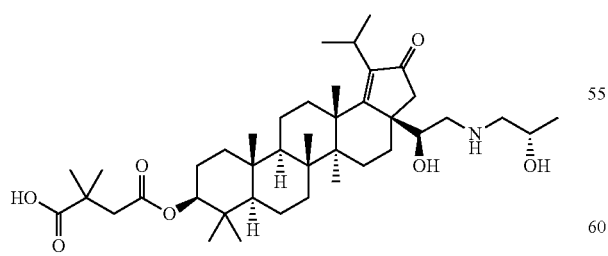

LC/MS: m/z calculated 671.5, found 672.4 (M+1)$^+$

Example 233

Compound 302

4-(((3aR,5aR,5bR,7aR,9S,11aR,11bR,13aS)-3a-((S)-2-((4-chlorophenyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

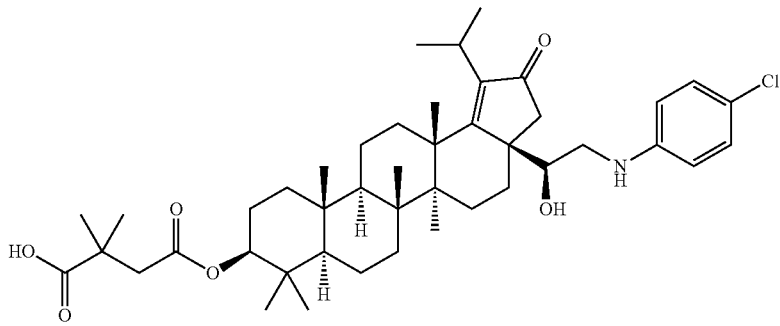

LC/MS: m/z calculated 723.4, found 724.4 (M+1)$^+$

Example 234

Compound 303

4-(((3aR,5aR,5bR,7aR,9S,11aR,11bR,13aS)-3a-((S)-1-hydroxy-2-(isoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

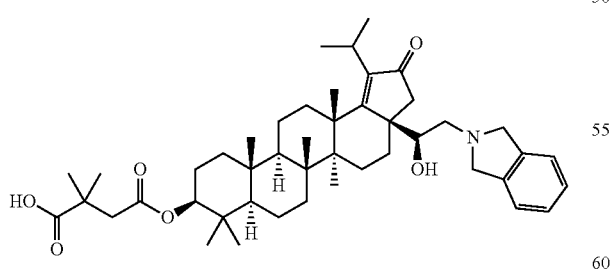

LC/MS: m/z calculated 715.5, found 716.5 (M+1)$^+$

Example 235

Compound 304

4-(((3aR,5aR,5bR,7aR,9S,11aR,11bR,13aS)-3a-((R)-2-(((S)-1-(5-chloropyridin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

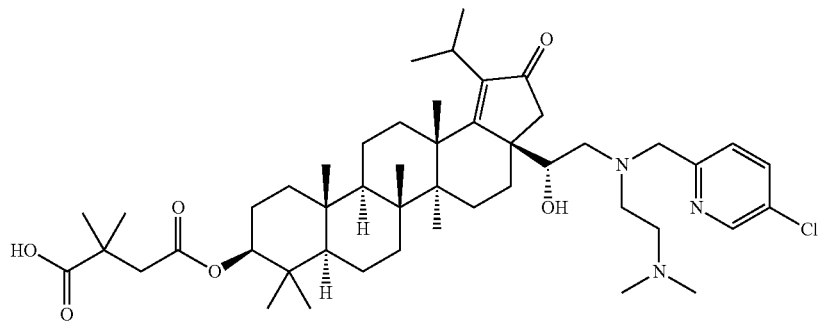

304

LC/MS: m/z calculated 823.5, found 824.5 (M+1)$^+$

Example 236

Compound 305

4-(((3aR,5aR,5bR,7aR,9S,11aR,11bR,13aS)-3a-((S)-2-(((S)-1-(5-chloropyridin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

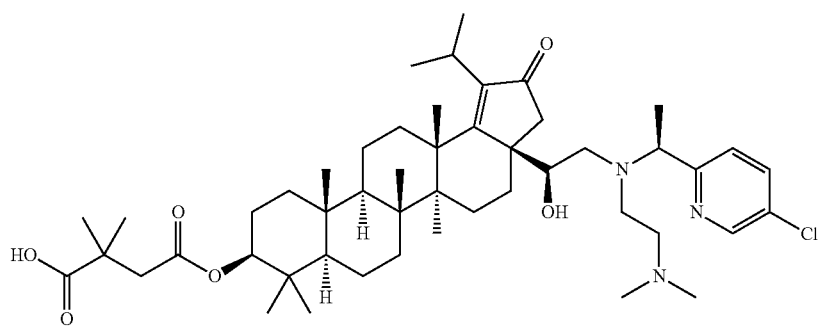

305

LC/MS: m/z calculated 823.5, found 824.5 (M+1)$^+$

Example 237

Compound 306

4-(((3aR,5aR,5bR,7aR,9S,11aR,11bR,13aS)-3a-((R)-1-hydroxy-2-(isoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

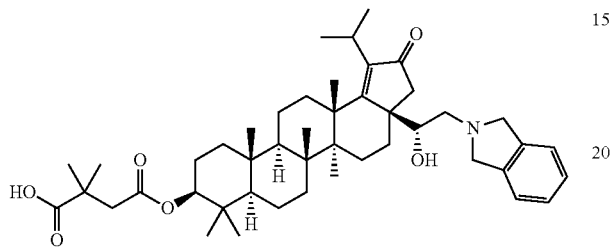

306

LC/MS: m/z calculated 715.5, found 716.5 (M+1)$^+$

Example 238

Compound 307

4-(((3aR,5aR,5bR,7aR,9S,11aR,11bR,13aS)-3a-((S)-2-((2-(5-chloropyridin-2-yl)propan-2-yl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

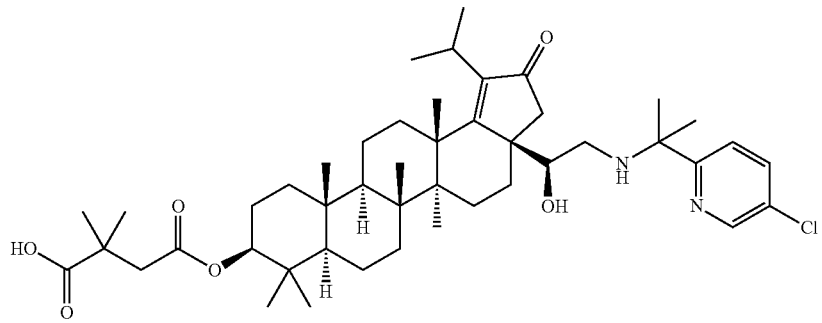

307

LC/MS: m/z calculated 766.5, found 767.5 (M+1)$^+$

Example 239

Compound 308

4-(((3aR,5aR,5bR,7aR,9S,11aR,11bR,13aS)-3a-((R)-2-((2-(5-chloropyridin-2-yl)propan-2-yl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

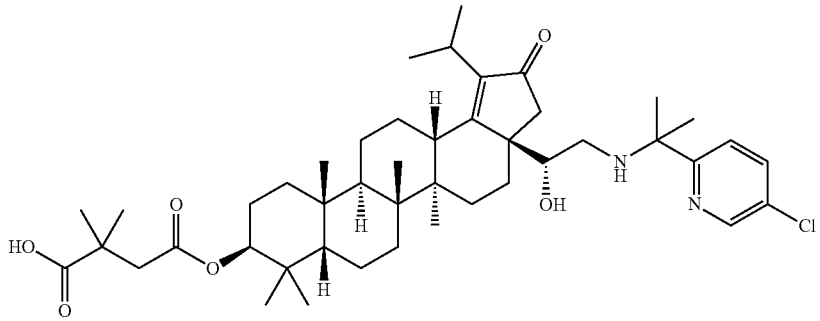

308

LC/MS: m/z calculated 766.5, found 767.6 (M+1)$^+$

Example 240

Compound 309

4-(((3aR,5aR,5bR,7aR,9S,11aR,11bR,13aS)-3a-((R)-1-hydroxy-2-(((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

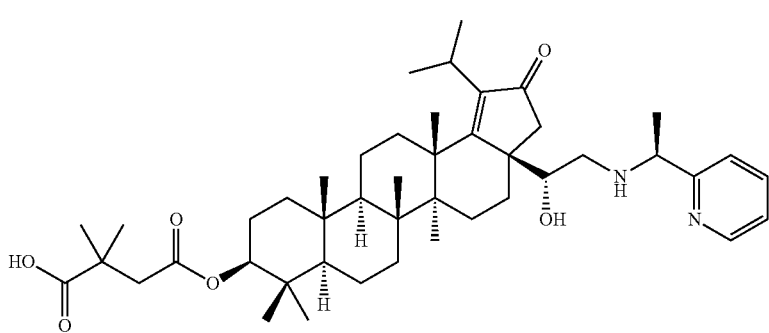

309

LC/MS: m/z calculated 718.5, found 719.5 (M+1)$^+$

Example 241

Compound 310

4-(((3aR,5aR,5bR,7aR,9S,11aR,11bR,13aS)-3a-((S)-1-hydroxy-2-((pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

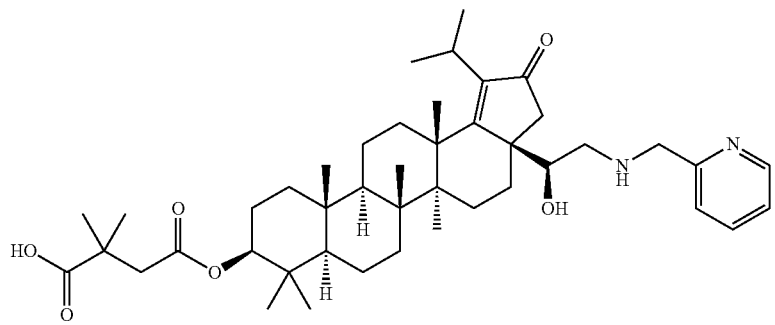

LC/MS: m/z calculated 704.5, found 705.5 (M+1)$^+$

Example 242

Compound 311

4-(((3aR,5aR,5bR,7aR,9S,11aR,11bR,13aS)-3a-((R)-1-hydroxy-2-((pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

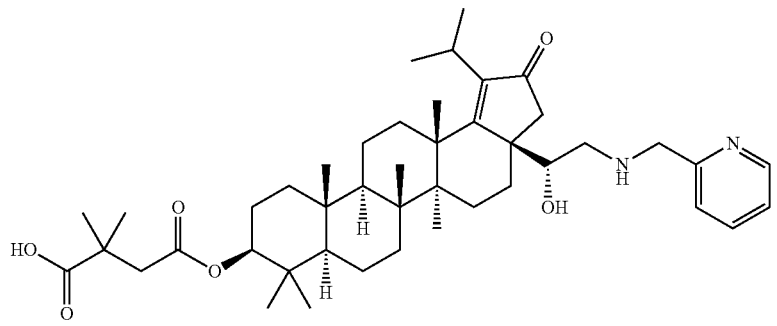

LC/MS: m/z calculated 704.5, found 705.5 (M+1)$^+$

Example 243

Compound 312

4-(((3aR,5aR,5bR,7aR,9S,11aR,11bR,13aS)-3a-((R)-2-((2-(dimethylamino)ethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

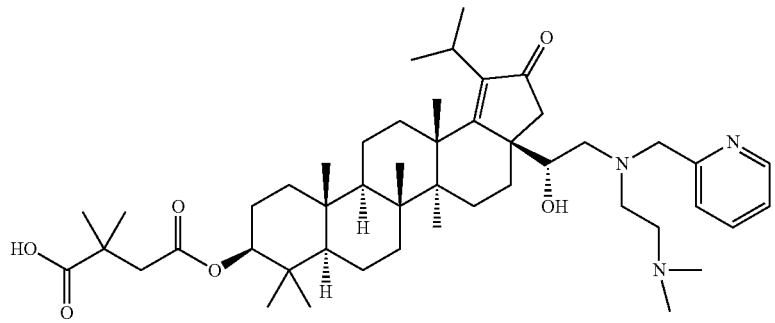

312

LC/MS: m/z calculated 775.5, found 776.5 (M+1)$^+$

Example 244

Compound 313

4-(((3aR,5aR,5bR,7aR,9S,11aR,11bR,13aS)-3a-((S)-1-hydroxy-2-(phenylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

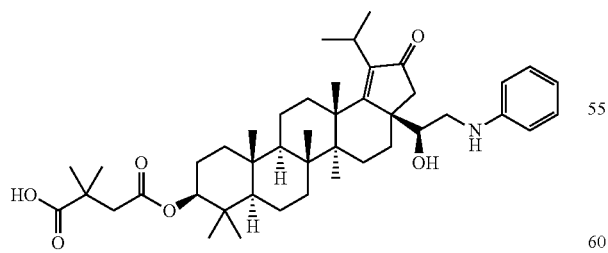

313

LC/MS: m/z calculated 689.5, found 690.5 (M+1)$^+$

Example 245

Compound 314

4-(((3aR,5aR,5bR,7aR,9S,11aR,11bR,13aS)-3a-((S)-1-hydroxy-2-((4-methoxyphenyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

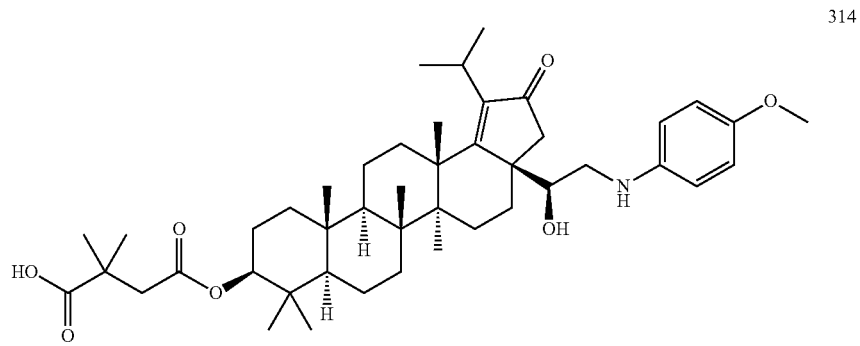

LC/MS: m/z calculated 719.5, found 720.5 (M+1)$^+$

Example 246

Compound 315

4-(((3aR,5aR,5bR,7aR,9S,11aR,11bR,13aS)-3a-((S)-1-hydroxy-2-((S)-2-(hydroxymethyl)pyrrolidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 247

Compound 316

4-(((3aR,5aR,5bR,7aR,9S,11aR,11bR,13aS)-3a-((S)-2-((R)-3-(ethoxycarbonyl)piperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

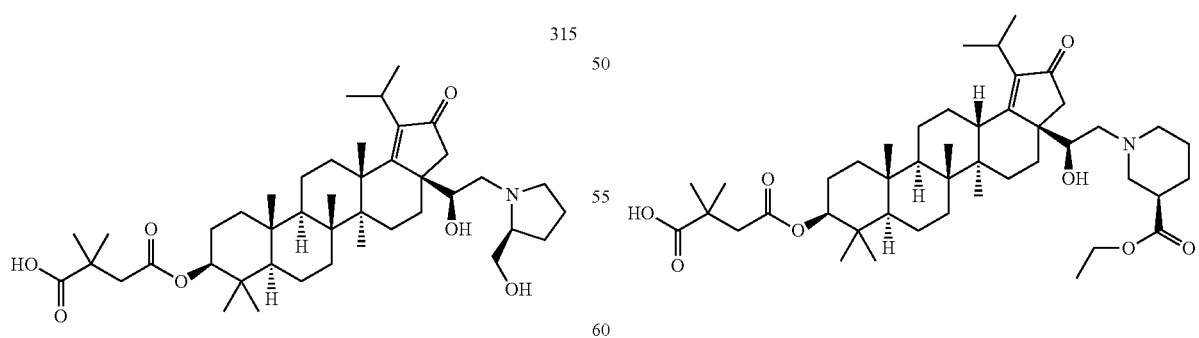

LC/MS: m/z calculated 697.5, found 698.5 (M+1)$^+$

LC/MS: m/z calculated 753.5, found 754.5 (M+1)$^+$

Example 248

Compound 317

4-(((3aR,5aR,5bR,7aR,9S,11aR,11bR,13aS)-3a-((S)-2-(4-formylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

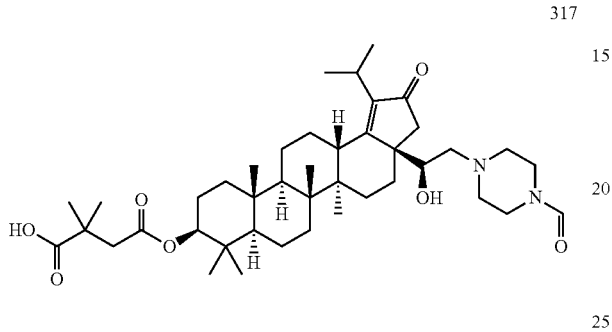

317

LC/MS: m/z calculated 710.5, found 711.5 (M+1)$^+$

Example 249

Compound 318

4-(((3aR,5aR,5bR,7aR,9S,11aR,11bR,13aS)-3a-((S)-2-(4-benzylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

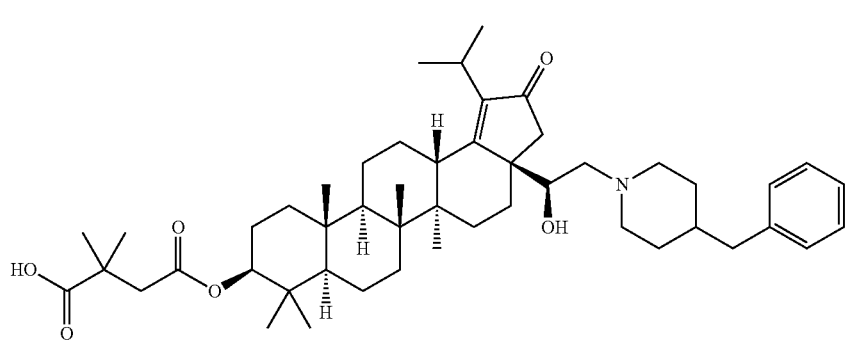

318

LC/MS: m/z calculated 771.5, found 772.5 (M+1)$^+$

Example 250

Compound 319

4-(((3aR,5aR,5bR,7aR,9S,11aR,11bR,13aS)-3a-((S)-2-(4-acetylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

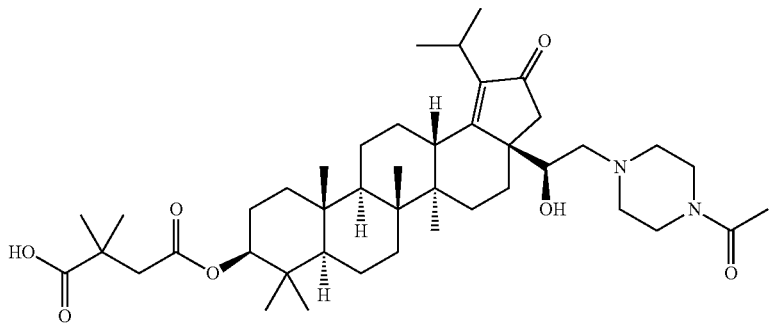

319

LC/MS: m/z calculated 724.5, found 725.5 (M+1)$^+$

Example 251

Compound 320

4-(((3aR,5aR,5bR,7aR,9S,11aR,11bR,13aS)-3a-((S)-1-hydroxy-2-(4-(2-morpholinoethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

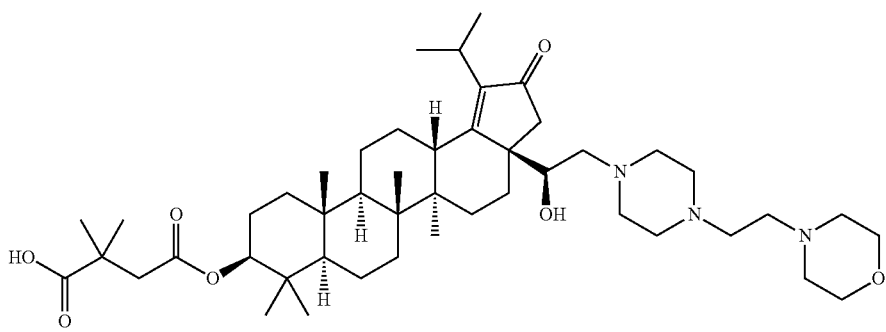

320

LC/MS: m/z calculated 795.6, found 796.5 (M+1)$^+$

Example 252

Compound 321

4-(((3aR,5aR,5bR,7aR,9S,11aR,11bR,13aS)-3a-((R)-2-(benzyl(carboxymethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

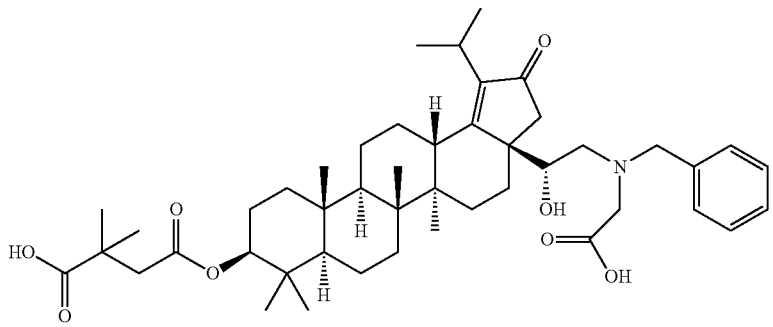

LC/MS: m/z calculated 761.5, found 762.5 (M+1)$^+$

Example 253

Compound 322

4-(((3aR,5aR,5bR,7aR,9S,11aR,11bR,13aS)-3a-((S)-1-hydroxy-2-(((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

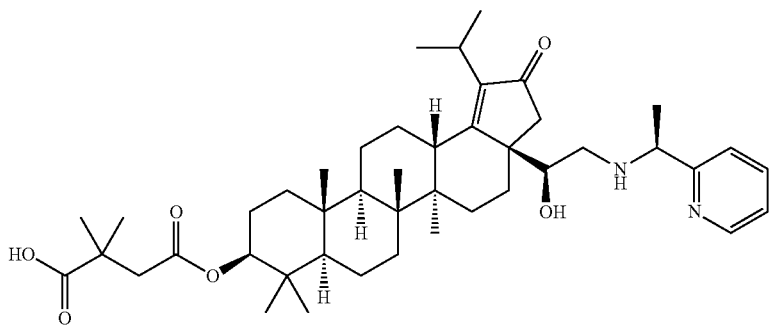

LC/MS: m/z calculated 718.5, found 719.5 (M+1)$^+$

Example 254

Compound 323

4-(((3aR,5aR,5bR,7aR,9S,11aR,11bR,13aS)-3a-((R)-2-(2-(dimethylamino)-N—((R)-1-(pyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

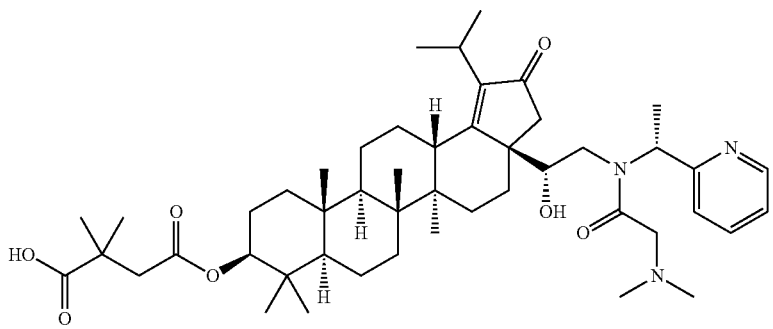

323

LC/MS: m/z calculated 803.5, found 804.5 (M+1)$^+$

Example 255

Compound 324

4-(((3aR,5aR,5bR,7aR,9S,11aR,11bR,13aS)-3a-((R)-1-hydroxy-2-((2-(methylamino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

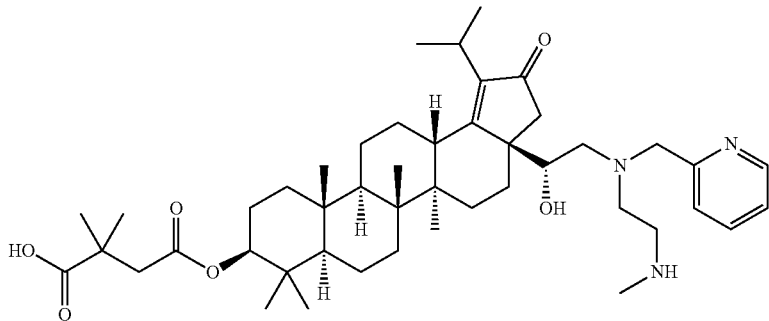

324

LC/MS: m/z calculated 761.5, found 762.5 (M+1)$^+$

Example 256

Compound 325

4-((3aR,5aR,5bR,7aR,9S,11aR,11bR,13aS)-3a-((R)-2-(bis(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate.

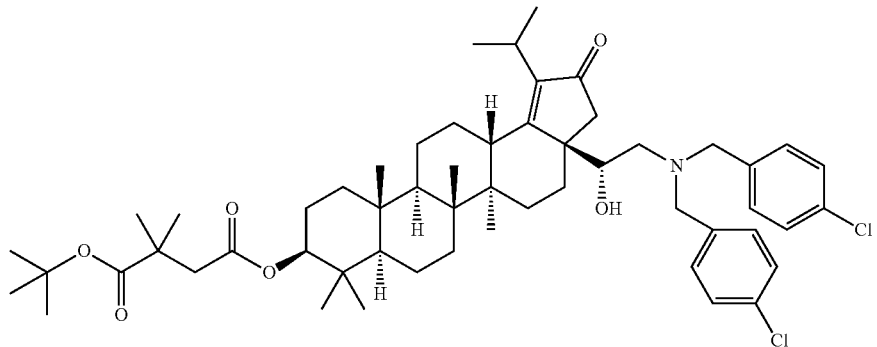

LC/MS: m/z calculated 917.5, found 918.5 (M+1)$^+$

Example 257

Compound 326

4-(((3aR,5aR,5bR,7aR,9S,11aR,11bR,13aS)-3a-((R)-2-(bis(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

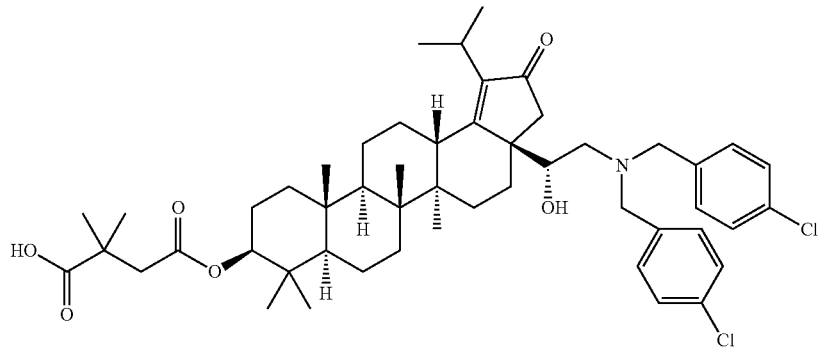

LC/MS: m/z calculated 861.4, found 862.4 (M+1)$^+$

Example 258

Compound 327

4-(((3aR,5aR,5bR,7aR,9S,11aR,11bR,13aS)-3a-((R)-1-hydroxy-2-((2-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

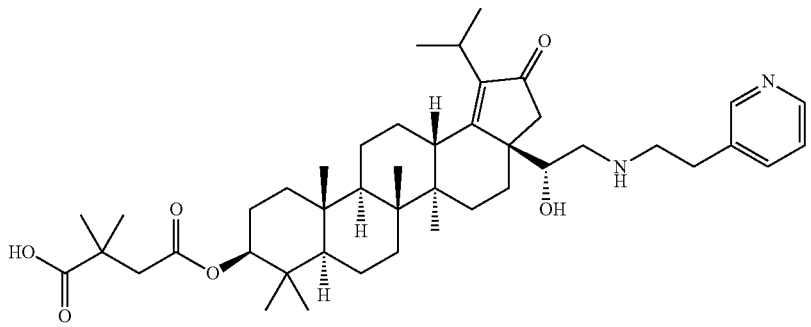

327

LC/MS: m/z calculated 718.5, found 719.5 (M+1)$^+$

Example 259

Compound 328

4-(((3aR,5aR,5bR,7aR,9S,11aR,11bR,13aS)-3a-((R)-1-hydroxy-2-((R)-3-hydroxypiperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

328

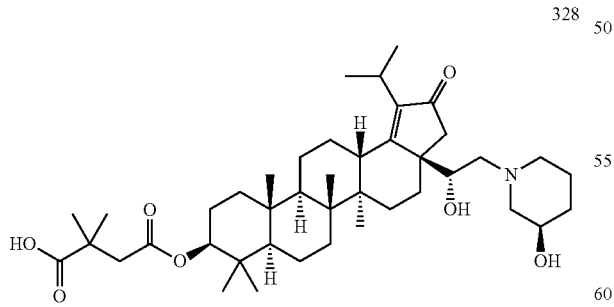

LC/MS: m/z calculated 697.5, found 698.5 (M+1)$^+$

Example 260

Compound 329

4-(((3aR,5aR,5bR,7aR,9S,11aR,11bR,13aS)-3a-((R)-1-hydroxy-2-((4-hydroxyphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

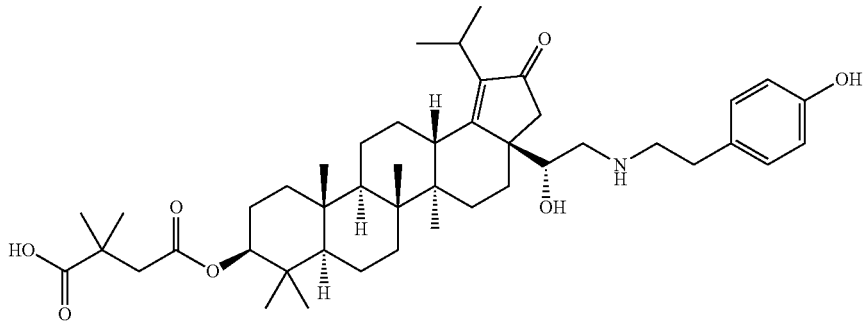

LC/MS: m/z calculated 733.5, found 734.4 $(M+1)^+$

Example 261

Compound 330

4-(((3aR,5aR,5bR,7aR,9S,11aR,11bR,13aS)-3a-((R)-1-hydroxy-2-(4-(2-hydroxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

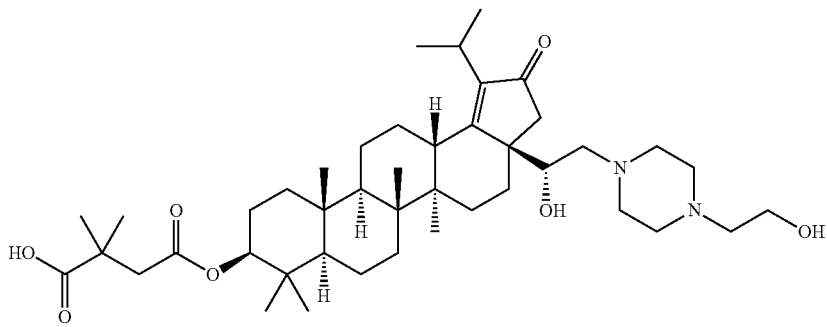

LC/MS: m/z calculated 726.5, found 727.5 $(M+1)^+$

Example 262

Compound 331

4-(((3aR,5aR,5bR,7aR,9S,11aR,11bR,13aS)-3a-((R)-1-hydroxy-2-thiomorpholinoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

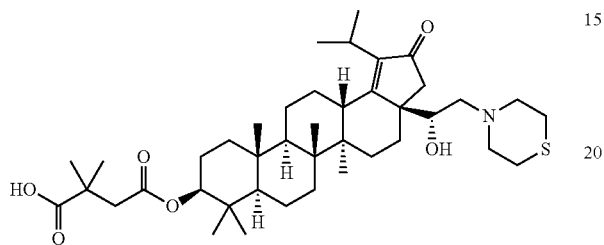

331

LC/MS: m/z calculated 699.4, found 700.4 (M+1)$^+$

Example 263

Compound 332

4-(((3aR,5aR,5bR,7aR,9S,11aR,11bR,13aS)-3a-((R)-1-hydroxy-2-(4-(pyridin-2-yl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

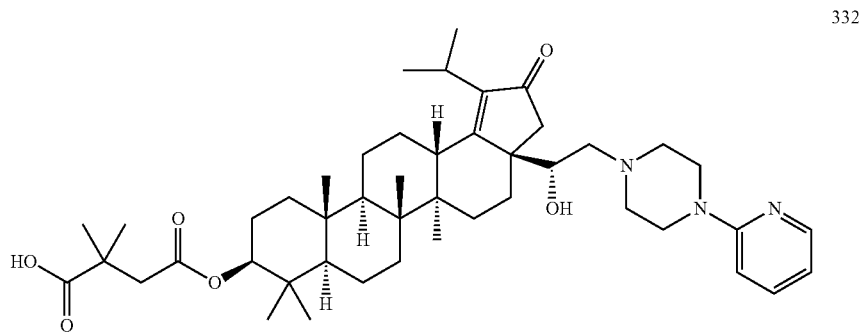

332

LC/MS: m/z calculated 759.5, found 760.5 (M+1)$^+$

Example 264

Compound 333

4-(((3aR,5aR,5bR,7aR,9S,11aR,11bR,13aS)-3a-((R)-1-hydroxy-2-(4-methyl-1,4-diazepan-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

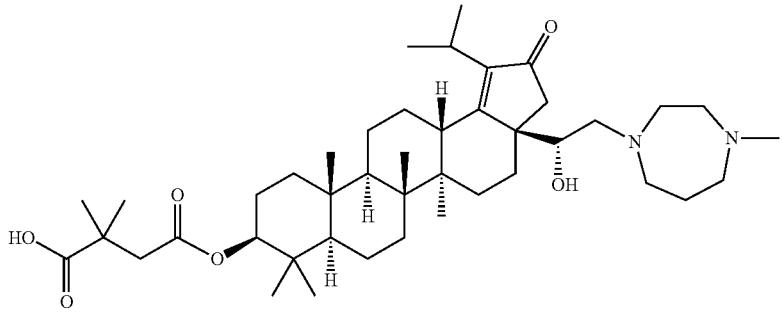

333

LC/MS: m/z calculated 710.5, found 711.5 (M+1)$^+$

Example 265

Compound 334

4-(((3aR,5aR,5bR,7aR,9S,11aR,11bR,13aS)-3a-((R)-2-(4-carbamoylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

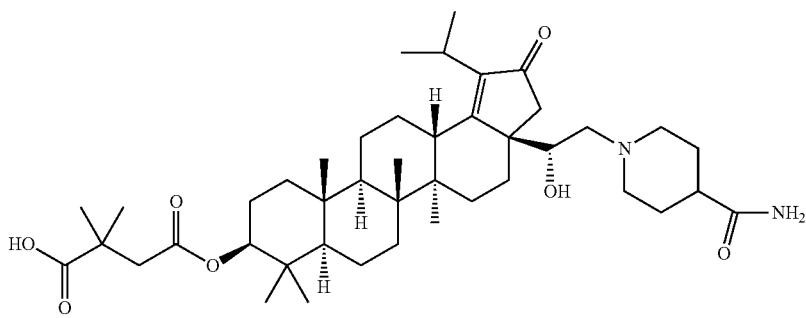

334

LC/MS: m/z calculated 724.5, found 725.5 (M+1)$^+$

Example 266

Compound 335

4-(((3aR,5aR,5bR,7aR,9S,11aR,11bR,13aS)-3a-((R)-1-hydroxy-2-(4-(2-methoxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

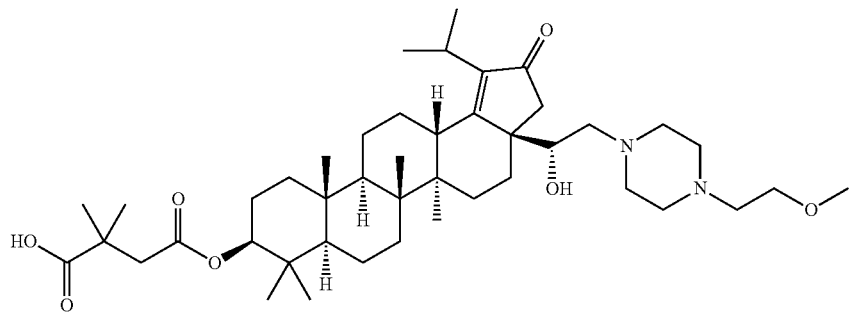

335

LC/MS: m/z calculated 740.5, found 741.5 (M+1)$^+$

Example 267

Compound 336

4-(((3aR,5aR,5bR,7aR,9S,11aR,11bR,13aS)-3a-((R)-1-hydroxy-2-(((R)-2-hydroxy-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

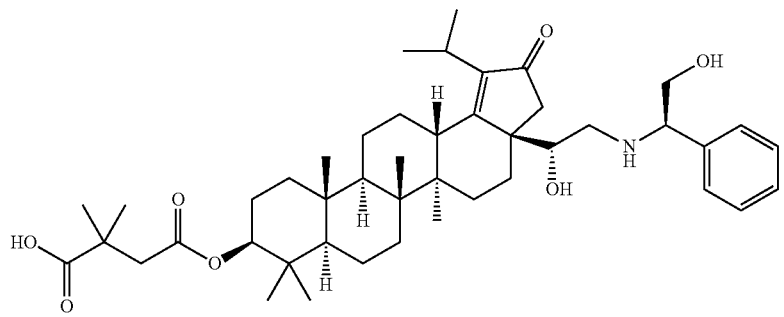

336

LC/MS: m/z calculated 733.5, found 734.5 (M+1)$^+$

Example 268

Compound 337

4-(((3aR,5aR,5bR,7aR,9S,11aR,11bR,13aS)-3a-((S)-1-hydroxy-2-((pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

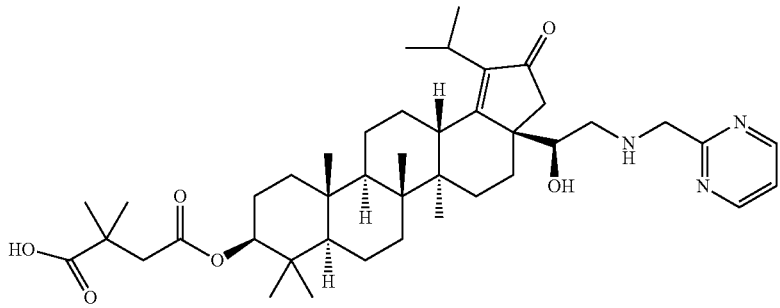

LC/MS: m/z calculated 705.5, found 706.4 (M+1)$^+$

Example 269

Compound 338

4-(((3aR,5aR,5bR,7aR,9S,11aR,11bR,13aS)-3a-((R)-1-hydroxy-2-((pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

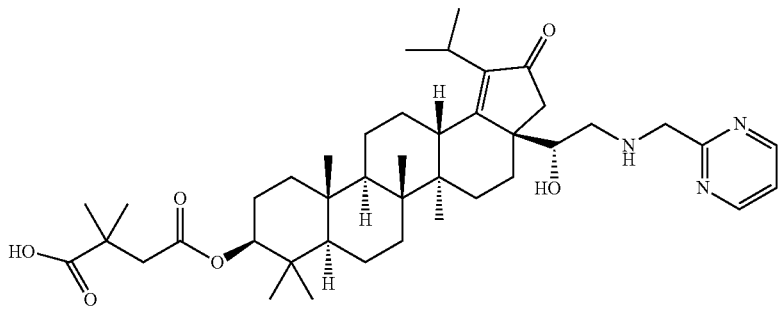

LC/MS: m/z calculated 705.5, found 706.4 (M+1)$^+$

Example 270

Compound 339

4-(((3aR,5aR,5bR,7aR,9S,11aR,11bR,13aS)-3a-((R)-2-(N-benzyl-2-(dimethylamino)-2-oxoacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

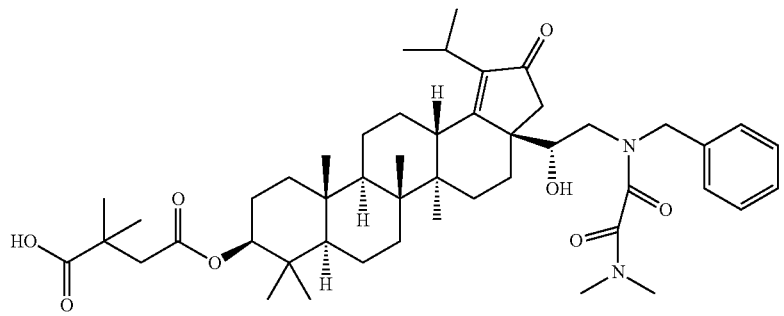

339

LC/MS: m/z calculated 802.5, found 803.5 $(M+1)^+$

Example 271

Compound 340

4-(((3aR,5aR,5bR,7aR,9S,11aR,11bR,13aS)-3a-((S)-2-((4-chloro-2-((dimethylamino)methyl)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

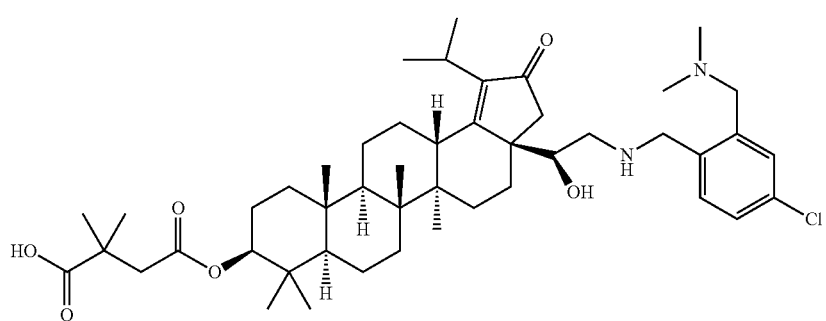

340

LC/MS: m/z calculated 794.5, found 795.5 $(M+1)^+$

Example 272

Compound 341

4-(((3aR,5aR,5bR,7aR,9S,11aR,11bR,13aS)-3a-((R)-2-((4-chloro-2-((dimethylamino)methyl)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

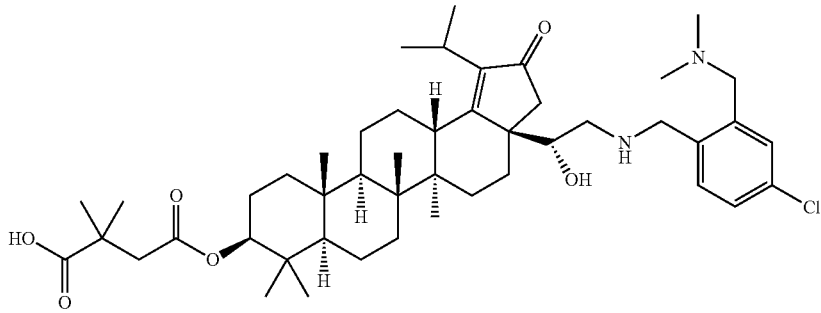

341

LC/MS: m/z calculated 794.5, found 795.5 (M+1)$^+$

Example 273

Compound 342

4-(((3aR,5aR,5bR,7aR,9S,11aR,11bR,13aS)-3a-((S)-2-((4-chloro-2-((dimethylamino)methyl)benzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

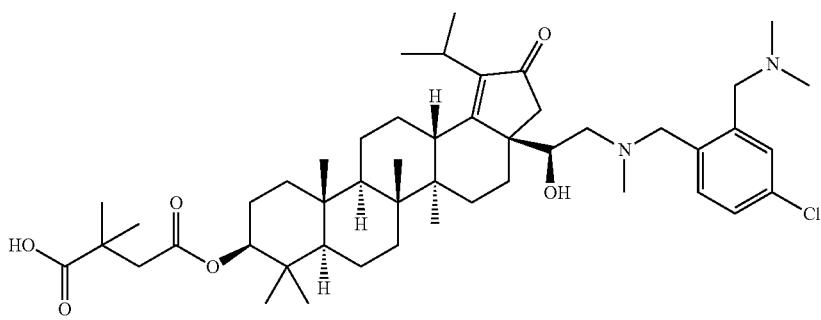

342

LC/MS: m/z calculated 808.5, found 809.5 (M+1)$^+$

Example 274

Compound 343

4-(((3aR,5aR,5bR,7aR,9S,11aR,11bR,13aS)-3a-((R)-2-(N-(4-chloro-2-((dimethylamino)methyl)benzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

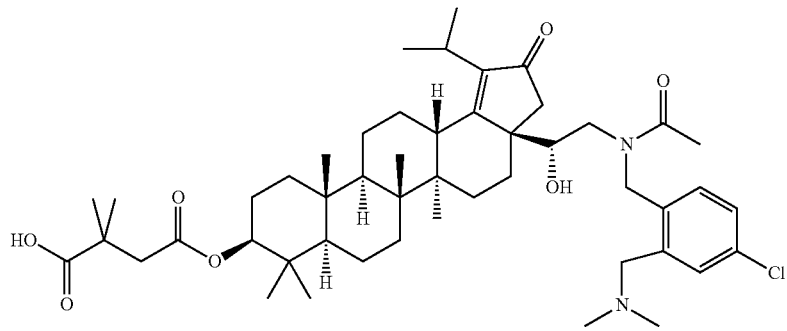

343

LC/MS: m/z calculated 836.5, found 837.5 (M+1)$^+$

Example 275

Compound 344

4-(((3aR,5aR,5bR,7aR,9S,11aR,11bR,13aS)-3a-((R)-2-((4-chloro-2-((dimethylamino)methyl)benzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

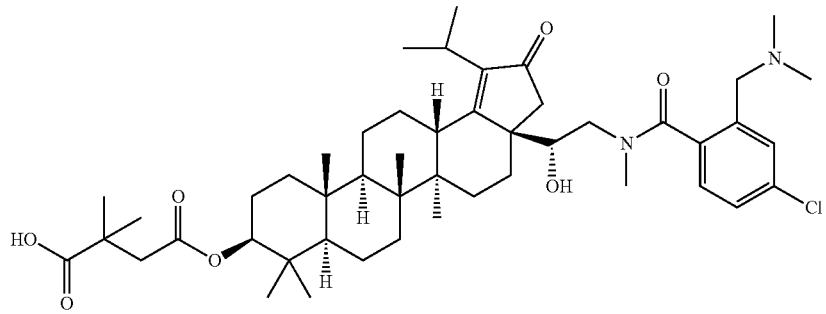

344

LC/MS: m/z calculated 808.5, found 809.5 (M+1)$^+$

Example 276

Compound 345

4-(((3aR,5aR,5bR,7aR,9S,11aR,11bR,13aS)-3a-((R)-2-(N-(cyclopropylmethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

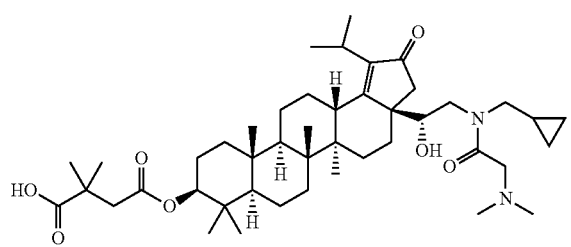

345

LC/MS: m/z calculated 752.5, found 753.5 (M+1)$^+$

Example 277

Compound 346

4-(((3aR,5aR,5bR,7aR,9S,11aR,11bR,13aS)-3a-((R)-2-(benzyl(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

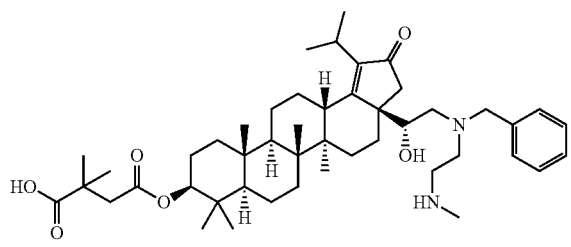

346

LC/MS: m/z calculated 760.5, found 761.5 (M+1)$^+$

Example 278

Compound 347

4-(((3aR,5aR,5bR,7aR,9S,11aR,11bR,13aS)-3a-((R)-2-((cyclopropylmethyl)(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

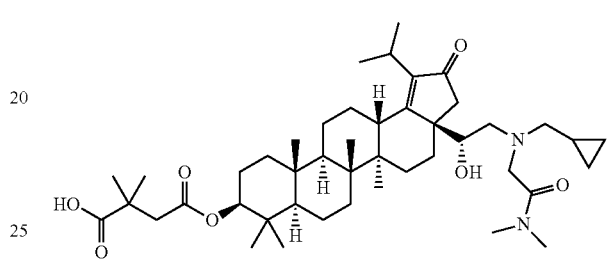

347

LC/MS: m/z calculated 752.5, found 753.5 (M+1)$^+$

Example 279

Compound 348

4-(((3aR,5aR,5bR,7aR,9S,11aR,11bR,13aS)-3a-((R)-2-((2-acetamidoethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

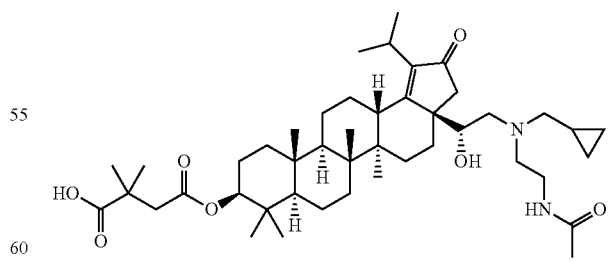

348

LC/MS: m/z calculated 752.5, found 753.5 (M+1)$^+$

Example 280

Compound 349

4-(((3aR,5aR,5bR,7aR,9S,11aR,11bR,13aS)-3a-((R)-2-((cyclopropylmethyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

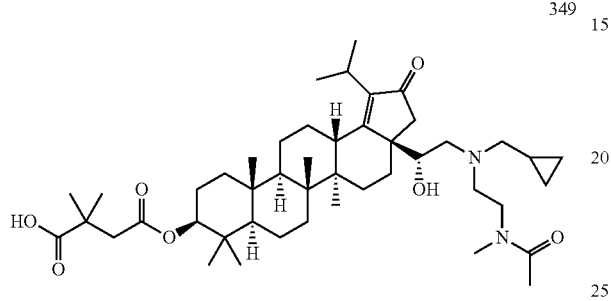

LC/MS: m/z calculated 766.5, found 767.5 (M+1)+

Example 281

Compound 350

4-(((3aR,5aR,5bR,7aR,9S,11aR,11bR,13aS)-3a-((R)-2-((2-amino-2-oxoethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

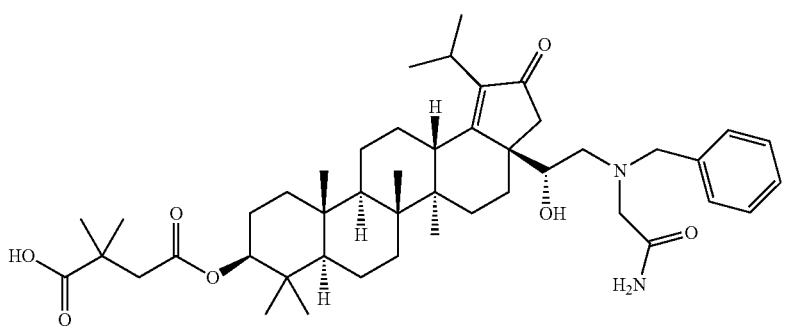

LC/MS: m/z calculated 760.5, found 761.5 (M+1)+

Example 282

Compound 351

4-(((3aR,5aR,5bR,7aR,9S,11aR,11bR,13aS)-3a-((R)-2-(benzyl(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

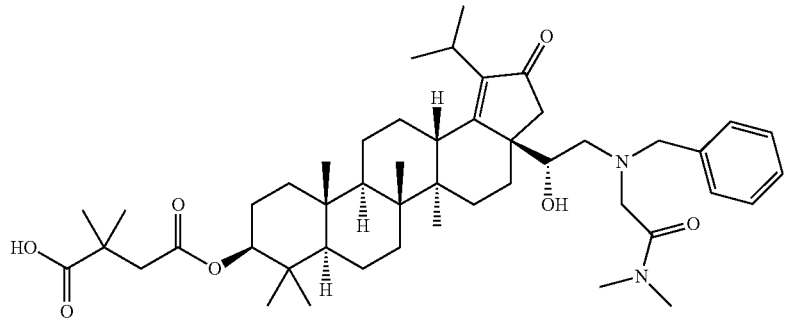

351

LC/MS: m/z calculated 788.5, found 789.5 (M+1)$^+$

Example 283

Compound 352

4-(((3aR,5aR,5bR,7aR,9S,11aR,11bR,13aS)-3a-((S)-1-hydroxy-2-(isobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 284

Compound 353

4-(((3aR,5aR,5bR,7aR,9S,11aR,11bR,13aS)-3a-((R)-2-(2-amino-N-(pyridin-3-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

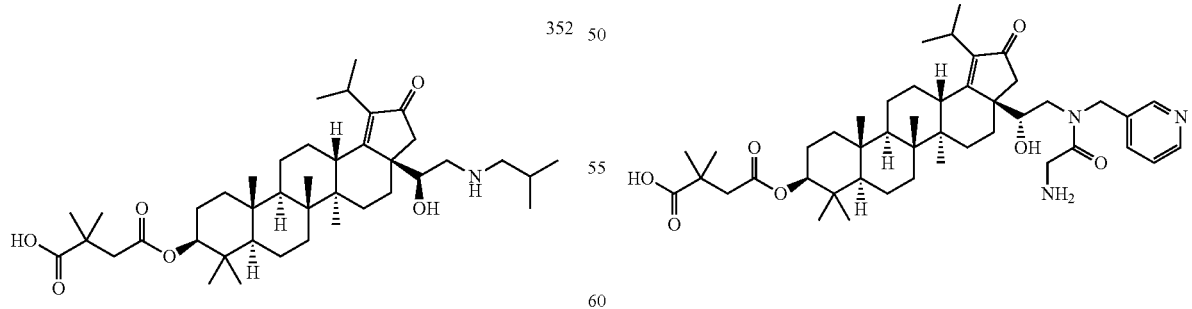

LC/MS: m/z calculated 669.5, found 670.5 (M+1)$^+$

LC/MS: m/z calculated 761.5, found 762.5 (M+1)$^+$

Example 285

Compound 354

4-(((3aR,5aR,5bR,7aR,9S,11aR,11bR,13aS)-3a-((R)-2-(2-(dimethylamino)-N-(pyridin-3-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

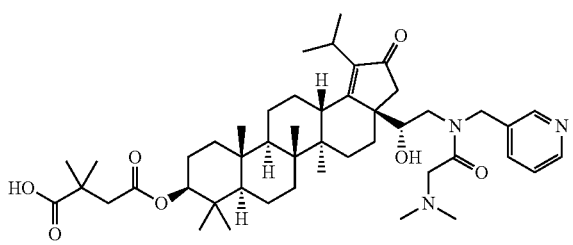

354

LC/MS: m/z calculated 789.5, found 790.5 (M+1)$^+$

Example 286

Compound 355

4-(((3aR,5aR,5bR,7aR,9S,11aR,11bR,13aS)-3a-((R)-1-hydroxy-2-(2-(methylamino)-N-(pyridin-3-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

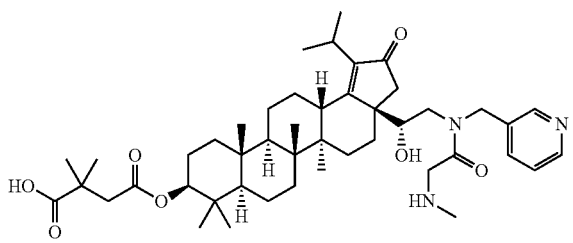

355

LC/MS: m/z calculated 775.5, found 776.5 (M+1)$^+$

Example 287

Compound 356

4-(((3aR,5aR,5bR,7aR,9S,11aR,11bR,13aS)-3a-((R)-1-hydroxy-2-((3-(trifluoromethyl)benzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

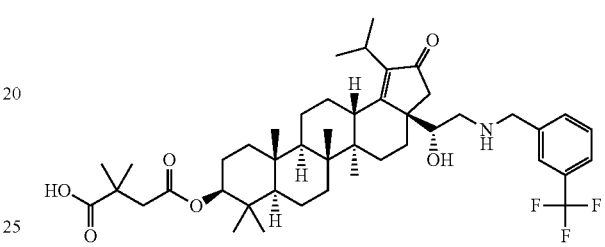

356

LC/MS: m/z calculated 771.5, found 772.4 (M+1)$^+$

Example 288

Compound 357

4-(((3aR,5aR,5bR,7aR,9S,11aR,11bR,13aS)-3a-((R)-1-hydroxy-2-((pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

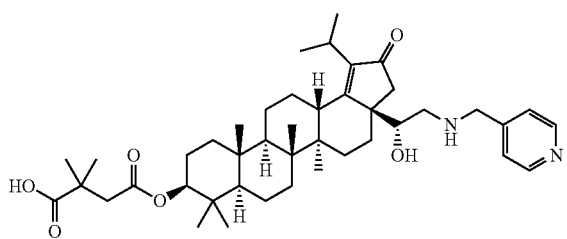

357

LC/MS: m/z calculated 704.5, found 705.5 (M+1)$^+$

Example 289

Compound 358

4-(((3aR,5aR,5bR,7aR,9S,11aR,11bR,13aS)-3a-((1R)-1-hydroxy-2-((((tetrahydrofuran-2-yl)methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

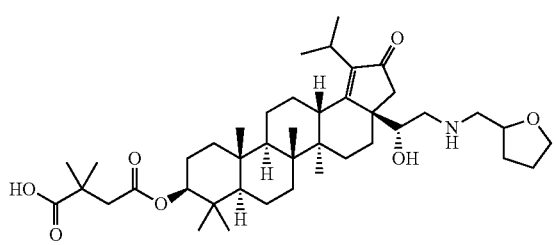

358

LC/MS: m/z calculated 697.5, found 698.5 (M+1)$^+$

Example 290

Compound 359

4-(((3aR,5aR,5bR,7aR,9S,11aR,11bR,13aS)-3a-((R)-2-(cyclohexyl(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

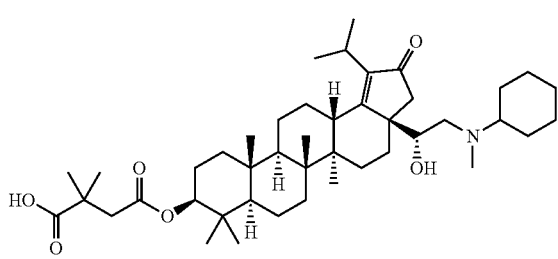

359

LC/MS: m/z calculated 709.5, found 710.5 (M+1)$^+$

Example 291

Compound 360

4-(((3aR,5aR,5bR,7aR,9S,11aR,11bR,13aS)-3a-((R)-1-hydroxy-2-(((S)-1-hydroxy-4-methylpentan-2-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

360

LC/MS: m/z calculated 713.5, found 714.5 (M+1)$^+$

Example 292

Compound 361

4-(((3aR,5aR,5bR,7aR,9S,11aR,11bR,13aS)-3a-((R)-1-hydroxy-2-((1-methylpiperidin-4-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

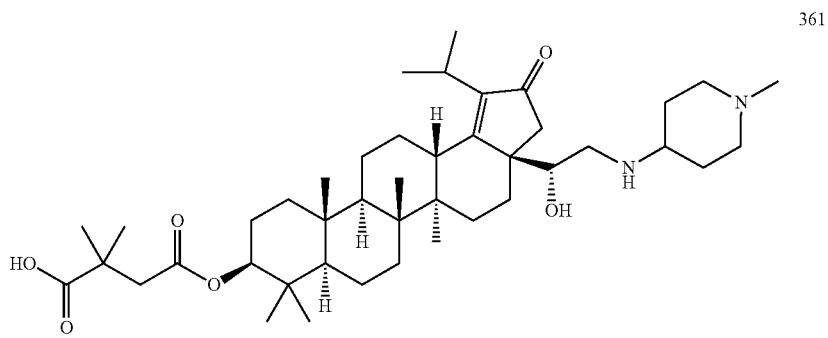

361

LC/MS: m/z calculated 710.5, found 711.5 (M+1)$^+$

Example 293

Compound 362

4-(((3aR,5aR,5bR,7aR,9S,11aR,11bR,13aS)-3a-((R)-2-(N-benzyl-1-carboxyformamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

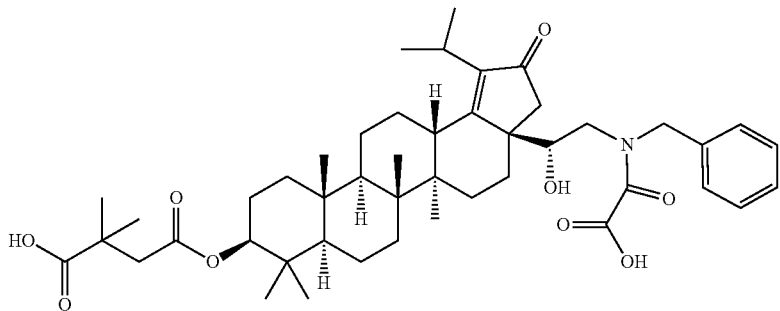

362

LC/MS: m/z calculated 775.5, found 776.5 (M+1)$^+$

Example 294

Compound 363

4-(((3aR,5aR,5bR,7aR,9S,11aR,11bR,13aS)-3a-((R)-2-(2-amino-N-benzyl-2-oxoacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

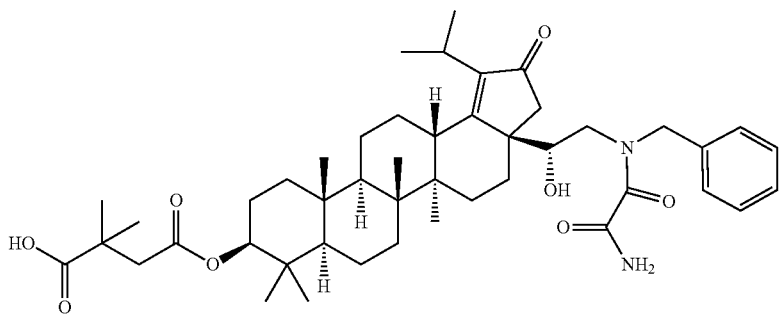

363

LC/MS: m/z calculated 774.5, found 775.5 (M+1)$^+$

Example 295

Compound 364

4-(((3aR,5aR,5bR,7aR,9S,11aR,11bR,13aS)-3a-((R)-1-hydroxy-2-(isobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

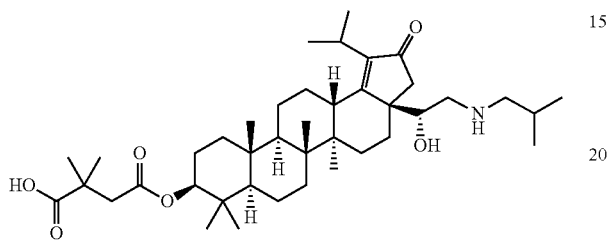

364

LC/MS: m/z calculated 669.5, found 670.5 (M+1)$^+$

Example 296

Compound 365

4-(((3aR,5aR,5bR,7aR,9S,11aR,11bR,13aS)-3a-((R)-1-hydroxy-2-(phenethylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

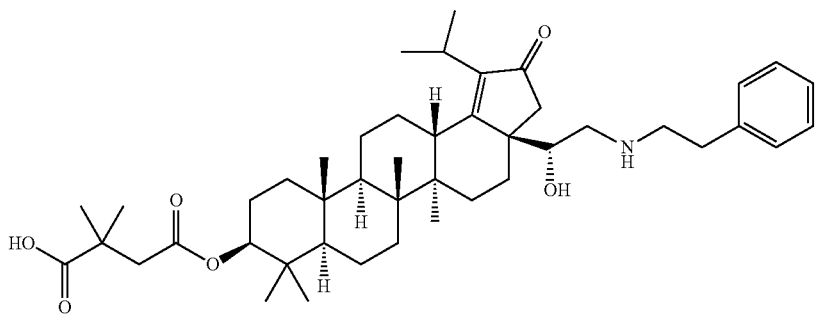

365

LC/MS: m/z calculated 717.5, found 718.5 (M+1)$^+$

Example 297

Compound 366

4-(((3aR,5aR,5bR,7aR,9S,11aR,11bR,13aS)-3a-((R)-2-((2-(dimethylamino)ethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

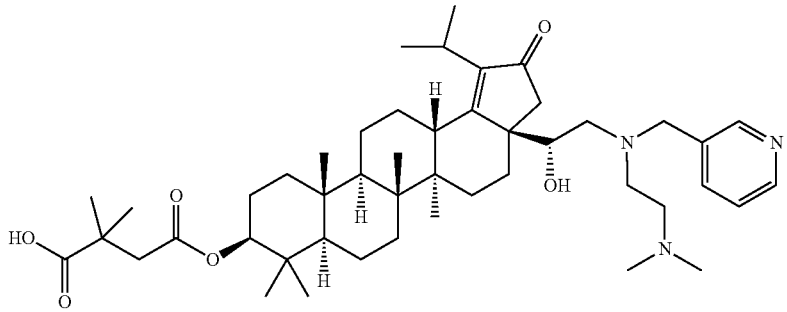

366

LC/MS: m/z calculated 775.5, found 776.5 $(M+1)^+$

Example 298

Compound 367

4-(((3aR,5aR,5bR,7aR,9S,11aR,11bR,13aS)-3a-((R)-2-((2-aminoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

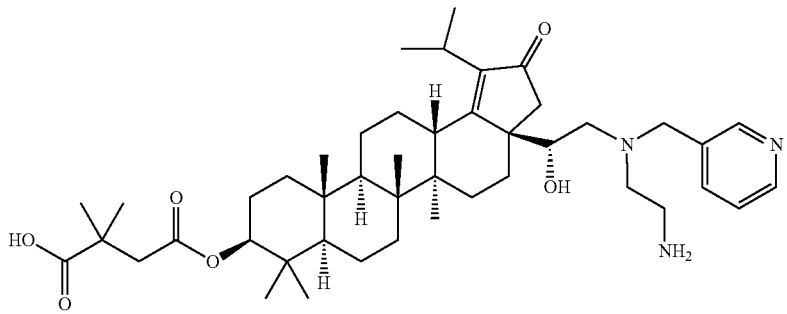

367

LC/MS: m/z calculated 747.5, found 748.5 $(M+1)^+$

Example 299

Compound 368

4-(((3aR,5aR,5bR,7aR,9S,11aR,11bR,13aS)-3a-((R)-2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

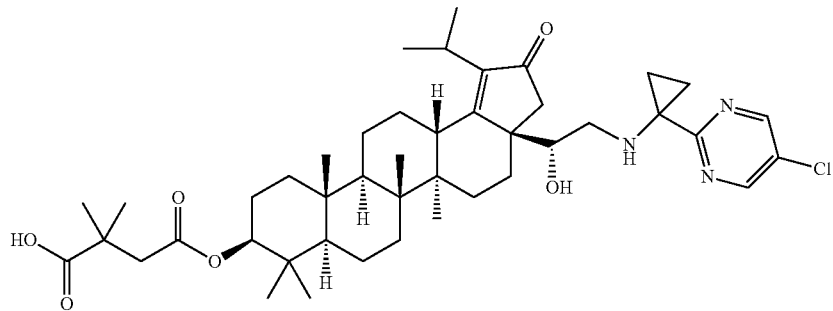

368

LC/MS: m/z calculated 765.5, found 766.5 (M+1)$^+$

Example 300

Compound 369

4-(((3aR,5aR,5bR,7aR,9S,11aR,11bR,13aS)-3a-((R)-2-(2-amino-N-(pyridin-4-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

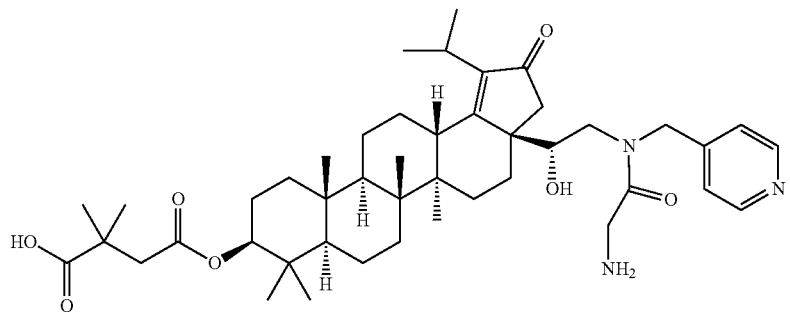

369

LC/MS: m/z calculated 761.5, found 762.5 (M+1)$^+$

Example 301

Compound 370

4-(((3aR,5aR,5bR,7aR,9S,11aR,11bR,13aS)-3a-((R)-1-hydroxy-2-(2-(methylamino)-N-(pyridin-4-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

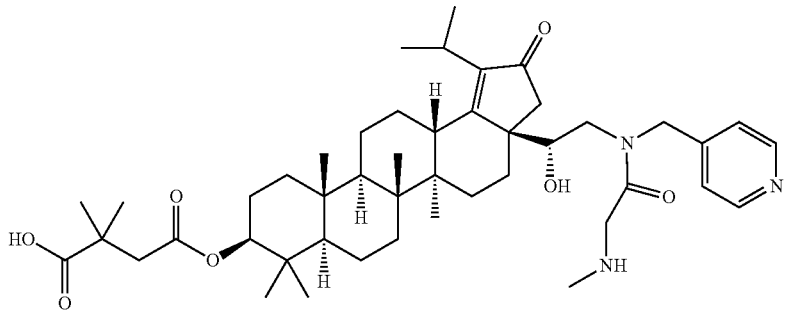

LC/MS: m/z calculated 775.5, found 776.5 (M+1)$^+$

Example 302

Compound 371

4-(((3aR,5aR,5bR,7aR,9S,11aR,11bR,13aS)-3a-((R)-2-(2-(dimethylamino)-N-(pyridin-4-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

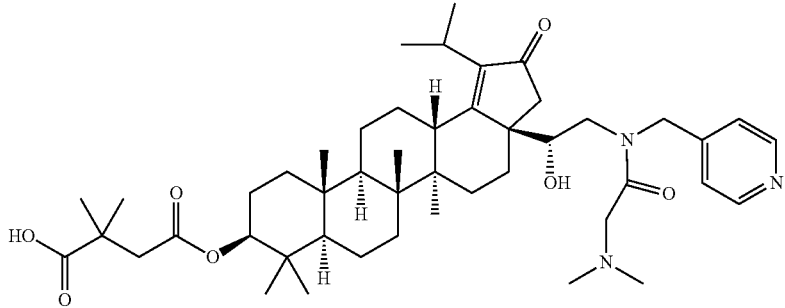

LC/MS: m/z calculated 789.5, found 790.5 (M+1)$^+$

Example 303

Compound 372

4-(((3aR,5aR,5bR,7aR,9S,11aR,11bR,13aS)-3a-((R)-2-((2-(dimethylamino)ethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

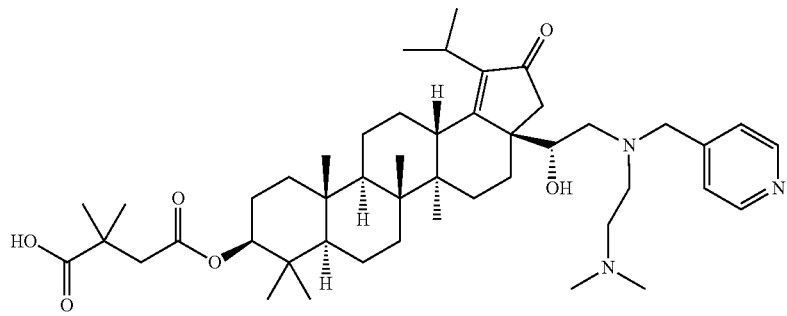

372

LC/MS: m/z calculated 775.5, found 776.5 (M+1)$^+$

Example 304

Compound 373

4-(((3aR,5aR,5bR,7aR,9S,11aR,11bR,13aS)-3a-((R)-1-hydroxy-2-((2-(methylamino)ethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

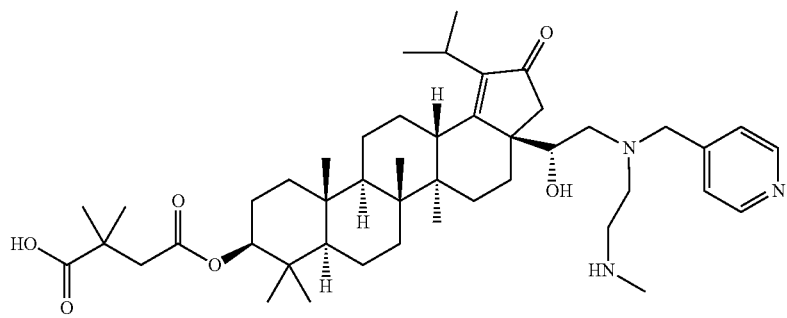

373

LC/MS: m/z calculated 761.5, found 762.5 (M+1)$^+$

Example 305

Compound 374

4-(((3aR,5aR,5bR,7aR,9S,11aR,11bR,13aS)-3a-(2-(cyclohexanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

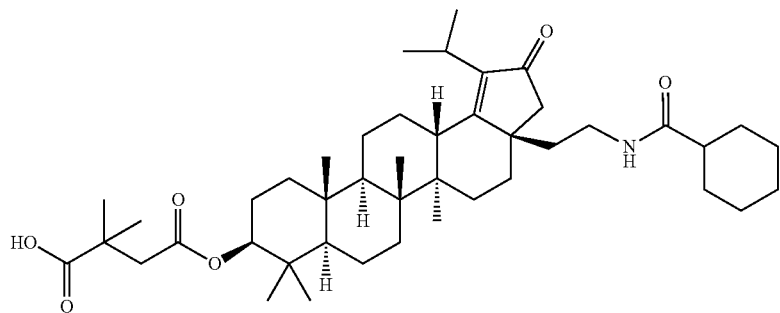

374

LC/MS: m/z calculated 707.5, found 708.5 (M+1)$^+$

Example 306

Compound 375

4-(((3aR,5aR,5bR,7aR,9S,11aR,11bR,13aS)-3a-((R)-2-((2-aminoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

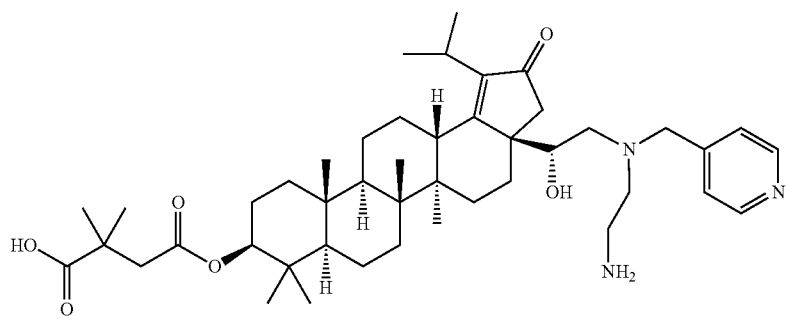

375

LC/MS: m/z calculated 747.5, found 748.5 (M+1)$^+$

Example 307

Compound 376

4-(((3aR,5aR,5bR,7aR,9S,11aR,11bR,13aS)-3a-((R)-2-((2-aminoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

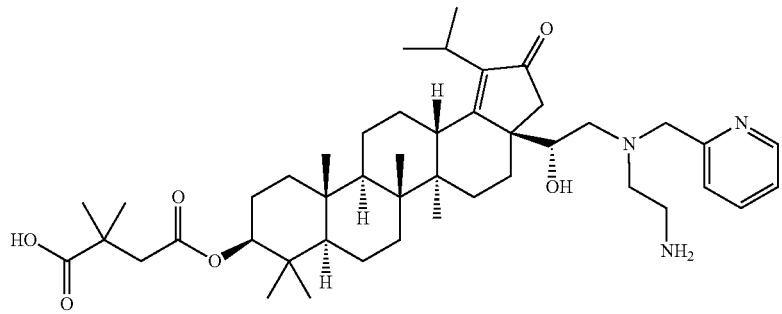

376

LC/MS: m/z calculated 747.5, found 748.5 (M+1)$^+$

Example 308

Compound 377

4-(((3aR,5aR,5bR,7aR,9S,11aR,11bR,13aS)-3a-((R)-1-hydroxy-2-((2-(N-methylacetamido)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

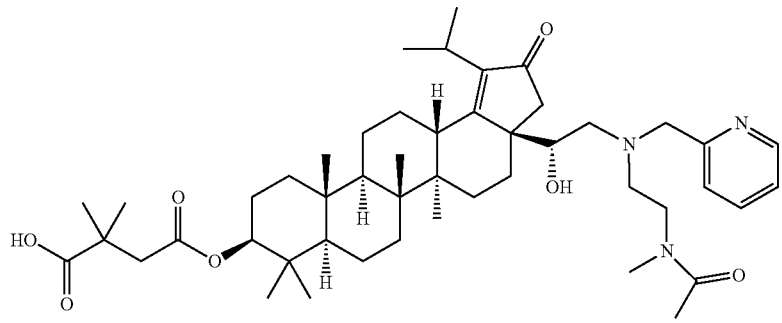

377

LC/MS: m/z calculated 803.5, found 804.5 (M+1)$^+$

Example 309

Compound 378

4-(((3aR,5aR,5bR,7aR,9S,11aR,11bR,13aS)-3a-((R)-2-((1-(5-chloropyrimidin-2-yl)cyclopropyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

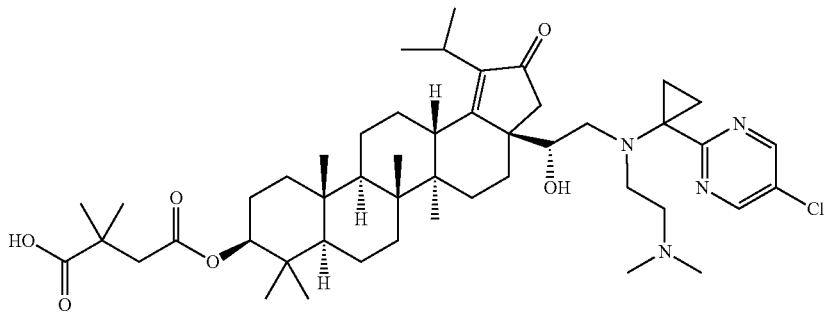

378

LC/MS: m/z calculated 836.5, found 837.5 (M+1)$^+$

Example 310

Compound 379

4-(((3aR,5aR,5bR,7aR,9S,11aR,11bR,13aS)-3a-((R)-2-(benzyl(2-(methylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

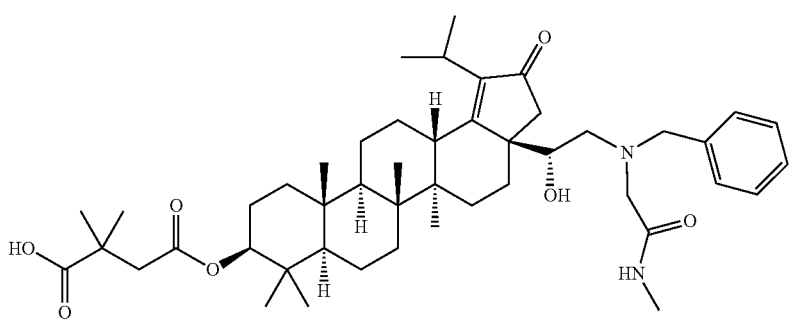

379

LC/MS: m/z calculated 774.5, found 775.5 (M+1)$^+$

Example 311

Compound 380

4-(((3aR,5aR,5bR,7aR,9S,11aR,11bR,13aS)-3a-((R)-2-((2-(dimethylamino)-2-oxoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

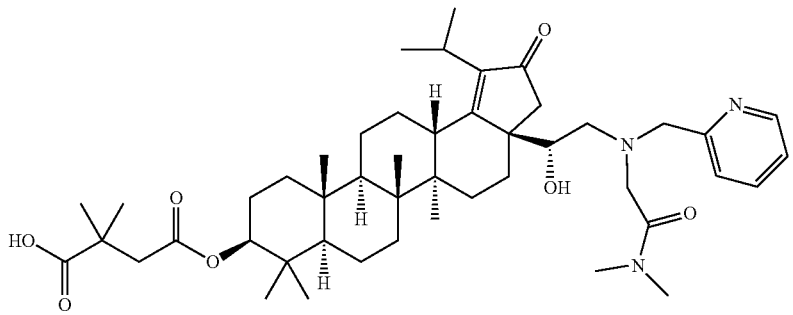

LC/MS: m/z calculated 789.5, found 790.5 (M+1)$^+$

Example 312

Compound 381

4-(((3aR,5aR,5bR,7aR,9S,11aR,11bR,13aS)-3a-((R)-2-(benzyl(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

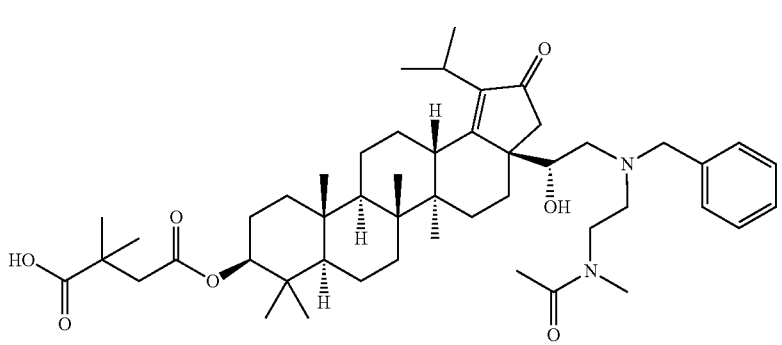

LC/MS: m/z calculated 802.5, found 803.5 (M+1)$^+$

Example 313

Compound 382

4-(((3aR,5aR,5bR,7aR,9S,11aR,11bR,13aS)-3a-((R)-2-(benzyl(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

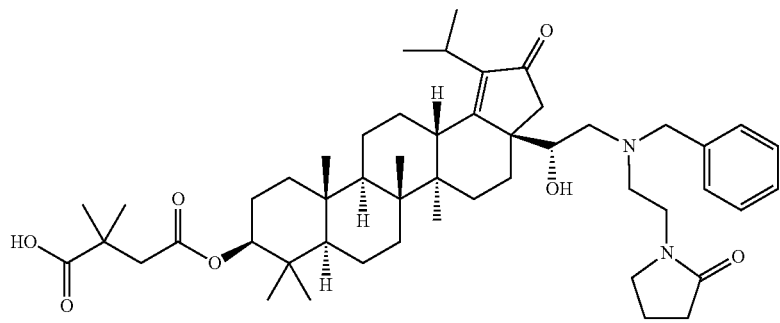

382

LC/MS: m/z calculated 814.5. found 815.5 (M+1)$^+$

Example 314

Compound 383

4-(((3aR,5aR,5bR,7aR,9S,11aR,11bR,13aS)-3a-((R)-2-(((1H-benzo[d]imidazol-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

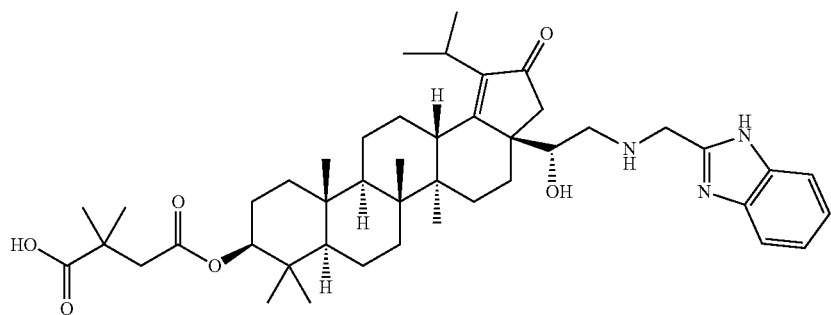

383

LC/MS: m/z calculated 743.5. found 744.5 (M+1)$^+$

Example 315

Compound 384

4-(((3aR,5aR,5bR,7aR,9S,11aR,11bR,13aS)-3a-((R)-2-(2-(aminomethyl)-1H-benzo[d]imidazol-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

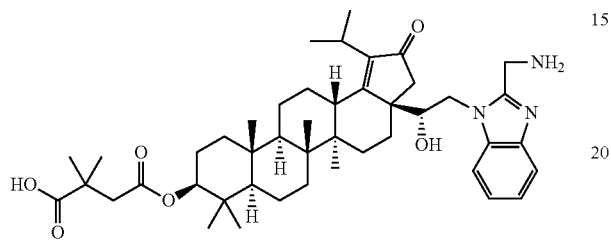

384

LC/MS: m/z calculated 743.5. found 744.5 (M+1)$^+$

Example 316

Compound 385

4-(((3aR,5aR,5bR,7aR,9S,11aR,11bR,13aS)-3a-((S)-2-((1-(4-chlorophenyl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

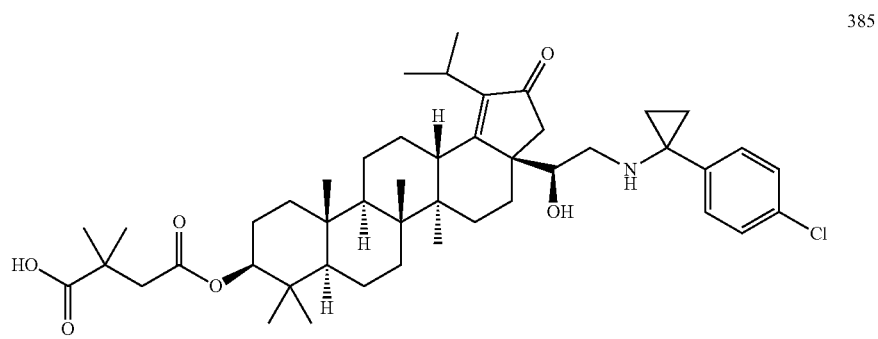

385

LC/MS: m/z calculated 763.5. found 764.5 (M+1)$^+$

Example 317

Compound 386

4-(((3aR,5aR,5bR,7aR,9S,11aR,11bR,13aS)-3a-((R)-2-((1-(4-chlorophenyl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

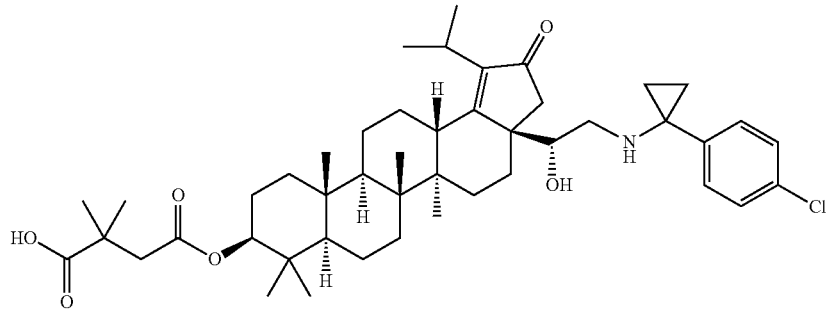

386

LC/MS: m/z calculated 763.5. found 764.5 (M+1)$^+$

Example 318

Compound 387

4-(((3aR,5aR,5bR,7aR,9S,11aR,11bR,13aS)-3a-((R)-1-hydroxy-2-((2-morpholinoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

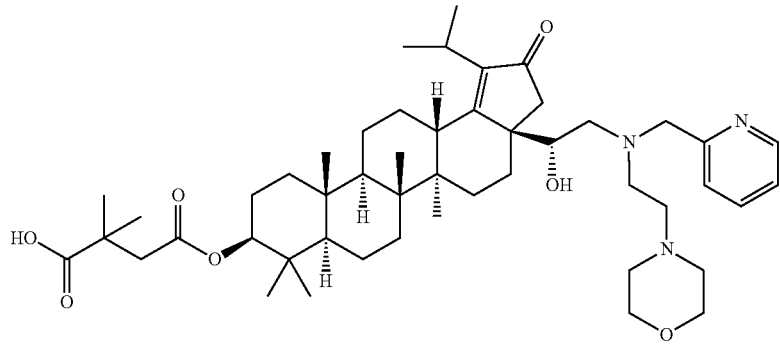

387

LC/MS: m/z calculated 817.6. found 818.5 (M+1)$^+$

Example 319

Compound 388

4-(((3aR,5aR,5bR,7aR,9S,11aR,11bR,13aS)-3a-((R)-1-hydroxy-2-((2-(2-oxopyrrolidin-1-yl)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

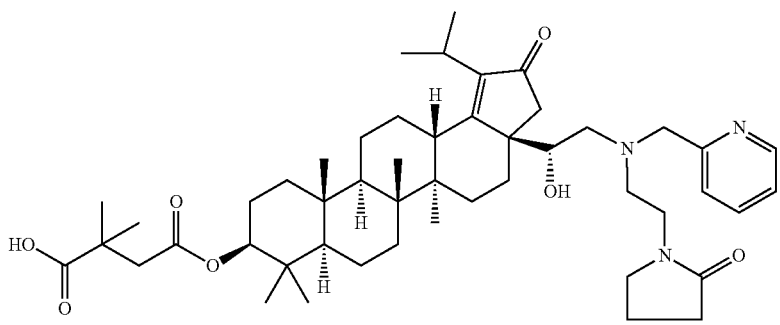

388

LC/MS: m/z calculated 815.5. found 816.5 (M+1)$^+$

Example 320

Compound 389

4-(((3aR,5aR,5bR,7aR,9S,11aR,11bR,13aS)-3a-((S)-1-hydroxy-2-(phenethylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

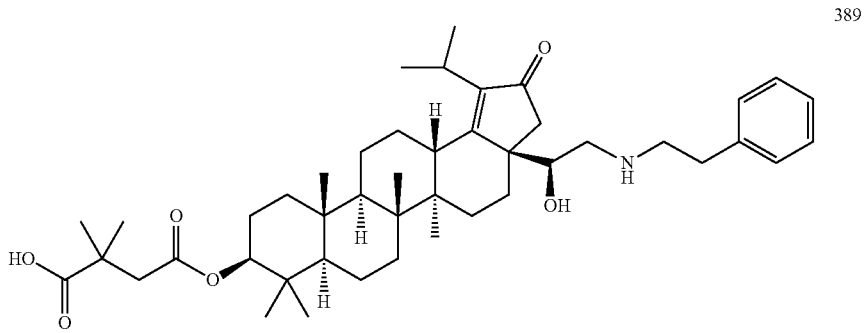

389

LC/MS: m/z calculated 717.5. found 718.5 (M+1)$^+$

Example 321

Compound 390

4-(((3aR,5aR,5bR,7aR,9S,11aR,11bR,13aS)-3a-((R)-1-hydroxy-2-((thiazol-5-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

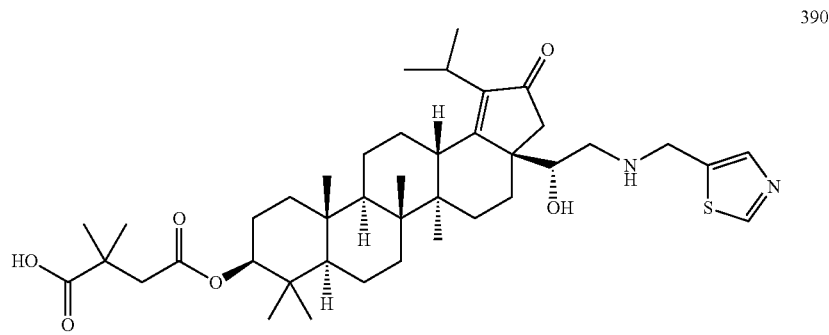

LC/MS: m/z calculated 710.4. found 711.4 (M+1)$^+$

Example 322

Compound 391

4-(((3aR,5aR,5bR,7aR,9S,11aR,11bR,13aS)-3a-(2-(cyclopentylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

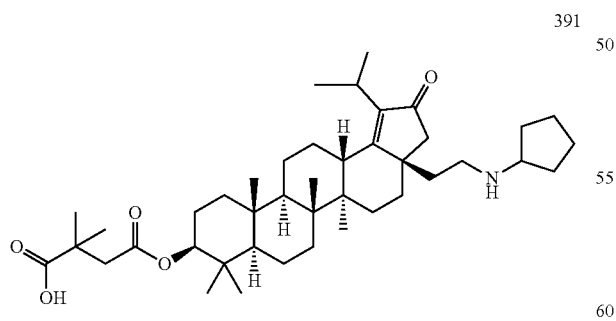

LC/MS: m/z calculated 665.5. found 666.5 (M+1)$^+$

Example 323

Compound 392

4-(((3aR,5aR,5bR,7aR,9S,11aR,11bR,13aS)-3a-((R)-2-((2-(dimethylamino)-2-oxoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

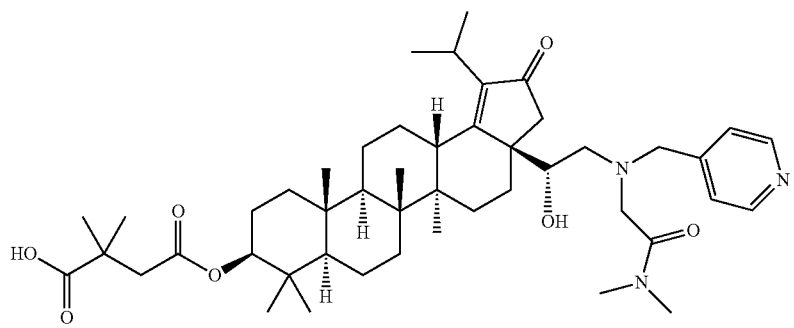

392

LC/MS: m/z calculated 789.5. found 790.5 (M+1)$^+$

Example 324

Compound 393

4-(((3aR,5aR,5bR,7aR,9S,11aR,11bR,13aS)-3a-((R)-2-((2-amino-2-oxoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

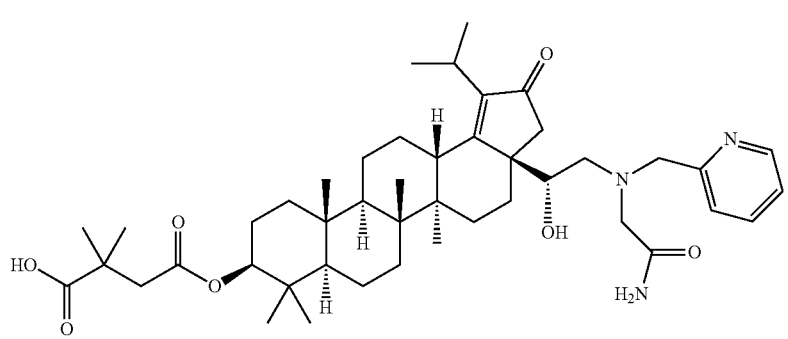

393

LC/MS: m/z calculated 761.5. found 762.5 (M+1)$^+$

Example 325

Compound 394

4-(((3aR,5aR,5bR,7aR,9S,11aR,11bR,13aS)-3a-((R)-1-hydroxy-2-((2-((2-hydroxyethyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

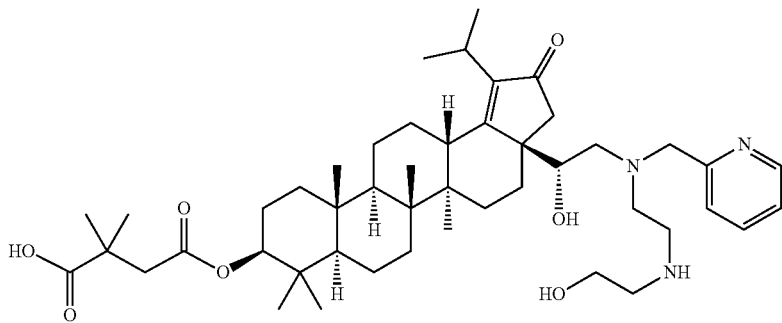

394

LC/MS: m/z calculated 791.5. found 792.5 (M+1)$^+$

Example 326

Compound 395

4-(((3aR,5aR,5bR,7aR,9S,11aR,11bR,13aS)-3a-((R)-1-hydroxy-2-((2-((2-methoxyethyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

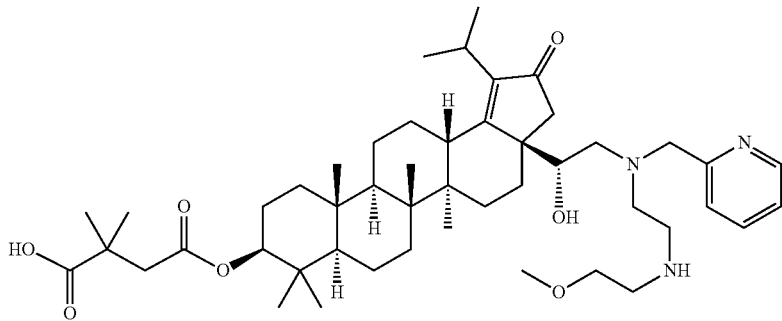

395

LC/MS: m/z calculated 805.6. found 806.5 (M+1)$^+$

Example 327

Compound 396

4-(((3aR,5aR,5bR,7aR,9S,11aR,11bR,13aS)-3a-((R)-2-((2-((tert-butoxycarbonyl)amino)ethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

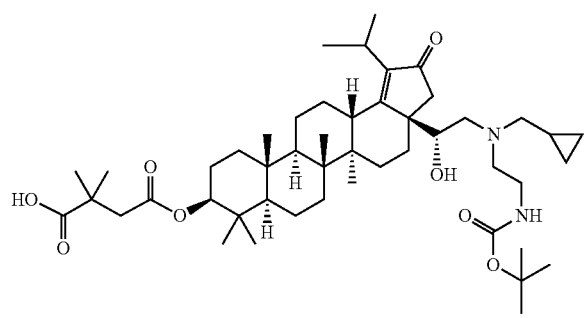

LC/MS: m/z calculated 810.6. found 811.5 (M+1)$^+$

Example 328

Compound 397

4-(((3aR,5aR,5bR,7aR,9S,11aR,11bR,13aS)-3a-((R)-2-((2-((tert-butoxycarbonyl)(methyl)amino)ethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

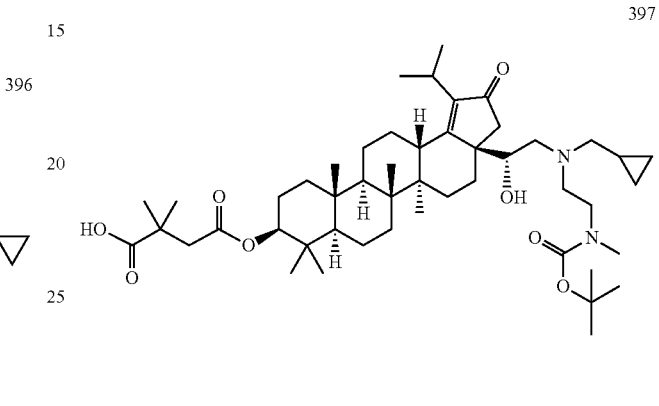

LC/MS: m/z calculated 824.6. found 825.5 (M+1)$^+$

Example 329

Compound 398

4-(((3aR,5aR,5bR,7aR,9S,11aR,11bR,13aS)-3a-(2-(N-benzyl-1-carboxyformamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

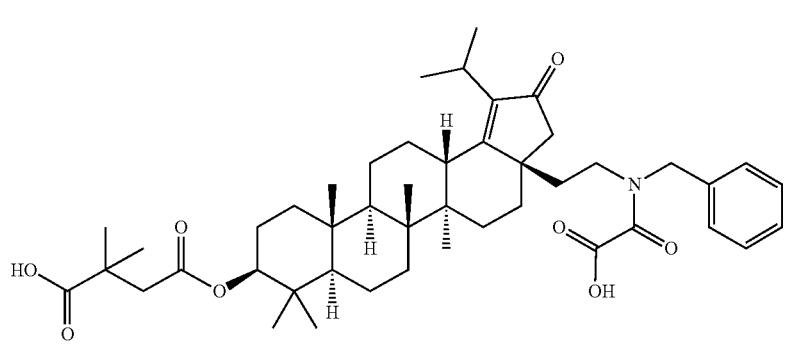

LC/MS: m/z calculated 759.5. found 760.5 (M+1)$^+$

Example 330

Compound 399

4-(((3aR,5aR,5bR,7aR,9S,11aR,11bR,13aS)-3a-((R)-2-((2-aminoethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

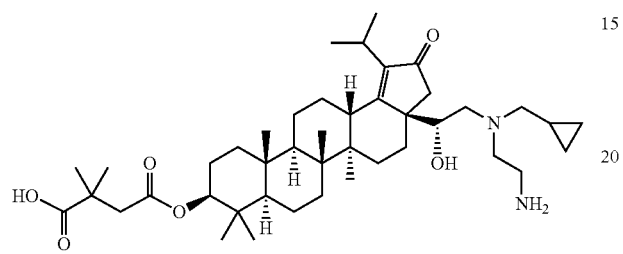

399

LC/MS: m/z calculated 710.5. found 711.5 (M+1)$^+$

Example 331

Compound 400

4-(((3aR,5aR,5bR,7aR,9S,11aR,11bR,13aS)-3a-((R)-2-((2-acetamidoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

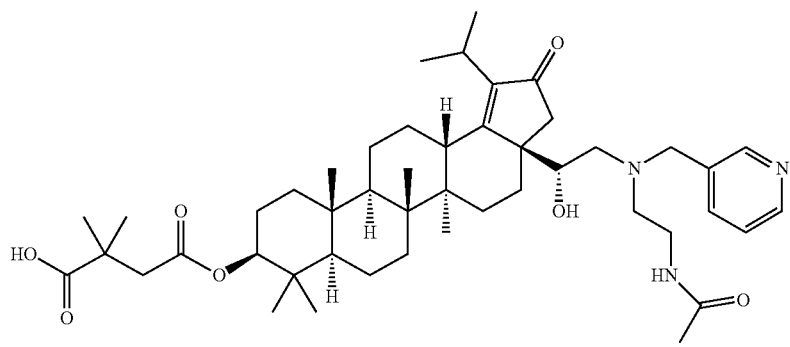

400

LC/MS: m/z calculated 789.5. found 790.5 (M+1)$^+$

Example 332

Compound 401

4-(((3aR,5aR,5bR,7aR,9S,11aR,11bR,13aS)-3a-((R)-1-hydroxy-2-((thiazol-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

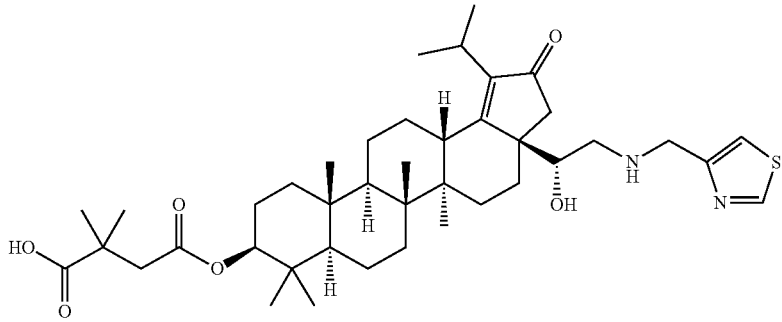

401

LC/MS: m/z calculated 710.4. found 711.4 (M+1)$^+$

Example 333

Compound 402

4-(((3aR,5aR,5bR,7aR,9S,11aR,11bR,13aS)-3a-((R)-1-hydroxy-2-((thiazol-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

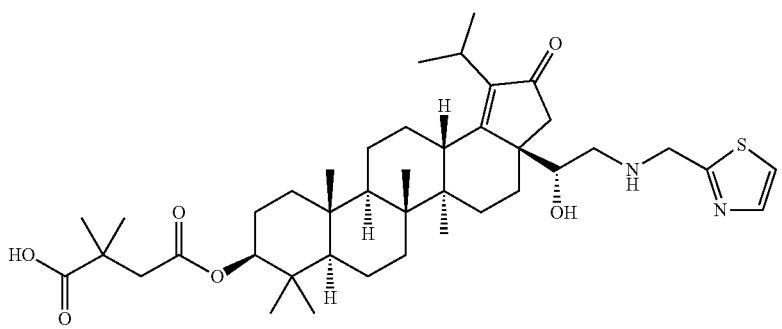

402

LC/MS: m/z calculated 710.4. found 711.4 (M+1)$^+$

Example 334

Compound 403

4-(((3aR,5aR,5bR,7aR,9S,11aR,11bR,13aS)-3a-((R)-2-((2-(dimethylamino)ethyl)(thiazol-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

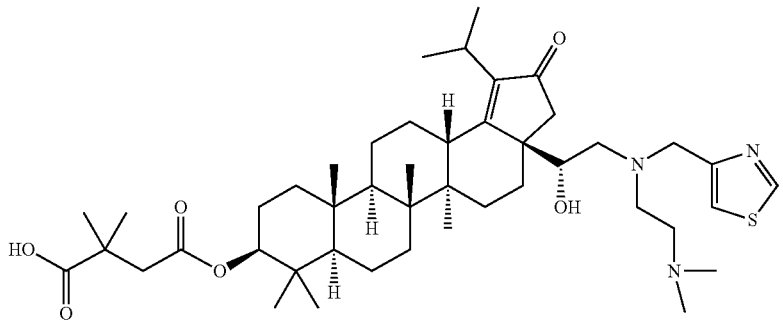

403

LC/MS: m/z calculated 781.5. found 782.5 (M+1)$^+$

Example 335

Compound 404

4-(((3aR,5aR,5bR,7aR,9S,11aR,11bR,13aS)-3a-(2-(benzyl(carboxymethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

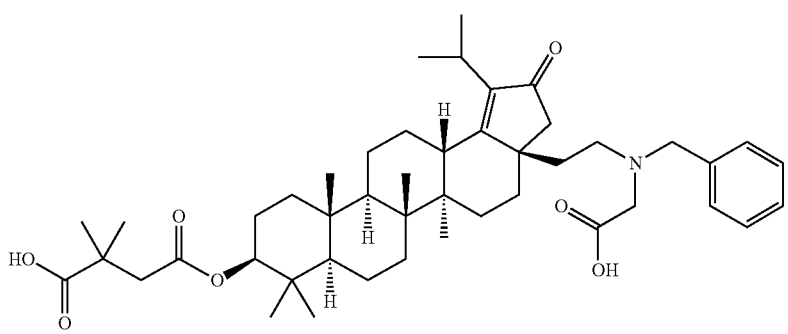

404

LC/MS: m/z calculated 745.5. found 746.5 (M+1)$^+$

Example 336

Compound 405

4-(((3aR,5aR,5bR,7aR,9S,11aR,11bR,13aS)-1-iso-propyl-5a,5b,8,8,11a-pentamethyl-3a-(2-(N-methyl-benzamido)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

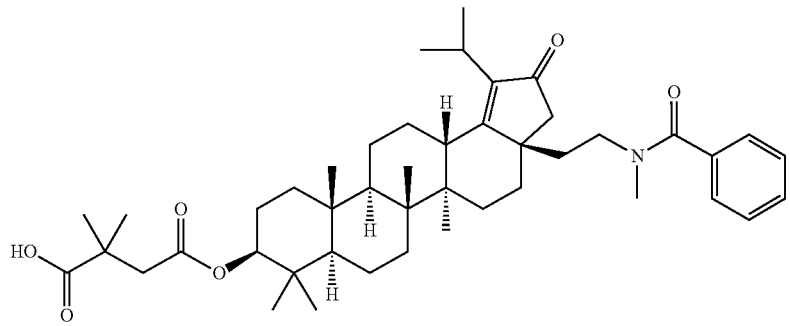

405

LC/MS: m/z calculated 715.5. found 716.5 (M+1)$^+$

Example 337

Compound 406

4-(((3aR,5aR,5bR,7aR,9S,11aR,11bR,13aS)-3a-(2-(N-benzyl-2-(dimethylamino)-2-oxoacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

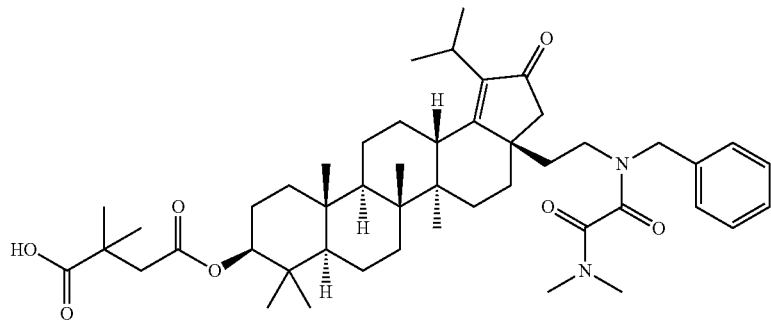

406

LC/MS: m/z calculated 786.5. found 787.5 (M+1)$^+$

Example 338

Compound 407

4-(((3aR,5aR,5bR,7aR,9S,11aR,11bR,13aS)-3a-((R)-2-((2-acetamidoethyl)(benzyl)amino)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

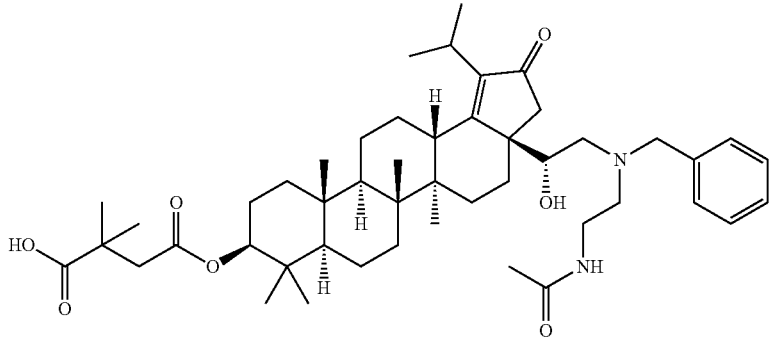

407

LC/MS: m/z calculated 788.5. found 789.5 (M+1)$^+$

Example 339

Compound 408

4-(((3aR,5aR,5bR,7aR,9S,11aR,11bR,13aS)-3a-(2-(2-amino-N-benzyl-2-oxoacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

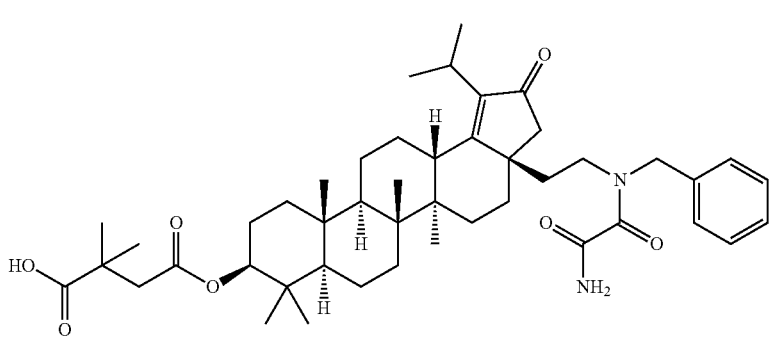

408

LC/MS: m/z calculated 758.5. found 759.5 (M+1)$^+$

Example 340

Compound 409

4-(((3aR,5aR,5bR,7aR,9S,11aR,11bR,13aS)-3a-((R)-2-((2-acetamidoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

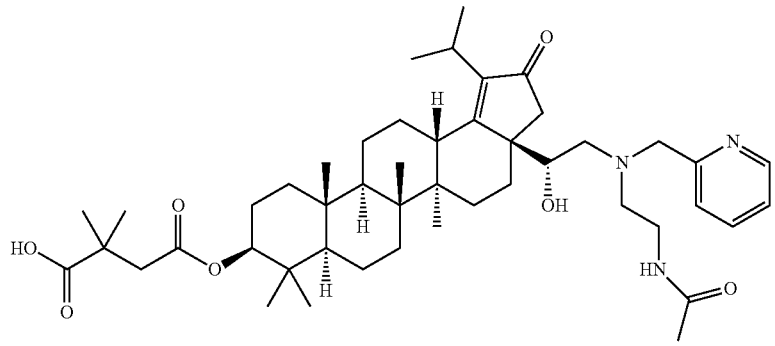

409

LC/MS: m/z calculated 789.5. found 790.5 (M+1)$^+$

Example 341

Compound 410

4-(((3aR,5aR,5bR,7aR,9S,11aR,11bR,13aS)-3a-((R)-2-((2-(dimethylamino)ethyl)(thiazol-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

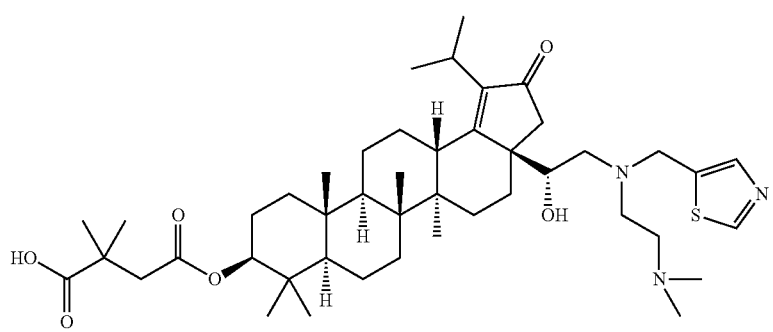

410

LC/MS: m/z calculated 781.5. found 782.5 (M+1)$^+$

Example 342

Compound 411

4-(((3aR,5aR,5bR,7aR,9S,11aR,11bR,13aS)-3a-((R)-2-((2-(dimethylamino)ethyl)(thiazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

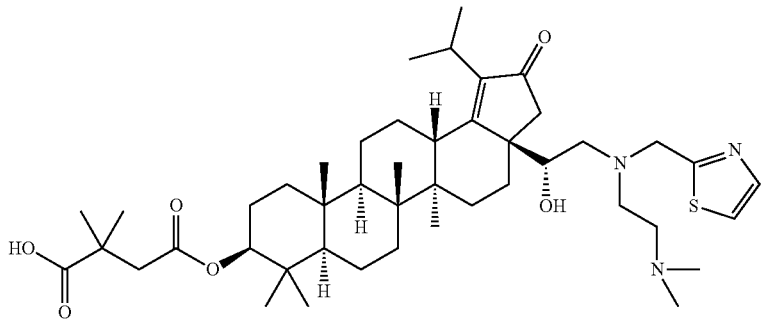

411

LC/MS: m/z calculated 781.5. found 782.5 (M+1)$^+$

Example 343

Compound 412

4-(((3aR,5aR,5bR,7aR,9S,11aR,11bR,13aS)-3a-((R)-2-((cyclopropylmethyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

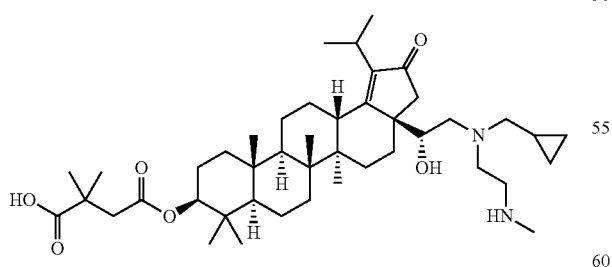

412

LC/MS: m/z calculated 724.5. found 725.5 (M+1)$^+$

Example 344

Compound 413

4-(((3aR,5aR,5bR,7aR,9S,11aR,11bR,13aS)-3a-((R)-2-((2-acetamidoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

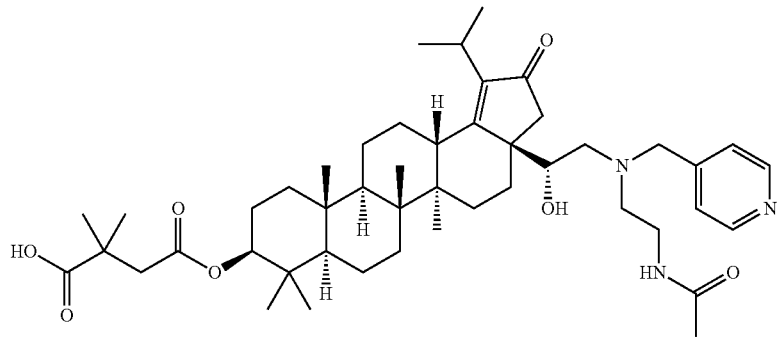

413

LC/MS: m/z calculated 789.5. found 790.5 (M+1)$^+$

Example 345

Compound 414

4-(((3aR,5aR,5bR,7aR,9S,11aR,11bR,13aS)-3a-((R)-2-((2-acetamidoethyl)(cyclopropylmethyl)amino)-1-acetoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

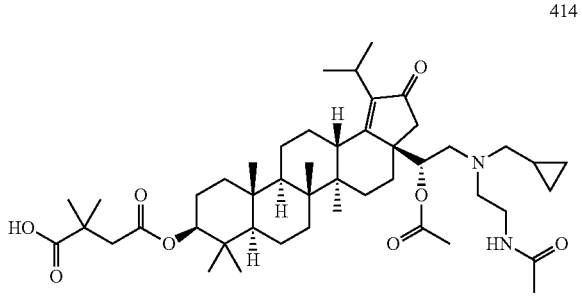

414

LC/MS: m/z calculated 794.5. found 795.5 (M+1)$^+$

Example 346

Compound 415

4-(((3aR,5aR,5bR,7aR,9S,11aR,11bR,13aS)-3a-((R)-1-acetoxy-2-((cyclopropylmethyl)(2-(N-methylacetamido)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

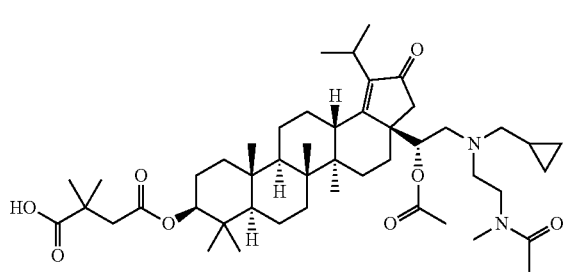

415

LC/MS: m/z calculated 808.6. found 809.5 (M+1)$^+$

Example 347

Compound 416

4-(((3aR,5aR,5bR,7aR,9S,11aR,11bR,13aS)-3a-((R)-2-(((5-chloropyrimidin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

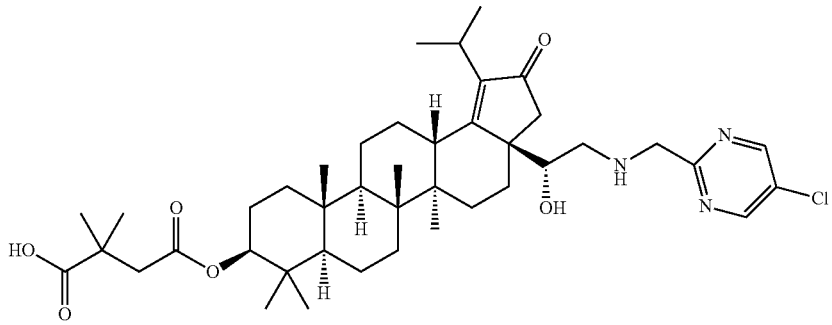

416

LC/MS: m/z calculated 739.4. found 740.4 (M+1)$^+$

Example 348

Compound 417

4-(((3aR,5aR,5bR,7aR,9S,11aR,11bR,13aS)-3a-((R)-2-((2-(dimethylamino)ethyl)(pyrimidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

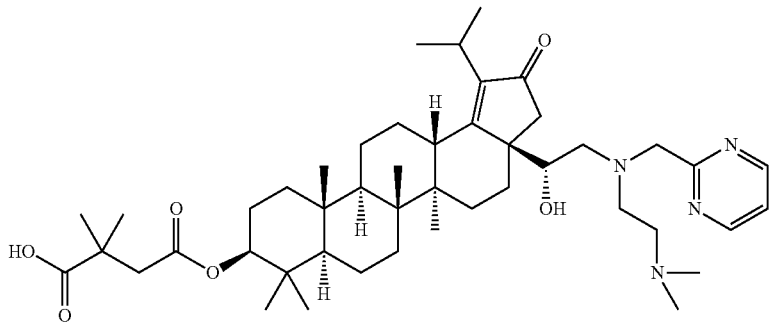

417

LC/MS: m/z calculated 776.5. found 777.5 (M+1)$^+$

Example 349

Compound 418

4-(((3aR,5aR,5bR,7aR,9S,11aR,11bR,13aS)-3a-((S)-2-(((5-chloropyrimidin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

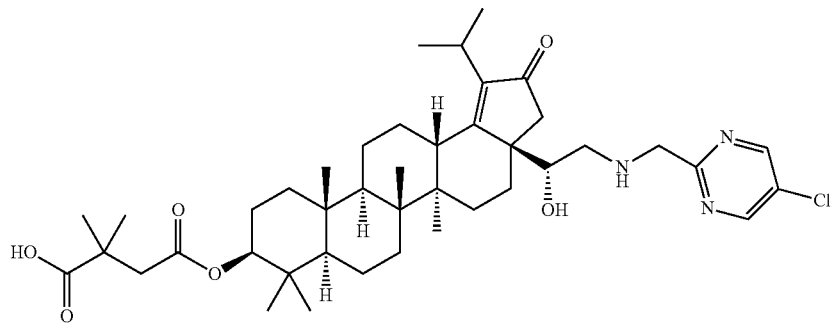

LC/MS: m/z calculated 739.4. found 740.4 (M+1)$^+$

Example 350

Compound 419

4-(((3aR,5aR,5bR,7aR,9S,11aR,11bR,13aS)-3a-((R)-1-hydroxy-2-((2-(methylamino)ethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

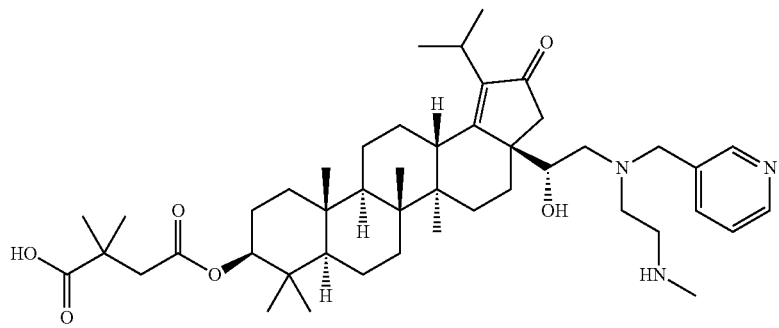

LC/MS: m/z calculated 761.5. found 762.5 (M+1)$^+$

Example 351

Compound 420

4-(((3aR,5aR,5bR,7aR,9S,11aR,11bR,13aS)-1-isopropyl-5a,5b,8,8,11a-pentamethyl-2-oxo-3a-((R)-2-oxo-3-(pyridin-2-ylmethyl) oxazolidin-5-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

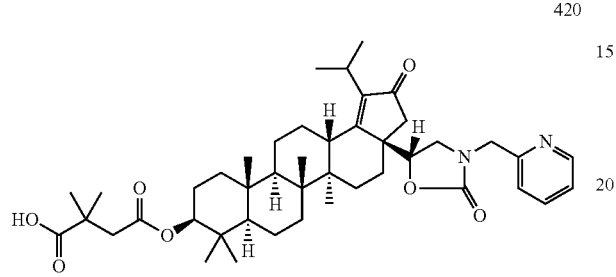

420

LC/MS: m/z calculated 730.5. found 731.4 (M+1)$^+$

Example 352

Compound 421

4-(((3aR,5aR,5bR,7aR,9S,11aR,11bR,13aS)-3a-((S)-2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

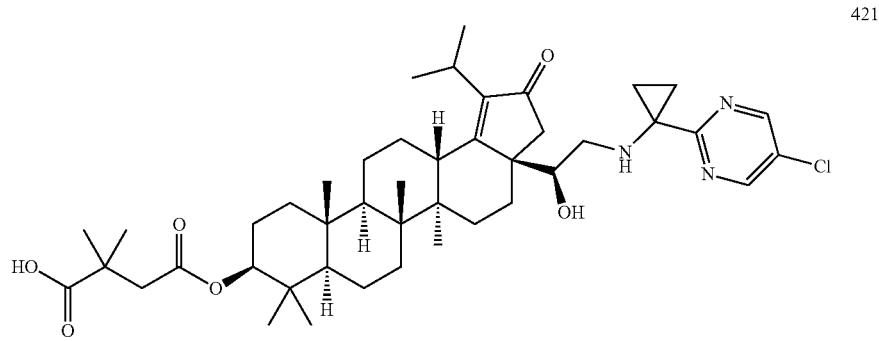

421

LC/MS: m/z calculated 765.4. found 766.4 (M+1)$^+$

Example 353

Compound 422

4-(((3aR,5aR,5bR,7aR,9S,11aR,11bR,13aS)-3a-((R)-2,11-dimethyl-3,10-dioxo-5-(pyridin-3-ylmethyl)-8-oxa-2,5,11-triazadodecan-7-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

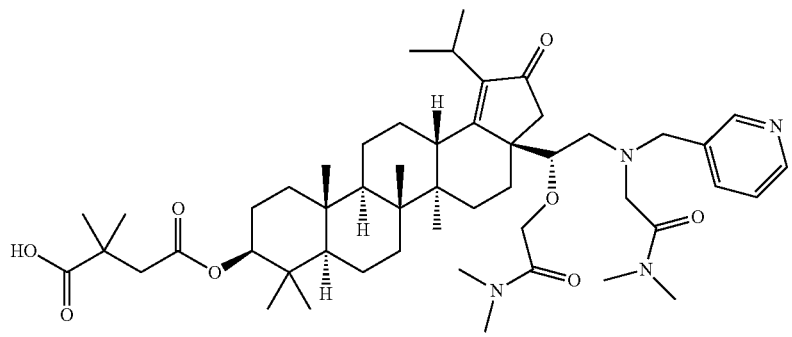

LC/MS: m/z calculated 874.6. found 875.6 (M+1)$^+$

Example 354

Compound 423

4-(((3aR,5aR,5bR,7aR,9S,11aR,11bR,13aS)-3a-((R)-1-hydroxy-2-((2-(methylamino)-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

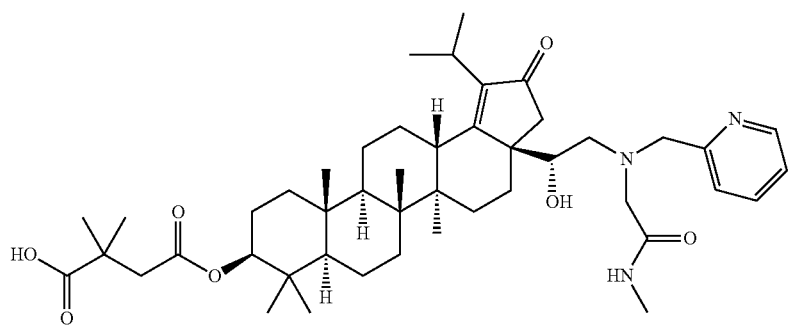

LC/MS: m/z calculated 775.5. found 776.5 (M+1)$^+$

Example 355

Compound 424

4-(((3aR,5aR,5bR,7aR,9S,11aR,11bR,13aS)-3a-((R)-2-((2-(dimethylamino)-2-oxoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

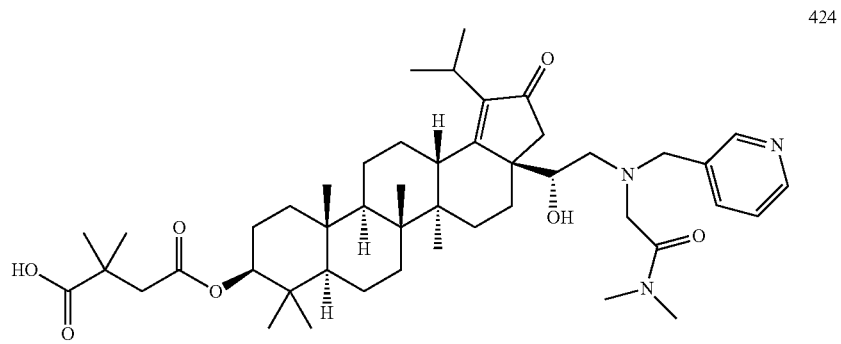

424

LC/MS: m/z calculated 789.5. found 790.5 (M+1)$^+$

Example 356

Compound 425

4-(((3aR,5aR,5bR,7aR,9S,11aR,11bR,13aS)-3a-((R)-2-(2-(dimethylamino)-N-(pyrimidin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,1b,12,13,13a-octadecahydro-2H-cyclopenta[a]chrysen-9-yl)oxy)-2,2-dimethyl-4-oxobutanoic acid.

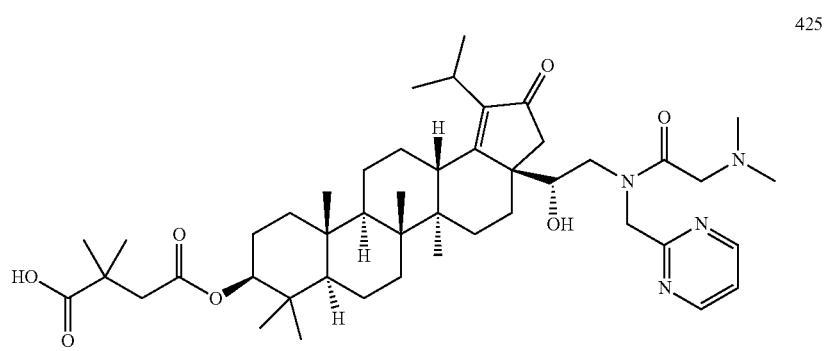

425

LC/MS: m/z calculated 790.5. found 791.5 (M+1)$^+$

Example 357

Compound 426

4-(((3aR,5aR,5bR,7aR,9S,11aR,11bR,13aS)-1-isopropyl-5a,5b,8,8,11a-pentamethyl-2-oxo-3a-(2-(picolinamido)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

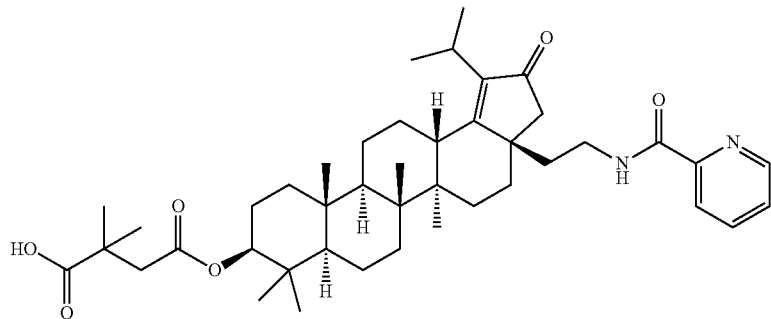

426

LC/MS: m/z calculated 702.5. found 703.4 (M+1)$^+$

Example 358

Compound 427

4-(((3aR,5aR,5bR,7aR,9S,11aR,11bR,13aS)-3a-((R)-2-((2-(1H-imidazol-1-yl)ethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

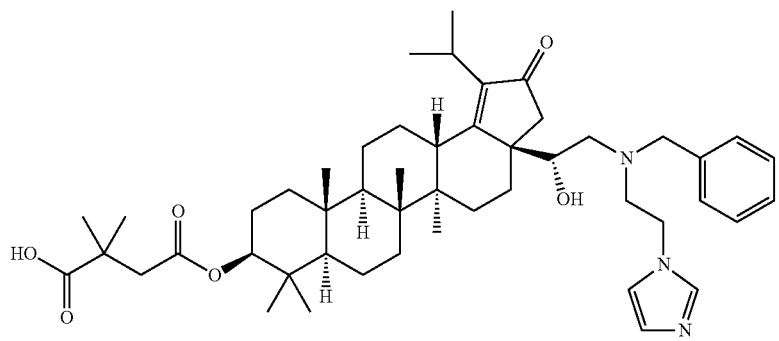

427

LC/MS: m/z calculated 797.5. found 798.5 (M+1)$^+$

Example 359

Compound 428

4-(((3aR,5aR,5bR,7aR,9S,11aR,11bR,13aS)-3a-((R)-2-((3-(1H-imidazol-1-yl)propyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

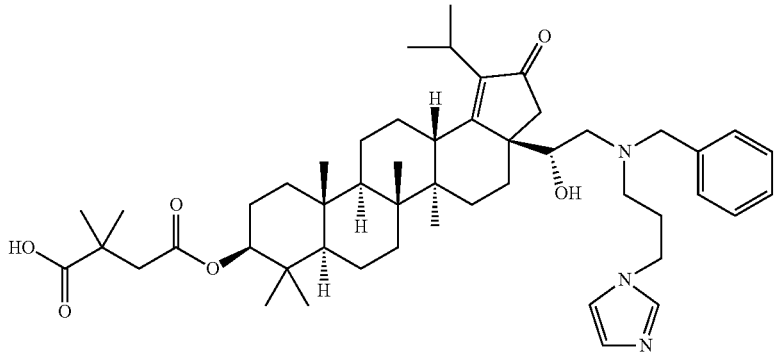

428

LC/MS: m/z calculated 811.5. found 812.5 (M+1)$^+$

Example 360

Compound 429

4-(((3aR,5aR,5bR,7aR,9S,11aR,11bR,13aS)-3a-((S)-2-((3-(1H-imidazol-1-yl)propyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

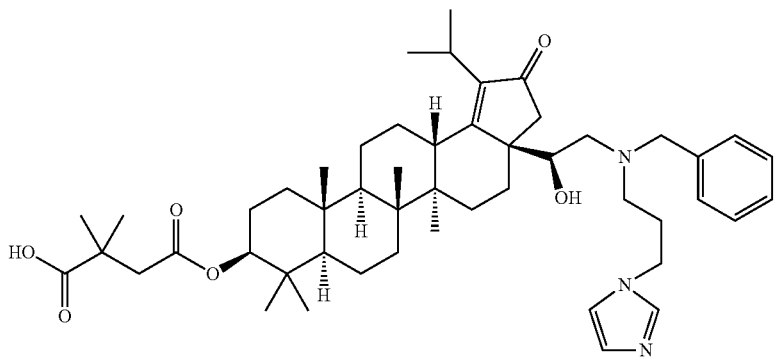

429

LC/MS: m/z calculated 811.5. found 812.5 (M+1)$^+$

Example 361

Compound 430

4-(((3aR,5aR,5bR,7aR,9S,11aR,11bR,13aS)-3a-(2-(N-benzyl-2-(dimethylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

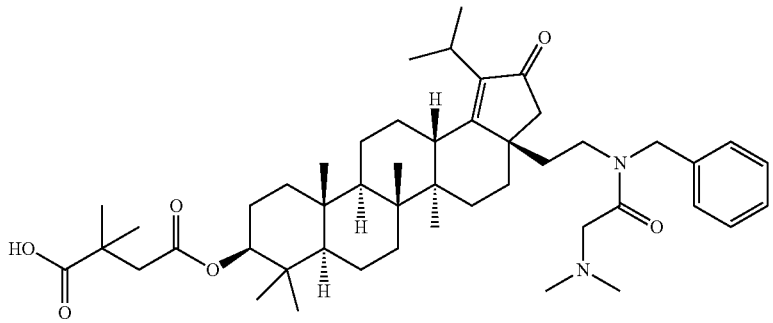

430

LC/MS: m/z calculated 772.5. found 773.5 (M+1)$^+$

Example 362

Compound 431

4-(((3aR,5aR,5bR,7aR,9S,11aR,11bR,13aS)-3a-((R)-2-(2-(dimethylamino)-N-isopropylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

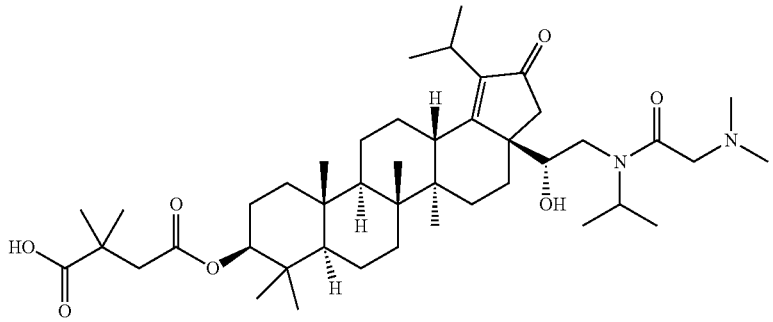

431

LC/MS: m/z calculated 740.5. found 741.5 (M+1)$^+$

Example 363

Compound 432

4-(((3aR,5aR,5bR,7aR,9S,11aR,11bR,13aS)-3a-((R)-1-hydroxy-2-(N-isopropyl-2-(methylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

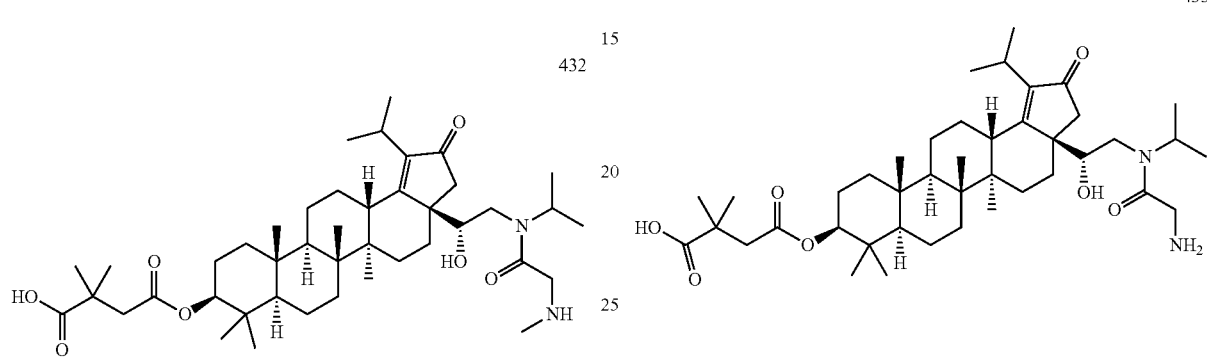

432

LC/MS: m/z calculated 726.5. found 727.5 (M+1)⁺

Example 364

Compound 433

4-(((3aR,5aR,5bR,7aR,9S,11aR,11bR,13aS)-3a-((R)-2-(2-amino-N-isopropylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

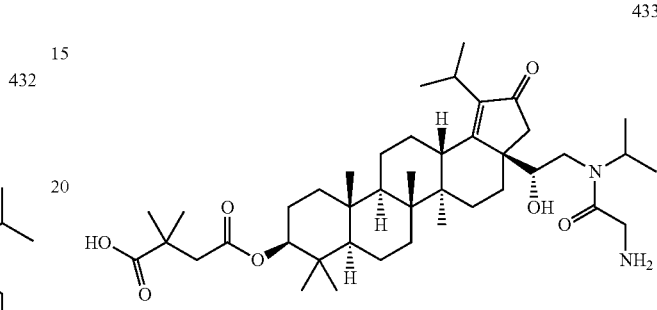

433

LC/MS: m/z calculated 712.5. found 713.5 (M+1)⁺

Example 365

Compound 434

4-(((3aR,5aR,5bR,7aR,9S,11aR,11bR,13aS)-3a-((R)-2-((2-(dimethylamino)ethyl)(3-(trifluoromethoxy)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

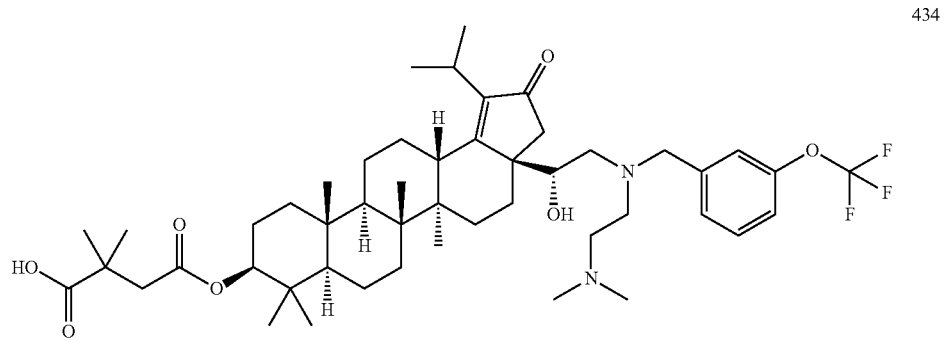

434

LC/MS: m/z calculated 858.5. found 859.5 (M+1)⁺

Example 366

Compound 435

4-(((3aR,5aR,5bR,7aR,9S,11aR,11bR,13aS)-3a-((R)-2-((2-(dimethylamino)ethyl)(4-(trifluoromethoxy)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

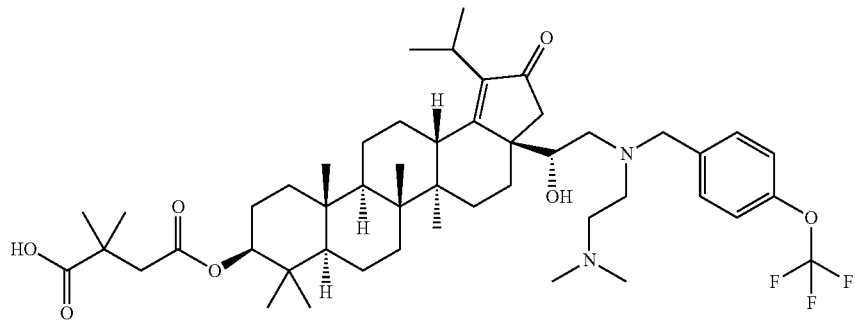

435

LC/MS: m/z calculated 858.5. found 859.5 (M+1)$^+$

Example 367

Compound 436

4-(((3aR,5aR,5bR,7aR,9S,11aR,11bR,13aS)-3a-(2-(2-(dimethylamino)-N-(pyridin-2-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

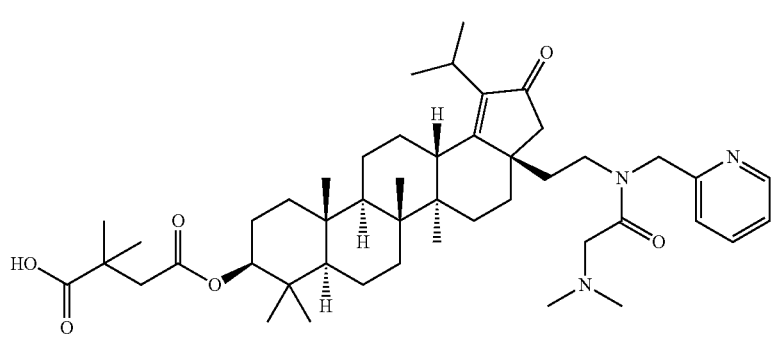

436

LC/MS: m/z calculated 773.5. found 774.5 (M+1)$^+$

Example 368

Compound 437

4-(((3aR,5aR,5bR,7aR,9S,11aR,11bR,13aS)-3a-((R)-2-((2-aminoethyl)(isopropyl)amino)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

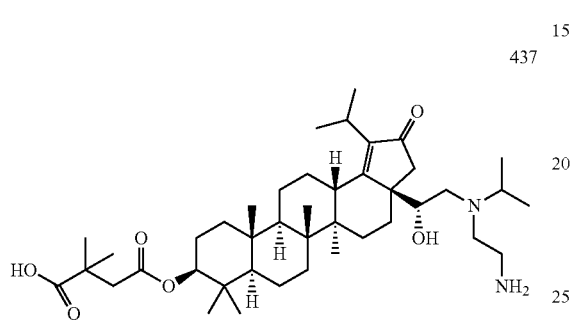

LC/MS: m/z calculated 698.5. found 699.5 (M+1)⁺.

Example 369

Compound 438

4-(((3aR,5aR,5bR,7aR,9S,11aR,11bR,13aS)-3a-((R)-2-((2-acetamidoethyl)(isopropyl)amino)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

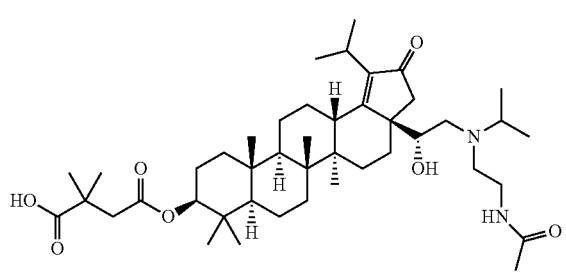

LC/MS: m/z calculated 740.5. found 741.5 (M+1)⁺

Example 370

Compound 439

4-(((3aR,5aR,5bR,7aR,9S,11aR,11bR,13aS)-3a-((R)-2-((2-(dimethylamino)-2-oxoethyl)(thiazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

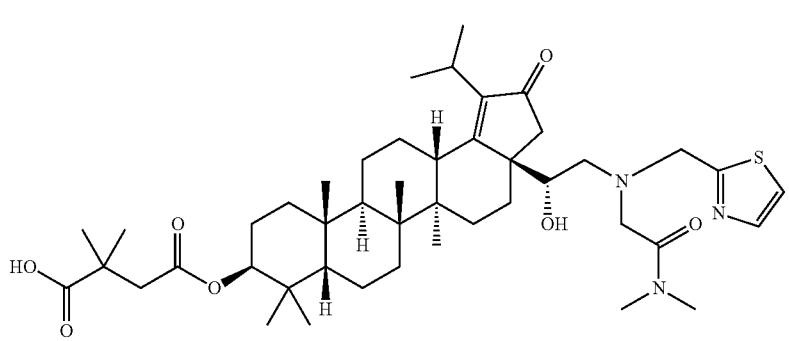

LC/MS: m/z calculated 795.5. found 796.4 (M+1)⁺

Example 371

Compound 440

4-(((3aR,5aR,5bR,7aR,9S,11aR,11bR,13aS)-1-isopropyl-5a,5b,8,8,11a-pentamethyl-3a-((R)-2-methyl-5-(pyridin-2-ylmethyl)-8, 11-dioxa-2, 5-diazadodecan-7-yl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

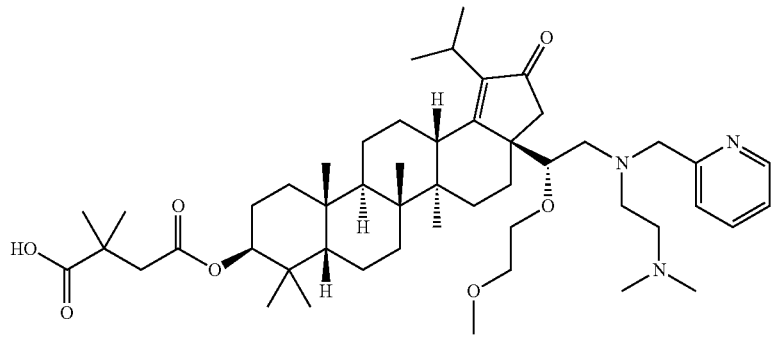

440

LC/MS: m/z calculated 833.6. found 834.5 (M+1)$^+$

Example 372

Compound 441

4-(((3aR,5aR,5bR,7aR,9S,11aR,11bR,13aS)-3a-((R)-2-((S)—N-benzyl-3, 4-dihydroxybutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

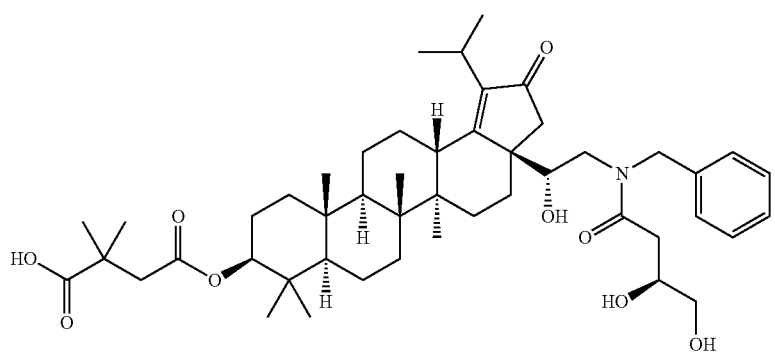

441

LC/MS: m/z calculated 805.5. found 806.5 (M+1)$^+$

Example 373

Compound 442

4-(((3aR,5aR,5bR,7aR,9S,11aR,11bR,13aS)-3a-((R)-2-((2-amino-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

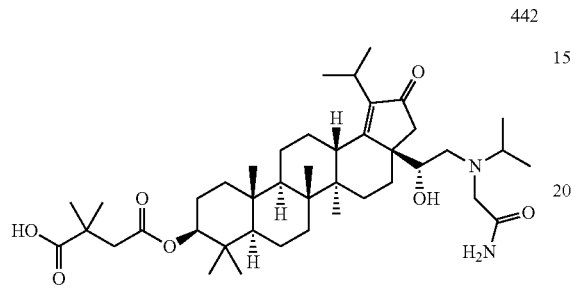

442

LC/MS: m/z calculated 712.5. found 713.5 $(M+1)^+$

Example 374

Compound 443

4-(((3aR,5aR,5bR,7aR,9S,11aR,11bR,13aS)-3a-((R)-2-((2-(dimethylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

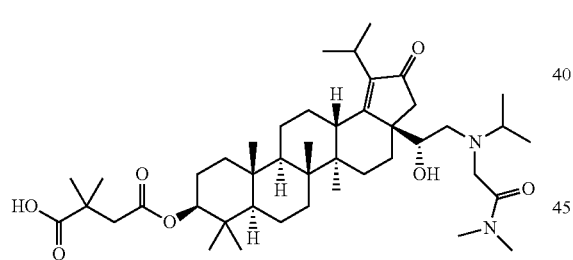

443

LC/MS: m/z calculated 740.5. found 741.5 $(M+1)^+$

Example 375

Compound 444

4-(((3aR,5aR,5bR,7aR,9S,11aR,11bR,13aS)-3a-((R)-1-hydroxy-2-(isopropyl(2-(methylamino)-2-oxoethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

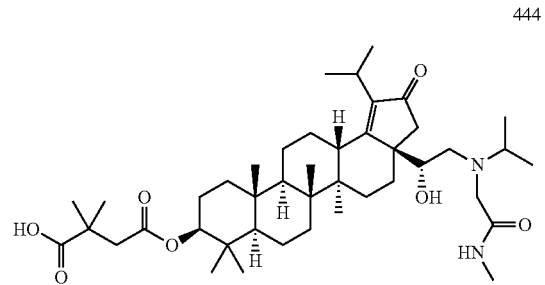

444

LC/MS: m/z calculated 726.5. found 727.5 $(M+1)^+$

Example 376

Compound 445

4-(((3aR,5aR,5bR,7aR,9S,11aR,11bR,13aS)-3a-((R)-2-((S)-3, 4-dihydroxy-N-(pyridin-2-ylmethyl)butanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

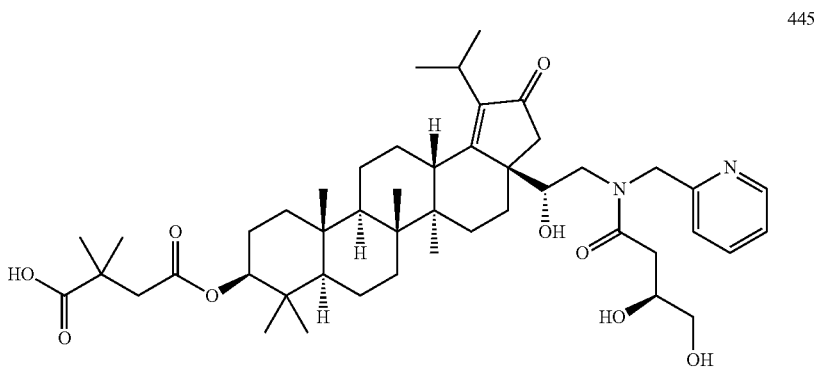

445

LC/MS: m/z calculated 806.5. found 807.5 $(M+1)^+$

Example 377

Compound 446

4-(((3aR,5aR,5bR,7aR,9S,11aR,11bR,13aS)-3a-((R)-2-((2-(ethylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

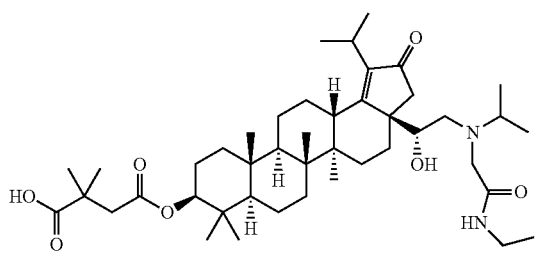

446

LC/MS: m/z calculated 740.5. found 741.5 (M+1)$^+$

Example 378

Compound 447

4-(((3aR,5aR,5bR,7aR,9S,11aR,11bR,13aS)-3a-((R)-2-((carboxymethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

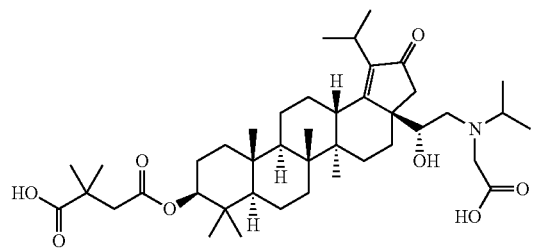

447

LC/MS: m/z calculated 713.5. found 714.5 (M+1)$^+$

Example 379

Compound 448

4-(((3aR,5aR,5bR,7aR,9S,11aR,11bR,13aS)-3a-((R)-2-((2-(cyclopropylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

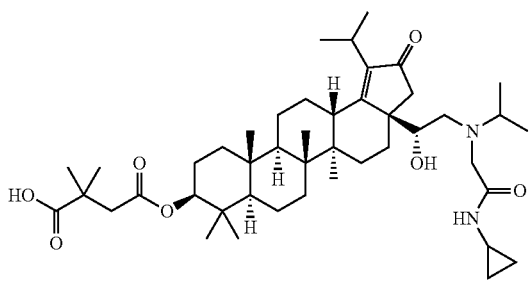

448

LC/MS: m/z calculated 752.5. found 753.5 (M+1)$^+$

Example 380

Compound 449

4-(((3aR,5aR,5bR,7aR,9S,11aR,11bR,13aS)-3a-((R)-2-(((5-chloropyrimidin-2-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

449

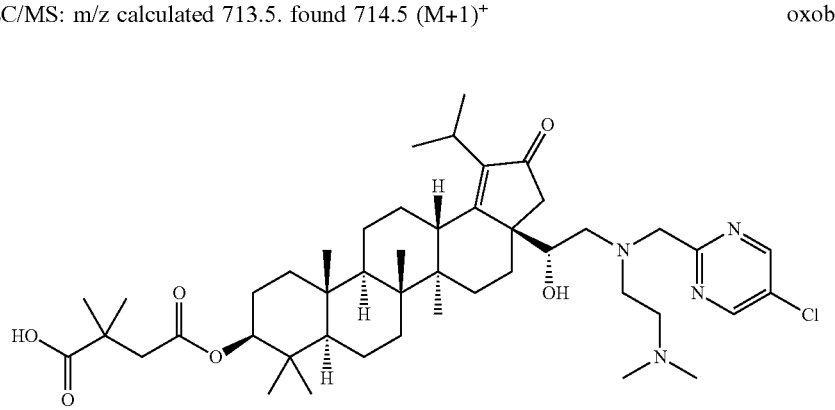

LC/MS: m/z calculated 810.5. found 811.5 (M+1)$^+$

Example 381

Compound 450

4-(((3aR,5aR,5bR,7aR,9S,11aR,11bR,13aS)-3a-((R)-2-(N-(cyclopropylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

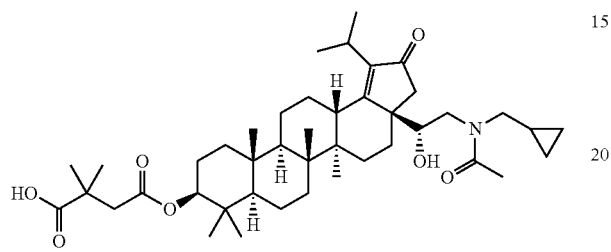

450

LC/MS: m/z calculated 709.5. found 710.5 (M+1)$^+$

Example 382

Compound 451

4-(((3aR,5aR,5bR,7aR,9S,11aR,11bR,13aS)-1-isopropyl-5a,5b,8,8,11a-pentamethyl-2-oxo-3a-(2-((pyridin-2-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

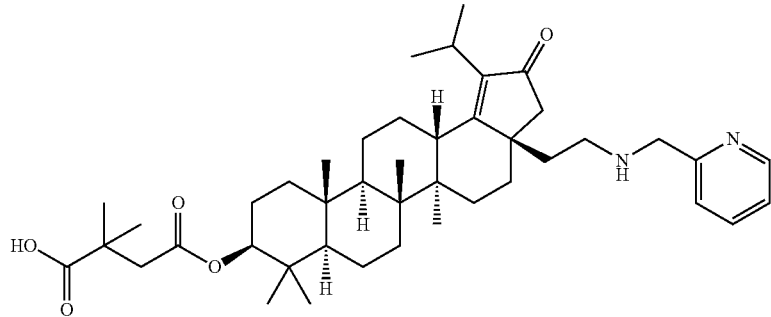

451

LC/MS: m/z calculated 688.5. found 689.5 (M+1)$^+$

Example 383

Compound 452

4-(((3aR,5aR,5bR,7aR,9S,11aR,11bR,13aS)-3a-((R)-2-((cyclopropylmethyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

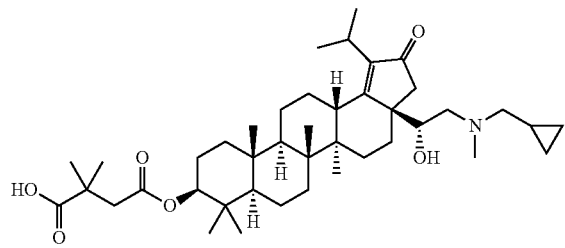

452

LC/MS: m/z calculated 681.5. found 682.5 (M+1)$^+$

Example 384

Compound 453

4-(((3aR,5aR,5bR,7aR,9S,11aR,11bR,13aS)-3a-((R)-2-(N-(cyclopropylmethyl)-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

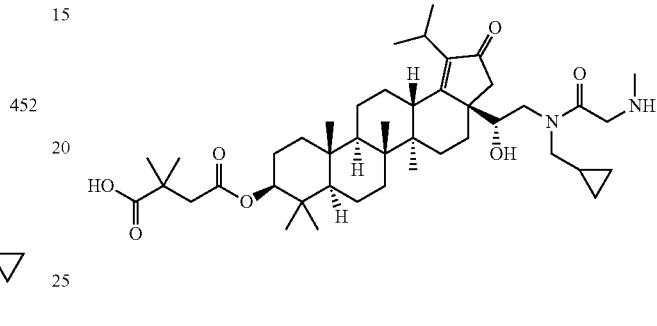

453

LC/MS: m/z calculated 738.5. found 739.5 (M+1)$^+$

Example 385

Compound 454

4-(((3aR,5aR,5bR,7aR,9S,11aR,11bR,13aS)-3a-((R)-2-(N-benzylisobutyramido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

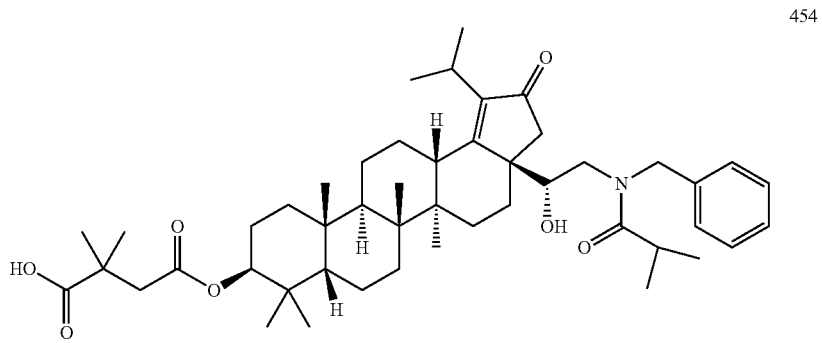

454

LC/MS: m/z calculated 773.5. found 774.5 (M+1)$^+$

Example 386

Compound 455

4-(((3aR,5aR,5bR,7aR,9S,11aR,11bR,13aS)-3a-((R)-2-(N-benzyl-3-methylbutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

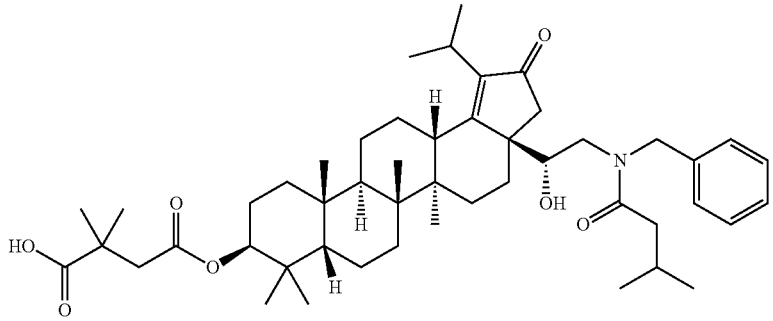

455

LC/MS: m/z calculated 787.5. found 788.5 (M+1)$^+$

Example 387

Compound 456

4-(((3aR,5aR,5bR,7aR,9S,11aR,11bR,13aS)-3a-((R)-2-(N-benzylpropionamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

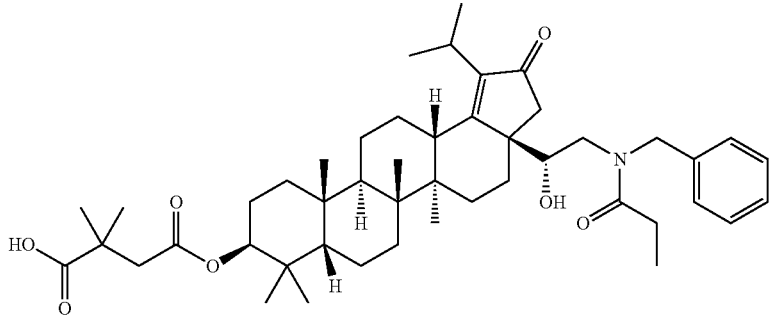

456

LC/MS: m/z calculated 759.5. found 760.5 (M+1)$^+$

Example 388

Compound 457

4-(((3aR,5aR,5bR,7aR,9S,11aR,11bR,13aS)-1-isopropyl-5a,5b,8,8,11a-pentamethyl-2-oxo-3a-(2-((pyridin-3-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

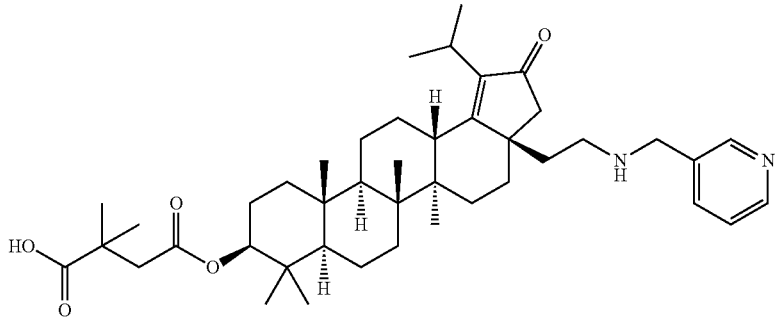

457

LC/MS: m/z calculated 688.5. found 689.5 (M+1)$^+$

Example 389

Compound 458

4-(((3aR,5aR,5bR,7aR,9S,11aR,11bR,13aS)-1-isopropyl-5a,5b,8,8,11a-pentamethyl-2-oxo-3a-(2-((pyridin-4-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

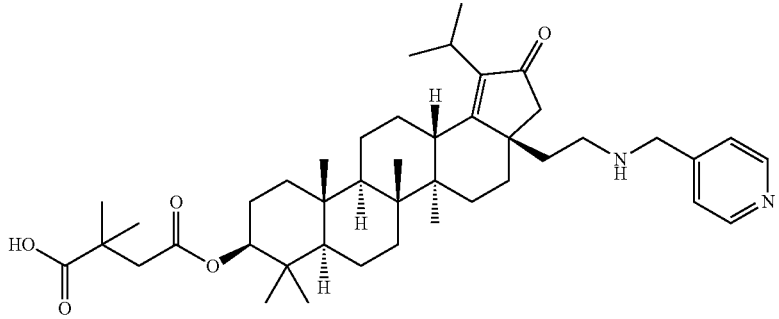

458

LC/MS: m/z calculated 688.5. found 689.5 (M+1)$^+$

Example 390

Compound 459

4-(((3aR,5aR,5bR,7aR,9S,11aR,11bR,13aS)-3a-((R)-2-((cyclopropylmethyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

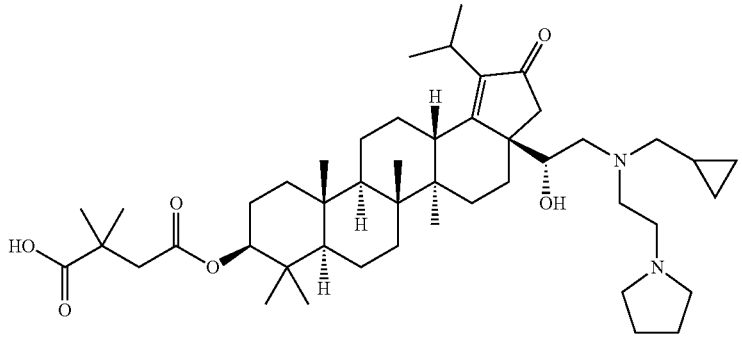

459

LC/MS: m/z calculated 764.6. found 765.5 (M+1)$^+$

Example 391

Compound 460

4-(((3aR,5aR,5bR,7aR,9S,11aR,11bR,13aS)-3a-((R)-2-(N-benzylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

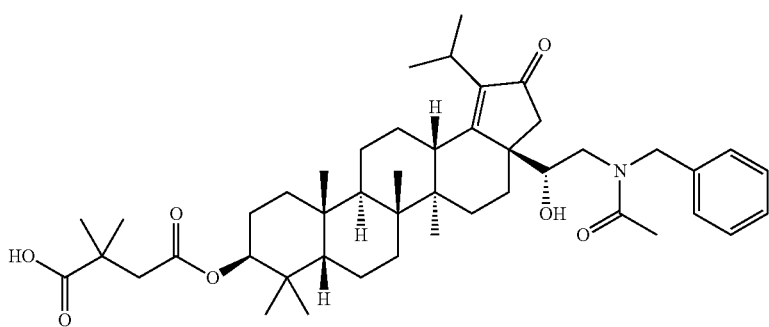

460

LC/MS: m/z calculated 745.5. found 746.5 (M+1)$^+$

Example 392

Compound 461

4-(((3aR,5aR,5bR,7aR,9S,11aR,11bR,13aS)-3a-((R)-2-(benzyl(2-morpholinoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

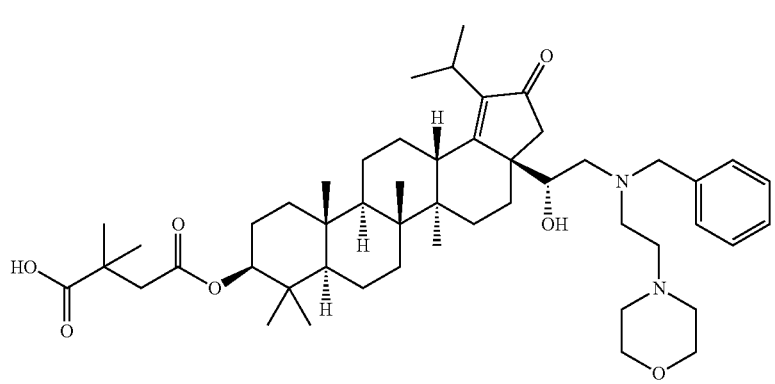

461

LC/MS: m/z calculated 816.6. found 817.5 (M+1)$^+$

Example 393

Compound 462

4-(((3aR,5aR,5bR,7aR,9S,11aR,11bR,13aS)-3a-((R)-2-(N, 3-dimethylbutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

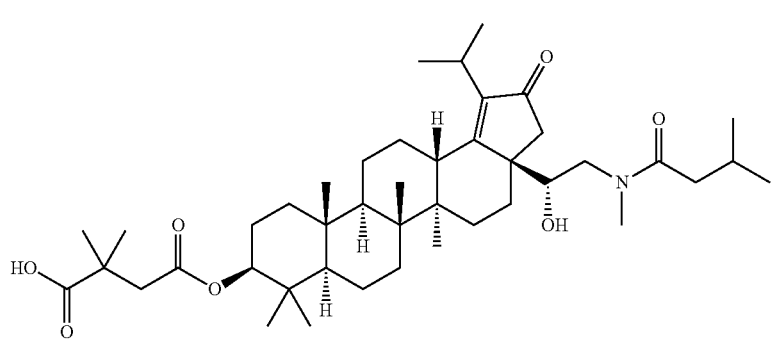

462

LC/MS: m/z calculated 711.5. found 712.5 (M+1)$^+$

Example 394

Compound 463

4-(((3aR,5aR,5bR,7aR,9S,11aR,11bR,13aS)-3a-((R)-2-(N-(cyclopropylmethyl)-2-(2-oxopyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

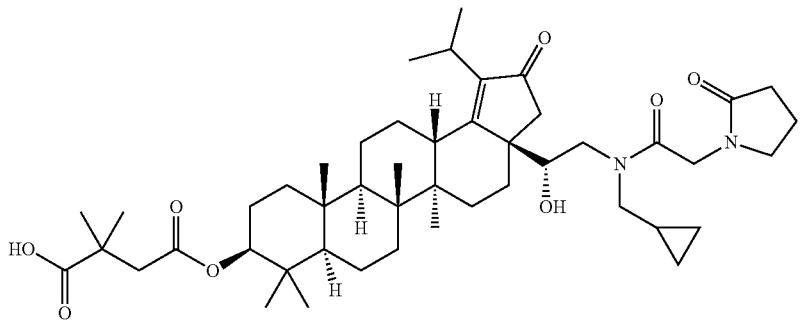

463

LC/MS: m/z calculated 792.5. found 793.5 (M+1)$^+$

Example 395

Compound 464

4-(((3aR,5aR,5bR,7aR,9S,11aR,11bR,13aS)-3a-((R)-1-(isobutyryloxy)-2-(methylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

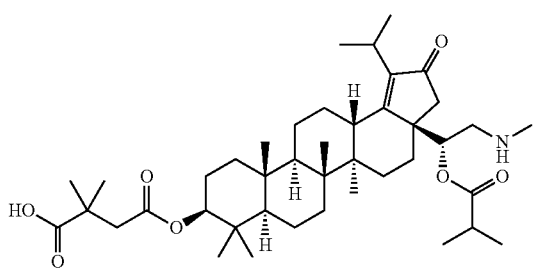

464

LC/MS: m/z calculated 697.5. found 698.5 (M+1)$^+$

Example 396

Compound 465

4-(((3aR,5aR,5bR,7aR,9S,11aR,11bR,13aS)-3a-(2-((cyclobutylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

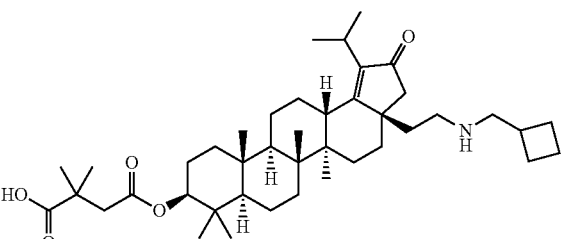

465

LC/MS: m/z calculated 665.5. found 666.5 (M+1)$^+$

Example 397

Compound 466

4-(((3aR,5aR,5bR,7aR,9S,11aR,11bR,13aS)-3a-(2-((cyclopropylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

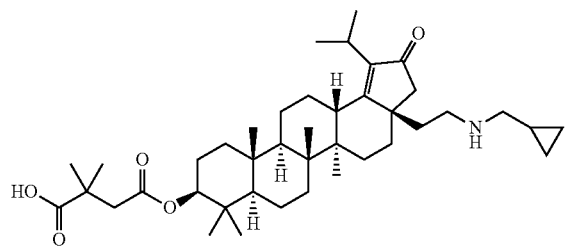

466

LC/MS: m/z calculated 651.5. found 652.5 (M+1)$^+$

Example 398

Compound 467

4-(((3aR,5aR,5bR,7aR,9S,11aR,11bR,13aS)-3a-((R)-2-(N-(cyclobutylmethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

467

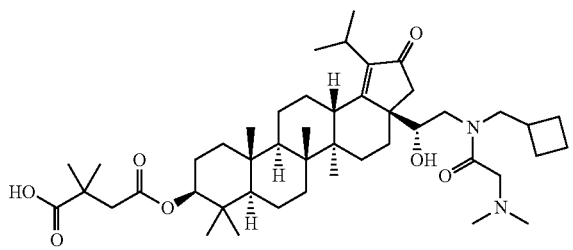

LC/MS: m/z calculated 766.5. found 767.5 (M+1)$^+$

Example 399

Compound 468

4-(((3aR,5aR,5bR,7aR,9S,11aR,11bR,13aS)-3a-(2-((cyclobutylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

468

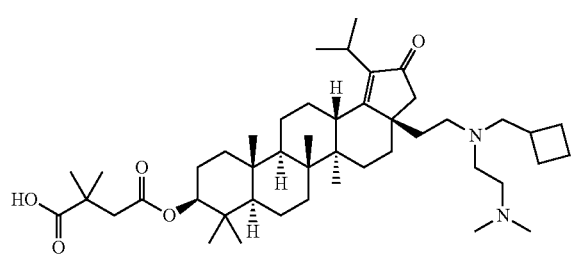

LC/MS: m/z calculated 736.6. found 737.5 (M+1)$^+$

Example 400

Compound 469

4-(((3aR,5aR,5bR,7aR,9S,11aR,11bR,13aS)-3a-((R)-1-hydroxy-2-((pyrimidin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

469

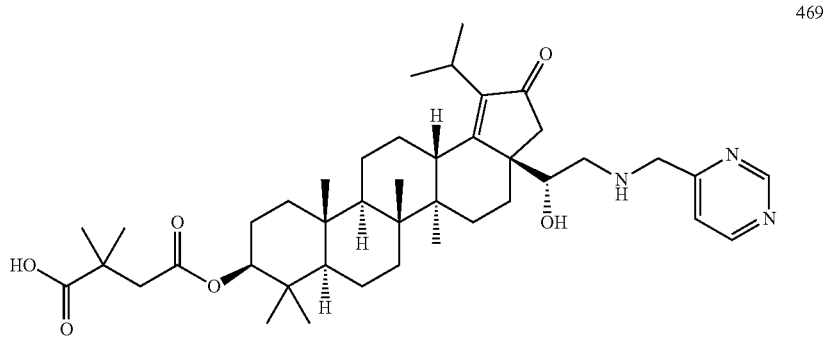

LC/MS: m/z calculated 705.5. found 706.5 (M+1)$^+$

Example 401

Compound 470

4-(((3aR,5aR,5bR,7aR,9S,11aR,11bR,13aS)-3a-((R)-2-(N-(cyclobutylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

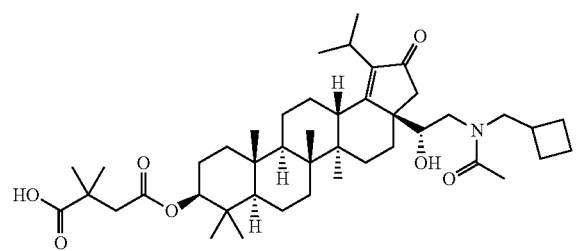

470

LC/MS: m/z calculated 723.5. found 724.5 (M+1)$^+$

Example 402

Compound 471

4-(((3aR,5aR,5bR,7aR,9S,11aR,11bR,13aS)-3a-((R)-1-((4-chlorobenzoyl)oxy)-2-(methylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

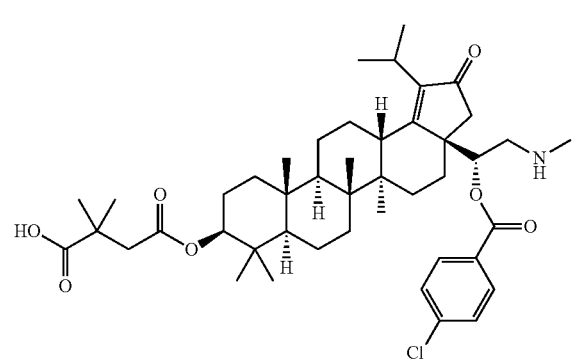

471

LC/MS: m/z calculated 765.4. found 766.4 (M+1)$^+$

Example 403

Compound 472

4-(((3aR,5aR,5bR,7aR,9S,11aR,11bR,13aS)-3a-((R)-1-(benzoyloxy)-2-((2-hydroxyethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

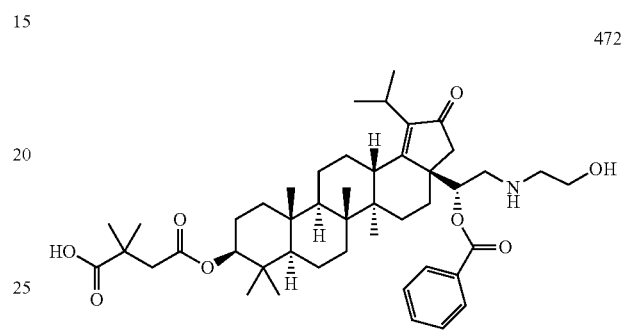

472

LC/MS: m/z calculated 761.5. found 762.4 (M+1)$^+$

Example 404

Compound 473

4-(((3aR,5aR,5bR,7aR,9S,11aR,11bR,13aS)-1-isopropyl-5a,5b,8,8,11a-pentamethyl-3a-((R)-2-(methylamino)-1-(2-phenylacetoxy)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

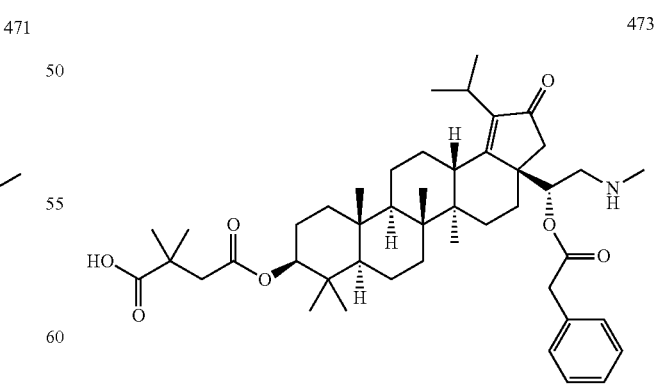

473

LC/MS: m/z calculated 745.5. found 746.5 (M+1)$^+$

Example 405

Compound 474

4-(((3aR,5aR,5bR,7aR,9S,11aR,11bR,13aS)-3a-((R)-1-hydroxy-2-(N-methylacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

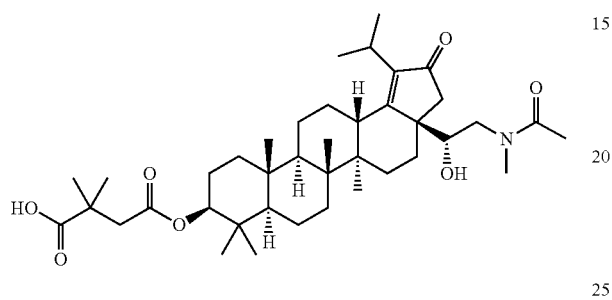

474

LC/MS: m/z calculated 669.5. found 670.4 (M+1)$^+$

Example 406

Compound 475

4-(((3aR,5aR,5bR,7aR,9S,11aR,11bR,13aS)-3a-((R)-2-(4-chloro-N-methylbenzamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

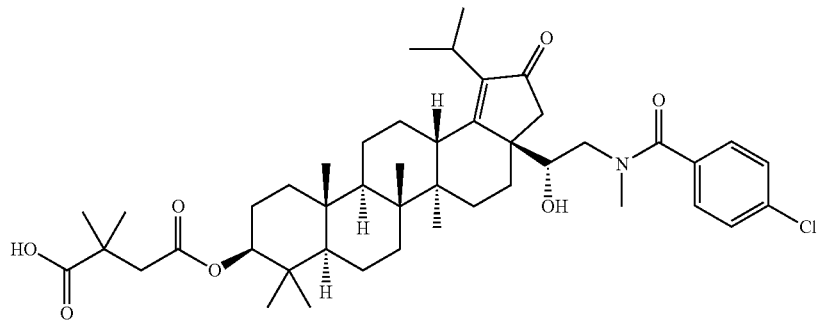

475

LC/MS: m/z calculated 765.4. found 766.4 (M+1)$^+$

Example 407

Compound 476

4-(((3aR,5aR,5bR,7aR,9S,11aR,11bR,13aS)-3a-((R)-1-hydroxy-2-(N-methyl-2-phenylacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

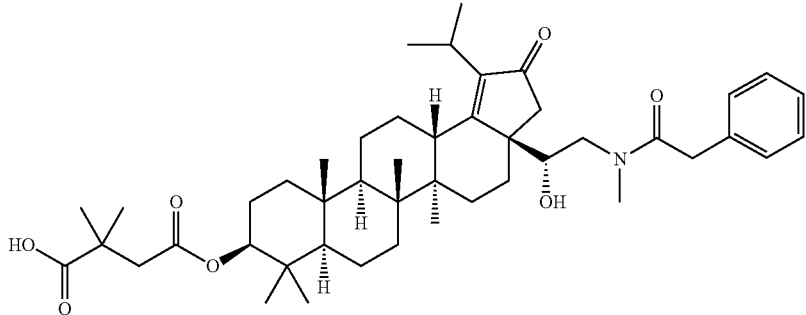

476

LC/MS: m/z calculated 745.5. found 746.5 (M+1)$^+$

Example 408

Compound 477

4-(((3aR,5aR,5bR,7aR,9S,11aR,11bR,13aS)-3a-((R)-1-hydroxy-2-(N-(2-hydroxyethyl)benzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

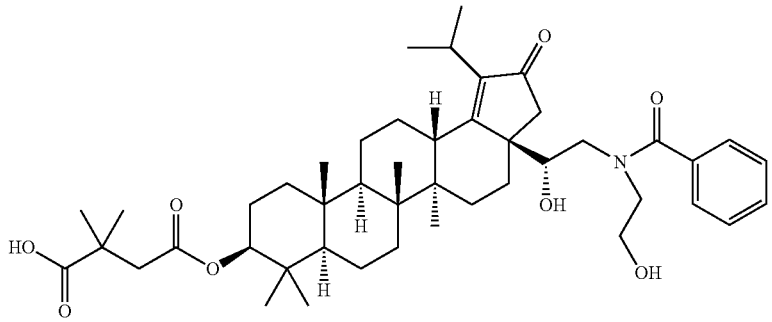

477

LC/MS: m/z calculated 761.5. found 762.4 (M+1)$^+$

Example 409

Compound 478

4-(((3aR,5aR,5bR,7aR,9S,11aR,11bR,13aS)-3a-((R)-1-hydroxy-2-((pyrimidin-5-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

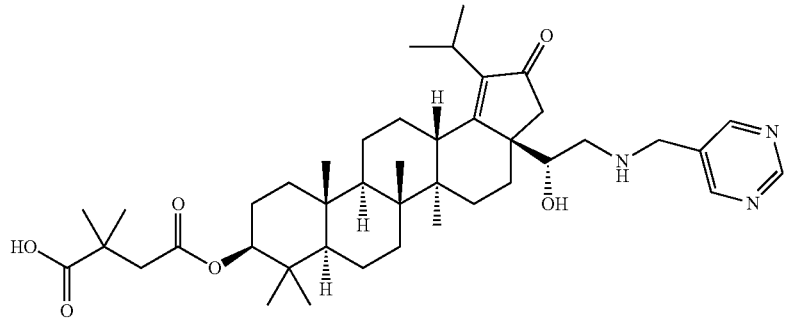

478

LC/MS: m/z calculated 705.5. found 706.5 (M+1)$^+$

Example 410

Compound 479

4-(((3aR,5aR,5bR,7aR,9S,11aR,11bR,13aS)-3a-((R)-2-((2-((cyclobutylmethyl)amino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

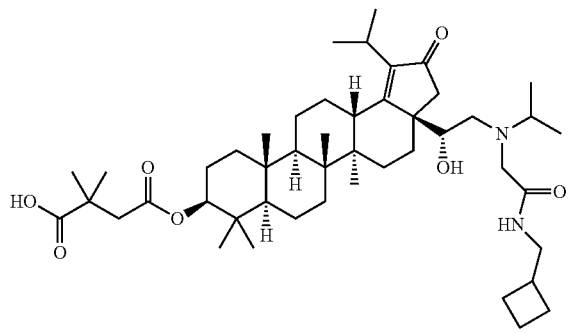

479

LC/MS: m/z calculated 780.6. found 781.6 (M+1)$^+$

Example 411

Compound 480

4-(((3aR,5aR,5bR,7aR,9S,11aR,11bR,13aS)-3a-((R)-1-hydroxy-2-(N-methylisobutyramido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

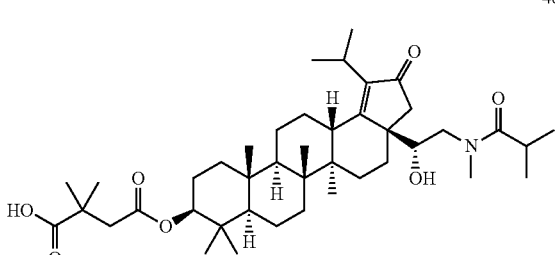

480

LC/MS: m/z calculated 697.5. found 698.5 (M+1)$^+$

Example 412

Compound 481

4-(((3aR,5aR,5bR,7aR,9S,11aR,11bR,13aS)-3a-((R)-1-hydroxy-2-(N-methylcyclopentanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

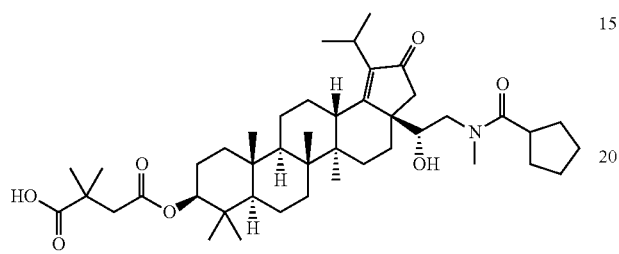

481

LC/MS: m/z calculated 723.5. found 724.5 (M+1)$^+$

Example 413

Compound 482

4-(((3aR,5aR,5bR,7aR,9S,11aR,11bR,13aS)-3a-((R)-1-hydroxy-2-(N-methylcyclohexanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

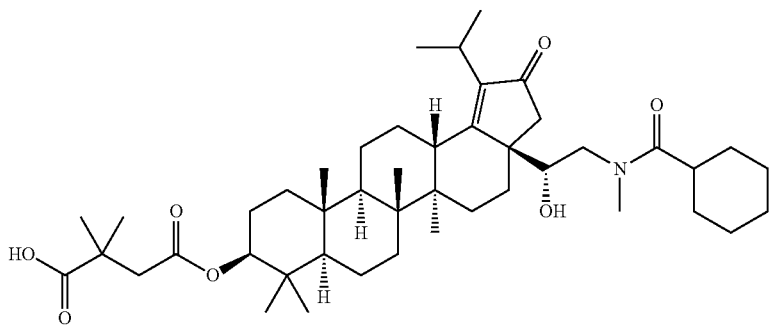

482

LC/MS: m/z calculated 737.5. found 738.5 (M+1)$^+$

Example 414

Compound 483

4-(((3aR,5aR,5bR,7aR,9S,11aR,11bR,13aS)-3a-(2-((cyclopropylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

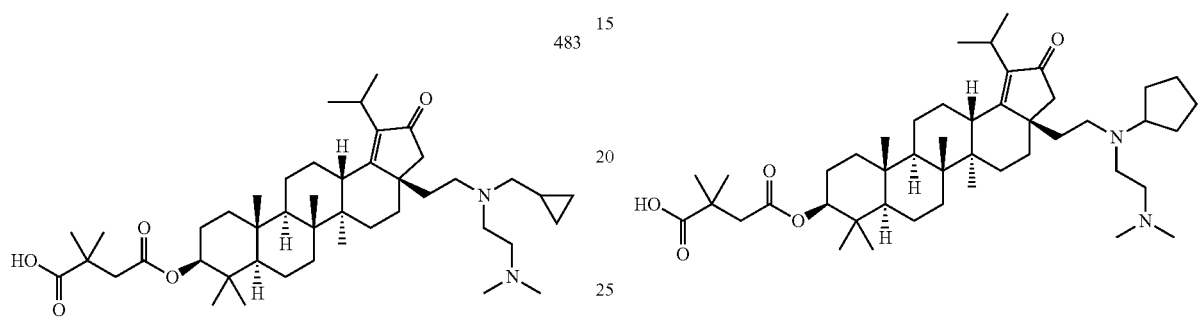

483

LC/MS: m/z calculated 722.6. found 723.6 (M+1)$^+$

Example 415

Compound 484

4-(((3aR,5aR,5bR,7aR,9S,11aR,11bR,13aS)-3a-(2-(cyclopentyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

484

LC/MS: m/z calculated 736.6. found 737.5 (M+1)$^+$

Example 416

Compound 485

4-(((3aR,5aR,5bR,7aR,9S,11aR,11bR,13aS)-3a-((R)-2-((2-(dimethylamino)ethyl)(pyrimidin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

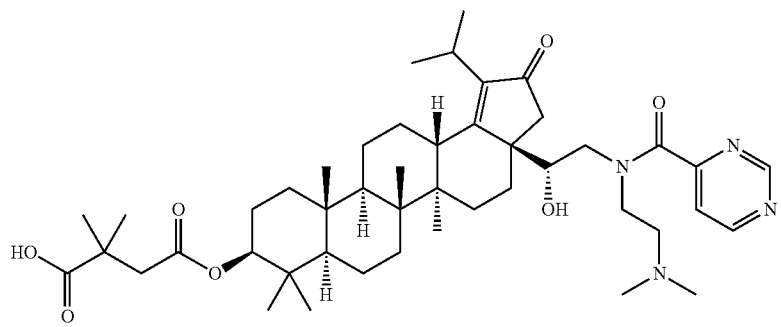

485

LC/MS: m/z calculated 776.5. found 777.5 (M+1)$^+$

Example 417

Compound 486

4-(((3aR,5aR,5bR,7aR,9S,11aR,11bR,13aS)-3a-((S)-2-(benzyl(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

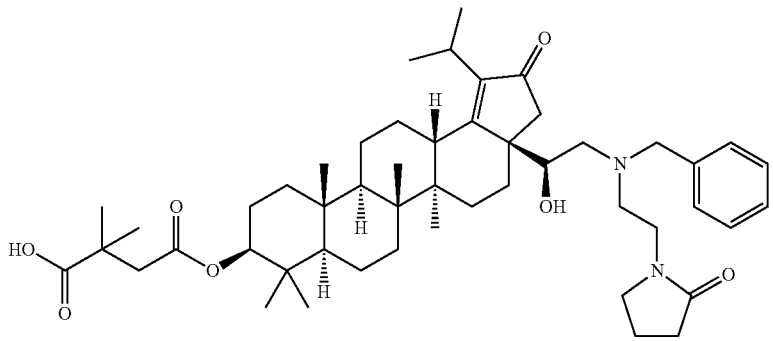

486

LC/MS: m/z calculated 814.5. found 815.5 (M+1)$^+$

Example 418

Compound 487

4-(((3aR,5aR,5bR,7aR,9S,11aR,11bR,13aS)-3a-((R)-1-hydroxy-2-(N-methylpicolinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

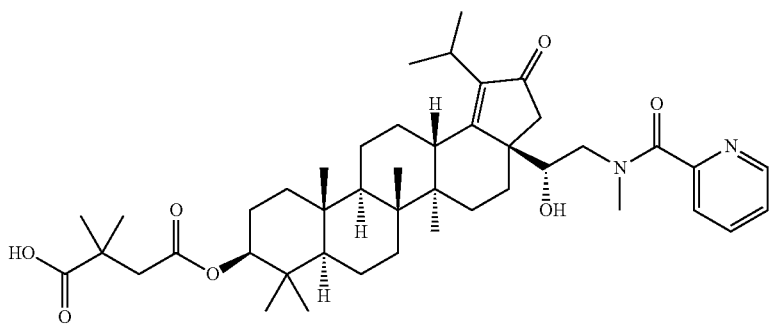

487

LC/MS: m/z calculated 732.5. found 733.5 (M+1)$^+$

Example 419

Compound 488

4-(((3aR,5aR,5bR,7aR,9S,11aR,11bR,13aS)-3a-((R)-2-(N-(4-chlorobenzyl)-2-hydroxyacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

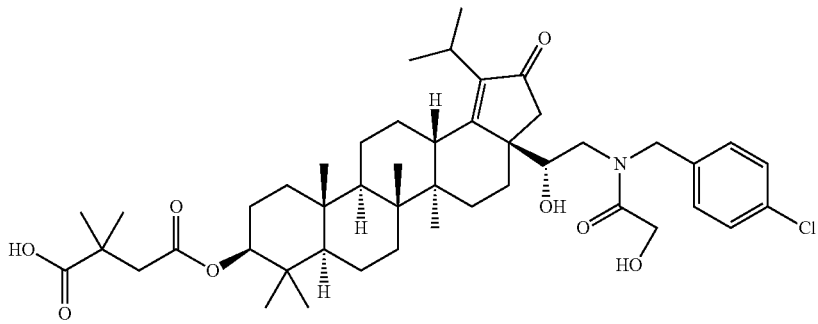

488

LC/MS: m/z calculated 795.4. found 796.3 (M+1)$^+$

Example 420

Compound 489

4-(((3aR,5aR,5bR,7aR,9S,11aR,11bR,13aS)-3a-((R)-1-hydroxy-2-(N-methylisonicotinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

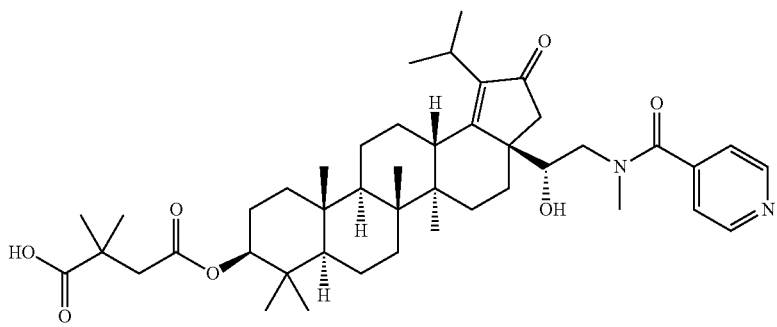

489

LC/MS: m/z calculated 732.5. found 733.5 (M+1)$^+$

Example 421

Compound 490

4-(((3aR,5aR,5bR,7aR,9S,11aR,11bR,13aS)-3a-((R)-1-hydroxy-2-(N-methylnicotinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

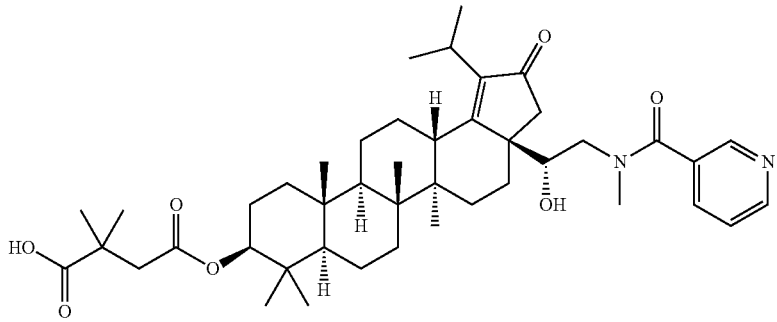

490

LC/MS: m/z calculated 732.5. found 733.4 (M+1)$^+$

Example 422

Compound 491

4-(((3aR,5aR,5bR,7aR,9S,11aR,11bR,13aS)-3a-((R)-2-(N-(4-chlorobenzyl)-2-methoxyacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

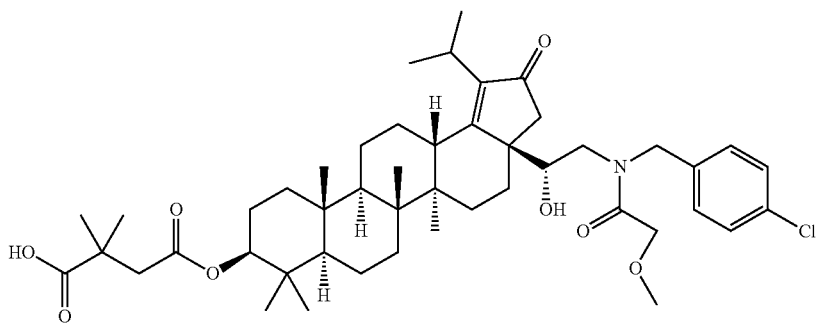

491

LC/MS: m/z calculated 809.5. found 810.3 (M+1)$^+$

Example 423

Compound 492

4-(((3aR,5aR,5bR,7aR,9S,11aR,11bR,3aS)-3a-((R)-2-(N-(4-chlorobenzyl)isobutyramido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

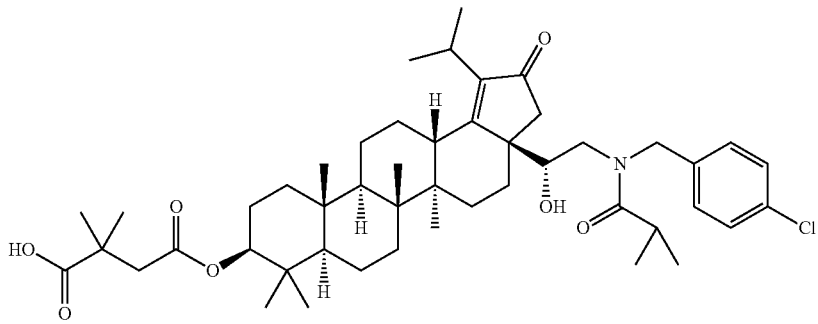

492

LC/MS: m/z calculated 807.5. found 808.5 (M+1)+

Example 424

Compound 493

4-(((3aR,5aR,5bR,7aR,9S,11aR,11bR,13aS)-3a-((R)-2-(N-(2-(dimethylamino)ethyl)-5-methyl-1,3,4-oxadiazole-2-carboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

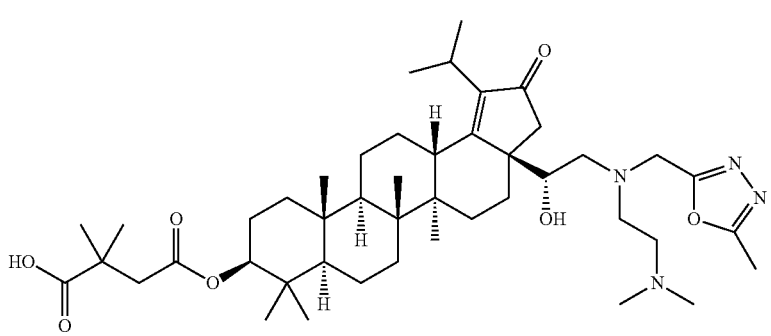

493

LC/MS: m/z calculated 794.5. found 795.5 (M+1)+

Example 425

Compound 494

4-(((3aR,5aR,5bR,7aR,9S,11aR,11bR,13aS)-1-isopropyl-5a,5b,8,8,11a-pentamethyl-2-oxo-3a-(2-((pyrimidin-2-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

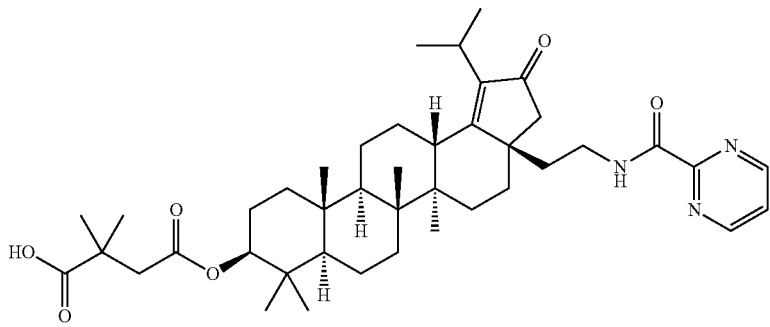

494

LC/MS: m/z calculated 689.5. found 690.4 (M+1)$^+$

Example 427

Compound 496

4-(((3aR,5aR,5bR,7aR,9S,11aR,11bR,13aS)-3a-((R)-2-((4-chlorobenzyl)amino)-1-sulfoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

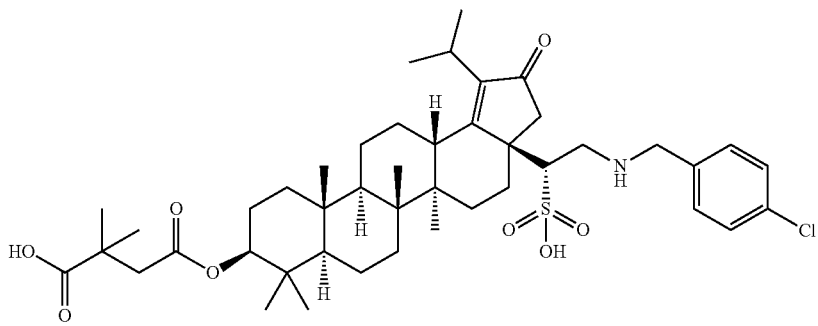

496

LC/MS: m/z calculated 801.4. found 802.2 (M+1)$^+$

Example 428

Compound 497

4-(((3aR,5aR,5bR,7aR,9S,11aR,11bR,13aS)-1-isopropyl-5a,5b,8,8,11a-pentamethyl-2-oxo-3a-(2-((pyrimidin-4-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

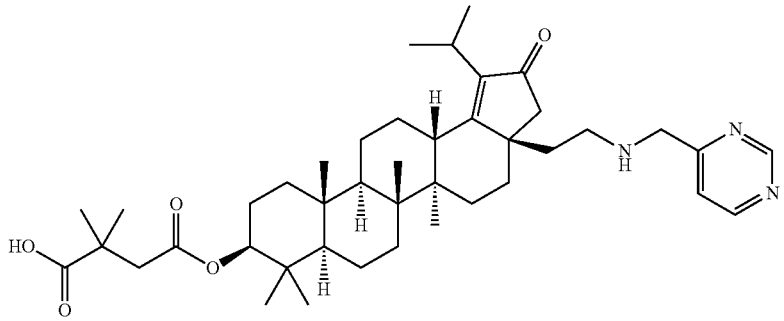

497

LC/MS: m/z calculated 689.5. found 690.4 (M+1)$^+$

Example 429

Compound 498

4-(((3aR,5aR,5bR,7aR,9S,11aR,11bR,13aS)-3a-(2-((2-(dimethylamino)-2-oxoethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

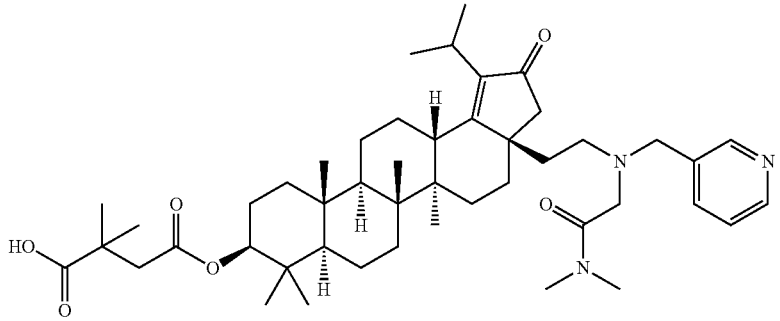

498

LC/MS: m/z calculated 773.5. found 774.5 (M+1)$^+$

Example 430

Compound 499

4-(((3aR,5aR,5bR,7aR,9S,11aR,11bR,13aS)-3a-(2-((2-(dimethylamino)-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

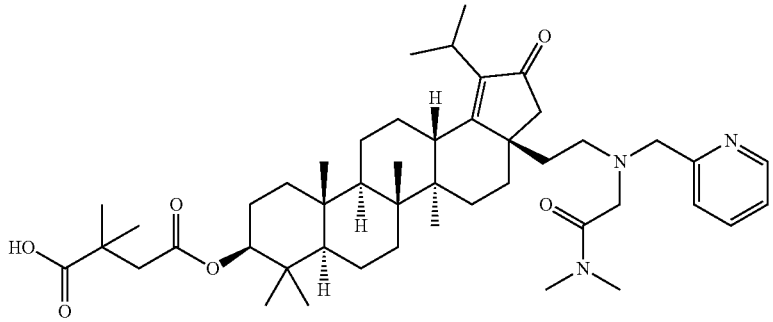

499

LC/MS: m/z calculated 773.5. found 774.5 (M+1)$^+$

Example 431

Compound 500

4-(((3aR,5aR,5bR,7aR,9S,11aR,11bR,13aS)-3a-((R)-2-((2-(dimethylamino)ethyl)(pyrimidin-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

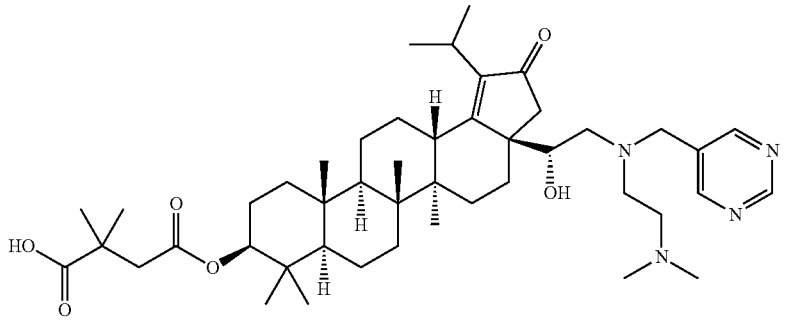

500

LC/MS: m/z calculated 776.5. found 777.4 (M+1)$^+$

Example 433

Compound 502

4-(((3aR,5aR,5bR,7aR,9S,11aR,11bR,13aS)-1-iso-propyl-5a,5b,8,8,11a-pentamethyl-2-oxo-3a-(2-(((R)-1-(pyridin-2-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

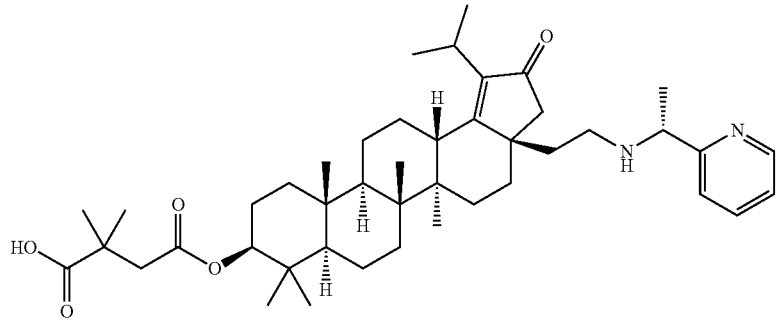

LC/MS: m/z calculated 702.5. found 703.3 (M+1)$^+$

Example 434

Compound 503

4-(((3aR,5aR,5bR,7aR,9S,11aR,11bR,13aS)-3a-((R)-2-(N-(cyclobutylmethyl)-2-(2-oxopyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 435

Compound 504

4-(((3aR,5aR,5bR,7aR,9S,11aR,11bR,13aS)-3a-((R)-2-((cyclobutylmethyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

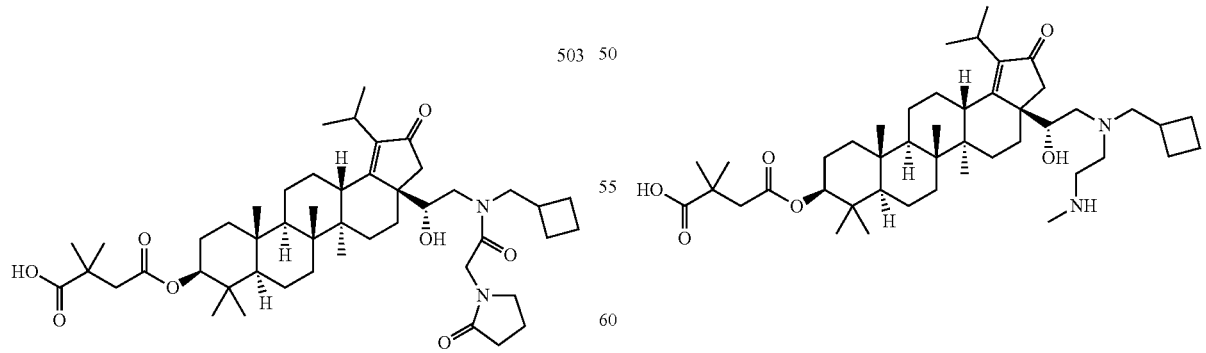

LC/MS: m/z calculated 806.5. found 806.9 (M+1)$^+$

LC/MS: m/z calculated 738.5. found 739.5 (M+1)$^+$

533

Example 436

Compound 505

4-(((3aR,5aR,5bR,7aR,9S,11aR,11bR,13aS)-3a-((R)-2-((2-(dimethylamino)ethyl)(oxazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

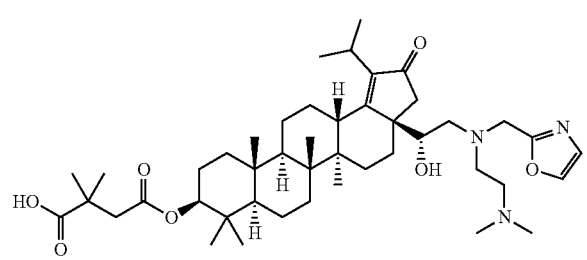

LC/MS: m/z calculated 765.5. found 765.9 (M+1)$^+$

Example 437

Compound 506

4-(((3aR,5aR,5bR,7aR,9S,11aR,11bR,13aS)-3a-((R)-1-hydroxy-2-(1-oxoisoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

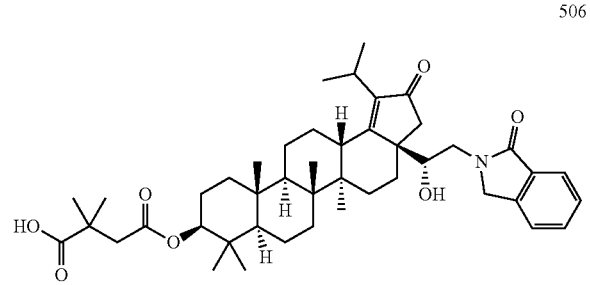

LC/MS: m/z calculated 729.5. found 729.9 (M+1)$^+$

534

Example 438

Compound 507

4-(((3aR,5aR,5bR,7aR,9S,11aR,11bR,13aS)-3a-(2-(cyclobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

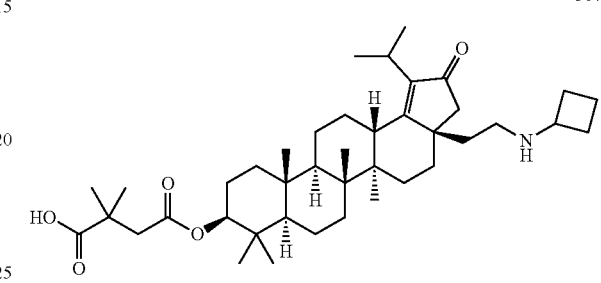

LC/MS: m/z calculated 651.5. found 652.0 (M+1)$^+$

Example 439

Compound 508

4-(((3aR,5aR,5bR,7aR,9S,11aR,11bR,13aS)-3a-(2-(cyclobutyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

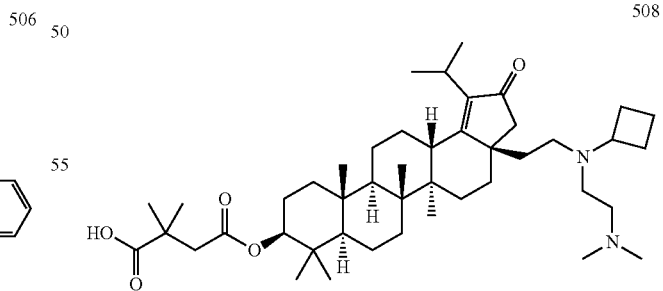

LC/MS: m/z calculated 722.6. found 723.0 (M+1)$^+$

Example 440

Compound 509

4-(((3aR,5aR,5bR,7aR,9S,11aR,11bR,13aS)-3a-((R)-2-((2-acetamidoethyl)(cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

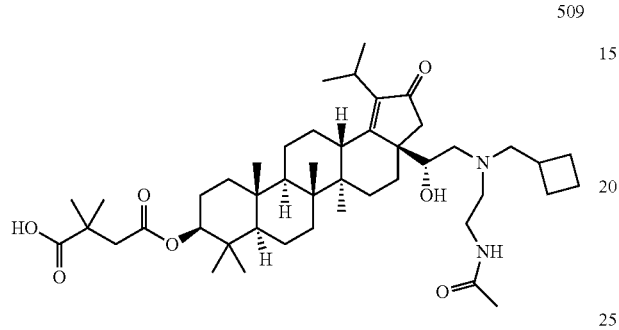

LC/MS: m/z calculated 766.5. found 766.9 (M+1)$^+$

Example 441

Compound 510

4-(((3aR,5aR,5bR,7aR,9S,11aR,11bR,13aS)-3a-(2-(2-(dimethylamino)-N-(pyridin-3-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

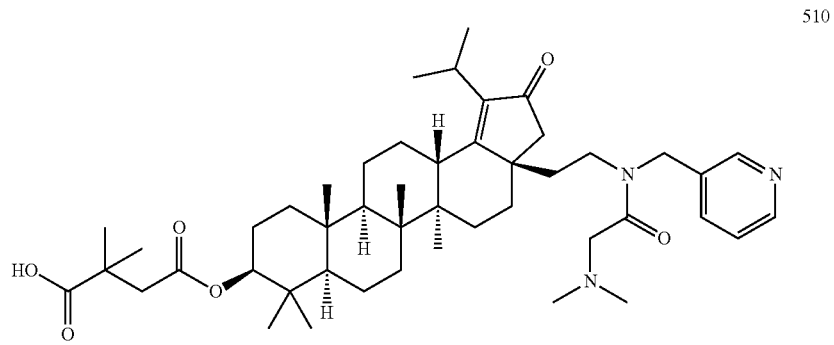

LC/MS: m/z calculated 773.5. found 774.5 (M+1)$^+$

Example 442

Compound 511

4-(((3aR,5aR,5bR,7aR,9S,11aR,11bR,13aS)-3a-(2-((2-(dimethylamino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

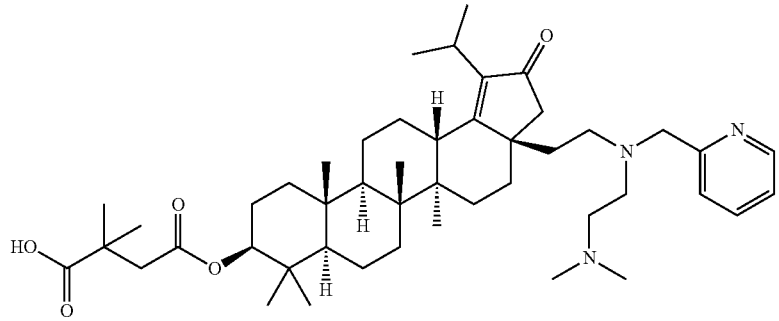

511

LC/MS: m/z calculated 759.6. found 760.5 (M+1)$^+$

Example 443

Compound 512

4-(((3aR,5aR,5bR,7aR,9S,11aR,11bR,13aS)-3a-((R)-2-((cyclobutylmethyl)(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

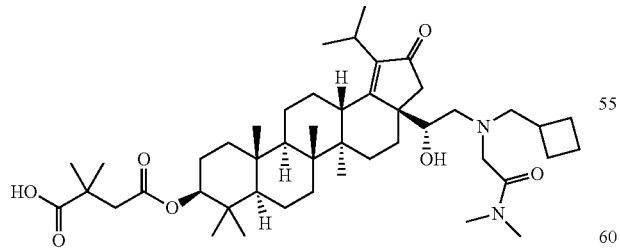

512

LC/MS: m/z calculated 766.5. found 767.5 (M+1)$^+$

Example 444

Compound 513

4-(((3aR,5aR,5bR,7aR,9S,11aR,11bR,13aS)-3a-(2-((2-(dimethylamino)ethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

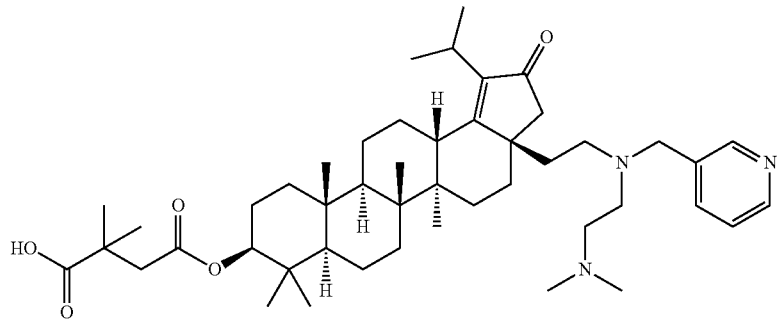

513

LC/MS: m/z calculated 759.6. found 760.5 (M+1)$^+$

Example 445

Compound 514

4-(((3aR,5aR,5bR,7aR,9S,11aR,11bR,13aS)-3a-(2-((2-(dimethylamino)ethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

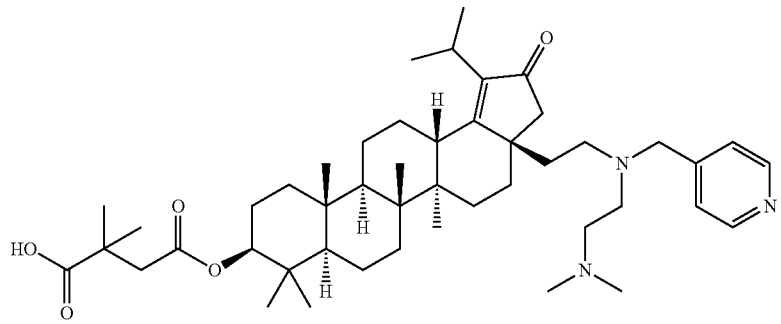

514

LC/MS: m/z calculated 759.6. found 760.5 (M+1)$^+$

Example 446

Compound 515

4-(((3aR,5aR,5bR,7aR,9S,11aR,11bR,13aS)-3a-(2-(2-(dimethylamino)-N-(pyridin-4-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

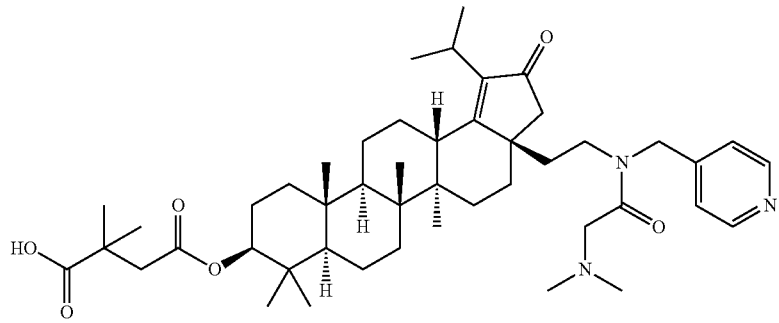

515

LC/MS: m/z calculated 773.5. found 774.5 (M+1)$^+$

Example 447

Compound 516

4-(((3aR,5aR,5bR,7aR,9S,11aR,11bR,13aS)-3a-((R)-2-((cyclobutylmethyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

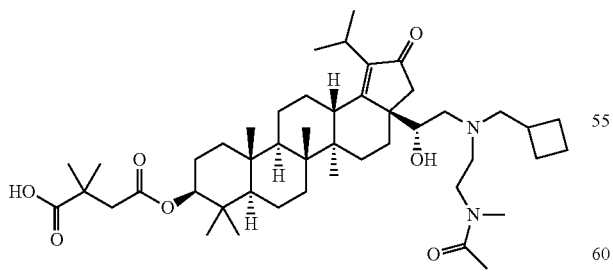

516

LC/MS: m/z calculated 780.6. found 781.4 (M+1)$^+$

Example 448

Compound 517

4-(((3aR,5aR,5bR,7aR,9S,11aR,11bR,13aS)-3a-((R)-1-hydroxy-2-(((R)-1-(pyrimidin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

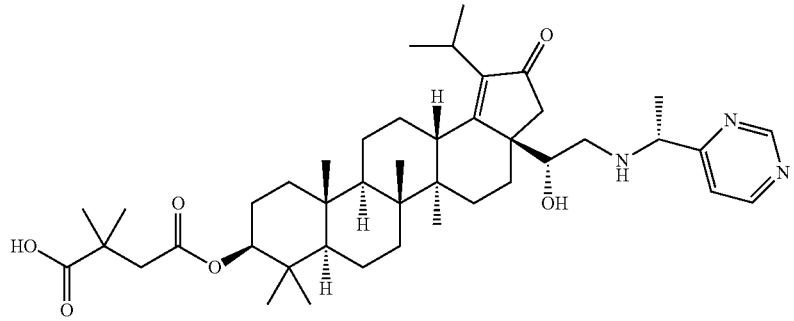

LC/MS: m/z calculated 719.5. found 720.4 (M+1)+

Example 449

Compound 518

4-(((3aR,5aR,5bR,7aR,9S,11aR,11bR,13aS)-3a-(2-((azetidin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

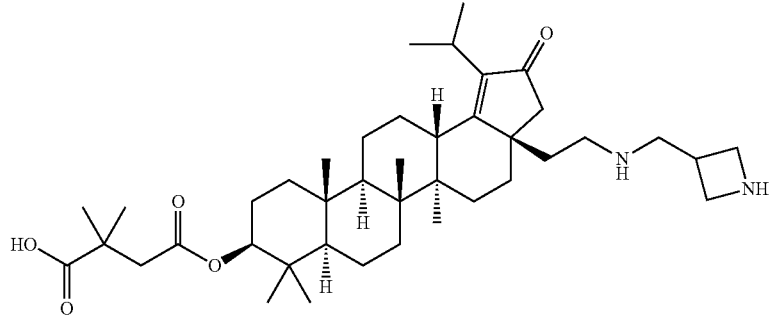

LC/MS: m/z calculated 666.5. found 667.4 (M+1)+

Example 450

Compound 519

4-(((3aR,5aR,5bR,7aR,9S,11aR,11bR,13aS)-3a-((R)-2-(N-(cyclopropylmethyl)-2-(pyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

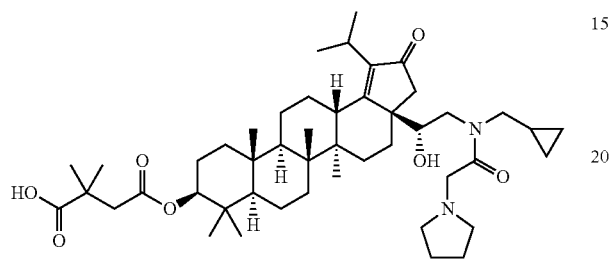

519

LC/MS: m/z calculated 778.5. found 779.5 (M+1)$^+$

Example 451

Compound 520

4-(((3aR,5aR,5bR,7aR,9S,11aR,11bR,13aS)-1-isopropyl-5a,5b,8,8,11a-pentamethyl-2-oxo-3a-(2-(((R)-1-(pyridin-4-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

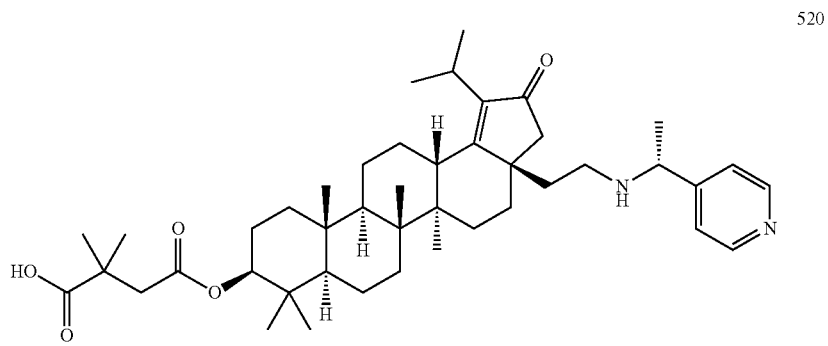

520

LC/MS: m/z calculated 702.5. found 703.5 (M+1)$^+$

Example 452

Compound 521

4-(((3aR,5aR,5bR,7aR,9S,11aR,11bR,13aS)-3a-(2-((azetidin-3-ylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

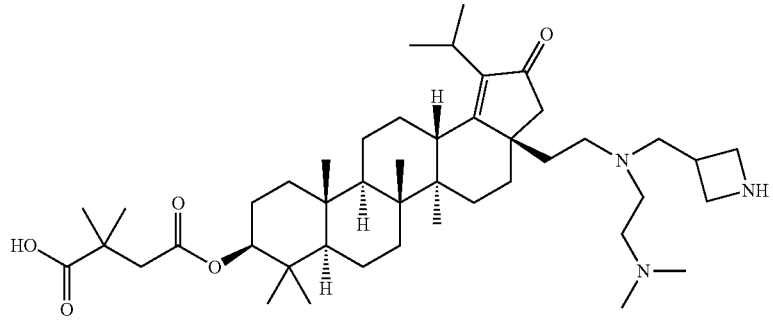

521

LC/MS: m/z calculated 737.6. found 738.7 (M+1)+

Example 454

Compound 523

4-(((3aR,5aR,5bR,7aR,9S,11aR,11bR,13aS)-3a-((R)-1-hydroxy-2-((2-morpholinoethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

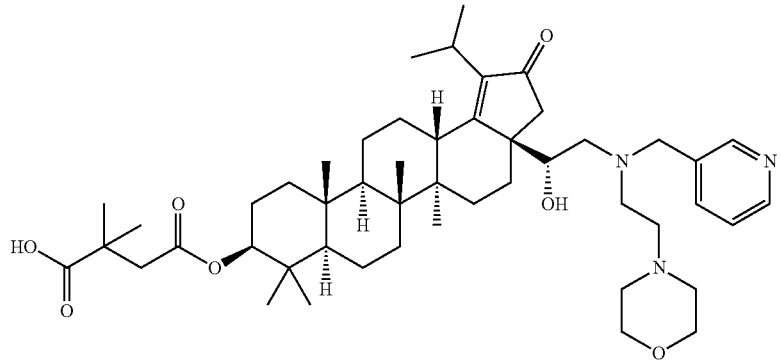

523

LC/MS: m/z calculated 817.6. found 818.5 (M+1)+

Example 455

Compound 524

4-(((3aR,5aR,5bR,7aR,9S,11aR,11bR,13aS)-3a-(2-((2-(dimethylamino)ethyl)((R)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

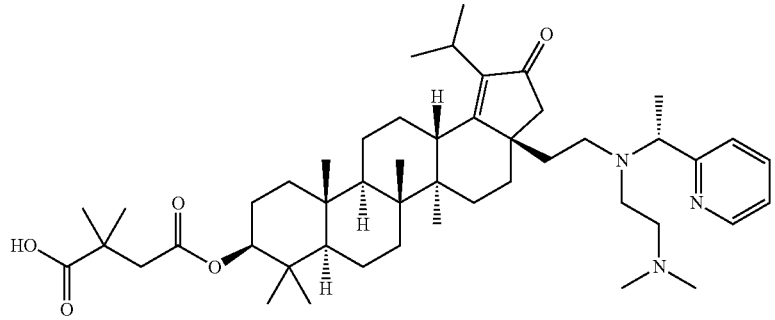

LC/MS: m/z calculated 773.6. found 774.5 (M+1)$^+$

Example 456

Compound 525

4-(((3aR,5aR,5bR,7aR,9S,11aR,11bR,13aS)-3a-((R)-2-((2-(dimethylamino)ethyl)((5-methyl-1,3,4-oxadiazol-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

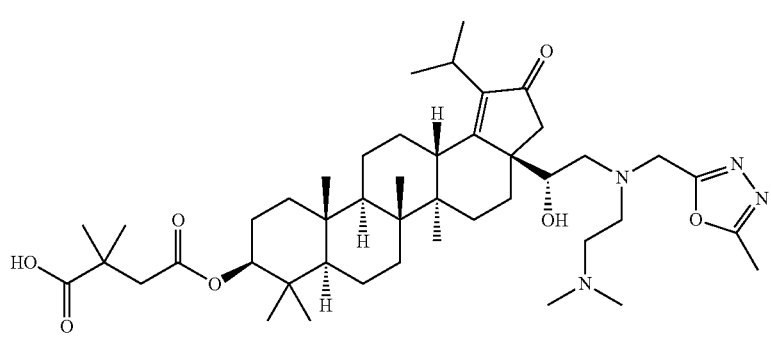

LC/MS: m/z calculated 780.6. found 781.5 (M+1)$^+$

Example 457

Compound 526

4-(((3aR,5aR,5bR,7aR,9S,11aR,11bR,13aS)-1-isopropyl-5a,5b,8,8,11a-pentamethyl-2-oxo-3a-(2-(((R)-1-(pyridin-3-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

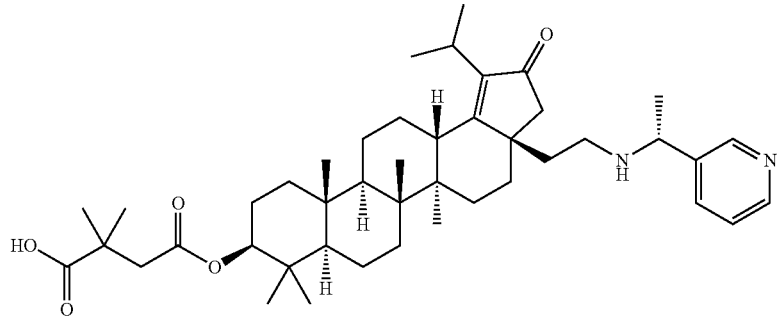

526

LC/MS: m/z calculated 702.5. found 703.5 (M+1)+

Example 458

Compound 527

4-(((3aR,5aR,5bR,7aR,9S,11aR,11bR,13aS)-3a-(2-(((1-acetylazetidin-3-yl)methyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

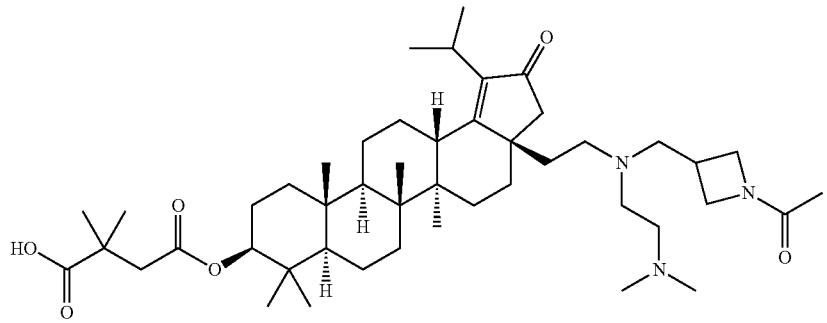

527

LC/MS: m/z calculated 779.6. found 780.7 (M+1)+

Example 459

Compound 528

4-(((3aR,5aR,5bR,7aR,9S,11aR,11bR,13aS)-3a-(2-((2-(dimethylamino)ethyl)(pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

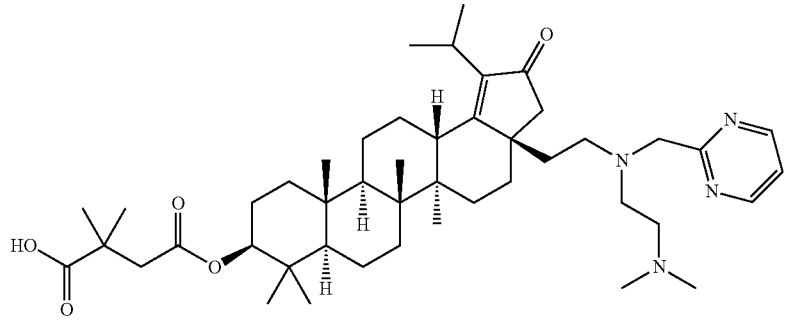

LC/MS: m/z calculated 760.5. found 761.7 (M+1)+

Example 460

Compound 529

4-(((3aR,5aR,5bR,7aR,9S,11aR,11bR,13aS)-3a-((R)-1-hydroxy-2-(((S)-1-(pyrimidin-5-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

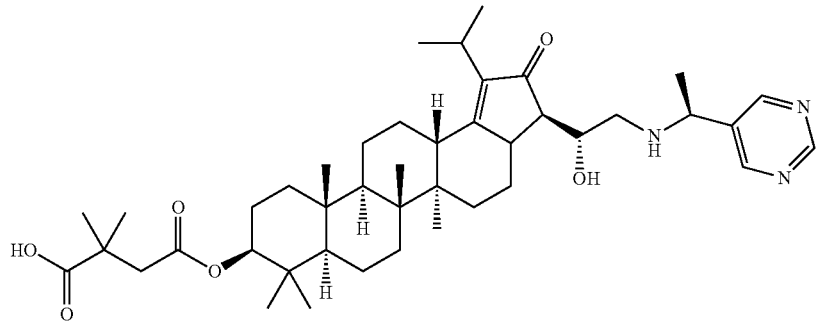

LC/MS: m/z calculated 719.5. found 720.5 (M+1)+

Example 461

Compound 530

4-(((3aR,5aR,5bR,7aR,9S,11aR,11bR,13aS)-3a-((R)-1-hydroxy-2-((2-morpholino-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

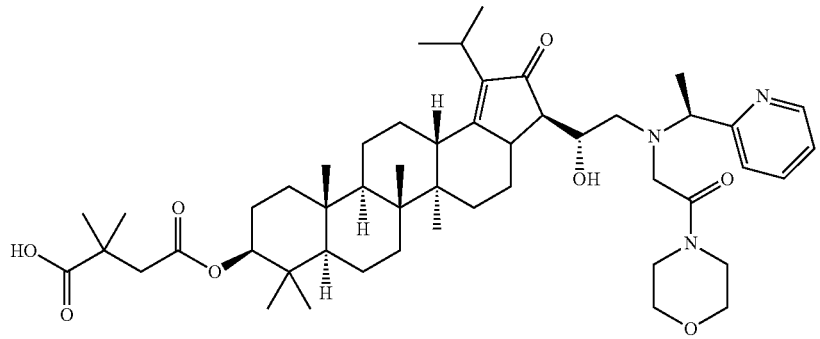

530

LC/MS: m/z calculated 831.5. found 832.7 (M+1)$^+$

Example 462

Compound 531

4-(((3aR,5aR,5bR,7aR,9S,11aR,11bR,13aS)-3a-(2-((2-(dimethylamino)ethyl)((R)-1-(pyridin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

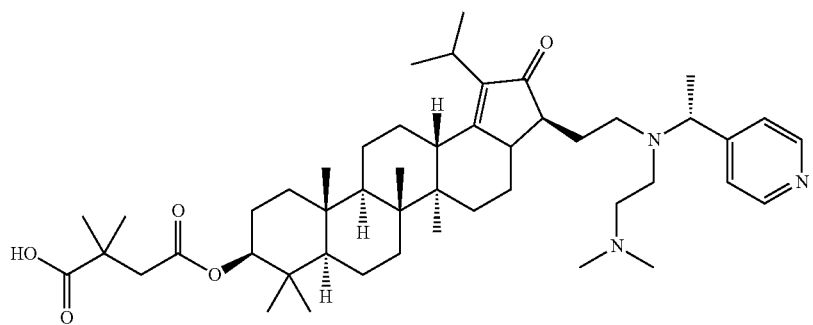

531

LC/MS: m/z calculated 773.6. found 774.7 (M+1)$^+$

Example 463

Compound 532

4-(((3aR,5aR,5bR,7aR,9S,11aR,11bR,13aS)-3a-((R)-2-(benzyl(2-morpholino-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

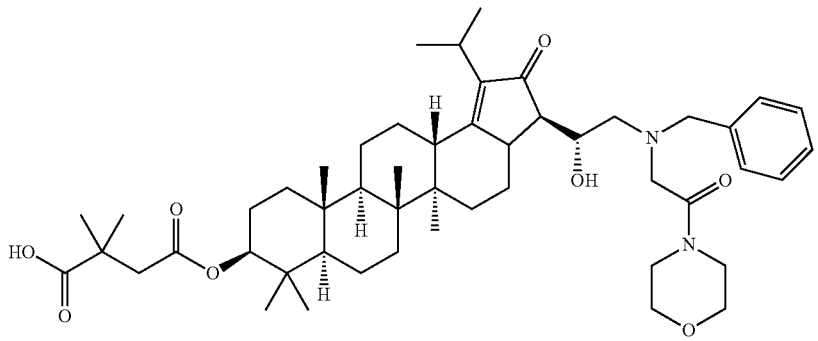

532

LC/MS: m/z calculated 830.5. found 831.5 (M+1)$^+$

Example 464

Compound 533

4-(((3aR,5aR,5bR,7aR,9S,11aR,11bR,13aS)-3a-(2-((cyclopentylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

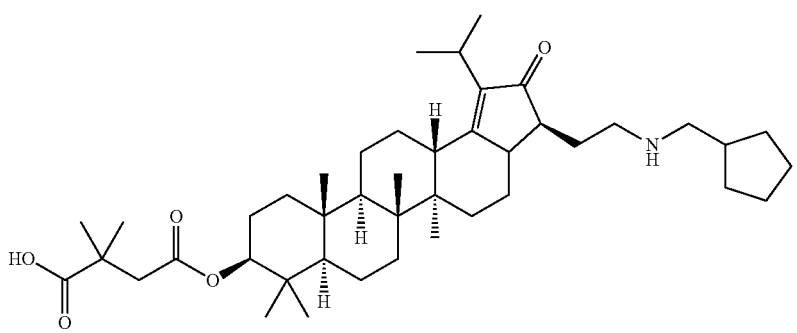

533

LC/MS: m/z calculated 679.5. found 680.7 (M+1)$^+$

Example 465

Compound 534

4-(((3aR,5aR,5bR,7aR,9S,11aR,11bR,13aS)-3a-(2-(((I-acetylazetidin-3-yl)methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

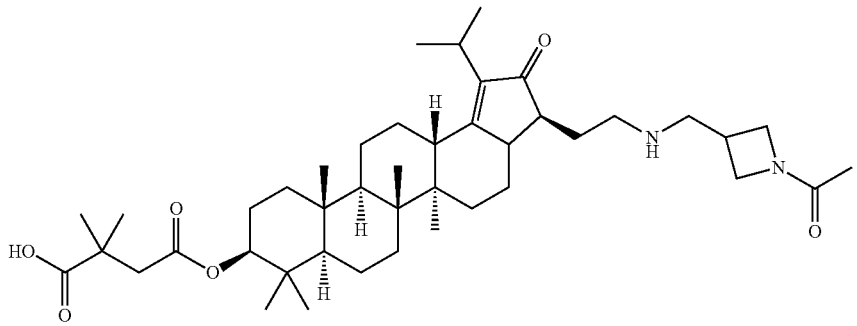

534

LC/MS: m/z calculated 708.5. found 709.7 (M+1)$^+$

Example 466

Compound 535

4-(((3aR,5aR,5bR,7aR,9S,11aR,11bR,13aS)-3a-((R)-1-hydroxy-2-((2-((2-methoxyethyl)(methyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

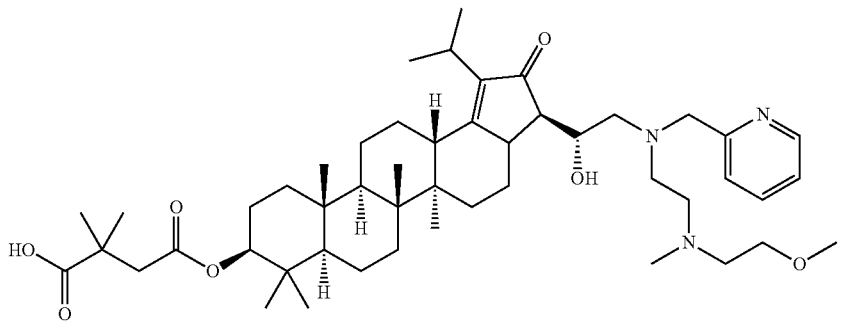

535

LC/MS: m/z calculated 819.6. found 820.5 (M+1)$^+$

Example 467

Compound 536

4-(((3aR,5aR,5bR,7aR,9S,11aR,11bR,13aS)-3a-(2-(N-(2-(dimethylamino)ethyl)benzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

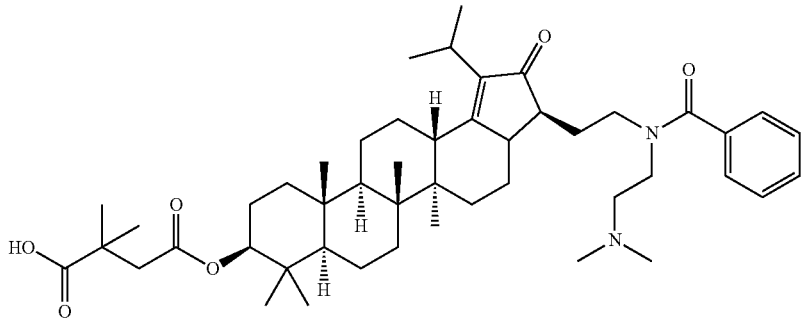

536

LC/MS: m/z calculated 772.5. found 773.5 (M+1)$^+$

Example 468

Compound 537

4-(((3aR,5aR,5bR,7aR,9S,11aR,11bR,13aS)-3a-((R)-1-hydroxy-2-(((S)-1-(pyrimidin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

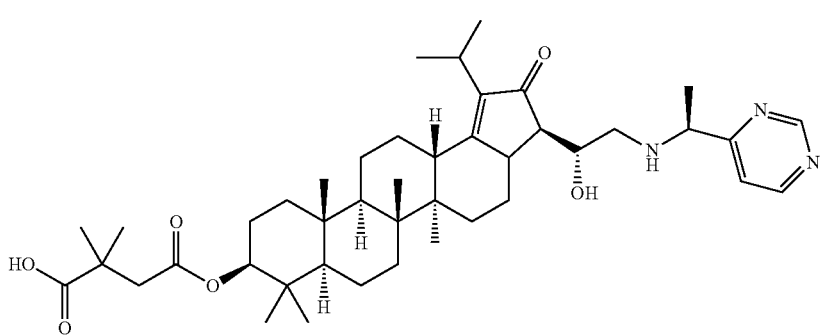

537

LC/MS: m/z calculated 719.5. found 720.5 (M+1)$^+$

Example 469

Compound 538

4-(((3aR,5aR,5bR,7aR,9S,11aR,11bR,13aS)-1-isopropyl-5a,5b,8,8,11a-pentamethyl-2-oxo-3a-(2-((1-(pyridin-2-yl)cyclopropyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

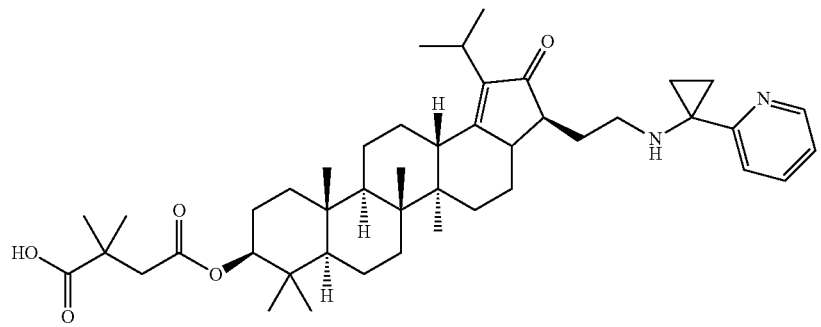

LC/MS: m/z calculated 714.5. found 715.5 (M+1)$^+$

Example 471

Compound 540

4-(((3aR,5aR,5bR,7aR,9S,11aR,11bR,13aS)-1-isopropyl-5a,5b,8,8,11a-pentamethyl-2-oxo-3a-(2-(piperidin-1-yl)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

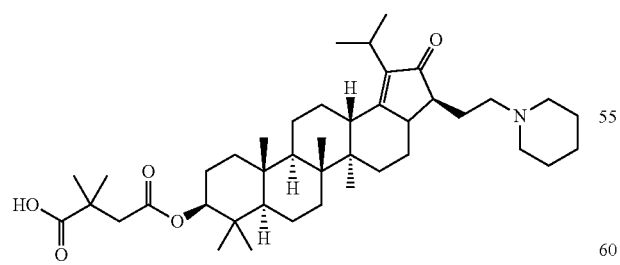

LC/MS: m/z calculated 665.5. found 666.5 (M+1)$^+$

Example 472

Compound 541

4-(((3aR,5aR,5bR,7aR,9S,11aR,11bR,13aS)-1-isopropyl-5a,5b,8,8,11a-pentamethyl-2-oxo-3a-(2-(((S)-1-(pyridin-3-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

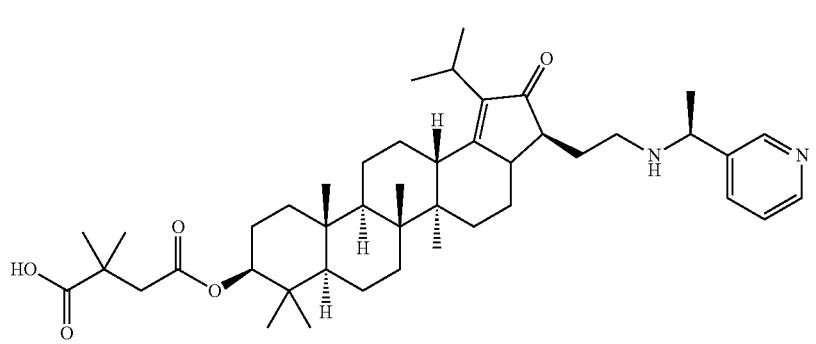

541

LC/MS: m/z calculated 702.5. found 703.4 (M+1)$^+$

Example 473

Compound 542

4-(((3aR,5aR,5bR,7aR,9S,11aR,11bR,13aS)-3a-(2-((2-(dimethylamino)ethyl)((S)-1-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

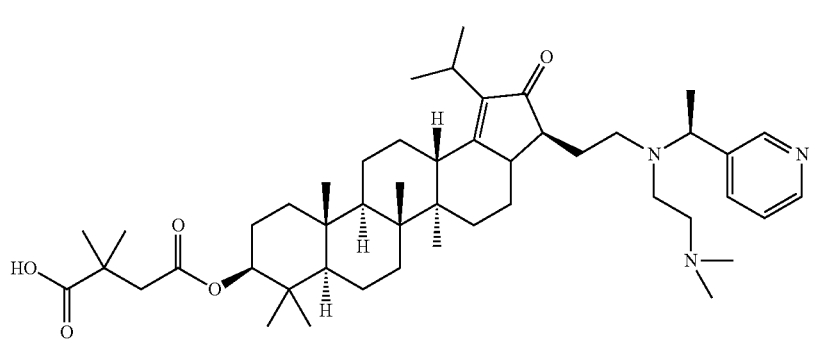

542

LC/MS: m/z calculated 773.6. found 774.7 (M+1)$^+$

Example 474

Compound 543

4-(((3aR,5aR,5bR,7aR,9S,11aR,11bR,13aS)-3a-(2-((2-(dimethylamino)ethyl)((R)-1-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

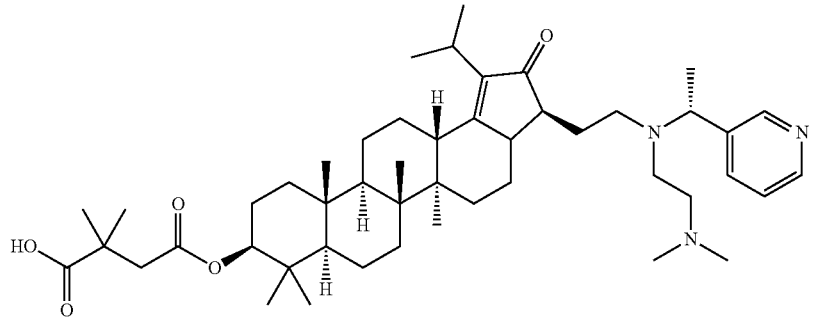

543

LC/MS: m/z calculated 773.6. found 774.7 (M+1)$^+$

Example 475

Compound 544

4-(((3aR,5aR,5bR,7aR,9S,11aR,11bR,13aS)-3a-((R)-1-hydroxy-2-(((R)-1-(pyrimidin-5-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

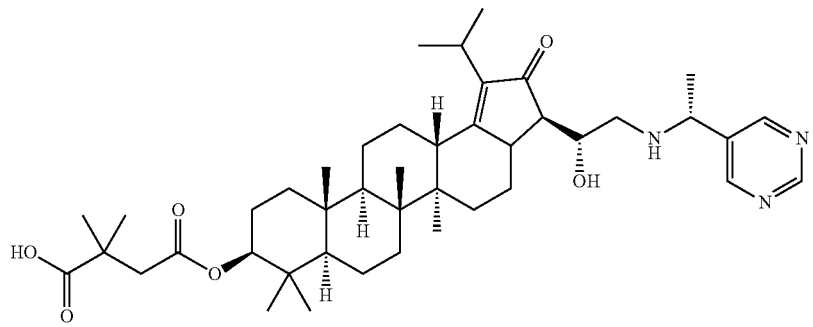

544

LC/MS: m/z calculated 719.5. found 719.8 (M+1)$^+$

Example 476

Compound 545

4-(((3aR,5aR,5bR,7aR,9S,11aR,11bR,13aS)-3a-((R)-2-(N-(2-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

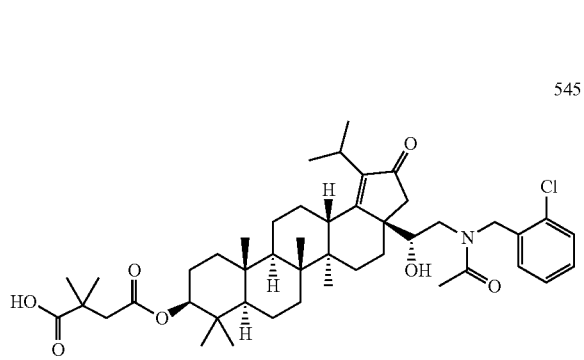

545

LC/MS: m/z calculated 779.4. found 780.3 (M+1)+

Example 477

Compound 546

4-(((3aR,5aR,5bR,7aR,9S,11aR,11bR,13aS)-3a-((R)-2-((4-chlorobenzyl)(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Example 478

Compound 547

4-(((3aR,5aR,5bR,7aR,9S,11aR,11bR,13aS)-1-isopropyl-5a,5b,8,8,11a-pentamethyl-3a-(2-((oxetan-3-ylmethyl)amino)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

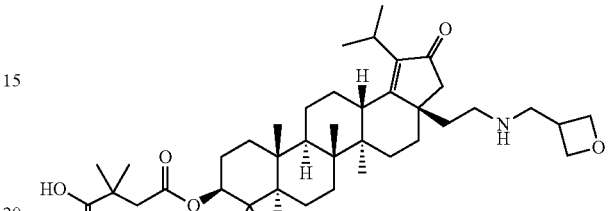

547

LC/MS: m/z calculated 667.5. found 668.4 (M+1)+

Example 479

Compound 548

4-(((3aR,5aR,5bR,7aR,9S,11aR,11bR,13aS)-1-isopropyl-5a,5b,8,8,11a-pentamethyl-2-oxo-3a-(2-(((S)-1-(pyridin-2-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

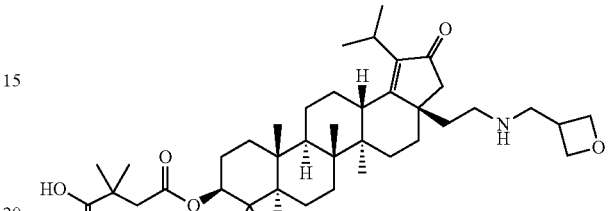

548

LC/MS: m/z calculated 702.5. found 703.5 (M+1)+

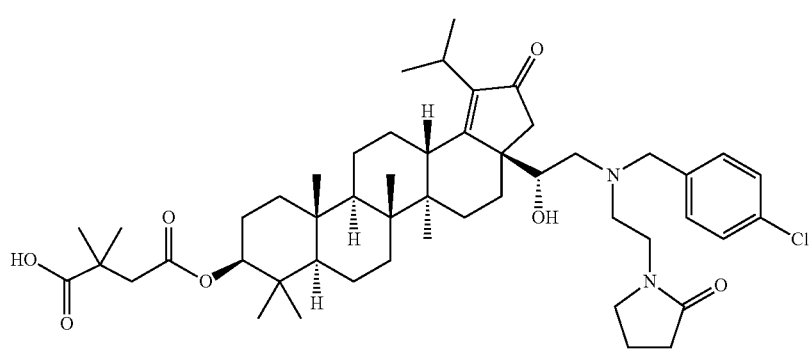

546

LC/MS: m/z calculated 848.5. found 849.5 (M+1)+

Example 480

Compound 549

4-(((3aR,5aR,5bR,7aR,9S,11aR,11bR,13aS)-1-isopropyl-5a,5b,8,8,11a-pentamethyl-2-oxo-3a-(2-(((S)-1-(pyridin-4-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

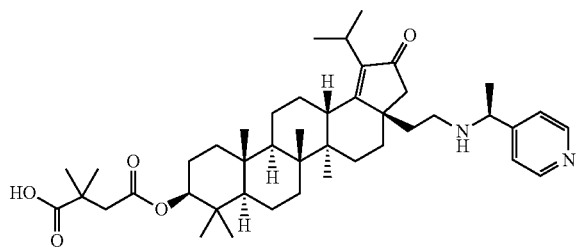

549

LC/MS: m/z calculated 702.5. found 703.4 (M+1)$^+$

Example 481

Compound 550

4-(((3aR,5aR,5bR,7aR,9S,11aR,11bR,13aS)-3a-((R)-2-((2-(dimethylamino)ethyl)((R)-1-(pyrimidin-4-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

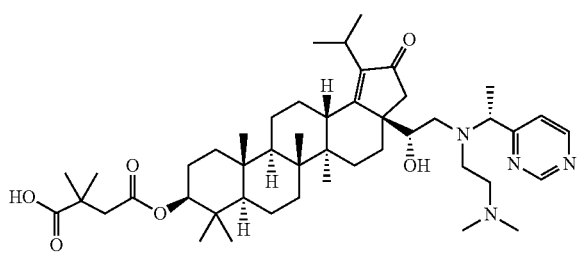

550

LC/MS: m/z calculated 790.6. found 791.5 (M+1)$^+$

Example 482

Compound 551

4-(((3aR,5aR,5bR,7aR,9S,11aR,11bR,13aS)-3a-(2-((2-(dimethylamino)ethyl)(1-(pyridin-2-yl)cyclopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

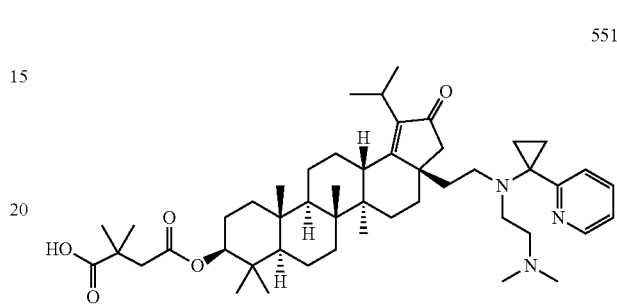

551

LC/MS: m/z calculated 785.6. found 786.5 (M+1)$^+$

Example 483

Compound 552

4-(((3aR,5aR,5bR,7aR,9S,11aR,11bR,13aS)-1-isopropyl-5a,5b,8,8,11a-pentamethyl-2-oxo-3a-(2-((2-(pyridin-2-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

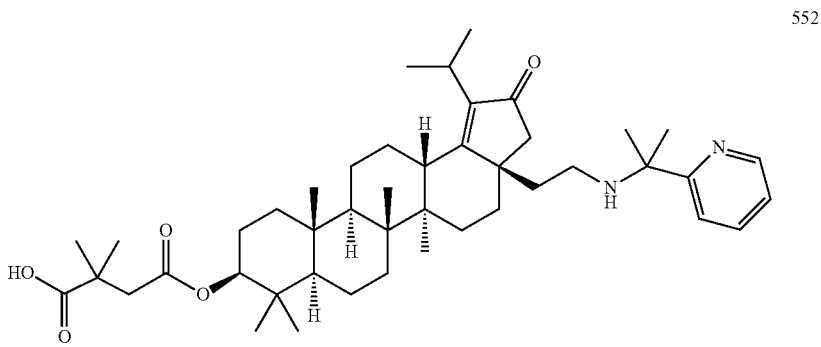

552

LC/MS: m/z calculated 716.5. found 717.5 (M+1)$^+$

Example 484

Compound 553

4-(((3aR,5aR,5bR,7aR,9S,11aR,11bR,13aS)-3a-(2-((2-(dimethylamino)ethyl)(oxetan-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

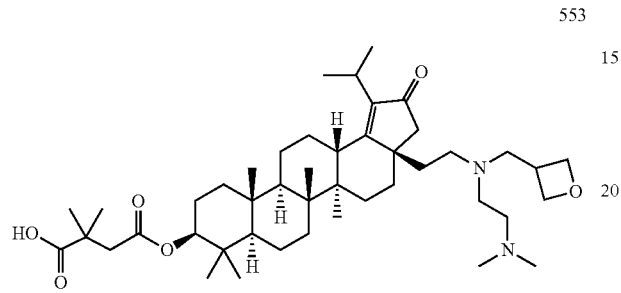

553

LC/MS: m/z calculated 738.5. found 739.5 (M+1)$^+$

Example 485

Compound 554

4-(((3aR,5aR,5bR,7aR,9S,11aR,11bR,13aS)-3a-(2-((2-(dimethylamino)ethyl)((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

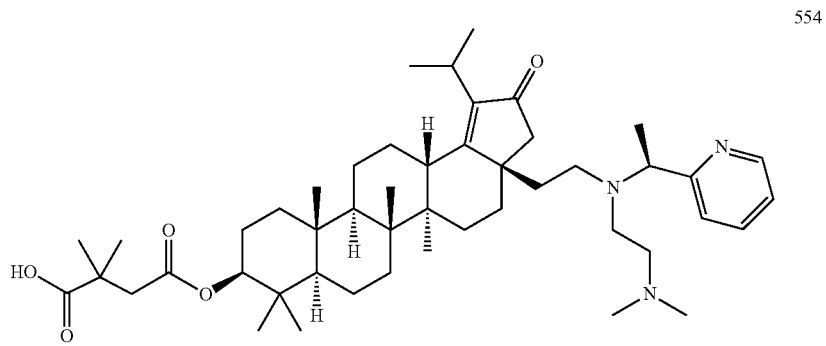

554

LC/MS: m/z calculated 773.6. found 774.5 (M+1)$^+$

Example 486

Compound 555

4-(((3aR,5aR,5bR,7aR,9S,11aR,11bR,13aS)-3a-(2-
((2-(dimethylamino)ethyl)((S)-1-(pyridin-4-yl)ethyl)
amino)ethyl)-1-isopropyl-5a,5b,8,8,11a-pentam-
ethyl-2-oxo-3,3a,4,5,5a,5b,6,7,7a,8,9,10,11,11a,11b,
12,13,13a-octadecahydro-2H-cyclopenta[a]chrysen-
9-yl)oxy)-2,2-dimethyl-4-oxobutanoic acid.

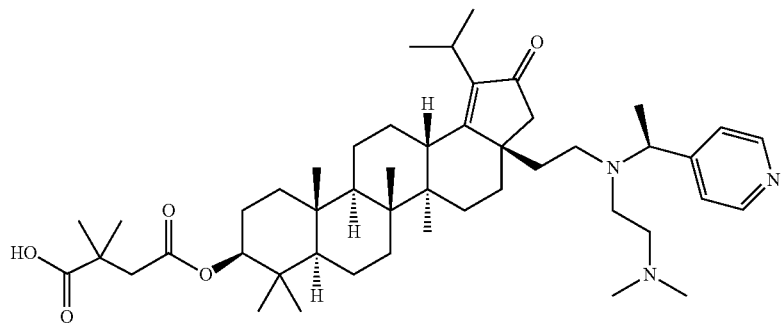

555

LC/MS: m/z calculated 773.6. found 774.5 (M+1)$^+$

Example 487

Compound 556

4-(((3aR,5aR,5bR,7aR,9S,11aR,11bR,13aS)-1-iso-
propyl-5a,5b,8,8,11a-pentamethyl-2-oxo-3a-(2-((1-
(pyrimidin-2-yl)cyclopropyl)amino)ethyl)-3,3a,4,5,
5a,5b,6,7,7a,8,9,10,11,11a,11b,12,13,13a-
octadecahydro-2H-cyclopenta[a]chrysen-9-yl)oxy)-
2,2-dimethyl-4-oxobutanoic acid.

556

LC/MS: m/z calculated 715.5. found 716.5 (M+1)$^+$

Example 488

Compound 557

4-(((3aR,5aR,5bR,7aR,9S,11aR,11bR,13aS)-3a-(2-((2-(dimethylamino)ethyl)(1-(pyrimidin-2-yl)cyclopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

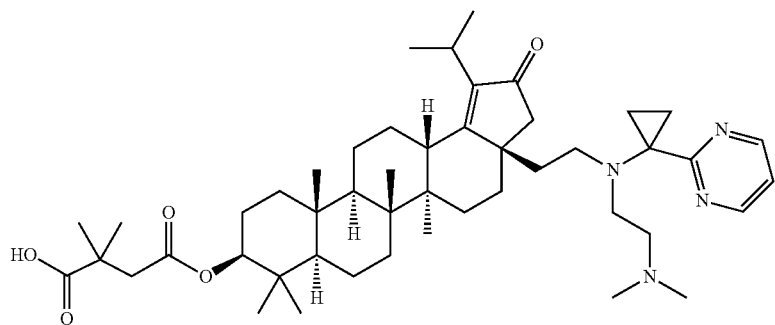

557

LC/MS: m/z calculated 786.6. found 787.5 (M+1)$^+$

Example 489

Compound 558

4-(((3aR,5aR,5bR,7aR,9S,11aR,11bR,13aS)-3a-(2-(N-(2-(dimethylamino)ethyl)picolinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

558

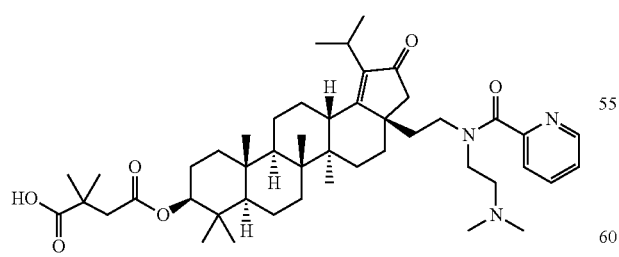

LC/MS: m/z calculated 773.5. found 774.5 (M+1)$^+$

Example 490

Compound 559

4-(((3aR,5aR,5bR,7aR,9S,11aR,11bR,13aS)-1-iso-propyl-5a,5b,8,8,11a-pentamethyl-2-oxo-3a-(2-((2-(pyridin-3-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

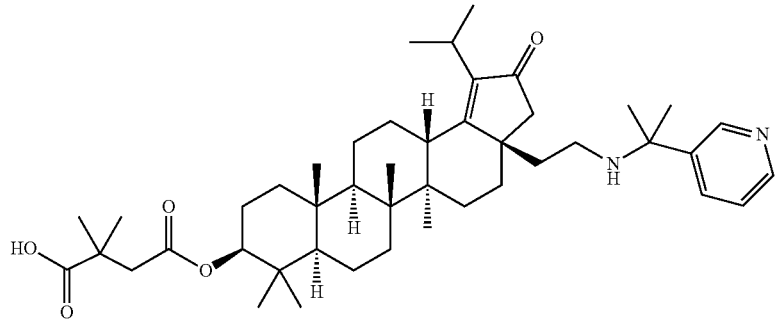

559

LC/MS: m/z calculated 716.5. found 717.5 (M+1)$^+$

Example 491

Compound 560

4-(((3aR,5aR,5bR,7aR,9S,11aR,11bR,13aS)-1-iso-propyl-5a,5b,8,8,11a-pentamethyl-2-oxo-3a-(2-((2-(pyridin-4-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

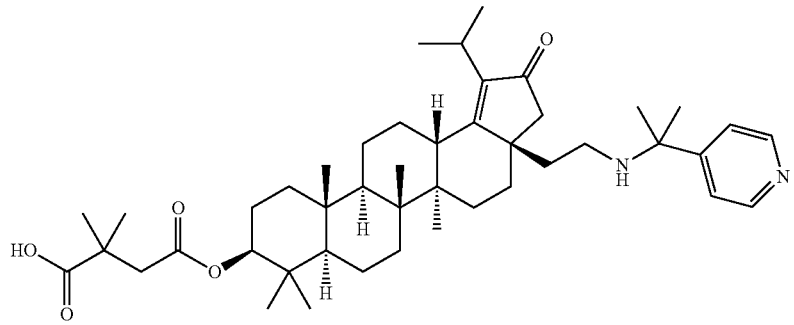

560

LC/MS: m/z calculated 716.5. found 717.5 (M+1)$^+$

Example 492

Compound 561

4-(((3aR,5aR,5bR,7aR,9S,11aR,11bR,13aS)-3a-((R)-2-(benzyl(2-(4-methylpiperazin-1-yl)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

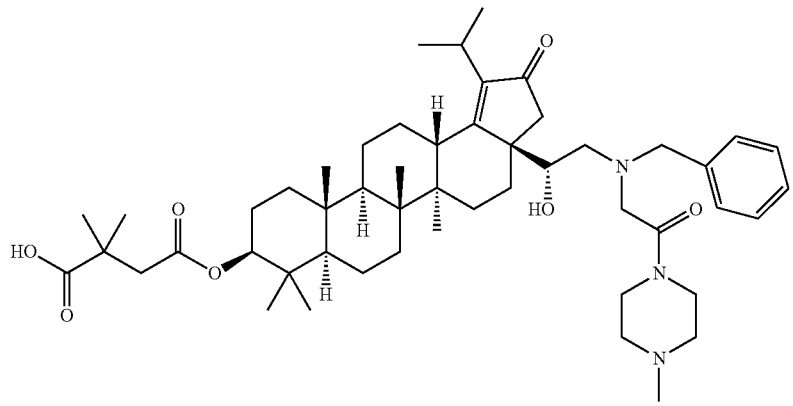

561

LC/MS: m/z calculated 843.6. found 844.5 (M+1)$^+$

Example 493

Compound 562

4-(((3aR,5aR,5bR,7aR,9S,11aR,11bR,13aS)-3a-((R)-2-((2-(dimethylamino)ethyl)(oxazol-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

562

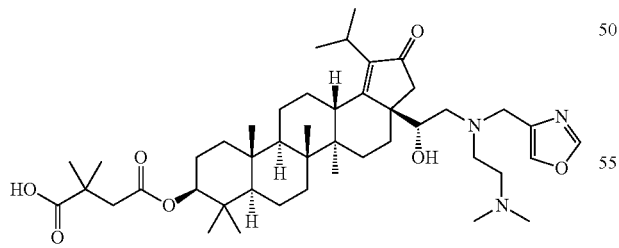

LC/MS: m/z calculated 765.5. found 766.5 (M+1)$^+$

Example 494

Compound 563

4-(((3aR,5aR,5bR,7aR,9S,11aR,11bR,13aS)-3a-(2-((2-(dimethylamino)ethyl)(2-(pyridin-2-yl)propan-2-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

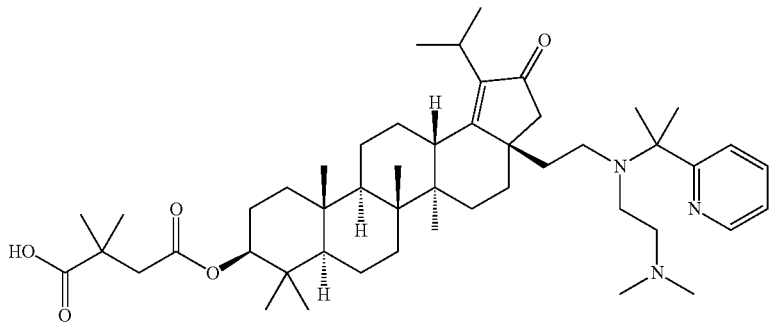

563

LC/MS: m/z calculated 787.6. found 788.5 (M+1)$^+$

Example 495

Compound 564

4-(((3aR,5aR,5bR,7aR,9S,11aR,11bR,13aS)-3a-(2-((2-(dimethylamino)-2-oxoethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

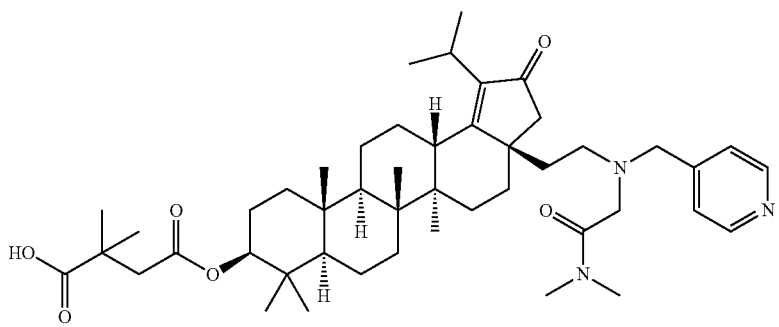

564

LC/MS: m/z calculated 773.6. found 774.5 (M+1)$^+$

Example 496
Compound 565
4-(((3aR,5aR,5bR,7aR,9S,11aR,11bR,13aS)-3a-((R)-2-((2-(dimethylamino)ethyl)(oxazol-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid
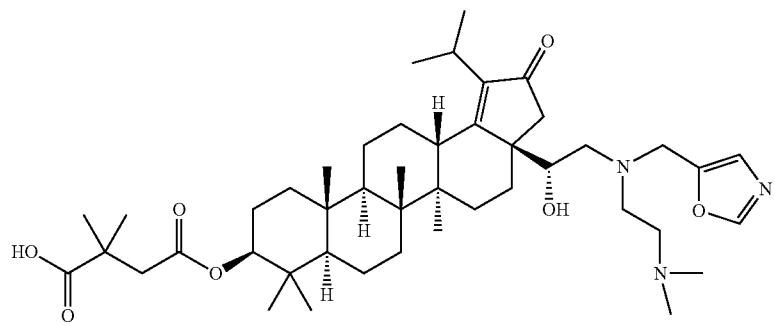
LC/MS: m/z calculated 765.5. found 766.5 (M+1)$^+$
Example 497
Compound 46
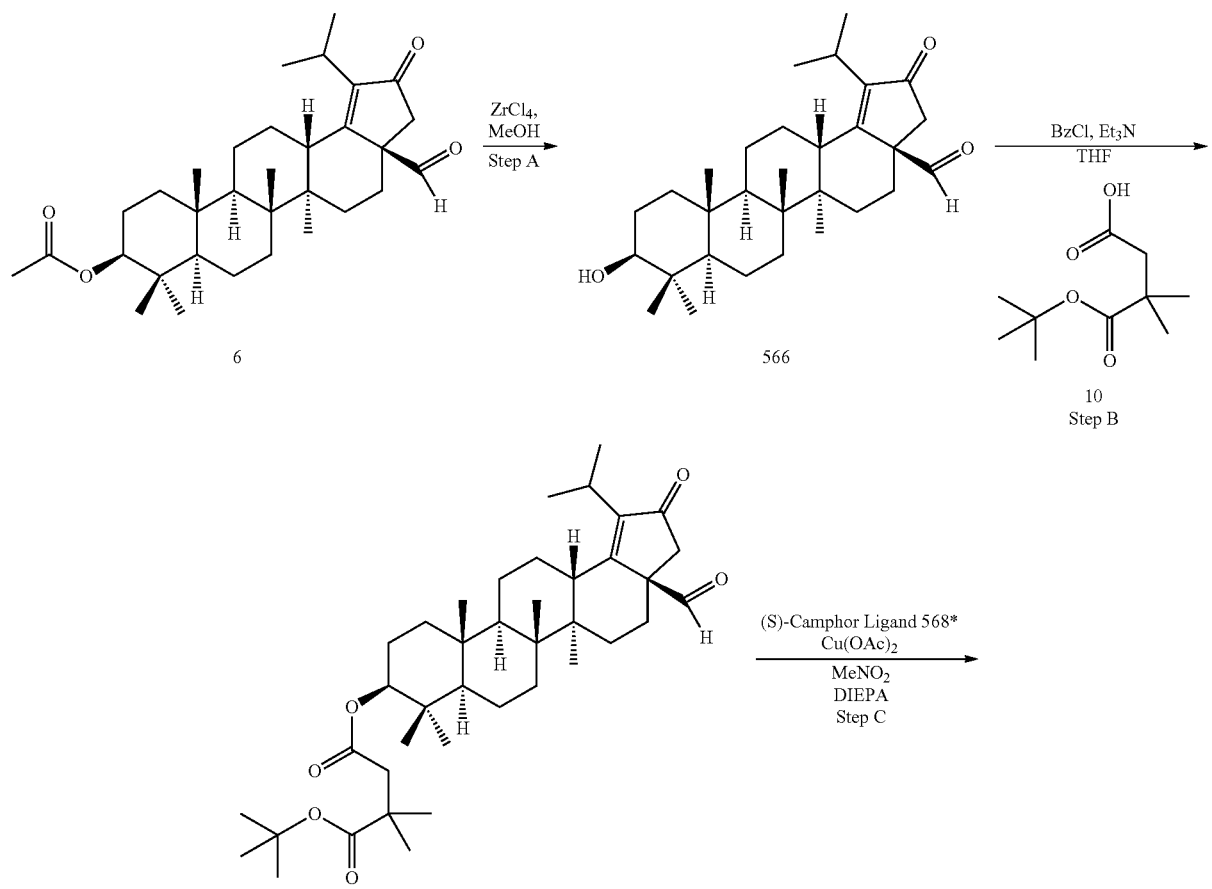

-continued
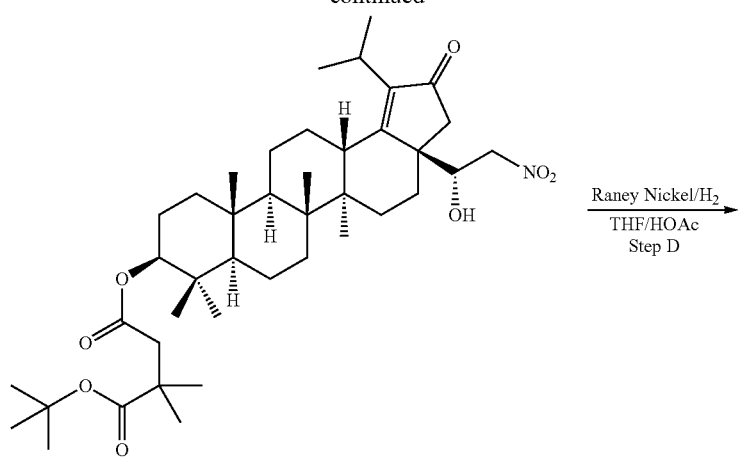
569
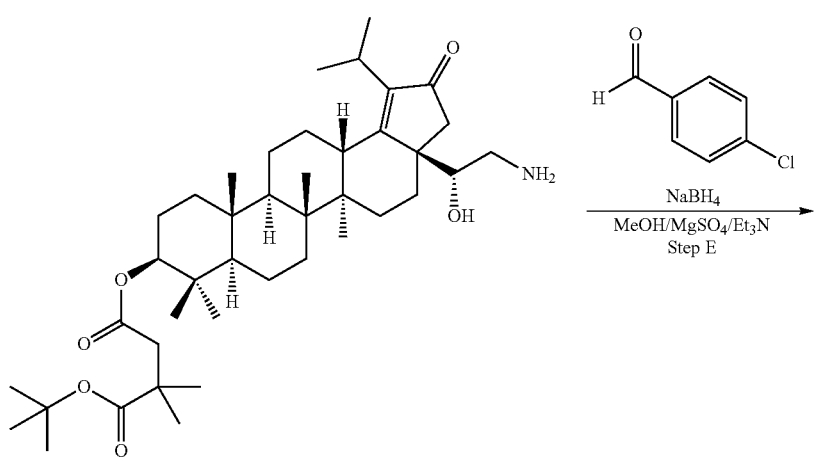
570
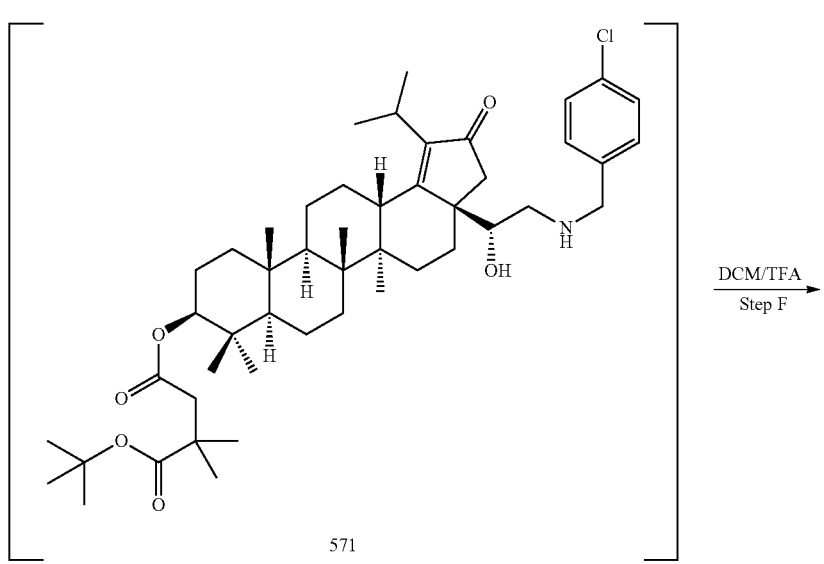
571

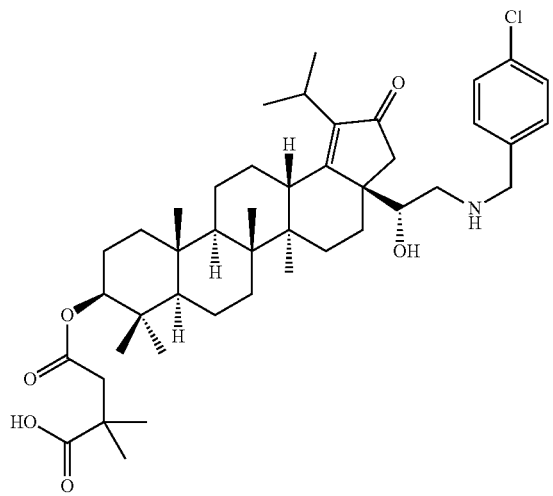

46

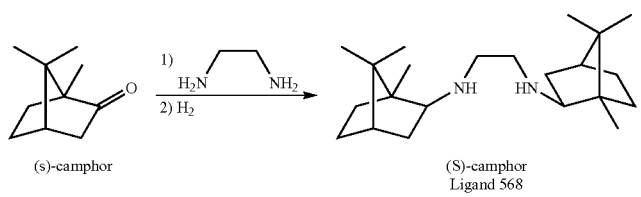

(s)-camphor (S)-camphor
Ligand 568

Step A: Intermediate 566

(3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde (3aR,5aR,5bR,7aR,9S,11aR,11bR,13aS)-3a-Formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (50 g) placed in a round bottomed flask with methanol (500 ml, 10 vol) and DCM ("dichloromethane"—200 ml, 4 vol) and stirred at ambient temp while adding solid ZrCl₄ (23.4 g, 1 equiv.) in portions. The reaction was warmed to approximately 60° C. and maintained for a total of 16 hours. The reaction was monitored for completion on HPLC (starting material and product formed an acetal derivative during the reaction). Once complete, the reaction was treated with water (5 equiv.) and maintained at 60 degrees for approximately 30 minutes.

Next, the reaction was cooled and evaporated under vacuum at a bath temp of approximately 40° C. to 200 ml (4 volumes). Ethyl acetate (500 ml, 10 vol) was added and reaction was then treated with 1N HCl (250 ml, 5 vol). The reaction was then mixed thoroughly and the layers were allowed to separate. The lower aqueous layer was drained off and back-washed with fresh ethyl acetate (100 ml, 2 vol).

The combined organic layer was washed with 1N HCl (250 ml, 5 vol) and evaporated under vacuum at a bath temp of 40° C. to 200 ml (4 vol) and then treated with acetonitrile (500 ml, 10 vol). The reaction was then evaporated to a final volume of approximately 150 ml (3 vol). Acetonitrile (500 ml, 10 vol) was then added and the reaction was warmed to a 60° C. forming solution. Next, was slowly added 3N HCl (100 ml, 2 vol), which resulted in precipitate formation. (see note 2). The reaction was then allowed to cool to ambient temperature and then it was filtered. The filtrated solid was next rinsed with acetonitrile (2 vol) and dried in vacuo to give a weight of 33.0 g, 72% yield of (3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde.

Note 1: The isolated solids were contaminated with a small amount of dimethyl acetal of product, which required reslurry in hot acetonitrile/3N HCl to complete the hydrolysis and resulted in loss of product (27 g recovered on re-treatment). It was determined that in process monitoring of reaction slurries during final hydrolysis require filtration of reaction aliquot in order to observe remaining dimethyl acetal. Dissolution of crude acetonitrile/aqueous HCl reaction solution for HPLC monitoring results in artificially low observed levels of dimethyl acetal due to hydrolysis in sample prep.

Note 2: Preferred procedure would be to add a portion of the 3N HCl (0.5 vol) and maintain reaction in solution at approximately 60° C. until dimethyl acetal hydrolysis is complete followed by addition of remainder (1.5 vol) of the 3N HCl and cooling to ambient temperature for filtration. Expected yield is 72%.

Step B: Intermediate 567

1-tert-butyl 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate.

(3aR,5aR,5bR,7aR,9S,11aR,11bR,13aS)-9-Hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde (26.9 g, 1 equiv), 4-(tert-butoxy)-3,3-dimethyl-4-oxobutanoic acid (14.96 g, 1.25 equiv) and THF (538 ml, 20 vol) were charged to a flask. Benzoyl chloride (10.4 g, 1.25 equiv) was added followed by slow addition of triethylamine (14.97 g, 2.5 equiv) forming a thick slurry. DMAP (0.1.81 g, 0.25 equiv) was added and the reaction was allowed to stir at ambient temperature for approximately 18 hours until complete by HPLC. Reaction was then charged with ethyl acetate (538 mL, 20 vol) and water (269 ml, 10 vol), stirred well and allowed to settle. Aqueous phase was removed and the organic phase washed with saturated sodium bicarbonate solution (2×10 vol) followed by water (269 mL, 10 vol). The reaction solution evaporated under vacuum to approximately 4 volumes to produce solids. Additional hexanes (269 ml, 10 vol) was added and reaction heated back to reflux to nearly form solution and slowly cooled to ambient temperature (seeding with desired product) and let stir for 15 minutes then cooled to 0° C. for approximately two hours and filtered solid. Washed solid with hexanes (2×10 vol) and dried at 50° C. under vacuum to a weight of 32.15 g, 85% yield of 1-tert-butyl 4-((3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate.

Step C: Intermediate 569

1-tert-butyl 4-((3aR,5aR,5bR,7aR,9S,11aR,11bR, 13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate.

The reaction was charged with 1-tert-butyl 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (15.75 g, 1 equiv), tert-butanol (157 ml, 10 vol) and toluene (47 ml, 3 vol) and stirred at ambient temperature. The ligand (N1,N2-bis(1,7,7-trimethylbicyclo[2.2.1]heptan-2-yl)ethane-1,2-diamine, derived from (S)-camphor, 0.492 g, 0.06 equiv) and copper (II) acetate mono hydrate (0.246 g, 0.05 equiv) were added in a single portion and reaction allowed to stir at ambient temperature for at least 2.5 hours (see note 1). The reaction is charged with nitromethane (7.52 g, 5 equiv) and Hunig's base ("N,N-diisopropylethylamine"—3.82 g, 1.2 equiv) and allowed to stir at ambient temperature for approximately 5 days. (See note 2). Reaction concentrated under vacuum at bath temp of no more than 35° C. to approximately 2 vols. (See note 3). Reaction charged with toluene (236 ml, 15 vols) and concentrated under vacuum again to approx 3 vols. Additional toluene (95 ml, 3 vol) was added to achieve a final reaction volume of approx 6 vols. Heptane (158 ml, 10 vols) was added slowly of to solution. Product began to crystallize out of solution upon seeding. Reaction was allowed to stir at ambient temperature for one to two hours and solids collected by filtration and washed with 10 vols of heptane. Solids were dried to a weight of 14.3 g (83% yield). Purity of isolated solid is typically ~90-95% with a 98/2 diastereomeric ratio favoring 1-tert-butyl 4-((3aR,5aR,5bR, 7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl) 2,2-dimethylsuccinate as the major diastereomer.

Step D: Intermediate 570

4-((3aR,5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate 1-tert-butyl 4-((3aR,5aR,5bR,7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) 2,2-dimethylsuccinate (12.9 g, 18.4 mmol) was placed in 1-L retreat curve impellor reactor and then added 22 vol of 90% THF-HOAc and stirred to dissolve at ambient temp. The reactor was purged 3× with nitrogen and then a slurry of water was added and then washed (pH ~8-9) RaNi catalyst (50% water, added 2.6 ml catalyst slurry, 1.3 g RaNi calculated) and then placed under hydrogen at 0.3 bar pressure for 3 hours and then raised the pressure to 2 bar and allowed to stir for 18 hours. Reaction was approximately 20% complete at this time. The temperature was raised to 35 deg C. and then the reaction was stirred for another 7 hours and sampled. The reaction was approximately 31% complete at this time. Reaction pressure was increased to 4 bar hydrogen and was allow to continue stirring at 35 deg for 20 hours. Reaction is 75% complete at this time and no change in impurity profile. Added another 0.15 wt of RaNi (3.0 ml of 50% slurry) to bring total RaNi loading up to 25 wt % and the reaction was allowed to stir at 35 deg under 4 bar Hydrogen for another 24 hours. The reaction was then determined to be complete by HPLC.

The reaction was then filtered through a 4 micron in-line filter, rinsing with THF (50 ml). Evaporated to approximately 3 vol and added ethyl acetate (195 ml, 15 vol) and washed with 1N NaOH solution (3×10 vol) and verified final wash to be basic pH. (Note: addition of 0.5 vol saturated NaCl solution was required on second and third washes to obtain efficient separation). Washed with saturated sodium chloride solution (5 vol) and evaporated to a solid foam that was azeotroped with 2×5 vol dichloromethane in order to obtain a solid foam. Dried on high vacuum pump to weight of 11.1 g (90% yield).

Recrystallized above sample (10.5 g) by dissolving in methanol (147 ml, 14 volumes) at reflux and then cooling with seeding to ambient temperature and allowed to stir 30 minutes). Mixture was further cooled to 15 degrees and filtered. Solids collected by filtration and washed with methanol (1 volume) and dried at 50 degrees in vacuo to a weight of 7.5 g (71% yield on recrystallization) of 4-((3aR, 5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate.

Step E and F: Compound 46

1-tert-butyl 4-((3aR,5aR,5bR,7aR,9S,11aR,11bR, 13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 2,2-dimethylsuccinate.

4-((3aR,5aR,5bR,7aR,9S,11aR,11bR,13aS)-3a-((R)-2-Amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate and p-Cl-benzaldehyde (1.1 equiv) were placed in a round bottomed flask with EtOH (10 vol) and added Na$_2$CO$_3$ powder (2.5 equiv) and allowed to stir overnight (16 hrs). The next day, the reaction slurry was cooled to approximately 10 degrees and added NaBH$_4$ to the reaction in a single portion and allowed reaction to stir while slowly warming to ambient temperature. Obtained HPLC after 45 minutes showing essentially complete conversion to desired product. p-Cl-benzyl alcohol present as well (using 220 nm wavelength). The reaction was then diluted with methylene chloride (30 ml, 10 vol) and water (30 ml, 10 vol) and the layers were allowed to separate. The DCM layer was then washed with additional water (10 vol) and evaporated to minimum volume on rotovap and added back DCM (10 vol) and treated with trifluoroacetic acid (6 ml, 2 vol) and the reaction was allowed to stir at ambient temperature. The reaction was almost complete after one hour, but it was left to stir overnight. After 18 hours reaction complete by HPLC and was evaporated to an oil.

Dissolved with warming to approximately 45 degrees in ethyl acetate (60 ml, 20 vol) and washed with NaHCO$_3$ solution (2×10 vol) to remove residual TFA. Then, washed with ethyl acetate and with half-saturated NaCl solution and evaporated to dryness and azeotroped dry with isopropanol (2×5 vol). Dissolved in isopropanol (5 vol) and diluted with acetonitrile to cloud point (10 vol) and then allowed to crystallize overnight. Cloudy mixture, but no filterable solids present. Meanwhile the test crystallization from ethyl acetate-heptane of the original isolated TFA salt solution had produced nice solids.

The entire reaction was then evaporated to dryness and azeotroped several portions of ethyl acetate on rotovap (3×10 vol) to remove all isopropanol and acetonitrile. Reaction dissolved with warming to reflux in ethyl acetate (30 ml, 10 vol). Added one equivalent trifluoroacetic acid (0.51 g) and slowly diluted with heptane to cloud point (15 ml, 3 volumes). Seeded with test crystallization seeds from above. Nice solids resulted almost immediately. Stirred with cooling to ambient temperature. Filtered solids and washed with heptane (15 ml, 3 vol). Dried on funnel to weight of 2.55 g, 67% yield of 4-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

Alternative Procedure 4-((3aR,5aR,5bR,7aR,9S,11aR,11bR,13aS)-3a-((R)-2-Amino-l-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (7 g, 1 equiv.) was placed in a round bottom flask and added MgSO$_4$ powder (2.5 equiv) and Et$_3$N (0.8 equiv) and p-Chlorobenzaldehyde and added MeOH (10 vol) and allowed to stir overnight (16 hrs). After this time an aliquot (0.5 ml) of the white slurry was removed and treated with approximately 25 mg NaBH$_4$ and allowed to stir for 5 minutes. Obtained HPLC of this aliquot indicating complete consumption of the amine starting material. The reaction mixture was cooled to 0 degrees on ice-brine bath and treated with solid NaBH$_4$ in a single portion (475 mg, 1.2 equiv) and allowed to stir at 0 degrees for approximately 45 minutes. HPLC after this time shows reaction is complete. The reaction was warmed to ambient temperature briefly and filtered through a CELITE™ diatomaceous earth bed. The solid was rinsed with additional methanol (35 ml, 5 vol) and then dichloromethane (70 ml, 10 vol). The filtrate/rinse was then treated with water (70ml, 10vol) and shaken in separatory funnel. The upper aqueous was washed well with additional dichloromethane (3×5 vol) and then the combined organic layers were washed with brine (10 vol). The organic phase was evaporated to a solid foam and azeotroped with dichloromethane. Dissolved in dichloromethane (70 ml, 10 vol) and treated with trifluoroacetic acid (14 ml, 2 vol) and allowed to stir at ambient temperature. The reaction almost complete in approximately 2 hours.

The reaction was allowed to sit over a weekend at which point the reaction was complete. The reaction was allowed to evaporate to a minimum volume and then ethyl acetate (10 vol) was added and evaporated to a minimum volume again. Repeated this evaporating to minimum volume and then dissolved in total of 10 volume ethyl acetate. Heated to near reflux and diluted with heptane (5 vol) and stirred while cooling to ambient temperature while solids were formed. Stirred for 30 minutes and filtered. Rinsed with heptane (3 vol) and dried to a weight of 4.85 g, 63% yield of 4-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid over two steps.

Example 498: Compound 51

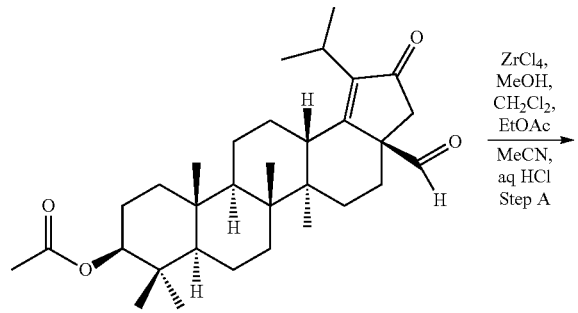

-continued
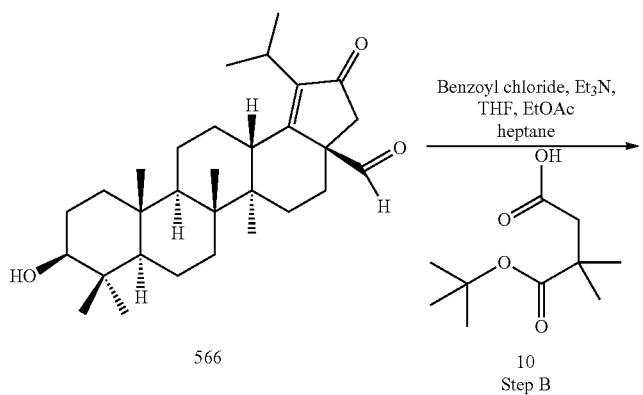
566
Benzoyl chloride, Et₃N,
THF, EtOAc
heptane
→
10
Step B
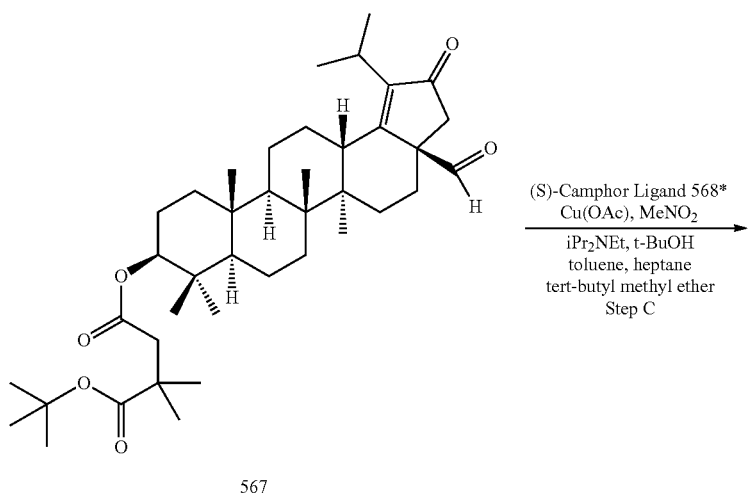
567
(S)-Camphor Ligand 568*
Cu(OAc), MeNO₂
─────────────
iPr₂NEt, t-BuOH
toluene, heptane
tert-butyl methyl ether
Step C
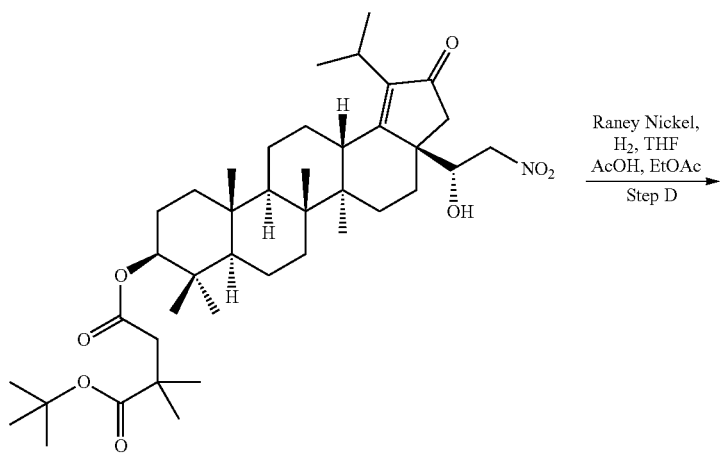
569
Raney Nickel,
H₂, THF
AcOH, EtOAc
─────────
Step D

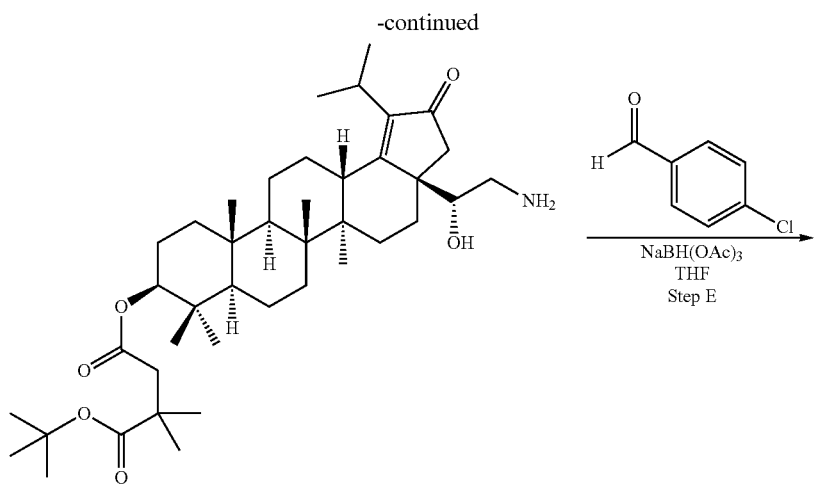
570
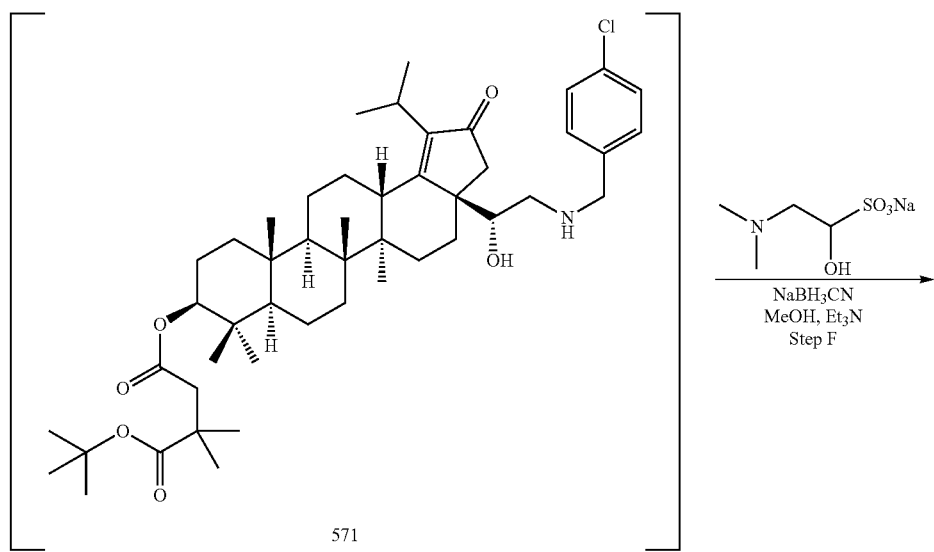
571
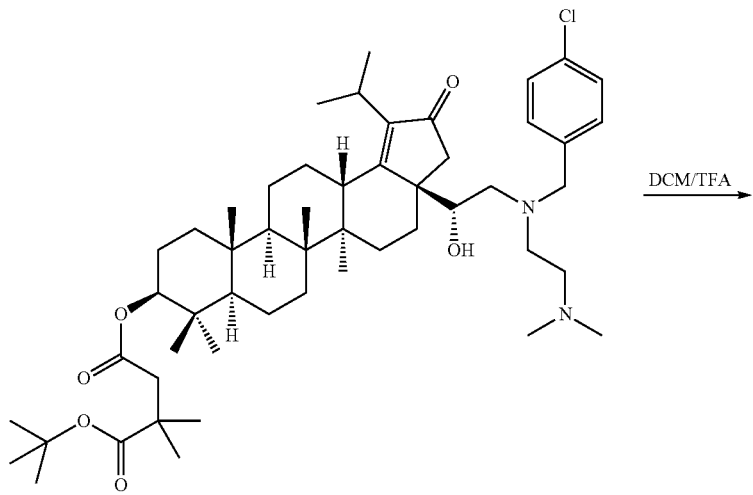
54

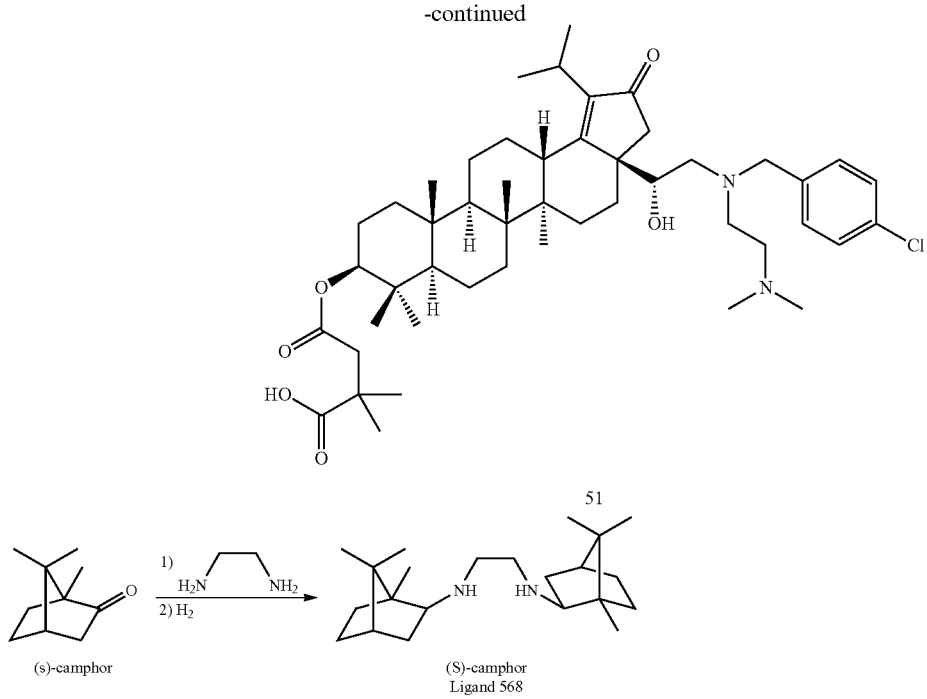

Step A: Intermediate 566

(3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde The compound (3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (400 g, 0.81 mol) was placed in a flask with methanol (4 L) and DCM (1.6 L) and stirred at ambient temp while adding solid $ZrCl_4$ (225.2 g, 0.97 mol) in portions. The reaction was warmed to approximately 45~55° C. and maintained for a total of 30~36 hours. The reaction was monitored for completion by HPLC.

Once complete, the reaction was then treated with water (120 mL) and maintained at 45~55° C. for approximately 30~60 minutes. The reaction was then cooled and evaporated under vacuum (at bath temp approximately 40° C.) to 1200 mL. Dichloromethane (4 L) was added and reaction was treated with 1N HCl (2 L), mixed thoroughly and the layers were allowed to separate. Afterwards, the upper aqueous layer was washed with fresh dichloromethane (800 mL). Next, the combined organic layer was washed with 1N HCl (2 L) and evaporated under vacuum (at bath temp of 40° C.) to 800 mL and treated with acetonitrile (4 L).

The reaction was then evaporated (at bath temp of 40° C.) to a final volume of approximately 800 mL. Acetonitrile (3.2 L) was added and the reaction was warmed to 50~60° C., thus forming a solution. Next was slowly added, 3N HCl (100 mL), which resulted in precipitate formation and which was maintained as a reaction in solution at approximately 50~60° C. until dimethyl acetal hydrolysis was complete followed by addition of water (4.8 L).

The reaction was allowed to cool to 0-10° C. and then the mixture was filtered and the resultant solid was rinsed with acetonitrile/water (1/1,800 mL). The solid was then slurryed in 10 volumes of heptane at 85~100° C. for 1~3 hours. The slurry was then cooled to ambient temperature and filtered. Washed the cake with 800 mL heptane then dried in vacuo at 40~50° C. to the 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl) 2,2-dimethylsuccinate 286 g. Yield is 72.6% corrected by assay.

$^1$H NMR (400 MHz, CDCl3) δ=9.33 (s, 1 H), 3.20-3.28 (m, 2 H), 2.57 (d, J=1 H), 2.36-2.42 (m, 2 H), 2.04-2.08 (m, 2 H), 1.86-1.90 (m, 2 H), 1.75-1.78 (m, 1 H), 1.23-1.66 (m, 35 H); LC/MS: m/z calculated 454.3. found 455.4 (M+1)$^+$

Step B: Intermediate 567

1-tert-butyl 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate The starting material (3aR,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde (32.4 g, 71 mmol), 4-(tert-butoxy)-3,3-dimethyl-4-oxobutanoic acid (18 g, 89 mmol) and THF (648 mL) were charged to a flask. Benzoyl chloride (12.5 g, 89 mmol) was added followed by slow addition of triethyl amine (18 g, 178 mmol) forming a thick slurry. DMAP (2.17 g, 18 mmol) was added and the reaction was allowed to stir at ambient temperature for approximately 24-30 hours until complete by HPLC. The reaction was then charged with ethyl acetate (648 mL) and water (324 mL), stirred well and allowed to settle. The aqueous phase was removed and the organic phase washed with saturated sodium bicarbonate solution (2×324 mL) followed by water (324 mL).

The reaction solution was then evaporated under vacuum to approximately 129 mL in order to produce solids. Additional heptane (324 mL) was added and the reaction heated back to reflux to a nearly formed solution and slowly cooled to ambient temperature and was stirred for 15 minutes then cooled to 0° C. for approximately two hours and the solids were filtered. The solids were then washed with heptane (2×324 mL) and dried at 50° C. under vacuum to give the desired compound as an off-white solid 1-tert-butyl 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl) 2,2-dimethylsuccinate 36.8 g. yield is 80%. 1H NMR (400 MHz, CDCl3) δ=9.24 (s, 1 H), 4.41-4.45 (m, 1 H), 3.19-3.20 (m, 1 H), 2.33-2.48 (m, 5 H), 0.96-1.60 (m, 37 H), 0.77-0.87 (m, 17 H); LC/MS: m/z calculated 638.4. found 639.4 (M+1)$^+$ Step C: Intermediate 569

1-tert-butyl 4-((3aR,5aR,5bR,7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate The reaction was charged with of 4-((3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (50 g, 78 mmol), tert-butanol (500 mL) and toluene (150 mL) and the temperature was adjusted to 20-25° C. The ligand (N1,N2-bis(1,7,7-trimethylbicyclo[2.2.1] heptan-2-yl)ethane-1,2-diamine (1.56 g, 4.7 mmol) and Copper(I) acetate (0.48 g, 3.9 mmol) were added in a single portion and the reaction was then stirred at 20-25° C. for 3-5 hrs.

The reaction was next allowed to cool to 7-13° C. The reaction was then charged with nitromethane (33 g, 0.55 mmol) and N,N-diisopropyl ethylamine (12.1 g, 94 mmol) and allowed to stir at 7-13° C. for approximately 30 hrs. The reaction was again charged with nitromethane (17 g, 0.3 mmol) and allowed to stir at 7-13° C. for approximately 40 hrs. The reaction was yet again charged with nitromethane (17 g, 0.3 mmol) and allowed to stir at 7-13° C. for approximately 20 hrs.

Next, the reaction was charged with MTBE (750 mL) and a 15% ammonium chloride solution (300 mL), allowed to stir for 30 min, and then separated into two phases. The organic phase was washed with water (250 mL) followed by brine (200 mL). The organic phase was then concentrated to 100 mL and MTBE (25 mL) was added. Next, n-heptane (500 mL) was slowly added and then stirred at 10-20° C. for 2 hrs. The reaction was then filtered and washed with n-heptane, and then dried under vacuum at 50-55° C. to give 4-((3aR,5aR,5bR,7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate as off-white solid 41.6 g. Yield is 75.9%, $^1$H NMR (400 MHz, CDCl3) δ=4.85 (bd, 1 H), 4.51-4.55 (dd, 1 H), 4.08-4.20 (m, 2 H), 3.15-3.22 (m, 1 H), 2.35-2.83 (m, 6 H), 0.80-2.03 (m, 54 H); LC/MS: m/z calculated 699.4. found 700.4 (M+1)$^+$ Step D: Intermediate 570

4-((3aR,5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate To 4-((3aR,5aR,5bR,7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (30 g, 42.6 mmol) in THF (600 mL) and AcOH (30 mL) was added Raney Ni (30 g, 5%) under $N_2$ at room temperature. The reaction was stirred at 45-55° C. under hydrogen gas (0.30-0.40 MPa) for 10-12 hours. The reaction mixture was filtered through a filter aid, washing with THF [2×90 mL] and the filtrate was adjusted to a pH of 7-8 with 5% $K_2CO_3$ aqueous.

Next, ethyl acetate (450 mL) was added to the reaction mixture and the two phases were separated. The aqueous layer was extracted with ethyl acetate (150 mL). The combined organic phase was washed two times with 7.5% NaCl aqueous (300 mL) and then washed with 17% NaCl aqueous (300 mL). The organic phase was concentrated under vacuum to give 25.7 g of 4-((3aR,5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate. Yield is 92%. $^1$H NMR (400 MHz, DMSO-d$_6$) δ=4.40-4.44 (dd, 1H), 3.79-3.80 (bd, 1H), 3.59-3.62 (M, 2H), 3.12-3.17 (m, 2H), 2.60-2.75 (m, 1H), 2.22-2.34 (m, 2H), 2.19-2.22 (m, 2H), 1.37-1.84 (m, 25H), 1.08-1.11 (m, 17H), 0.81-0.91 (m, 13H); LC/MS: m/z calculated 669.5. found 670.4 (M+1)$^+$ Step E: Intermediate 571

1-tert-butyl 4-((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of 4-((3aR,5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate in THF (5 g, 7.6 mmol in 100 mL THF) was added 4-chlorobenzaldehyde (0.96 g, 6.84 mmol) and then stirred at −2-2° C. for 0.5 hours. Next, NaHB(OAc)$_3$ (3.53 g, 16.7 mmol) was added to the reaction and stirred at −2-2° C. for 0.5 hours. The reaction was then warmed to 3-7° C. and again stirred at 3-7° C. for 10-15 hours and then stirred at 8-12° C. for 5-8 hours.

The reaction was quenched by saturated NH$_4$Cl (aqueous) (50 mL) and water (20 mL) and then stirred at 10~20° C. for 0.5 hours. The reaction was then extracted with MTBE (75 mL) and the aqueous layer was extracted with MTBE (25 mL). The combined organic phase was washed with water (25 mL) and the pH adjusted to 7-8 with 5% $K_2CO_3$ aqueous. The organic phase was separated and washed two times with 7.5% NaCl aqueous (50 mL) and then washed with 20% NaCl aqueous (50 mL). The organic phase was concentrated under vacuum again to approx 20 mL. Additional DCM (60 mL) was added and concentrated under vacuum to approx 20 mL. Additional DCM (60 mL) was again added and concentrated under vacuum to approx 20 mL. Additional DCM (60 mL) was again added and concentrated under vacuum to approx 20 mL. Then, 50 mL MeOH was charged and concentrated under vacuum again to approx 20 mL. An additional 50 mL MeOH was charged to give a solution of 4-((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate in MeOH. This mixture was used in the next step directly. 1HNMR (400 MHz, DMSO-d6) δ=0.81-1.78 (m, 49H), 1.91 (s, 6H), 2.18-2.20 (m, 2H) 2.32-2.37 (m, 3H), 3.02-3.08 (M, 2H?] 3.56-3.62 (m, 4H) 4.00-4.04 (d, 1H) 4.12-4.15 (d, 1H) 4.27-4.40 (m, 1H) 4.39-4.43 (m, 1H), 7.43-7.45 (d, 2H), 7.52-7.54 (d, 2H); LC/MS: m/z calculated 793.5. found 794.4 (M+1)+

Step F: Intermediate 54

1-tert-butyl 4-((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate Added a solution of 4-((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinatee (55 g, 69.3 mmol) dissolved in methanol (825 mL), dimethyl amino acetaldehyde hydrogen sulfite sodium salt (66.8 g, 0.35 mol) and Et₃N(38.7 g, 0.38 mol) into a reactor. The reaction was stirred for 2-3 hrs at 30-40° C. under nitrogen protection. NaBH₃CN (8.8 g, 0.14 mol) was added and stirred at 30-40° C. under nitrogen protection for 13-15 hrs. Next, the reaction temperature was adjusted to 50-60° C. and stirred for 3-5 hrs. The reaction mixture was then concentrated to 275 mL and then DCM (550 mL) was added, followed by water (440 mL). The two phases were separated and the water phase was extracted with DCM (twice with 385 mLs each time). The organic phase was washed with water (twice with 358 mLs each time). Next, the organic phase was concentrated to give 1-tert-butyl 4-((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate 43 g oil. Yield is 71%. 1HNMR (400 MHz, CDCl3) δ=7.27-7.29 (m, 4H), 4.46-4.50 (m, 1H), 4.08-4.13 (m, 2 H), 4.00-4.02 (m, 1H), 3.59-3.60 (m, 1H), 3.09 (m, 1H), 2.03-2.67 (m, 14H), 0.62-1.42 (m, 57 H); LC/MS: m/z calculated 864.5. found 865.6 (M+1)+

Step G: Compound 51

4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid From the last step, dissolved the 1-tert-butyl 4-((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (0.8 g, 0.92 mmol) in 3.2 mL DCM, then charged 1.6 mL TFA into the solution.

The reaction mixture was then stirred at 15-25° C. for 1~3 hrs. Next, the reaction was charged with 4 mL DCM and 4 mL water, stirred well and then allowed to settle. The aqueous phase was then removed and the organic phase washed two times with water (4 mLs each). The aqueous phase was then extracted with DCM (1.6 mL). The combined organic phase was then washed with saturated sodium bicarbonate until the pH was between 7-8, followed by two more washes with water (4 mLs each).

Next, the organic phase was evaporated under vacuum to give 0.69 g crude product. The crude product was then dissolved in 4.8 mL isopropanol and heated to reflux to dissolve all material. Acetonitrile (19 mL) was added and brought to a gentle reflux and allowed to start cooling while seeded with 2 mg seed material at 45° C. The mixture was then stirred at 45° C. for 2 hours. Solids began form and they were cooled to 10~20° C. and stirred for 3 hours. The solution solids were filtered and then rinsed twice with 1 g acetonitrile each time.

The solids were then dried in a vacuum oven at 45 deg C. for 18 hours to give the desired product: 4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (0.59 g, yield was 78%).

Example 499

Compound 51

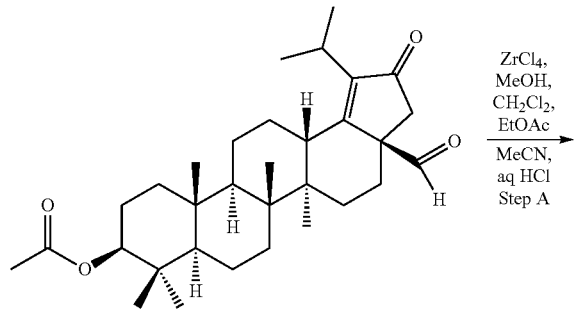

-continued
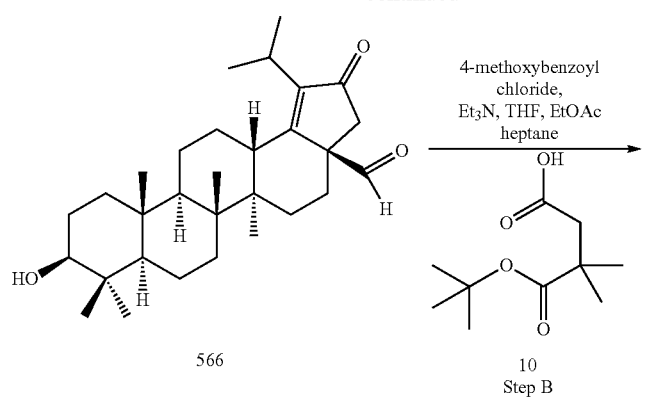
566
4-methoxybenzoyl chloride,
Et₃N, THF, EtOAc
heptane
10
Step B
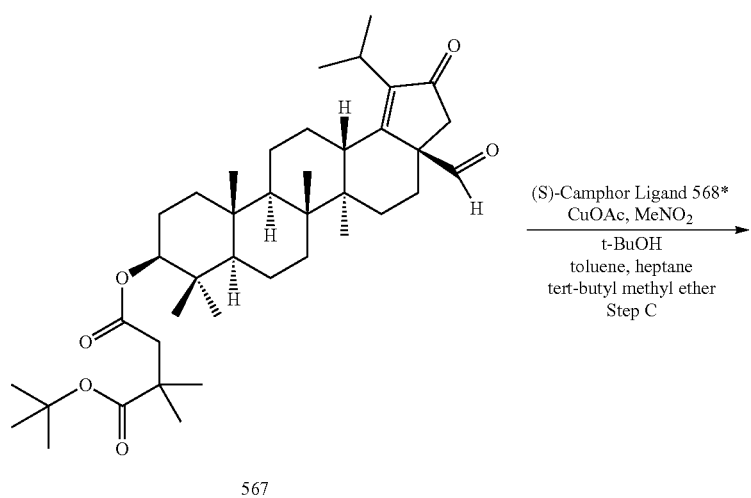
567
(S)-Camphor Ligand 568*
CuOAc, MeNO₂
────────────────
t-BuOH
toluene, heptane
tert-butyl methyl ether
Step C
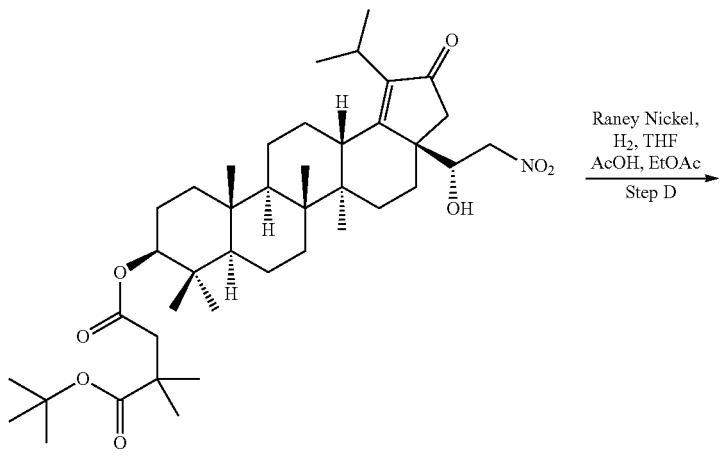
569
Raney Nickel,
H₂, THF
AcOH, EtOAc
─────────
Step D -continued
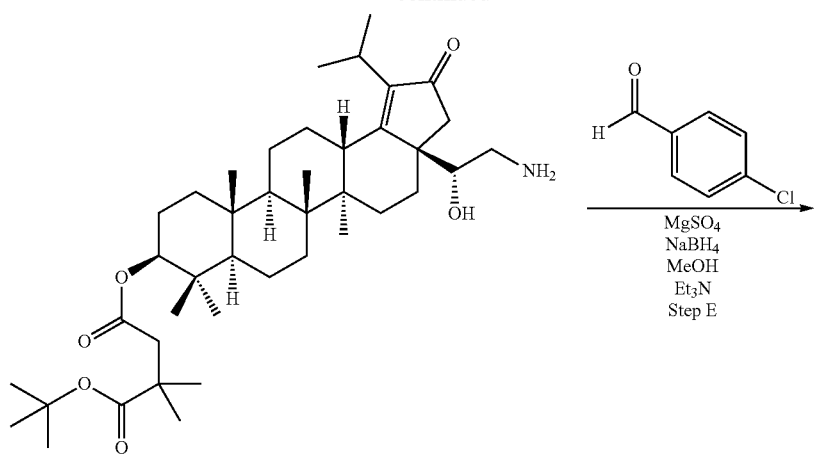
570
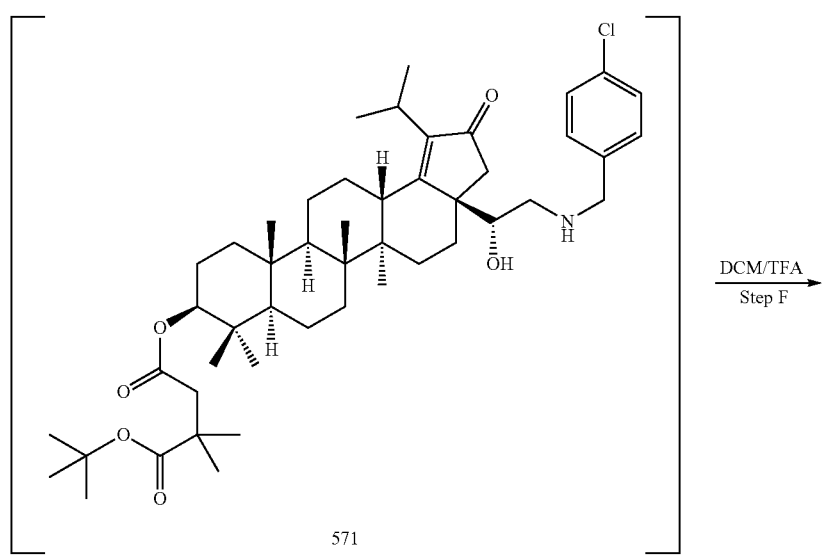
571
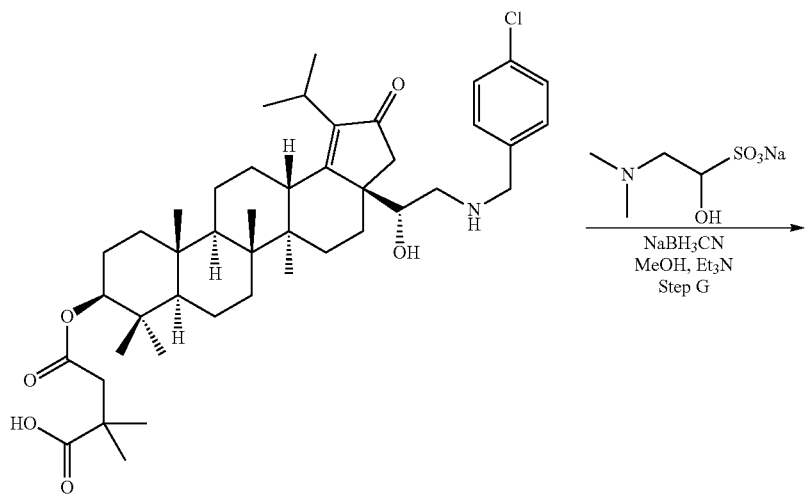
46

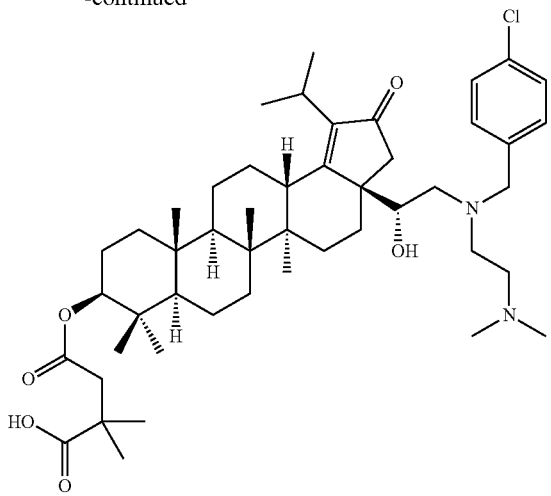

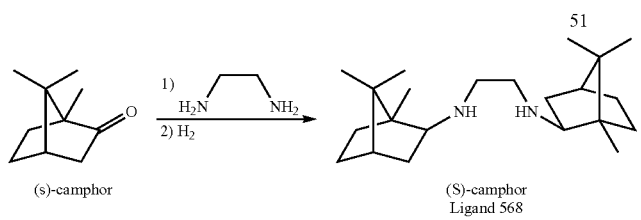

(s)-camphor → (S)-camphor Ligand 568

Procedures for steps A and D below are not included and are similar to those reported in previous examples and will be understood by one skilled in the art.

Step B: Intermediate 567

1-tert-butyl 4-((3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) 2,2-dimethylsuccinate The starting material (3aR,5aR,5bR,7aR,9S,11aR,11bR, 13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carbaldehyde (5 g, 11 mmol), 4-(tert-butoxy)-3,3-dimethyl-4-oxobutanoic acid (3.4 g, 16.5 mmol), THF ("tetrahydrofuran"—100 mL) and triethylamine (3.4 g, 33 mmol) were charged to a flask.

The mixture was then stirred for 20~30 mins at 0~5° C. Then, 4-methoxybenzoyl chloride (2.8 g, 16.5 mmol) was added through a dropping funnel while the reaction temperature was maintained at 0~5° C. The reaction was then stirred for an additional 1 hour, then DMAP ("dimethylaminopyridine"—0.2 g, 1.65 mmol) was added and the reaction allowed to stir at ambient temperature for approximately 24~30 hours until complete by HPLC.

Next, the reaction was charged with ethyl acetate (100 mL) and water (50 mL), stirred well and allowed to settle. The aqueous phase was removed and the organic phase washed with saturated sodium bicarbonate solution (2×50 mL) followed by water (50 mL). The reaction solution was evaporated under vacuum to approximately 5-10 mL to produce solids. An additional amount of heptane (50 mL) was added and the reaction heated back to reflux to nearly form solution and slowly cooled to ambient temperature and let stir for 15 minutes then cooled to 0° C. for approximately two hours and the solids were filtered out. Next, the solids were washed with heptane (2×50 mL) and dried at 50° C. under vacuum to give the desired compound as off-white solid 1-tert-butyl 4-((3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate. (4.7 g, yield is 67%).

Step C: Intermediate 569

1-tert-butyl 4-((3aR,5aR,5bR,7aR,9S,11aR,11bR, 13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate A reaction was charged with 4-((3aR,5aR,5bR,7aR,9S, 11aR,11bR,13aS)-3a-formyl-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) 2,2-dimethylsuccinate (6 g, 9.4 mmol), tert-butanol (60 mL) and toluene (18 mL) and temperature was adjusted to 20-25° C. The ligand (N1,N2-bis(1,7,7-trimethylbicyclo [2.2.1] heptan-2-yl)ethane-1,2-diamine (0.2 g, 0.57 mmol)) and Copper(I) acetate (0.06 g, 0.47 mmol) were added in a single portion and the reaction allowed to stir at 20-25° C. for 3-5 hrs.

The reaction was then cooled to a temperature of 7-13° C. Afterwards, the reaction was charged with nitromethane (3.9 g, 63 mmol) and allowed to stir at 7-13° C. for approximately 30 hrs. The reaction was charged with additional nitromethane (2.2 g, 35.7 mmol) and allowed to stir at 7-13° C. for approximately 40 hrs. The reaction was charged again with additional nitromethane (2.2 g, 35.7 mmol) and allowed to stir at 7-13° C. for approximately 20 hrs.

Next, the reaction was charged with MTBE ("methyl tertiary butyl ether"—90 mL) and a 15% ammonium chloride solution (36 mL), and allowed to stir for 30 min and then allowed to separate out into two phases. The organic phase was washed with water (30 mL) followed by brine (24 mL). The organic phase was then concentrated to 12 mL and MTBE (3 mL) was added. Next, n-heptane (60 mL) was slowly added and then stirred at 10-20° C. for 2 hrs. The solution was then filtered and washed with n-heptane, the cake was then dried under vacuum at 50-55° C. to give 4-((3aR,5aR,5bR,7aR,9S,11aR,11bR,13aS)-3a-((R)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate as off-white solid 4.27 g. (65% yield)

Step E: Intermediate 571

1-tert-butyl 4-((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate 4-((3aR,5aR,5bR,7aR,9S,11aR,11bR,13aS)-3a-((R)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate (15 g, 22.4 mmol) was placed in a round bottomed flask and then the following were also added: $MgSO_4$ powder (8.1 g, 56 mmol) and $Et_3N$ (3.6 g, 35.8 mmol) and p-Chlorobenzaldehyde (5.05 g, 29.1 mmol) and added MeOH (300 mL). The reaction was then allowed to stir for 2 hrs.

The reaction mixture was then cooled to 0 degrees C. on ice-brine bath and treated with solid NaBH4 (1.61 g, 42.56 mmol) under 10 degrees C. and allowed to stir at 20 degrees for approximately 45 minutes. HPLC after this time showed the reaction was complete. The reaction was then filtered through a CELITE™ diatomaceous earth bed. The solids were rinsed with additional methanol (75 mL) and then dichloromethane (150 mL). The filtrate/rinse was treated with water (150 mL) and shaken in a separation funnel. The organic layers were then washed with water (150 mL). Next, the organic phase was evaporated to give 15 g of 1-tert-butyl 4-((3aR,5aR,5bR,7aR,9S,11aR,11bR,13aS)-3a-((R)-24-chlorobenzyl)amino)-1- hydroxyethyl)-1-isopropyl-5a,5b,8,8,11a-pentamethyl-2-oxo-3,3a,4,5,5a,5b6,7,7a,8,9,10,11,11a,11b,12,13,13a-octadecahydro-2H-cyclopenta[a]chrysen-9-yl) 2,2-dimethyl succinate as a foamy solid, 84% yield. The crude product was used for the next step directly.

Step F: Compound 46

4-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, 2,2,2-trifluoroacetic acid salt (1:1)

Dissolved 1-tert-butyl 4-((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (15 g, 18.9 mmol) in dichloromethane (150 mL) and treated with trifluoroacetic acid (30 mL) and allowed to stir at ambient temperature. The reaction was complete in approximately 10 hours. Next, the reaction washed with water (2×150 mL) and the organic phase was evaporated to a minimum volume and ethyl acetate (150 mL vol) was added and then evaporated again to a minimum volume. Evaporated again to a minimum volume and then dissolved in a total of 150 mL volume ethyl acetate.

Next, the resultant solution was heated to near reflux and then diluted with heptane (90 mL) and stirred while cooling to ambient temperature, at which point, solids were formed. The solution was then stirred for 30 minutes and filtered. The filtered solids were rinsed with heptane (30 mL) and dried to give 13 g 4-(((3aR,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, 2,2,2-trifluoroacetic acid salt (1:1), 81% yield. 1HNMR (400 MHz, DMSO-d6) δ=0.60-1.89 (m, 46H) 2.16-2.19 (d, 1H) 2.32-2.68 (m, 4H) 3.02-3.11 (m, 1H) 4.10-4.26 (m, 3H), 4.38-4.42 (dd, 1H) 5.93 (s, 1H) 7.51 (s, 4H), 8.80-8.98 (d, 2H); LC-MS: m/z calculated (free base) 737.4. found 738.1 (M+1)+.

Step G: Compound 51

4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid From Step F above, the 4-(((3aR,5aR,5bR,7aR,9S,11aR,11bR,13aS)-3a-((R)-2-((4-chlorobenzyl)amino)-1-hydroxyethyl)-1isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoicacid trifluoroacetic acid salt (9.0 g, 10.56 mmol) was placed in a round bottomed flask and added dimethylamino acetaldehyde hydrogen sulfite salt (5.05 g, 26.4 mmol) and $CH_3COONa$ (3.46 g, 42.23 mmol) and added MeOH (180 mL) and allowed to stir for 1 hour.

To the reaction mixture was added $NaBH_3CN$ (2.65 g, 42.23 mmol) and allowed to stir at 25 degrees C. for approximately 36 hrs. HPLC after this time showed reaction was complete. Next, the reaction was filtered through a CELITE™ diatomaceous earth bed. The solids were then rinsed with additional methanol (45 mL) and then dichloromethane (90 mL). The filtrate/rinse was treated with water (45 mL) and shaken in separatory funnel. The organic layers were then washed with $NaHCO_3$(4 times -45 mL each) and water (two times-45 mL each).

The organic phase was then evaporated to a minimum volume and i-PrOH (36 mL) was added and heated to 75 degrees C. for 2 hours. The resulting solution was then diluted with $CH_3CN$ (45 mL) at 75 degrees C. The solution was then cooled to 5 degrees C. over 4 hours. The solution was then stirred at 5 degrees C. for 2 hours and filtered. The filtrate was then rinsed with $CH_3CN$ (9 mL) and dried to give crude 4-(((3aR,5aR,5bR,7aR,9S,11aR,11bR,13aS)-3a-((R)-2-((4-chlorobenzyl)(2-(dimethylamino)ethyl)amino)-

1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (5.6 g, 65% yield).

Re-crystallization

From Step G above, the crude 4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (5.6 g) was placed in a round bottomed flask and added i-PrOH (36 mL) and heated to 75 degrees C. for 2 hours. Next, the reaction was diluted with $CH_3CN$ (45 mL) at 75 degrees C. The reaction was then cooled to 5 degrees C. over 4 hours.

The reaction was then stirred at 5 degrees C. for 2 hours and filtered. The filtrate was then rinsed with $CH_3CN$ (9 mL) and dried to give 4.8 g 4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, 84% yield. 1HNMR (400 MHz, DMSO-d6) δ=0.80-0.29 (m, 14H), 0.97-1.17 (m, 21H), 1.32-1.91 (m, 13), 2.08-2.23 (m, 12H) 2.27-2.38 (m, 3H) 2.40-2.46 (m, 1H) 2.51-2.20 (m, 1H) 2.66-2.70 (m, 1H) 3.00-3.04 (m, 1.0H) 3.71-3.78 (m, 1H) 3.89-3.91 (d, 1H) 4.37-4.41 (dd, 1H), 7.31-7.37 (m, 4H); LC-MS: m/z calculated 808.5. found 809.1 (M+1)+.

Synthesis of Intermediate 11S (3aR,5aR,5bR,7aR,9S,11aR,11bR,13aS)-3a-((S)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (2.0 g, 4.03 mmol) was placed in a flask with n-BuOH (10 ml) and diamine catalyst derived from (R)-camphor (N1,N2-bis(1,7,7-trimethylbicyclo[2.2.1]heptan-2-yl)ethane-1,2-diamine, 0.08 g, 0.242 mmol) diamine catalyst and $Cu(OAc)_2$ (0.037 g, 0.201 mmol) and stirred approximately 16 hours at ambient temperature.

The reaction was then cooled to approximately 0° C. and treated with nitromethane (1.23 g, 20.1 mmol) and Hunig's base (("N,N-diisopropylethylamine"—0.053 g, 0.40 mmol) and allowed to held at 5° C. for 24 hours. Additional BuOH (25 ml) and Hunig's base ("N,N-diisopropylethylamine") were added and the reaction held at −10° C. for 24 hours and then at ambient temperature for 24 hours. Solids present in the reaction were filtered to provide the title compound as an off white solid (1.1 g, 49% as 95:5 mixture of diastereomers). $^1$H NMR (500 MHz, CDCl3) δ=4.89 (bd, 1 H), 4.57 (d, 1 H), 4.49 (dd, 1 H), 4.34 (dd, 1 H), 3.21 (m, 1H) 2.94 (dd, 1H) 2.38 (m, 2H) 2.08 to 0.8 (m, 54H) *Note: Integration of the 2.4 to 0.8 region of the spectrum is higher due to the presence of impurities in the sample.

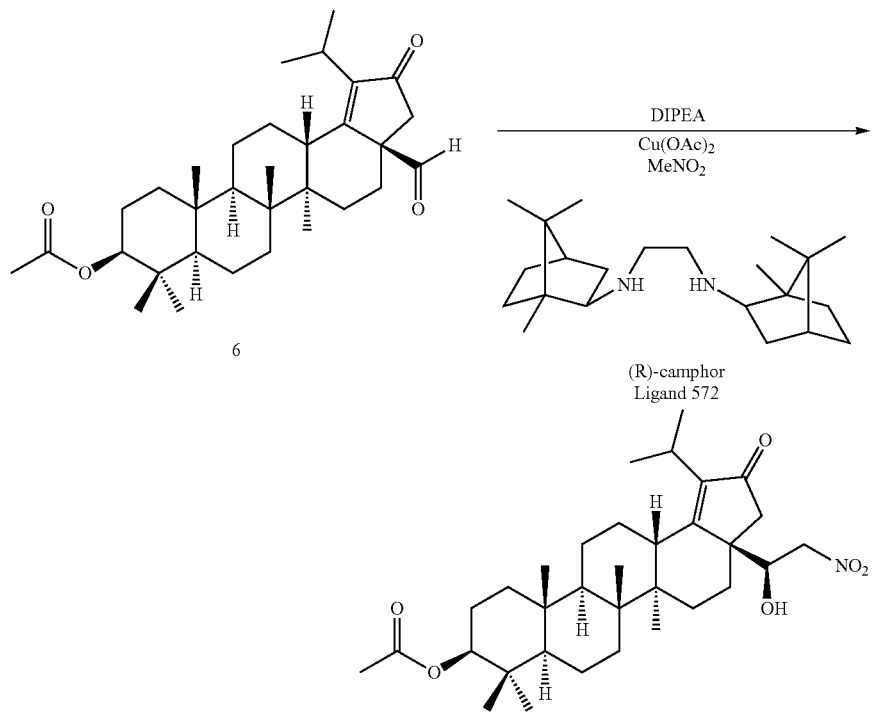

615
Synthesis of Intermediate 12S

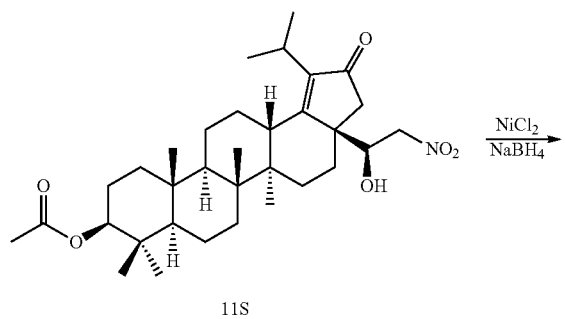

(3aR,5aR,5bR,7aR,9S,11aR,11bR,13aS)-3a-((S)-2-
amino-1-hydroxyethyl)-1-isopropyl-5a,5b,8,8,11a-
pentamethyl-2-oxo-3,3a,4,5,5a,5b,6,7,7a,8,9,10,11,
11a,11b,12,13,13a-octadecahydro-2H-cyclopenta[a]
chrysen-9-yl acetate To a flask containing (3aR,5aR,5bR,7aR,9S,11aR,11bR,13aS)-3a-((S)-1-hydroxy-2-nitroethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (~95% single diastereomer from the previous Intermediate 11S stage, 0.5 g, 0.89 mmol) in methanol and cooled to −5° C. was added $NiCl_2$ (0.232 g, 1.79 mmol). The contents were stirred and treated with $NaBH_4$ (0.475 g, 12.5 mmol), which was added slowly in portions over a 30 minute period while maintaining at approximately −5° C.

An extremely exothermic reaction resulted in some material loss. The reaction was warmed to ambient temperature slowly over a 30 minute period and allowed to stir for approximately 2 hours. The reaction was then quenched with $NH_4Cl$ soln and diluted with methylene chloride. The liquid layers were separated and the organic layer was washed several times with $NH_4Cl$ soln. Next, the organic layer was evaporated to dryness and the residue was chromatographed on silica gel column and eluted with 10% methanol-dichloromethane. The product containing fractions were evaporated to give title compound as grey solid (250 mg, 53% yield). Sample was carried on to next stage without further characterization.

616
Synthesis of Intermediate 13S

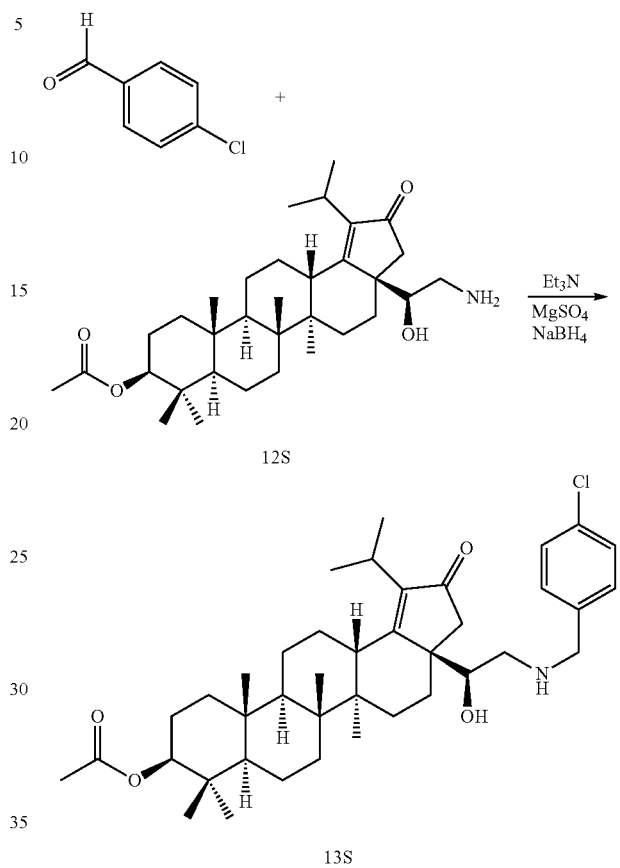

(3aR,5aR,5bR,7aR,9S,11aR,11bR,13aS)-3a-((S)-2-
((4-chlorobenzyl)amino)-1-hydroxyethyl)-1-isopro-
pyl-5a,5b,8,8,11a-pentamethyl-2-oxo-3,3a,4,5,5a,5b,
6,7,7a,8,9,10,11,11a,11b,12,13,13a-octadecahydro-
2H-cyclopenta[a]chrysen-9-yl acetate To a flask containing (3aR,5aR,5bR,7aR,9S,11aR,11bR,13aS)-3a-((S)-2-amino-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (200 mg, 379 mmol) and methanol (15 ml) was added triethylamine (15 mg, 0.152 mmol), magnesium sulfate (68 mg, 0.168 mmol) and 4-chlorobenzaldehyde (64 mg, 0.455 mmol). The contents were allowed to stir at ambient temperature for approximately 2 hours. To the resulting mixture was added sodium borohydride (17 mg, 455 mmol) in a single portion and the reaction was allowed to stir at ambient temperature for two and a half days. The reaction was then charged with an additional 20% excess of the p-Cl-benzaldehyde and sodium borohydride and allowed to stir an additional 2 hours. Finally, the reaction was quenched with water, allowed to stir 15 minutes and solids filtered to provide title compound contaminated with impurities. LC/MS: m/z calculated 651.4. found 652 $(M+1)^+$.

Synthesis of (S) Camphor Derived Chiral Diamine Ligand 568

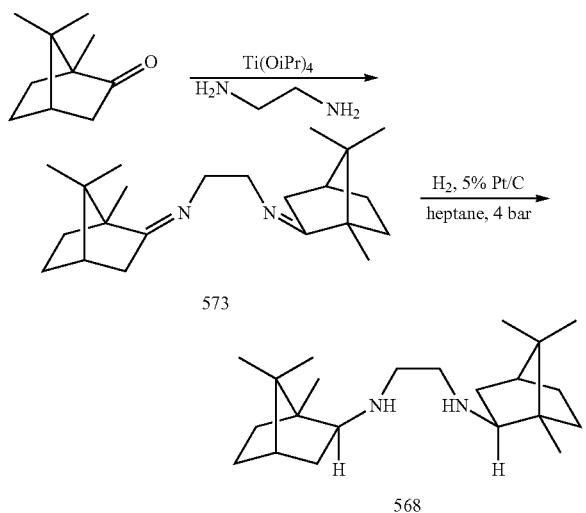

Step A: N,N'-bis(isobornyl)ethylenediimine (573).

Titanium (IV) isopropoxide (235.4 g, 830 mmol, 1.04 eq) was added to a flask containing (1S)-(-)-camphor (121.43 g, 798 mmol, 1 eq) at ambient temperature. The reaction was then heated to ~50° C. Next, ethylenediamine (31.2 g, 518 mmol, 0.65 eq) was charged to the reaction. The temperature was then kept above 45° C. during the addition. The reaction was then heated to ~91° C. for 17 hours. Next, the reaction was cooled to 20-25° C. and heptane (1.2 L) was added. Water (29.9 g, 1659 mmol, 2.08 eq) was added over at least 15 minutes. The slurry was then stirred for 20 minutes at ambient temperature, cooled to ~0° C., and stirred for 30 minutes at ~0° C. The slurry was then filtered and the solids washed with heptane (607 mL). The diimine solution was stored ~5° C. overnight. The solution was then warmed to ambient temperature and filtered to remove additional salts. Next, the solution was partially concentrated and filtered through CELITE™ diatomaceous earth. Finally, the solution was concentrated to ~608 mL and used as is in the next reaction.

Step B: N,N'-bis(isobornyl)ethylenediamine ligand (568).

To a 1 L Jacketed Lab Reactor (JLR) was added the above diimine solution followed by 5% Pt/C (Johnson-Matthey, B501018-5, 6.6 g). The reaction was hydrogenated for ~15 hours at 4 par at ambient temperature. The reaction was filtered and washed with heptane (300 mL). The solution was concentrated to provide a white solid (115.07 g). This two step procedure was repeated. Both batches were combined. Attempts to crystallize the material from i-PrOH and water failed. The product was extracted with heptane. The heptane layer was then washed with water, brine, dried over sodium sulfate, filtered and concentrated on rotovapor and then high vacuum. The product 568 (222.18 g) was obtained as a white solid and used as is in the asymmetric Henry reaction during the camphor ligand addition step. $^1$H NMR (500 MHz, CDCl$_3$) δ 2.69-2.61 (m, 1 H), 2.53-2.47 (m, 2 H), 1.71-1.63 (m, 2 H), 1.6-1.43 (m, 3 H), 1.1-1.01 (m, 2H), 1.01-0.98 (m, 3H), 0.89-0.83 (m, 3H), 0.81-0.78 (m, 3H)

Synthesis of (R) Camphor Derived Chiral Diamine Ligand 572

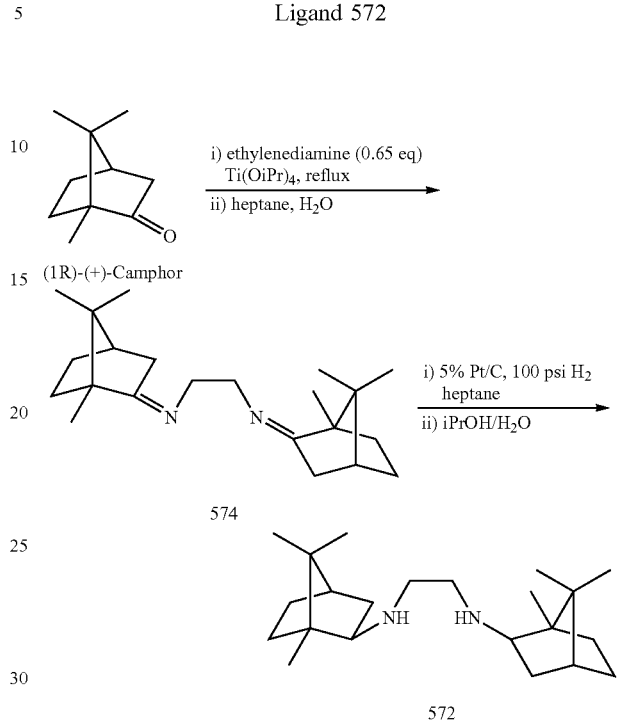

This material was prepared with modifications to methods shown in Tetrahedron: *Asymmetry* 14 (2003) 1451-1454.

Step A: N,N'-bis(isobornyl)ethylenediimine (574)

Titanium isopropoxide (100 mL, 341 mmol, 1.04 eq) was charged to a roundbottom flask containing (1R)-(+)-camphor (50 g, 328 mmol) at 20-25° C. The reaction mixture was then heated to 50° C., at which time ethylenediamine (14.3 mL, 213 mmol, 0.65 eq) was charged to the reaction. Note: The ethylenediamine addition was exothermic, but it is important to conduct the charge above 45° C. to prevent solidification of the reaction mixture as titanium/ethylenediamine complexes are formed. The solution was then heated to reflux (~90-92° C.) for 20-24 hours. At that time, the reaction is cooled to 20-25° C. and diluted with heptane (500 mL), followed by slow addition of H$_2$O (12.3 mL, 2.08 eq) over ~15 minutes to initiate the formation (and subsequent precipitation) of TiO$_2$ from the reaction. The slurry was stirred for 20 minutes at 20-25° C., cooled to 0° C., and stirred for 20 minutes at 0° C. Finally, the precipitate was filtered and washed with heptane (250 mL) to obtain a solution of diimine (573) in heptane, which was concentrated to 250 mL of heptane (~4.6 vol) prior to use in the subsequent hydrogenation stage.

Step B: N,N'-bis(isobornyl)ethylenediamine ligand (572).

Johnson-Matthey Yellow Kit #28 [5% Pt/C, B501018-5] catalyst (2.7 g, 5 wt % wrt 6) was charged to a Parr vessel, followed by a solution of diimine (6) in heptane (~54 g in 250 mL heptane). The reaction was hydrogenated for 15 h at 100 psi H$_2$, 20° C., at which time the only product was observed by LCMS. The mixture was then filtered through a CELITE™diatomaceous earth pad and washed with heptane (130 mL). The filtrate solvent was swapped from heptanes to isopropanol (270 mL, 5 vol), after which water (86 mL, 1.5 vol) was charged and the reaction was heated to reflux to dissolve all material. Slow cooling of the solution to 20° C. resulted in crystallization of the product. Additional water (200 mL, 3.7 vol) was charged over 15 minutes and the reaction was held for an additional 20 minutes. The slurry was then cooled to 0° C. and held for 30 minutes, at which time the product was filtered and washed with a 0° C. mixture of 1:1 water/isopropanol (130 mL) to yield 46.05 g (572) (84.3%) after drying overnight.

The above intermediates 11S, 12S, and 13S serve to demonstrate application of the asymmetric Henry reaction in the camphor ligand step to produce the S alcohol on a useful intermediate in consistent yield and selectivity with the earlier examples that provide the R diastereomeric alcohol. It will be apparent to one skilled in the art that this methodology can be employed in combination with the appropriate triterpene derived scaffolds to give either the R or S diastereomer upon chosing the appropriate camphor derived diamine chiral ligand under the conditions outlined herein. Furthermore, it is shown that the above nitroalcohol intermediates, whether a mixture of diastereomeric alcohols or in optically enriched form, are useful to provide compounds of Formula I or Formula II.

Example 500

Compound 575

4-(((3aR,5aR,5bR,7aR,9S,11aR,11bR,13aS)-3a-((R)-2-(((5-chloropyrimidin-2-yl)methyl)(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

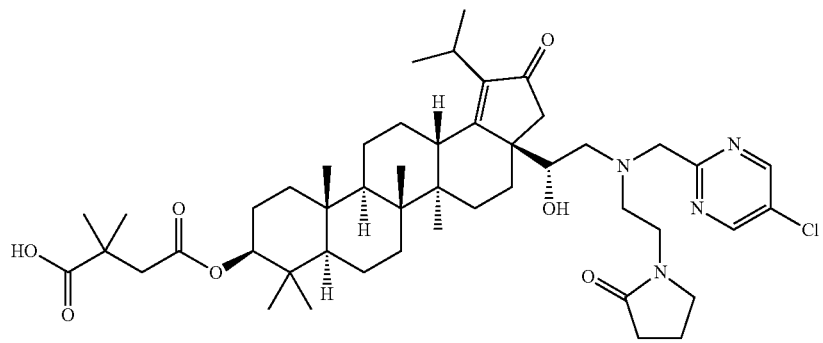

575

LC/MS: m/z calculated 850.5. found 851.5 (M+1)$^+$

Example 501

Compound 576

4-(((3aR,5aR,5bR,7aR,9S,11aR,11bR,13aS)-3a-((R)-2-(((5-chloropyrimidin-2-yl)methyl)(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

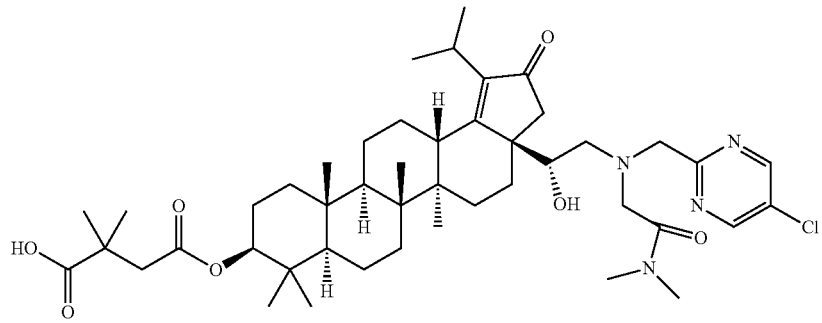

576

LC/MS: m/z calculated 824.5. found 825.5 (M+1)$^+$

Example 502

Compound 577

(R)-4-(((3aR,5aR,5bR,7aR,9S,11aR,11bR,13aS)-3a-((R)-2-((cyclopropylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-methyl-4-oxobutanoic acid

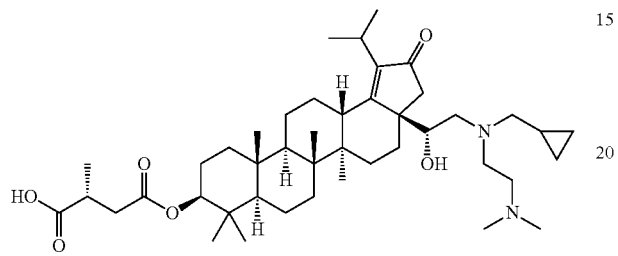

577

LC/MS: m/z calculated 724.5. found 725.5 (M+1)$^+$

Example 503

Compound 578

(R)-4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-methyl-4-oxobutanoic acid.

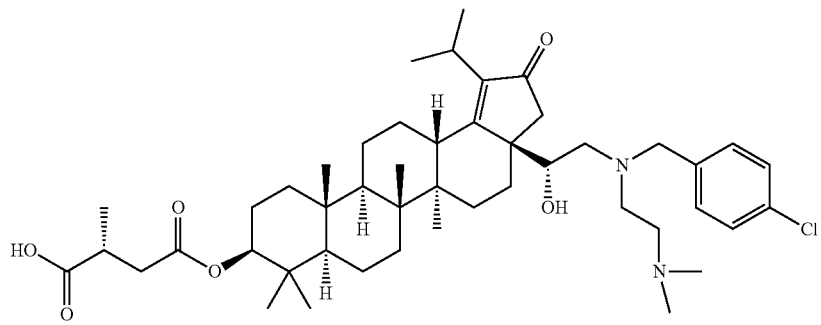

578

LC/MS: m/z calculated 794.5. found 795.5 (M+1)$^+$

Example 504

Compound 579

4-(((3aR,5aR,5bR,7aR,9S,11aR,11bR,3aS)-3a-((R)-2-((2-(dimethylamino)ethyl)(pyridazin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

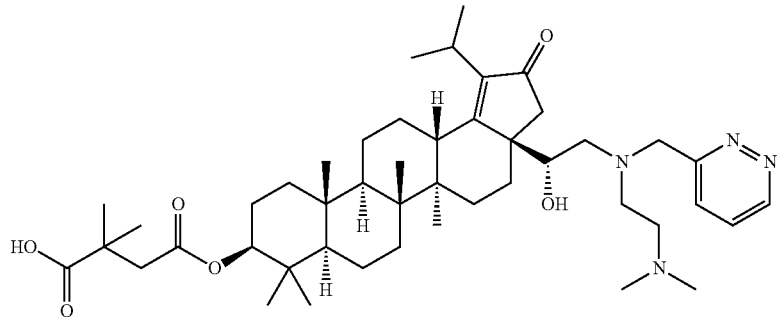

579

LC/MS: m/z calculated 776.5. found 777.6 (M+1)$^+$

Example 505

Compound 580

4-(((3aR,5aR,5bR,7aR,9S,11aR,11bR,13aS)-3a-((R)-2-((cyclobutylmethyl)(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

580

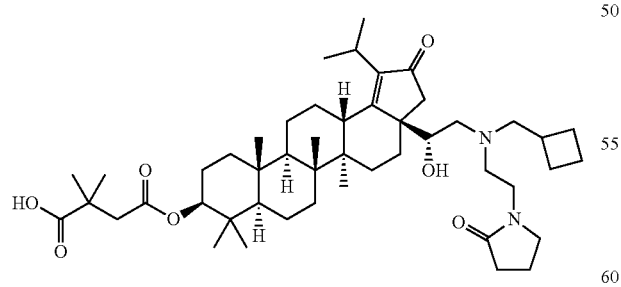

LC/MS: m/z calculated 792.6. found 793.6 (M+1)$^+$

Example 506

Compound 581

4-(((3aR,5aR,5bR,7aR,9S,11aR,11bR,13aS)-3a-((R)-2-(((S)-1-(5-chloropyrimidin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

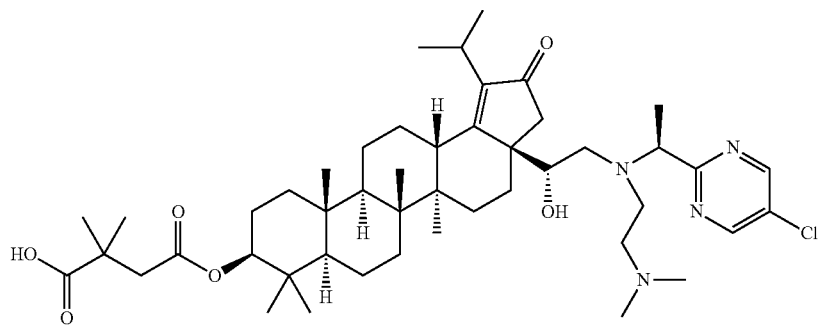

581

LC/MS: m/z calculated 824.5. found 825.5 (M+1)$^+$

Example 507

Compound 582

4-(((3aR,5aR,5bR,7aR,9S,11aR,11bR,13aS)-3a-((R)-2-(((R)-1-(5-chloropyrimidin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

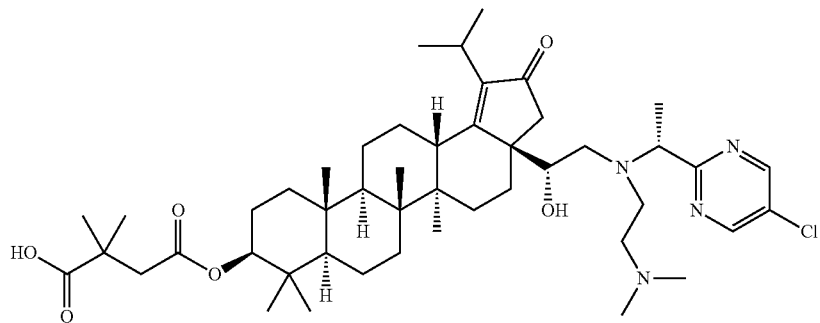

582

LC/MS: m/z calculated 824.5. found 825.5 (M+1)$^+$

Example 508

Compound 583

(R)-4-(((3aR,5aR,5bR,7aR,9S,11aR,11bR,13aS)-3a-((R)-2-((2-(dimethylamino)ethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-methyl-4-oxobutanoic acid.

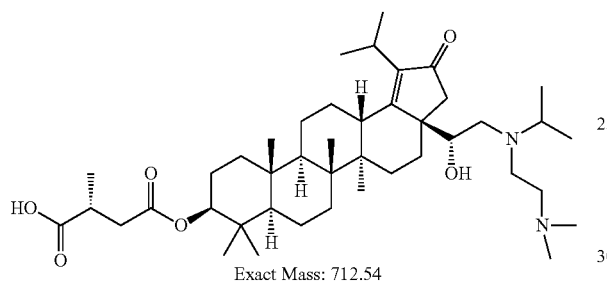

Exact Mass: 712.54

LC/MS: m/z calculated 712.5. found 713.7 (M+1)$^+$

Example 509

Compound 584

4-(((3aR,5aR,5bR,7aR,9S,11aR,11bR,13aS)-3a-((R)-2-((cyclopropylmethyl)(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid.

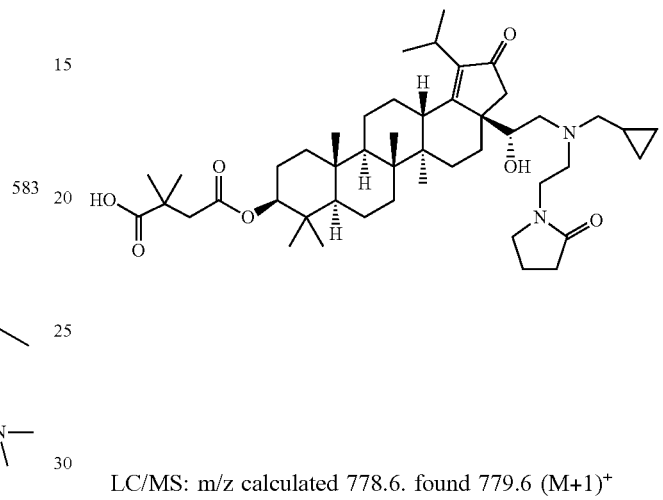

LC/MS: m/z calculated 778.6. found 779.6 (M+1)$^+$

Example 510

Compound 585

(S)-4-(((3aR,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-methyl-4-oxobutanoic acid.

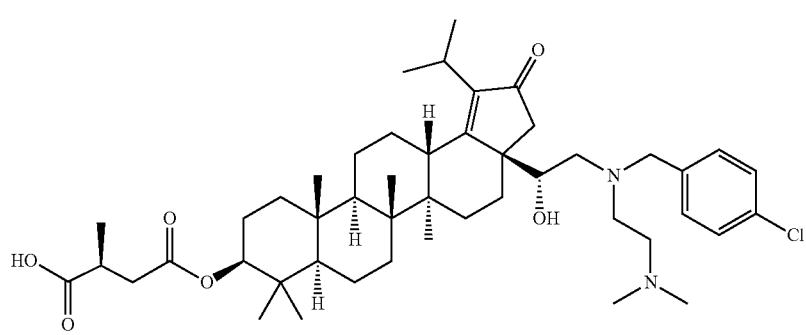

LC/MS: m/z calculated 794.5. found 795.5 (M+1)$^+$.

After the above description of synthesis procedures for the compounds described herein, there is provided in accordance with other embodiments of the present invention, a process for preparing a compound of Formula (I) having the structure:

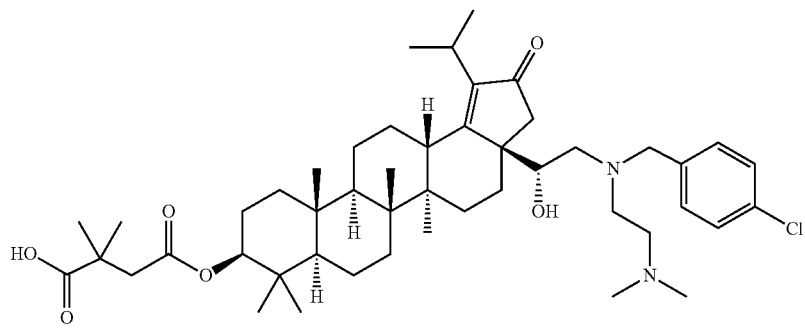

comprising the steps of:
(1) saponifying a compound having the structure:

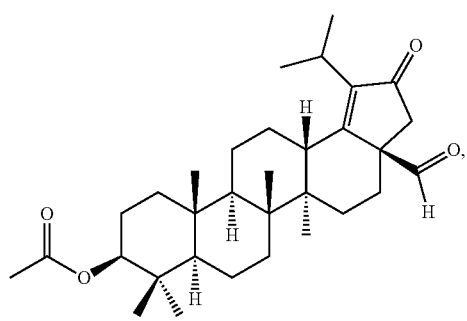

in the presence of a first metal catalyst, in order to provide a compound having the structure:

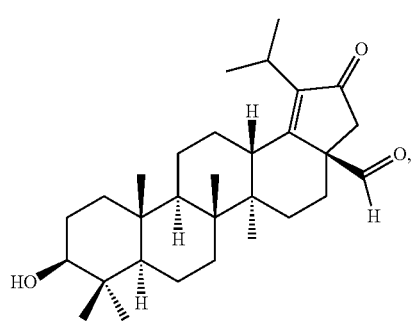

(2) reacting the compound product of Step (1), with a compound having the structure:

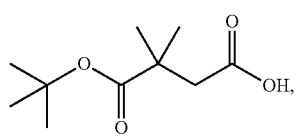

in the presence of an acid chloride and a tertiary amine in order to provide a compound having the structure:

[Structure]

(3) reacting nitromethane with the compound product of Step (2) in the presence of a chiral ligand, an optional base, and a second metal catalyst in order to provide a compound having the structure:

[Structure]

(4) reducing the compound product of Step (3), in the presence of a third metal catalyst and hydrogen gas in order to provide a compound having the structure:

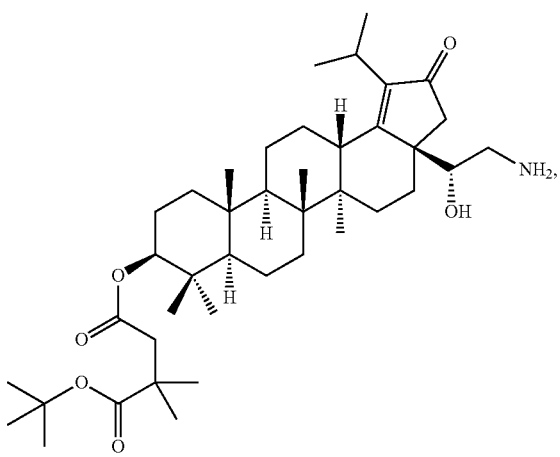

(5) reacting p-chlorobenzaldehyde with the compound product of Step (4), in the presence of a metal hydride, to provide a compound having the structure:

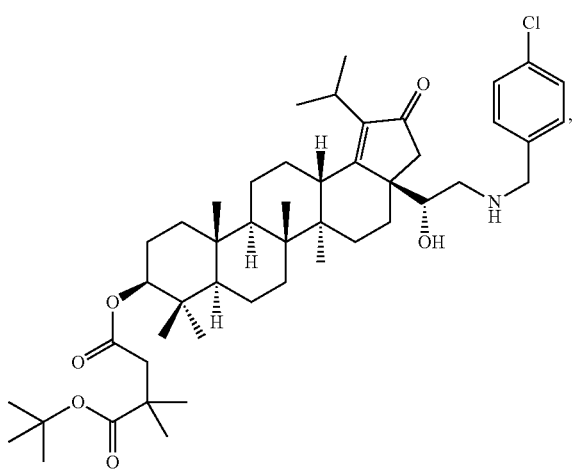

(6) acidifying the compound product of Step (5), in the presence of an acid in order to provide the compound having the structure:

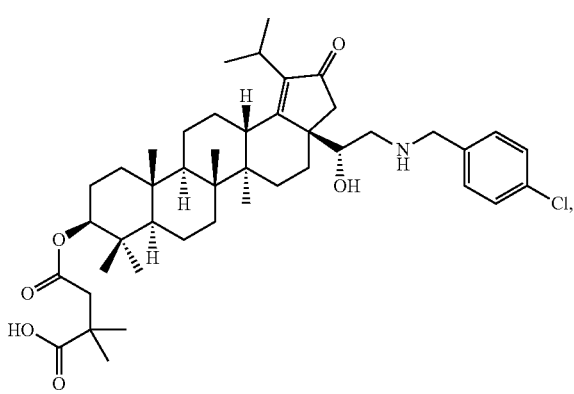

(7) reacting the compound product of Step (6) with a compound having the structure according to Formula III:

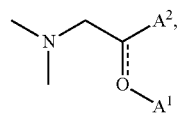

(III)

wherein $A^1$ is either optionally absent or is selected from the group consisting —H, methyl, and ethyl; and $A^2$ is selected from the group consisting of —H, hydroxyl, methoxy, ethoxy, and —$SO_3^-Na^+$; while in the presence of a metal hydride in order to provide the compound having the structure:

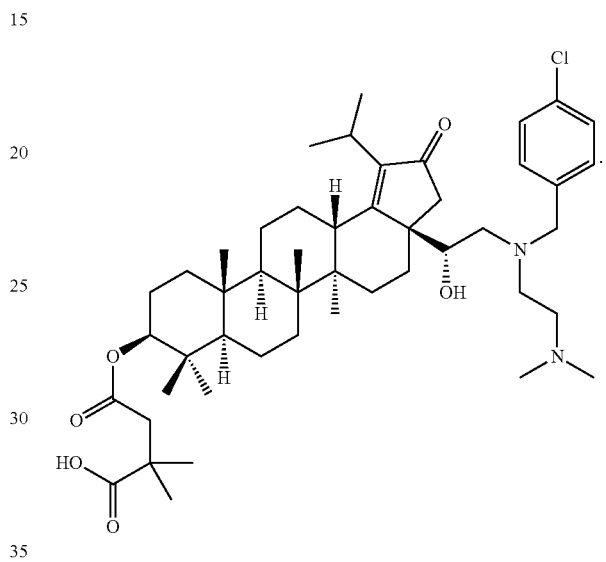

As will be known to one of skill in the art after reading the synthetic procedures described here and the process steps described above and below, several suitable chemical components can be used to carry out the process steps. Such suitable chemical components can be used interchangeably with any process step description described herein according to knowledge in the art.

In accordance with other embodiments of the present invention, there is provided a process for preparing a compound of Formula (I), wherein one or more of Steps (1)-(7) are conducted in the presence of a solvent.

In accordance with other embodiments of the present invention, there is provided a process for preparing a compound of Formula (I), wherein one or more of Steps (1)-(7) are conducted in the presence of an organic solvent.

In accordance with other embodiments of the present invention, there is provided a process for preparing a compound of Formula (I), wherein one or more of Steps (1)-(7) are conducted in the presence of a solvent that is selected from the group consisting of water, dichloromethyl, methanol, tetrahydrofuran, tetrahydrofuran acetate, ethanol, ethyl acetate, heptane, isopropanol, tert-butanol, toluene, acetonitrile, and tert-butyl methyl ether.

In accordance with other embodiments of the present invention, there is provided a process for preparing a compound of Formula (I), wherein the first metal catalyst of Step (1) is a metal halide.

In accordance with other embodiments of the present invention, there is provided a process for preparing a compound of Formula (I), wherein the first metal catalyst of Step (1) is zirconium tetrachloride.

In accordance with other embodiments of the present invention, there is provided a process for preparing a compound of Formula (I), wherein the acid chloride of Step (2) is selected from the group consisting of benzoyl chloride and methoxybenzoyl chloride.

In accordance with other embodiments of the present invention, there is provided a process for preparing a compound of Formula (I), wherein the acid chloride of Step (2) is methoxybenzoyl chloride.

In accordance with other embodiments of the present invention, there is provided a process for preparing a compound of Formula (I), wherein the tertiary amine of Step (2) is a tertiary amine coupling agent.

In accordance with other embodiments of the present invention, there is provided a process for preparing a compound of Formula (I), wherein the tertiary amine of Step (2) is selected from the group consisting of triethylamine, N,N-diisopropylethylamine, and 1-ethyl-3-[3-dimethylaminopropyl]carbodiimide hydrochloride.

In accordance with other embodiments of the present invention, there is provided a process for preparing a compound of Formula (I), wherein the tertiary amine of Step (2) is 1-ethyl-3-[3-dimethylaminopropyl]carbodiimide hydrochloride.

In accordance with other embodiments of the present invention, there is provided a process for preparing a compound of Formula (I), wherein the tertiary amine of Step (2) is triethylamine.

In accordance with other embodiments of the present invention, there is provided a process for preparing a compound of Formula (I), wherein the second metal catalyst of Step (3) is a compound comprising a metal selected from the group consisting of Zn, Co, Cu, Mg, and Cr.

In accordance with other embodiments of the present invention, there is provided a process for preparing a compound of Formula (I), wherein the second metal catalyst of Step (3) is a compound comprising a metal selected from the group consisting of Cu(I) and Cu(II).

In accordance with other embodiments of the present invention, there is provided a process for preparing a compound of Formula (I), wherein the second metal catalyst of Step (3) is a compound comprising Cu(I).

In accordance with other embodiments of the present invention, there is provided a process for preparing a compound of Formula (I), wherein the second metal catalyst of Step (3) is selected from the group consisting of Copper(I) acetate and Cu(II) acetate.

In accordance with other embodiments of the present invention, there is provided a process for preparing a compound of Formula (I), wherein the second metal catalyst of Step (3) is Copper(I) acetate.

In accordance with other embodiments of the present invention, there is provided a process for preparing a compound of Formula (I), wherein the second metal catalyst of Step (3) is Copper(II) acetate.

In accordance with other embodiments of the present invention, there is provided a process for preparing a compound of Formula (I), wherein the optional base of Step (3) is selected from the group consisting of alkali metal hydroxides, alkoxides, carbonates, fluoride anions, and nonionic organic amine bases.

In accordance with other embodiments of the present invention, there is provided a process for preparing a compound of Formula (I), wherein the optional base of Step (3) is $^i$Pr$_2$Net.

In accordance with other embodiments of the present invention, there is provided a process for preparing a compound of Formula (I), wherein the chiral ligand of Step (3) is a derivative of S-Camphor.

In accordance with other embodiments of the present invention, there is provided a process for preparing a compound of Formula (I), wherein the chiral ligand of Step (3) is a compound having the structure:

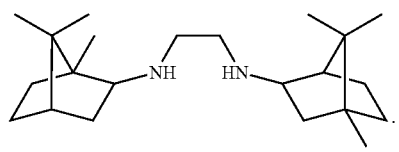 [SMILES: CC12CCC(C(NCCNC3CC4CCC3(C)C4(C)C)C1)C2(C)C]

In accordance with other embodiments of the present invention, there is provided a process for preparing a compound of Formula (I), wherein the third metal catalyst of Step (4) is selected from the group consisting of Raney Nickel, nickel, nickel chloride, aluminum, palladium, copper, zinc, chromium, iridium, rhodium, platinum, and combinations thereof.

In accordance with other embodiments of the present invention, there is provided a process for preparing a compound of Formula (I), wherein the third metal catalyst of Step (4) is Raney Nickel.

In accordance with other embodiments of the present invention, there is provided a process for preparing a compound of Formula (I), wherein the hydrogen of Step (4) is hydrogen gas.

In accordance with other embodiments of the present invention, there is provided a process for preparing a compound of Formula (I), wherein the metal hydride of Step (5) is a borohydride.

In accordance with other embodiments of the present invention, there is provided a process for preparing a compound of Formula (I), wherein the metal hydride of Step (5) is selected from the group consisting of NaBH$_4$ and NaBH(OAc)$_3$.

In accordance with other embodiments of the present invention, there is provided a process for preparing a compound of Formula (I), wherein the metal hydride of Step (5) is NaBH$_4$.

In accordance with other embodiments of the present invention, there is provided a process for preparing a compound of Formula (I), wherein the metal hydride of Step (5) is NaBH(OAc)$_3$.

In accordance with other embodiments of the present invention, there is provided a process for preparing a compound of Formula (I), wherein the acid of Step (6) is selected from the group consisting of trifluoroacetic acid, HCl, and trichloroacetic acid, In accordance with other embodiments of the present invention, there is provided a process for preparing a compound of Formula (I), wherein the acid of Step (6) is trifluoroacetic acid.

In accordance with other embodiments of the present invention, there is provided a process for preparing a compound of Formula (I), wherein the $A^2$ of Step (7) is —SO$_3$Na.

In accordance with other embodiments of the present invention, there is provided a process for preparing a compound of Formula (I), wherein the $A^2$ of Step (7) is —H.

In accordance with other embodiments of the present invention, there is provided a process for preparing a compound of Formula (I), wherein the $A^1$ of Step (7) is absent.

In accordance with other embodiments of the present invention, there is provided a process for preparing a compound of Formula (I), wherein the A¹ of Step (7) is —H.

In accordance with other embodiments of the present invention, there is provided a process for preparing a compound of Formula (I), wherein the compound of Formula III of Step (7) has the following structure:

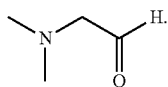

In accordance with other embodiments of the present invention, there is provided a compound of Formula (I), wherein the compound of Formula III of Step (7) has the following structure:

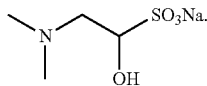

In accordance with other embodiments of the present invention, there is provided a process for preparing a compound of Formula (I), wherein the compound of Formula III of Step (7) has the following structure:

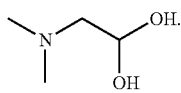

In accordance with other embodiments of the present invention, there is provided a process for preparing a compound of Formula (I), wherein the compound of Formula III of Step (7) has the following structure:

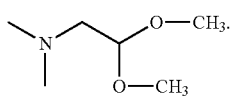

In accordance with other embodiments of the present invention, there is provided a process for preparing a compound of Formula (I), wherein the compound of Formula III of Step (7) has the following structure:

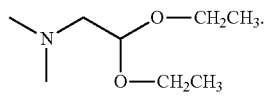

In accordance with other embodiments of the present invention, there is provided a process for preparing a compound of Formula (I), wherein the metal hydride of Step (7) is a borohydride.

In accordance with other embodiments of the present invention, there is provided a process for preparing a compound of Formula (I), wherein the metal hydride of Step (7) is NaBH₃CN.

In accordance with other embodiments of the present invention, there is provided a process for preparing a compound of Formula (I) having the structure:

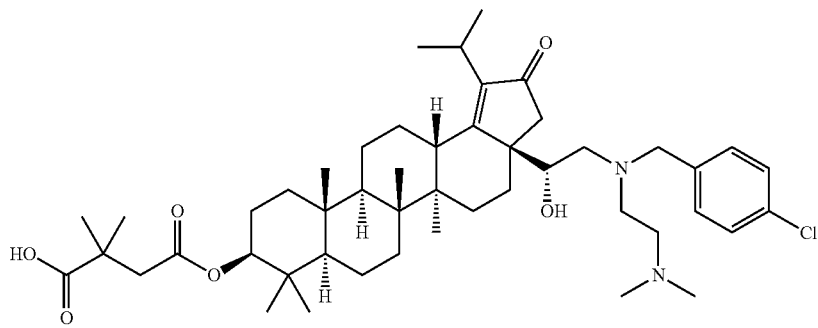

comprising the steps of:

(1) saponifying a compound having the structure:

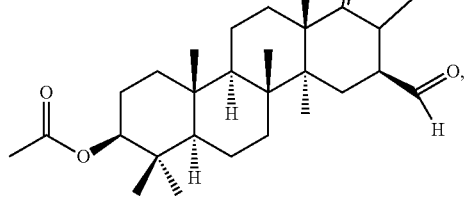

in the presence of a first metal catalyst, in order to provide a compound having the structure:

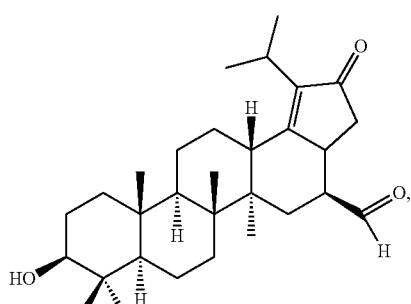
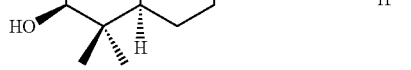

(2) reacting the compound product of Step (1), with a compound having the structure:

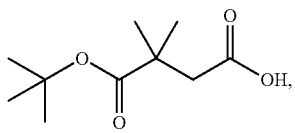

in the presence of an acid chloride and a tertiary amine in order to provide a compound having the structure:

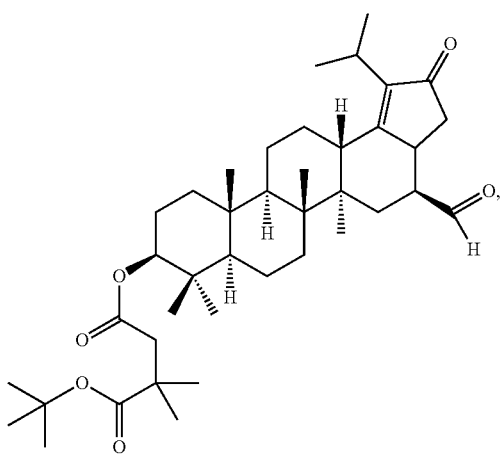

(3) reacting nitromethane with the compound product of Step (2) in the presence of a chiral ligand and a base and a second metal catalyst in order to provide a compound having the structure:

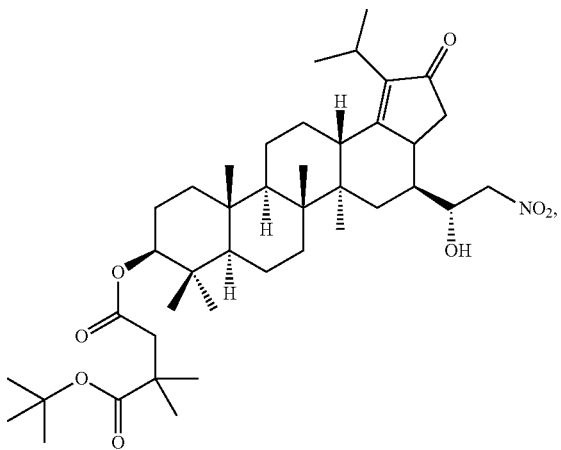

(4) reducing the compound product of Step (3), in the presence of a third metal catalyst and hydrogen gas in order to provide a compound having the structure:

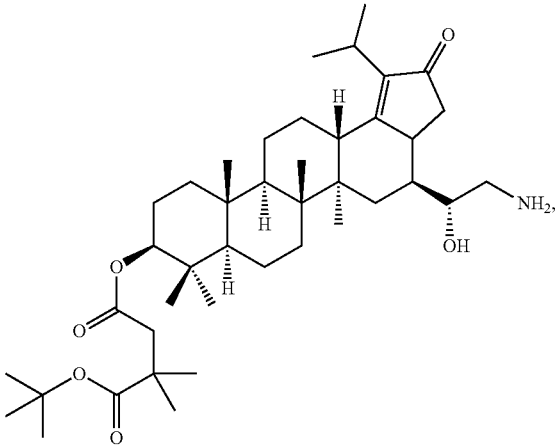

(5) reacting p-chlorobenzaldehyde with the compound product of Step (4), in the presence of a metal hydride and a tertiary amine, to provide a compound having the structure:

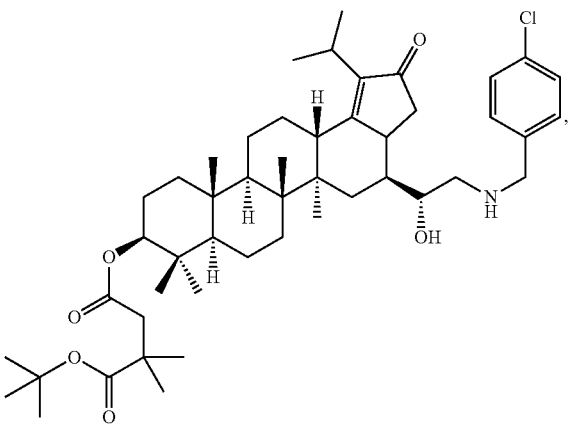

(6) reacting the compound product of Step (5) with a compound having the structure according to Formula III:

(III)

wherein $A^1$ is either optionally absent or is selected from the group consisting —H, methyl, and ethyl; and $A^2$ is selected from the group consisting of —H, methoxy, ethoxy, hydroxyl, and —SO$_3^-$Na$^+$; while in the presence of a metal hydride in order to provide the compound having the structure:

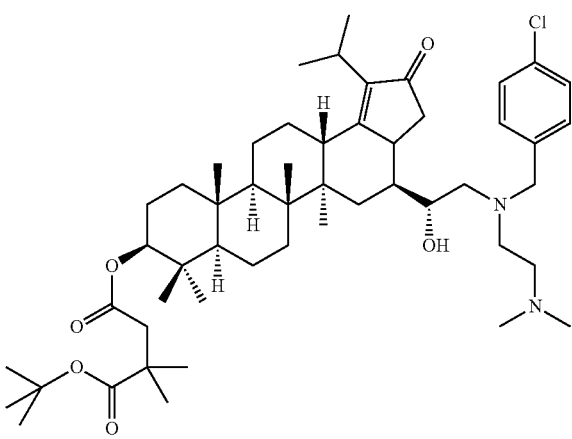

(7) acidifying the compound product of Step (6), in the presence of an acid in order to provide the compound having the structure:

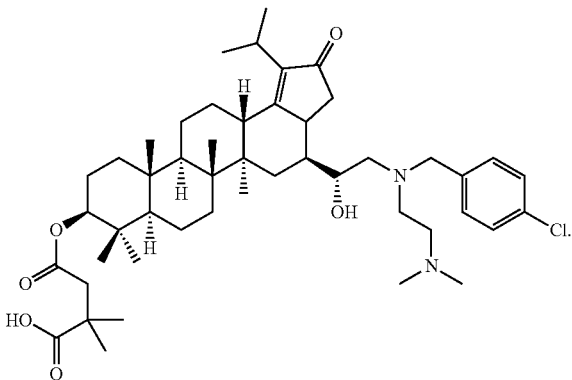

With regards to the synthesis procedures herein, and in accordance with other embodiments of the present invention, there is also provided a process for preparing a compound of Formula (I), wherein one or more of Steps (1)-(7) are conducted in the presence of a solvent.

In accordance with other embodiments of the present invention, there is provided a process for preparing a compound of Formula (I), wherein one or more of Steps (1)-(7) are conducted in the presence of an organic solvent.

In accordance with other embodiments of the present invention, there is provided a process for preparing a compound of Formula (I), wherein one or more of Steps (1)-(7) are conducted in the presence of a solvent that is selected from the group consisting of water, dichloromethyl, methanol, tetrahydrofuran, tetrahydrofuran acetate, ethanol, ethyl acetate, heptane, isopropanol, tert-butanol, toluene, acetonitrile, and tert-butyl methyl ether.

In accordance with other embodiments of the present invention, there is provided a process for preparing a compound of Formula (I), wherein the base of Step (3) is selected from the group consisting of alkali metal hydroxides, alkoxides, carbonates, fluoride anions, and nonionic organic amine bases.

In accordance with other embodiments of the present invention, there is provided a process for preparing a compound of Formula (I), wherein the base of Step (3) is $^iPr_2Net$.

In accordance with other embodiments of the present invention, there is provided a process for preparing a compound of Formula (I), wherein the tertiary amine of Step (5) is selected from the group consisting of triethylamine and 1-ethyl-3-[3-dimethylaminopropyl]carbodiimide hydrochloride.

In accordance with other embodiments of the present invention, there is provided a process for preparing a compound of Formula (I), wherein the tertiary amine of Step (5) is triethylamine.

In accordance with other embodiments of the present invention, there is provided a process for preparing a compound of Formula (I), wherein the metal hydride of Step (5) is a borohydride.

In accordance with other embodiments of the present invention, there is provided a process for preparing a compound of Formula (I), wherein the metal hydride of Step (5) is selected from the group consisting of $NaBH_4$ and $NaBH(OAc)_3$.

In accordance with other embodiments of the present invention, there is provided a process for preparing a compound of Formula (I), wherein the metal hydride of Step (5) is $NaBH_4$.

In accordance with other embodiments of the present invention, there is provided a process for preparing a compound of Formula (I), wherein the tertiary amine of Step (6) is triethylamine.

In accordance with other embodiments of the present invention, there is provided a process for preparing a compound of Formula (I), having the structure:

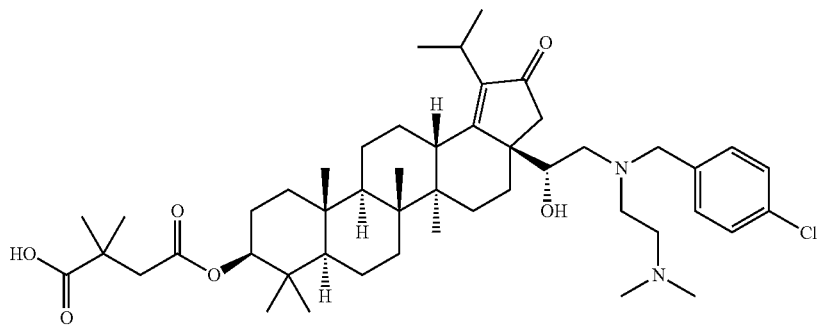

comprising the steps of:
  (1) reacting a compound having the structure:

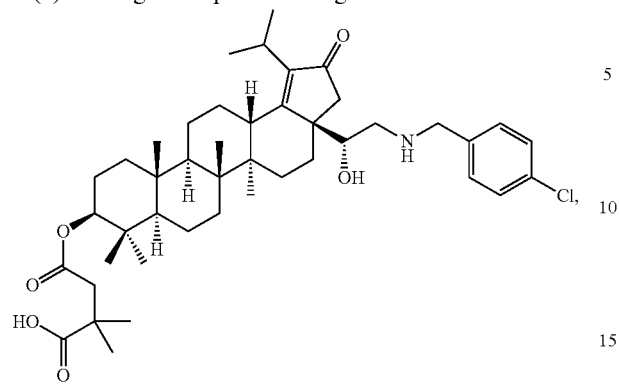

with a compound having the structure according to Formula III:

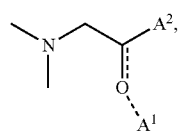

(III)

wherein $A^1$ is either optionally absent or is selected from the group consisting —H, methyl, and ethyl; and $A^2$ is selected from the group consisting of —H, methoxy, ethoxy, hydroxyl, and —$SO_3^-Na^+$; while in the presence of a metal hydride in order to provide the compound having the structure:

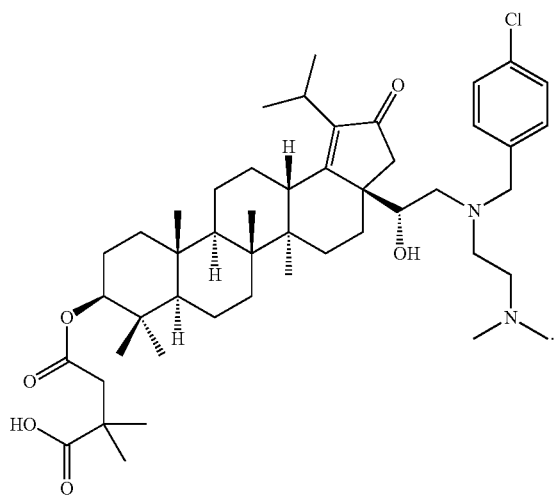

In accordance with other embodiments of the present invention and the suitable process step components recited above, there is provided a process for preparing a compound of Formula (I), having the structure:

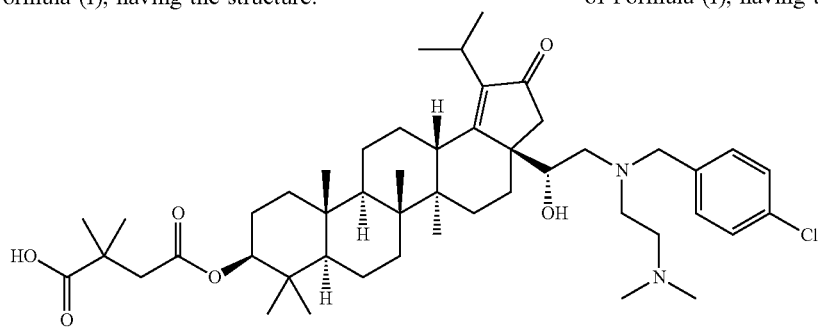

comprising the steps of:
  (1) acidifying a compound having the structure:

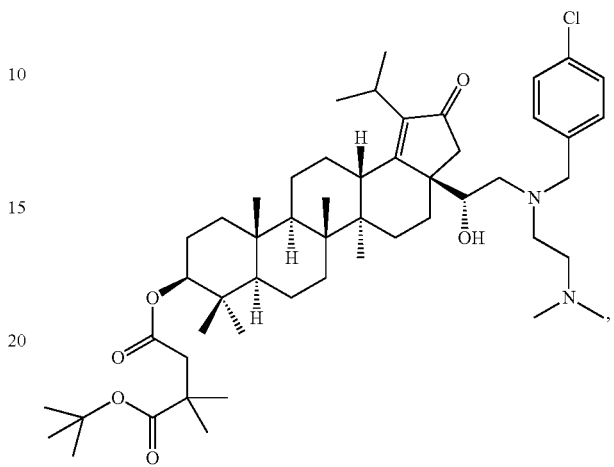

in the presence of an acid in order to provide the compound having the structure:

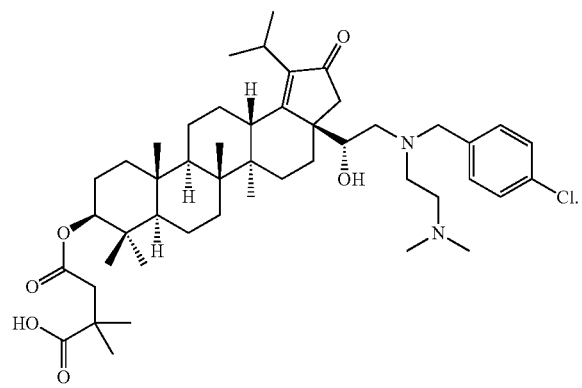

In accordance with other embodiments of the present invention and the suitable process step components recited above, there is provided a process for preparing a compound of Formula (I), having the structure:

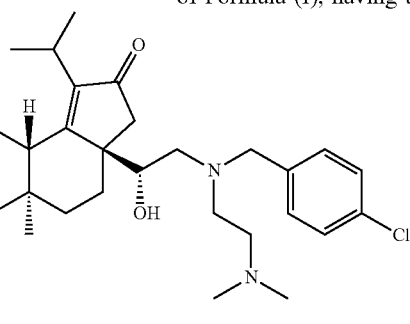

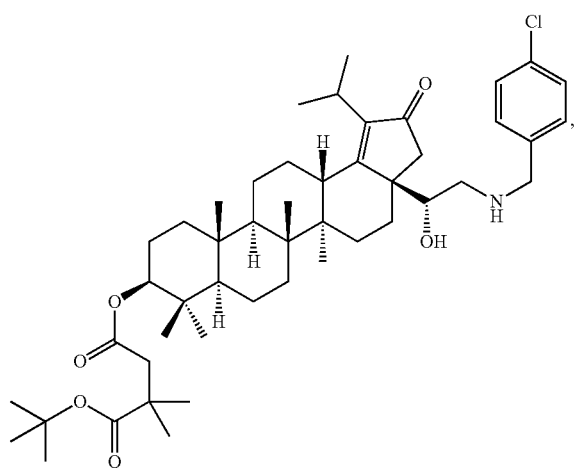

comprising the steps of:
(1) reacting p-chlorobenzaldehyde with a compound having the structure:

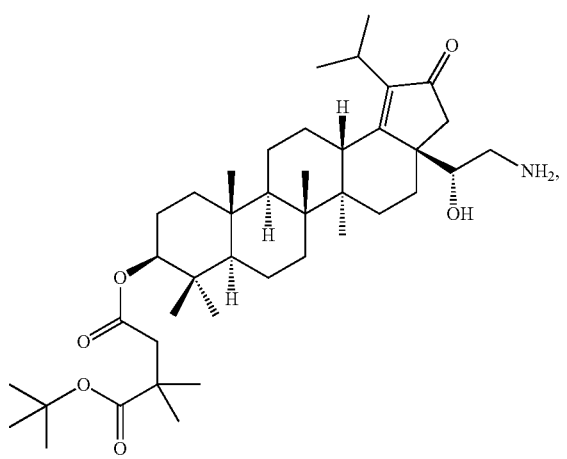

in the presence of a metal hydride to provide the compound having the structure:

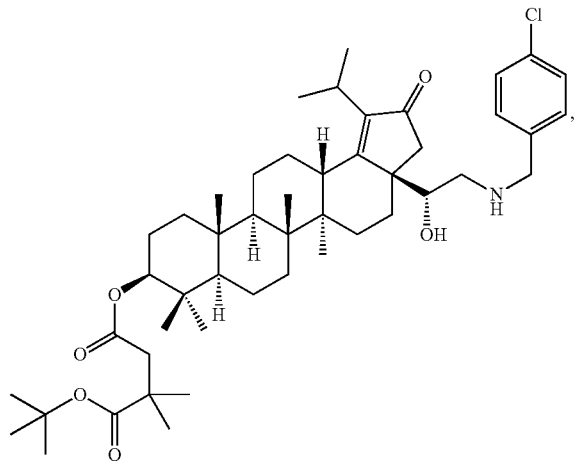

In accordance with other embodiments of the present invention and the suitable process step components recited above, there is provided a process for preparing a compound of Formula (I), having the structure:

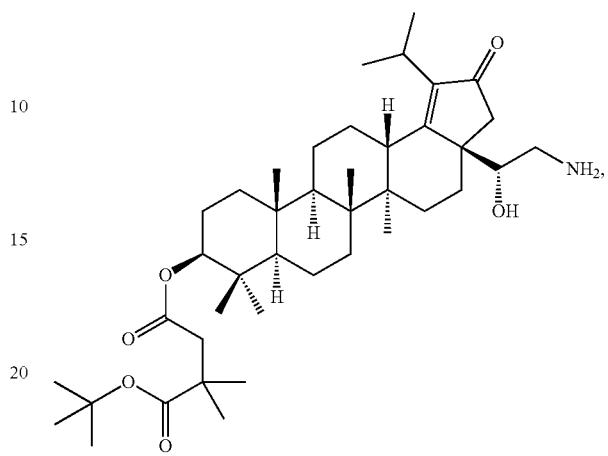

comprising the steps of:
(1) reducing a compound having the structure:

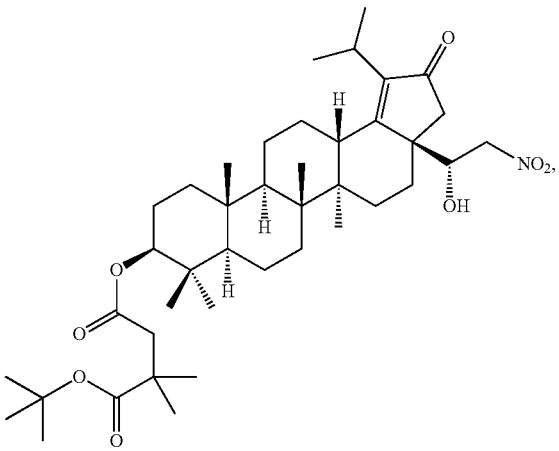

in the presence of a metal catalyst and hydrogen gas in order to provide the compound having the structure:

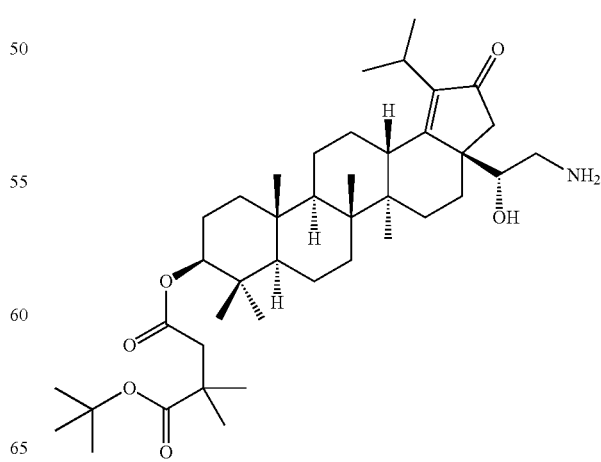

In accordance with other embodiments of the present invention and the suitable process step components recited above, there is provided a process for preparing a compound of Formula (I), having the structure:

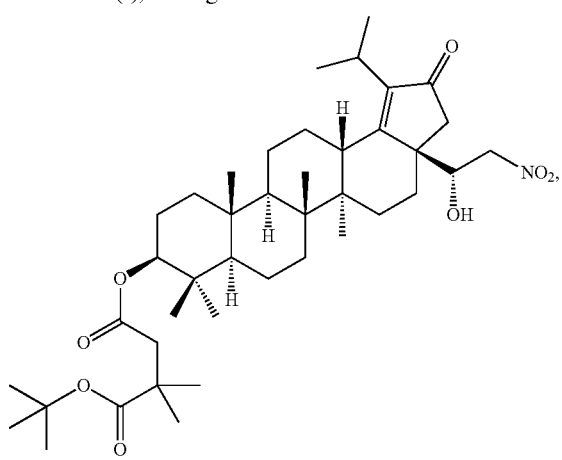

comprising the steps of:
(1) reacting nitromethane with a compound having the structure:

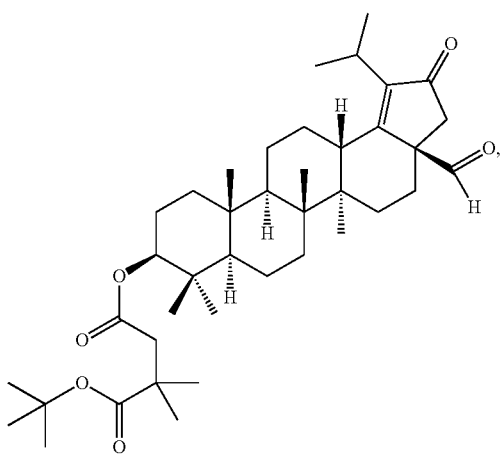

in the presence of a chiral ligand and a metal catalyst in order to provide a compound having the structure:

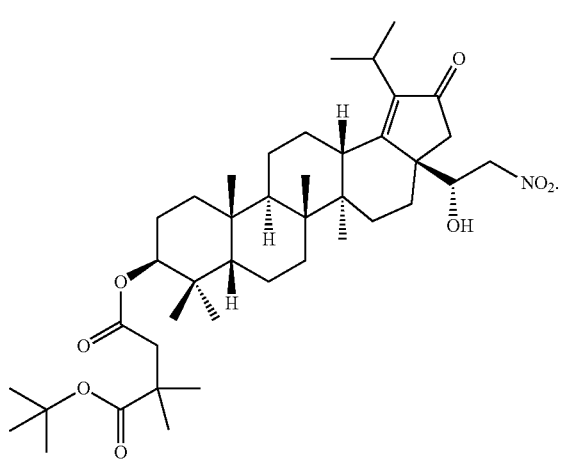

In accordance with other embodiments of the present invention and the suitable process step components recited above, there is provided a process for preparing a compound of Formula (I), having the structure:

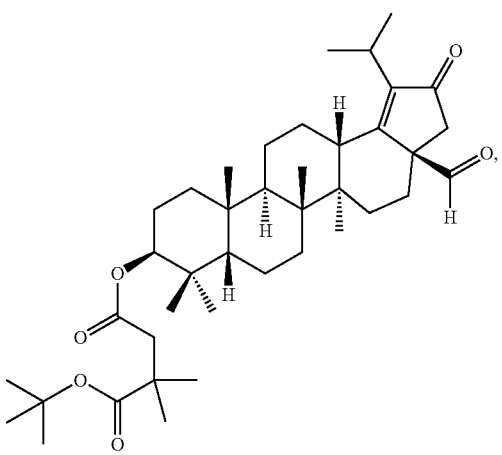

comprising the steps of:
(1) reacting a compound having the structure:

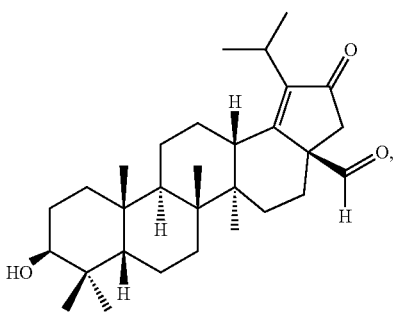

with a compound having the structure:

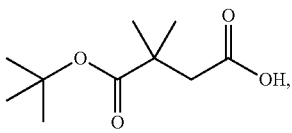

in the presence of an acid chloride and a tertiary amine in order to provide the compound having the structure:

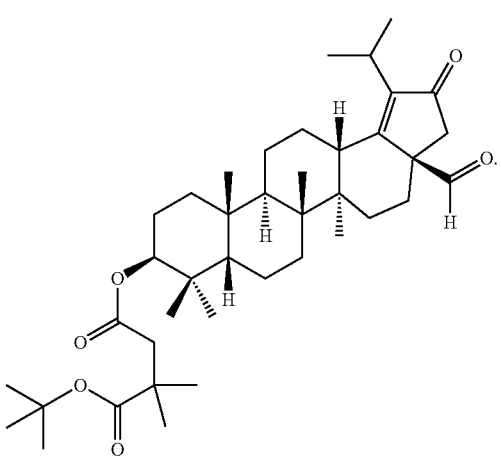

In accordance with other embodiments of the present invention and the suitable process step components recited above, there is provided a process for preparing a compound of Formula (I), having the structure:

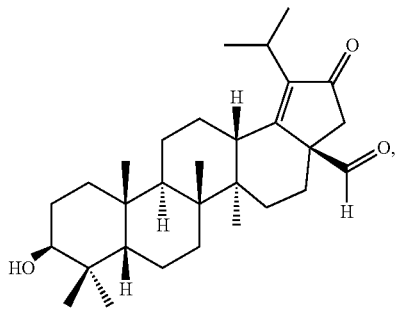

comprising the steps of:
(1) saponifying a compound having the structure:

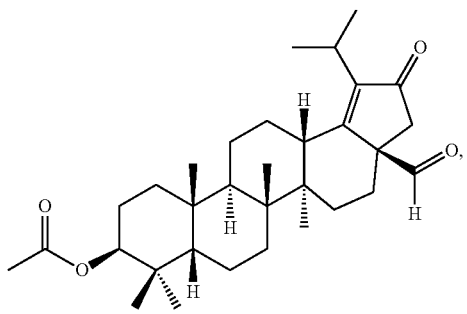

in the presence of a metal catalyst, in order to provide the compound having the structure:

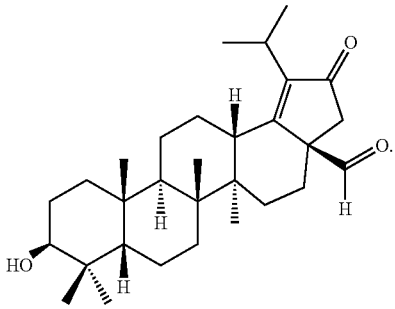

In accordance with other embodiments of the present invention and the suitable process step components recited above, there is provided a process for preparing a compound of Formula (I), having the structure:

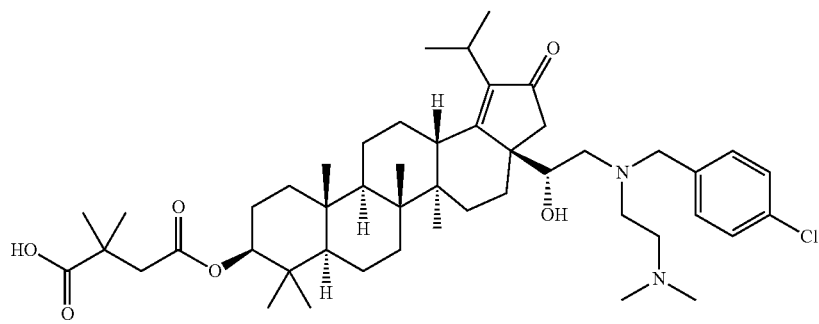

comprising the steps according to the following synthesis scheme. As will be known to one of skill in the art, the above reagents recited in still other synthesis schemes may be substituted within the synthesis scheme below as described above.

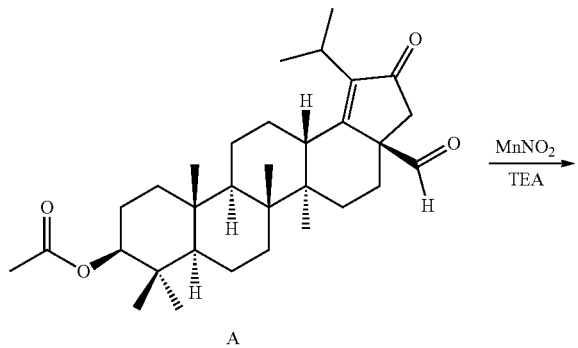

A

-continued
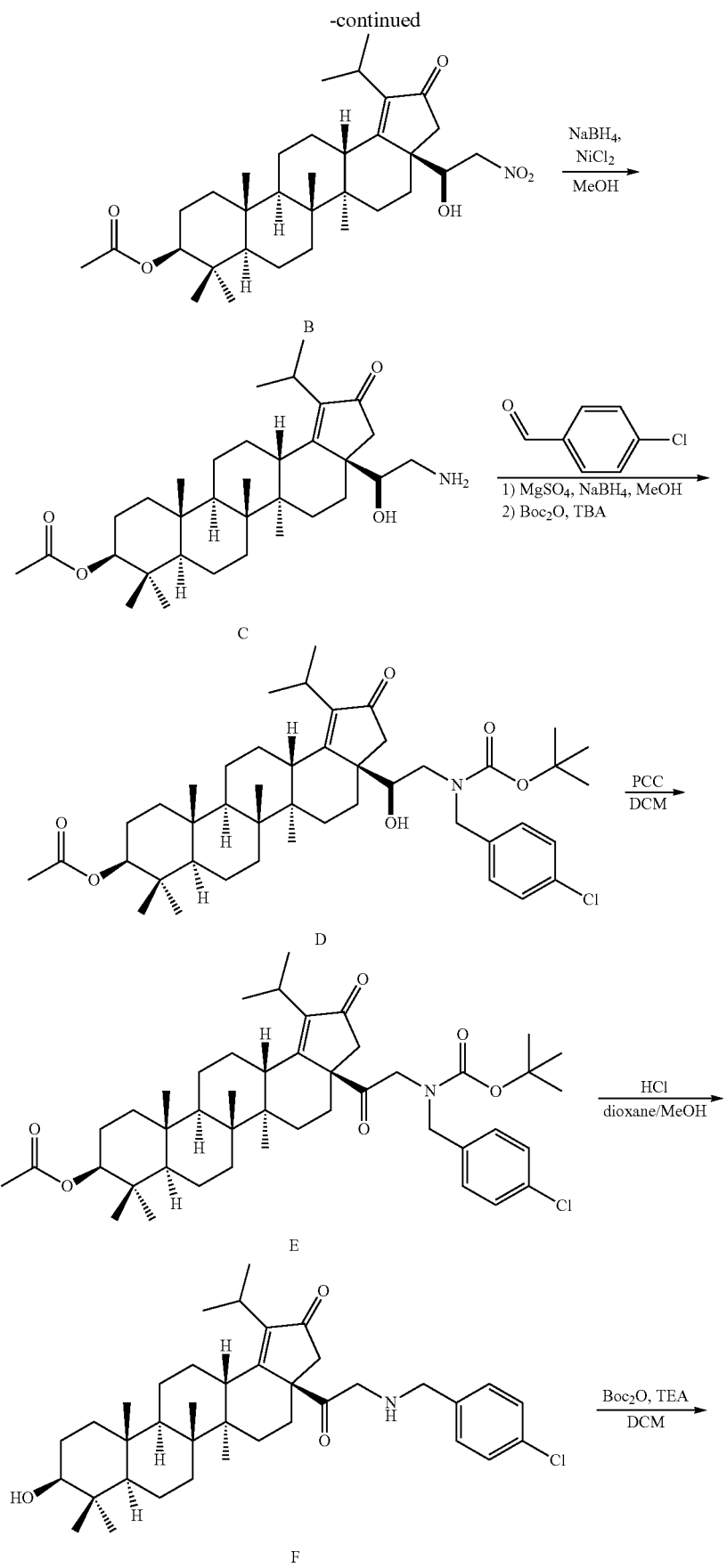

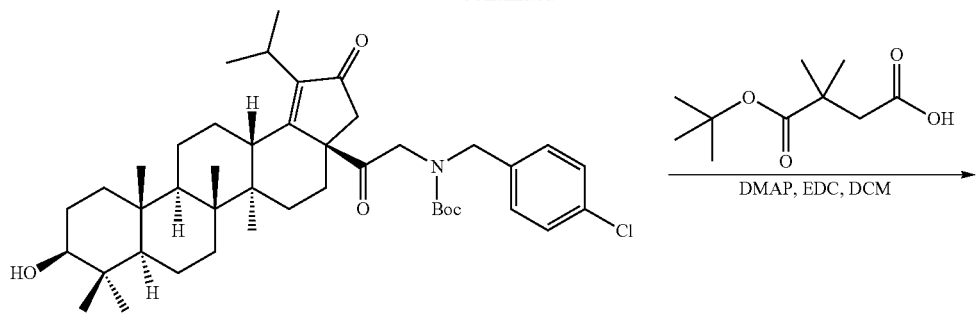
G
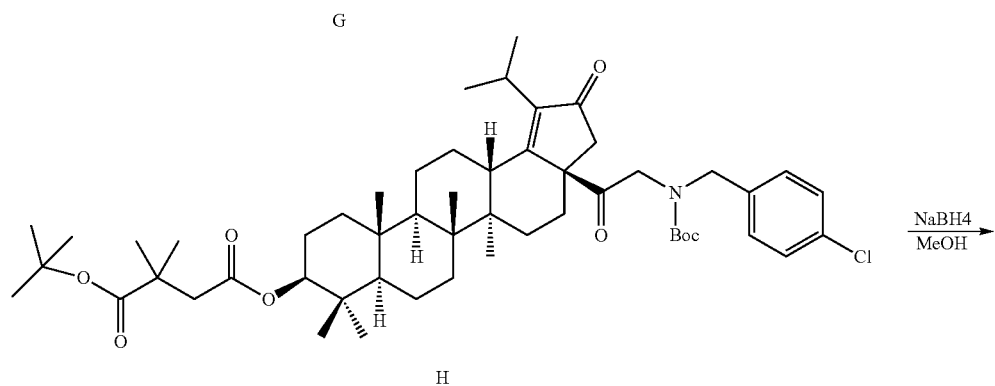
H
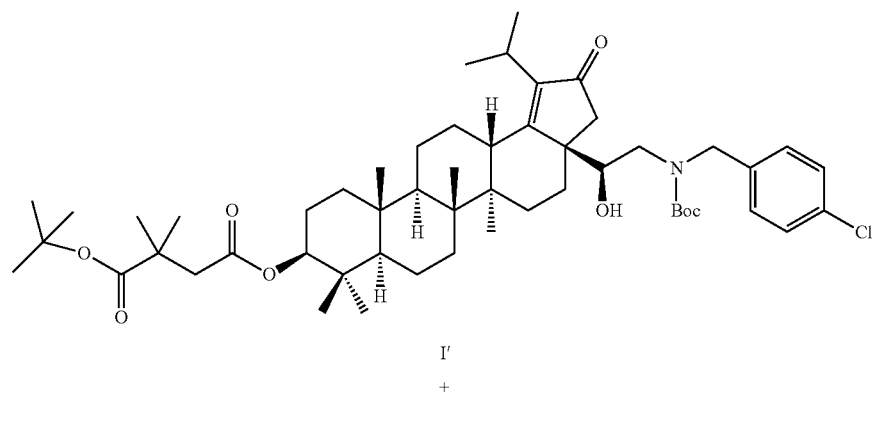
I'
+
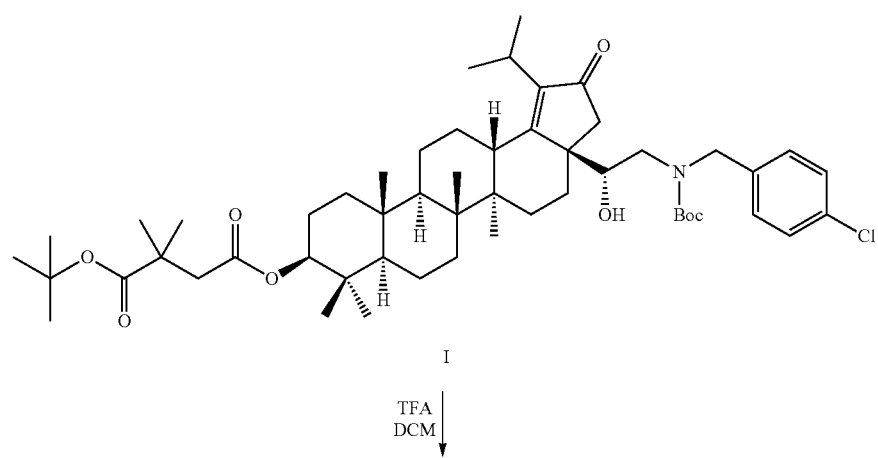
I

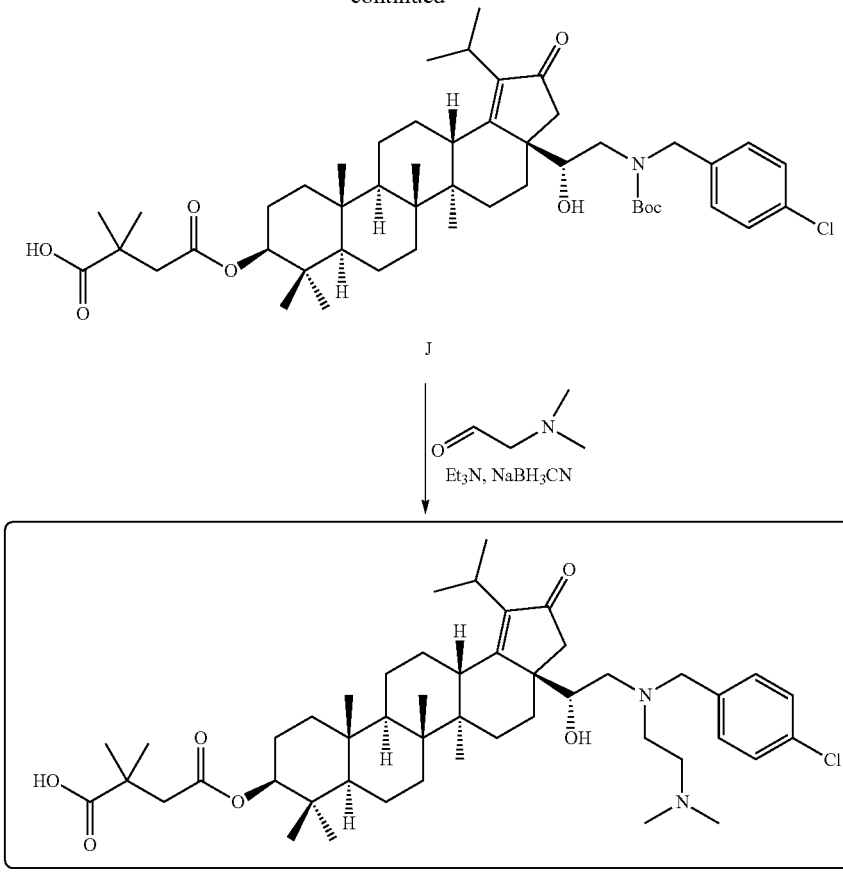

Administration and Formulation

In another embodiment, there is provided a pharmaceutical composition comprising a pharmaceutically acceptable diluent and a therapeutically effective amount of a compound of Formula I or Formula II or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula I or Formula II may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences,* 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula I or Formula II containing one or more asymmetric carbon atoms can exist as two or more stereoisomers. Where a compound of Formula I or Formula II contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formula I or Formula II, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I or Formula II contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula I or Formula II wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I or Formula II, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds of Formula I or Formula II can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of Formula I or Formula II, which may have little or no pharmacological activity themselves can, when administered into or onto the body, be converted into compounds of Formula I or Formula II as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

Example 84

MT4 Cell Antiviral Assay

Experimental Procedure:

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of 5×105 cells/ml. Cell aliquots were infected by the addition of HIV-1 (strain IIIB) diluted to give a viral multiplicity of infection of 100×TCID50. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 µl of the cell suspension was added to each well of the plate containing pre-diluted compound. Plates were then placed in a tissue culture incubator with humidified 5% $CO_2$ for 5 days. At the end of the incubation period, cell number and hence HIV-induced cytopathy was estimated by either (A) propidium iodide staining, or by an (B) MTS tetrazolium staining method.

For propidium iodide readout, 27 µl of 5% Nonidet-40 was added to each well of the incubation plate. After thorough mixing with a Costar multitip pipetter, 60 µl of the mixture was transferred to filter-bottomed 96-well plates. The plates were analyzed in an automated assay instrument (Screen Machine, Idexx Laboratories). The control and standard used was 3'-azido-3'-deoxythymidine tested over a concentration range of 0.01 to 1 µM in every assay. The expected range of $IC_{50}$ values for 3'-azido-3'-deoxythymidine is 0.04 to 0.12 µM. The assay makes use of a propidium iodide dye to estimate the DNA content of each well.

For MTS readout, 20 µl CellTiter 96 AQ One Solution reagent (Promega #G3582) was added to each well. At 75 minutes following the addition of MTS reagent, absobance was read at 492 nM using a Tecan Sunrise 96-well plate reader.

Analysis:

The antiviral effect of a test compound is reported as an $EC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program, version 5.00, 10 Jul. 1995.

For each assay plate, the results (relative fluorescence units, rfU, or OD values) of wells containing uninfected cells or infected cells with no compound were averaged, respectively. For measurements of compound-induced cytotoxicty, results from wells containing various compound concentrations and uninfected cells were compared to the average of uninfected cells without compound treatment. Percent of cells remaining is determined by the following formula:

Percent of cells remaining=(compound-treated uninfected cells, rfU, or *OD* values/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $EC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100.

Results:

Compounds of the present invention have anti-HIV activity in the range $EC_{50}$=1-1000 nM.

TABLE 3

| Example number | $EC_{50}$ NL4-3 wt (nM) | $EC_{50}$ V370A (nM) |
|---|---|---|
| 1 | 41.1 | 34.6 |
| 2 | 5.2 | 4.7 |
| 3 | 61.7 | 242.7 |

TABLE 3-continued

| Example number | EC$_{50}$ NL4-3 wt (nM) | EC$_{50}$ V370A (nM) |
|---|---|---|
| 4 | 10.1 | 9.3 |
| 5 | 2.6 | 3.2 |
| 6 | 0.5 | 3.8 |
| 7 | 6.1 | 23.1 |
| 8 | 5.9 | 14.3 |
| 9 | 12.3 | 13.5 |
| 10 | 2.3 | 2.4 |
| 11 | 6.3 | 6.7 |
| 12 | 4.5 | 5.1 |
| 13 | 1.6 | 2.1 |
| 14 | 2.1 | 3.6 |
| 15 | 6.9 | 31.1 |
| 16 | 11.0 | 7.6 |
| 17 | 8.7 | 29.2 |
| 18 | 0.8 | 0.7 |
| 19 | 3.9 | 4.1 |
| 20 | 2.3 | 4.1 |
| 21 | 76.5 | 103.5 |
| 22 | 3.3 | 3.5 |
| 23 | 4.9 | 11.7 |
| 24 | 40.4 | 1528.0 |
| 25 | 14.7 | 27.8 |
| 26 | 4.9 | 545.0 |
| 27 | 8.2 | 8.9 |
| 29 | 17.5 | 28.6 |
| 31 | 5.4 | 22.5 |
| 33 | 5.3 | ND |
| 34 | 7.1 | 21.1 |
| 35 | 4.2 | 124.0 |
| 36 | 4.0 | 9.4 |
| 37 | 26.9 | 556.6 |
| 38 | 5.2 | 20.9 |
| 39 | 6.6 | 217.1 |
| 40 | 11.1 | 18.9 |
| 44 | 1.8 | 2.6 |
| 45 | 1.9 | 2.5 |
| 46 | 11.1 | 64.8 |
| 47 | 7.7 | 72.9 |
| 49 | 21.8 | 192.3 |
| 50 | 1.1 | 1.4 |
| 51 | 3.5 | 6.3 |
| 52 | 4.6 | 7.0 |
| 53 | 6.2 | 494.3 |
| 56 | 3.4 | 3.4 |
| 57 | 4.2 | 8.0 |
| 58 | 31.5 | 379.0 |
| 59 | 5.3 | 17.2 |
| 60 | 60.2 | 8409.0 |
| 61 | 129.7 | 10000.0 |
| 62 | 103.6 | 213.2 |
| 63 | 3.2 | 5.0 |
| 64 | 7.2 | 120.2 |
| 65 | 83.8 | 3077.0 |
| 66 | 9.2 | 16.1 |
| 67 | 135.5 | 411.1 |
| 68 | 10.5 | 110.2 |
| 69 | 1.0 | 4.1 |
| 70 | 1.6 | 2.1 |
| 71 | 31.2 | 35.3 |
| 72 | 5.1 | 10.8 |
| 73 | 31.8 | 62.3 |
| 74 | 2.9 | 4.8 |
| 75 | 0.6 | 1.0 |
| 76 | 0.7 | 0.9 |
| 77 | 4.7 | 5.0 |
| 78 | 2.1 | 2.7 |
| 79 | 14.7 | 76.1 |
| 80 | 2.4 | 2.7 |
| 81 | 3.0 | 5.4 |
| 82 | 8.9 | 70.5 |
| 83 | 7.3 | 143.5 |

Table 3 shows EC$_{50}$ values for representative compounds of Table 2 after the HIV MT4 Antiviral Cell Assay of Example 84.

Example 86

This example shows the EC$_{50}$ potencies of Bevirimat, compound 51, compound A, and compound B against wild type HIV, site directed HIV mutants, and clinical HIV isolates. As can be seen in Table 5, compound 51 demostrates higher potency than the other compounds when measured against HIV among wildtype, certain site directed mutants, and against several clinical HIV isolates. Surprisingly, compound 51 continues to have excellent potency against HIV relative to the other compounds, when protein binding is taken into account as can be seen in Table 6.

The results in Tables 5 and 6 for compound 51 demostrate an unexpected result taken in light of Bevirimat and compounds A and B. The results in the above tables are indicative of the unpredictability in developing anti-HIV compounds where a subtle change in the chemical structure can have a large impact on the clinical result. Where compounds A and B show alternating efficacy in their both their EC$_{50}$ values for polymorphism and protein binding, compound 51 shows none of this variability and is therefor unexpectedly superior when viewed in terms of potential clinical applicability. A direct comparison between compound 51 and compounds A and B, demostrate how subtle chemical substitutions can have a dramatic effect on the in vitro efficacy of a putative anti-HIV compound.

A similar advantage for compound 51 can be seen in Table 6 where protein binding and serum shift for the above compounds are compared. This table shows both a significant decrease in the EC$_{50}$ and a reduced serum effect for compound 51 relative to the other compounds tested.

TABLE 5

Wild-type, Polymorphisms, & PBLs - EC$_{50}$ (nM)

| | MT4 NL. wt* | MT4 NL. V370A | HIV-1 B CC1/85 (V370A) | HIV-1 B ASJM108 (V370A+) | HIV-1 C 97ZA009 (V370A+) |
|---|---|---|---|---|---|
| Bevirimat | 223 | 6062 | >10000 | >10000 | 13435 |
| Compound A | 14 | 16 | 5 | 51 | 1159 |
| CompoundB | 8 | 8 | 13 | 6 | 2000 |
| Compound51 | 0.8 | 0.7 | 1.2 | 1.0 | 4 |

*Consensus Clade B Sp1 Genotype.

TABLE 6

Protein Binding Effects on Potency

| | LHIV IC$_{50}$ (nM) | LHIV IC$_{50}$ (nM) with 40% HuS | Fold shift with 40% HuS |
|---|---|---|---|
| Bevirimat | 42 | 6600 | 157 |
| Compound A | 9.3 | 73 | 7.9 |
| CompoundB | 3.2 | 43 | 13.4 |
| Compound51 | 1.9 | 10.6 | 5.5[a] |

[a]Definitive protein shift value determined in PBL's by titration at SRI is 1X

Example 87

It is suspected that many anti-HIV compounds might potentially be less effective in the treatment of patients who have failed a previous protease inhibitor-containing regimen and whose viruses have developed drug resistance mutations within the protease gene.

A major obstacle to their long-term efficacy of anti-HIV therapies has been the emergence of resistance to current antiretroviral drugs. One method for comparing the effectiveness of anti-HIV compounds is the characterization of such compounds' polymorphism at drug resistant sites.

Figure 2:
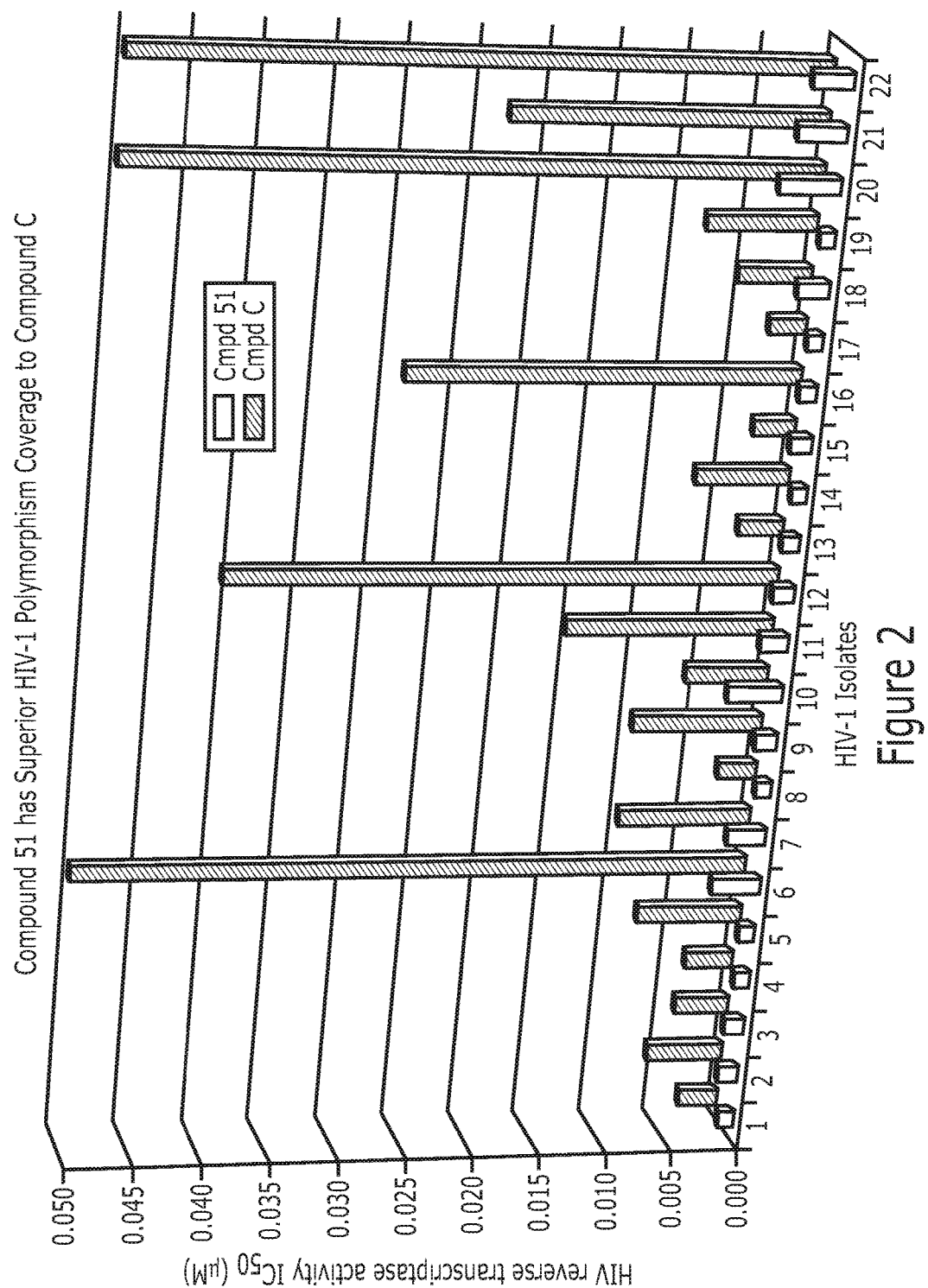
FIG. 2 shows a bar graph representing a comparison between compound 51 and compound C of their relative ability to inhibit HIV reverse transcriptase activity across a broad panel of HIV-1 isolates.

A comparison of compound 51 versus Bevirimet ("BVM") against a broad panel of HIV isolates is shown in FIG. 1. From FIG. 1, it can be seen that compound 51 shows superior polymorphism coverage across this panel of HIV isolates to Bevirimat. Likewise, compound 51 shows superior polymorphism coverage as compared to compound C as shown in FIG. 2.

This example was performed as follows. Crude human primary blood mononuclear cells (PBMCs) were collected from healthy donors via leukapheresis and determined to be negative for HIV exposure, among a variety of additional infectious diseases. PBMCs were isolated via Ficoll-Hypaque density gradient separation followed by aspiration of the banded leukocytes from the gradient. Purified PBMCs from 10 individual donors were combined and cryopreserved in liquid nitrogen as a PBMC pool. Various PBMC pools were utilized.

Various HIV-1 isolates were obtained from different sources. A stock of the virus was generated in a pool of CD4+ PBMCs and frozen. Viral replication for each virus stock was measured on PHA-blasted PBMC pools to determine the appropriate virus input for anti-viral assays. HIV gag sequences were determined for each isolate by the Sanger di-deoxy sequencing method.

Cryo-preserved PBMC pools were thawed and stimulated with 2 µg/mL PHA in media (RPMI1640, 20% FBS, 10% T cell growth factor, antibiotics) for 3 days. Blasts were then washed, counted, and cultured in media at $2\times10^6$ cells/mL in media with 10 U/mL recombinant IL-2 for an additional 24 hours. Stimulated PBMCs were counted for trypan blue exclusion viability and seeded in 96-well round bottom plates at a final density of $1\times10^6$ cells/well. A volume of the drug dose titration was added to the cells followed by a predetermined amount of virus. The plates were incubated for 7 days at 37° C., 5% $CO_2$. to allow for viral replication and inhibition by compound to assess anti-viral potency.

In order to determine anti-viral potency, HIV reverse transcriptase activity in cell culture supernatants was measured as a measure of viral replication in the presence or absence of compound. At the end of the incubation period, fifty (50) µL of PBMC culture supernatants were transferred to a new 96-well plate; 10 µL of RT extraction buffer was added followed by the addition of 40 µL of RT assay buffer. The RT plates were thoroughly mixed and placed in a humidified incubator at 37° C., 5% $CO_2$ for 2 h. DE-81 96-well plates were placed on a vacuum manifold and 100 uL of the RT reaction transferred to the ion-exchange chromatography plates. After applying the solution phase of the RT reaction to the DE-81 plate, the plate was then washed once with prepared 5% $Na_2HPO_4$, followed by a wash of $dH_2O$. Plates were then allowed to dry overnight at room temperature. The plates were sealed and 50 µL scintillation fluid added prior to reading on a Topcount (Packard) luminometer at 10 s/well.

Below are the particular HIV-1 isolates tested as shown in FIG. 1:
1—HIV-1 A_UG275
2—HIV-1 AE_42368
3—HIV-1 C_97/ZA/009
4—HIV-1 C_ETH2220
5—HIV-1 C_ZAM18
6—HIV-1 C_I-2516
7—HIV-1 B_CC1/85
8—HIV-1 B_ASJM108
9—HIV-1 B_SF162
10—HIV-1 B_92US657
11—HIV-1 B_BR92030
12—HIV-1 B_ASM42
13—HIV-1 B_BR92023
14—HIV-1 B_ASM44
15—HIV-1 B_92US660
16—HIV-1 B_THA92014
17—HIV-1 B_IIIB
18—HIV-1 B_301596
19—HIV-1 B_ASM34
20—HIV-1 B_BK132
21—HIV-1 B_ASM57
22—HIV-1 B_ASM54
23—HIV-1 B_92HT599
24—HIV-1 B_CM237
25—HIV-1 B_92HT593
26—HIV-1 B_BZ167
27—HIV-1 B_92US723

Below are the particular HIV isolates tested as shown in FIG. 2:
1—HIV-1 A_UG275
2—HIV-1 AE_42368
3—HIV-1 B_301596
4—HIV-1 B_92HT593
5—HIV-1 B_92HT599
6—HIV-1 B_92US657
7—HIV-1 B_92US660
8—HIV-1 B_92US723
9—HIV-1 B_ASJM108
10—HIV-1 B_ASM34
11—HIV-1 B_ASM42
12—HIV-1 B_ASM44
13—HIV-1 B_ASM54
14—HIV-1 B_BK132
15—HIV-1 B_BZ167
16—HIV-1 B_CC1/85
17—HIV-1 B_CM237
18—HIV-1 B_IIIB
19—HIV-1 B_SF162
20—HIV-1 C_97/ZA/009
21—HIV-1 C_ETH2220
22—HIV-1 C_ZAM18

Example 88

This example shows in Table 7 a direct comparison between compound 51, compound 56, and compound C. Intrinsic HIV wild type potency for compound 51 relative to compound C is about 10× better (0.8 nM vs. 6 nM). In the HIV polymorphic strain, V370, the potency for compound 51 relative to compound C is even more dramatic (0.7 nM vs. 19 nM). In terms of human protein shift listed as human serum (HS) in this example, is another factor of 10 fold better for compound 51 relative to compound C (5.5 fold shift vs. a 48.9 fold shift).

All taken together, as can be seen in Table 7 there is a factor of 238 fold improvement for compound 51 over compound C for the $C_{trough}$ target, which is the $PAEC_{50}$ (or $PAEC_{90}$ which is the same factor just higher for each by a factor of 3-4 fold). In fact, the reported 5.5 fold shift in Table 7 for 40% human serum in a multicell HIV full life cycle reporter based assay.

Table 7 also depicts the protein adjusted $EC_{50}$ for the V370A polymorphic virus (which represents up to 40% of patients in clade B and maybe more outside clade B) you can see that compound 51 potency is unexpectedly greater at 3.9 nM, while compound C potency is lower at 929 nM.

TABLE 7

| Compound Identity | HIV w/t $^{MT4}EC_{50}$ | V370A $^{MT4}EC_{50}$ | Human Serum Fold Shift** | V370A $PAEC_{50}$*** |
|---|---|---|---|---|
| Compound 51 ('232) | 0.8 nM | 0.7 nM | 5.5X | 3.9 nM |
| Compound 56 ('233) | 4 nM | 4 nM | 16.2X | 65 nM |
| Compound C ('363) | 6 nM | 19 nM | 48.9X | 929 nM |

**Human Serum fold shift values determined using 40% human serum in a HIV multicell full life cycle assay.
***V370A $PAEC_{50}$ is determined by the product of V370A $^{MT4}EC_{50}$ and human serum fold shift.

Example 89

The PBL assay in this example was performed as follows in order to study the effect of human serum on the HIV antiviral activity of certain compounds. In particular, the effect of the presence of human serum on the antiviral activity of compound 51 and Bevirimat ("BVM") was evaluated in a modified PMBC assay.

In the standard assay, PHA/IL-2 stimulated PBMCs ($5 \times 10^4$ cells/well) were incubated with virus and compound 51 or BVM (both compounds tested at range of 0.06 nM to 25 mM) for 7 days.

In the modified PBMC assay, PHA/IL-2 stimulated PBMCs were pre-incubated with HIV-1 strain JR-CSF prior to addition of compound 51 or BVM and human serum. In this assay, $8 \times 10^6$ cells from pooled donors were incubated with virus for 1 hour, followed by centrifugation for 1 hour. Cells were then gently re-suspended and incubated an additional 2 hours. During this second incubation period, $2.5 \times 10^4$ uninfected PBMCs from pooled donors were added to the interior 60 wells of a 96 well plate, followed by the addition of compound 51 or BVM (both compounds tested at range of 0.06 nM to 25 mM) and human serum (10%, 20%, 30% and 40%) to the appropriate wells. At the end of the second incubation period, infected cells were diluted in media ($5 \times 10^5$ cells/mL) (without washout of virus) and 50 mL ($2.5 \times 10^4$ cells) were added to each well of the plate and incubated for 7 days.

Following incubation in both the standard and modified assays, supernatants were assayed for reverse transcriptase (RT) activity and p24 antigen content by ELISA and spectrophotometric analysis at 450 nM.

Compound 51 maintained antiviral activity in the presence of human serum at all serum concentrations tested, with no apparent shift in $IC_{50}$ values (range: 0.52 to 3.07 nM) compared to the $IC_{50}$ value (0.69 nM) in the standard assay (0% serum). These results indicate that the inhibitory activity of compound 51 is minimally or not at all impacted by serum proteins. Extrapolating from the normalized $IC_{50}$ values observed in the presence of the various human serum concentrations gave an estimated $IC_{50}$ value of 0.33 nM for 100% human serum (assuming a linear relationship). BVM also maintained antiviral activity in the presence of human serum at all concentrations, however, there was a large increase in the $IC_{50}$ values (range: 1.38 mM to 13 mM) associated with increasing human serum concentrations compared to the standard assay (9.76 nM). Extrapolating from the normalized $IC_{50}$ values observed in the presence of the various concentrations of human serum there is a 2,310-fold change in the $IC_{50}$ value in the presence of 100% serum (compared to the control experiment, suggesting that BVM is highly bound by serum proteins).

The effect of human serum on antiviral activity of compound 51 and BVM was also evaluated in the LHIV assay. Using the same format as the standard LHIV assay, the addition of 40% human serum caused a 5.6-fold shift in the $IC_{50}$ value (10.6 nM) for compound 51 and a 174.9-fold shift in $IC_{50}$ value (3.88 mM) for BVM.

Figure 3:
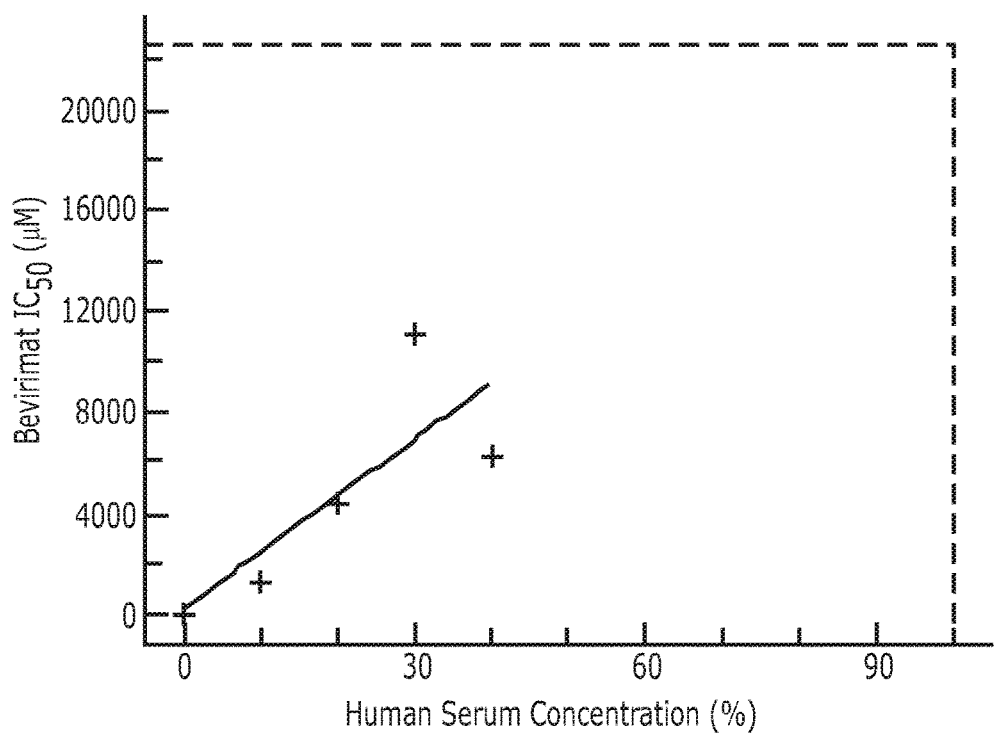
FIG. 3 shows a line graph representing an extrapolation of Bevirimat normalized IC$_{50}$ values to 100% human serum.
Figure 4:
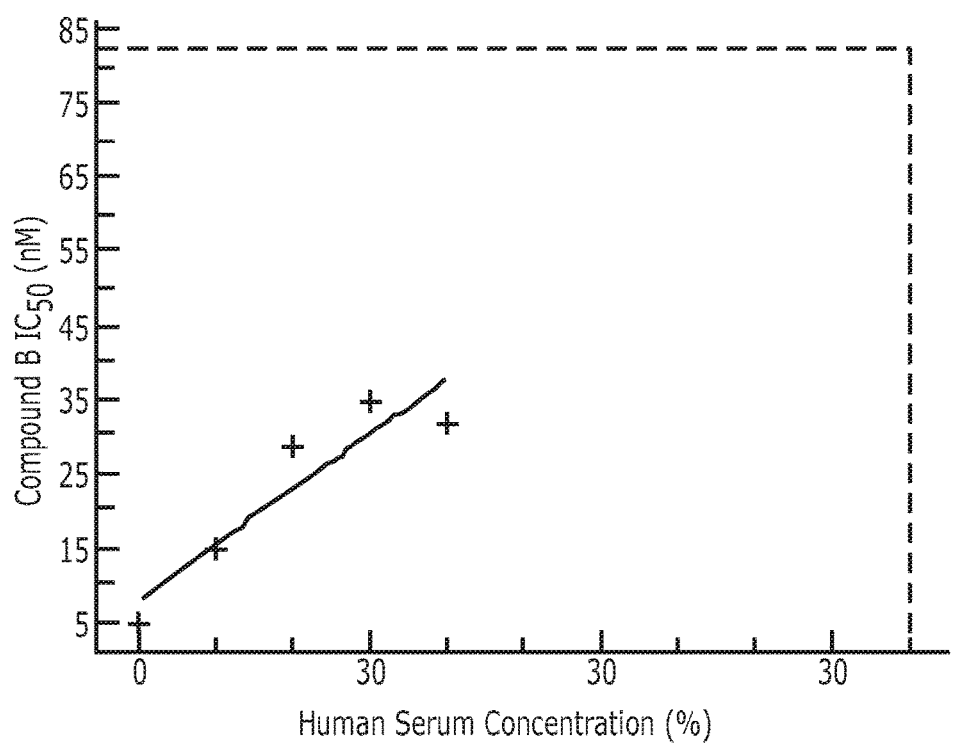
FIG. 4 shows a line graph representing an extrapolation of compound B normalized IC$_{50}$ values to 100% human serum.
Figure 5:
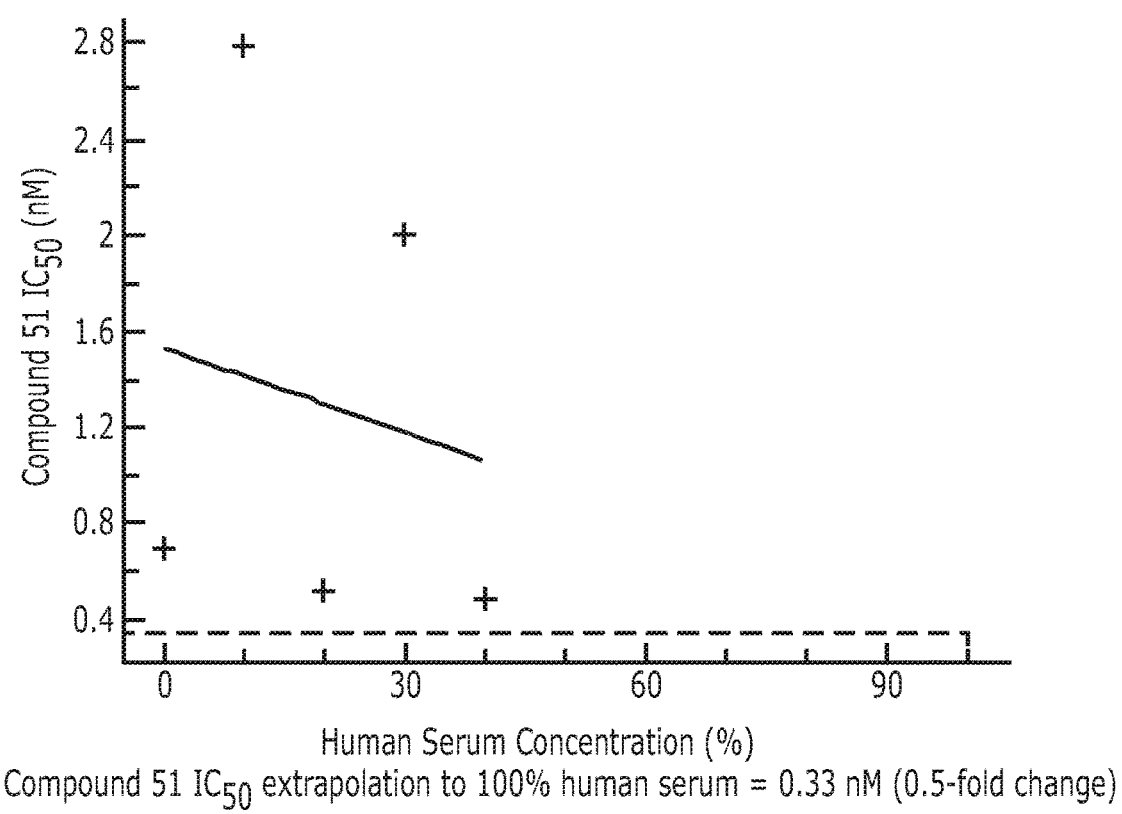
FIG. 5 shows a line graph representing an extrapolation of compound 51 normalized IC$_{50}$ values to 100% human serum.

However, when determined in a PBL assay containing a titration between 0 and 40% human serum the extrapolated value is 1 fold or less. Therefore, the improvement of compound 51 over compound C, in terms of potency while in the presence of human serum, is likely >1300 fold better when a more typical baseline is taken into account. See FIGS. 3, 4, and 5.

What is claimed is:

1. A composition comprising a compound of the structure:

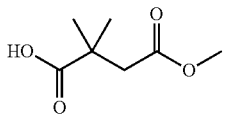

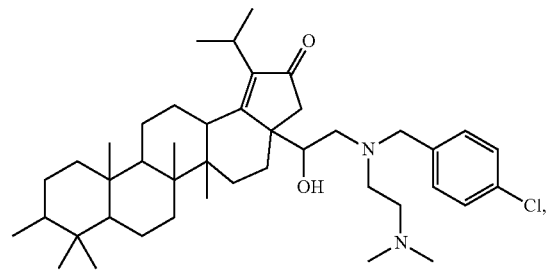

or a pharmaceutically acceptable salt thereof, in combination with an additional agent active against HIV selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

2. A composition comprising a compound of the structure:

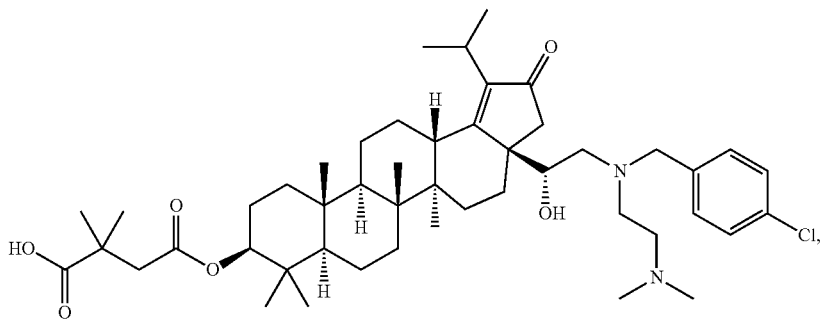

or a pharmaceutically acceptable salt thereof,
in combination with an additional agent active against HIV selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fos-amprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

3. A method of ameliorating an HIV infection in a subject in need thereof comprising 1) administering to the subject a compound of the structure:

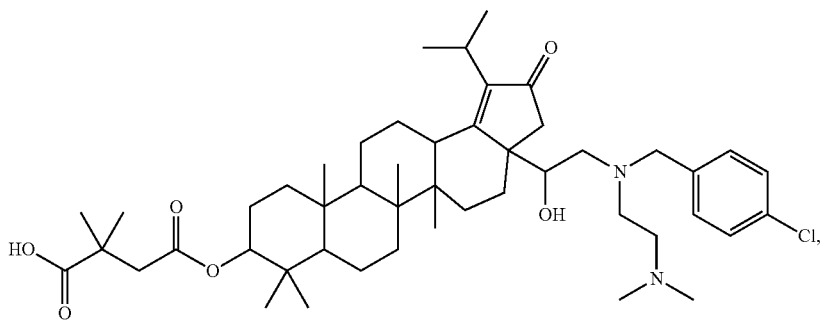

or a pharmaceutically acceptable salt thereof,
and 2) administering to the subject an additional agent active against HIV selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fos-amprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

4. The method according to claim 3, wherein the administering of said additional agent is performed separately.

5. The method according to claim 3, wherein the administering of said additional agent is performed simultaneously.

6. A method of ameliorating an HIV infection in a subject in need thereof comprising 1) administering to the subject a compound of the structure:

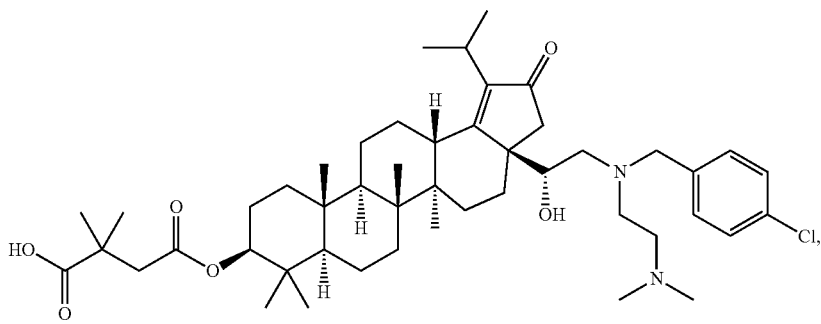

or a pharmaceutically acceptable salt thereof,
and 2) administering to the subject an additional agent active against HIV selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

7. The method according to claim 6, wherein the administering of said second agent is performed separately.

8. The method according to claim 6, wherein the administering of said second agent is performed simultaneously.

* * * * *